United States Patent
Marx et al.

(10) Patent No.: US 12,391,697 B2
(45) Date of Patent: Aug. 19, 2025

(54) CONDENSED BI-HETEROCYCLES AS INHIBITING AGENTS FOR BRUTON'S TYROSINE KINASE

(71) Applicant: BIOGEN MA INC., Cambridge, MA (US)

(72) Inventors: Isaac Marx, Arlington, MA (US); Jürgen Schulz, Boston, MA (US); Brian T. Hopkins, Newton, MA (US); Bin Ma, Arlington, MA (US); Robin Prince, Sharon, MA (US); Marta Nevalainen, Holliston, MA (US)

(73) Assignee: BIOGEN MA INC., Cambridge, MA (US)

( * ) Notice: Subject to any disclaimer, the term of this patent is extended or adjusted under 35 U.S.C. 154(b) by 755 days.

(21) Appl. No.: 17/773,418

(22) PCT Filed: Oct. 29, 2020

(86) PCT No.: PCT/US2020/057961
§ 371 (c)(1),
(2) Date: Apr. 29, 2022

(87) PCT Pub. No.: WO2021/087112
PCT Pub. Date: May 6, 2021

(65) Prior Publication Data
US 2023/0025892 A1 Jan. 26, 2023

Related U.S. Application Data

(60) Provisional application No. 62/928,058, filed on Oct. 30, 2019.

(51) Int. Cl.
*C07D 519/00* (2006.01)
*C07D 487/04* (2006.01)

(52) U.S. Cl.
CPC ......... *C07D 487/04* (2013.01); *C07D 519/00* (2013.01)

(58) Field of Classification Search
CPC .................... C07D 487/04; C07D 519/00
See application file for complete search history.

(56) References Cited

U.S. PATENT DOCUMENTS

2024/0287076 A1* 8/2024 Guckian .............. C07D 495/02

FOREIGN PATENT DOCUMENTS

| WO | 2014/173289 A1 | 10/2014 |
|---|---|---|
| WO | 2015/089327 A1 | 6/2015 |

OTHER PUBLICATIONS

Guo et al., Discovery of Zanubrutinib (BGB-3111), a Novel, Potent, and Selective Covalent Inhibitor of Bruton's Tyrosine Kinase. J Med Chem. Sep. 12, 2019;62(17):7923-7940.
International Search Report and Written Opinion for Application No. PCT/US2020/057961, dated Mar. 10, 2021, 10 pages.

* cited by examiner

*Primary Examiner* — Erich A Leeser
(74) *Attorney, Agent, or Firm* — McCarter & English, LLP; Xin Zhang

(57) ABSTRACT

Provided are compounds of Formula (I): Formula (I) or pharmaceutically acceptable salts thereof, wherein $R^1$, $R^2$, $R^3$, $R^4$, $R^5$, $R^6$, $A^1$, $B^1$, $B^2$, $Q^1$ and $Q^2$ are as defined herein; and methods for their use and production.

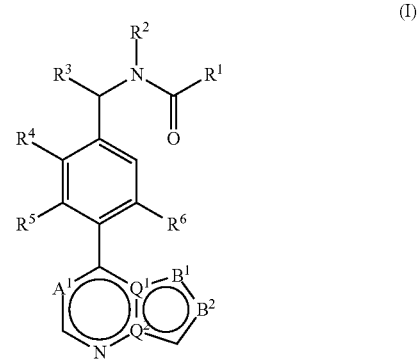

(I)

20 Claims, No Drawings

CONDENSED BI-HETEROCYCLES AS INHIBITING AGENTS FOR BRUTON'S TYROSINE KINASE

RELATED APPLICATIONS

This application is a 35 U.S.C. § 371 national stage filing of International Application No. PCT/US2020/057961, filed on Oct. 29, 2020, which claims the benefit of the filing date, under 35 U.S.C. § 119 (e), of U.S. Provisional Application No. 62/928,058, filed on Oct. 30, 2019, the. The entire contents of which each of the aforementioned applications are incorporated herein by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCy), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I):

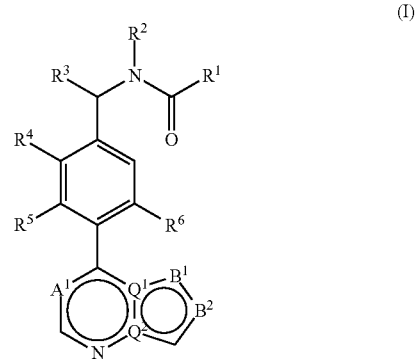

or a pharmaceutically acceptable salt thereof, wherein:
$A^1$ is selected from $CR^7$ and N;
$B^1$ and $B^2$ are each independently selected from $CR^8$, N, and $NR^8$;
one of $Q^1$ and $Q^2$ is N, and the other one is C;
$R^1$ is selected from $-N(R^{1a})_2$, 3- to 7-membered monocyclic carbocyclyl, 3- to 7-membered monocyclic heterocyclyl, 7- to 10-membered bicyclic carbocyclyl, and 7- to 10-membered bicyclic heterocyclyl; wherein the 3- to 7-membered monocyclic carbocyclyl, 3- to 7-membered monocyclic heterocyclyl, 7- to 10-membered bicyclic carbocyclyl, and 7- to 10-membered bicyclic heterocyclyl represented by $R^1$ are each optionally substituted with one or more (e.g., one, two, three, four, five, or six etc.) $R^{10}$;
$R^{1a}$, for each occurrence, is independently selected from H, $C_{1-6}$ alkyl, $C_{2-6}$ alkenyl, $C_{2-6}$ alkynyl, wherein the $C_{1-6}$ alkyl, $C_{2-6}$ alkenyl, and $C_{2-6}$ alkynyl represented by $R^{1a}$ are each optionally substituted with one or more (e.g., one, two, three, four, five, or six etc.) $R^{10}$;
$R^{10}$, for each occurrence, is independently selected from halogen, $-OR^{10a}$, $-S(O)_2R^{10a}$, $-CN$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{10}$ are each optionally substituted with one or more (e.g., one, two, three, four, five, or six etc.) $R^{15}$;
$R^{10a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;
$R^{15}$, for each occurrence, is independently selected from $C_{1-6}$ alkyl, halogen, $-CN$, and $-OR^{15a}$; or two $R^{15}$, taken together with their intervening atom, form 3- to 7-membered monocyclic carbocyclyl or 4- to 6-membered monocyclic heterocyclyl;
$R^{15a}$ is H or $C_{1-6}$ alkyl;
$R^2$ is selected from H, $C_{1-6}$ alkyl, $C_{2-6}$ alkenyl, and $C_{2-6}$ alkynyl;
$R^3$ is selected from H, $C_{1-6}$ alkyl, $C_{2-6}$ alkenyl, $C_{2-6}$ alkynyl, $-C(O)N(R^{3a})_2$, $-C(O)OR^{3a}$, and $-C(O)R^{3a}$, wherein the $C_{1-6}$ alkyl, $C_{2-6}$ alkenyl, and $C_{2-6}$ alkynyl represented by $R^3$ are each optionally substituted with one or more (e.g., one, two, three, four, five, or six etc.) $R^{30}$;

$R^{3a}$, for each occurrence, is independently selected from H, $C_{1-6}$ alkyl, $C_{2-6}$ alkenyl, $C_{2-6}$ alkynyl, wherein the $C_{1-6}$ alkyl, $C_{2-6}$ alkenyl, and $C_{2-6}$ alkynyl represented by $R^{3a}$ are each optionally substituted with one or more (e.g., one, two, three, four, five, or six etc.) $R^{30}$;

$R^{30}$, for each occurrence, is independently selected from halogen, $—OR^{30a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{30a}$ is selected from H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl;

or alternatively $R^2$ and $R^3$, taken together with their intervening atoms, form a Ring A that is selected from 3- to 7-membered monocyclic heterocyclyl and 7- to 10-membered bicyclic heterocyclyl; wherein Ring A is optionally substituted with one or more (e.g., one, two, three, four, five, or six etc.) $R^{200}$;

$R^{200}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $—CN$, $—C(O)R^{200a}$, $—C(O)_2R^{200a}$, $—C(O)N(R^{200a})_2$, $—N(R^{200a})_2$, $—N(R^{200a})C(O)R^{200a}$, $—N(R^{200a})C(O)_2R^{200a}$, $—N(R^{200a})C(O)N(R^{200a})_2$, $—N(R^{200a})S(O)_2R^{200a}$, $—OR^{200a}$, $—OC(O)R^{200a}$, $—OC(O)N(R^{200a})_2$, $—SR^{200a}$, $—S(O)R^{200a}$, $—S(O)_2R^{200a}$, $—S(O)N(R^{200a})_2$, $—S(O)_2N(R^{200a})_2$; wherein the $C_{1-6}$alkyl, $C_{2-6}$alkenyl, $C_{2-6}$alkynyl, 3- to 7-membered monocyclic carbocyclyl, 4- to 6-membered monocyclic heterocyclyl represented by $R^{200}$ are each optionally substituted with one or more (e.g., one, two, three, four, five, or six etc.) $R^{250}$; or two $R^{200}$ taken together with their intervening atom, form 4- to 6-membered monocyclic heterocyclyl or 3- to 7-membered monocyclic carbocyclyl, each of which is optionally substituted with one or more (e.g., one, two, three, four, five, or six etc.) $R^{250}$;

$R^{200a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{200a}$ are each optionally substituted with one or more (e.g., one, two, three, four, five, or six etc.) $R^{250}$;

$R^{250}$, for each occurrence, is independently selected from $C_{1-6}$ alkyl, halogen and $—OR^{250a}$;

$R^{250a}$ is H or $C_{1-6}$ alkyl;

$R^4$ is selected from H, $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $—NO_2$, $—CN$, $—OR^{4a}$, $—SR^{4a}$, $—N(R^{4a})_2$, $—C(O)R^{4a}$, $—C(O)OR^{4a}$, $—S(O)R^{4a}$, $—S(O)_2R^{4a}$, $—C(O)N(R^{4a})_2$, $—SO_2N(R^{4a})_2$, $—OC(O)R^{4a}$, $—N(R)C(O)R^{4a}$, $—N(R)C(O)OR^{4a}$, $—N(R)SO_2R^{4a}$, and $—OC(O)N(R^{4a})_2$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^4$ are each optionally substituted with one or more (e.g., one, two, three, four, five, or six etc.) $R^{40}$;

$R^{4a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{4a}$ are each optionally substituted with one or more (e.g., one, two, three, four, five, or six etc.) $R^{40}$;

$R^{40}$, for each occurrence, is independently selected from halogen, $—OR^{40a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{40}$ are each optionally substituted with one or more (e.g., one, two, three, four, five, or six etc.) $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl are each optionally substituted with one or more (e.g., one, two, three, four, five, or six etc.) $R^{45}$;

$R^{45}$, for each occurrence, is independently selected from $C_{1-6}$ alkyl, halogen and $—OR^{45a}$;

$R^{45a}$ is H or $C_{1-6}$ alkyl;

or alternatively $R^3$ and $R^4$, taken together with their intervening atoms form Ring B that is selected from 5- to 7-membered monocyclic carbocyclyl and 5- to 7-membered monocyclic heterocyclyl having 1-2 heteroatoms independently selected from O, N and S; wherein Ring B is optionally substituted with one or more (e.g., one, two, three, four, five, or six etc.) $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $—C(O)R^{300a}$, $—OR^{300a}$, and $—S(O)_2R^{300a}$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more (e.g., one, two, three, four, five, or six etc.) $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more (e.g., one, two, three, four, five, or six etc.) $R^{350}$;

$R^{350}$, for each occurrence, is independently selected from $C_{1-6}$ alkyl, halogen, $—CN$, $—C(O)R^{350a}$, $—C(O)N(R^{350a})_2$, $—C(R^{350a})_2N(R^{350a})_2$, and $—OR^{350a}$;

$R^{350a}$, for each occurrence, is independently H or $C_{1-6}$ alkyl optionally substituted with one to three halogen, or two $R^{350a}$ together with the N atom from which they are attached form 4- to 6-membered monocyclic heterocyclyl with 1-2 heteroatoms selected from N and O;

$R^5$ is selected from H, $C_{1-6}$ alkyl, $C_{2-6}$ alkenyl, $C_{2-6}$ alkynyl, halogen, and $—OR^{5a}$; wherein the $C_{1-6}$ alkyl, $C_{2-6}$ alkenyl, and $C_{2-6}$ alkynyl represented by $R^5$ are optionally substituted with one or more (e.g., one, two, three, four, five, or six etc.) halogen;

$R^{5a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl represented by $R^{5a}$ are each optionally substituted with one or more (e.g., one, two, three, four, five, or six etc.) halogen;

$R^6$ is selected from H, $C_{1-6}$ alkyl, $C_{2-6}$ alkenyl, $C_{2-6}$ alkynyl, halogen, —$OR^{6a}$; wherein the $C_{1-6}$ alkyl, $C_{2-6}$ alkenyl and $C_{2-6}$ alkynyl represented by $R^6$ are each optionally substituted with one or more (e.g., one, two, three, four, five, or six etc.) halogen;

$R^{6a}$ is H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{6a}$ are each optionally substituted with one or more (e.g., one, two, three, four, five, or six etc.) halogen;

$R^7$ is selected from H, $C_{1-6}$ alkyl, $C_{2-6}$ alkenyl, $C_{2-6}$ alkynyl, —CN, —$OR^{7a}$, —$C(O)N(R^{7a})_2$, —$C(O)OR^{7a}$, and —$C(O)R^{7a}$; wherein the $C_{1-6}$ alkyl, $C_{2-6}$ alkenyl, and $C_{2-6}$ alkynyl represented by $R^7$ are each optionally substituted one or more (e.g., one, two, three, four, five, or six etc.) $R^{70}$;

$R^{7a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{7a}$ are each optionally substituted with one or more (e.g., one, two, three, four, five, or six etc.) $R^7$;

$R^{70}$, for each occurrence, is independently selected from halogen, —$OR^{70a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$alkyl, $C_{2-6}$alkenyl, $C_{2-6}$alkynyl, 3- to 7-membered monocyclic carbocyclyl and 4- to 6-membered monocyclic heterocyclyl represented by $R^{70}$ are optionally substituted with one or more (e.g., one, two, three, four, five or six etc.) $R^{75}$;

$R^{70a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{70a}$ are each optionally substituted one or more (e.g., one, two, three, four, five, or six etc.) $R^{75}$;

$R^{75}$, for each occurrence, is independently selected from $C_{1-6}$ alkyl, halogen and —$OR^{75a}$;

$R^{75a}$ is H or $C_{1-6}$ alkyl;

$R^8$, for each occurrence, is independently selected from H, halogen, $C_{1-6}$ alkyl, $C_{2-6}$ alkenyl, $C_{2-6}$ alkynyl, —CN, —$C(O)R^{8a}$, —$C(O)_2R^{8a}$, —$C(O)N(R^{8a})_2$, —$N(R^{8a})_2$, —$N(R^{8a})C(O)R^{8a}$, —$N(R^{8a})C(O)_2R^{8a}$, —$N(R^{8a})C(O)N(R^{8a})_2$, —$N(R^{8a})S(O)_2R^{8a}$, —$OR^{8a}$, —$OC(O)R^{8a}$, —$OC(O)N(R^{8a})_2$, —$SR^{8a}$, —$S(O)R^{8a}$, —$S(O)_2R^{8a}$, —$S(O)N(R^{8a})_2$, —$S(O)_2N(R^{8a})_2$, 3- to 7-membered monocyclic carbocyclyl, 4- to 6-membered monocyclic heterocyclyl, and 7- to 10-membered bicyclic heterocyclyl; wherein the $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl and 7- to 10-membered bicyclic heterocyclyl represented by $R^8$ are each optionally substituted with one or more (e.g., one, two, three, four, five, or six etc.) $R^{80}$;

$R^{8a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{8a}$ are each optionally substituted with one or more (e.g., one, two, three, four, five, or six etc.) $R^{80}$; or two $R^{8a}$, taken together with their intervening atom, form 4- to 6-membered monocyclic heterocyclyl optionally substituted with one or more (e.g., one, two, three, four, five, or six etc.) $R^{80}$;

$R^{80}$, for each occurrence, is independently selected from halogen, $C_{1-6}$ alkyl, $C_{2-6}$ alkenyl, $C_{2-6}$ alkynyl, —CN, —$C(O)R^{80a}$, —$C(O)_2R^{80a}$, —$C(O)N(R^{80a})_2$, —$N(R^{80a})_2$, —$N(R^{80a})C(O)R^{80a}$, —$N(R^{80a})C(O)_2R^{80a}$, —$N(R^{80a})C(O)N(R^{80a})_2$, —$N(R^{80a})S(O)_2R^{80a}$, —$OR^{80a}$, —$OC(O)R^{80a}$, —$OC(O)N(R^{80a})_2$, —$SR^{80a}$, —$S(O)R^{80a}$, —$S(O)_2R^{80a}$, —$S(O)N(R^{80a})_2$, —$S(O)_2N(R^{80a})_2$, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{80}$ are each optionally substituted with one or more (e.g., one, two, three, four, five, or six etc.) $R^{85}$; or two $R^{80}$ together the carbon atom from which they are attached form an oxo group (—C=O)—);

$R^{80a}$, for each occurrence, is independently selected from H, $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl; wherein the $C_{1-6}$ alkyl, $C_{2-6}$ alkenyl, $C_{2-6}$alkynyl, 3- to 6-membered monocyclic carbocyclyl, and 4- to 6-membered monocyclic heterocyclyl represented by $R^{80a}$ are each optionally substituted with one or more (e.g., one, two, three, four, five, or six etc.) $R^{85}$;

$R^{85}$, for each occurrence, is independently $C_{1-6}$ alkyl, halogen and —$OR^{85a}$; and $R^{85a}$ is H or $C_{1-6}$ alkyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to the subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof for use in treating a disorder responsive to inhibition of Btk.

Other features or advantages will be apparent from the following detailed description of several embodiments, and also from the appended claims.

DETAILED DESCRIPTION

The compounds or pharmaceutically acceptable salts thereof as described herein, can have activity as Btk modulators. In particular, compounds or pharmaceutically acceptable salts thereof as described herein, can be Btk inhibitors.

In a second embodiment, a compound of the present invention is represented by formula (I), or a pharmaceutically acceptable salt thereof, wherein $A^1$ is N, $Q^1$ is C, and $Q^2$ is N; and the definitions for the other variables are as defined in the first embodiment.

In a third embodiment, a compound of the present invention is represented by formula (I), or a pharmaceutically acceptable salt thereof, wherein $A^1$ is CH, $Q^1$ is N, and $Q^2$ is C; and the definitions for the other variables are as defined in the first embodiment.

In a fourth embodiment, a compound of the present invention is represented by formula (I), or a pharmaceutically acceptable salt thereof, wherein $A^1$ is CH; $Q^1$ is C and $Q^2$ is N; and the definitions for the other variables are as defined in the first embodiment.

In a fifth embodiment, a compound of the present invention is represented by any one of the following formulas:

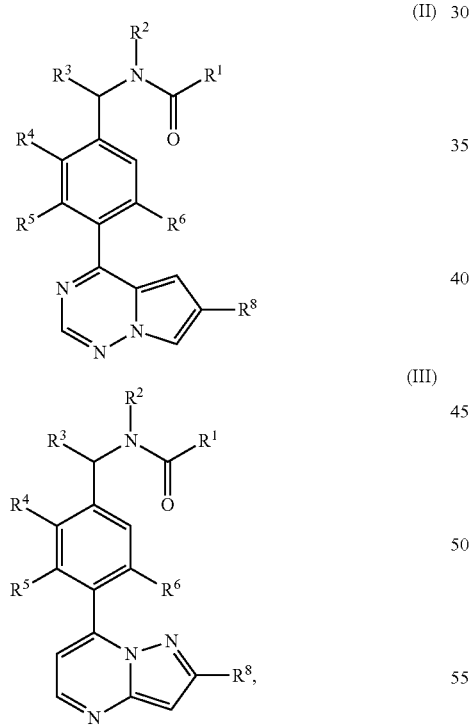

or a pharmaceutically acceptable salt thereof; and the definitions for the variables are as defined in the first embodiment.

In a sixth embodiment, a compound of the present invention is represented by formula (I), (II), or (III) or a pharmaceutically acceptable salt thereof, wherein $R^1$ is 5- to 6-membered monocyclic heteroaryl having 1-4 heteroatoms independently selected from O, N and S; wherein the 5- to 6-membered monocyclic heteroaryl represented by $R^1$ is optionally substituted with one or two $R^{10}$; and the definitions for the other variables are as defined in the first, second, third, fourth or fifth embodiment.

In a seventh embodiment, a compound of the present invention is represented by formula (I), (II), or (III) or a pharmaceutically acceptable salt thereof, wherein $R^1$ is a 5-membered heteroaryl selected from pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl, each of which is optionally substituted with one or two $R^{10}$; and the definitions for the other variables are as defined in the first, second, third, fourth, fifth or sixth embodiment.

In an eighth embodiment, a compound of the present invention is represented by formula (I), (II), or (III) or a pharmaceutically acceptable salt thereof, wherein $R^1$ is represented by one of the following formulas:

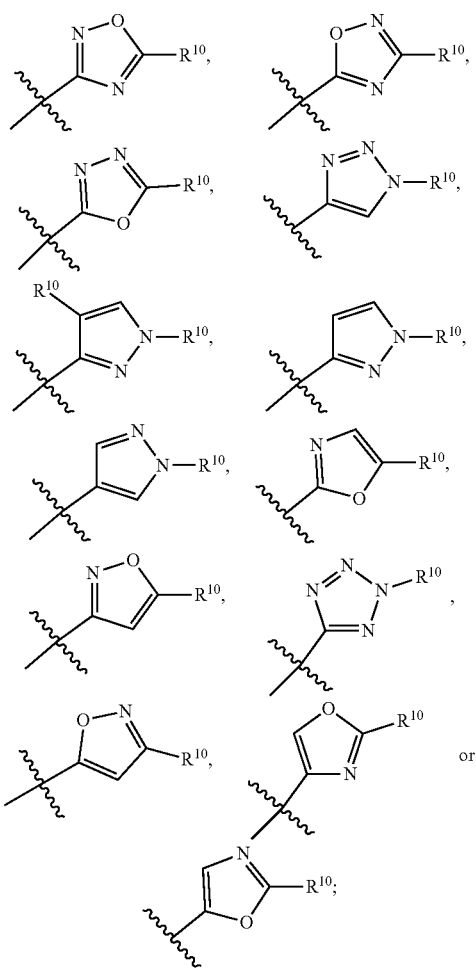

and the definitions for the other variables are as defined in the first, second, third, fourth, fifth or seventh embodiment.

In a ninth embodiment, a compound of the present invention is represented by formula (I), (II), or (III), or a pharmaceutically acceptable salt thereof, wherein $R^{10}$, for each occurrence, is independently selected from halogen, —$OR^{10a}$, —$S(O)_2R^{10a}$, —CN, $C_{1-6}$ alkyl, $C_{3-6}$ cycloalkyl, and phenyl; wherein the $C_{1-6}$ alkyl, $C_{3-6}$ cycloalkyl, and phenyl represented by $R^{10}$ are each optionally substituted with one to three $R^{15}$;

$R^{10a}$, for each occurrence, is independently selected from H and $C_{1-3}$ alkyl;

$R^{15}$, for each occurrence, is independently selected from $C_{1-6}$alkyl, halogen, —CN and —$OR^{15a}$; and $R^{15a}$ is H or $C_{1-3}$ alkyl; and the definitions for the other variables are as defined in the first, second, third, fourth, fifth, sixth, seventh or eighth embodiment.

In a tenth embodiment, a compound of the present invention is represented by formula (I), (II), or (III), or a pharmaceutically acceptable salt thereof, wherein $R^{10}$, for each occurrence, is independently selected from —F, —CN, —$CH_2OH$, —$CF_3$, —$CH_3$, —$C(CH_3)_3$, —$CH(CH_3)_2$, —$C(CH_3)_2CHF_2$, —$C(CH_3)_2CH_2F$, —$C(CH_3)_2CN$, —$CH_2CH(CH_3)_2$, 1-methylcyclopropyl, 2,2-difluorocyclopropyl, phenyl, and —$S(O)_2CH_3$; and the definitions for the other variables are as defined in the first, second, third, fourth, fifth, sixth, seventh or eighth embodiment.

In a eleventh embodiment, a compound of the present invention is represented by formula (I), (II), or (III), or a pharmaceutically acceptable salt thereof, wherein $R^{10}$, for each occurrence, is independently selected from $C_{1-6}$ alkyl and $C_{3-6}$ cycloalkyl, wherein the $C_{1-6}$ alkyl and $C_{3-6}$ cycloalkyl are each optionally substituted with one to three $R^{15}$; and wherein $R^{15}$ for each occurrence is independently halogen or $C_{1-3}$ alkyl; and the definitions for the other variables are as defined in the first, second, third, fourth, fifth, sixth, seventh, or eighth embodiment.

In a twelfth embodiment, a compound of the present invention is represented by formula (I), (II), or (III), or a pharmaceutically acceptable salt thereof, wherein $R^2$ is H or methyl; and the definitions for the other variables are as defined in the first, second, third, fourth, fifth, sixth, seventh, eighth, ninth, tenth, or eleventh embodiment.

In a thirteenth embodiment, a compound of the present invention is represented by formula (I), (II), or (III), or a pharmaceutically acceptable salt thereof, wherein $R^3$ is H; and the definitions for the other variables are as defined in the first, second, third, fourth, fifth, sixth, seventh, eighth, ninth, tenth, eleventh, or twelfth embodiment.

In a fourteenth embodiment, a compound of the present invention is represented by formula (I), (II), or (III), or a pharmaceutically acceptable salt thereof, wherein $R^4$ is selected from halogen, —CN, —$OR^{4a}$, $C_{1-6}$ alkyl, and $C_{3-6}$ cycloalkyl, wherein the $C_{1-6}$ alkyl and $C_{3-6}$cycloalkyl represented by $R^4$ are each optionally substituted with one to three halogen; and $R^{4a}$ is $C_{1-4}$alkyl optionally substituted with one to three halogen; and the definitions for the other variables are as defined in the first, second, third, fourth, fifth, sixth, seventh, eighth, ninth, tenth, eleventh, twelfth, or thirteenth embodiment.

In a fifteenth embodiment, a compound of the present invention is represented by formula (I), (II), or (III), or a pharmaceutically acceptable salt thereof, wherein $R^4$ is selected from —F, —Cl, —$OCH_3$, —$CH_3$, —$CF_3$, —$CHF_2$, —$CH_2CHF_2$, and cyclopropyl; and the definitions for the other variables are as defined in the first, second, third, fourth, fifth, sixth, seventh, eighth, ninth, tenth, eleventh, twelfth, or thirteenth embodiment.

In a sixteenth embodiment, a compound of the present invention is represented by formula (I), (II), or (III), or a pharmaceutically acceptable salt thereof, wherein $R^3$ and $R^4$, taken together with their intervening atoms form Ring B that is a 7-membered monocyclic carbocyclyl or 7-membered monocyclic heterocyclyl having one heteroatom selected from O and N; and the definitions for the other variables are as defined in the first, second, third, fourth, fifth, sixth, seventh, eighth, ninth, tenth, eleventh or twelfth embodiment.

In a seventeenth embodiment, a compound of the present invention is represented by any one of the following formulas:

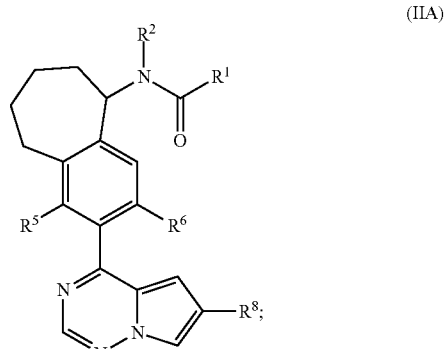

(IIA)

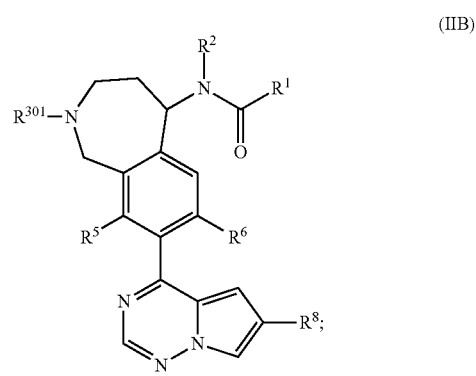

(IIB)

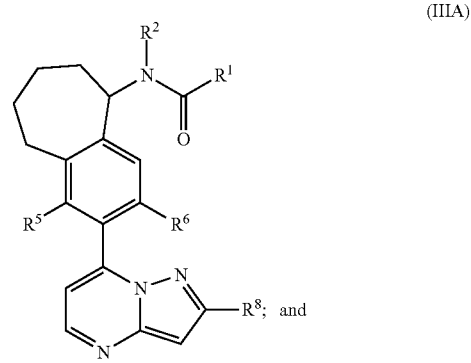

(IIIA)

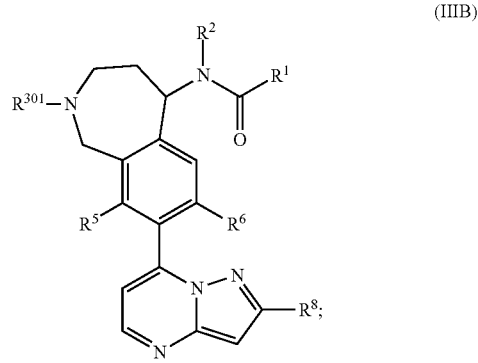

(IIIB)

or a pharmaceutically acceptable salt thereof, wherein:
$R^{301}$ is H or $R^{300}$;
$R^{300}$ is selected from $C_{1-6}$ alkyl, $C_{2-6}$ alkenyl, $C_{2-6}$ alkynyl, 4- to 6-membered monocyclic heterocyclyl, $-C(O)R^{300a}$, $-OR^{300a}$, and $-S(O)_2R^{300a}$; wherein the $C_{1-6}$ alkyl, $C_{2-6}$ alkenyl, $C_{2-6}$ alkynyl and 4- to 6-membered monocyclic heterocyclyl represented by $R^{300}$ are each optionally substituted with one to three $R^{350}$;
$R^{300a}$ is selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl are each optionally substituted with one to three $R^{350}$;
$R^{350}$, for each occurrence, is independently selected from $C_{1-6}$ alkyl, halogen, —CN, $-N(R^{350a})_2$, $-C(O)R^{350a}$, $-C(O)N(R^{350a})_2$, $-C(R^{350a})_2N(R^{350a})_2$, and $-OR^{350a}$, wherein the $C_{1-6}$alkyl is optionally substituted with one to three halogen;
$R^{350}$, for each occurrence, is independently H or $C_{1-6}$alkyl optionally substituted with one to three halogen; or two $R^{350a}$ together with the N atom from which they are attached form 4- to 6-membered monocyclic heterocyclyl with 1-2 heteroatoms selected from N and O; and the definitions for the variables are as defined in the first, second, third, fourth, fifth, sixth, seventh, eighth, ninth, tenth, eleventh, twelfth, thirteenth fourteenth, or fifteenth embodiment.

In a specific embodiment, $R^{300}$ is represented by one of the following formula:

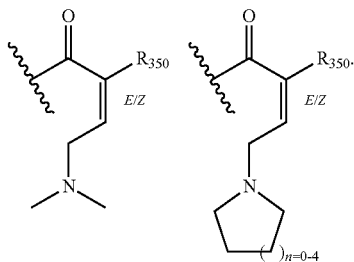

In an eighteenth embodiment, a compound of the present invention is represented by formula (I), (II), (III), (IIA), (IIB), (IIIA), or (IIIB), or a pharmaceutically acceptable salt thereof, wherein $R^5$ is H or halogen; and the definitions for the variables are as defined in the first, second, third, fourth, fifth, sixth, seventh, eighth, ninth, tenth, eleventh, twelfth, thirteenth fourteenth, fifteenth, sixteenth, or seventeenth embodiment.

In a nineteenth embodiment, a compound of the present invention is represented by formula (I), (II), (III), (IIA), (IIB), (IIIA), or (IIIB), or a pharmaceutically acceptable salt thereof, wherein $R^5$ is H or F; and the definitions for the variables are as defined in the first, second, third, fourth, fifth, sixth, seventh, eighth, ninth, tenth, eleventh, twelfth, thirteenth fourteenth, fifteenth, sixteenth, or seventeenth embodiment.

In a twentieth embodiment, a compound of the present invention is represented by formula (I), (II), (III), (IIA), (IIB), (IIIA), or (IIIB), or a pharmaceutically acceptable salt thereof, wherein $R^6$ is H or halogen; and the definitions for the variables are as defined in the first, second, third, fourth, fifth, sixth, seventh, eighth, ninth, tenth, eleventh, twelfth, thirteenth fourteenth, fifteenth, sixteenth, seventeenth, eighteenth, or nineteenth embodiment.

In a twenty-first embodiment, a compound of the present invention is represented by formula (I), (II), (III), (IIA), (IIB), (IIIA), or (IIIB), or a pharmaceutically acceptable salt thereof, wherein $R^6$ is H or F; and the definitions for the variables are as defined in the first, second, third, fourth, fifth, sixth, seventh, eighth, ninth, tenth, eleventh, twelfth, thirteenth fourteenth, fifteenth, sixteenth, seventeenth, eighteenth, or nineteenth embodiment.

In a twenty-second embodiment, a compound of the present invention is represented by formula (I), (II), (III), (IIA), (IIB), (IIIA), or (IIIB), or a pharmaceutically acceptable salt thereof, wherein $R^8$, for each occurrence, is independently selected from H, halogen, $C_{2-6}$ alkynyl, —C(O)$R^{8a}$, —C(O)N($R^{8a})_2$, —N($R^{8a})_2$, —O$R^{8a}$, —CN, $C_{1-6}$ alkyl, $C_{2-6}$ alkenyl, phenyl, $C_{3-6}$ cycloalkyl, 4- to 6-membered monocyclic heterocyclyl having 1-2 heteroatoms independently selected from O, N and S, and 7- to 10-membered bicyclic heterocyclyl having 1-4 heteroatoms independently selected from O, N and S; wherein the $C_{1-6}$ alkyl, $C_{2-6}$ alkenyl, $C_{2-6}$ alkynyl, phenyl, $C_{3-6}$ cycloalkyl, 4- to 6-membered monocyclic heterocyclyl, and 7- to 10-membered bicyclic heterocyclyl represented by $R^8$ are each optionally substituted with one to three $R^{80}$;
$R^{8a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{8a}$ are each optionally substituted with one or three $R^{80}$; or two $R^{8a}$, taken together with their intervening atom, form 4- to 6-membered monocyclic heterocyclyl optionally substituted with one to three $R^{80}$;
$R^{80}$, for each occurrence, is independently selected from halogen, —CN, —C(O)$R^{80a}$, —O$R^{80a}$, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{80}$ are each optionally substituted with one or three $R^{85}$; or two $R^{80}$ together the carbon atom from which they are attached form an oxo group (—C=O—); and
$R^{80a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl having 1-2 heteroatoms independently selected from O, N and S;
$R^{85}$, for each occurrence, is independently selected from halogen and —O$R^{85a}$;
$R^{85a}$ is H or $C_{1-6}$ alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, or twenty-first embodiment.

In a twenty-third embodiment, a compound of the present invention is represented by formula (I), (II), (III), (IIA), (IIB), (IIIA), or (IIIB), or a pharmaceutically acceptable salt thereof, wherein $R^8$, for each occurrence, is independently selected from H, halogen, $C_{1-6}$ alkyl, $C_{2-6}$ alkynyl, —C(O)$R^{8a}$, —C(O)N($R^{8a})_2$, —N($R^{8a})_2$, —O$R^{8a}$, —CN, phenyl, 4- to 6-membered monocyclic heterocyclyl having 1-2 heteroatoms independently selected from O, N and S, and 7- to 10-membered bicyclic heterocyclyl having 1-3 heteroatoms independently selected from O, N and S; wherein the $C_{1-6}$ alkyl, $C_{2-6}$ alkynyl, phenyl, 4- to 6-membered monocyclic heterocyclyl, and 7- to 10-membered bicyclic heterocyclyl represented by $R^8$ are each optionally substituted with one to three $R^{80}$;

$R^{8a}$, for each occurrence, is independently selected from $C_{1-6}$ alkyl and 4- to 6-membered monocyclic heterocyclyl, wherein the $C_{1-6}$ alkyl and 4- to 6-membered monocyclic heterocyclyl represented by $R^{8a}$ are each optionally substituted with one to three $R^{80}$;

$R^{80}$, for each occurrence, is independently selected from halogen, —CN, —C(O)$R^{80a}$, —OR$^{80a}$, $C_{1-6}$ alkyl, $C_{3-6}$ cycloalkyl, and 4- to 6-membered monocyclic heterocyclyl, wherein the $C_{1-6}$ alkyl, $C_{3-6}$ cycloalkyl, and 4- to 6-membered monocyclic heterocyclyl represented by $R^{80}$ are each optionally substituted with one to three $R^{85}$; or two $R^{80}$ together the carbon atom from which they are attached form an oxo group (—C=O—);

$R^{80a}$, for each occurrence, is independently selected from H, $C_{1-6}$ alkyl and $C_{2-6}$ alkenyl;

$R^{85}$, for each occurrence, is independently selected from halogen and —OR$^{85a}$; and $R^{85a}$ is H or $C_{1-3}$ alkyl; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, or twenty-first embodiment.

In a twenty-fourth embodiment, a compound of the present invention is represented by formula (I), (II), (III), (IIA), (IIB), (IIIA), or (IIIB), or a pharmaceutically acceptable salt thereof, wherein $R^8$ is selected from H, —CH$_3$, —CH$_2$OCH$_3$, F, Br, —CN, —OCH$_3$, —OC$_2$H$_5$OCH$_3$, —N(CH$_3$)(CH$_2$CH$_2$OCH$_3$), —C(O)N(CH$_3$)$_2$,

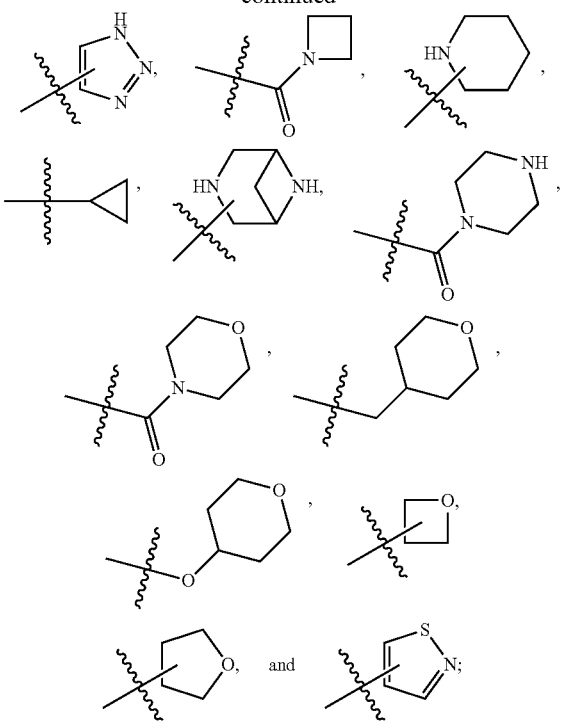

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, or twenty-second embodiment.

In a twenty-fifth embodiment, a compound of the present invention is represented by formula (I), (II), (III), (IIA), (IIB), (IIIA), or (IIIB), or a pharmaceutically acceptable salt thereof, wherein $R^{80}$ is selected from halogen, —CN, —C(O)$R^{80a}$, —OR$^{80a}$, $C_{1-3}$ alkyl, $C_{3-6}$ cycloalkyl, and 4- to 6-membered monocyclic heterocyclyl having 1-2 heteroatoms selected from O and N; wherein the $C_{1-3}$ alkyl, $C_{3-6}$ cycloalkyl, and 4- to 6-membered monocyclic heterocyclyl represented by $R^{80}$ are each optionally substituted with one to three $R^{85}$; or two $R^{80}$ together with the carbon atom from which they are attached from an oxo (—C(=O)) group;

$R^{80a}$, for each occurrence, is independently selected from $C_{1-4}$alkyl and $C_{2-4}$ alkenyl;

$R^{85}$, for each occurrence, is independently selected from F, —OH or $C_{1-3}$alkoxy; and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third or twenty-fourth embodiment.

In a twenty-sixth embodiment, a compound of the present invention is represented by formula (I), (II), (III), (IIA), (IIB), (IIIA), or (IIIB), or a pharmaceutically acceptable salt thereof, wherein $R^{80}$, for each occurrence, is independently selected from —F, —CH$_3$, —CHF$_2$, —CH$_2$OH, —CH(CH$_3$)$_2$, —C$_2$H$_5$, —CH$_2$CHF$_2$, —CN, —OCH$_3$, —C(O)(CH$_2$C=CH), —C(O)(CH=CCH$_3$), —CH$_2$CH$_2$OCH$_3$,

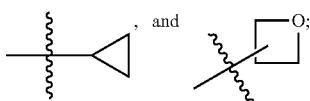

and the definitions for the other variables are as defined in the first, second, third, fourth, fifth, sixth, seventh, eighth, ninth, tenth, eleventh, twelfth, thirteenth, fourteen, fifteenth, seventeenth, eighteenth, nineteenth, twentieth, twenty-first, twenty-second, twenty-third or twenty-fourth embodiment.

In a twenty-seventh embodiment, a compound of the present invention is represented by any one of the following formulas:

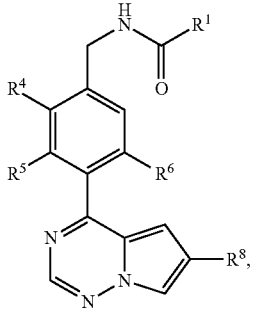

(IV)

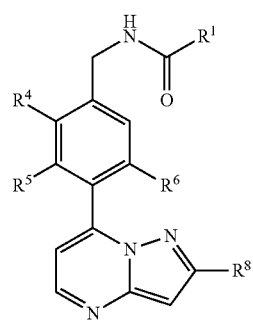

(V)

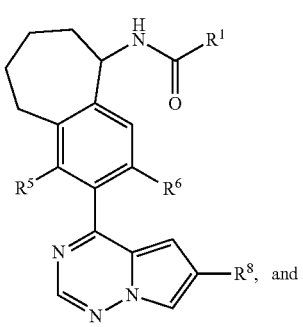

(VI)

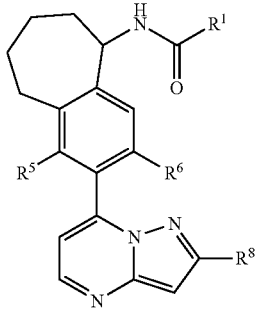

(VII)

or a pharmaceutically acceptable salt thereof, wherein:
- $R^1$ is a 5-membered heteroaryl selected from 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl, each of which is optionally substituted with one or two $R^{10}$;
- $R^{10}$, for each occurrence, is independently selected from halogen, $-OR^{10a}$, $-S(O)_2R^{10a}$, $-CN$, $C_{1-6}$ alkyl, $C_{3-6}$ cycloalkyl, and phenyl; wherein the $C_{1-6}$ alkyl, $C_{3-6}$cycloalkyl, and phenyl represented by $R^{10}$ are each optionally substituted with one to three $R^{15}$;
- $R^{10a}$, for each occurrence, is independently selected from H and $C_{1-3}$alkyl;
- $R^{15}$, for each occurrence, is independently selected from $C_{1-6}$ alkyl, halogen, $-CN$ and $-OR^{15a}$.
- $R^{15a}$ is H or $C_{1-3}$ alkyl;
- $R^4$ is selected from halogen, $-CN$, $-OR^{4a}$, $C_{1-6}$ alkyl, and $C_{3-6}$ cycloalkyl; wherein the $C_{1-6}$ alkyl and $C_{3-6}$ cycloalkyl represented by $R^4$ are each optionally substituted with 1-3 halogen; and
- $R^{4a}$ is $C_{1-4}$ alkyl optionally substituted with one to three halogen;
- $R^5$ is H or halogen;
- $R^6$ is H or halogen;
- $R^8$ is H, $-OR^{8a}$ or 4- to 6-membered monocyclic heterocyclyl having 1-2 heteroatoms independently selected from O and N, wherein the 4- to 6-membered monocyclic heterocyclyl is optionally substituted with one or two $R^{80}$;
- $R^{8a}$ is $C_{1-6}$ alkyl optionally substituted with one to three $R^{80}$;
- $R^{80}$, for each occurrence, is independently selected from halogen, $-OR^{80a}$, and $C_{1-3}$ alkyl optionally substituted with one to three $R^{85}$;
- $R^{80a}$, for each occurrence, is independently selected from H, $C_{1-6}$ alkyl and $C_{2-6}$ alkenyl;
- $R^{85}$, for each occurrence, is independently selected from halogen and $-OR^{85a}$; and
- $R^{85a}$ is H or $C_{1-3}$ alkyl; and the definitions for the other variables are as defined in the first embodiment.

In a twenty-eighth embodiment, a compound of the present invention is represented by formula (I), (II), (III), (IIA), (IIB), (IIIA), (IIIB), (IV), (V), (VI), (VII), or a pharmaceutically acceptable salt thereof, wherein $R^1$ is

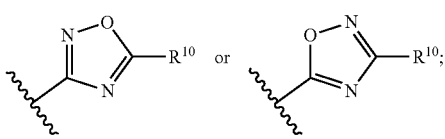

and $R^{10}$ is $C_{1-4}$alkyl or $C_{3-6}$cycloalkyl optionally substituted with halogen or $C_{1-3}$ alkyl; and the definitions for the other variables are as defined in the first or twenty-seventh embodiment.

In a twenty-ninth embodiment, a compound of the present invention is represented by formula (I), (II), (III), (IIA), (IIB), (IIIA), (IIIB), (IV), (V), (VI), or (VII), or a pharmaceutically acceptable salt thereof, wherein $R^{10}$ is —C(CH$_3$)$_3$ or 1-methylcyclopropyl; and the definitions for the other variables are as defined in the first, twenty-seventh, or twenty-eighth embodiment.

In a thirtieth embodiment, a compound of the present invention is represented by formula (I), (II), (III), (IIA), (IIB), (IIIA), (IIIB), (IV), (V), (VI), or (VII), or a pharmaceutically acceptable salt thereof, wherein $R^4$ is F, Cl, —CH$_3$, —CHF$_2$, —CF$_3$, —OCH$_3$, or cyclopropyl;
$R^5$ is H or F; and
$R^6$ is H or F; and the definitions for the other variables are as defined in the first, twenty-seventh, twenty-eighth, or twenty-ninth embodiment.

In a thirty-first embodiment, a compound of the present invention is represented by formula (I), (II), (III), (IIA), (IIB), (IIIA), (IIIB), (IV), (V), (VI), or (VII), or a pharmaceutically acceptable salt thereof, wherein $R^8$ is selected from H, —OR$^{8a}$,

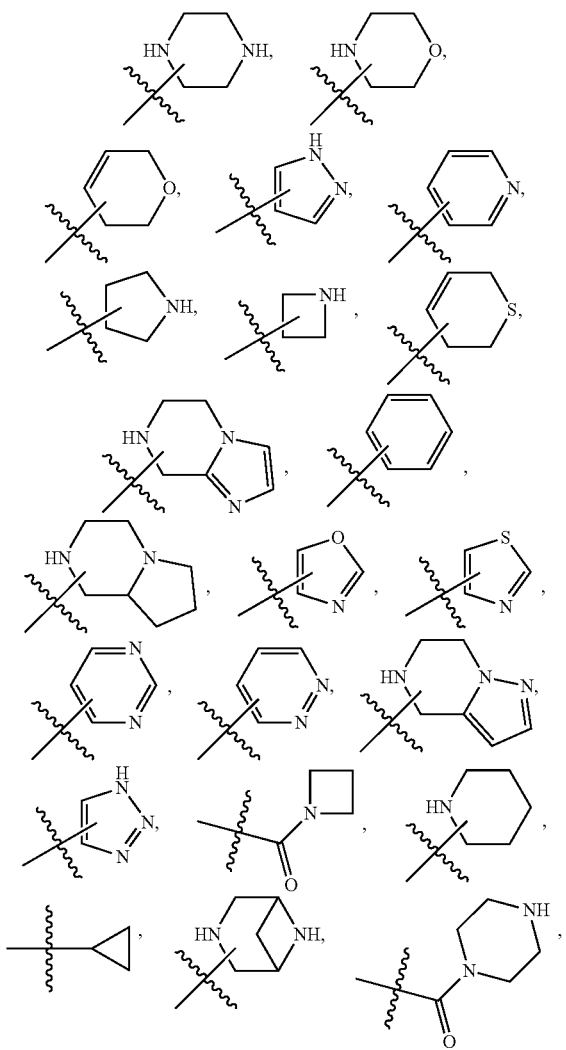

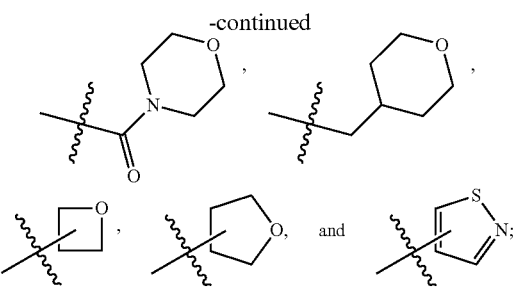

and the definitions for the other variables are as defined in the first, twenty-seventh, twenty-eighth, twenty-ninth, thirtieth or thirty-first embodiment.

In a thirty-second embodiment, a compound of the present invention is represented by formula (I), (II), (III), (IIA), (IIB), (IIIA), (IIIB), (IV), (V), (VI), (VII), or a pharmaceutically acceptable salt thereof, wherein $R^8$ is H,

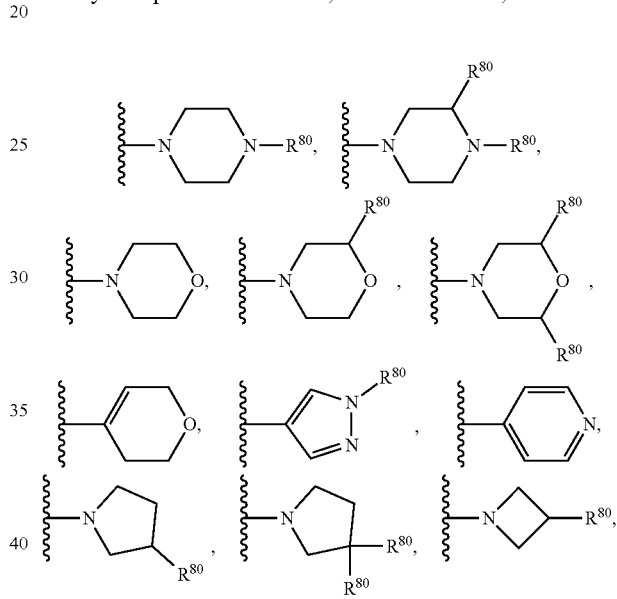

or —OR$^{8a}$; and the definitions for the other variables are as defined in the first, twenty-seventh, twenty-eighth, twenty-ninth, thirtieth or thirty-first embodiment.

In a thirty-third embodiment, a compound of the present invention is represented by formula (I), (II), (III), (IIA), (IIB), (IIIA), (IIIB), (IV), (V), (VI), or (VII), or a pharmaceutically acceptable salt thereof, wherein $R^{80}$, for each occurrence, is independently selected from F, —CH$_3$,

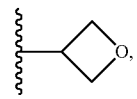

—CH$_2$CH$_2$OCH$_3$, —OCH$_3$, and —CH$_2$CHF$_2$; and the definitions for the other variables are as defined in the first, twenty-seventh, twenty-eighth, twenty-ninth, thirtieth, thirty-first, or thirty-second embodiment.

In a thirty-fourth embodiment of the present invention, the compound of the present invention is selected from:
5-tert-butyl-N-[[2-chloro-5-fluoro-4-(6-morpholinopyrrolo[2,1-f][1,2,4]triazin-4-yl)phenyl]methyl]-1,2,4-oxadiazole-3-carboxamide;

3-(tert-butyl)-N-(3-fluoro-2-methyl-4-(6-morpholinopyrrolo[2,1-f][1,2,4]triazin-4-yl)benzyl)-1,2,4-oxadiazole-5-carboxamide;

5-(1,1-difluoro-2-methylpropan-2-yl)-N-(2-methyl-4-(6-(1-methyl-1H-pyrazol-4-yl)pyrrolo[2,1-f][1,2,4]triazin-4-yl)benzyl)-1,3,4-oxadiazole-2-carboxamide;

5-(tert-butyl)-N-(2-methyl-4-(6-(4-methylpiperazin-1-yl)pyrrolo[2,1-f][1,2,4]triazin-4-yl)benzyl)-1,2,4-oxadiazole-3-carboxamide;

5-(tert-butyl)-N-(2-methyl-4-(6-morpholinopyrrolo[2,1-f][1,2,4]triazin-4-yl)benzyl)-1,2,4-oxadiazole-3-carboxamide;

3-(tert-butyl)-N-(4-(6-(3,6-dihydro-2H-pyran-4-yl)pyrrolo[2,1-f][1,2,4]triazin-4-yl)-2-methylbenzyl)-1,2,4-oxadiazole-5-carboxamide;

5-(tert-butyl)-N-(4-(6-(1-(2-methoxyethyl)-1H-pyrazol-4-yl)pyrrolo[2,1-f][1,2,4]triazin-4-yl)-2-methylbenzyl)-1,2,4-oxadiazole-3-carboxamide;

5-(tert-butyl)-N-(4-(6-(3-methoxyazetidin-1-yl)pyrrolo[2,1-f][1,2,4]triazin-4-yl)-2-methylbenzyl)-1,2,4-oxadiazole-3-carboxamide;

5-(tert-butyl)-N-(2-methyl-4-(6-(1-methyl-1H-pyrazol-3-yl)pyrrolo[2,1-f][1,2,4]triazin-4-yl)benzyl)-1,2,4-oxadiazole-3-carboxamide;

5-(tert-butyl)-N-(4-(6-(1-(2,2-difluoroethyl)-1H-pyrazol-4-yl)pyrrolo[2,1-f][1,2,4]triazin-4-yl)-2-methylbenzyl)-1,2,4-oxadiazole-3-carboxamide;

5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide;

5-(tert-butyl)-N-(4-(6-(3,3-difluoropyrrolidin-1-yl)pyrrolo[2,1-f][1,2,4]triazin-4-yl)-2-methylbenzyl)-1,2,4-oxadiazole-3-carboxamide;

3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide;

5-(tert-butyl)-N-(2-chloro-4-(6-morpholinopyrrolo[2,1-f][1,2,4]triazin-4-yl)benzyl)-1,2,4-oxadiazole-3-carboxamide;

5-(tert-butyl)-N-(2-methyl-4-(2-(1-methyl-1H-pyrazol-4-yl)pyrazolo[1,5-a]pyrimidin-7-yl)benzyl)-1,2,4-oxadiazole-3-carboxamide;

5-(tert-butyl)-N-(2-methyl-4-(pyrrolo[1,2-b]pyridazin-4-yl)benzyl)-1,2,4-oxadiazole-3-carboxamide;

3-(tert-butyl)-N-(2-methyl-4-(pyrrolo[1,2-b]pyridazin-4-yl)benzyl)-1,2,4-oxadiazole-5-carboxamide;

5-(tert-butyl)-N-(4-(5-fluoropyrrolo[2,1-f][1,2,4]triazin-4-yl)-2-methylbenzyl)-1,2,4-oxadiazole-3-carboxamide;

2-(1,1-difluoroethyl)-N-(2-methyl-4-(pyrrolo[2,1-f][1,2,4]triazin-4-yl)benzyl)oxazole-4-carboxamide;

5-(tert-butyl)-N-(4-(imidazo[1,2-b]pyridazin-8-yl)-2-methylbenzyl)-1,2,4-oxadiazole-3-carboxamide;

5-(tert-butyl)-N-(2-methyl-4-(2-morpholinopyrazolo[1,5-a]pyrimidin-7-yl)benzyl)-1,2,4-oxadiazole-3-carboxamide;

(R)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide;

(S)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide;

(R)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide;

(S)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide;

(S)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide;

(R)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide;

(R)-5-(tert-butyl)-N-(1-(3-fluoro-2-methyl-4-(6-morpholinopyrrolo[2,1-f][1,2,4]triazin-4-yl)phenyl)ethyl)-1,2,4-oxadiazole-3-carboxamide;

5-(tert-butyl)-N-(2-methyl-4-(6-(4-(oxetan-3-yl)piperazin-1-yl)pyrrolo[2,1-f][1,2,4]triazin-4-yl)benzyl)-1,2,4-oxadiazole-3-carboxamide;

N-(3-fluoro-2-methyl-4-(6-(1-methyl-1H-pyrazol-4-yl)pyrrolo[2,1-f][1,2,4]triazin-4-yl)benzyl)-5-(1-fluoro-2-methylpropan-2-yl)-1,2,4-oxadiazole-3-carboxamide;

5-(tert-butyl)-N-(4-(6-morpholinopyrrolo[2,1-f][1,2,4]triazin-4-yl)-2-(trifluoromethyl)benzyl)-1,2,4-oxadiazole-3-carboxamide;

5-(tert-butyl)-N-(2-methoxy-4-(6-(1-methyl-1H-pyrazol-4-yl)pyrrolo[2,1-f][1,2,4]triazin-4-yl)benzyl)-1,2,4-oxadiazole-3-carboxamide;

5-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,2,4-oxadiazole-3-carboxamide hydrochloride;

5-(tert-butyl)-N-(2-cyclopropyl-4-(6-morpholinopyrrolo[2,1-f][1,2,4]triazin-4-yl)benzyl)-1,2,4-oxadiazole-3-carboxamide;

5-(tert-butyl)-N-(2-methyl-4-(6-(pyridin-4-yl)pyrrolo[2,1-f][1,2,4]triazin-4-yl)benzyl)-1,2,4-oxadiazole-3-carboxamide;

5-(tert-butyl)-N-(4-(6-((2,6-syn)-2,6-dimethylmorpholino)pyrrolo[2,1-f][1,2,4]triazin-4-yl)-2-methylbenzyl)-1,2,4-oxadiazole-3-carboxamide;

N-(2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide;

5-(1-fluoro-2-methylpropan-2-yl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide;

N-(3-fluoro-2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide hydrochloride;

5-(1-fluoro-2-methylpropan-2-yl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide;

N-(3-fluoro-2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide hydrochloride;

5-(tert-butyl)-N-(4-(6-((2R,6R)-2,6-dimethylmorpholino)pyrrolo[2,1-f][1,2,4]triazin-4-yl)-2-methylbenzyl)-1,2,4-oxadiazole-3-carboxamide;

5-(tert-butyl)-N-(4-(6-((2S,6S)-2,6-dimethylmorpholino)pyrrolo[2,1-f][1,2,4]triazin-4-yl)-2-methylbenzyl)-1,2,4-oxadiazole-3-carboxamide;

3-(tert-butyl)-N-(3-fluoro-2-methoxy-4-(6-(1-methyl-1H-pyrazol-4-yl)pyrrolo[2,1-f][1,2,4]triazin-4-yl)benzyl)-1,2,4-oxadiazole-5-carboxamide;

5-(tert-butyl)-N-(2-methyl-4-(2-methylpyrazolo[1,5-a]pyrimidin-7-yl)benzyl)-1,2,4-oxadiazole-3-carboxamide;

N-(4-([1,2,4]triazolo[4,3-b]pyridazin-8-yl)-2-methylbenzyl)-5-(tert-butyl)-1,2,4-oxadiazole-3-carboxamide;

5-(tert-butyl)-N-(2-methyl-4-(5-methylimidazo[5,1-f][1,2,4]triazin-4-yl)benzyl)-1,2,4-oxadiazole-3-carboxamide;

5-(tert-butyl)-N-(2-methyl-4-(5-methylpyrrolo[2,1-f][1,2,4]triazin-4-yl)benzyl)-1,2,4-oxadiazole-3-carboxamide;

5-(tert-butyl)-N-(2-methyl-4-(pyrazolo[1,5-a]pyrimidin-7-yl)benzyl)-1,2,4-oxadiazole-3-carboxamide;

N-(4-(6-bromopyrrolo[2,1-f][1,2,4]triazin-4-yl)-2-methylbenzyl)-5-(tert-butyl)-1,2,4-oxadiazole-3-carboxamide;
5-tert-butyl-N-[(4-imidazo[2,1-f][1,2,4]triazin-4-yl-2-methyl-phenyl)methyl]-1,2,4-oxadiazole-3-carboxamide;
5-tert-butyl-N-[[4-(3-cyanopyrrolo[1,2-b]pyridazin-4-yl)-2-methyl-phenyl]methyl]-1,2,4-oxadiazole-3-carboxamide;
5-tert-butyl-N-[(4-imidazo[5,1-f][1,2,4]triazin-4-yl-2-methyl-phenyl)methyl]-1,2,4-oxadiazole-3-carboxamide;
5-(tert-butyl)-N-(2-methyl-4-(6-methylpyrrolo[2,1-f][1,2,4]triazin-4-yl)benzyl)-1,2,4-oxadiazole-3-carboxamide;
(R)-5-(tert-butyl)-N-(1-fluoro-2-(pyrrolo[2,1-f][1,2,4]triazin-4-yl)-6,7,8,9-tetrahydro-5H-benzo[7]annulen-5-yl)-1,2,4-oxadiazole-3-carboxamide;
(R)-3-(tert-butyl)-N-(1-(2-methyl-4-(6-(1-methyl-1H-pyrazol-4-yl)pyrrolo[2,1-f][1,2,4]triazin-4-yl)phenyl)ethyl)-1,2,4-oxadiazole-5-carboxamide;
5-(tert-butyl)-N-(4-(6-(2-methoxyethoxy)pyrrolo[2,1-f][1,2,4]triazin-4-yl)-2-methylbenzyl)-1,2,4-oxadiazole-3-carboxamide;
N-(4-(6-(1-acryloyl-1H-pyrazol-4-yl)pyrrolo[2,1-f][1,2,4]triazin-4-yl)-2-methylbenzyl)-5-(tert-butyl)-1,2,4-oxadiazole-3-carboxamide;
5-(tert-butyl)-N-(2-methyl-4-(6-(1-methylazetidin-3-yl)pyrrolo[2,1-f][1,2,4]triazin-4-yl)benzyl)-1,2,4-oxadiazole-3-carboxamide;
1-(tert-butyl)-N-(4-(6-(1-methyl-1H-pyrazol-4-yl)pyrrolo[2,1-f][1,2,4]triazin-4-yl)-2-(trifluoromethyl)benzyl)-1H-pyrazole-4-carboxamide;
5-(tert-butyl)-N-(2-cyclopropyl-3-fluoro-4-(pyrrolo[2,1-f][1,2,4]triazin-4-yl)benzyl)-1,2,4-oxadiazole-3-carboxamide;
5-(tert-butyl)-N-(3,5-difluoro-2-methyl-4-(pyrrolo[2,1-f][1,2,4]triazin-4-yl)benzyl)-1,2,4-oxadiazole-3-carboxamide;
1-(tert-butyl)-N-(2-(difluoromethyl)-4-(6-(1-methyl-1H-pyrazol-4-yl)pyrrolo[2,1-f][1,2,4]triazin-4-yl)benzyl)-1H-1,2,3-triazole-4-carboxamide;
3-(tert-butyl)-N-(2-(2,2-difluoroethyl)-4-(6-morpholinopyrrolo[2,1-f][1,2,4]triazin-4-yl)benzyl)-1,2,4-oxadiazole-5-carboxamide;
3-(tert-butyl)-N-(2-(2,2-difluoroethyl)-3-fluoro-4-(6-(1-methyl-1H-pyrazol-4-yl)pyrrolo[2,1-f][1,2,4]triazin-4-yl)benzyl)-1,2,4-oxadiazole-5-carboxamide hydrochloride;
5-(tert-butyl)-N-(4-(6-(dimethylcarbamoyl)pyrrolo[2,1-f][1,2,4]triazin-4-yl)-2-methylbenzyl)-1,2,4-oxadiazole-3-carboxamide;
5-(tert-butyl)-N-(2-methyl-4-(6-(pyrimidin-2-yl)pyrrolo[2,1-f][1,2,4]triazin-4-yl)benzyl)-1,2,4-oxadiazole-3-carboxamide;
3-(tert-butyl)-N-(2-methyl-4-(6-(4-methylpiperazin-1-yl)pyrrolo[2,1-f][1,2,4]triazin-4-yl)benzyl)-1,2,4-oxadiazole-5-carboxamide;
(R)-5-(tert-butyl)-N-(4-(6-(2,4-dimethylpiperazin-1-yl)pyrrolo[2,1-f][1,2,4]triazin-4-yl)-2-methylbenzyl)-1,2,4-oxadiazole-3-carboxamide;
5-(tert-butyl)-N-(2-methyl-4-(6-(oxetan-3-yl)pyrrolo[2,1-f][1,2,4]triazin-4-yl)benzyl)-1,2,4-oxadiazole-3-carboxamide;
3-(tert-butyl)-N-(2-methyl-4-(6-(tetrahydro-2H-pyran-4-yl)pyrrolo[2,1-f][1,2,4]triazin-4-yl)benzyl)-1,2,4-oxadiazole-5-carboxamide;
N-(4-(6-(3,3-bis(hydroxymethyl)azetidin-1-yl)pyrrolo[2,1-f][1,2,4]triazin-4-yl)-2-methylbenzyl)-5-(tert-butyl)-1,2,4-oxadiazole-3-carboxamide;
5-(tert-butyl)-N-(4-(6-cyclopropylpyrrolo[2,1-f][1,2,4]triazin-4-yl)-2-methylbenzyl)-1,2,4-oxadiazole-3-carboxamide;
(S)-5-(tert-butyl)-N-(2-methyl-4-(6-(2-methyl-4-(oxetan-3-yl)piperazin-1-yl)pyrrolo[2,1-f][1,2,4]triazin-4-yl)benzyl)-1,2,4-oxadiazole-3-carboxamide;
5-(tert-butyl)-N-(4-(6-ethynylpyrrolo[2,1-f][1,2,4]triazin-4-yl)-2-methylbenzyl)-1,2,4-oxadiazole-3-carboxamide;
5-(tert-butyl)-N-(4-(6-(methoxymethyl)pyrrolo[2,1-f][1,2,4]triazin-4-yl)-2-methylbenzyl)-1,2,4-oxadiazole-3-carboxamide;
5-(tert-butyl)-N-(4-(6-(2,2-dimethylmorpholino)pyrrolo[2,1-f][1,2,4]triazin-4-yl)-2-methylbenzyl)-1,2,4-oxadiazole-3-carboxamide;
5-(tert-butyl)-N-(2-methyl-4-(6-((tetrahydro-2H-pyran-4-yl)oxy)pyrrolo[2,1-f][1,2,4]triazin-4-yl)benzyl)-1,2,4-oxadiazole-3-carboxamide;
5-(tert-butyl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide;
5-tert-butyl-N-[[3-fluoro-2-methyl-4-(6-morpholinopyrrolo[2,1-f][1,2,4]triazin-4-yl)phenyl]methyl]-1,3,4-oxadiazole-2-carboxamide;
5-tert-butyl-N-[[3-fluoro-2-methyl-4-[2-(1-methylpyrazol-4-yl)pyrazolo[1,5-a]pyrimidin-7-yl]phenyl]methyl]-1,2,4-oxadiazole-3-carboxamide;
3-tert-butyl-N-[[3-fluoro-2-methyl-4-[2-(1-methylpyrazol-4-yl)pyrazolo[1,5-a]pyrimidin-7-yl]phenyl]methyl]-1,2,4-oxadiazole-5-carboxamide;
5-(tert-butyl)-N-(3-fluoro-2-methyl-4-(2-morpholinopyrazolo[1,5-a]pyrimidin-7-yl)benzyl)-1,2,4-oxadiazole-3-carboxamide;
5-tert-butyl-N-[[2-methyl-4-[6-(1H-pyrazol-4-yl)pyrrolo[2,1-f][1,2,4]triazin-4-yl]phenyl]methyl]-1,2,4-oxadiazole-3-carboxamide;
5-(tert-butyl)-N-(3-fluoro-2-methyl-4-(6-morpholinopyrrolo[2,1-f][1,2,4]triazin-4-yl)benzyl)-1,2,4-oxadiazole-3-carboxamide;
1-(tert-butyl)-N-(3-fluoro-2-methyl-4-(6-morpholinopyrrolo[2,1-f][1,2,4]triazin-4-yl)benzyl)-1H-1,2,3-triazole-4-carboxamide;
1-(tert-butyl)-N-(3-fluoro-2-methyl-4-(6-morpholinopyrrolo[2,1-f][1,2,4]triazin-4-yl)benzyl)-1H-pyrazole-4-carboxamide;
1-(tert-butyl)-N-(3-fluoro-2-methyl-4-(6-morpholinopyrrolo[2,1-f][1,2,4]triazin-4-yl)benzyl)-1H-pyrazole-3-carboxamide;
2-(tert-butyl)-N-(2-methyl-4-(6-(2-methylmorpholino)pyrrolo[2,1-f][1,2,4]triazin-4-yl)benzyl)-2H-tetrazole-5-carboxamide;
2-(tert-butyl)-N-(2-methyl-4-(6-(2-methylmorpholino)pyrrolo[2,1-f][1,2,4]triazin-4-yl)benzyl)oxazole-4-carboxamide;
(S)-5-(tert-butyl)-N-(4-(6-(2,4-dimethylpiperazin-1-yl)pyrrolo[2,1-f][1,2,4]triazin-4-yl)-2-methylbenzyl)-1,2,4-oxadiazole-3-carboxamide;
5-(tert-butyl)-N-(2-methyl-4-(6-((1S,4S)-5-methyl-2,5-diazabicyclo[2.2.1]heptan-2-yl)pyrrolo[2,1-f][1,2,4]triazin-4-yl)benzyl)-1,2,4-oxadiazole-3-carboxamide;
5-(tert-butyl)-N-(2-methyl-4-(6-((tetrahydro-2H-pyran-4-yl)methyl)pyrrolo[2,1-f][1,2,4]triazin-4-yl)benzyl)-1,2,4-oxadiazole-3-carboxamide;
5-(tert-butyl)-N-(2-methyl-4-(6-(tetrahydrofuran-3-yl)pyrrolo[2,1-f][1,2,4]triazin-4-yl)benzyl)-1,2,4-oxadiazole-3-carboxamide;
5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide;

3-(tert-butyl)-N-(4-(6-(4-methoxypiperidin-1-yl)pyrrolo[2,1-f][1,2,4]triazin-4-yl)-2-methylbenzyl)-1,2,4-oxadiazole-5-carboxamide;

2-(tert-butyl)-N-(4-(6-(3,4-dimethylpiperazin-1-yl)pyrrolo[2,1-f][1,2,4]triazin-4-yl)-2-methylbenzyl)-2H-tetrazole-5-carboxamide;

3-(tert-butyl)-N-(4-(6-(3,4-dimethoxypyrrolidin-1-yl)pyrrolo[2,1-f][1,2,4]triazin-4-yl)-2-methylbenzyl)-1,2,4-oxadiazole-5-carboxamide;

3-(tert-butyl)-N-(4-(6-(2-isopropylmorpholino)pyrrolo[2,1-f][1,2,4]triazin-4-yl)-2-methylbenzyl)-1,2,4-oxadiazole-5-carboxamide;

5-(tert-butyl)-N-(4-(6-(3,6-dihydro-2H-thiopyran-4-yl)pyrrolo[2,1-f][1,2,4]triazin-4-yl)-2-methylbenzyl)-1,2,4-oxadiazole-3-carboxamide;

5-(tert-butyl)-N-(4-(6-cyanopyrrolo[2,1-f][1,2,4]triazin-4-yl)-2-methylbenzyl)-1,2,4-oxadiazole-3-carboxamide;

3-(tert-butyl)-N-(4-(6-(3,6-dihydro-2H-pyran-4-yl)pyrrolo[2,1-f][1,2,4]triazin-4-yl)-2-methylbenzyl)-1,2,4-oxadiazole-5-carboxamide;

5-(tert-butyl)-N-(2-methyl-4-(6-(1-(oxetan-3-yl)-1H-pyrazol-4-yl)pyrrolo[2,1-f][1,2,4]triazin-4-yl)benzyl)-1,2,4-oxadiazole-3-carboxamide;

3-(tert-butyl)-N-(2-methyl-4-(6-morpholinopyrrolo[2,1-f][1,2,4]triazin-4-yl)benzyl)-1,2,4-oxadiazole-5-carboxamide;

5-(tert-butyl)-N-(2-methyl-4-(6-(1-methyl-1H-1,2,3-triazol-4-yl)pyrrolo[2,1-f][1,2,4]triazin-4-yl)benzyl)-1,2,4-oxadiazole-3-carboxamide;

5-(tert-butyl)-N-(4-(6-(1-(difluoromethyl)-1H-pyrazol-4-yl)pyrrolo[2,1-f][1,2,4]triazin-4-yl)-2-methylbenzyl)-1,2,4-oxadiazole-3-carboxamide;

5-(tert-butyl)-N-(4-(6-(1,3-dimethyl-1H-pyrazol-4-yl)pyrrolo[2,1-f][1,2,4]triazin-4-yl)-2-methylbenzyl)-1,2,4-oxadiazole-3-carboxamide;

5-(tert-butyl)-N-(4-(6-(1,5-dimethyl-1H-pyrazol-4-yl)pyrrolo[2,1-f][1,2,4]triazin-4-yl)-2-methylbenzyl)-1,2,4-oxadiazole-3-carboxamide;

5-(tert-butyl)-N-(2-methyl-4-(6-(oxazol-5-yl)pyrrolo[2,1-f][1,2,4]triazin-4-yl)benzyl)-1,2,4-oxadiazole-3-carboxamide;

5-(tert-butyl)-N-(2-methyl-4-(6-(1-methyl-1H-imidazol-4-yl)pyrrolo[2,1-f][1,2,4]triazin-4-yl)benzyl)-1,2,4-oxadiazole-3-carboxamide;

5-(tert-butyl)-N-(3-fluoro-2-methyl-4-(6-(1-methyl-1H-pyrazol-4-yl)pyrrolo[2,1-f][1,2,4]triazin-4-yl)benzyl)-1,2,4-oxadiazole-3-carboxamide;

5-(tert-butyl)-N-(3-fluoro-2-methyl-4-(6-(1-methyl-1H-pyrazol-4-yl)pyrrolo[2,1-f][1,2,4]triazin-4-yl)benzyl)-1,2,4-oxadiazole-3-carboxamide;

2-(tert-butyl)-N-(2-methyl-4-(6-(1-methyl-1H-pyrazol-4-yl)pyrrolo[2,1-f][1,2,4]triazin-4-yl)benzyl)-2H-tetrazole-5-carboxamide;

2-(tert-butyl)-N-(2-methyl-4-(6-morpholinopyrrolo[2,1-f][1,2,4]triazin-4-yl)benzyl)-2H-tetrazole-5-carboxamide;

3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide;

(S)-5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide;

(R)-5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide;

3-(tert-butyl)-N-(3-fluoro-2-methyl-4-(2-morpholinopyrazolo[1,5-a]pyrimidin-7-yl)benzyl)-1,2,4-oxadiazole-5-carboxamide;

(S)-5-(tert-butyl)-N-(4-(6-(7,7-difluorohexahydropyrrolo[1,2-a]pyrazin-2(1H)-yl)pyrrolo[2,1-f][1,2,4]triazin-4-yl)-2-methylbenzyl)-1,2,4-oxadiazole-3-carboxamide;

5-(tert-butyl)-N-(4-(6-(5,6-dihydroimidazo[1,2-a]pyrazin-7(8H)-yl)pyrrolo[2,1-f][1,2,4]triazin-4-yl)-2-methylbenzyl)-1,2,4-oxadiazole-3-carboxamide trifluoroacetate;

-(tert-butyl)-N-(4-(6-(5,6-dihydroimidazo[1,2-a]pyrazin-7(8H)-yl)pyrrolo[2,1-f][1,2,4]triazin-4-yl)-2-methylbenzyl)-1,2,4-oxadiazole-5-carboxamide trifluoroacetate;

5-(tert-butyl)-N-(4-(6-((3R,4S)-3,4-difluoropyrrolidin-1-yl)pyrrolo[2,1-f][1,2,4]triazin-4-yl)-2-methylbenzyl)-1,2,4-oxadiazole-3-carboxamide;

(S)-3-(tert-butyl)-N-(4-(6-(7,7-difluorohexahydropyrrolo[1,2-a]pyrazin-2(1H)-yl)pyrrolo[2,1-f][1,2,4]triazin-4-yl)-2-methylbenzyl)-1,2,4-oxadiazole-5-carboxamide;

2-(tert-butyl)-N-(4-(6-(3,6-dihydro-2H-pyran-4-yl)pyrrolo[2,1-f][1,2,4]triazin-4-yl)-2-methylbenzyl)oxazole-4-carboxamide;

2-(tert-butyl)-N-(4-(6-(3,6-dihydro-2H-pyran-4-yl)pyrrolo[2,1-f][1,2,4]triazin-4-yl)-2-methylbenzyl)oxazole-5-carboxamide;

1-(tert-butyl)-N-(4-(6-(3,6-dihydro-2H-pyran-4-yl)pyrrolo[2,1-f][1,2,4]triazin-4-yl)-2-methylbenzyl)-1H-pyrazole-4-carboxamide;

1-(tert-butyl)-N-(4-(6-(3,6-dihydro-2H-pyran-4-yl)pyrrolo[2,1-f][1,2,4]triazin-4-yl)-2-methylbenzyl)-1H-pyrazole-3-carboxamide;

2-(tert-butyl)-N-(4-(6-(3,6-dihydro-2H-pyran-4-yl)pyrrolo[2,1-f][1,2,4]triazin-4-yl)-2-methylbenzyl)-2H-tetrazole-5-carboxamide;

1-(tert-butyl)-N-(4-(6-(1,5-dimethyl-1H-pyrazol-4-yl)pyrrolo[2,1-f][1,2,4]triazin-4-yl)-2-methylbenzyl)-1H-pyrazole-4-carboxamide;

2-(tert-butyl)-N-(4-(6-(1,5-dimethyl-1H-pyrazol-4-yl)pyrrolo[2,1-f][1,2,4]triazin-4-yl)-2-methylbenzyl)-2H-tetrazole-5-carboxamide;

2-(tert-butyl)-N-(4-(6-(1,5-dimethyl-1H-pyrazol-4-yl)pyrrolo[2,1-f][1,2,4]triazin-4-yl)-2-methylbenzyl)oxazole-4-carboxamide;

5-(tert-butyl)-N-(2-chloro-5-fluoro-4-(pyrrolo[2,1-f][1,2,4]triazin-4-yl)benzyl)-1,2,4-oxadiazole-3-carboxamide;

3-(tert-butyl)-N-(2-chloro-5-fluoro-4-(pyrrolo[2,1-f][1,2,4]triazin-4-yl)benzyl)-1,2,4-oxadiazole-5-carboxamide;

2-(tert-butyl)-N-(2-chloro-5-fluoro-4-(pyrrolo[2,1-f][1,2,4]triazin-4-yl)benzyl)oxazole-4-carboxamide;

5-(tert-butyl)-N-(2-chloro-5-fluoro-4-(pyrrolo[2,1-f][1,2,4]triazin-4-yl)benzyl)isoxazole-3-carboxamide;

2-(tert-butyl)-N-(2-chloro-5-fluoro-4-(pyrrolo[2,1-f][1,2,4]triazin-4-yl)benzyl)-2H-tetrazole-5-carboxamide;

(R)-3-(tert-butyl)-N-(2-methyl-4-(6-(2-methylmorpholino)pyrrolo[2,1-f][1,2,4]triazin-4-yl)benzyl)-1,2,4-oxadiazole-5-carboxamide;

(S)-3-(tert-butyl)-N-(2-methyl-4-(6-(2-methylmorpholino)pyrrolo[2,1-f][1,2,4]triazin-4-yl)benzyl)-1,2,4-oxadiazole-5-carboxamide;

(R)-2-(tert-butyl)-N-(2-methyl-4-(6-(2-methylmorpholino)pyrrolo[2,1-f][1,2,4]triazin-4-yl)benzyl)-2H-tetrazole-5-carboxamide;

(S)-2-(tert-butyl)-N-(2-methyl-4-(6-(2-methylmorpholino)pyrrolo[2,1-f][1,2,4]triazin-4-yl)benzyl)-2H-tetrazole-5-carboxamide;

(S)-5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide;

(R)-5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide;

(R)-2-(tert-butyl)-N-(2-methyl-4-(6-(2-methylmorpholino)pyrrolo[2,1-f][1,2,4]triazin-4-yl)benzyl)oxazole-4-carboxamide;

(S)-2-(tert-butyl)-N-(2-methyl-4-(6-(2-methylmorpholino)pyrrolo[2,1-f][1,2,4]triazin-4-yl)benzyl)oxazole-4-carboxamide;

1-(tert-butyl)-N-(4-(6-(1-(2,2-difluoroethyl)-1H-pyrazol-4-yl)pyrrolo[2,1-f][1,2,4]triazin-4-yl)-2-methylbenzyl)-1H-pyrazole-4-carboxamide;

2-(tert-butyl)-N-(4-(6-(1-(2,2-difluoroethyl)-1H-pyrazol-4-yl)pyrrolo[2,1-f][1,2,4]triazin-4-yl)-2-methylbenzyl)-2H-tetrazole-5-carboxamide;

N-(4-(6-(1-(but-2-enoyl)-1H-pyrazol-4-yl)pyrrolo[2,1-f][1,2,4]triazin-4-yl)-2-methylbenzyl)-5-(tert-butyl)-1,2,4-oxadiazole-3-carboxamide;

5-(tert-butyl)-N-(2-methyl-4-(6-(6-methyl-3,6-diazabicyclo[3.1.1]heptan-3-yl)pyrrolo[2,1-f][1,2,4]triazin-4-yl)benzyl)-1,2,4-oxadiazole-3-carboxamide trifluoroacetate;

5-(tert-butyl)-N-(2-methyl-4-(6-(1-methylpyrrolidin-3-yl)pyrrolo[2,1-f][1,2,4]triazin-4-yl)benzyl)-1,2,4-oxadiazole-3-carboxamide;

N-(4-(2-aminopyrrolo[2,1-f][1,2,4]triazin-4-yl)-2-methylbenzyl)-5-(tert-butyl)-1,2,4-oxadiazole-3-carboxamide;

5-(tert-butyl)-N-(2-methyl-4-(pyrrolo[2,1-f][1,2,4]triazin-4-yl)benzyl)-1,2,4-oxadiazole-3-carboxamide;

3-(tert-butyl)-N-(2-methyl-4-(pyrrolo[2,1-f][1,2,4]triazin-4-yl)benzyl)-1,2,4-oxadiazole-5-carboxamide;

3-(tert-butyl)-N-(2-cyclopropyl-3-fluoro-4-(pyrrolo[2,1-f][1,2,4]triazin-4-yl)benzyl)-1,2,4-oxadiazole-5-carboxamide;

5-(tert-butyl)-N-(2-chloro-3-fluoro-4-(6-morpholinopyrrolo[2,1-f][1,2,4]triazin-4-yl)benzyl)-1,2,4-oxadiazole-3-carboxamide;

1-(tert-butyl)-N-(2-chloro-3-fluoro-4-(6-morpholinopyrrolo[2,1-f][1,2,4]triazin-4-yl)benzyl)-1H-pyrazole-4-carboxamide;

5-(tert-butyl)-N-(2-chloro-3-fluoro-4-(6-morpholinopyrrolo[2,1-f][1,2,4]triazin-4-yl)benzyl)-1,3,4-oxadiazole-2-carboxamide;

1-(tert-butyl)-N-(2-chloro-3-fluoro-4-(6-morpholinopyrrolo[2,1-f][1,2,4]triazin-4-yl)benzyl)-1H-1,2,3-triazole-4-carboxamide;

1-(tert-butyl)-N-(2-chloro-3-fluoro-4-(6-morpholinopyrrolo[2,1-f][1,2,4]triazin-4-yl)benzyl)-1H-pyrazole-3-carboxamide;

3-(tert-butyl)-N-(2-chloro-4-(6-morpholinopyrrolo[2,1-f][1,2,4]triazin-4-yl)benzyl)-1,2,4-oxadiazole-5-carboxamide;

1-(tert-butyl)-N-(2-chloro-4-(6-morpholinopyrrolo[2,1-f][1,2,4]triazin-4-yl)benzyl)-1H-pyrazole-4-carboxamide;

5-(tert-butyl)-N-(2-chloro-4-(6-morpholinopyrrolo[2,1-f][1,2,4]triazin-4-yl)benzyl)-1,3,4-oxadiazole-2-carboxamide;

1-(tert-butyl)-N-(2-chloro-4-(6-morpholinopyrrolo[2,1-f][1,2,4]triazin-4-yl)benzyl)-1H-1,2,3-triazole-4-carboxamide;

5-(tert-butyl)-N-(2-cyclopropyl-3-fluoro-4-(6-morpholinopyrrolo[2,1-f][1,2,4]triazin-4-yl)benzyl)-1,3,4-oxadiazole-2-carboxamide;

1-(tert-butyl)-N-(2-cyclopropyl-3-fluoro-4-(6-morpholinopyrrolo[2,1-f][1,2,4]triazin-4-yl)benzyl)-1H-1,2,3-triazole-4-carboxamide;

5-(tert-butyl)-N-(2-methyl-4-(6-(1-methyl-1H-pyrazol-4-yl)pyrrolo[2,1-f][1,2,4]triazin-4-yl)benzyl)-1,3,4-oxadiazole-2-carboxamide;

1-(tert-butyl)-N-(2-methyl-4-(6-(1-methyl-1H-pyrazol-4-yl)pyrrolo[2,1-f][1,2,4]triazin-4-yl)benzyl)-1H-1,2,3-triazole-4-carboxamide;

1-(tert-butyl)-N-(2-methyl-4-(6-(1-methyl-1H-pyrazol-4-yl)pyrrolo[2,1-f][1,2,4]triazin-4-yl)benzyl)-1H-pyrazole-4-carboxamide;

1-(tert-butyl)-N-(2-methyl-4-(6-(1-methyl-1H-pyrazol-4-yl)pyrrolo[2,1-f][1,2,4]triazin-4-yl)benzyl)-1H-pyrazole-3-carboxamide;

5-(tert-butyl)-N-(2-methyl-4-(6-(pyridin-3-yl)pyrrolo[2,1-f][1,2,4]triazin-4-yl)benzyl)-1,2,4-oxadiazole-3-carboxamide;

5-(tert-butyl)-N-(2-methyl-4-(6-(6-methylpyridazin-4-yl)pyrrolo[2,1-f][1,2,4]triazin-4-yl)benzyl)-1,2,4-oxadiazole-3-carboxamide;

3-(tert-butyl)-N-(2-methyl-4-(6-(6-methylpyridazin-4-yl)pyrrolo[2,1-f][1,2,4]triazin-4-yl)benzyl)-1,2,4-oxadiazole-5-carboxamide;

5-(tert-butyl)-N-(4-(6-(isothiazol-4-yl)pyrrolo[2,1-f][1,2,4]triazin-4-yl)-2-methylbenzyl)-1,2,4-oxadiazole-3-carboxamide;

3-(tert-butyl)-N-(4-(6-(isothiazol-4-yl)pyrrolo[2,1-f][1,2,4]triazin-4-yl)-2-methylbenzyl)-1,2,4-oxadiazole-5-carboxamide;

5-(tert-butyl)-N-(4-(6-((2-methoxyethyl)(methyl)amino)pyrrolo[2,1-f][1,2,4]triazin-4-yl)-2-methylbenzyl)-1,2,4-oxadiazole-3-carboxamide;

1-(tert-butyl)-N-(2-methyl-4-(6-morpholinopyrrolo[2,1-f][1,2,4]triazin-4-yl)benzyl)-1H-pyrazole-3-carboxamide;

2-(tert-butyl)-N-(2-methyl-4-(6-morpholinopyrrolo[2,1-f][1,2,4]triazin-4-yl)benzyl)oxazole-4-carboxamide;

5-(tert-butyl)-N-(2-methyl-4-(6-(4-methyl-3-oxopiperazin-1-yl)pyrrolo[2,1-f][1,2,4]triazin-4-yl)benzyl)-1,2,4-oxadiazole-3-carboxamide;

5-(tert-butyl)-N-(2-chloro-4-(pyrrolo[2,1-f][1,2,4]triazin-4-yl)benzyl)-1,2,4-oxadiazole-3-carboxamide;

5-(tert-butyl)-N-(4-(pyrrolo[2,1-f][1,2,4]triazin-4-yl)-2-(trifluoromethyl)benzyl)-1,2,4-oxadiazole-3-carboxamide;

5-(tert-butyl)-N-(3-fluoro-2-methoxy-4-(pyrrolo[2,1-f][1,2,4]triazin-4-yl)benzyl)-1,2,4-oxadiazole-3-carboxamide;

5-(tert-butyl)-N-(2-(difluoromethyl)-4-(pyrrolo[2,1-f][1,2,4]triazin-4-yl)benzyl)-1,2,4-oxadiazole-3-carboxamide;

1-(tert-butyl)-N-(2-methyl-4-(pyrrolo[2,1-f][1,2,4]triazin-4-yl)benzyl)-1H-pyrazole-3-carboxamide;

1-(tert-butyl)-N-(2-methyl-4-(pyrrolo[2,1-f][1,2,4]triazin-4-yl)benzyl)-1H-pyrazole-4-carboxamide;

1-(tert-butyl)-N-(2-methyl-4-(pyrrolo[2,1-f][1,2,4]triazin-4-yl)benzyl)-1H-1,2,3-triazole-4-carboxamide;

5-(tert-butyl)-N-(2-methyl-4-(pyrrolo[2,1-f][1,2,4]triazin-4-yl)benzyl)-1,3,4-oxadiazole-2-carboxamide;

3-(tert-butyl)-N-(4-(6-morpholinopyrrolo[2,1-f][1,2,4]triazin-4-yl)-2-(trifluoromethyl)benzyl)-1,2,4-oxadiazole-5-carboxamide;

1-(tert-butyl)-N-(4-(6-morpholinopyrrolo[2,1-f][1,2,4]triazin-4-yl)-2-(trifluoromethyl)benzyl)-1H-1,2,3-triazole-4-carboxamide;

1-(tert-butyl)-N-(2-methoxy-4-(6-(1-methyl-1H-pyrazol-4-yl)pyrrolo[2,1-f][1,2,4]triazin-4-yl)benzyl)-1H-1,2,3-triazole-4-carboxamide;

3-(tert-butyl)-N-(2-methoxy-4-(6-(1-methyl-1H-pyrazol-4-yl)pyrrolo[2,1-f][1,2,4]triazin-4-yl)benzyl)-1,2,4-oxadiazole-5-carboxamide;

3-(tert-butyl)-N-(2-(difluoromethyl)-4-(6-(1-methyl-1H-pyrazol-4-yl)pyrrolo[2,1-f][1,2,4]triazin-4-yl)benzyl)-1,2,4-oxadiazole-5-carboxamide;

5-(tert-butyl)-N-(2-(difluoromethyl)-4-(6-(1-methyl-1H-pyrazol-4-yl)pyrrolo[2,1-f][1,2,4]triazin-4-yl)benzyl)-1,3,4-oxadiazole-2-carboxamide;

3-(tert-butyl)-N-(2-(difluoromethyl)-4-(6-morpholinopyrrolo[2,1-f][1,2,4]triazin-4-yl)benzyl)-1,2,4-oxadiazole-5-carboxamide;

5-(tert-butyl)-N-(2-(difluoromethyl)-4-(6-morpholinopyrrolo[2,1-f][1,2,4]triazin-4-yl)benzyl)-1,3,4-oxadiazole-2-carboxamide;

3-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,2,4-oxadiazole-5-carboxamide;

1-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1H-1,2,3-triazole-4-carboxamide;

5-(tert-butyl)-N-(2-methoxy-4-(6-(1-methyl-1H-pyrazol-4-yl)pyrrolo[2,1-f][1,2,4]triazin-4-yl)benzyl)-1,3,4-oxadiazole-2-carboxamide;

2-(tert-butyl)-N-(2-(difluoromethyl)-4-(6-morpholinopyrrolo[2,1-f][1,2,4]triazin-4-yl)benzyl)oxazole-4-carboxamide;

5-(tert-butyl)-N-(2-(difluoromethyl)-3-fluoro-4-(6-morpholinopyrrolo[2,1-f][1,2,4]triazin-4-yl)benzyl)-1,3,4-oxadiazole-2-carboxamide;

1-(tert-butyl)-N-(3-fluoro-2-methoxy-4-(6-(1-methyl-1H-pyrazol-4-yl)pyrrolo[2,1-f][1,2,4]triazin-4-yl)benzyl)-1H-1,2,3-triazole-4-carboxamide;

5-(tert-butyl)-N-(3-fluoro-2-methoxy-4-(6-(1-methyl-1H-pyrazol-4-yl)pyrrolo[2,1-f][1,2,4]triazin-4-yl)benzyl)-1,3,4-oxadiazole-2-carboxamide;

1-(tert-butyl)-N-(3-fluoro-2-methoxy-4-(6-morpholinopyrrolo[2,1-f][1,2,4]triazin-4-yl)benzyl)-1H-pyrazole-3-carboxamide formate;

3-(tert-butyl)-N-(3-fluoro-2-methoxy-4-(6-morpholinopyrrolo[2,1-f][1,2,4]triazin-4-yl)benzyl)-1,2,4-oxadiazole-5-carboxamide formate;

(R)-5-(tert-butyl)-N-(1-(2-chloro-4-(6-morpholinopyrrolo[2,1-f][1,2,4]triazin-4-yl)phenyl)ethyl)-1,3,4-oxadiazole-2-carboxamide;

1-(tert-butyl)-N-(2-cyclopropyl-4-(6-morpholinopyrrolo[2,1-f][1,2,4]triazin-4-yl)benzyl)-1H-1,2,3-triazole-4-carboxamide formate;

3-(tert-butyl)-N-(2-cyclopropyl-4-(6-morpholinopyrrolo[2,1-f][1,2,4]triazin-4-yl)benzyl)-1,2,4-oxadiazole-5-carboxamide;

3-(tert-butyl)-N-(2-(2,2-difluoroethyl)-4-(6-(1-methyl-1H-pyrazol-4-yl)pyrrolo[2,1-f][1,2,4]triazin-4-yl)benzyl)-1,2,4-oxadiazole-5-carboxamide;

1-(tert-butyl)-N-(2-(difluoromethyl)-4-(6-(3,6-dihydro-2H-pyran-4-yl)pyrrolo[2,1-f][1,2,4]triazin-4-yl)benzyl)-1H-pyrazole-4-carboxamide;

1-(tert-butyl)-N-(4-(6-(1-(2,2-difluoroethyl)-1H-pyrazol-4-yl)pyrrolo[2,1-f][1,2,4]triazin-4-yl)-2-(difluoromethyl)benzyl)-1H-pyrazole-4-carboxamide;

2-(tert-butyl)-N-(4-(6-(1-(2,2-difluoroethyl)-1H-pyrazol-4-yl)pyrrolo[2,1-f][1,2,4]triazin-4-yl)-2-(difluoromethyl)benzyl)oxazole-4-carboxamide;

2-(tert-butyl)-N-(2-(difluoromethyl)-4-(6-(1-methyl-1H-pyrazol-4-yl)pyrrolo[2,1-f][1,2,4]triazin-4-yl)benzyl)oxazole-4-carboxamide;

1-(tert-butyl)-N-(2-(difluoromethyl)-4-(6-(1-methyl-1H-pyrazol-4-yl)pyrrolo[2,1-f][1,2,4]triazin-4-yl)benzyl)-1H-pyrazole-4-carboxamide;

5-(tert-butyl)-N-(2-(difluoromethyl)-4-(6-(3,6-dihydro-2H-pyran-4-yl)pyrrolo[2,1-f][1,2,4]triazin-4-yl)benzyl)-1,3,4-oxadiazole-2-carboxamide;

2-(tert-butyl)-N-(2-methyl-4-(pyrrolo[2,1-f][1,2,4]triazin-4-yl)benzyl)-2H-tetrazole-5-carboxamide;

5-(tert-butyl)-N-(2-methyl-4-(6-(morpholine-4-carbonyl)pyrrolo[2,1-f][1,2,4]triazin-4-yl)benzyl)-1,2,4-oxadiazole-3-carboxamide;

5-(tert-butyl)-N-(2-methyl-4-(6-(4-methylpiperazine-1-carbonyl)pyrrolo[2,1-f][1,2,4]triazin-4-yl)benzyl)-1,2,4-oxadiazole-3-carboxamide;

5-(tert-butyl)-N-(4-(6-(3-methoxyazetidine-1-carbonyl)pyrrolo[2,1-f][1,2,4]triazin-4-yl)-2-methylbenzyl)-1,2,4-oxadiazole-3-carboxamide;

5-(tert-butyl)-N-(3-fluoro-2-methyl-4-(pyrrolo[2,1-f][1,2,4]triazin-4-yl)benzyl)-1,2,4-oxadiazole-3-carboxamide;

5-(tert-butyl)-N-(2-(difluoromethyl)-4-(6-(1-methyl-1H-pyrazol-4-yl)pyrrolo[2,1-f][1,2,4]triazin-4-yl)benzyl)-1,2,4-oxadiazole-3-carboxamide;

5-(tert-butyl)-N-(2-(difluoromethyl)-4-(6-morpholinopyrrolo[2,1-f][1,2,4]triazin-4-yl)benzyl)-1,2,4-oxadiazole-3-carboxamide;

5-(tert-butyl)-N-(2-(difluoromethyl)-3-fluoro-4-(6-morpholinopyrrolo[2,1-f][1,2,4]triazin-4-yl)benzyl)-1,2,4-oxadiazole-3-carboxamide;

4-(tert-butyl)-N-(2-(difluoromethyl)-4-(6-morpholinopyrrolo[2,1-f][1,2,4]triazin-4-yl)benzyl)oxazole-2-carboxamide;

5-(tert-butyl)-N-(3-fluoro-2-methoxy-4-(6-morpholinopyrrolo[2,1-f][1,2,4]triazin-4-yl)benzyl)-1,2,4-oxadiazole-3-carboxamide;

5-(tert-butyl)-N-(4-(6-(4-fluorophenyl)pyrrolo[2,1-f][1,2,4]triazin-4-yl)-2-methylbenzyl)-1,2,4-oxadiazole-3-carboxamide;

5-(tert-butyl)-N-(4-(6-(4-cyanophenyl)pyrrolo[2,1-f][1,2,4]triazin-4-yl)-2-methylbenzyl)-1,2,4-oxadiazole-3-carboxamide;

5-(tert-butyl)-N-(2-methyl-4-(6-(pyrimidin-5-yl)pyrrolo[2,1-f][1,2,4]triazin-4-yl)benzyl)-1,2,4-oxadiazole-3-carboxamide;

5-(tert-butyl)-N-(2-methyl-4-(6-(2-methylpyridin-4-yl)pyrrolo[2,1-f][1,2,4]triazin-4-yl)benzyl)-1,2,4-oxadiazole-3-carboxamide;

5-(tert-butyl)-N-(4-(6-(2-methoxypyridin-4-yl)pyrrolo[2,1-f][1,2,4]triazin-4-yl)-2-methylbenzyl)-1,2,4-oxadiazole-3-carboxamide;

5-(tert-butyl)-N-(2-methyl-4-(6-(3-methylmorpholino)pyrrolo[2,1-f][1,2,4]triazin-4-yl)benzyl)-1,2,4-oxadiazole-3-carboxamide;

5-(tert-butyl)-N-(2-methyl-4-(6-(pyridin-2-yl)pyrrolo[2,1-f][1,2,4]triazin-4-yl)benzyl)-1,2,4-oxadiazole-3-carboxamide;

5-(tert-butyl)-N-(2-(2,2-difluoroethyl)-4-(6-(1-methyl-1H-pyrazol-4-yl)pyrrolo[2,1-f][1,2,4]triazin-4-yl)benzyl)-1,2,4-oxadiazole-3-carboxamide;

5-(tert-butyl)-N-(2-(2,2-difluoroethyl)-4-(6-morpholinopyrrolo[2,1-f][1,2,4]triazin-4-yl)benzyl)-1,2,4-oxadiazole-3-carboxamide; and 5-(tert-butyl)-N-(2-(2,2-difluoroethyl)-3-fluoro-4-(6-(1-methyl-1H-pyrazol-4-yl)pyrrolo[2,1-f][1,2,4]triazin-4-yl)benzyl)-1,2,4-oxadiazole-3-carboxamide hydrochloride;

5-(tert-butyl)-N-(2-(2,2-difluoroethyl)-3-fluoro-4-(6-morpholinopyrrolo[2,1-f][1,2,4]triazin-4-yl)benzyl)-1,2,4-oxadiazole-3-carboxamide hydrochloride;

5-(tert-butyl)-N-(3-fluoro-2-methoxy-4-(6-(1-methyl-1H-pyrazol-4-yl)pyrrolo[2,1-f][1,2,4]triazin-4-yl)benzyl)-1,2,4-oxadiazole-3-carboxamide hydrochloride;

5-(tert-butyl)-N-(4-(6-(1-ethyl-1H-pyrazol-4-yl)pyrrolo[2,1-f][1,2,4]triazin-4-yl)-2-methylbenzyl)-1,2,4-oxadiazole-3-carboxamide hydrochloride;

5-(tert-butyl)-N-(4-(6-(1-cyclopropyl-1H-pyrazol-4-yl)pyrrolo[2,1-f][1,2,4]triazin-4-yl)-2-methylbenzyl)-1,2,4-oxadiazole-3-carboxamide hydrochloride;

or a pharmaceutically acceptable salt thereof, such as a trifluoroacetate salt or a hydrochloride salt.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 10-ring members, or in particular 3- to 8-ring members, 3- to 7-ring members, 3- to 6-ring members or 5- to 7-ring members, 4- to 7-ring members or 4- to 6-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings.

In one embodiment, a heterocyclyl is a 3- to 7-membered monocyclic heterocyclyl (saturated or partially unsaturated (i.e., non-aromatic)) having 1-2 heteroatoms selected from O, S and N. Examples of 3- to 7-membered monocyclic heterocyclyl include, but are not limited to, aziridinyl, oxiranyl, thirranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl. In one embodiment, a heterocyclyl is a 5- to 7-membered monocyclic heterocyclyl (saturated or partially unsaturated).

In one embodiment, a heterocyclyl is a 4- to 6-membered monocyclic heterocyclyl (saturated or partially unsaturated) having 1-2 heteroatoms selected from O, S and N. Examples of a 4- to 6-membered monocyclic heterocyclyl include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl having 1-2 heteroatoms selected from O, S and N. Examples of saturated 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is oxetanyl, tetrahydrofuranyl, or tetrahydropyranyl.

In one embodiment, a 4- to 6-membered monocyclic heterocyclyl is selected from

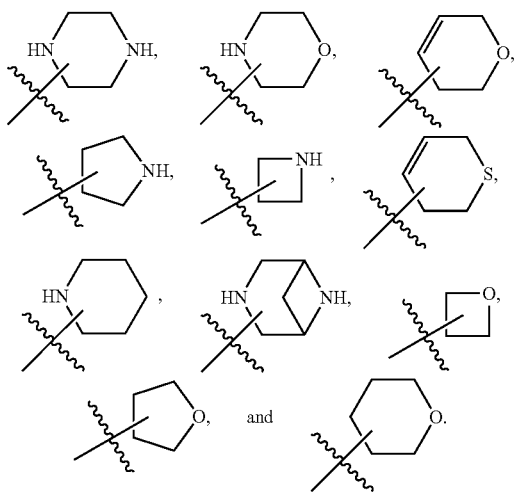

In one embodiment, a heterocyclyl is a 7-membered monocyclic heterocyclyl (saturated or partially unsaturated), such as a 7-membered monocyclic heterocyclyl having one heteroatom selected from O and N. Examples of a 7-membered monocyclic heterocyclyl include, but are not limited to, azepanyl, azepinyl, oxepanyl, oxepinyl, thiepanyl, thiepinyl, diazepanyl, diazepinyl, and thiazepinyl.

In another embodiment, a heterocyclyl is a 7- to 10-membered bicyclic heterocyclyl. In yet another embodiment, a heterocyclyl is a 9- to 10-membered non-aromatic bicyclic heterocyclyl. In another embodiment, a heterocyclyl is 9- to 10-membered fused non-aromatic bicyclic heterocyclyl. The heterocyclyl group can be attached to the rest of a compound of the invention at a heteroatom or a carbon atom. In one embodiment, a 9- to 10-membered fused non-aromatic bicyclic heterocyclyl is selected from N

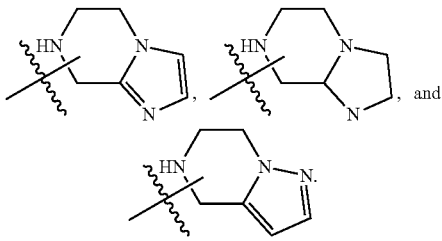

In another embodiment, a heterocyclyl is a 7- to 8-membered bridged non-aromatic bicyclic heterocyclyl, such as.

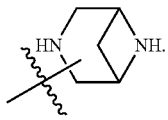

As used herein, the term "heteroaryl" refers to an aromatic 5- to 6-membered monocyclic ring system, having 1 to 4 heteroatoms independently selected from O, N and S, and wherein N can be oxidized (e.g., N(O)) or quaternized, and S can be optionally oxidized to sulfoxide and sulfone. Examples of 5- to 6-membered monocyclic heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, and the like. In one embodiment, a heteroaryl is a 5-membered heteroaryl. Examples of a 5-membered heteroaryl include, but are not limited to, pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl. In one embodiment, a 5-membered heteroaryl is selected from

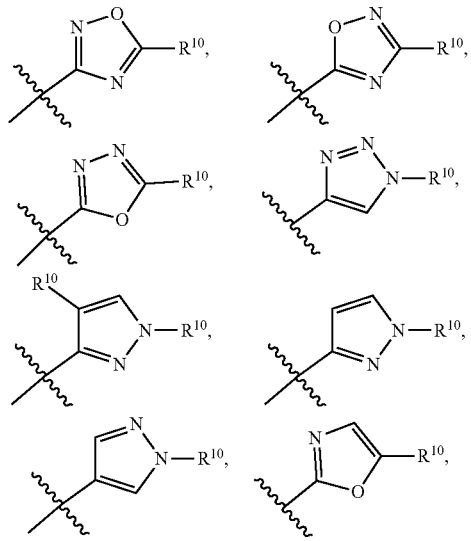

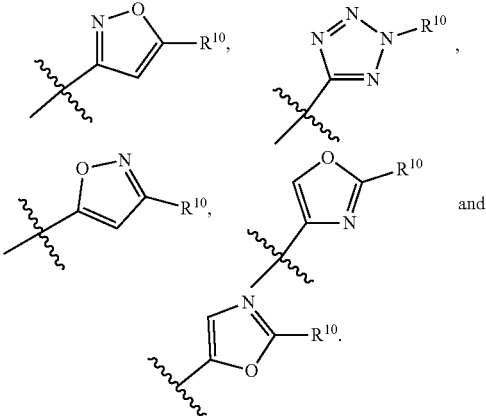

The term "fused ring system", as used herein, is a ring system that has two rings each of which are independently selected from a carbocyclyl or a heterocyclyl, wherein the two ring structures share two adjacent ring atoms. In one embodiment, a fused ring system have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, and S. In one embodiment, a bridged ring system have from 6 to 8 ring members.

The term "spiro ring system," as used herein, is a ring system that has two rings each of which are independently selected from a carbocyclyl or a heterocyclyl, wherein the two ring structures having one ring atom in common. In one embodiment, spiro ring systems have from 5 to 8 ring members.

As used herein, the term "carbocyclyl" refers to saturated or unsaturated monocyclic or bicyclic hydrocarbon groups of 3-7 carbon atoms, 3-5, 3-6, 4-6, or 5-7 carbon atoms. The term "carbocyclyl" encompasses cycloalkyl groups and aromatic groups (i.e., aryl). The term "cycloalkyl" refers to completely saturated monocyclic or bicyclic or spiro hydrocarbon groups of 3-7 carbon atoms, 3-6 carbon atoms, or 5-7 carbon atoms. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

In one embodiment, the carbocyclyl is a 3- to 7-membered monocyclic carbocyclyl. Exemplary 3- to 7-membered monocyclic carbocyclyls include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. In one embodiment, the carbocyclyl is a 5- to 7-membered monocyclic carbocyclyl. In another embodiment, the carbocyclyl is a 4- to 6-membered monocyclic carbocyclyl, such as but not limited to cycloheptyl. In another embodiment, the carbocyclyl is a 4- to 6-membered monocyclic carbocyclyl. In another embodiment, the carbocyclyl is a 3- to 6-membered carbocyclyl. In another embodiment, the carbocyclyl is a 3- to 6-membered cycloalkyl. In yet another embodiment, the carbocyclyl is phenyl. In yet another embodiment, the carbocyclyl is cyclopropyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the invention provides deuterated compounds disclosed herein, in which any or more positions occupied by hydrogen can include enrichment by deuterium above the natural abundance of deuterium. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance.

The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to the subject an effective amount of at least one compound described herein, or a pharmaceutically acceptable salt thereof.

In one embodiment, the present invention provides methods of treating autoimmune disorders, inflammatory disorders, and cancers in a subject in need thereof comprising administering to the subject an effective amount of at least one compound described herein, or a pharmaceutically acceptable salt thereof.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis. In some embodiments, the present invention provides a method of treating systemic lupus erythematosus or atopic dermatitis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

Abbreviations and acronyms used herein include the following:
AcCl means acetyl chloride;
AcOH means acetic acid;
$AgNO_3$ means silver nitrate;
Aq. means aqueous;
Ar means argon;
BBBPY means 4,4'-di-tert-butyl-2,2'-dipyridyl;
$BH_3 \cdot Me_2S$ means borane dimethyl sulfide complex solution;
$BH_3 \cdot THF$ means borane tetrahydrofuran complex solution;
BINAP means (±)-2,2'-Bis(diphenylphosphino)-1,1'-binaphthalene;
Bn means benzyl;
Boc means tert-butoxy carbonyl;
$Boc_2O$ means di-tert-butyl decarbonate;
BPO means 2-(4-biphenyl)-5-phenyloxazole;
$(BPin)_2$ means bis(pinacolato)diboron;
br means broad;
nBuOH means n-butanol;
tBuOH means tert butanol;
n-BuLi means n-butyl lithium;
° C. means degrees Celsius;
$CCl_4$ means carbon tetrachloride;
$CHCl_3$ means chloroform;
$CDCl_3$ means deutero-chloroform;
CDI means 1,1'-carbonyldiimidazole;
CO means carbon monoxide;
$CO_2$ means carbon dioxide;
$(COCl)_2$ means oxalyl chloride;
$Cs_2CO_3$ means cesium carbonate;
CuBr means copper bromide;
CuCN means copper cyanide;
δ means chemical shift;
d means doublet;
dd means double doublet;
DCM means dichloromethane;
DABAL-$Me_3$ means bis(trimethylaluminium)-1,4-diazabicyclo[2.2.2]octane adduct;
DAST means (diethylamino)sulfur trichloride;
DIBAL-H means diisobutylaluminium hydride;
DIPEA means N-ethyldiisopropylamine or N,N-diisopropylethylamine;
DEA means diethylamine;
DME means 1,2-dimethoxyethane;
DMF means N,N-dimethylformamide;
DMSO means dimethylsulfoxide;
DMSO-$d_6$ means hexadeuterodimethyl sulfoxide;
$D_2O$ means deuterated water;
Et means ethyl;
$Et_2O$ means ether;
EtOH means ethanol;
EtOAc means ethyl acetate;
Eq. means equivalent;
g means gram;
HBr means hydrogen bromide;
HCHO means formaldehyde;
HCl means hydrochloric acid;
$HCO_2H$ means formic acid;
Hept means heptanes;

$^1$H NMR means proton nuclear magnetic resonance; H$_2$O means water;
HOAt means 1-hydroxy-7-azabenzotriazole;
HPLC means high pressure liquid chromatography;
h means hour;
JosiPhos means (R)-1-[(SP)-2-(Dicyclohexylphosphino)ferrocenyl]ethyldi-tert-butylphosphine;
K$_2$CO$_3$ means potassium carbonate;
KF means potassium fluoride;
KHSO$_4$ means potassium bisulfate;
KI means potassium iodide;
KOAc means potassium acetate;
KOH means potassium hydroxide;
K$_3$PO$_4$ means potassium phosphate tribasic;
L means litre;
LCMS means liquid chromatography mass spectrometry;
LiALH$_4$ means lithium aluminium hydride;
LiBr means lithium bromide;
LiOH means lithium hydroxide;
m means multiplet;
M means molar;
Me means methyl;
MeCN means acetonitrile;
MeOH means methanol;
MeOH-d$_4$ means deutero-methanol;
MeTHF means 2-methyltetrahydrofuran;
mg means milligram;
MgSO$_4$ means magnesium sulfate;
MHz means mega Hertz;
mins means minutes;
mL means millilitres;
mmol means millimole;
MS m/z means mass spectrum peak;
MsCl means methanesulfonyl chloride;
M/V means Mass volume ratio;
N$_2$ means nitrogen;
NaBH$_3$CN means sodium cyanoborohydride;
NaBH$_4$ means sodium borohydride;
NatBuO means sodium tert-butoxide;
Na$_2$CO$_3$ means sodium carbonate;
NaH means sodium hydride;
NaHCO$_3$ means sodium bicarbonate;
NaI means sodium iodide;
NaOH means sodium hydroxide;
Na$_2$SO$_3$ means sodium thiosulfate;
Na$_2$SO$_4$ means sodium sulfate;
NBS means N-bromosuccinimide;
NH$_3$ means ammonia;
NH$_4$Cl means ammonium chloride;
NH$_4$HCO$_3$ means ammonium bicarbonate;
NH$_4$OH is ammonium hydroxide;
NiCl$_2$ glyme means nickel(II) chloride ethylene glycol dimethyl ether complex;
OMs means mesylate;
P(cy)$_3$ means tricyclohexylphosphine;
Pd/C means palladium on carbon;
Pd(OAc)$_2$ means palladium acetate;
Pd$_2$(dba)$_3$ means tris(dibenzylideneacetone)dipalladium (0);
Pd(dppf)Cl$_2$ means [1,1'-bis(diphenylphosphino)ferrocene]dichloropalladium(II);
Pd(dppf)Cl$_2$·DCM means [1,1'-bis(diphenylphosphino)ferrocene]dichloropalladium(II), complex with dichloromethane;
Pd(dtbpf)Cl$_2$ means [1,1'-bis(di-tert-butylphosphino)ferrocene]dichloropalladium(II);
Pd(PPh$_3$)$_4$ means tetrakis(triphenylphosphine)palladium (0);
PE means petroleum ether;
iPrOH means iso-propanol;
q means quartet;
RT means room temperature;
s means singlet;
sat. means saturated;
SCX means strong cation exchange;
SFC means supercritical fluid chromatography;
SiO$_2$ means silicon dioxide;
SOCl$_2$ means thionyl chloride;
soln. means solution;
STAB means sodium triacetoxyborohydride;
t means triplet;
TBAF means tetrabutylammonium fluoride;
TBDMS means tert-butyldimethylsilyl;
TBME means tert-butyl methyl ether;
t-BuONa means sodium tert-butoxide;
TEA means triethylamine;
TFA means trifluoroacetic acid;
Ti(OEt)$_4$ means titanium ethoxide;
Tf$_2$O means trifluoromethanesulfonic anhydride;
THF means tetrahydrofuran;
TLC means thin layer chromatography;
TMS means trimethylsilyl;
TMSCHN$_2$ means (trimethylsilyl)diazomethane;
μL means micro litres;
μmol means micromole;
Zn(CN)$_2$ means zinc cyanide;
ZnCl$_2$ means zinc chloride;

Preparative HPLC Conditions

In the Example sections below, the following preparative HPLC methods were used.

Method A:
Column: Phenomenex Synergi C18 150×30 mm; 4 μm
Mobile phase A: MeCN
Mobile phase B: H$_2$O
Modifier: 0.05% HCl
Gradient (% organic): 0-100% optimized for each example Method B:
Column: Sunfire C18 50×30 mm, 5 μm
Mobile phase A: MeCN
Mobile phase B: H$_2$O
Modifier: 0.1% TFA
Gradient (% organic): 5-95% optimized for each example.

Method C:
Column: XSelect C18 100×19 mm; 5 μm
Mobile phase A: MeCN
Mobile phase B: H$_2$O
Modifier: 0.1% NH$_4$OH
Gradient (% organic): 0-100% optimized for each example.

Method D:
Column: Xtimate C18 150×25 mm; 5 μm
Mobile phase A: MeCN
Mobile phase B: H$_2$O
Modifier: 10 mM NH$_4$HCO$_3$
Gradient (% organic): 0-100% optimized for each example.

Method E:
Column: YMC-Actus C18 100×30 mm; 5 μm
Mobile phase A: MeCN
Mobile phase B: H$_2$O
Modifier: 0.225% HCO$_2$H
Gradient (% organic): 0-100% optimized for each example.

General Procedures

First Process

According to a first process, compounds of formula (I'), such as compounds of formula (I), (II), (III) or a pharmaceutically acceptable salt thereof may be prepared using the general procedure as illustrated in Scheme 1.

Scheme 1

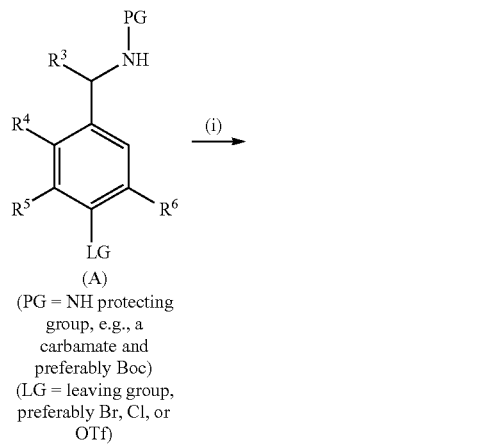

(A)
(PG = NH protecting group, e.g., a carbamate and preferably Boc)
(LG = leaving group, preferably Br, Cl, or OTf)

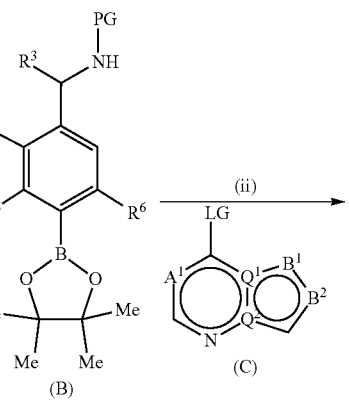

(B)

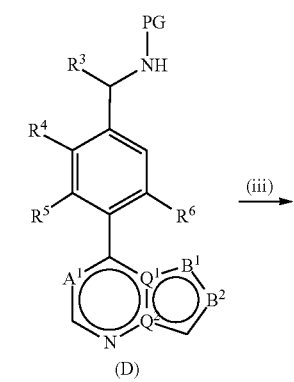

(D)

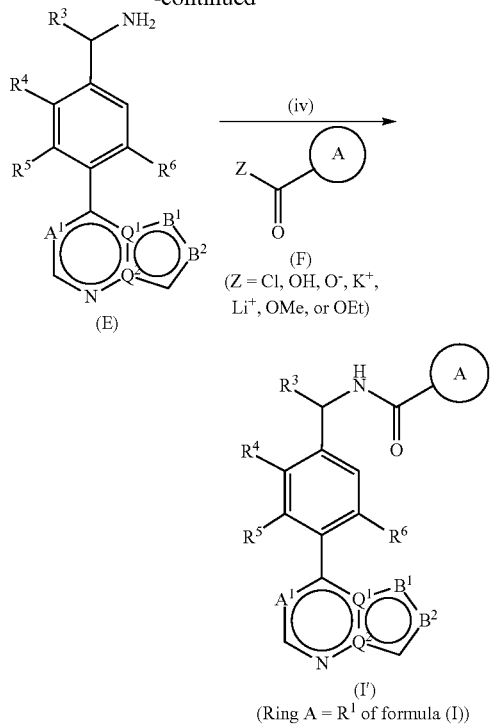

(F)
(Z = Cl, OH, O⁻, K⁺, Li⁺, OMe, or OEt)

(I')
(Ring A = $R^1$ of formula (I))

The compound of Formula (B) may be prepared from the compound of Formula (A), according to step (i), a boronate ester formation achieved by treatment with a suitable boronate such as $(BPin)_2$, in the presence of a suitable inorganic base, such as $K_2CO_3$ or KOAc and a suitable catalyst, such as, $Pd(dppf)Cl_2$ or $Pd_2(dba)_3$ with a suitable phosphine ligand such as $P(cy)_3$ or XPhos or $Pd(PPh_3)_4$. in a suitable non-polar solvent at between RT and elevated temperature. Preferred conditions comprise, treatment of the compound of Formula (A) with $(BPin)_2$ in the presence of $Pd(dppf)Cl_2$ or $Pd_2(dba)_3$ with XPhos or $P(cy)_3$, in the presence of KOAc in DMSO, toluene or dioxane at between 85° C. and 90° C.

The compound of Formula (D) may be prepared from the compound of Formula (B) and heterocycle of Formula (C) according to step (ii) an organometallic catalysed cross-coupling reaction. Typical cross-coupling conditions comprise a palladium catalyst containing suitable phosphine ligands, in the presence of an inorganic or organic base, in aqueous solvent at between RT and the reflux temperature of the reaction. Preferred conditions comprise reaction of the compounds of Formulae (B) and (D) in the presence of $Pd(dppf)Cl_2$ or $Pd(dtbpf)Cl_2$, and a suitable base such as $Na_2CO_3$, $K_2CO_3$ or $K_3PO_4$ in a suitable solvent such as aqueous dioxane at between 70° C. and 100° C.

The amine of Formula (E) may be prepared by the deprotection of the compound of Formula (D) according to process step (iii). Typically the compound of Formula (D) is treated with a suitable acid such as HCl or TFA in a suitable aprotic solvent such as DCM, MeOH, EtOAc or dioxane at between RT and reflux temperature. Preferred conditions comprise, reaction of the compound of Formula (D) with TFA or HCl in DCM, MeOH, EtOAc or dioxane at between RT and 50° C.

The compound of Formula (I') may be prepared by an amide bond formation of the compound of Formula (F) with the amine of Formula (E) in the presence of a suitable coupling agent and organic base in a suitable polar aprotic solvent.

When Z is OH, O⁻K⁺, O⁻Li⁺ preferred conditions, comprise reaction of the compound of Formula (F) with the amine of Formula (E) in the presence of a coupling agent preferably, T3P® or HATU, in the presence of a suitable organic base such as TEA or DIPEA; or DABAL-Me₃, in a suitable solvent, such as DMF, DCM or THF, at between rt and 45° C.

Alternatively, the compound of Formula (I') may be prepared from the ester of Formula (F) by reaction of the amine of Formula (E) in the presence of a suitable coupling agent, typically DABAL-Me₃ according to the method described by Novak et al (Tet. Lett. 2006, 47, 5767).

Alternatively, the compound of Formula (I') may be prepared from the acid chloride of Formula (F) by reaction of the amine of Formula (E) in the presence of a suitable organic base in a suitable solvent. Preferred conditions comprise reaction of the amine of Formula (E) with the acid chloride of Formula (F) in the presence of DIPEA in DCM at RT.

Second Process

According to a second process, compounds of formula (I'), such as formula (I), (II), (III) or a pharmaceutically acceptable salt thereof may be prepared using the general procedure as illustrated in Scheme 2, where PG, LG and Z are as defined in Scheme 1.

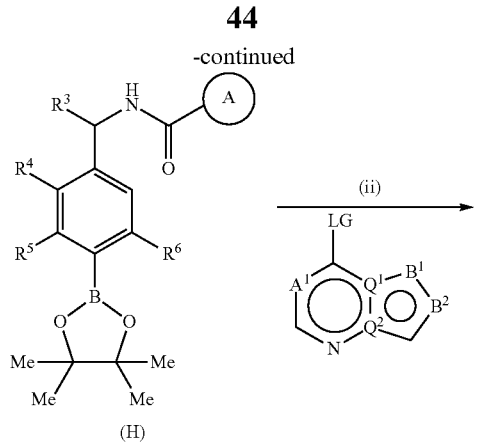

(H)

Scheme 2

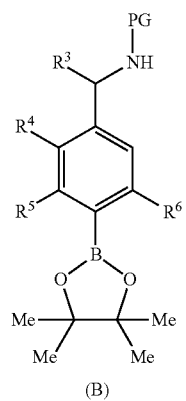

(B)

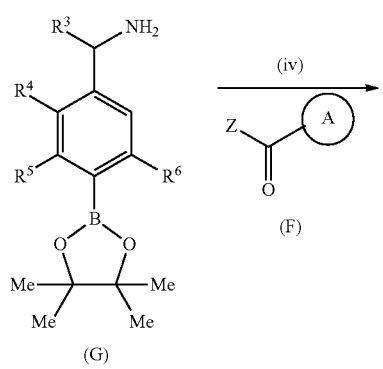

(G)

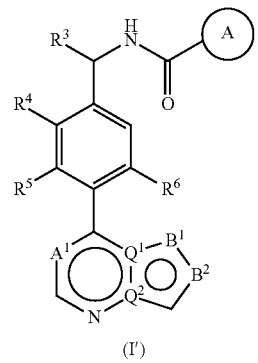

(I')

The compound of Formula (G) may be prepared from the protected amine of Formula (B) according to step (iii) a deprotection reaction, as described previously in Scheme 1.

The compound of Formula (H) may be prepared from the amine of Formula (G) and the compound of Formula (F) according to step (iv) an amide bond formation, as previously described in Scheme 1. Preferred conditions, comprise reaction of the acid of Formula (F) with the amine of Formula (G) in the presence of a coupling agent preferably, T3P®, HBTU or HATU, in the presence of a suitable organic base such as DIPEA or pyridine, optionally in a suitable solvent such as DMF at between rt and 50° C.

The compound of Formula (I') may be prepared according to step (ii) an organometallic catalysed cross-coupling reaction coupling reaction, as previously described in Scheme 1.

Third Process

According to a third process, compounds of Formula (M), wherein $R^8$ is a C-linked unsaturated heterocycle, may be prepared from compounds of Formulae (J), wherein $R^8$ is Br and the compounds of Formulae (K) and (C) as illustrated by the general procedure of Scheme 3, where PG is as defined in Scheme 1.

Scheme 3

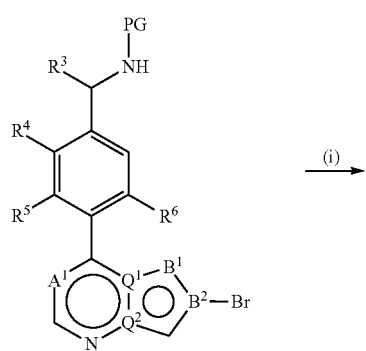

(J)

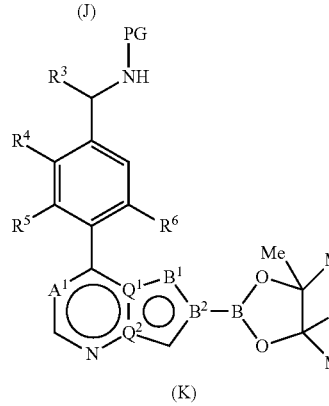

(K)

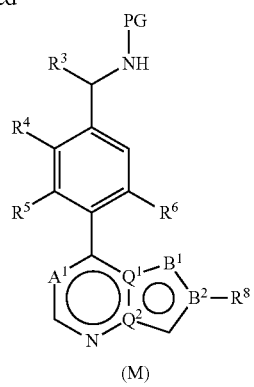

(M)

The compound of Formula (K) may be prepared from the compound of Formula (J), according to step (i), a boronate ester formation, as previously described in Scheme 1.

The compound of Formula (V) may be prepared from the compounds of Formula (K) and (L) according to step (ii) an organometallic catalysed cross-coupling reaction, as previously described in Scheme 1.

Fourth Process

According to a fourth process, compounds of Formula (M) may be prepared from compounds of Formula (J), wherein $R^8$ is Br and the compounds of Formulae (L), (N) and (O) as illustrated by the general procedure of Scheme 4, where PG and LG as defined in Scheme 1.

Scheme 4

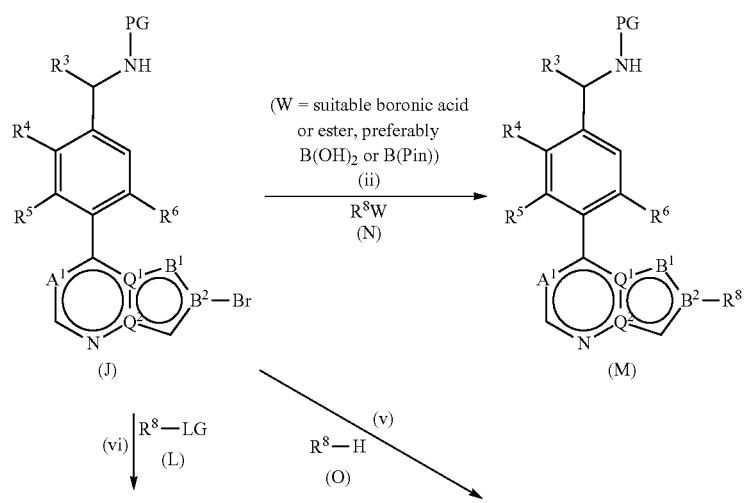

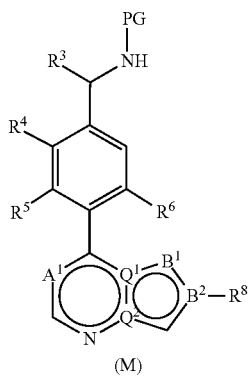

(M)

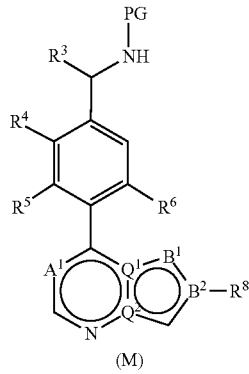

(M)

Where R⁸ is a C-linked unsaturated substituent, the compound of Formula (M) may be prepared according to process step (ii) the organometallic catalysed cross coupling of the compound of Formula (J) with the compound of Formula (N), as previously described in Scheme 1. Preferred conditions comprise reaction of the compounds of Formulae (J) and (N) in the presence of Pd(dppf)Cl$_2$, and a suitable base such as Na$_2$CO$_3$ or K$_2$CO$_3$ in a suitable solvent such as aqueous dioxane at between 70° C. and 100° C.

Alternatively, wherein R⁸ is an alkynyl group, the compound of Formula (M), may be prepared by a Sonagashira reaction as described in *Journal of Organic Chemistry.* 1998; 63; 23; 8551-8553.

Where R⁸ is an N-linked substituent, the compound of Formula (M) may be prepared according to process step (v) a Buchwald-Hartwig cross coupling reaction. Typical conditions comprise, reaction of the amine of Formula (O) with the bromide of Formula (J) in the presence of a suitable inorganic base, a suitable palladium catalyst in a suitable solvent at elevated temperature. Preferred conditions comprise, reaction of the compounds of Formulae (J) and (O) in the presence DavePhos, RuPhos, XPhos or JosiPhos optionally in combination with of Pd$_2$(dba)$_3$, or RuPhos Pd G3, BrettPhos Pd G1 methyl t-butyl adduct, RuPhos Pd G1 methyl t-butyl ether adduct, tBuXPhos-Pd-G3, optionally in the presence of a suitable base such as K$_3$PO$_4$, Cs$_2$CO$_3$, Na$_2$CO$_3$, NatBuO or phosphazene base P2-Et, in a suitable solvent such as dioxane, t-amyl alcohol, THF or toluene at between 70° C. and 110° C.

Where R⁸ is a C-linked saturated substituent, the compound of Formula (M) may be prepared according to process step (vi) a photo-catalysed iridium-nickel cross coupling reaction. Typical conditions comprise, reaction of the amine of Formula (O) with the bromide of Formula (J) in the presence of a suitable Nickel/Iridium catalyst combination such as NiCl$_2$ glyme, BBBPY and Ir[dF(CF$_3$)ppy]$_2$(dtbbpy) PF$_6$, in the presence of a suitable base such as LiOH with tris(trimethylsilyl)silane in a suitable solvent such as DME at RT under blue light.

Compounds of Formulae (I'), (B) and (M) may be converted to alternative compounds of Formulae (I'), (B) and (M) by standard chemical transformations such as for example, organometallic catalysed cross-coupling reactions, reduction of carboxylic acid esters, O-alkylations, fluorinations, hydrogenation, reductive amination, hydrolysis of esters, For example, see Example 77, step 1, Example 77, step 2, Example 19, step 2, Example 21, step 2 and Example 32, step 4, Example 67, step 4.

The compounds of Formulae (A), (M), (F), (L), (N) and (O) are commercially available, may be prepared by analogy to methods known in the literature, or the methods described in the examples described below.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in a conventional manner. See, for example, those described in 'Greene's Protective Groups in Organic Synthesis' by Theodora W. Greene and Peter G. M. Wuts, Fifth Edition, (John Wiley and Sons, 2014), in particular Chapter 7 ("Protection for the amino group") and Chapter 5 ("Protection for the Carboxyl group"), each incorporated herein by reference in its entirety, which also describes methods for the removal of such groups.

Example 1. 5-tert-butyl-N-[[2-chloro-5-fluoro-4-(6-morpholinopyrrolo[2,1-f][1,2,4]triazin-4-yl)phenyl]methyl]-1,2,4-oxadiazole-3-carboxamide

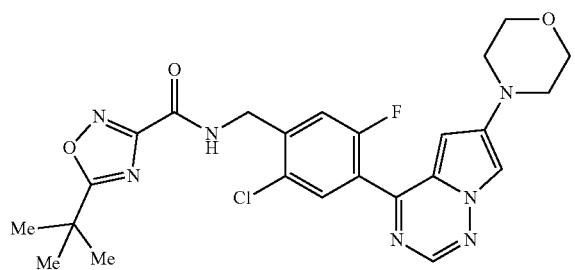 [SMILES: CC(C)(C)c1nc(C(=O)NCc2cc(F)c(-c3ncnn4cc(N5CCOCC5)cc34)cc2Cl)no1]

1. Synthesis of tert-butyl (2-chloro-5-fluoro-4-(4,4,5,5-tetramethyl-1,3,2-dioxaborolan-2-yl)benzyl)carbamate

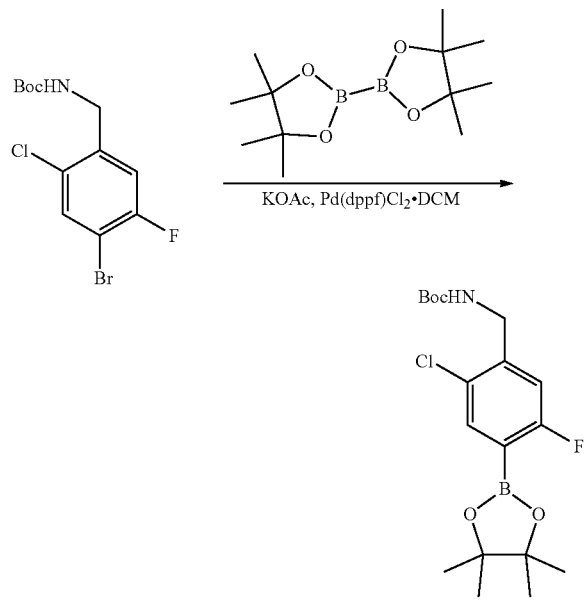

To a solution of tert-butyl (4-bromo-2-chloro-5-fluorophenyl)carbamate (WO2015089327, [0229], 1.47 g, 4.3 mmol) and (bispinacolato)diboron (1.42 g, 5.6 mmol) in dioxane (20 mL) were added Pd(dppf)Cl$_2$·DCM (300 mg, 0.36 mmol) and KOAc (843 mg, 8.6 mmol) at 16° C. and the reaction was heated to 100° C. under N$_2$ and stirred at that temperature for 16 h. The cooled reaction mixture was concentrated in vacuo and the crude product was purified by silica gel column chromatography (petroleum ether/EtOAc=20:1 to 4:1) to afford the title compound (1 g, crude) as a pale white solid which was used for the next step without further purification. LCMS m/z=330.1 [M+H]$^+$

2. Synthesis of tert-butyl (4-(6-bromopyrrolo[2,1-f][1,2,4]triazin-4-yl)-2-chloro-5-fluorobenzyl)carbamate

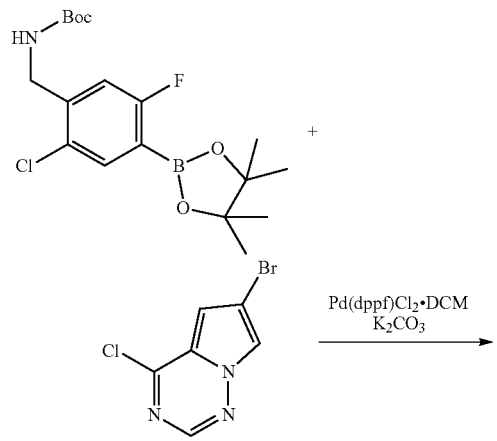

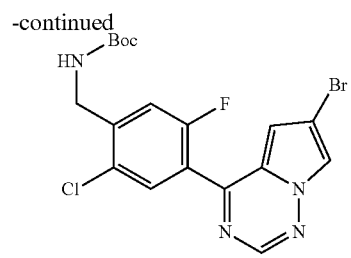

A mixture of tert-butyl (2-chloro-5-fluoro-4-(4,4,5,5-tetramethyl-1,3,2-dioxaborolan-2-yl)benzyl)carbamate (618 mg, 1.6 mmol), 6-bromo-4-chloro-pyrrolo[2,1-f][1,2,4]triazine (410 mg, 1.8 mmol), Pd(dppf)Cl$_2$·DCM (131 mg, 0.2 mmol) and K$_2$CO$_3$ (443 mg, 3.2 mmol) in dioxane (13.7 mL) and water (3.2 mL) was purged with N$_2$ for 5 min. The reaction mixture was stirred at 100° C. under N$_2$ for 1 h. The cooled reaction was concentrated in vacuo, the residue partitioned between water (25 mL) and EtOAc (25 mL) and the layers separated. The aqueous phase was extracted with EtOAc (2×25 mL), the combined organic layers washed with brine (75 mL), dried over Na$_2$SO$_4$, filtered and concentrated in vacuo. The residue was purified by silica gel column chromatography (0-100% EtOAc/Hept) to afford the title compound as a yellow solid (471 mg, 61%). LCMS m/z=485.1 [M+H]$^+$

3. Synthesis of tert-butyl (2-chloro-5-fluoro-4-(6-morpholinopyrrolo[2,1-f][1,2,4]triazin-4-yl)benzyl)carbamate

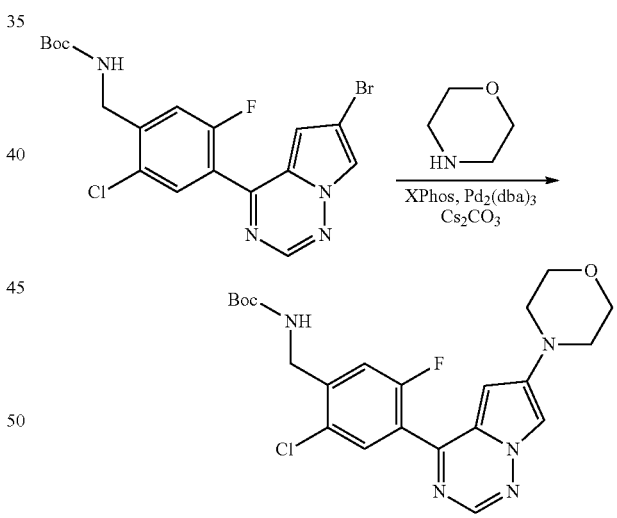

A mixture of tert-butyl (4-(6-bromopyrrolo[2,1-f][1,2,4]triazin-4-yl)-2-chloro-5-fluorobenzyl)carbamate (100 mg, 0.2 mmol), morpholine (29 mg, 0.3 mmol, 28 µL), Pd$_2$(dba)$_3$ (20 mg, 0.02 mmol), Cs$_2$CO$_3$ (214 mg, 0.7 mmol) and XPhos (21 mg, 0.04 mmol) in dioxane (2.2 mL) was purged with N$_2$ and the reaction stirred at 100° C. overnight. The cooled mixture was filtered through Celite® and the filtrate was concentrated in vacuo. The crude material was purified by silica gel column chromatography (2-100% EtOAc/Hept). The crude material was further purified by SFC using a CHIRALPAK AD-H 30×250 mm, 5um column eluting with 35% MeOH w/0.1% DEA in CO$_2$ (flow rate: 100 mL/min) to afford the title compound as a yellow solid (12 mg, 13%). LCMS m/z=462.3 [M+H]+

4. Synthesis of (2-chloro-5-fluoro-4-(6-morpholino-pyrrolo[2,1-f][1,2,4]triazin-4-yl)phenyl)meth-anamine hydrochloride

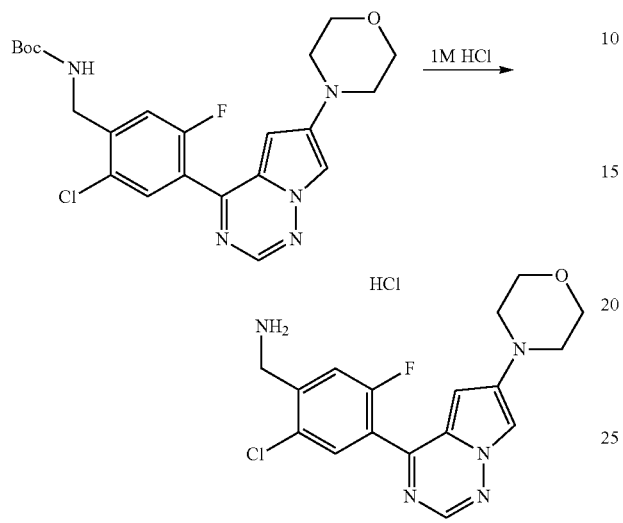

1M HCl (26 µL) was added to a solution of tert-butyl (2-chloro-5-fluoro-4-(6-morpholinopyrrolo[2,1-f][1,2,4]triazin-4-yl)benzyl)carbamate (12 mg, 0.03 mmol) in EtOAc (0.25 mL) and the reaction stirred at RT for 18 h. The mixture was evaporated in vacuo to afford the title compound, which was carried forward assuming quantitative yield. LCMS m/z=362.2 [M+H]+

5. Synthesis of 5-tert-butyl-N-[[2-chloro-5-fluoro-4-(6-morpholinopyrrolo[2,1-f][1,2,4]triazin-4-yl)phe-nyl]methyl]-1,2,4-oxadiazole-3-carboxamide To an ice-cold solution of potassium 5-(tert-butyl)-1,2,4-oxadiazole-3-carboxylate (8 mg, 0.04 mmol) in THF (0.1 mL) was added Et3N (11 mg, 0.1 mmol) and HATU (20 mg, 0.05 mmol). Additional THF (1 mL) was added and the mixture was stirred at 0° C. for 10 min before (2-chloro-5-fluoro-4-(6-morpholinopyrrolo[2,1-f][1,2,4]triazin-4-yl)phenyl)methanamine hydrochloride (10 mg, 0.03 mmol) was added. The reaction mixture was warmed to 23° C. and stirred at that temperature for 60 h. The reaction was quenched with H2O (5 mL) and extracted with EtOAc (3×5 mL). The combined organics were washed with brine, dried (Na2SO4), and evaporated in vacuo. The residue was purified by prep-HPLC (Method C; 20-80%) to afford the title compound (4 mg, 30%). LCMS m/z=514.5 [M+H]+; 1H NMR (500 MHz, MeOH-d4) δ: 8.38 (s, 1H), 7.87 (s, 1H), 7.81 (d, 1H), 7.38 (d, 1H), 6.34 (s, 1H), 4.74 (s, 2H), 3.86-3.78 (m, 4H), 3.19-3.13 (m, 4H), 1.52-1.48 (m, 9H).

Example 2. 3-(tert-butyl)-N-(3-fluoro-2-methyl-4-(6-morpholinopyrrolo[2,1-f][1,2,4]triazin-4-yl)ben-zyl)-1,2,4-oxadiazole-5-carboxamide

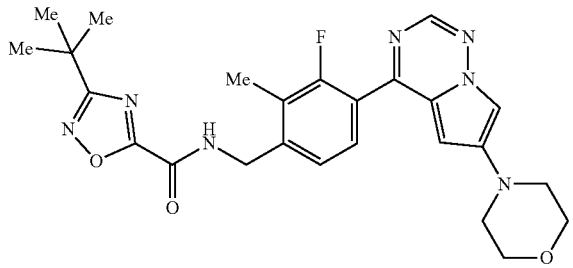 [SMILES: Cc1c(CNC(=O)c2nc(C(C)(C)C)no2)ccc(-c2ncnn3cc(N4CCOCC4)cc23)c1F]

1. Synthesis of tert-butyl (3-fluoro-2-methyl-4-(6-morpholinopyrrolo[2,1-f][1,2,4]triazin-4-yl)benzyl) carbamate (100014-481)

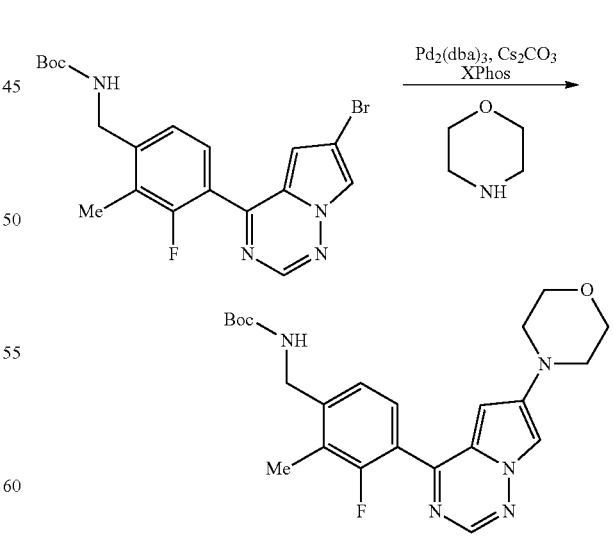

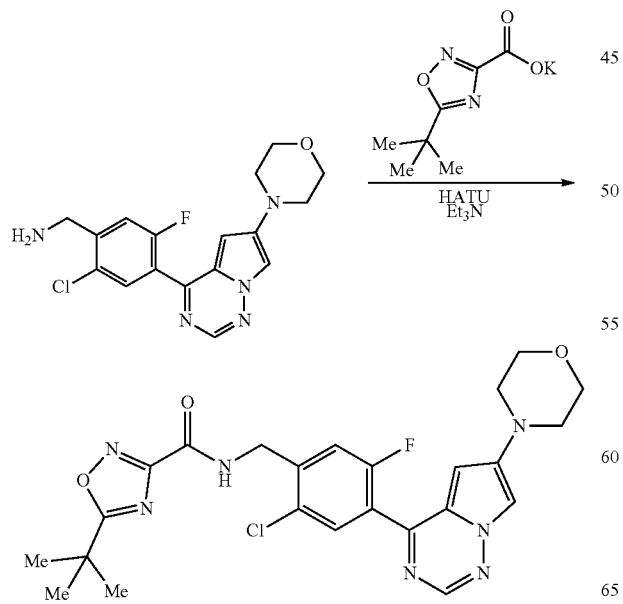

A mixture of tert-butyl (4-(6-bromopyrrolo[2,1-f][1,2,4] triazin-4-yl)-3-fluoro-2-methylbenzyl)carbamate (500 mg, 1.2 mmol), morpholine (150 mg, 1.7 mmol), Pd2(dba)3 (106 mg, 0.12 mmol), Cs2CO3 (1.12 g, 3.5 mmol) and XPhos (110 mg, 0.23 mmol) in dioxane (11.5 mL) was purged with N₂ for 5 minutes and the reaction was heated to 100° C. and stirred at that temperature overnight. The cooled mixture was filtered through Celite® and the filtrate was concentrated in vacuo. The crude was purified by silica gel column chromatography (2-100% EtOAc/Hept) to afford the title compound as a yellow solid (354 mg, 70%). LCMS m/z=442.3 [M+H]⁺; ¹H NMR (500 MHz, MeOH-d₄) δ: 8.35 (s, 1H), 7.84 (d, 1H), 7.51 (t, 1H), 7.27 (br d, 1H), 7.20 (br d, 1H), 6.31 (s, 1H), 4.40-4.28 (m, 2H), 3.89-3.75 (m, 4H), 3.20-3.11 (m, 4H), 2.33 (d, 3H), 1.47 (s, 9H)

2. Synthesis of (3-fluoro-2-methyl-4-(6-morpholino-pyrrolo[2,1-f][1,2,4]triazin-4-yl)phenyl)methanamine

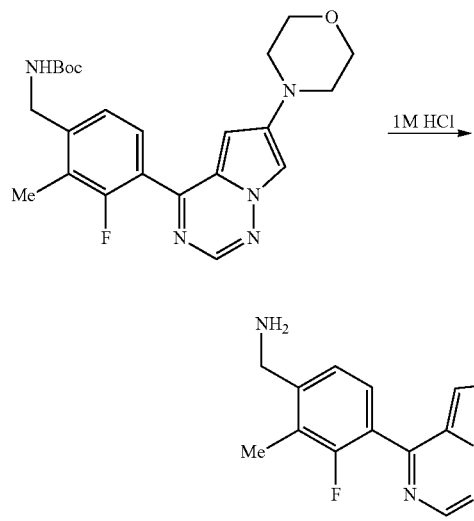

1M HCl (29 mg, 0.8 mmol) was added to a solution of tert-butyl (3-fluoro-2-methyl-4-(6-morpholinopyrrolo[2,1-f][1,2,4]triazin-4-yl)benzyl)carbamate (354 mg, 0.8 mmol) in EtOAc (8 mL) and the reaction was stirred at RT for 24 h. The mixture was partitioned between water (10 mL) and EtOAc (10 mL) and the layers were separated. The aqueous phase was basified to pH 10 using saturate aqueous NaHCO₃ and extracted with EtOAc (3×10 mL). The combined organic extracts were washed with brine, dried (Na₂SO₄), filtered, and concentrated in vacuo to afford the title compound as a yellow solid (278 mg, 100%). LCMS m/z=342.3 [M+H]⁺; ¹H NMR (500 MHz, MeOH-d₄) δ: 8.40-8.38 (m, 1H), 7.89 (d, 1H), 7.63 (t, 1H), 7.41 (d, 1H), 6.29 (t, 1H), 4.27 (s, 2H), 3.89-3.78 (m, 4H), 3.20-3.12 (m, 4H), 2.42 (d, 3H).

3. Synthesis of potassium 3-(tert-butyl)-1,2,4-oxadiazole-5-carboxylate

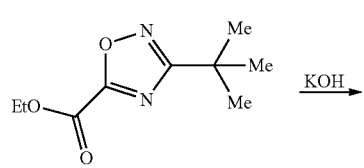

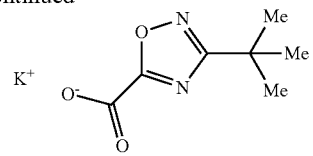

To a stirred solution of ethyl 3-tert-butyl-1,2,4-oxadiazole-5-carboxylate (2.7 g, 13.6 mmol) in EtOH/water (4/1 v/v, 35 mL) was added powdered KOH (765 mg, 13.6 mmol) and the reaction stirred at 23° C. for 4 d. The solvent was removed in vacuo with no heating, the resulting white solid was triturated with Et₂O, and the crude material was dried in vacuo to afford the title compound as a white solid (2.6 g, 92%) which was used without further purification.

4. Synthesis of 3-(tert-butyl)-N-(3-fluoro-2-methyl-4-(6-morpholinopyrrolo[2,1-f][1,2,4]triazin-4-yl)benzyl)-1,2,4-oxadiazole-5-carboxamide

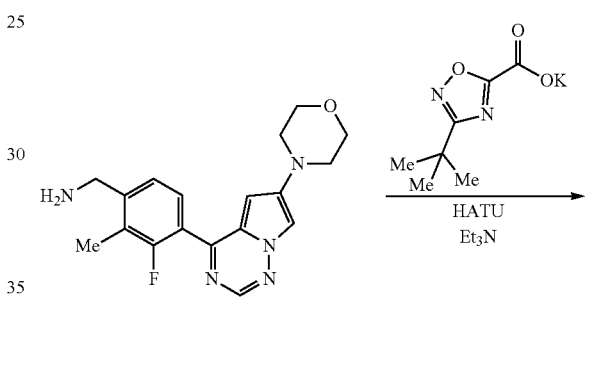

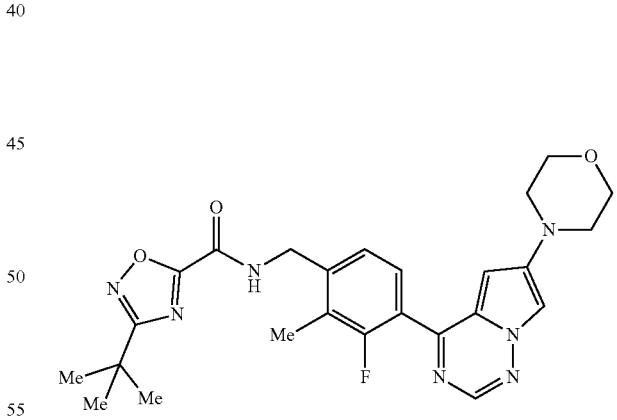

The crude product was obtained from potassium 3-(tert-butyl)-1,2,4-oxadiazole-5-carboxylate and (3-fluoro-2-methyl-4-(6-morpholinopyrrolo[2,1-f][1,2,4]triazin-4-yl)phenyl)methanamine, following the procedure described in Example 1, Step 5. The crude product was purified by HPLC method C to afford the title compound as a yellow solid (31 mg, 19%). LCMS m/z=494.3 [M+H]⁺; ¹H NMR (500 MHz, MeOH-d₄) δ: 8.36 (s, 1H), 7.85 (d, 1H), 7.54 (t, 1H), 7.35 (d, 1H), 6.32 (t, 1H), 4.69 (s, 2H), 3.88-3.76 (m, 4H), 3.20-3.11 (m, 4H), 2.40 (d, 3H), 1.42 (s, 9H).

Example 3. 5-(1,1-difluoro-2-methylpropan-2-yl)-N-(2-methyl-4-(6-(1-methyl-1H-pyrazol-4-yl)pyrrolo[2,1-f][1,2,4]triazin-4-yl)benzyl)-1,3,4-oxadiazole-2-carboxamide

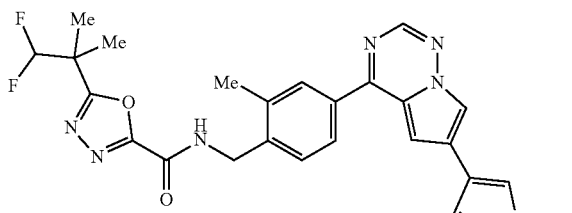

1. Synthesis of 3-acetoxy-2,2-dimethylpropanoic Acid

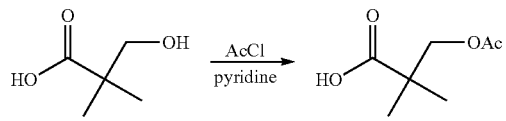

3-hydroxy-2,2-dimethylpropanoic acid (47.2 g, 400 mmol) was dissolved in pyridine (120 mL), and the reaction mixture was cooled to 0° C. Acetyl chloride (47.2 g, 600 mmol) was added dropwise, and then the reaction mixture was stirred at RT for 16 h. The reaction was acidified with 1 N HCl to pH=3-4 and extracted with EtOAc (3×100 mL). The organic extracts were washed with 1 N HCl (5×30 mL), dried over MgSO$_4$, and concentrated in vacuo to give the title compound (60.0 g, 94%). LCMS m/z=161.1 [M+H]$^+$. $^1$H NMR (400 MHz, CDCl$_3$) δ: 4.13 (s, 2H), 2.08 (s, 3H), 1.26 (s, 6H).

2. Synthesis of tert-butyl 2-(3-acetoxy-2,2-dimethylpropanoyl)hydrazine-1-carboxylate

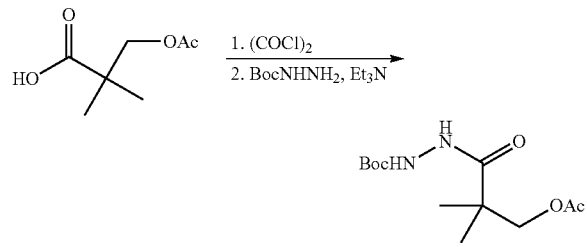

To a solution of 3-acetoxy-2,2-dimethylpropanoic acid (0.8 g, 8.0 mmol) in DCM (40 mL) were added oxalyl chloride (3.0 g, 24.0 mmol) and DMF (1 drop, cat). The mixture was stirred at RT for 3 h. After concentration, the freshly prepared acid chloride was dissolved in DCM (30 mL), and BocNH—NH$_2$ (1.1 g, 8.0 mmol) and Et$_3$N (1.6 g, 16 mmol) were added. The mixture was stirred at RT for 8 h. Then water (50 mL) was added and the mixture was extracted with DCM (3×100 mL). The combined organic extracts were washed with brine (2×80 mL), dried (Na$_2$SO$_4$), and concentrated in vacuo. The crude product was purified by silica gel column chromatography (petroleum ether/EtOAc=8:1) to give the title compound as a white solid (1.2 g, 86%). LCMS m/z=275.2 [M+H]$^+$. $^1$H NMR (400 MHz, CDCl$_3$) δ: 7.68 (br, 1H), 6.56 (br, 1H), 4.12 (s, 2H), 2.10 (s, 3H), 1.47 (s, 9H), 1.27 (s, 6H).

3. Synthesis of 3-hydrazineyl-2,2-dimethyl-3-oxopropyl acetate hydrochloride

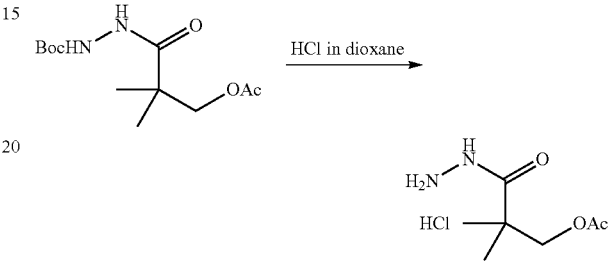

A solution of tert-butyl 2-(3-acetoxy-2,2-dimethylpropanoyl)hydrazine-1-carboxylate (5.5 g, 9.3 mmol) in an HCl solution (4M in dioxane, 20 mL) was stirred at RT for 2 h. The reaction mixture was concentrated in vacuo to give the title compound (3.8 g, 89%), which was carried forward without further purification. LCMS m/z=175.1 [M+H]$^+$. $^1$H NMR (400 MHz, CDCl$_3$) δ: 10.35 (br, 2H), 4.13 (s, 2H), 2.08 (s, 3H), 1.29 (s, 6H).

4. Synthesis of ethyl 2-(2-(3-acetoxy-2,2-dimethylpropanoyl)hydrazineyl)-2-oxoacetate

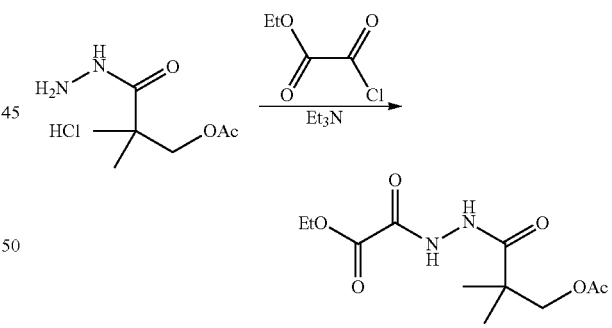

To a solution of 3-hydrazineyl-2,2-dimethyl-3-oxopropyl acetate hydrochloride (800 mg, 4.6 mmol) in DCM (20 mL) were added ethyl 2-chloro-2-oxoacetate (628 mg, 4.6 mmol) and Et$_3$N (1.42 g, 14.0 mmol). The mixture was stirred at RT for 16 h. After diluting with DCM (150 mL), the mixture was washed with brine (60 mL), dried (Na$_2$SO$_4$), filtered, and concentrated in vacuo. The crude product was purified by silica gel column chromatography (petroleum ether/EtOAc=1:1) to give the title compound as a yellow oil (905 mg, 72%). LCMS m/z=275.1 [M+H]$^+$; $^1$H NMR (400 MHz, CDCl$_3$) δ: 8.95 (s, 1H), 4.39 (q, 2H), 4.13 (s, 2H) 2.12 (s, 3H), 1.39 (t, 3H), 1.30 (s, 6H)

5. Synthesis of ethyl 5-(1-acetoxy-2-methylpropan-2-yl)-1,3,4-oxadiazole-2-carboxylate

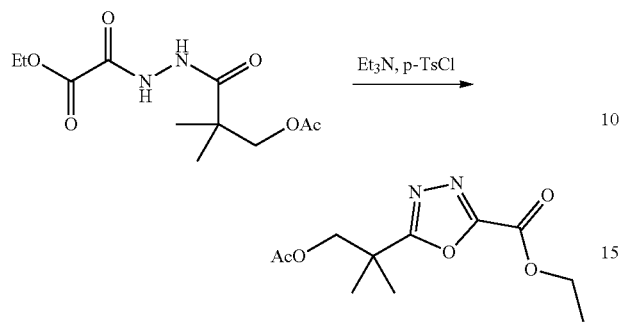

To a solution of ethyl 2-(2-(3-acetoxy-2,2-dimethylpropanoyl)hydrazineyl)-2-oxoacetate (1.5 g, 5.6 mmol) in DCM (20 mL) were added p-TsCl (1.3 g, 6.7 mmol) and Et₃N (735 mg, 7.3 mmol). The mixture was stirred at RT for 8 h. After diluting with DCM (100 mL), the mixture was washed with brine (60 mL), dried (Na₂SO₄), filtered, and concentrated in vacuo. The crude product was purified by silica gel column chromatography (petroleum ether/EtOAc=2:1) to give the title compound as a yellow solid (1.0 g, 72%). LCMS m/z=257.1 [M+H]⁺; ¹H NMR (400 MHz, CDCl₃) δ: 4.52 (q, 2H), 4.28 (s, 2H), 2.03 (s, 3H), 1.52 (s, 6H), 1.46 (t, 3H).

6. Synthesis of ethyl 5-(1-hydroxy-2-methylpropan-2-yl)-1,3,4-oxadiazole-2-carboxylate

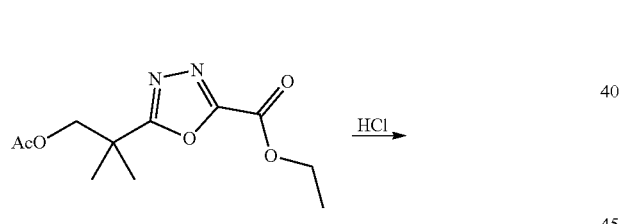

To a solution of ethyl 5-(1-acetoxy-2-methylpropan-2-yl)-1,3,4-oxadiazole-2-carboxylate (4.0 g, 15.6 mmol) in EtOH (40 mL) was added conc HCl (4 mL). The mixture was stirred at RT for 16 h. The reaction mixture was concentrated in vacuo and the crude material was purified by silica gel column chromatography (petroleum ether/EtOAc=2:1) to give the title compound as a yellow oil (1.2 g, 36%). LCMS m/z=215.1 [M+H]⁺; ¹H NMR (400 MHz, CDCl₃) δ: 4.52 (q, 2H), 3.84 (s, 2H), 1.47-1.44 (m, 9H).

7. Synthesis of ethyl 5-(2-methyl-1-oxopropan-2-yl)-1,3,4-oxadiazole-2-carboxylate

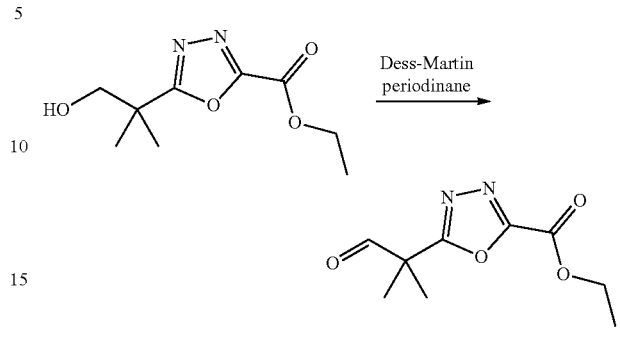

To a solution of ethyl 5-(1-hydroxy-2-methylpropan-2-yl)-1,3,4-oxadiazole-2-carboxylate (1.0 g, 4.7 mmol) in DCM (150 mL) was added Dess-Martin periodinane (2.4 g, 5.6 mmol). The mixture was stirred at RT for 16 h. After dilution with water (20 mL), the mixture was extracted with DCM (2×30 mL). The combined organic layers were washed with H₂O (2×20 mL), dried (Na₂SO₄), filtered, and concentrated in vacuo to give the title compound as a yellow solid (500 mg, 51%). LCMS m/z=213.1 [M+H]⁺; ¹H NMR (400 MHz, CDCl₃) δ: 9.68 (s, 1H), 4.53 (q, 2H), 1.66 (s, 6H), 1.26 (t, 3H).

8. Synthesis of ethyl 5-(1,1-difluoro-2-methylpropan-2-yl)-1,3,4-oxadiazole-2-carboxylate

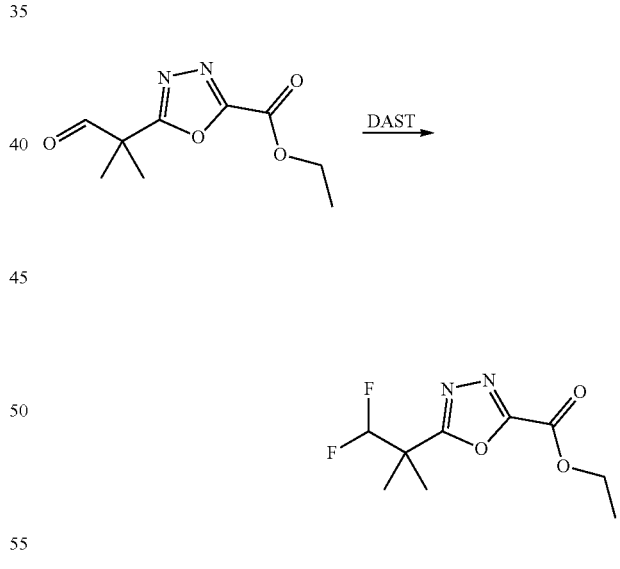

A solution of ethyl 5-(2-methyl-1-oxopropan-2-yl)-1,3,4-oxadiazole-2-carboxylate (1.4 g, 6.6 mmol) in DAST (10 mL) was stirred at 40° C. for 16 h. The reaction mixture was concentrated, and ice was added, followed by EtOAc (50 mL). The layers were separated, and the organic phase was dried (Na₂SO₄), filtered, and concentrated in vacuo. The residue was purified by silica gel column chromatography (petroleum ether/EtOAc=3:1) to give the title compound as a yellow oil (720 mg, 47%). LCMS m/z=235.1 [M+H]⁺; ¹H NMR (400 MHz, CDCl₃) δ: 6.01 (t, 1H), 4.53 (q, 2H), 1.58 (s, 6H), 1.46 (t, 3H).

9. Synthesis of potassium 5-(1,1-difluoro-2-methyl-propan-2-yl)-1,3,4-oxadiazole-2-carboxylate

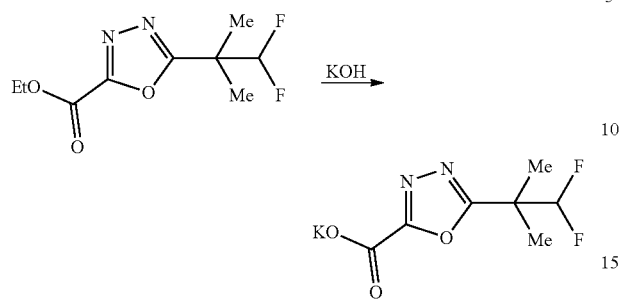

The title compound was obtained from ethyl 5-(1,1-difluoro-2-methylpropan-2-yl)-1,3,4-oxadiazole-2-carboxylate using an analogous method to that described for Example 2, Step 3.

10. Synthesis of 5-(1,1-difluoro-2-methylpropan-2-yl)-N-(2-methyl-4-(6-(1-methyl-1H-pyrazol-4-yl)pyrrolo[2,1-f][1,2,4]triazin-4-yl)benzyl)-1,3,4-oxadiazole-2-carboxamide

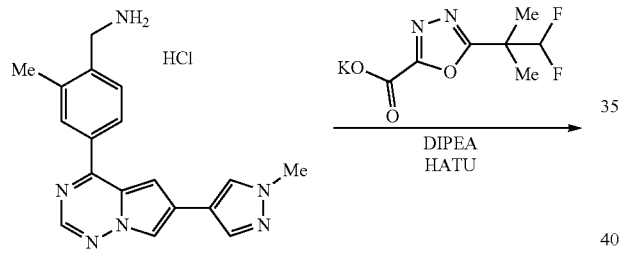

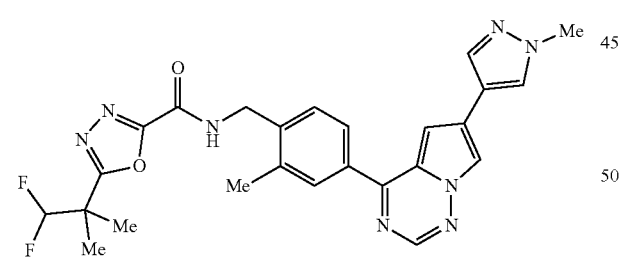

The title compound was prepared (57.1 mg, 34%) using an analogous method to that described for Example 1, Step 5 using (2-methyl-4-(6-(1-methyl-1H-pyrazol-4-yl)pyrrolo[2,1-f][1,2,4]triazin-4-yl)phenyl)methanamine hydrochloride and potassium 5-(1,1-difluoro-2-methylpropan-2-yl)-1,3,4-oxadiazole-2-carboxylate with DIPEA as base and DCM as solvent. LCMS m/z=507.2 [M+H]$^+$; $^1$H NMR (400 MHz, MeOH-$d_4$) δ: 8.91-8.98 (m, 1H), 8.33-8.44 (m, 1H), 8.15-8.25 (m, 1H), 7.96-8.03 (m, 1H), 7.87-7.93 (m, 2H), 7.82-7.86 (m, 1H), 7.50-7.58 (m, 1H), 7.18-7.28 (m, 1H), 6.12 (s, 1H), 4.70 (s, 2H), 3.92 (s, 3H), 2.51 (s, 3H), 1.53-1.61 (m, 6H).

Example 4. 5-(tert-butyl)-N-(2-methyl-4-(6-(4-methylpiperazin-1-yl)pyrrolo[2,1-f][1,2,4]triazin-4-yl)benzyl)-1,2,4-oxadiazole-3-carboxamide trifluoroacetate

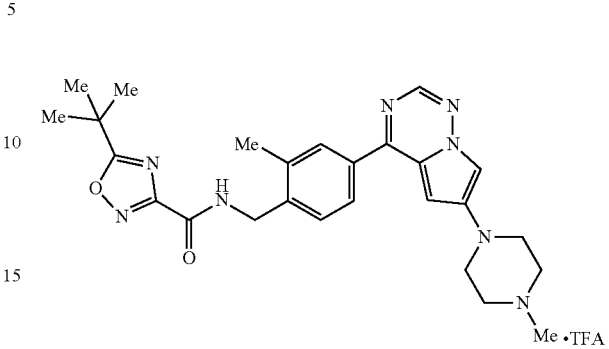

1. Synthesis of tert-butyl (4-(6-bromopyrrolo[2,1-f][1,2,4]triazin-4-yl)-2-methylbenzyl)carbamate

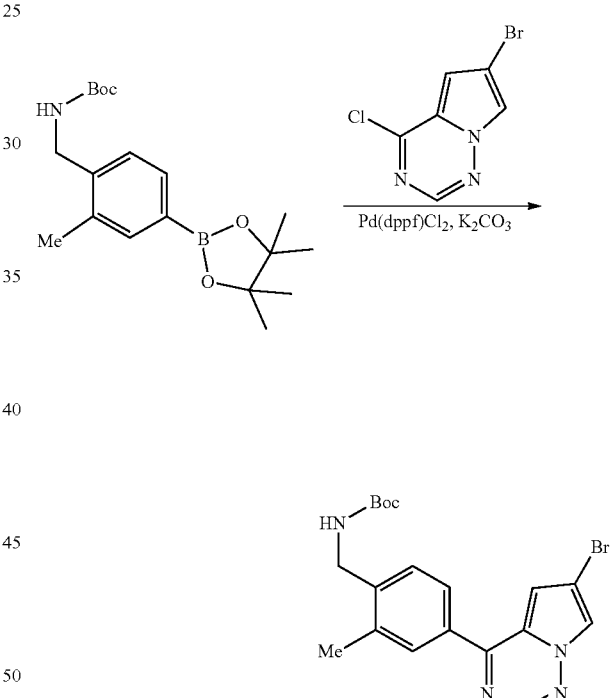

A mixture of tert-butyl (2-methyl-4-(4,4,5,5-tetramethyl-1,3,2-dioxaborolan-2-yl)benzyl)carbamate (10.0 g, 28.8 mmol), 6-bromo-4-chloro-pyrrolo[2,1-f][1,2,4]triazine (13.4 g, 57.6 mmol), K$_2$CO$_3$ (11.9 g, 86.4 mmol) and Pd(dppf)C$_2$ (1.1 g, 1.4 mmol) in dioxane (100 mL) and water (25 mL) was purged with N$_2$ for 5 min. The reaction mixture was heated to 100° C. under N$_2$ and stirred at that temperature for 18 h. The cooled reaction was diluted with H$_2$O (100 mL) and EtOAc (200 mL), filtered, and the layers separated. The organic layers were washed with brine (100 mL), dried (Na$_2$SO$_4$), and concentrated in vacuo. The crude was purified by silica gel column chromatography (EtOAc/Hept=1:3) to afford the title compound as a yellow solid (10.1 g, 84%). LCMS m/z=417.1 [M+H]$^+$

2. Synthesis of tert-butyl (2-methyl-4-(6-(4-methylpiperazin-1-yl)pyrrolo[2,1-f][1,2,4]triazin-4-yl)benzyl)carbamate

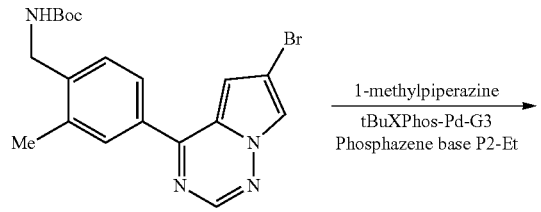

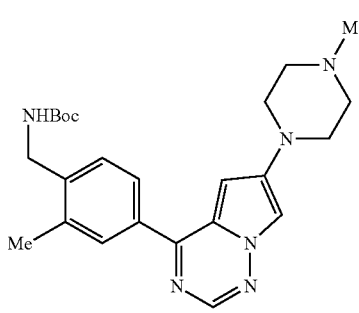

N₂ was bubbled through a mixture of tert-butyl (4-(6-bromopyrrolo[2,1-f][1,2,4]triazin-4-yl)-2-methylbenzyl)carbamate (350 mg, 0.84 mmol) and tBuXPhos-Pd-G3 (67 mg, 0.08 mmol) in t-amyl alcohol (4.2 mL) for 5 mins. Phosphazene base P2-Et (569 mg, 1.7 mmol) and 1-methylpiperazine (126 mg, 1.3 mmol) were added and the reaction stirred at RT for 4 h. The reaction was diluted with saturated NH₄Cl solution and extracted with EtOAc (2×25 mL). The combined organic layers were washed with brine (50 mL), dried (Na₂SO₄), filtered, and concentrated in vacuo. The crude was purified by silica gel column chromatography (0-10% MeOH/DCM with 1% NH₄OH modifier) to afford the title compound as a bright yellow solid (75 mg, 20%). LCMS m/z=437.3 [M+H]⁺

3. Synthesis of (2-methyl-4-(6-(4-methylpiperazin-1-yl)pyrrolo[2,1-f][1,2,4]triazin-4-yl)phenyl)methanamine hydrochloride

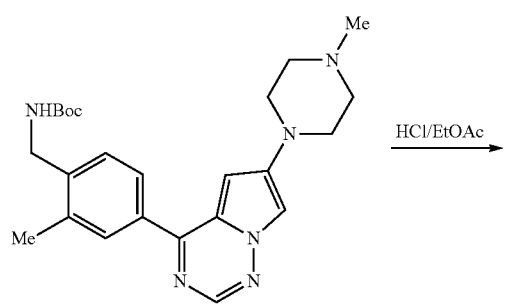

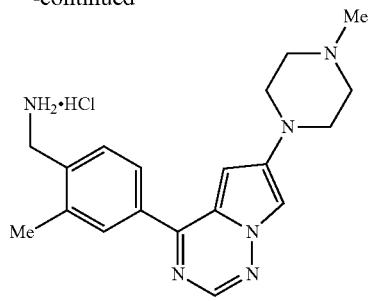

A solution of HCl in EtOAc (4 M, 2 mL) was added to tert-butyl (2-methyl-4-(6-(4-methylpiperazin-1-yl)pyrrolo[2,1-f][1,2,4]triazin-4-yl)benzyl)carbamate and the mixture stirred at RT for 18 h. The mixture was concentrated in vacuo to give the title compound as a yellow solid (4.3 mg) which was used in next step without further purification. LCMS m/z=337.0 [M+H]⁺

4. Synthesis of 5-(tert-butyl)-N-(2-methyl-4-(6-(4-methylpiperazin-1-yl)pyrrolo[2,1-f][1,2,4]triazin-4-yl)benzyl)-1,2,4-oxadiazole-3-carboxamide trifluoroacetate

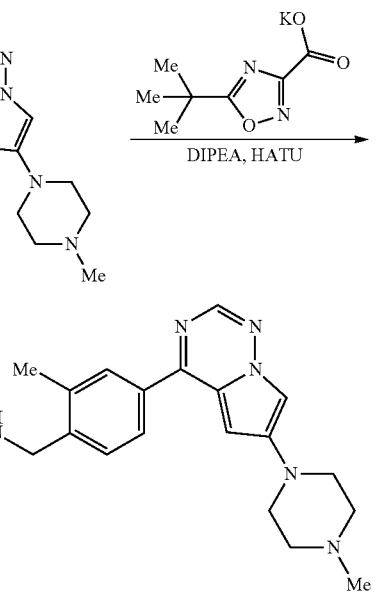

A vial was charged with (2-methyl-4-(6-(4-methylpiperazin-1-yl)pyrrolo[2,1-f][1,2,4]triazin-4-yl)phenyl)methanamine hydrochloride (40 mg, 0.08 mmol), potassium 5-tert-butyl-1,2,4-oxadiazole-3-carboxylate (21 mg, 0.1 mmol) and DCM (1 mL) followed by DIPEA (107 mg, 0.8 mmol). The mixture was cooled to 0° C. and HATU (38 mg, 0.1 mmol) was added in a single portion and the reaction was stirred overnight at RT. The reaction was concentrated in vacuo and the residue was dissolved in MeOH and passed through a fritted filter. The filtrate was evaporated in vacuo and the residue purified by reverse phase HLPC (Method A, 5-45%) to afford the title compound as a red solid (20 mg, 40%). LCMS m/z=489.2 [M+H]⁺; ¹H NMR (500 MHz, DMSO-d₆) δ: 9.52 (t, 1H), 8.51 (s, 1H), 8.06 (d, 1H), 7.89-7.98 (m, 2H), 7.43 (d, 1H), 6.81 (d, 1H), 4.54 (d, 2H), 3.91 (br d, 2H), 3.51 (br d, 2H), 3.14-3.24 (m, 2H), 3.00-3.10 (m, 2H), 2.85 (d, 3H), 2.46 (s, 3H), 1.44 (s, 9H).

Example 5. 5-(tert-butyl)-N-(2-methyl-4-(6-morpholinopyrrolo[2,1-f][1,2,4]triazin-4-yl)benzyl)-1,2,4-oxadiazole-3-carboxamide trifluoroacetate

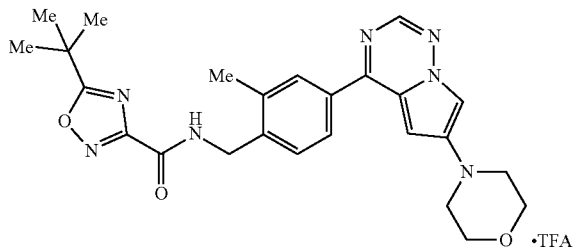 [SMILES: Cc1cc(-c2ncnn3cc(N4CCOCC4)cc23)ccc1CNC(=O)c1noc(C(C)(C)C)n1]

1. Synthesis of tert-butyl (2-methyl-4-(6-morpholinopyrrolo[2,1-f][1,2,4]triazin-4-yl)benzyl)carbamate

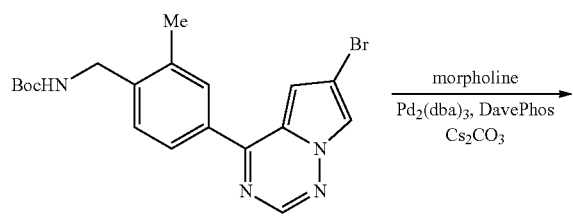

A mixture of tert-butyl (4-(6-bromopyrrolo[2,1-f][1,2,4]triazin-4-yl)-2-methylbenzyl)carbamate (501 mg, 1.2 mmol), morpholine (157 mg, 1.8 mmol), Pd$_2$(dba)$_3$ (55 mg, 0.06 mmol), DavePhos (47 mg, 0.12 mmol) and Cs$_2$CO$_3$ (782 mg, 2.4 mmol) in dioxane (12 mL) was purged with N$_2$ for 5 mins and then stirred at 100° C. for 16 h. Additional morpholine (157 mg, 1.8 mmol), Pd$_2$(dba)$_3$ (55 mg, 0.06 mmol), DavePhos (47 mg, 0.12 mmol) and Cs$_2$CO$_3$ (782 mg, 2.4 mmol) were added and the reaction was stirred for a further 24 h at 110° C. The cooled reaction was concentrated in vacuo and the crude product was purified by silica gel column chromatography (0-100% EtOAc/Hept) to afford the title compound as a yellow solid (279 mg, 55%). LCMS m/z=424.3 [M+H]$^+$

2. Synthesis of (2-methyl-4-(6-morpholinopyrrolo[2,1-f][1,2,4]triazin-4-yl)phenyl)methanamine hydrochloride

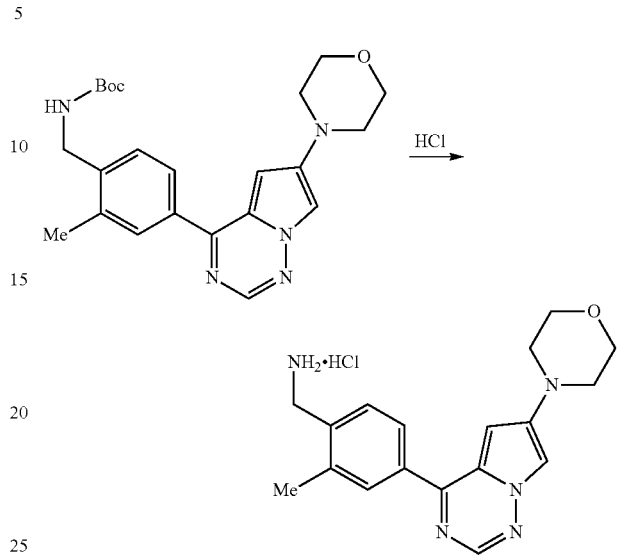

An HCl solution (1.4 mL, 1.8 mmol, 1.25 M in MeOH) was added to a solution of tert-butyl (2-methyl-4-(6-morpholinopyrrolo[2,1-f][1,2,4]triazin-4-yl)benzyl)carbamate (64 mg, 0.18 mmol) in MeOH (1.8 mL) and the reaction stirred at 50° C. for 18 h. The cooled reaction mixture was concentrated in vacuo to afford the title compound as a dark red film (52.0 mg), which was carried forward without further purification. LCMS m/z=264.1 [M+H]$^+$

3. Synthesis of 5-(tert-butyl)-N-(2-methyl-4-(6-morpholinopyrrolo[2,1-f][1,2,4]triazin-4-yl)benzyl)-1,2,4-oxadiazole-3-carboxamide trifluoroacetate

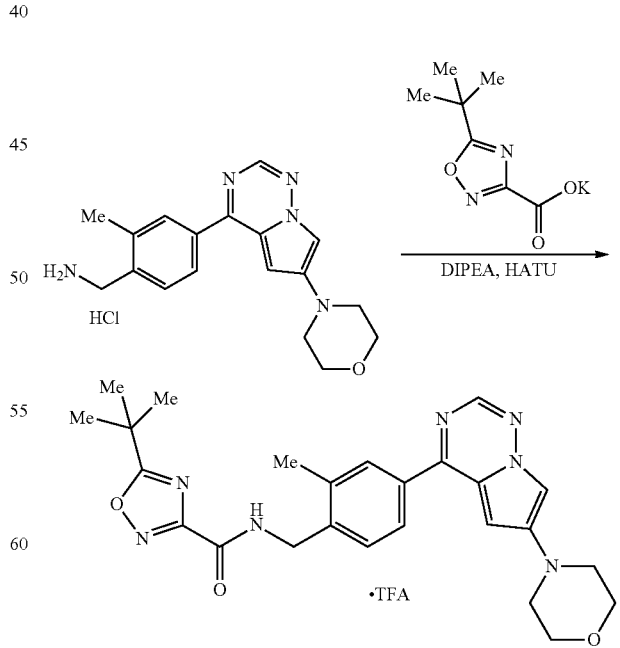

The crude product was obtained from (2-methyl-4-(6-morpholinopyrrolo[2,1-f][1,2,4]triazin-4-yl)phenyl)methanamine hydrochloride and potassium 5-(tert-butyl)-1,2,4-oxadiazole-3-carboxylate following the procedure described in Example 4, Step 4. The crude product was purified by reverse phase HPLC (Method B, 5-55%) to afford title compound as a red solid (33 mg, 47%). LCMS m/z=476.2 [M+H]+; 1H NMR (500 MHz, DMSO-$d_6$) δ: 9.50 (t, 1H), 8.48 (s, 1H), 8.02 (d, 1H), 7.89-7.96 (m, 2H), 7.43 (d, 1H), 6.73 (d, 1H), 4.54 (d, 2H), 3.72-3.81 (m, 4H), 3.13-3.22 (m, 4H), 2.45 (s, 3H), 1.44 (s, 9H).

Example 6. 5-(tert-butyl)-N-(4-(6-(3,6-dihydro-2H-pyran-4-yl)pyrrolo[2,1-f][1,2,4]triazin-4-yl)-2-methylbenzyl)-1,2,4-oxadiazole-3-carboxamide 1. Synthesis of tert-butyl (4-(6-(3,6-dihydro-2H-pyran-4-yl)pyrrolo[2,1-f][1,2,4]triazin-4-yl)-2-methylbenzyl)carbamate

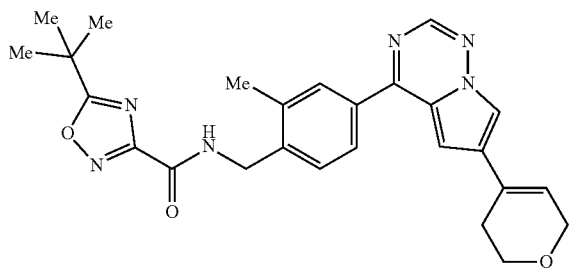 [SMILES: Cc1cc(-c2ncnn3cc(C4=CCOCC4)cc23)ccc1CNC(=O)c1noc(C(C)(C)C)n1]

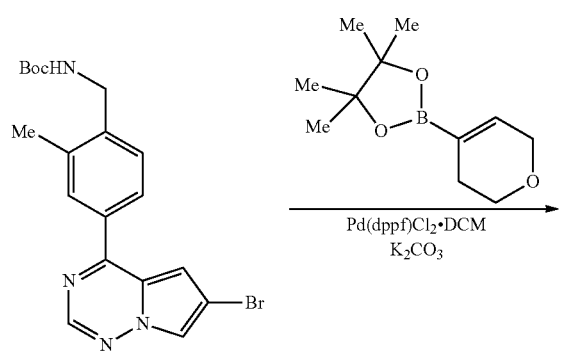

A mixture of tert-butyl (4-(6-bromopyrrolo[2,1-f][1,2,4]triazin-4-yl)-2-methylbenzyl)carbamate (75 mg, 0.2 mmol), 2-(3,6-dihydro-2H-pyran-4-yl)-4,4,5,5-tetramethyl-1,3,2-dioxaborolane (113 mg, 0.5 mmol), Pd(dppf)Cl$_2$·DCM (15 mg, 0.02 mmol) and K$_2$CO$_3$ (75 mg, 0.5 mmol) in dioxane (1.2 mL) and water (0.6 mL) was purged with nitrogen for 5 minutes and then heated at 100° C. overnight. The reaction mixture was concentrated in vacuo and the residue was purified by silica gel column chromatography (0-100% EtOAc:Hept) to afford the title compound as a light yellow solid (91 mg, 120%). LCMS m/z=421.1 [M+H]+

2. Synthesis of (4-(6-(3,6-dihydro-2H-pyran-4-yl)pyrrolo[2,1-f][1,2,4]triazin-4-yl)-2-methylphenyl)methanamine trifluoroacetate

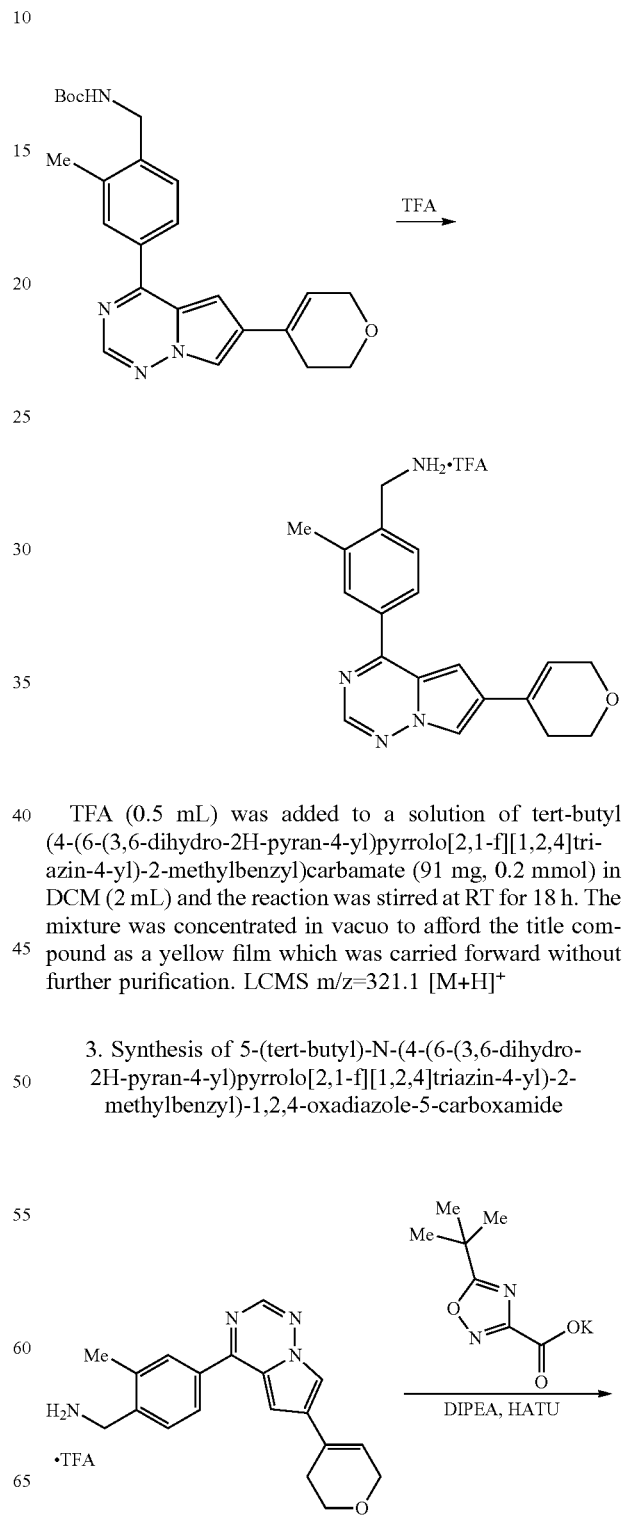

TFA (0.5 mL) was added to a solution of tert-butyl (4-(6-(3,6-dihydro-2H-pyran-4-yl)pyrrolo[2,1-f][1,2,4]triazin-4-yl)-2-methylbenzyl)carbamate (91 mg, 0.2 mmol) in DCM (2 mL) and the reaction was stirred at RT for 18 h. The mixture was concentrated in vacuo to afford the title compound as a yellow film which was carried forward without further purification. LCMS m/z=321.1 [M+H]+

3. Synthesis of 5-(tert-butyl)-N-(4-(6-(3,6-dihydro-2H-pyran-4-yl)pyrrolo[2,1-f][1,2,4]triazin-4-yl)-2-methylbenzyl)-1,2,4-oxadiazole-5-carboxamide -continued

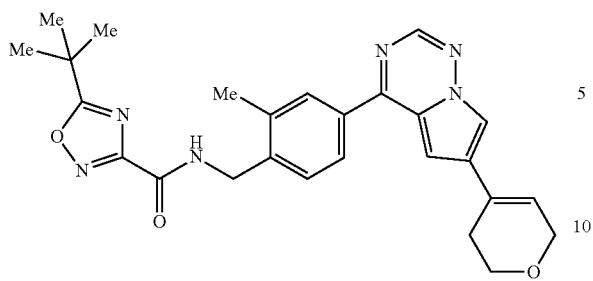

The compound was obtained from [4-[6-(3,6-dihydro-2H-pyran-4-yl)pyrrolo[2,1-f][1,2,4]triazin-4-yl]-2-methyl-phenyl]methanamine trifluoroacetate and potassium 5-tert-butyl-1,2,4-oxadiazole-3-carboxylate following the procedure described in Example 4, Step 4. The crude product was purified by silica gel column chromatography (0-100% [3:1 EtOAc:EtOH]:Hept) to afford the title compound as a light yellow solid (21 mg, 49%). LCMS m/z=473.2 [M+H]$^+$; $^1$H NMR (500 MHz, DMSO-d$_6$) δ: 9.52 (t, 1H), 8.57 (s, 1H), 8.34 (d, 1H), 7.98 (d, 1H), 7.96 (s, 1H), 7.45 (d, 1H), 7.28 (d, 1H), 6.48 (br s, 1H), 4.55 (d, 2H), 4.24 (br d, 2H), 3.83 (t, 2H), 2.46 (s, 3H), 1.44 (s, 9H).

Example 7. 5-(tert-butyl)-N-(4-(6-(1-(2-methoxyethyl)-1H-pyrazol-4-yl)pyrrolo[2,1-f][1,2,4]triazin-4-yl)-2-methylbenzyl)-1,2,4-oxadiazole-3-carboxamide

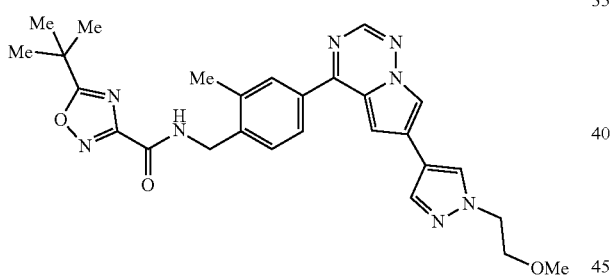

1. Synthesis of tert-butyl (4-(6-(1-(2-methoxyethyl)-1H-pyrazol-4-yl)pyrrolo[2,1-f][1,2,4]triazin-4-yl)-2-methylbenzyl)carbamate

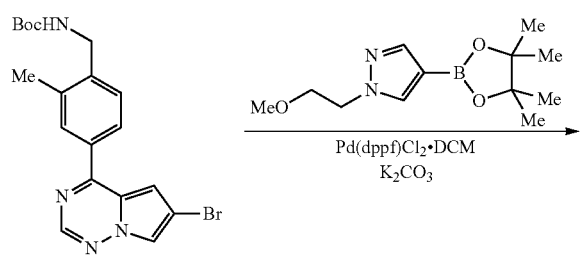

-continued

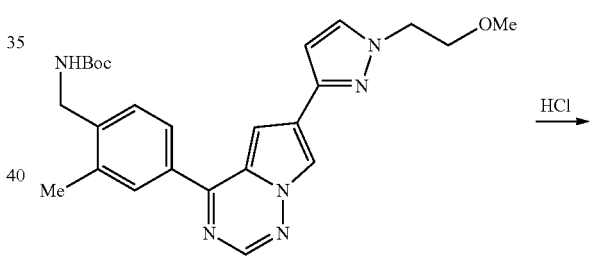

A mixture of tert-butyl (4-(6-bromopyrrolo[2,1-f][1,2,4]triazin-4-yl)-2-methylbenzyl)carbamate (75 mg, 0.2 mmol), 1-(2-methoxyethyl)-1H-pyrazole-4-boronic acid pinacol ester (135 mg, 0.5 mmol), Pd(dppf)Cl$_2$·DCM (15 mg, 0.02 mmol) and K$_2$CO$_3$ (75 mg, 0.5 mmol) in dioxane (1.2 mL) and water (0.6 mL) was purged with nitrogen for 5 minutes and then heated at 100° C. overnight. The reaction mixture was concentrated in vacuo and the residue was purified by silica gel column chromatography (0-100% EtOAc:Hept) to afford the title compound as a light yellow solid (90 mg, 120%). LCMS m/z=463.3 [M+H]$^+$ 2. Synthesis of (4-(6-(1-(2-methoxyethyl)-1H-pyrazol-4-yl)pyrrolo[2,1-f][1,2,4]triazin-4-yl)-2-methylphenyl)methanamine hydrochloride HCl (4 M, 0.5 mL) was added to tert-butyl (4-(6-(1-(2-methoxyethyl)-1H-pyrazol-4-yl)pyrrolo[2,1-f][1,2,4]triazin-4-yl)-2-methylbenzyl)carbamate (90 mg, 0.2 mmol) in MeOH (2 mL) and was stirred overnight at RT. The mixture was concentrated in vacuo to afford the title compound (90 mg, crude) which was used in the next step without further purification. LCMS m/z=363.2 [M+H]$^+$ 3. Synthesis of 5-(tert-butyl)-N-(4-(6-(1-(2-methoxyethyl)-1H-pyrazol-4-yl)pyrrolo[2,1-f][1,2,4]triazin-4-yl)-2-methylbenzyl)-1,2,4-oxadiazole-3-carboxamide

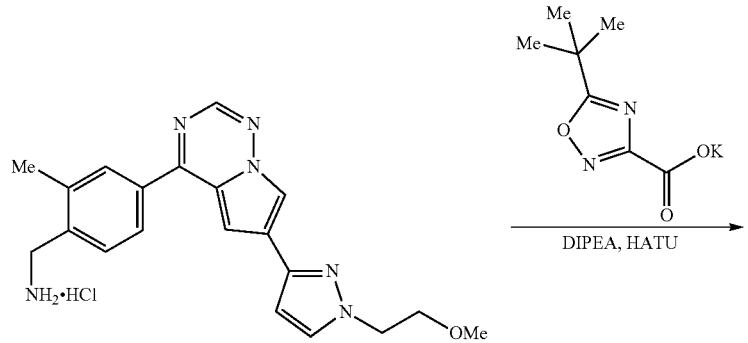

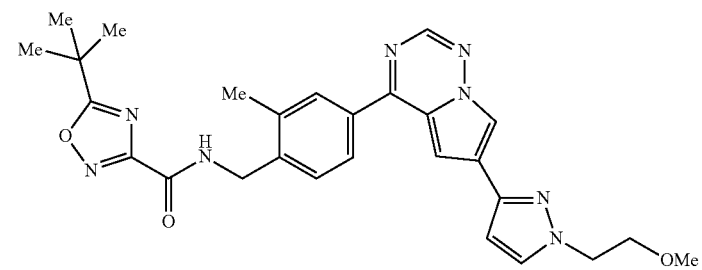

The compound was obtained from (4-(6-(1-(2-methoxyethyl)-1H-pyrazol-4-yl)pyrrolo[2,1-f][1,2,4]triazin-4-yl)-2-methylphenyl)methanamine hydrochloride and potassium 5-tert-butyl-1,2,4-oxadiazole-3-carboxylate following the procedure described in Example 4, Step 4. The crude product was purified by silica gel column chromatography (0-75% EtOAc/EtOH (3:1):Hept) to afford the title compound as a yellow solid (32 mg, 60%). LCMS m/z=515.3 [M+H]$^+$; $^1$H NMR (500 MHz, DMSO-$d_6$) δ: 9.53 (t, 1H), 8.56 (s, 1H), 8.47 (d, 1H), 8.23 (s, 1H), 8.00 (br d, 1H), 7.97 (s, 2H), 7.46 (d, 1H), 7.41 (d, 1H), 4.56 (d, 2H), 4.27 (t, 2H), 3.71 (t, 2H), 3.24 (s, 3H), 2.48 (s, 3H), 1.44 (s, 9H).

Example 8. 5-(tert-butyl)-N-(4-(6-(3-methoxyazetidin-1-yl)pyrrolo[2,1-f][1,2,4]triazin-4-yl)-2-methylbenzyl)-1,2,4-oxadiazole-3-carboxamide

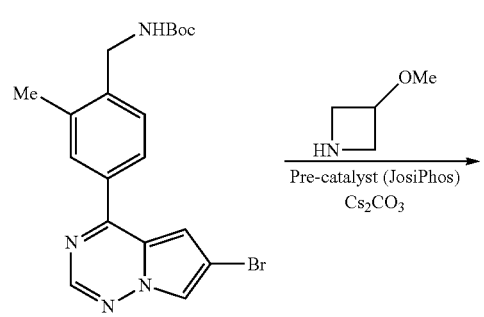

1. Synthesis of tert-butyl (4-(6-(3-methoxyazetidin-1-yl)pyrrolo[2,1-f][1,2,4]triazin-4-yl)-2-methylbenzyl)carbamate (100098-698)

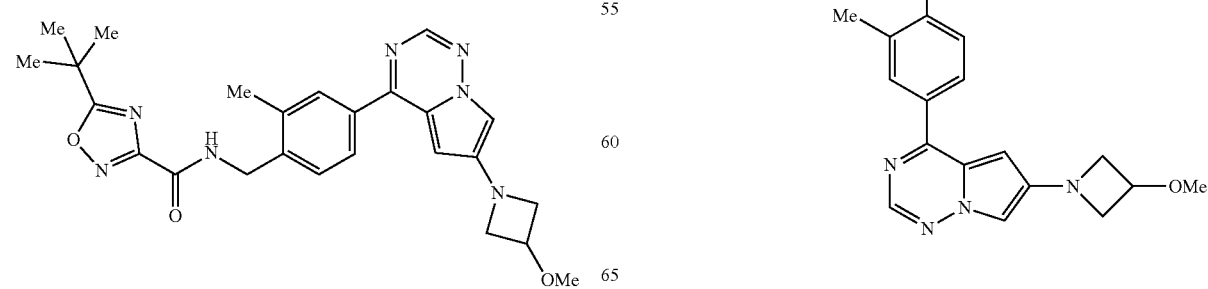

A mixture of tert-butyl (4-(6-bromopyrrolo[2,1-f][1,2,4]triazin-4-yl)-2-methylbenzyl)carbamate (95 mg, 0.2 mmol), Pd₂(dba)₃ (10 mg, 0.01 mmol), JosiPhos (13 mg, 0.02 mmol) and Cs₂CO₃ (223 mg, 0.7 mmol) were dissolved in dioxane (2.3 mL) and the mixture purged with N₂ for 5 min. 3-Methoxyazetidine (30 mg, 0.3 mmol) was added and the reaction was stirred at 100° C. overnight. The cooled reaction was concentrated in vacuo and the crude was purified by silica gel column chromatography (0-100% EtOAc:Hept) to afford the title compound as a yellow solid (85 mg, 88%). LCMS m/z=424.3 [M+H]⁺

2. Synthesis of (4-(6-(3-methoxyazetidin-1-yl)pyrrolo[2,1-f][1,2,4]triazin-4-yl)-2-methylphenyl)methanamine

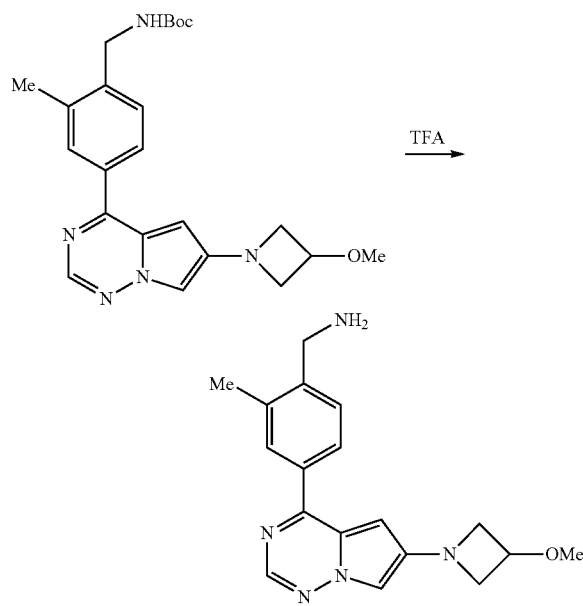

TFA (229 mg, 2.0 mmol) was added to a solution of tert-butyl (4-(6-(3-methoxyazetidin-1-yl)pyrrolo[2,1-f][1,2,4]triazin-4-yl)-2-methylbenzyl)carbamate (85 mg, 0.2 mmol) in DCM (2.0 mL) and the reaction was stirred at RT for 18 h. The reaction was concentrated in vacuo, the residue dissolved in MeOH, and passed through an SCX ion exchange column flushing through with MeOH followed by 2M methanolic NH₃. The combined organic phases were concentrated in vacuo to afford the title compound (67 mg, crude) which was carried forward without further purification. LCMS m/z=324.2 [M+H]⁺

3. Synthesis of 5-(tert-butyl)-N-(4-(6-(3-methoxyazetidin-1-yl)pyrrolo[2,1-f][1,2,4]triazin-4-yl)-2-methylbenzyl)-1,2,4-oxadiazole-3-carboxamide

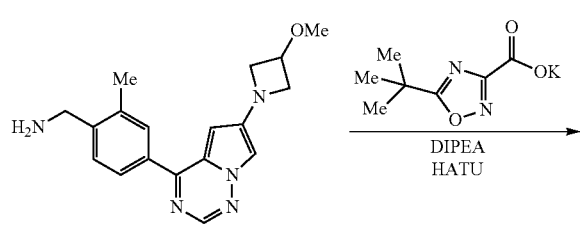

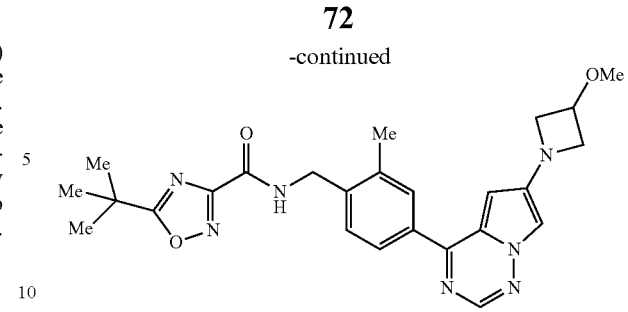

The compound was obtained from (4-(6-(3-methoxyazetidin-1-yl)pyrrolo[2,1-f][1,2,4]triazin-4-yl)-2-methylphenyl)methanamine and potassium 5-tert-butyl-1,2,4-oxadiazole-3-carboxylate following the procedure described in Example 4, Step 4. The crude product was purified by silica gel column chromatography (0-100% (EtOAc/EtOH (3:1):Hept) to afford the title compound as a yellow solid (28 mg, 28%). LCMS m/z=476.3 [M+H]⁺; ¹H NMR (500 MHz, DMSO-d₆) δ: 9.49 (t, 1H), 8.46 (s, 1H), 7.84-7.96 (m, 2H), 7.71 (d, 1H), 7.42 (d, 1H), 6.43 (d, 1H), 4.54 (d, 2H), 4.30-4.38 (m, 1H), 4.09 (dd, 2H), 3.67 (dd, 2H), 3.31 (s, 3H), 2.45 (s, 3H), 1.44 (s, 9H).

Example 9. 5-(tert-butyl)-N-(2-methyl-4-(6-(1-methyl-1H-pyrazol-3-yl)pyrrolo[2,1-f][1,2,4]triazin-4-yl)benzyl)-1,2,4-oxadiazole-3-carboxamide trifluoroacetate

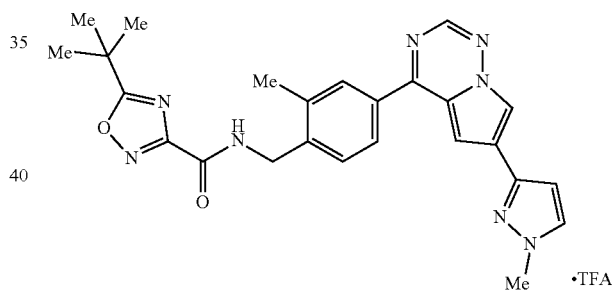

1. Synthesis of tert-butyl (2-methyl-4-(6-(1-methyl-1H-pyrazol-3-yl)pyrrolo[2,1-f][1,2,4]triazin-4-yl)benzyl)carbamate

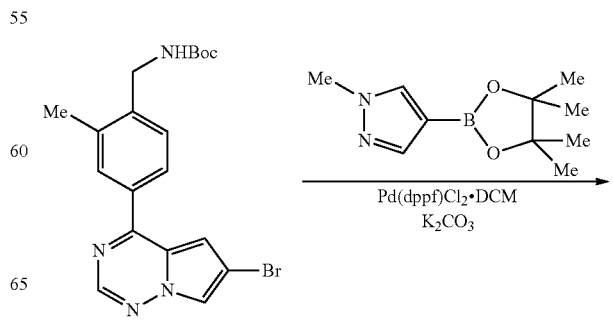

3. Synthesis of 5-(tert-butyl)-N-(2-methyl-4-(6-(1-methyl-1H-pyrazol-3-yl)pyrrolo[2,1-f][1,2,4]triazin-4-yl)benzyl)-1,2,4-oxadiazole-3-carboxamide trifluoroacetate

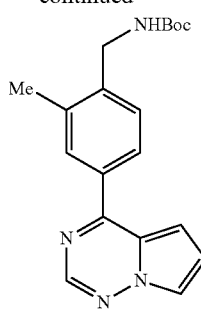

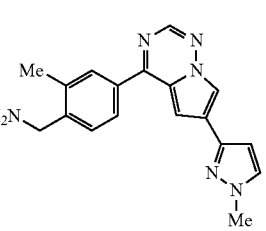 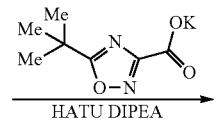

N₂ was bubbled for 5 min through a mixture of tert-butyl (4-(6-bromopyrrolo[2,1-f][1,2,4]triazin-4-yl)-2-methylbenzyl)carbamate (500 mg, 1.2 mmol), 1-methyl-4-(4,4,5,5-tetramethyl-1,3,2-dioxaborolan-2-yl)pyrazole (499 mg, 2.4 mmol), Pd(dppf)Cl₂·DCM (98 mg, 0.12 mmol) and K₂CO₃ (498 mg, 3.6 mmol) in dioxane (8 mL) and H₂O (4 mL). The reaction mixture was then heated to 100° C. overnight. The reaction was concentrated in vacuo and the crude purified by silica gel column chromatography (0-100% EtOAc:Hept) to afford the title compound as a yellow solid (461 mg, 92%). LCMS m z=419.3 [M+H]⁺.

2. Synthesis of (2-methyl-4-(6-(1-methyl-1H-pyrazol-3-yl)pyrrolo[2,1-f][1,2,4]triazin-4-yl)phenyl)methanamine hydrochloride

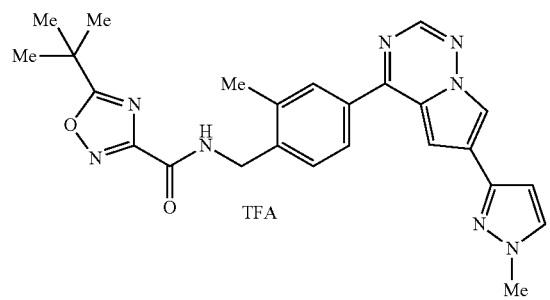

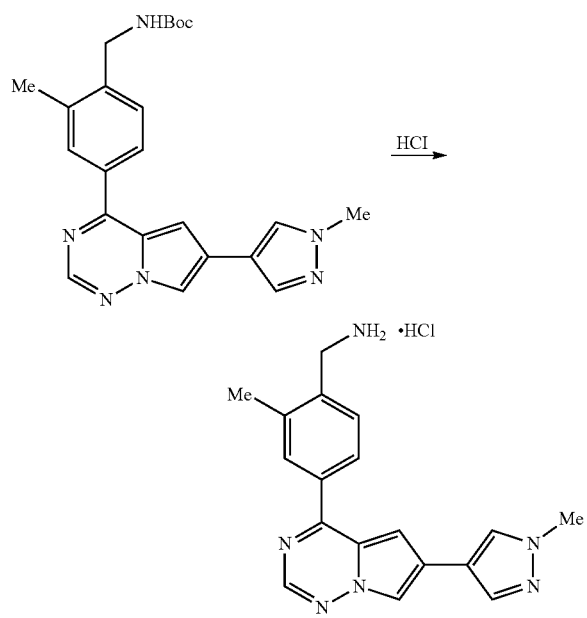

tert-Butyl (2-methyl-4-(6-(1-methyl-1H-pyrazol-3-yl)pyrrolo[2,1-f][1,2,4]triazin-4-yl)benzyl)carbamate (460 mg, 1.1 mmol) was dissolved in an HCl solution (8.8 mL, 1.25 M in MeOH) and the reaction was stirred overnight at 50° C. The reaction mixture was concentrated in vacuo to afford the title compound as a yellow solid (445 mg, crude) which was used without further purification. LCMS m/z=319.2 [M+H]⁺

The compound was obtained from (2-methyl-4-(6-(1-methyl-1H-pyrazol-3-yl)pyrrolo[2,1-f][1,2,4]triazin-4-yl)phenyl)methanamine hydrochloride and potassium 5-tert-butyl-1,2,4-oxadiazole-3-carboxylate following the procedure described in Example 4, Step 4. The crude product was purified by silica gel column chromatography (0-100% EtOAc/Hept), followed by prep-HPLC (Method B; 10-90%) to afford the title compound as a yellow solid (30 mg, 32%). LCMS m/z=471.3 [M+H]⁺; ¹H NMR (400 MHz, DMSO-d₆) δ: 9.52 (t, 1H), 8.60 (s, 1H), 8.46 (d, 1H), 7.94-8.02 (m, 2H), 7.74 (d, 1H), 7.48 (d, 1H), 7.42 (d, 1H), 6.77 (d, 1H), 4.56 (d, 2H), 3.89 (s, 3H), 2.48 (s, 3H), 1.44 (s, 9H).

Example 10. 5-(tert-butyl)-N-(4-(6-(1-(2,2-difluoroethyl)-1H-pyrazol-4-yl)pyrrolo[2,1-f][1,2,4]triazin-4-yl)-2-methylbenzyl)-1,2,4-oxadiazole-3-carboxamide trifluoroacetate

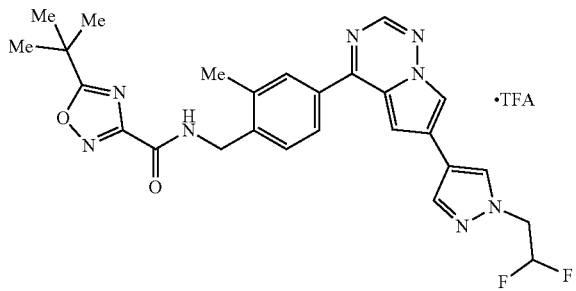 [SMILES: Cc1cc(-c2ncnn3cc(-c4cnn(CC(F)F)c4)cc23)ccc1CNC(=O)c1noc(C(C)(C)C)n1]

1. Synthesis of tert-butyl (4-(6-(1-(2,2-difluoroethyl)-1H-pyrazol-4-yl)pyrrolo[2,1-f][1,2,4]triazin-4-yl)-2-methylbenzyl)carbamate

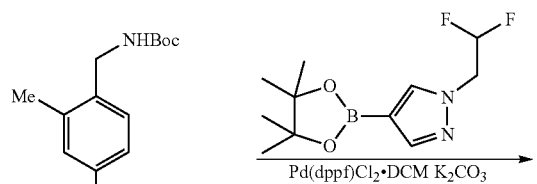

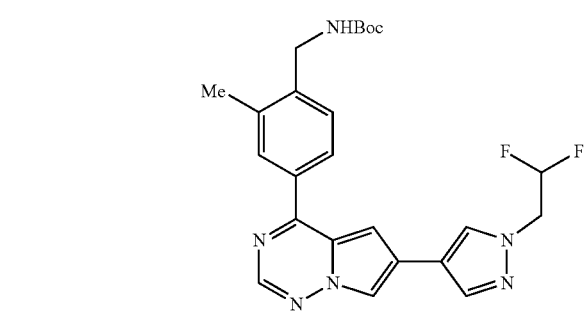

N₂ was bubbled for 5 min through a mixture of tert-butyl (4-(6-bromopyrrolo[2,1-f][1,2,4]triazin-4-yl)-2-methylbenzyl)carbamate (100 mg, 0.2 mmol), 1-(2,2-difluoroethyl)-1H-pyrazole-4-boronic acid pinacol ester (124 mg, 0.5 mmol), Pd(dppf)Cl₂·DCM (20 mg, 0.02 mmol) and K₂CO₃ (99 mg, 0.5 mmol) in dioxane (1.6 mL) and H₂O (0.8 mL). The reaction mixture was heated to 100° C. and was stirred at that temperature overnight. The cooled reaction was concentrated in vacuo and purified by silica gel column chromatography (0-100% EtOAc:Hept) to afford the title compound as a yellow solid (92 mg, 82%). LCMS m z=469.2 [M+H]⁺.

2. Synthesis of (4-(6-(1-(2,2-difluoroethyl)-1H-pyrazol-4-yl)pyrrolo[2,1-f][1,2,4]triazin-4-yl)-2-methylphenyl)methanamine hydrochloride

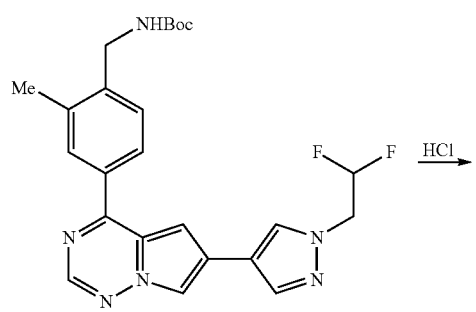

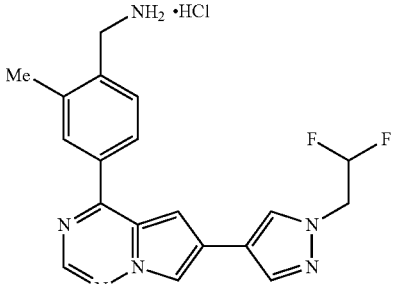

tert-Butyl (4-(6-(1-(2,2-difluoroethyl)-1H-pyrazol-4-yl)pyrrolo[2,1-f][1,2,4]triazin-4-yl)-2-methylbenzyl)carbamate (93 mg, 0.2 mmol) was dissolved in an HCl solution (1.5 mL, 1.25 M in MeOH) and the reaction was stirred overnight at 50° C. The reaction mixture was concentrated in vacuo to afford the title compound as a yellow solid (80 mg, 92% yield) which was used without further purification. LCMS m/z=369.2 [M+H]⁺.

3. Synthesis of 5-(tert-butyl)-N-(4-(6-(1-(2,2-difluoroethyl)-1H-pyrazol-4-yl)pyrrolo[2,1-f][1,2,4]triazin-4-yl)-2-methylbenzyl)-1,2,4-oxadiazole-3-carboxamide trifluoroacetate

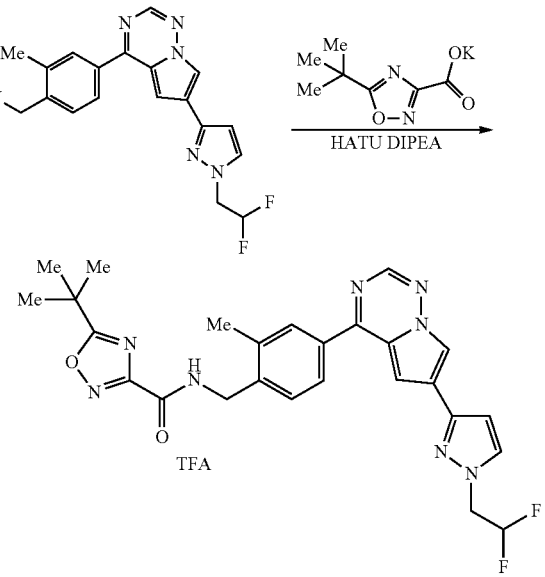

The compound was obtained from (4-(6-(1-(2,2-difluoroethyl)-1H-pyrazol-4-yl)pyrrolo[2,1-f][1,2,4]triazin-4-yl)-2-methylphenyl)methanamine hydrochloride and potassium 5-tert-butyl-1,2,4-oxadiazole-3-carboxylate following the procedure described in Example 4, Step 4. The crude product was purified by silica gel column chromatography (0-100% EtOAc/Hept), followed by prep-HPLC (Method B; 10-90%) to afford the title compound as a yellow solid (23 mg, 32%). LCMS m/z=521.2 [M+H]⁺; ¹H NMR (400 MHz, DMSO-d₆) δ: 9.53 (t, 1H), 8.57 (s, 1H), 8.51 (d, 1H), 8.30 (s, 1H), 8.08 (d, 1H), 7.94-8.03 (m, 2H), 7.39-7.52 (m, 2H), 6.18-6.59 (m, 1H), 4.65 (td, 2H), 4.56 (d, 2H), 2.48 (s, 3H), 1.44 (s, 9H).

Example 11. 5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide trifluoroacetate

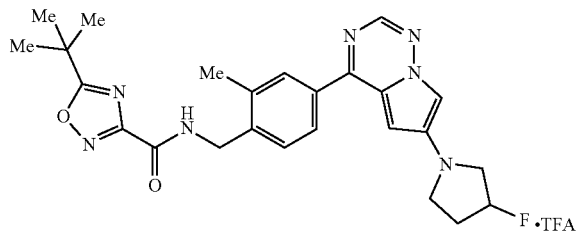 [SMILES: Cc1cc(-c2ncnn3cc(N4CCC(F)C4)cc23)ccc1CNC(=O)c1noc(C(C)(C)C)n1]

1. Synthesis of tert-butyl (4-(6-(3-fluoropyrrolidin-1-yl)pyrrolo[2,1-f][1,2,4]triazin-4-yl)-2-methylbenzyl)carbamate

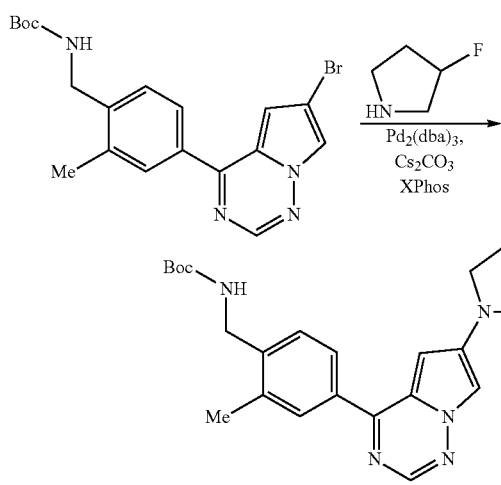

The title compound was obtained as a yellow solid, from tert-butyl (4-(6-bromopyrrolo[2,1-f][1,2,4]triazin-4-yl)-2-methylbenzyl)carbamate and 3-fluoropyrrolidine following the procedure described in Example 2, Step 1. (78 mg, 38% yield). LCMS m/z=426.2 [M+H]$^+$

2. Synthesis of (4-(6-(3-fluoropyrrolidin-1-yl)pyrrolo[2,1-f][1,2,4]triazin-4-yl)-2-methylphenyl)methanamine hydrochloride

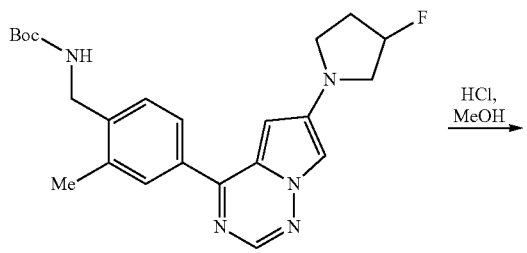

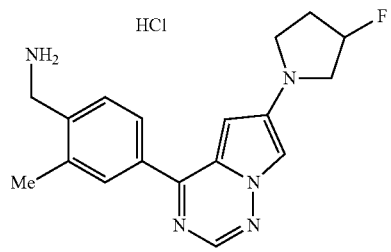

To a solution of tert-butyl (4-(6-(3-fluoropyrrolidin-1-yl)pyrrolo[2,1-f][1,2,4]triazin-4-yl)-2-methylbenzyl)carbamate (78 mg, 0.2 mmol) in MeOH (1.8 mL) was added an HCl solution (1.5 mL, 1.25 M in MeOH). The reaction was heated to 50° C. and was stirred at that temperature overnight. The cooled reaction was concentrated in vacuo to afford the title compound as a red solid (66 mg, crude), which was carried forward without further purification. LCMS m/z=326.1 [M+H]$^+$

3. Synthesis of 5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide trifluoroacetate

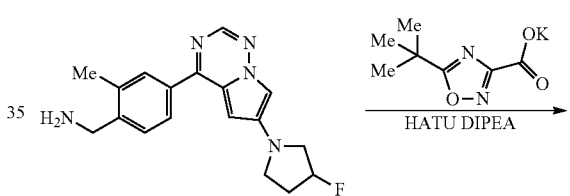

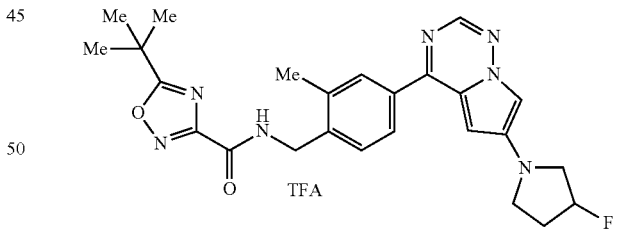

The compound was obtained from (4-(6-(3-fluoropyrrolidin-1-yl)pyrrolo[2,1-f][1,2,4]triazin-4-yl)-2-methylphenyl)methanamine hydrochloride and potassium 5-tert-butyl-1,2,4-oxadiazole-3-carboxylate following the procedure described in Example 4, Step 4. The residue was purified by prep-HPLC (Method B, 5-60%) to afford the title compound as a red solid (81 mg, 67%). LCMS m/z=478.2 [M+H]$^+$; $^1$H NMR (500 MHz, DMSO-d$_6$) δ: 9.45-9.60 (m, 1H), 8.44-8.54 (m, 1H), 7.87-7.98 (m, 2H), 7.44 (d, 1H), 6.51 (s, 1H), 5.38-5.56 (m, 1H), 4.55 (d, 2H), 3.40-3.70 (m, 4H), 2.46 (s, 2H), 2.16-2.33 (m, 2H), 1.44 (s, 9H)

Example 12. 5-(tert-butyl)-N-(4-(6-(3,3-difluoropyrrolidin-1-yl)pyrrolo[2,1-f][1,2,4]triazin-4-yl)-2-methylbenzyl)-1,2,4-oxadiazole-3-carboxamide trifluoroacetate

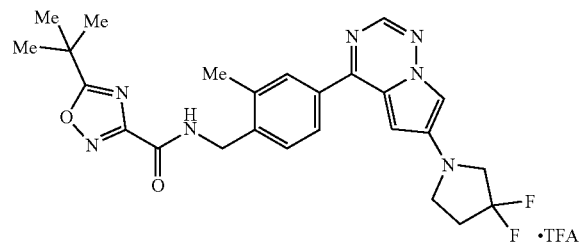 [SMILES: Cc1cc(-c2ncnn3cc(N4CCC(F)(F)C4)cc23)ccc1CNC(=O)c1noc(C(C)(C)C)n1]

1. Synthesis of tert-butyl (4-(6-(3,3-difluoropyrrolidin-1-yl)pyrrolo[2,1-f][1,2,4]triazin-4-yl)-2-methylbenzyl)carbamate

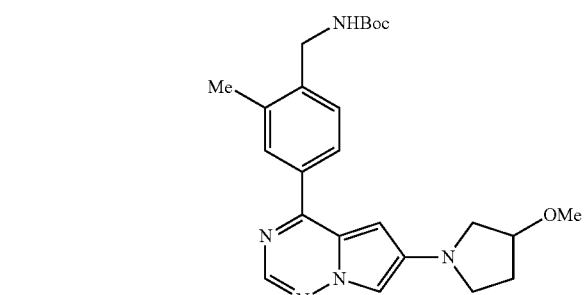

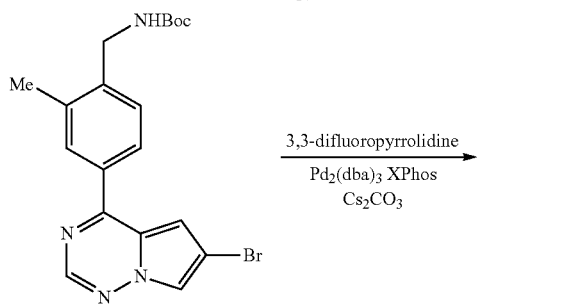

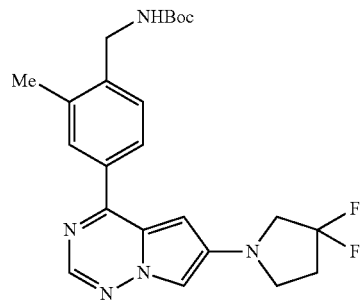

The title compound was obtained as a yellow solid from tert-butyl (4-(6-bromopyrrolo[2,1-f][1,2,4]triazin-4-yl)-2-methylbenzyl)carbamate and 3,3-difluoropyrrolidine, following the procedure described in Example 11, Step 1. (88 mg, 41%). LCMS m/z=444.2 [M+H]$^+$ 2. Synthesis of (4-(6-(3,3-difluoropyrrolidin-1-yl)pyrrolo[2,1-f][1,2,4]triazin-4-yl)-2-methylphenyl)methanamine hydrochloride

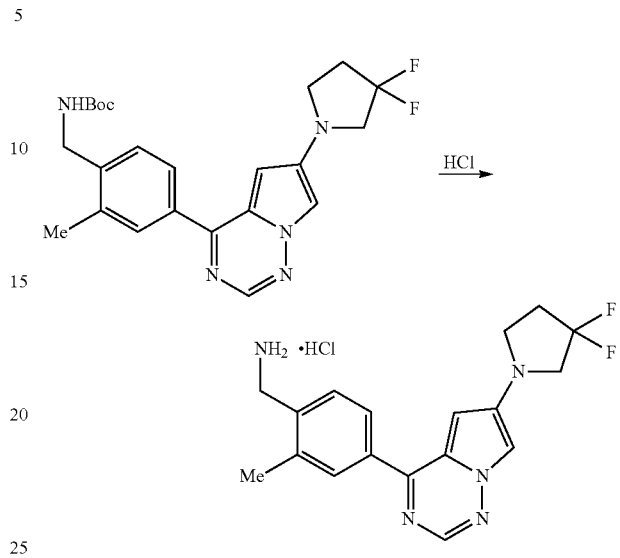

tert-Butyl (4-(6-(3,3-difluoropyrrolidin-1-yl)pyrrolo[2,1-f][1,2,4]triazin-4-yl)-2-methylbenzyl)carbamate (93 mg, 0.2 mmol) was dissolved in an HCl solution (1.5 mL, 1.25 M in MeOH) and the reaction was heated to 50° C. and stirred at that temperature overnight. The reaction mixture was concentrated in vacuo to afford the title compound as a red solid (85 mg, crude) which was used without further purification. LCMS m/z=344.2 [M+H]$^+$ 3. Synthesis of 5-(tert-butyl)-N-(4-(6-(3,3-difluoropyrrolidin-1-yl)pyrrolo[2,1-f][1,2,4]triazin-4-yl)-2-methylbenzyl)-1,2,4-oxadiazole-3-carboxamide trifluoroacetate

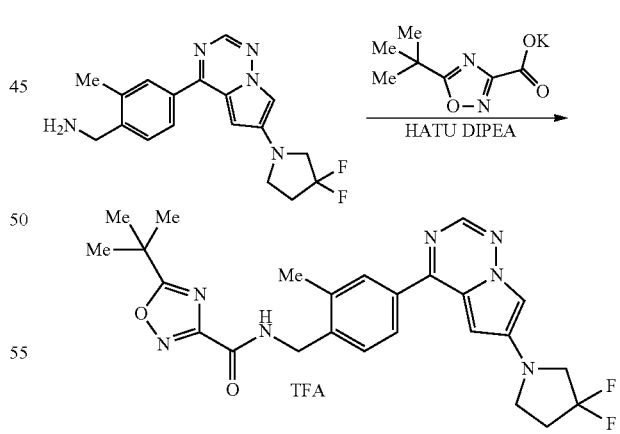

The compound was obtained from (4-(6-(3,3-difluoropyrrolidin-1-yl)pyrrolo[2,1-f][1,2,4]triazin-4-yl)-2-methylphenyl)methanamine hydrochloride and potassium 5-tert-butyl-1,2,4-oxadiazole-3-carboxylate following the procedure described in Example 4, Step 4. The crude product was purified by prep-HPLC (Method B, 5-65%) to afford the title compound as a red solid (32.5 mg, 48%). LCMS m/z=496.0 [M+H]$^+$; $^1$H NMR (400 MHz, DMSO-d$_6$) δ: 9.52

(t, 1H), 8.50 (s, 1H), 7.91-7.96 (m, 2H), 7.44 (d, 1H), 6.60 (d, 1H), 4.55 (d, 2H), 3.72 (t, 2H), 3.51 (t, 1H), 2.51-2.60 (m, 2H), 2.46 (s, 3H), 2.08 (s, 1H), 1.44 (s, 9H).

Example 13. 3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide

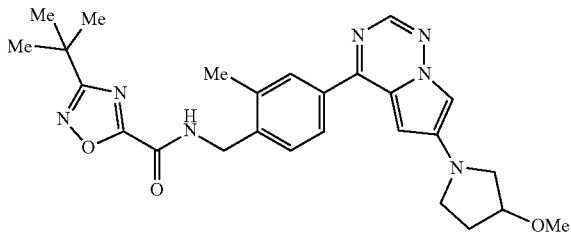 [SMILES: COC1CCN(c2cc3c(-c4ccc(CNC(=O)c5nc(C(C)(C)C)no5)c(C)c4)ncnn3c2)C1]

1. Synthesis of tert-butyl (4-(6-(3-methoxypyrrolidin-1-yl)pyrrolo[2,1-f][1,2,4]triazin-4-yl)-2-methylbenzyl)carbamate

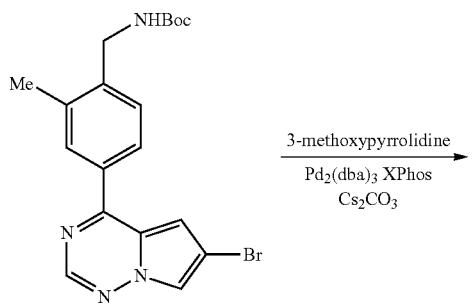

The title compound was obtained from tert-butyl (4-(6-bromopyrrolo[2,1-f][1,2,4]triazin-4-yl)-2-methylbenzyl)carbamate and 3-methoxypyrrolidine, following the procedure described in Example 2, Step 1 (47 mg, 22%). LCMS m/z=438.3 [M+H]⁺

2. Synthesis of 4-(6-(3-methoxypyrrolidin-1-yl)pyrrolo[2,1-f][1,2,4]triazin-4-yl)-2-methylphenyl)methanamine hydrochloride

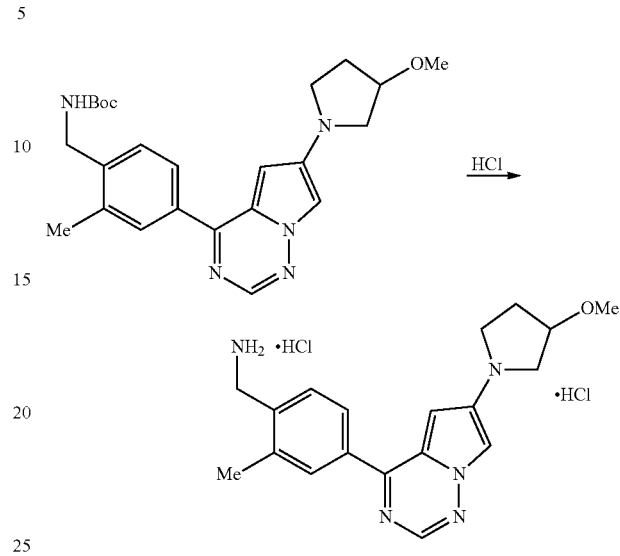

HCl (4 M, 0.1 mL) was added to tert-butyl (4-(6-(3-methoxypyrrolidin-1-yl)pyrrolo[2,1-f][1,2,4]triazin-4-yl)-2-methylbenzyl)carbamate (47 mg, 0.1 mmol) in MeOH (2 mL) and the mixture was stirred at RT for 16 h. The reaction was concentrated in vacuo to afford the title compound (43 mg, crude) which was used in the next step without additional purification.

3. Synthesis of 3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide

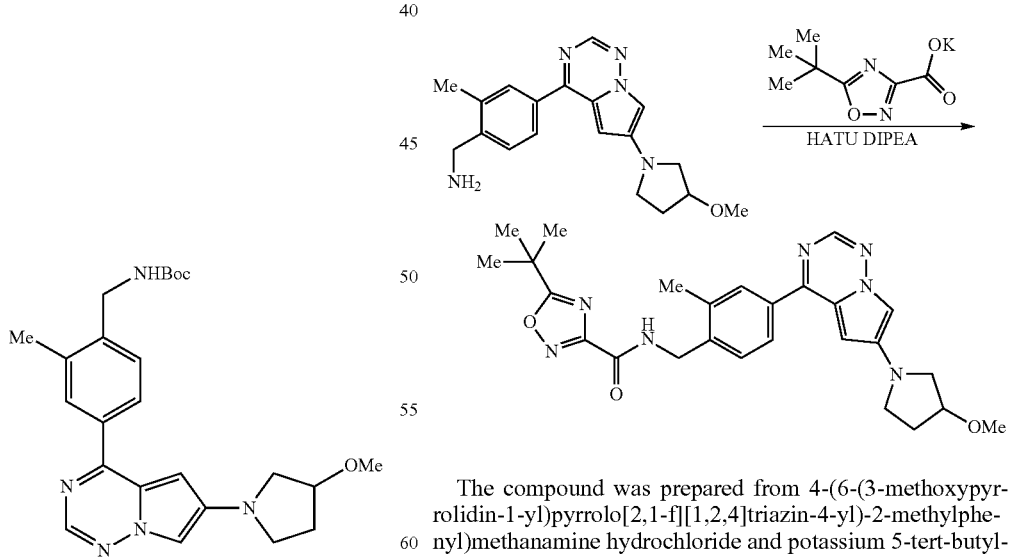

The compound was prepared from 4-(6-(3-methoxypyrrolidin-1-yl)pyrrolo[2,1-f][1,2,4]triazin-4-yl)-2-methylphenyl)methanamine hydrochloride and potassium 5-tert-butyl-1,2,4-oxadiazole-3-carboxylate following the procedure described in Example 4, Step 4. The residue was purified by prep-HPLC (Method B, 5-60%) to afford the title compound as a red solid (81 mg, 67%). LCMS m/z=478.2 [M+H]⁺; ¹H NMR (400 MHz, MeOH-d₄) δ: 8.25-8.34 (m, 1H), 7.80-7.90 (m, 2H), 7.60-7.66 (m, 1H), 7.48-7.54 (m, 1H), 6.32-6.39 (m, 1H), 4.65-4.74 (m, 2H), 4.12-4.21 (m, 1H), 3.48 (dd, 1H), 3.37-3.39 (m, 3H), 3.34-3.36 (m, 1H), 3.31 (m, 2H), 2.52 (s, 3H), 2.13-2.22 (m, 2H), 1.48-1.52 (m, 9H).

Example 14. 3-(tert-butyl)-N-(2-chloro-3-fluoro-4-(6-morpholinopyrrolo[2,1-f][1,2,4]triazin-4-yl)benzyl)-1,2,4-oxadiazole-5-carboxamide trifluoroacetate

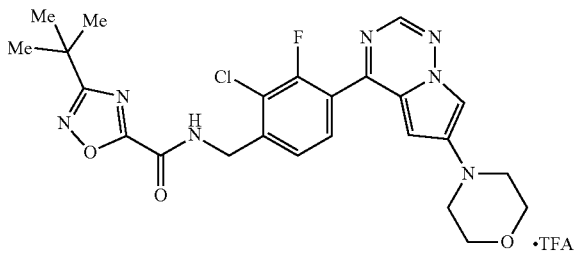 [SMILES: CC(C)(C)c1noc(C(=O)NCc2ccc(-c3ncnn4cc(N5CCOCC5)cc34)c(F)c2Cl)n1]

1. Synthesis of 2-chloro-3-fluoro-4-iodobenzonitrile

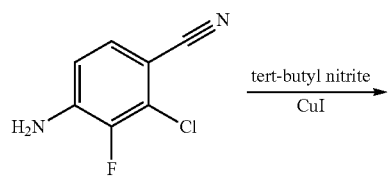

tert-Butyl nitrite (70 mL, 526 mmol) was added to a mixture of CuI (100 g, 526 mmol) in MeCN (455 mL) and the brown suspension was heated to 65-66° C. (internal). A solution of 4-amino-2-chloro-3-fluorobenzonitrile (44.8 g, 263 mmol) in MeCN (385 mL) was added dropwise over 50 min, the dropping funnel was washed with MeCN (400 mL), and the reaction was stirred at 65° C. for 18 h. The cooled mixture was filtered through Celite®, washing through with MeCN. The filtrate was concentrated in vacuo, the resulting black solid was suspended in DCM and a small amount of MeCN, and filtered through silica gel, grading from 0% to 33% EtOAc/Hept to give the title compound as a grey/brown solid (44.6 g, 60%). ¹H NMR (300 MHz, CDCl₃) δ: 7.80 (dd, 1H), 7.23 (dd, 1H).

2. Synthesis of (2-chloro-3-fluoro-4-iodophenyl)methanamine hydrochloride

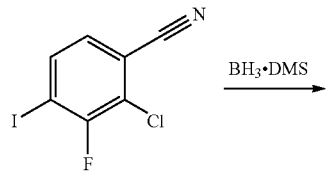

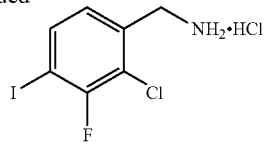

A solution of BH₃·Me₂S in THF (119 mL, 238 mmol, 2 M) was added over 5 min to a solution of 2-chloro-3-fluoro-4-iodobenzonitrile (44.6 g, 159 mmol) in THF (350 mL) and the reaction was stirred at 65° C. for 4 h. The reaction was quenched with MeOH (50 mL), allowed to cool to RT, and concentrated in vacuo. The residue was suspended in DCM (250 mL), the mixture acidified with conc. HCl solution (37%, 100 mL), and the suspension was filtered off and washed with DCM and TBME. The solids were dried in vacuo, the mother liquor was concentrated in vacuo, and the residue was re-suspended in DCM. The solids were filtered off and washed with DCM and TBME to give a second crop of title compound as a light-yellow solid (total: 39.2 g, 77%). ¹H NMR (300 MHz, DMSO-d₆) δ: 8.63 (br s, 3H), 7.89 (dd, 1H), 7.26 (dd, 1H), 4.10 (s, 2H).

3. Synthesis of tert-butyl (2-chloro-3-fluoro-4-iodobenzyl)carbamate

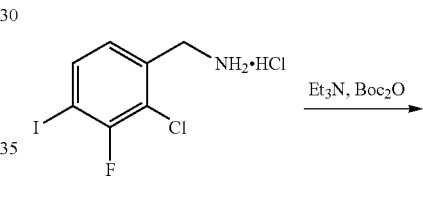

Et₃N (78.9 mL, 566 mmol), followed by Boc₂O (32 mL, 136 mmol), were added to a suspension of (2-chloro-3-fluoro-4-iodophenyl)methanamine hydrochloride (36.5 g, 113 mmol) in DCM (350 mL) and the reaction was stirred at RT for 72 h. H₂O (100 mL) was added and the layers were separated. The organic layer was washed with brine (200 mL) and saturated aqueous NaHCO₃ (200 mL). The organic layer was filtered through a glass filter (P4) and washed sequentially with water (2×100 mL) and brine (2×100 mL). The organic phase was dried (Na₂SO₄), filtered, and concentrated in vacuo to give a dark-brown oil. The oil was suspended in TBME and the precipitate was filtered off and washed with TBME. The filtrate was concentrated in vacuo to give the product as a dark-brown solid (35.1 g, 80%). ¹H NMR (300 MHz, CDCl₃) δ: 7.60 (dd, 1H), 6.96 (dd, 1H), 4.35 (s, 2H), 1.44 (s, 9H).

4. Synthesis of tert-butyl (2-chloro-3-fluoro-4-(4,4,5,5-tetramethyl-1,3,2-dioxaborolan-2-yl)benzyl) carbamate

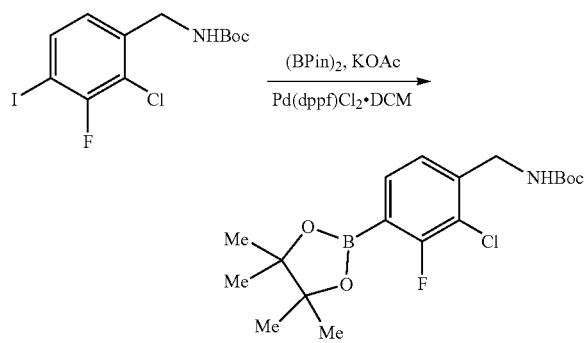

(Bispinacolato)diboron (27.7 g, 109 mmol) and KOAc (17.9 g, 182 mmol) were added to tert-butyl (2-chloro-3-fluoro-4-iodobenzyl)carbamate (35.1 g, 91.1 mmol) and the mixture was purged with $N_2$ for 5 mins. Pd(dppf)Cl$_2$·DCM (7.44 g, 9.11 mmol) was added and the red suspension was stirred at 80° C. for 44 h. The mixture was cooled to RT and additional (bispinacolato)diboron (13.7 g, 53.8 mmol), KOAc (17.9 g, 182 mmol) and Pd(dppf)Cl$_2$·DCM (7.44 g, 9.11 mmol) were added. The mixture was stirred at 80° C. for a further 18 h. The cooled mixture was poured into $H_2O$ (1 L) and the suspension stirred for 30 min at RT. The mixture was extracted with DCM (500 mL+2×250 mL), the combined organic layers were washed with brine (500 mL), then filtered through Celite® and concentrated in vacuo. The solid was azeotroped with toluene (3×) and heptane (3×) and the residue suspended in heptane and stirred for 1.5 h. The solids were filtered off, washed with heptane, and dried to afford the title compound as a yellow solid (47.6 g, crude). $^1$H NMR (300 MHz, CDCl$_3$) δ: 7.58 (dd, 1H), 7.17 (d, 1H), 5.00 (br s, 1H), 4.41 (d, 2H), 1.44 (s, 9H), 1.35 (s, 12H).

5. Synthesis of tert-butyl (4-(6-bromopyrrolo[2,1-f][1,2,4]triazin-4-yl)-2-chloro-3-fluorobenzyl)carbamate

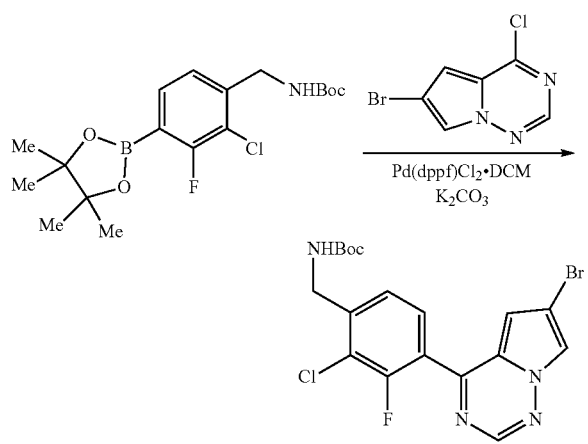

A mixture of tert-butyl (2-chloro-3-fluoro-4-(4,4,5,5-tetramethyl-1,3,2-dioxaborolan-2-yl)benzyl)carbamate (2.26 g, 5.9 mmol), K$_2$CO$_3$ (2.43 g, 17.6 mmol), 6-bromo-4-chloro-pyrrolo[2,1-f][1,2,4]triazine (2.72 g, 11.7 mmol) and Pd(dppf)Cl$_2$·DCM (479 mg, 0.59 mmol) in dioxane (24 mL) and water (8 mL) was purged with $N_2$ and the reaction was stirred at 100° C. for 18 h. The cooled mixture was diluted with EtOAc and filtered, washing through with EtOAc.

The filtrate was concentrated in vacuo and the residue was purified by silica gel column chromatography (EtOAc/Hept=5:1). The product was recrystallized from EtOAc/Hept (2:1) to afford the title compound as a yellow solid (1.9 g, 64%). LCMS m/z=457.1 [M+H]$^+$

6. Synthesis of tert-butyl (2-chloro-3-fluoro-4-(6-morpholinopyrrolo[2,1-f][1,2,4]triazin-4-yl)benzyl) carbamate

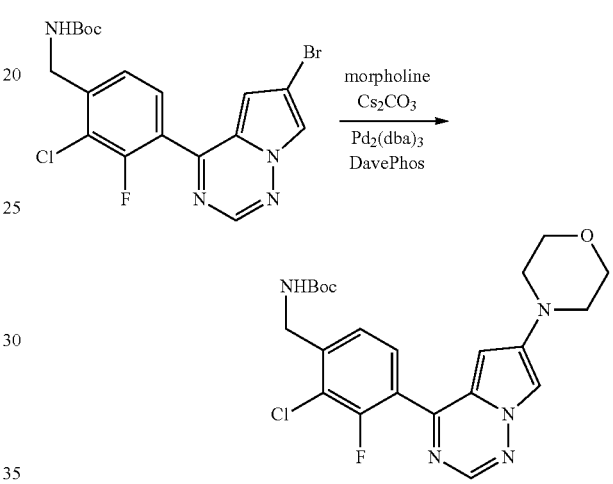

t-Amyl alcohol (2 mL), followed by morpholine (29 mg, 0.3 mmol) were added to a mixture of tert-butyl (4-(6-bromopyrrolo[2,1-f][1,2,4]triazin-4-yl)-2-chloro-3-fluorobenzyl)carbamate (100 mg, 0.2 mmol), Cs$_2$CO$_3$ (143 mg, 0.4 mmol), Pd$_2$(dba)$_3$ (20 mg, 0.02 mmol), and DavePhos (17 mg, 0.04 mmol) and the reaction was purged with $N_2$. The reaction was stirred at RT for 5 mins and then was stirred at 100° C. for 18 h. The cooled mixture was diluted with EtOAc and filtered. The filtrate was concentrated in vacuo and the crude purified by silica gel column chromatography (EtOAc/Hept=1:2) to afford the title compound as a yellow-orange semi-solid (43 mg, 34%). LCMS m/z=462.3 [M+H]$^+$

7. Synthesis of (2-chloro-3-fluoro-4-(6-morpholinopyrrolo[2,1-f][1,2,4]triazin-4-yl)phenyl)methanamine

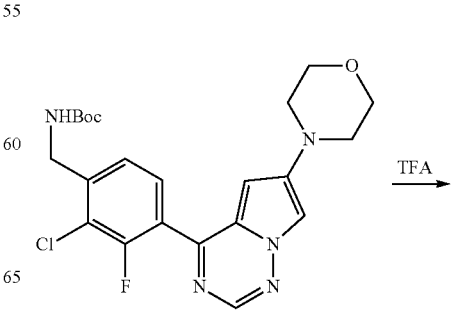

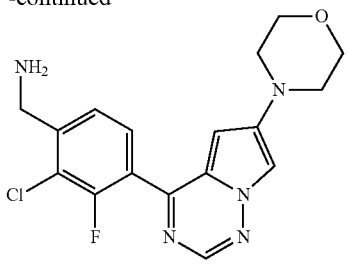

TFA (114 mg, 0.7 mmol) was added to a solution of tert-butyl (2-chloro-3-fluoro-4-(6-morpholinopyrrolo[2,1-f][1,2,4]triazin-4-yl)benzyl)carbamate (43 mg, 0.07 mmol) in DCM (2 mL) and the reaction was stirred at RT for 18 h. The reaction was concentrated in vacuo, the residue dissolved in MeOH, and passed through an SCX ion exchange column flushing through with MeOH followed by 2M methanolic NH$_3$. The combined organic phases were concentrated in vacuo to afford the title compound as an orange gum (22 mg, 59%). LCMS m/z=362.0 [M+H]$^+$ 8. Synthesis of 3-(tert-butyl)-N-(2-chloro-3-fluoro-4-(6-morpholinopyrrolo[2,1-f][1,2,4]triazin-4-yl)benzyl)-1,2,4-oxadiazole-5-carboxamide trifluoroacetate

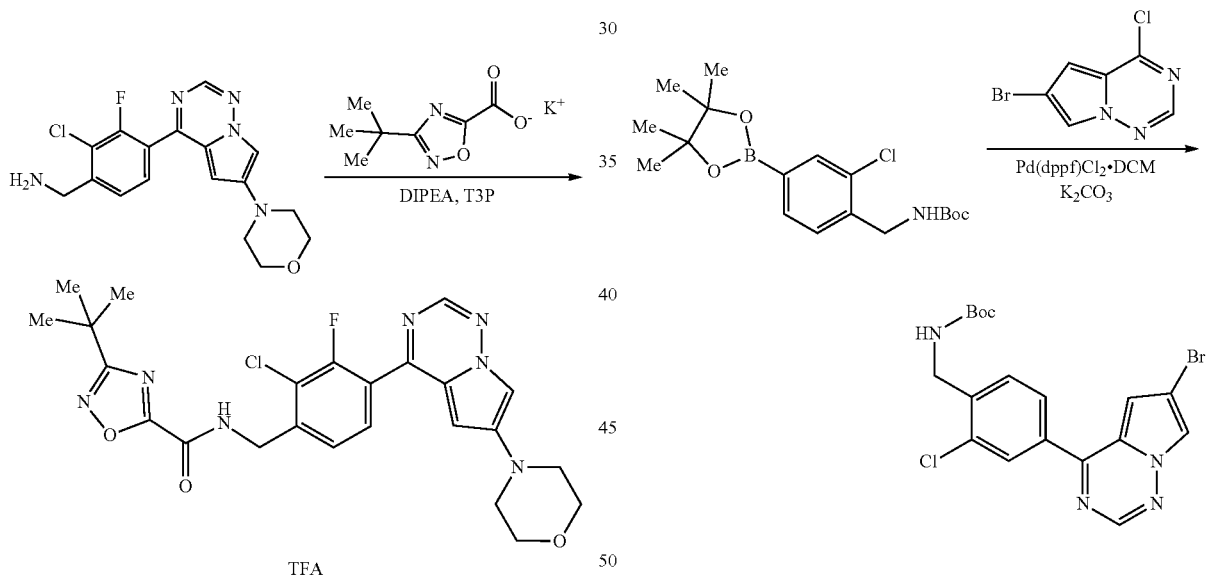

DIPEA (70 mg, 0.54 mmol) was added to a mixture of (2-chloro-3-fluoro-4-(6-morpholinopyrrolo[2,1-f][1,2,4]triazin-4-yl)phenyl)methanamine (65 mg, 0.18 mmol), potassium 3-(tert-butyl)-1,2,4-oxadiazole-5-carboxylate (150 mg, 0.72 mmol) in DMF (1 mL) and cooled in an ice-water bath and stirred for 5 min. T3P® (343 mg, 0.54 mmol, 50% solution in DMF) was added dropwise and stirring continued in the ice-water bath for 30 minutes. The reaction was warmed to RT and was stirred overnight. The reaction mixture was diluted with EtOAc and washed (NaHCO$_3$). The aqueous phase was back-extracted with EtOAc and the combined organics were dried (Na$_2$SO$_4$) and concentrated in vacuo. The residue was purified by prep-HPLC (Method B, 10-95%) to afford the title compound as a red solid (7.1 mg, 6%). LCMS m/z=514.3 [M+H]$^+$. $^1$H NMR (500 MHz, CDCl$_3$) δ: 8.56 (s, 1H), 7.78 (d, 1H), 7.68 (dd, 1H), 7.64-7.58 (m, 1H), 7.47 (d, 1H), 6.30 (t, 1H), 4.86 (d, 2H), 3.91-3.87 (m, 4H), 3.23-3.20 (m, 4H), 1.42 (s, 9H).

Example 15. 5-(tert-butyl)-N-(2-chloro-4-(6-morpholinopyrrolo[2,1-f][1,2,4]triazin-4-yl)benzyl)-1,2,4-oxadiazole-3-carboxamide trifluoroacetate

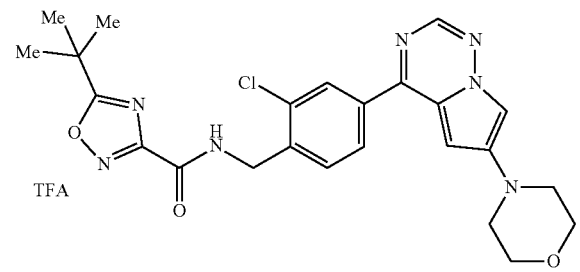 [SMILES: CC(C)(C)c1nc(C(=O)NCc2ccc(-c3ncnn4cc(N5CCOCC5)cc34)cc2Cl)no1]

1. Synthesis of tert-butyl (4-(6-bromopyrrolo[2,1-f][1,2,4]triazin-4-yl)-2-chlorobenzyl)carbamate A mixture of tert-butyl (2-chloro-4-(4,4,5,5-tetramethyl-1,3,2-dioxaborolan-2-yl)benzyl)carbamate (2.0 g, 5.4 mmol), 6-bromo-4-chloro-pyrrolo[2,1-f][1,2,4]triazine (1.9 g, 8.2 mmol) and K$_2$CO$_3$ (2.3 g, 16.3 mmol) were suspended in dioxane (20 mL) and H$_2$O (2 mL) and N$_2$ was bubbled through the mixture for 5 min. Pd(dppf)Cl$_2$·DCM (398 mg, 0.54 mmol) was added and the reaction was stirred at 100° C. for 2 h. The cooled reaction was diluted with EtOAc and washed with H$_2$O and brine. The aqueous layer was extracted with EtOAc and the combined organic extracts were dried (MgSO$_4$), filtered, and concentrated in vacuo. The residue was purified by silica gel column chromatography (0-40% EtOAc/Hept) and the product was recrystallized from hexane/EtOAc (2:1) to afford the title compound as an ochre-colored solid (1.3 g, 55% yield). LCMS m/z=437.0 [M+H]$^+$

2. Synthesis of tert-butyl (2-chloro-4-(6-morpholinopyrrolo[2,1-f][1,2,4]triazin-4-yl)benzyl)carbamate

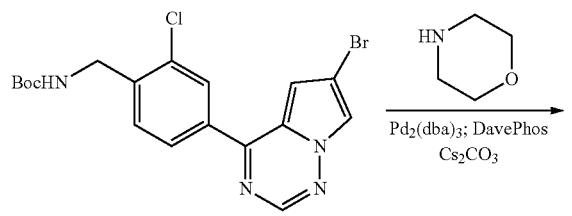

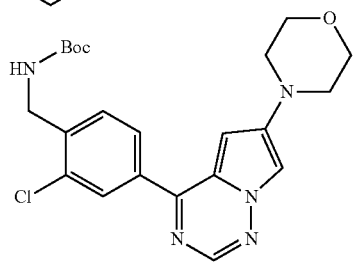

A mixture of tert-butyl (4-(6-bromopyrrolo[2,1-f][1,2,4]triazin-4-yl)-2-chlorobenzyl)carbamate (1.3 g, 3.0 mmol), morpholine (388 mg, 4.5 mmol) and $Cs_2CO_3$ (1.9 g, 5.9 mmol) in dry dioxane (15 mL) was purged with $N_2$ for 5 min. DavePhos (175 mg, 0.45 mmol) and $Pd_2(dba)_3$ (272 mg, 0.30 mmol) were added and the reaction was heated to 90° C. for 17 h. The cooled mixture was diluted with EtOAc and washed with water and brine. The aqueous layer was extracted with EtOAc and the combined organic layers were dried ($MgSO_4$), filtered, and concentrated in vacuo. The residue was purified by silica gel column chromatography (0-40% EtOAc/Hept) to afford the title compound as an orange solid (407 mg, 31% yield). LCMS m/z=444.2 [M+H]+

3. Synthesis of (2-chloro-4-(6-morpholinopyrrolo[2,1-f][1,2,4]triazin-4-yl)phenyl)methanamine hydrochloride

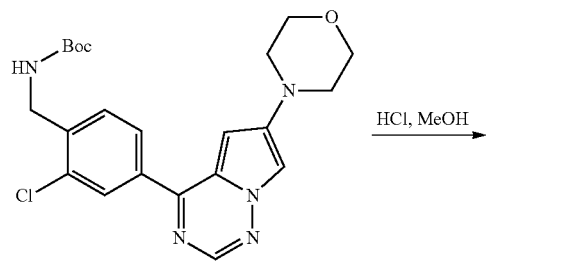

HCl (4 M, 0.5 mL) was added to tert-butyl (2-chloro-4-(6-morpholinopyrrolo[2,1-f][1,2,4]triazin-4-yl)benzyl)carbamate (407 mg, 0.092 mmol) in MeOH (2 mL) and the reaction was stirred overnight at RT. The mixture was concentrated in vacuo to afford the title compound (80 mg, 32%) which was used in the next step without further purification. LCMS m/z=344.2 [M+H]+

4. Synthesis of 5-(tert-butyl)-N-(2-chloro-4-(6-morpholinopyrrolo[2,1-f][1,2,4]triazin-4-yl)benzyl)-1,2,4-oxadiazole-3-carboxamide trifluoroacetate

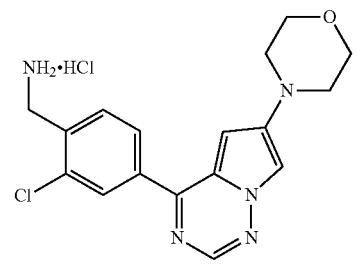

The crude product was obtained from (2-chloro-4-(6-morpholinopyrrolo[2,1-f][1,2,4]triazin-4-yl)phenyl)methanamine hydrochloride and lithium 5-(tert-butyl)-1,2,4-oxadiazole-3-carboxylate following the procedure described in Example 14, Step 8. The residue was purified by prep-HPLC (Method B; 10-90%) to afford the title compound as a yellow solid (15 mg, 15%). LCMS m/z=496.2 [M+H]+; $^1$H NMR (500 MHz, $CDCl_3$) δ: 8.48-8.42 (m, 1H), 8.09 (d, 1H), 7.96-7.90 (m, 1H), 7.64 (d, 1H), 7.59 (d, 1H), 7.57-7.47 (m, 1H), 6.45 (d, 1H), 4.84 (d, 2H), 3.93-3.86 (m, 4H), 3.22-3.13 (m, 4H), 1.50-1.46 (m, 9H).

Example 16. 5-(tert-butyl)-N-(2-methyl-4-(2-(1-methyl-1H-pyrazol-4-yl)pyrazolo[1,5-a]pyrimidin-7-yl)benzyl)-1,2,4-oxadiazole-3-carboxamide trifluoroacetate

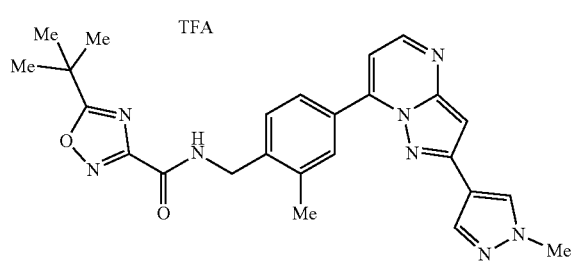 [SMILES: Cc1cc(-c2ccnc3cc(-c4cnn(C)c4)nn23)ccc1CNC(=O)c1noc(C(C)(C)C)n1]

1. Synthesis of tert-butyl tert-butyl (4-(2-bromopyrazolo[1,5-a]pyrimidin-7-yl)-2-methylbenzyl)carbamate

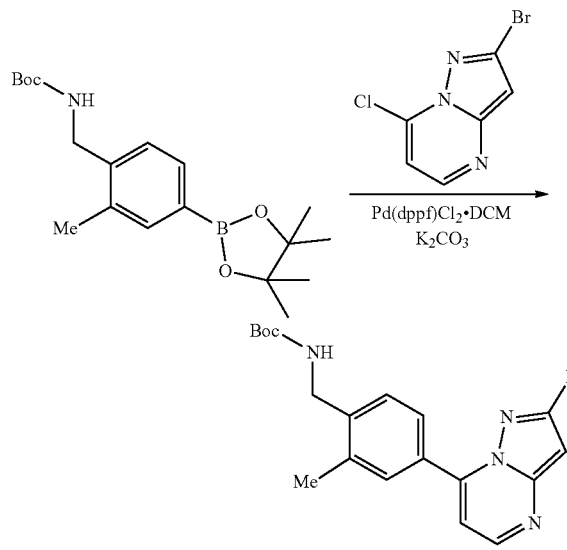

A mixture of tert-butyl (2-methyl-4-(4,4,5,5-tetramethyl-1,3,2-dioxaborolan-2-yl)benzyl)carbamate (WO 2015089327 Example 1, 630 mg, 1.8 mmol), 2-bromo-7-chloro-pyrazolo[1,5-a]pyrimidine (842 mg, 3.6 mmol) and K$_2$CO$_3$ (750 mg, 5.4 mmol) were suspended in dioxane (8 mL) and water (1 mL) and N$_2$ was bubbled through for 5 min. Pd(dppf)Cl$_2$·DCM (132 mg, 0.18 mmol) was added and the reaction was stirred at 100° C. for 2 h. The cooled mixture was diluted with EtOAc and water, filtered through Celite® and the layers separated. The aqueous layer was extracted with EtOAc, and the combined organic extracts were dried (MgSO$_4$), filtered, and concentrated in vacuo. The residue was purified by silica gel column chromatography (0-100% EtOAc/Hept) to afford the title compound as a yellow solid (750 mg, 99%). LCMS m/z=417.1 [M+H]$^+$; $^1$H NMR (500 MHz, CDCl$_3$) δ: 8.53 (d, 1H), 7.87 (dd, 1H), 7.85-7.80 (m, 1H), 7.51-7.45 (m, 1H), 6.94-6.87 (m, 1H), 6.86-6.79 (m, 1H), 4.84 (br s, 1H), 4.42 (br d, 2H), 2.49-2.42 (m, 3H), 1.53-1.48 (s, 9H).

2. Synthesis of tert-butyl (2-methyl-4-(2-(1-methyl-1H-pyrazol-4-yl)pyrazolo[1,5-a]pyrimidin-7-yl)benzyl)carbamate

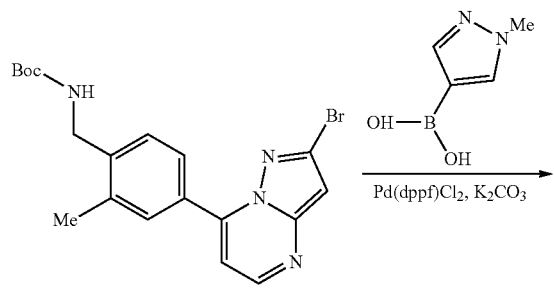

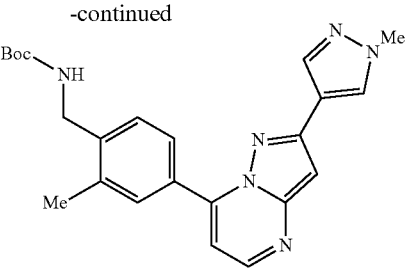

A suspension of tert-butyl (4-(2-bromopyrazolo[1,5-a]pyrimidin-7-yl)-2-methylbenzyl)carbamate (100 mg, 0.24 mmol) and (1-methylpyrazol-4-yl)boronic acid (60 mg, 0.48 mmol) in dioxane (1 mL) and H$_2$O (0.1 mL) was purged with N$_2$ for 5 min. K$_2$CO$_3$ (99 mg, 0.72 mmol) and Pd(dppf)Cl$_2$ (26 mg, 0.04 mmol) were added and the reaction was stirred at 110° C. for 2 hr. The cooled mixture was diluted with EtOAc and H$_2$O, filtered through a plug of Celite®, and the layers separated. The aqueous layer was extracted with EtOAc and the combined organic extracts were dried (MgSO$_4$), filtered, and concentrated in vacuo. The residue was purified by silica gel column chromatography (0-100% EtOAc/Hept) to afford the title compound as a yellow solid (89 mg, 89%). LCMS m/z=419.3 [M+H]$^+$; $^1$H NMR (400 MHz, CDCl$_3$) δ: 8.48 (br d, 1H), 8.00 (br d, 1H), 7.97 (s, 1H), 7.94 (s, 1H), 7.88 (s, 1H), 7.49 (d, 1H), 6.91-6.85 (m, 2H), 4.86 (br s, 1H), 4.50-4.40 (m, 2H), 4.00 (s, 3H), 2.47 (s, 3H), 1.51 (s, 9H).

3. Synthesis of (2-methyl-4-(2-(1-methyl-1H-pyrazol-4-yl)pyrazolo[1,5-a]pyrimidin-7-yl)phenyl)methanamine hydrochloride

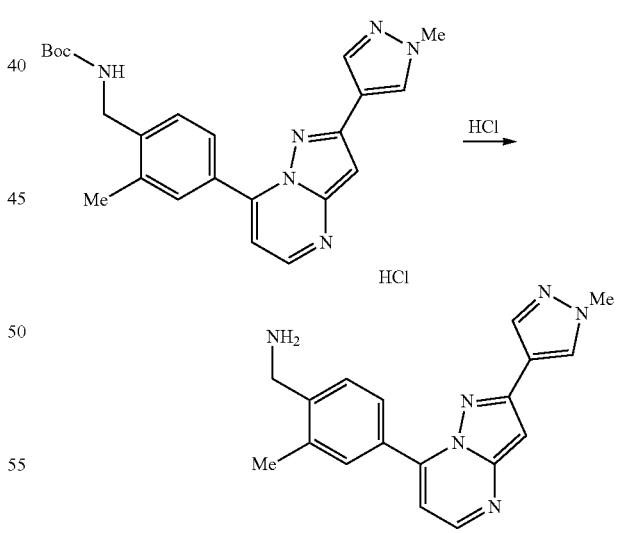

To a solution of tert-butyl (2-methyl-4-(2-(1-methyl-1H-pyrazol-4-yl)pyrazolo[1,5-a]pyrimidin-7-yl)benzyl)carbamate (85 mg, 0.2 mmol) in MeOH (1 mL) was added 4 M HCl in dioxane (0.5 mL) and the reaction was stirred at RT for 1 h. The reaction mixture was concentrated in vacuo to afford the title compound as a yellow solid, which was carried forward without further purification. LCMS m/z=319.2 [M+H]$^+$

4. Synthesis of 5-(tert-butyl)-N-(2-methyl-4-(2-(1-methyl-1H-pyrazol-4-yl)pyrazolo[1,5-a]pyrimidin-7-yl)benzyl)-1,2,4-oxadiazole-3-carboxamide trifluoroacetate

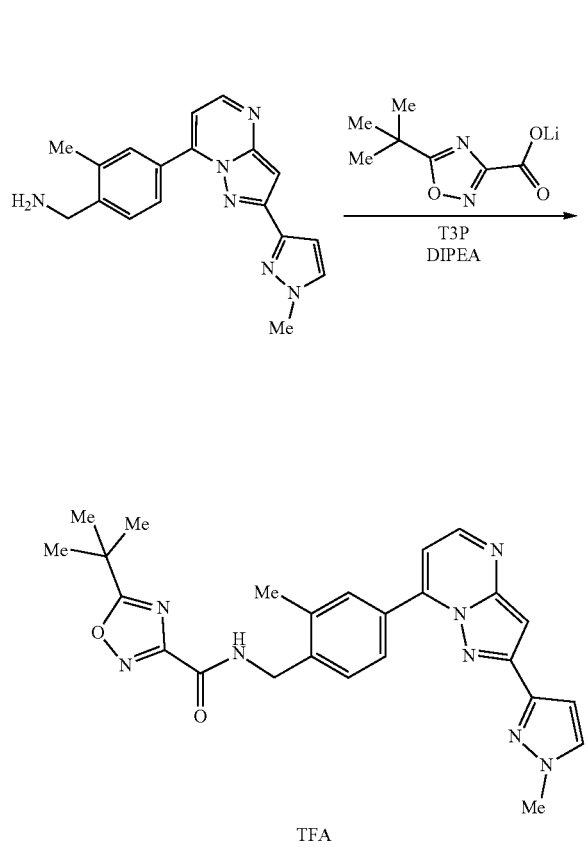

The crude product was obtained from (2-methyl-4-(2-(1-methyl-1H-pyrazol-4-yl)pyrazolo[1,5-a]pyrimidin-7-yl)phenyl)methanamine hydrochloride and lithium 5-(tert-butyl)-1,2,4-oxadiazole-3-carboxylate following the procedure described in Example 14, Step 8. The crude product was purified by prep HPLC, using Method B, 10-90% to afford the title compound as a yellow solid (23 mg, 25%). LCMS m/z=471.2 [M+H]$^+$; $^1$H NMR (500 MHz, MeOH-d$_4$) δ: 8.37 (d, 1H), 8.02 (s, 1H), 7.92 (br d, 1H), 7.88 (s, 2H), 7.45 (d, 1H), 6.93 (d, 1H), 6.78 (s, 1H), 4.66 (s, 2H), 3.90 (s, 3H), 2.45 (s, 3H), 1.48 (s, 9H).

Example 17. 5-(tert-butyl)-N-(2-methyl-4-(pyrrolo[1,2-b]pyridazin-4-yl)benzyl)-1,2,4-oxadiazole-3-carboxamide

1. Synthesis of tert-butyl (2-methyl-4-(pyrrolo[1,2-b]pyridazin-4-yl)benzyl)carbamate

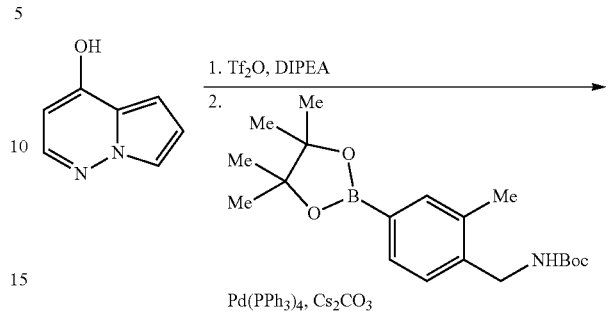

Tf$_2$O (505 mg, 1.8 mmol) was added dropwise via syringe to a solution of pyrrolo[1,2-b]pyridazin-4-ol (200 mg, 1.5 mmol) and DIPEA (385 mg, 3.0 mmol) in DCM (10 mL) cooled in an ice bath and the mixture was stirred at RT for 18 hr. The mixture was diluted with DCM and washed with H$_2$O. The organic phase was dried (Na$_2$SO$_4$) and concentrated in vacuo to provide pyrrolo[1,2-b]pyridazin-4-yl trifluoromethanesulfonate (400 mg, 91%) as a viscous dark liquid. Dioxane (6 mL) and H$_2$O (2 mL) were added to a mixture of pyrrolo[1,2-b]pyridazin-4-yl trifluoromethanesulfonate (400 mg, 1.5 mmol), tert-butyl (2-methyl-4-(4,4,5,5-tetramethyl-1,3,2-dioxaborolan-2-yl)benzyl)carbamate (WO 2015089327 Example 1, 1.03 g, 3.0 mmol), Cs$_2$CO$_3$ (971 mg, 3.0 mmol) and Pd(PPh$_4$)$_3$ (172 mg, 0.15 mmol) under N$_2$ and the reaction was stirred at 100° C. for 18 h. The cooled mixture was diluted with EtOAc and the solids removed by filtration and washed with additional EtOAc. The combined filtrates were concentrated in vacuo and the residue purified by silica gel column chromatography (20% EtOAc/Hept) to afford the title compound as a sticky yellow gum (410 mg, 73%). LCMS m/z=338.5 [M+H]$^+$

2. Synthesis of (2-methyl-4-(pyrrolo[1,2-b]pyridazin-4-yl)phenyl)methanamine

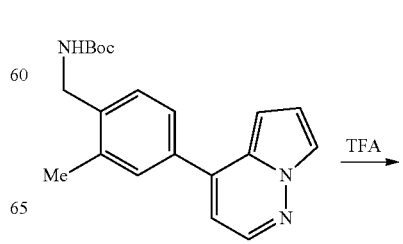

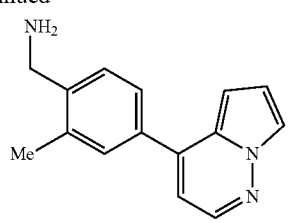

The title compound was obtained as a reddish brown gum (220 mg, 68%) from tert-butyl (2-methyl-4-(pyrrolo[1,2-b]pyridazin-4-yl)benzyl)carbamate following the procedure described in Example 14, Step 7. LCMS m/z=238.5 [M+H]⁺

3. Synthesis of 5-(tert-butyl)-N-(2-methyl-4-(pyrrolo[1,2-b]pyridazin-4-yl)benzyl)-1,2,4-oxadiazole-3-carboxamide

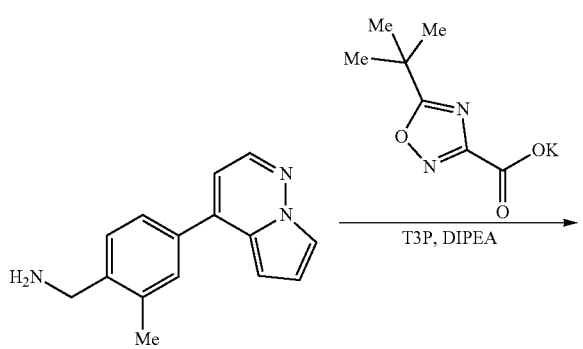

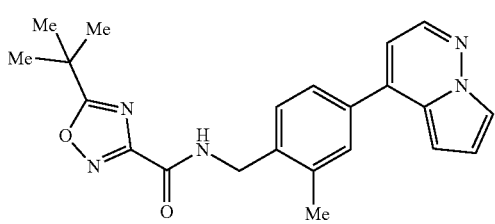

The compound was prepared using an analogous method to that described for Example 14, Step 8 using (2-methyl-4-(pyrrolo[1,2-b]pyridazin-4-yl)phenyl)methanamine and potassium 5-(tert-butyl)-1,2,4-oxadiazole-3-carboxylate. The crude product was purified by prep-HPLC (Method C; 0-100%) to afford the title compound as a yellow solid (13 mg, 13%). LCMS m/z=390.5 [M+H]⁺; ¹H NMR (400 MHz, CDCl₃) δ: 8.09 (d, 1H), 7.84 (s, 1H), 7.59 (br s, 2H), 7.46 (d, 1H), 7.2 (br s, 1H), 6.93-6.90 (m, 1H), 6.66 (d, 1H), 6.54 (d, 1H), 4.76 (d, 2H), 2.47 (s, 3H), 1.48 (s, 9H).

Example 18. 3-(tert-butyl)-N-(2-methyl-4-(pyrrolo[1,2-b]pyridazin-4-yl)benzyl)-1,2,4-oxadiazole-5-carboxamide

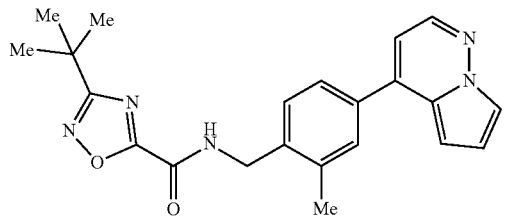 [SMILES: Cc1cc(-c2ccnn3cccc23)ccc1CNC(=O)c1nc(C(C)(C)C)no1]

1. Synthesis of 3-(tert-butyl)-N-(2-methyl-4-(pyrrolo[1,2-b]pyridazin-4-yl)benzyl)-1,2,4-oxadiazole-5-carboxamide

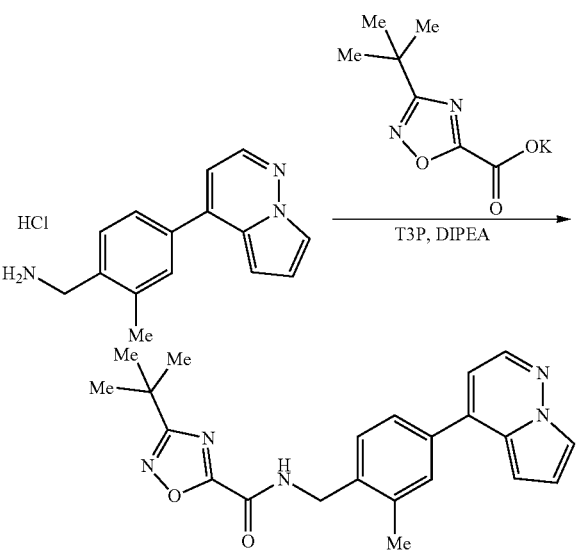

The compound was prepared using an analogous method to that described for Example 14, Step 8 using (2-methyl-4-(pyrrolo[1,2-b]pyridazin-4-yl)phenyl)methanamine and potassium 3-(tert-butyl)-1,2,4-oxadiazole-5-carboxylate. The crude product was purified by prep-HPLC (Method C; 0-100%) to afford the title compound as a yellow solid (3.6 mg, 3.8%). LCMS m/z=390.6 [M+H]⁺

Example 19. 5-(tert-butyl)-N-(4-(5-fluoropyrrolo[2,1-f][1,2,4]triazin-4-yl)-2-methylbenzyl)-1,2,4-oxadiazole-3-carboxamide trifluoroacetate

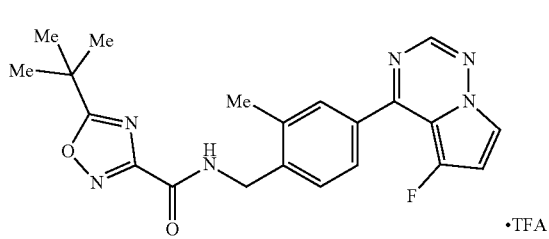 [SMILES: Cc1cc(-c2ncnn3ccc(F)c23)ccc1CNC(=O)c1noc(C(C)(C)C)n1]

1. Synthesis of tert-butyl (2-methyl-4-(pyrrolo[2,1-f][1,2,4]triazin-4-yl)benzyl)carbamate

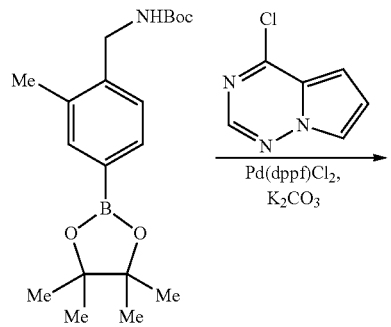

To a solution of tert-butyl (2-methyl-4-(4,4,5,5-tetramethyl-1,3,2-dioxaborolan-2-yl)benzyl)carbamate (1.0 g, 2.9 mmol) in 1,4-dioxane/water (v/v=10/1, 66 mL) was added 4-chloropyrrolo[2,1-f][triazine] (486 mg, 3.2 mmol), Pd(dppf)Cl$_2$ (105 mg, 0.14 mmol) and K$_2$CO$_3$ (796 mg, 5.8 mmol) and the mixture stirred at 90° C. for 15 h. The mixture was concentrated in vacuo and the residue purified by silica gel column chromatography (petroleum ether/EtOAc=10:1 to 8:1) to afford the title compound as a yellow oil (1.00 g, 89%). LCMS m/z=339.1 [M+H]$^+$

2. Synthesis of tert-butyl (4-(5-fluoropyrrolo[2,1-f][1,2,4]triazin-4-yl)-2-methylbenzyl)carbamate

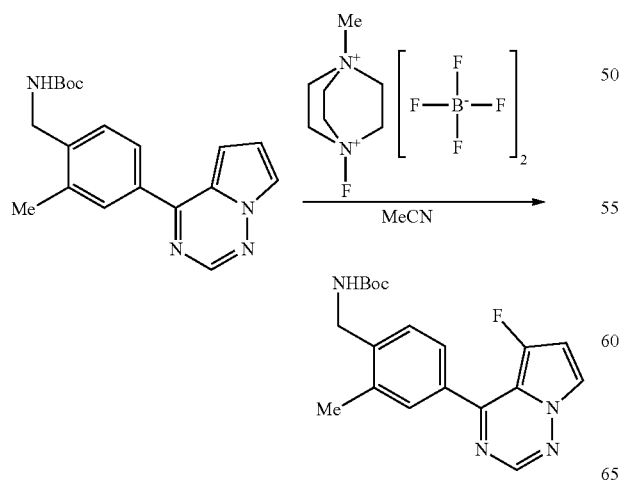

1-Fluoro-4-methyl-1,4-diazoniabicyclo[2.2.2]octanebis(tetrafluoroborate) (1.7 g, 5.3 mmol) was added to a solution of tert-butyl (2-methyl-4-(pyrrolo[2,1-f][1,2,4]triazin-4-yl)benzyl)carbamate (600 mg, 1.8 mmol) in MeCN (30 mL) cooled in an ice bath and the reaction was stirred at RT for 18 hr. The mixture was diluted with DCM and filtered, washing through with additional DCM. The filtrate was concentrated in vacuo and the residue purified by prep HPLC Method A (5-95%) to afford the title compound as a yellow sticky gum (26 mg, 4% yield). LCMS m/z=357.5 [M+H]$^+$

3. Synthesis of (4-(5-fluoropyrrolo[2,1-f][1,2,4]triazin-4-yl)-2-methylphenyl)methanamine

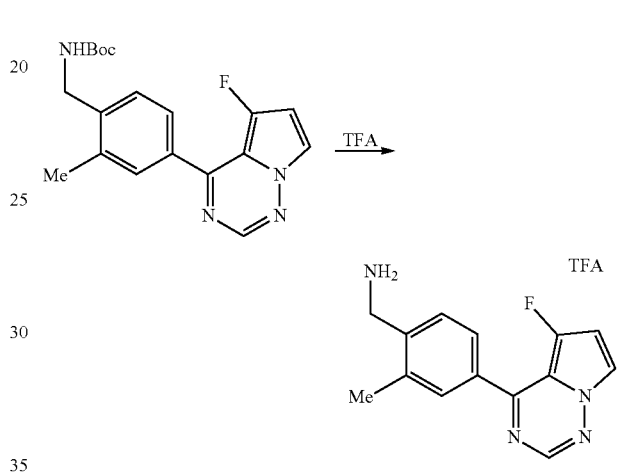

TFA (404 mg, 3.6 mmol) was added to a solution tert-butyl (4-(5-fluoropyrrolo[2,1-f][1,2,4]triazin-4-yl)-2-methylbenzyl)carbamate (26 mg, 0.07 mmol) in DCM (2 mL) and the reaction was stirred at RT for 18 h. The reaction was concentrated in vacuo, the residue dissolved in MeOH, and passed through an SCX ion exchange column flushing through with MeOH followed by 2M methanolic NH$_3$. The combined organic phases were concentrated in vacuo to afford the title compound as a sticky yellow oil (20 mg, 99%). LCMS m/z=257.4 [M+H]$^+$

4. Synthesis of 5-(tert-butyl)-N-(4-(5-fluoropyrrolo[2,1-f][1,2,4]triazin-4-yl)-2-methylbenzyl)-1,2,4-oxadiazole-3-carboxamide

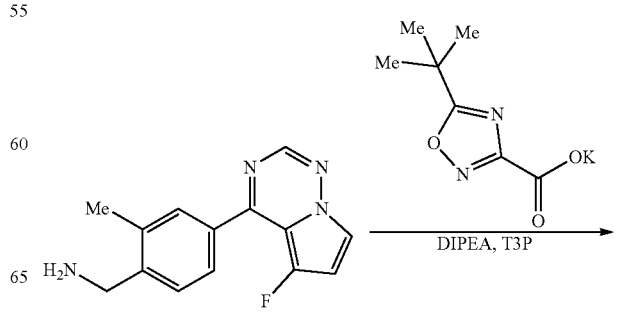

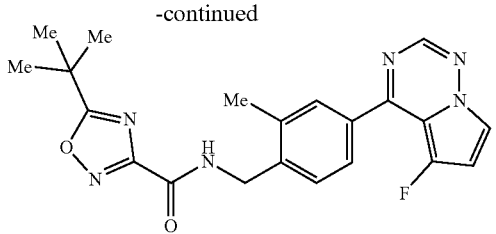

The title compound was prepared using an analogous method to that described for Example 14, Step 8 using (4-(5-fluoropyrrolo[2,1-f][1,2,4]triazin-4-yl)-2-methylphenyl)methanamine and potassium 5-(tert-butyl)-1,2,4-oxadiazole-3-carboxylate. The crude product was purified by prep-HPLC (Method B; 5-95%) to afford the title compound as a yellow solid (22 mg, 55%). LCMS m/z=409.5 [M+H]$^+$; $^1$H NMR (400 MHz, CDCl$_3$) δ: 8.51 (s, 1H), 7.91 (dd, 1H), 7.79-7.72 (m, 2H), 7.54 (d, 1H), 7.33 (br d, 1H), 6.82 (d, 1H), 4.79 (d, 2H), 2.49 (s, 3H), 1.48 (s, 9H).

Example 20. 2-(1,1-difluoroethyl)-N-(2-methyl-4-(pyrrolo[2,1-f][1,2,4]triazin-4-yl)benzyl)oxazole-4-carboxamide trifluoroacetate

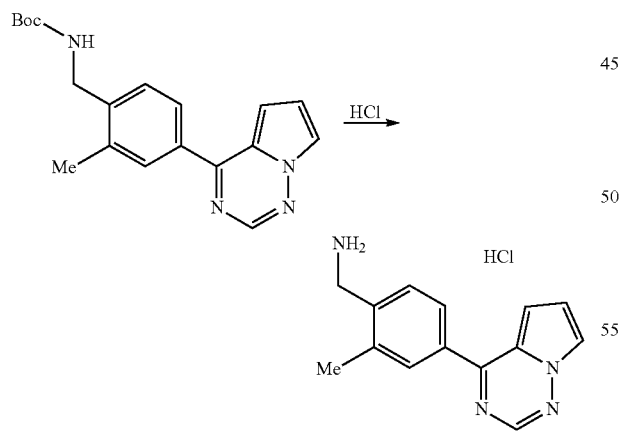

1. Synthesis of (2-methyl-4-(pyrrolo[2,1-f][1,2,4]triazin-4-yl)phenyl)methanamine hydrochloride An HCl solution (10 mL, 4M in EtOAc) was added to a solution of tert-butyl (2-methyl-4-(pyrrolo[2,1-f][1,2,4]triazin-4-yl)benzyl)carbamate (1 g, 2.6 mmol) in DCM (20 mL) and the reaction was stirred at RT for 1 h. The mixture was filtered and the solid was dried in vacuo to afford the title compound as a yellow solid (710 mg, 99%). LCMS m/z=239.0 [M+H]$^+$ 2. Synthesis of lithium 2-(1,1-difluoroethyl)oxazole-4-carboxylate

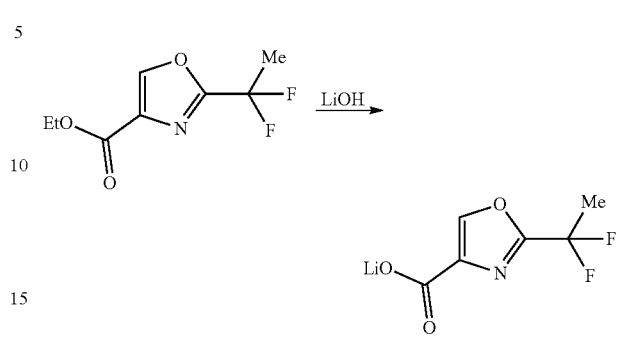

The title compound was obtained from ethyl 2-(1,1-difluoroethyl)oxazole-4-carboxylate and LiOH following an analogous procedure to that described in Example 2, Step 3. The crude product was carried forward without further purification.

3. Synthesis of 2-(1,1-difluoroethyl)-N-(2-methyl-4-(pyrrolo[2,1-f][1,2,4]triazin-4-yl)benzyl)oxazole-4-carboxamide trifluoroacetate

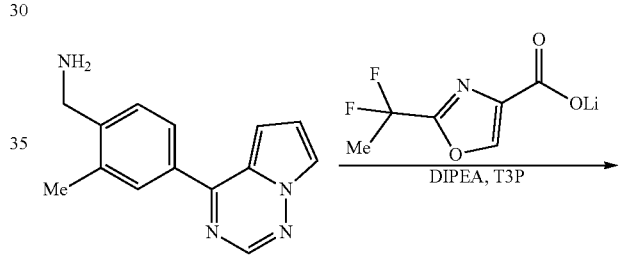

The title compound was prepared using an analogous method to that described for Example 14, Step 8 using (2-methyl-4-(pyrrolo[2,1-f][1,2,4]triazin-4-yl)phenyl)methanamine hydrochloride and lithium 2-(1,1-difluoroethyl)oxazole-4-carboxylate. The compound was purified by prep-HPLC (Method B; 10-95%) to afford the title compound as a yellow solid (8.5 mg, 9%). LCMS m/z=398.5 [M+H]$^+$; $^1$H NMR (400 MHz, CDCl$_3$) δ: 8.66 (s, 1H), 8.36 (s, 1H), 8.15 (dd, 1H), 7.89-7.83 (m, 2H), 7.56 (d, 1H), 7.38-7.30 (m, 2H), 7.22 (dd, 1H), 4.75 (d, 2H), 2.50 (s, 3H), 2.11 (t, 3H).

Example 21. 5-(tert-butyl)-N-(4-(imidazo[1,2-b]pyridazin-8-yl)-2-methylbenzyl)-1,2,4-oxadiazole-3-carboxamide trifluoroacetate

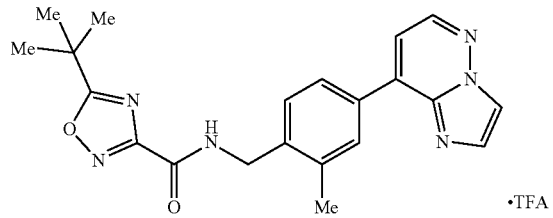 [SMILES: Cc1cc(-c2ccnn3ccnc23)ccc1CNC(=O)c1noc(C(C)(C)C)n1]

1. Synthesis of tert-butyl (4-(6-chloroimidazo[1,2-b]pyridazin-8-yl)-2-methylbenzyl)carbamate

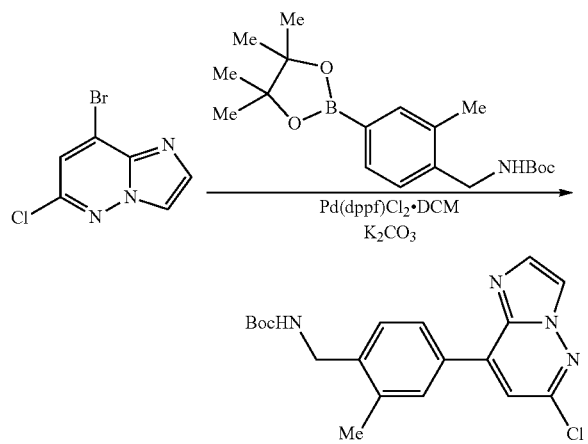

Dioxane (3 mL) and H₂O (1 mL) were added to a mixture of 8-bromo-6-chloro-imidazo[1,2-b]pyridazine (232 mg, 1.0 mmol), tert-butyl (2-methyl-4-(4,4,5,5-tetramethyl-1,3,2-dioxaborolan-2-yl)benzyl)carbamate (WO 2015089327 Example 1, 347 mg, 1.0 mmol), K₂CO₃ (553 mg, 4.0 mmol) and Pd(dppf)Cl₂·DCM (82 mg, 0.10 mmol) under N₂ and the reaction was stirred at RT for 5 mins and then at 95° C. for 14 h. The cooled mixture was diluted with EtOAc and filtered, washing through with additional EtOAc. The filtrate was concentrated in vacuo and the residue was purified by silica gel column chromatography (EtOAc/Hept, 1:1) to afford the title compound as a yellow gum (360 mg, 87%). LCMS m/z=373.2 [M+H]⁺

2. Synthesis of tert-butyl (4-(imidazo[1,2-b]pyridazin-8-yl)-2-methylbenzyl)carbamate

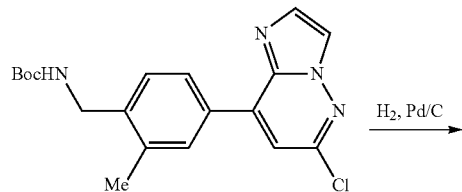

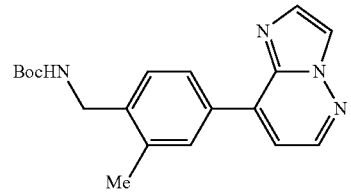

10% Pd/C (57 mg, 0.05 mmol) was added to a solution of tert-butyl (4-(6-chloroimidazo[1,2-b]pyridazin-8-yl)-2-methylbenzyl)carbamate (100 mg, 0.27 mmol) in MeOH (10 mL) and the reaction was stirred under an atmosphere of H₂ for 5 days. The reaction mixture was filtered, washing through with MeOH. The filtrate was concentrated in vacuo and the residue purified by silica gel column chromatography (EtOAc/Hept, 1:1) to afford the title compound as a yellow gum (55 mg, 30%). LCMS m/z=339.2 [M+H]⁺

3. Synthesis of (4-(imidazo[1,2-b]pyridazin-8-yl)-2-methylphenyl)methanamine

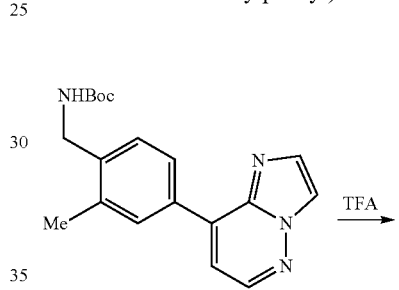

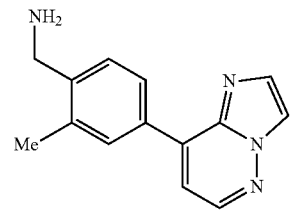

TFA (909 mg, 8.0 mmol) was added to a solution of tert-butyl (4-(imidazo[1,2-b]pyridazin-8-yl)-2-methylbenzyl)carbamate (50 mg, 0.4 mmol) in DCM (5 mL) and the reaction was stirred at RT for 5 days. The reaction was concentrated in vacuo, the residue dissolved in MeOH, and passed through an SCX ion exchange column flushing through with MeOH followed by 2M methanolic NH₃. The combined organic phases were concentrated in vacuo to afford the title compound as a sticky yellow-orange gum (53 mg, 50%). LCMS m/z=239.2 [M+H]⁺

4. Synthesis of 5-(tert-butyl)-N-(4-(imidazo[1,2-b]pyridazin-8-yl)-2-methylbenzyl)-1,2,4-oxadiazole-3-carboxamide trifluoroacetate

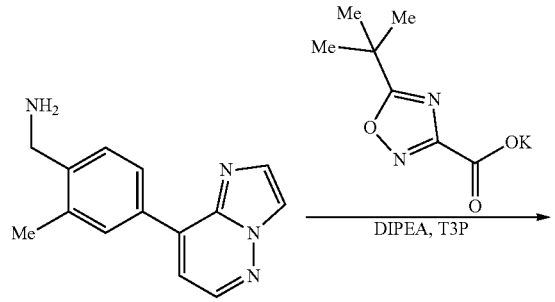

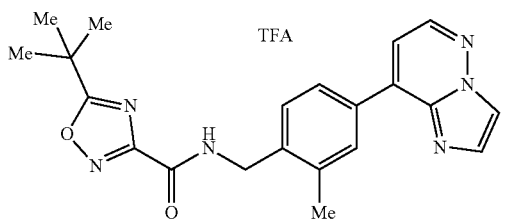

The title compound was prepared using an analogous method to that described for Example 14, Step 8 using (4-(imidazo[1,2-b]pyridazin-8-yl)-2-methylphenyl)methanamine and potassium 5-(tert-butyl)-1,2,4-oxadiazole-3-carboxylate. The compound was purified by prep-HPLC (Method B; 5-95%) to afford the title compound as a yellow solid (21.6 mg, 18%). LCMS m/z=391.3 [M+H]+; 1H NMR (400 MHz, DMSO-d6) δ: 9.49 (t, 1H), 8.65 (d, 1H), 8.43 (d, 1H), 8.11 (s, 1H), 8.08-8.04 (m, 1H), 7.94 (d, 1H), 7.55 (d, 1H), 7.43 (d, 1H), 4.53 (d, 2H), 2.44 (s, 3H), 1.43 (s, 9H).

Example 22. 5-(tert-butyl)-N-(2-methyl-4-(2-morpholinopyrazolo[1,5-a]pyrimidin-7-yl)benzyl)-1,2,4-oxadiazole-3-carboxamide

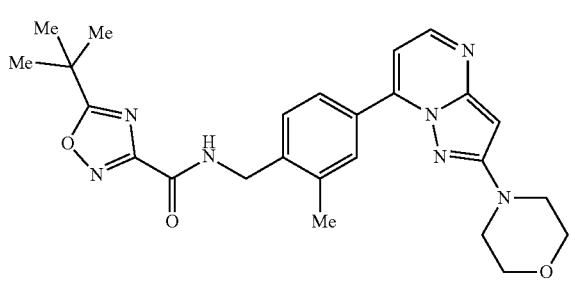 [SMILES: Cc1cc(-c2ccnc3cc(N4CCOCC4)nn23)ccc1CNC(=O)c1noc(C(C)(C)C)n1]

1. Synthesis of tert-butyl tert-butyl (4-(2-bromopyrazolo[1,5-a]pyrimidin-7-yl)-2-methylbenzyl)carbamate

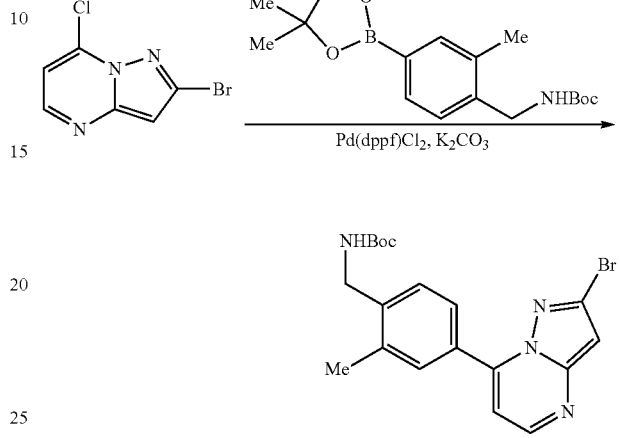

A mixture of tert-butyl (2-methyl-4-(4,4,5,5-tetramethyl-1,3,2-dioxaborolan-2-yl)benzyl)carbamate (WO 2015089327 Example 1, 630 mg, 1.8 mmol), 2-bromo-7-chloro-pyrazolo[1,5-a]pyrimidine (842 mg, 3.6 mmol) and K2CO3 (750 mg, 5.4 mmol) were suspended in dioxane (8 mL) and water (1 mL) and degassed with N2 for 5 min. Pd(dppf)Cl2 (132 mg, 0.18 mmol) was added and the reaction stirred at 100° C. for 2 h. The cooled mixture was diluted with EtOAc and water, filtered through Celite®, and the layers separated. The aqueous layer was extracted with EtOAc and the combined organic extracts were dried (MgSO4), filtered, and concentrated in vacuo. The residue was purified by silica gel column chromatography (0-100% EtOAc/Hept) to afford the title compound as a yellow solid (750 mg, 99%). 1H NMR (500 MHz, CDCl3) δ: 8.53 (d, 1H), 7.87 (dd, 1H), 7.85-7.80 (m, 1H), 7.51-7.45 (m, 1H), 6.94-6.87 (m, 1H), 6.86-6.79 (m, 1H), 4.84 (br s, 1H), 4.42 (br d, 2H), 2.49-2.42 (m, 3H), 1.53-1.48 (s, 9H). LCMS m/z=417.1 [M+H]+

2. Synthesis of tert-butyl (2-methyl-4-(2-morpholinopyrazolo[1,5-a]pyrimidin-7-yl)benzyl)carbamate

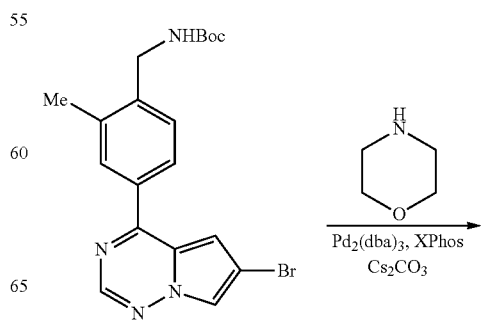

4. Synthesis of 5-(tert-butyl)-N-(2-methyl-4-(2-morpholinopyrazolo[1,5-a]pyrimidin-7-yl)benzyl)-1,2,4-oxadiazole-3-carboxamide

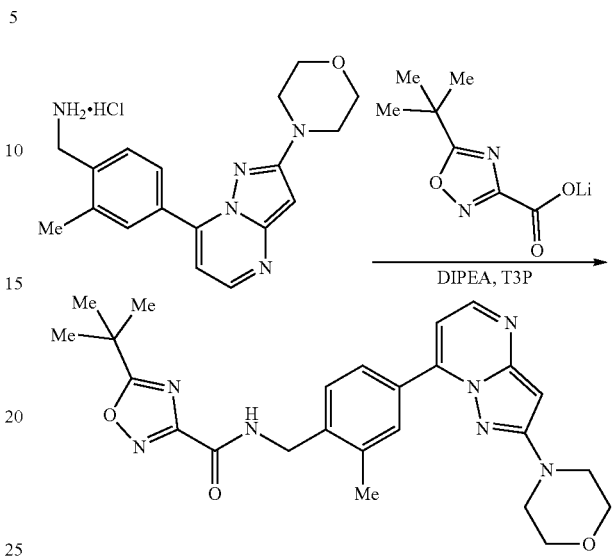

The title compound was prepared using an analogous method to that described for Example 14, Step 8 using (2-methyl-4-(2-morpholinopyrazolo[1,5-a]pyrimidin-7-yl)phenyl)methanamine hydrochloride and lithium 5-(tert-butyl)-1,2,4-oxadiazole-3-carboxylate. The crude material was purified by silica gel column chromatography (0-100% EtOAc/Hept) to give the title compound as a yellow solid (60 mg, 46% over 2 steps). LCMS m/z=476.2 [M+H]$^+$; $^1$H NMR (500 MHz, CDCl$_3$) δ: 8.33 (d, 1H), 8.00 (dd, 1H), 7.92 (s, 1H), 7.50 (d, 1H), 7.20 (br s, 1H), 6.74 (d, 1H), 6.12 (s, 1H), 4.76 (d, 2H), 3.87-3.82 (m, 4H), 3.45-3.38 (m, 4H), 2.48 (s, 3H), 1.51-1.45 (m, 9H).

Example 23 and Example 24. (S)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide and (R)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide

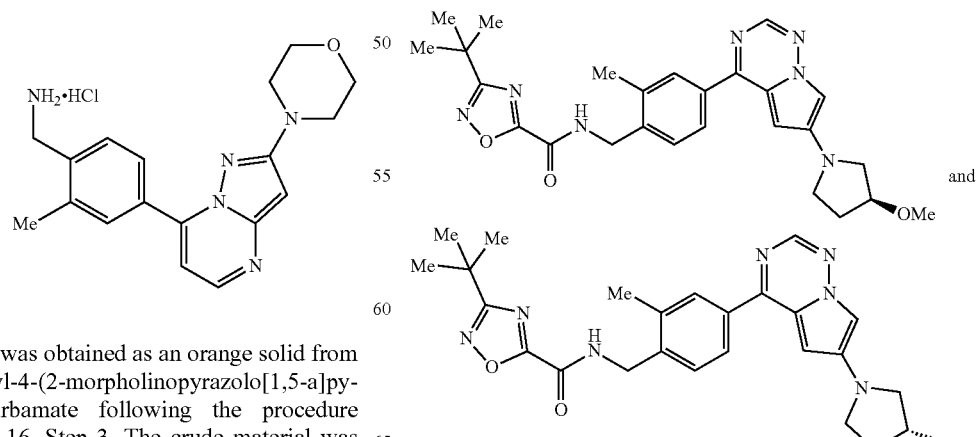

---

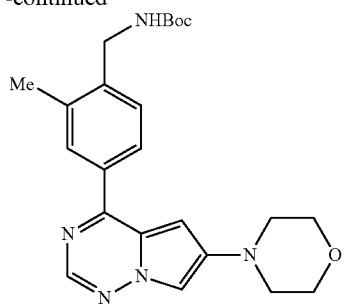

The title compound was obtained as an orange solid (79 mg, 55%) from tert-butyl (4-(2-bromopyrazolo[1,5-a]pyrimidin-7-yl)-2-methylbenzyl)carbamate and morpholine following the procedure described in Example 13, Step 1. LCMS m/z=424.2 [M+H]$^+$; $^1$H NMR (500 MHz, CDCl$_3$) δ: 8.34 (d, 1H), 7.97 (d, 1H), 7.90 (s, 1H), 7.44 (d, 1H), 6.73 (d, 1H), 6.09 (s, 1H), 4.84 (br s, 1H), 4.42 (br d, 2H), 3.89-3.84 (m, 4H), 3.46-3.38 (m, 4H), 2.47-2.41 (s, 3H), 1.52-1.47 (s, 9H).

3. Synthesis of (2-methyl-4-(2-morpholinopyrazolo[1,5-a]pyrimidin-7-yl)phenyl)methanamine hydrochloride

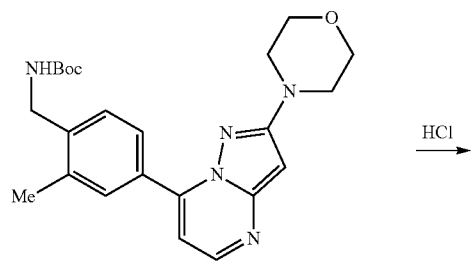

The title compound was obtained as an orange solid from tert-butyl (2-methyl-4-(2-morpholinopyrazolo[1,5-a]pyrimidin-7-yl)benzyl)carbamate following the procedure described in Example 16, Step 3. The crude material was carried forward without further purification. LCMS m/z=324.2 [M+H]$^+$ Absolute Stereochemistry Arbitrarily Assigned 1. Synthesis of (S)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide (Example 23) and (R)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide (Example 24)

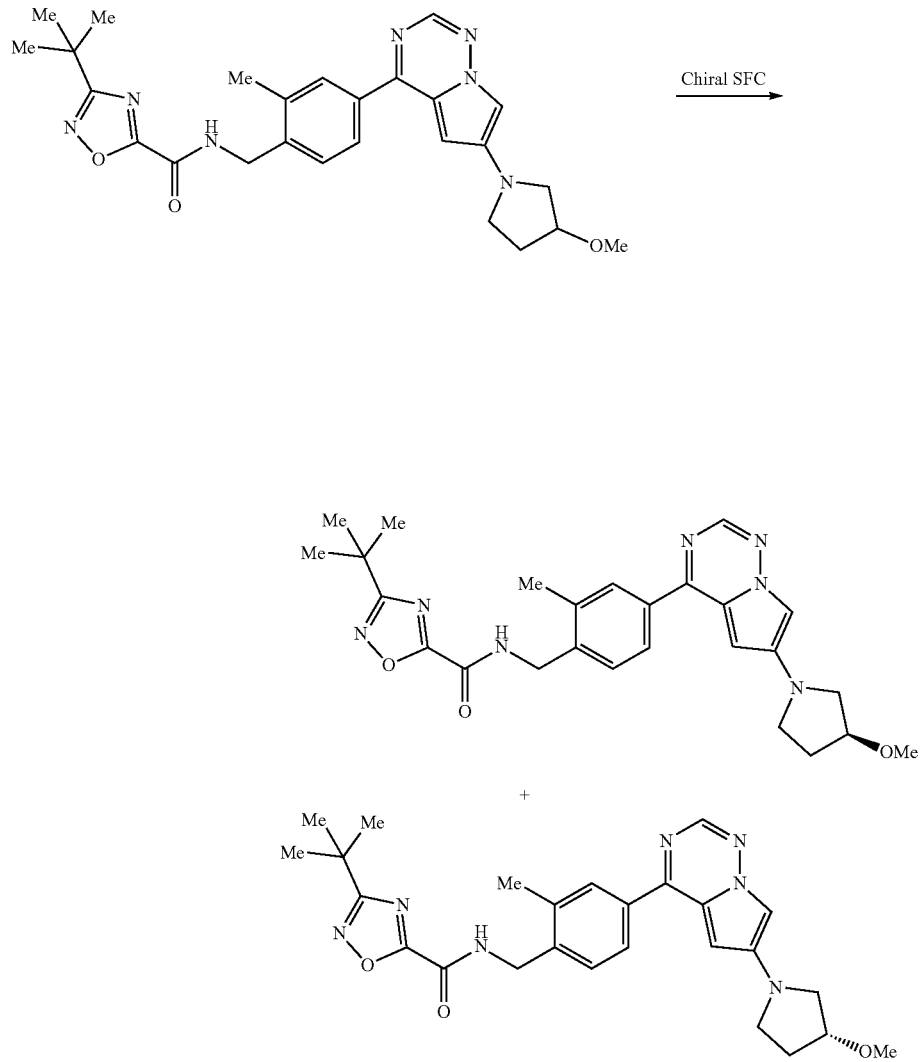

3-(tert-Butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide (Example 13; 65 mg) was purified by chiral SFC (CHIRALPAK AD-H 30×250 mm, 5 μm; 30% IPA+0.1% DEA in $CO_2$ to afford the title compounds. Absolute stereochemical configurations were arbitrarily assigned.

Example 23; Peak 1: (S)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide (4.4 mg). LCMS m/z=490.3 [M+H]$^+$; $^1$H NMR (400 MHz, MeOH-$d_4$) δ: 8.25-8.34 (m, 1H), 7.80-7.90 (m, 2H), 7.60-7.66 (m, 1H), 7.48-7.54 (m, 1H), 6.32-6.39 (m, 1H), 4.65-4.74 (m, 2H), 4.12-4.21 (m, 1H), 3.48 (dd, 1H), 3.37-3.39 (m, 3H), 3.34-3.36 (m, 1H), 3.31 (m, 2H), 2.52 (s, 3H), 2.13-2.22 (m, 2H), 1.48-1.52 (m, 9H).

Example 24; Peak 2: (R)-3-(tert-butyl)-N-(4-(6-(3-methoxypyrrolidin-1-yl)pyrrolo[2,1-f][1,2,4]triazin-4-yl)-2-methylbenzyl)-1,2,4-oxadiazole-5-carboxamide (5.9 mg). LCMS m/z=490.3 [M+H]$^+$; $^1$H NMR (400 MHz, MeOH-$d_4$) δ: 8.26-8.33 (m, 1H), 7.81-7.89 (m, 2H), 7.59-7.64 (m, 1H), 7.46-7.54 (m, 1H), 6.30-6.40 (m, 1H), 4.70 (s, 2H), 4.16 (br s, 1H), 3.44-3.53 (m, 1H), 3.37-3.39 (m, 3H), 3.34-3.36 (m, 1H), 3.27-3.32 (m, 2H), 2.51 (s, 3H), 2.13-2.20 (m, 2H), 1.49-1.52 (m, 9H).

Example 25 and Example 26. (R)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide and (S)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide

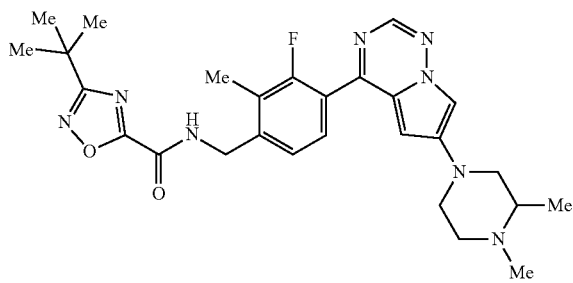 [SMILES: Cc1c(CNC(=O)c2nc(C(C)(C)C)no2)ccc(-c2ncnn3cc(N4CCN(C)C(C)C4)cc23)c1F]

1. Synthesis of 4-bromo-2-fluoro-3-methylaniline

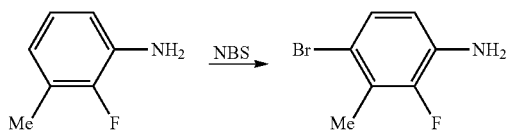

A solution of NBS (28.4 g, 160 mmol) in DCM was added dropwise to an ice-cooled solution of 2-fluoro-3-methylaniline (20.0 g, 160 mmol) in DCM (200 mL) and the reaction was stirred at 20° C. for 5 h. The mixture was diluted with saturated aqueous $Na_2CO_3$ solution (100 mL), the layers were separated, and the aqueous phase was extracted with DCM (2×100 mL). The combined organic layers were dried ($Na_2SO_4$), filtered, and concentrated in vacuo. The crude product was purified by silica gel column chromatography (petroleum ether/EtOAc=10:1) to afford the title compound as a brown oil (32.0 g, crude). LCMS m/z=205.8 $[M+H]^+$

2. Synthesis of 4-amino-3-fluoro-2-methylbenzonitrile

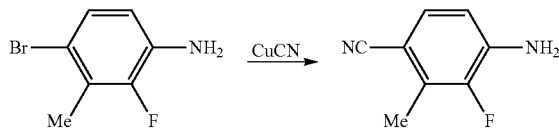

CuCN (35.6 g, 397 mmol) was added to a solution of 4-bromo-2-fluoro-3-methylaniline (27 g, 132 mmol) in DMF (200 mL) under $N_2$ and the reaction was stirred at 140° C. for 16 h. $NH_3·H_2O$ (300 mL) was added to the cooled reaction, the mixture was filtered to remove the solid, the filtrate was poured into $H_2O$ (300 mL) and extracted with EtOAc (2×300 mL). The aqueous phase was extracted with EtOAc (2×300 mL) and the combined organic layers were dried ($Na_2SO_4$), filtered and concentrated in vacuo. The crude product was purified by silica gel column chromatography (petroleum ether/EtOAc=70:30) to afford the title compound as a brown oil (15 g, 75% yield). LCMS m/z=151.0 $[M+H]^+$

3. Synthesis of 4-bromo-3-fluoro-2-methylbenzonitrile

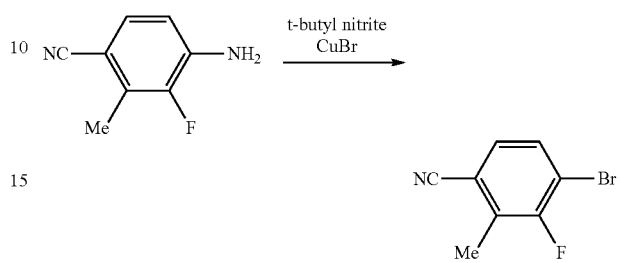

A solution of 4-amino-3-fluoro-2-methylbenzonitrile (15 g, 100 mmol) in MeCN (250 mL) was added to a solution of tert-butyl nitrite (17.8 mL, 150 mmol) and CuBr (21.5 g, 150 mmol) in MeCN at 65° C. and the reaction was stirred at 65° C. for 3 h under $N_2$. The cooled mixture was filtered, the filtrate concentrated in vacuo, and the crude product purified by silica gel column chromatography (petroleum ether/EtOAc=9:1) to afford the title compound as an orange solid (11.5 g, crude). $^1$H NMR (400 MHz, $CDCl_3$) δ: 7.51 (dd, 1H), 7.28 (dd, 1H), 2.52 (s, 3H).

4. Synthesis of tert-butyl (4-bromo-3-fluoro-2-methylbenzyl)carbamate

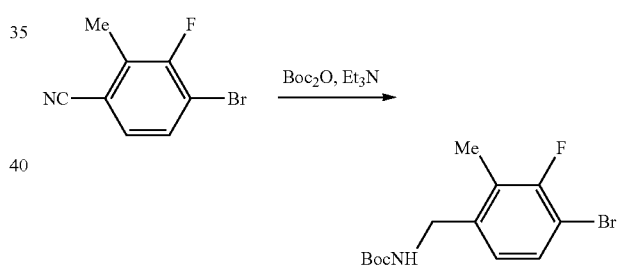

To a solution of (4-bromo-3-fluoro-2-methylphenyl)methanamine (14 g, 64 mmol) in DCM (100 mL) were added $Et_3N$ (13 g, 128 mmol) and $Boc_2O$ (16.8 g, 77 mmol) and the mixture was stirred at 25° C. for 2 h. The mixture was concentrated in vacuo and the residue was purified by silica gel column chromatography (petroleum ether/EtOAc=50:1) to afford the title compound as a white solid (12.0 g, 59%). $^1$H NMR (400 MHz, DMSO-$d_6$) δ: 7.47 (dd, 1H), 7.37 (dd, 1H), 6.96 (d, 1H), 4.07 (d, 2H), 2.19 (d, 3H), 1.37 (s, 9H).

5. Synthesis of tert-butyl (3-fluoro-2-methyl-4-(4,4,5,5-tetramethyl-1,3,2-dioxaborolan-2-yl)benzyl)carbamate

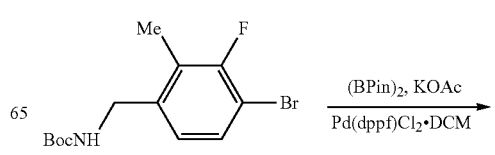

-continued

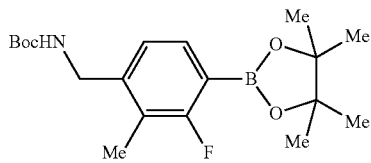

To a solution of tert-butyl (4-bromo-3-fluoro-2-methylbenzyl)carbamate (10 g, 31 mmol) in dioxane (150 mL) were added (bispinacolato)diboron (9.6 g, 38 mmol) and KOAc (6.2 g, 63 mmol). Pd(dppf)Cl$_2$·DCM (2.1 g, 2.5 mmol) was added and the reaction was stirred at 80° C. for 17 h under N$_2$. The reaction mixture was concentrated in vacuo and the crude material was purified by silica-gel column chromatography (petroleum ether/EtOAc=20:1) to give the title compound as a yellow solid (13.0 g, crude). LCMS m/z=310.1 [M-tBu+H]$^+$ 6. Synthesis of tert-butyl (4-(6-bromopyrrolo[2,1-f] [1,2,4]triazin-4-yl)-3-fluoro-2-methylbenzyl)carbamate

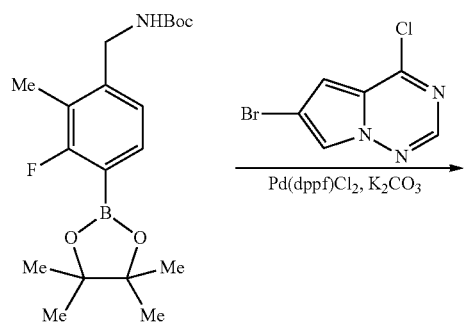

A mixture of tert-butyl (3-fluoro-2-methyl-4-(4,4,5,5-tetramethyl-1,3,2-dioxaborolan-2-yl)benzyl)carbamate (786 mg, 2.2 mmol), 6-bromo-4-chloro-pyrrolo[2,1-f][1,2,4]triazine (1.0 g, 4.3 mmol), Pd(dppf)Cl$_2$ (157 mg, 0.2 mmol) and K$_2$CO$_3$ (891 mg, 6.5 mmol) in dioxane (8 mL) and H$_2$O (0.8 mL) was degassed and heated to 95° C. for 16 h. The cooled mixture was filtered through Celite®, and the filtrate concentrated in vacuo. The crude product was purified by silica gel column chromatography (0-100% EtOAc/Hept) to afford the title compound as a red solid (960 mg, 100%). LCMS m/z=437.1 [M+H]$^+$ 7. Synthesis of tert-butyl (4-(6-(3,4-dimethylpiperazin-1-yl)pyrrolo[2,1-f][1,2,4]triazin-4-yl)-3-fluoro-2-methylbenzyl)carbamate

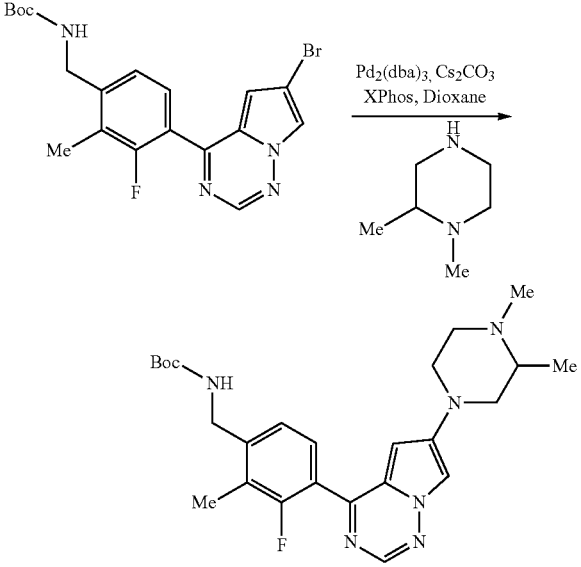

The title compound was obtained from tert-butyl (4-(6-bromopyrrolo[2,1-f][1,2,4]triazin-4-yl)-3-fluoro-2-methylbenzyl)carbamate and 1,2-dimethylpiperazine following the procedure described in Example 13, Step 1. The residue was purified by silica gel column chromatography (0-30% MeOH/DCM) to afford the title compound (73 mg, 34%). LCMS m/z=469.3 [M+H]$^+$ 8. Synthesis of (4-(6-(3,4-dimethylpiperazin-1-yl) pyrrolo[2,1-f][1,2,4]triazin-4-yl)-3-fluoro-2-methylphenyl)methanamine trifluoroacetate

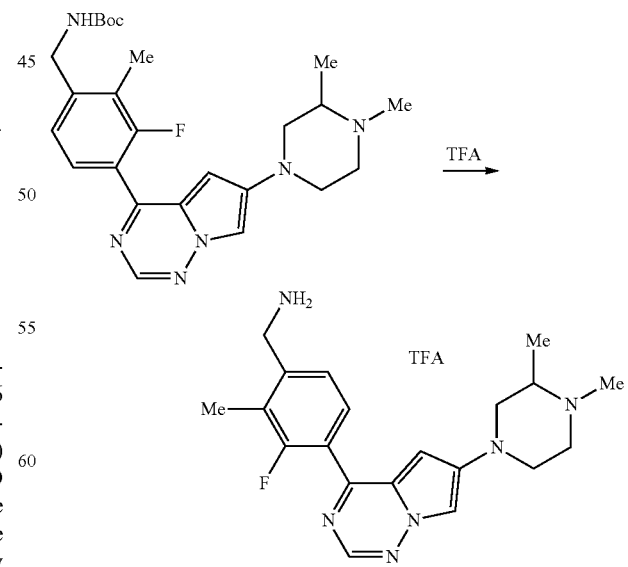

A solution of tert-butyl (4-(6-(3,4-dimethylpiperazin-1-yl)pyrrolo[2,1-f][1,2,4]triazin-4-yl)-3-fluoro-2-methylbenzyl)carbamate (73 mg, 0.16 mmol) and TFA (0.5 mL) in DCM (1.50 mL) was stirred at RT for 16 h. The mixture was concentrated in vacuo to afford the title compound, which was carried forward without further purification. LCMS m/z=369.2 [M+H]$^+$ 9. Synthesis of 3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide

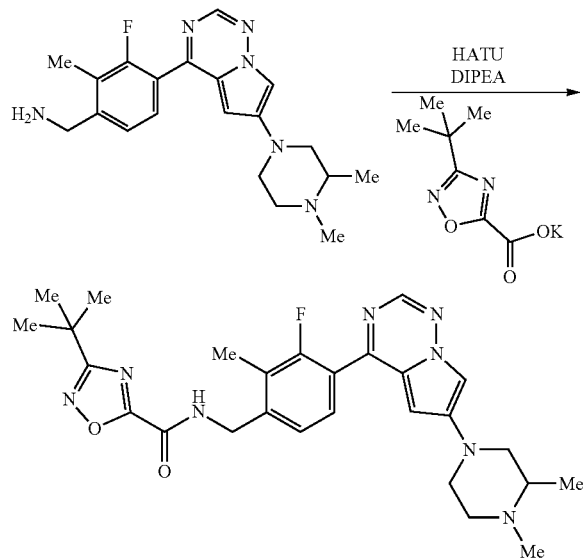

A mixture of (4-(6-(3,4-dimethylpiperazin-1-yl)pyrrolo[2,1-f][1,2,4]triazin-4-yl)-3-fluoro-2-methylphenyl)methanamine trifluoroacetate (131 mg, 0.36 mmol), potassium 3-(tert-butyl)-1,2,4-oxadiazole-5-carboxylate (89 mg, 0.43 mmol), HATU (163 mg, 0.43 mmol) and DIPEA (184 mg, 1.4 mmol) in DCM (2 mL) was stirred at RT for 16 h. The crude was filtrated through Celite® and the filtrate concentrated in vacuo. The crude was purified by silica gel column chromatography (0-30% MeOH/DCM) to afford the title compound (130 mg, 70%). LCMS m/z=521.3 [M+H]$^+$ 10. Synthesis of (R)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide and (S)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide

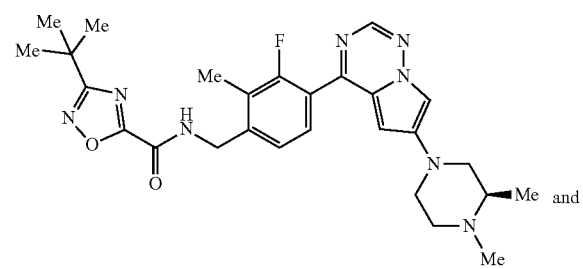

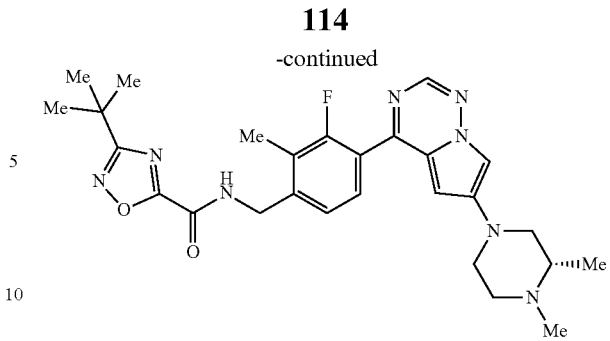

Absolute Stereochemistry Arbitrarily Assigned 3-(tert-Butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide (130 mg) was purified by chiral SFC (CHIRALPAK AD-H 30×250 mm, 5 μm; 30% EtOH+0.1% DEA in CO$_2$ to afford the title compounds.

Example 25; Peak 1: (R)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide (3.7 mg, 2.7%). LCMS m/z=521.3 [M+H]$^+$; $^1$H NMR (400 MHz, MeOH-d$_4$) δ: 8.35 (s, 1H), 7.85 (d, 1H), 7.54 (t, 1H), 7.36 (d, 1H), 6.30 (t, 1H), 4.70 (s, 2H), 3.43-3.60 (m, 2H), 2.86-3.00 (m, 3H), 2.51-2.60 (m, 1H), 2.44-2.49 (m, 1H), 2.42 (d, 3H), 2.35 (s, 3H), 1.38-1.48 (m, 9H), 1.17 (d, 3H).

Example 26; Peak 2: (S)-3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide (4.8 mg, 3.5%). LCMS m/z=521.3 [M+H]$^+$; $^1$H NMR (400 MHz, MeOH-d$_4$) δ: 8.33-8.38 (m, 1H), 7.82-7.89 (m, 1H), 7.51-7.59 (m, 1H), 7.32-7.41 (m, 1H), 6.25-6.33 (m, 1H), 4.67-4.73 (m, 2H), 3.46-3.59 (m, 2H), 2.88-2.99 (m, 2H), 2.52-2.59 (m, 1H), 2.44-2.50 (m, 1H), 2.40-2.43 (m, 3H), 2.36 (s, 3H), 1.43 (s, 9H), 1.15-1.19 (m, 3H).

Example 27 and Example 28. (R)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide and (S)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide

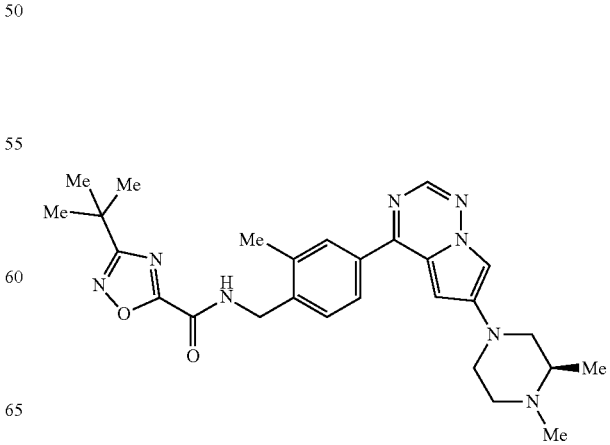

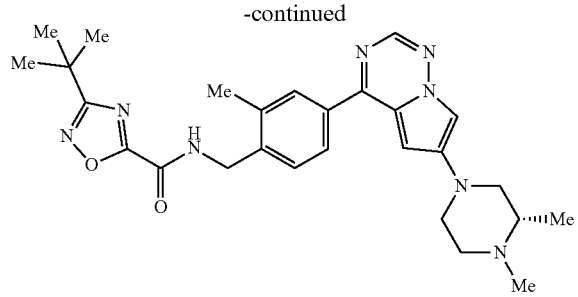

1. Synthesis of tert-butyl (4-(6-(3,4-dimethylpiperazin-1-yl)pyrrolo[2,1-f][1,2,4]triazin-4-yl)-2-methylbenzyl)carbamate

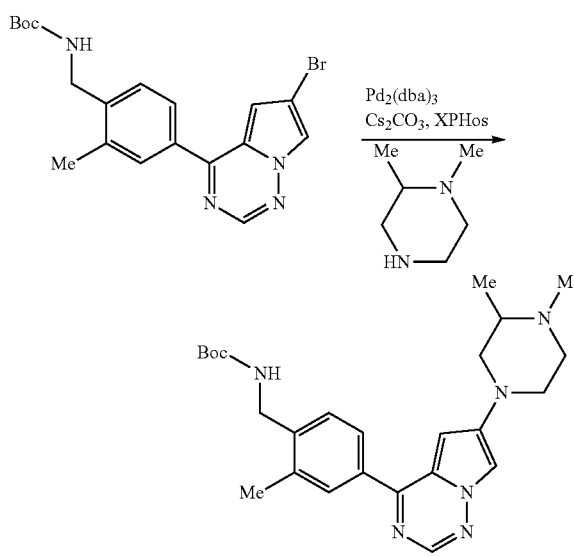

The crude product was obtained from tert-butyl (4-(6-bromopyrrolo[2,1-f][1,2,4]triazin-4-yl)-2-methylbenzyl)carbamate and 1,2-dimethylpiperazine following the procedure described in Example 2, Step 1. The crude product was purified by silica gel column chromatography (0-30% MeOH/DCM) to afford the title compound (265 mg, crude), which was used without further purification. LCMS m/z=451.2 [M+H]+

2. Synthesis of (4-(6-(3,4-dimethylpiperazin-1-yl)pyrrolo[2,1-f][1,2,4]triazin-4-yl)-2-methylphenyl)methanamine hydrochloride

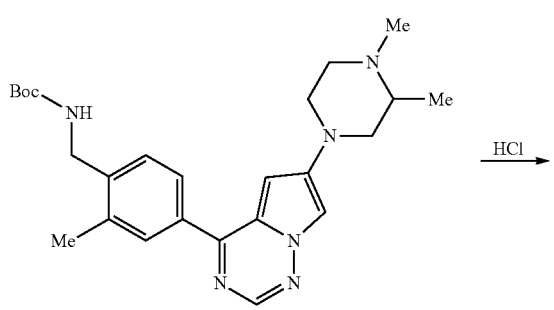

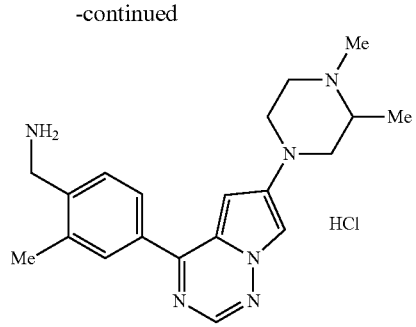

The title compound was obtained (230 mg, crude) from tert-butyl (4-(6-(3,4-dimethylpiperazin-1-yl)pyrrolo[2,1-f][1,2,4]triazin-4-yl)-2-methylbenzyl)carbamate following the procedure described in Example 16, Step 3. LCMS m/z=351.1 [M+H]+

3. Synthesis of 3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide The compound was obtained from (4-(6-(3,4-dimethylpiperazin-1-yl)pyrrolo[2,1-f][1,2,4]triazin-4-yl)-2-methylphenyl)methanamine hydrochloride and potassium 3-(tert-butyl)-1,2,4-oxadiazole-5-carboxylate following the procedure described in Example 4, Step 4. The residue was purified by silica gel column chromatography (0-30% MeOH/DCM) to afford the title compound (25 mg, 29%). LCMS m/z=503.2 [M+H]+

4. Synthesis of (R)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide and (S)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide

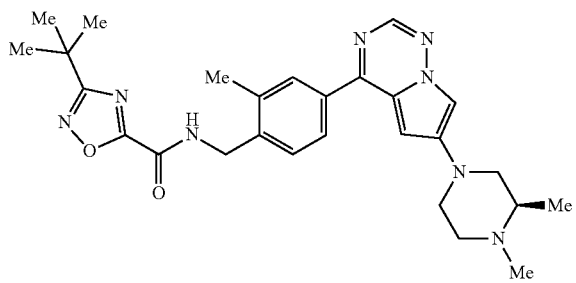

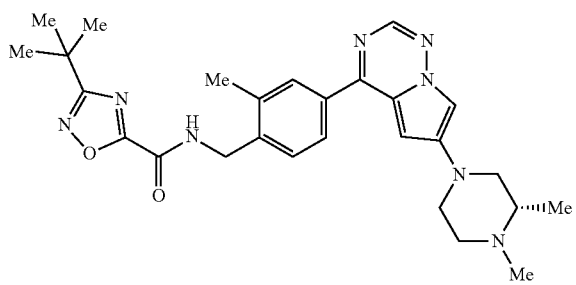

Absolute Stereochemistry Arbitrarily Assigned 3-(tert-Butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide (20 mg) was purified by chiral SFC (CHIRALPAK IA 30×250 mm, 5 μm; 40% MeOH+0.1% DEA in $CO_2$ to afford the title compounds.

Example 27; Peak 1: (R)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide (7.8 mg, 37%). LCMS m/z=504.3 [M+H]$^+$; $^1$H NMR (400 MHz, MeOH-d$_4$) δ: 8.29-8.40 (m, 1H), 7.75-7.92 (m, 3H), 7.53 (d, 1H), 6.61 (d, 1H), 4.70 (s, 2H), 3.45-3.63 (m, 2H), 2.73-3.01 (m, 3H), 2.42-2.62 (m, 5H), 2.28-2.39 (m, 4H), 1.38-1.48 (m, 9H), 1.19 (d, 3H).

Example 28; Peak 2: (S)-3-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-5-carboxamide (7.6 mg, 36%). LCMS m/z=504.3 [M+H]$^+$; $^1$H NMR (400 MHz, MeOH-d$_4$) δ: 8.30-8.39 (m, 1H), 7.76-7.90 (m, 3H), 7.49-7.56 (m, 1H), 6.62 (br s, 1H), 4.70 (s, 2H), 3.48-3.61 (m, 2H), 2.86-3.01 (m, 2H), 2.80 (br s, 1H), 2.45-2.63 (m, 5H), 2.24-2.39 (m, 4H), 1.40-1.45 (m, 9H), 1.19 (br d, 3H).

Example 29 and Example 30. (S)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide and (R)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide 1. Synthesis of tert-butyl (2-methyl-4-(6-(2-methylmorpholino)pyrrolo[2,1-f][1,2,4]triazin-4-yl)benzyl) carbamate

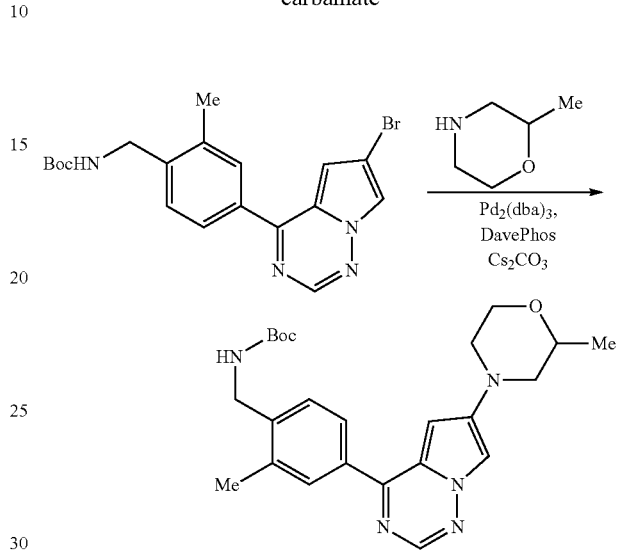

The title compound was prepared from tert-butyl (4-(6-bromopyrrolo[2,1-f][1,2,4]triazin-4-yl)-2-methylbenzyl) carbamate and 2-methylmorpholine using an analogous method to that described for Example 5, Step 1 and was obtained as a yellow solid (184 mg, 35%). LCMS m/z=438.2 [M+H]$^+$ 2. Synthesis of (2-methyl-4-(6-(2-methylmorpholino)pyrrolo[2,1-f][1,2,4]triazin-4-yl)phenyl)methanamine hydrochloride

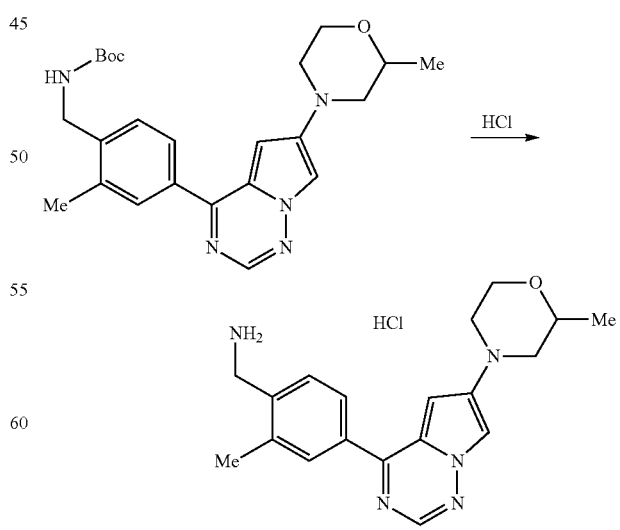

The title compound was prepared from tert-butyl (2-methyl-4-(6-(2-methylmorpholino)pyrrolo[2,1-f][1,2,4]

triazin-4-yl)benzyl)carbamate using an analogous method to that described for Example 5, Step 2 and was obtained as a red solid (168 mg, crude). LCMS m/z=338.2 [M+H]+

3. Synthesis of 5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide

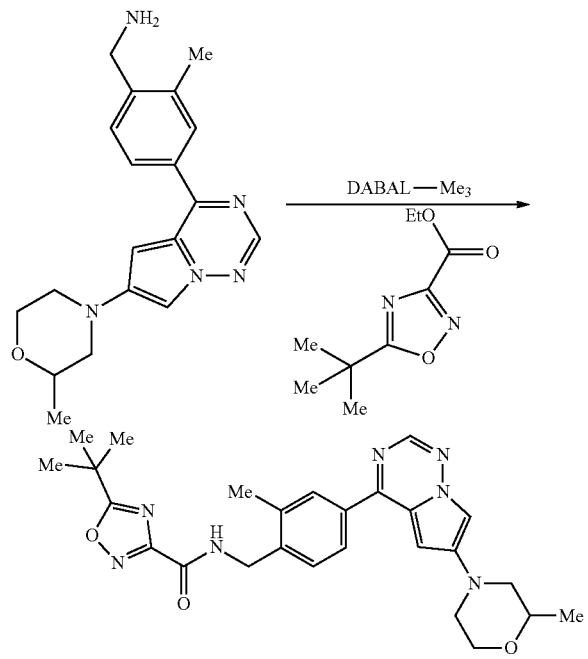

To a solution of (2-methyl-4-(6-(2-methylmorpholino)pyrrolo[2,1-f][1,2,4]triazin-4-yl)phenyl)methanamine hydrochloride (40 mg, 0.12 mmol) and ethyl 5-tert-butyl-1,2,4-oxadiazole-3-carboxylate (35 mg, 0.18 mmol) in THF (1.2 mL) at RT was added DABAL-Me3 (46 mg, 0.18 mmol). The reaction mixture was heated at 45° C. overnight. The reaction was diluted with MeOH, filtered, and concentrated in vacuo. The residue re-dissolved in MeOH, filtered and concentrated in vacuo. The residue was purified by silica gel column chromatography (0-100% EtOAc/Hept) to afford the title compound as a yellow solid (26 mg, 45%). LCMS m/z=490 [M+H]+

4. Synthesis of (S)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide and (R)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide

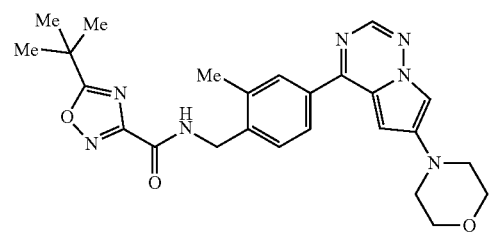 and 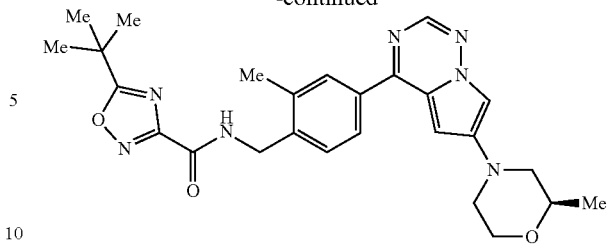

Absolute Stereochemistry Arbitrarily Assigned

The title compounds were obtained by chiral SFC (Chiralpak AD-H, 30×250 mm, 5 μm, 40% IPA+0.1% DEA in $CO_2$) purification of 5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide. Example 29, Peak 1; (S)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide (12 mg). LCMS m/z=490.2 [M+H]+; 1H NMR (500 MHz, DMSO-d6) δ: 9.59-9.44 (m, 1H), 8.64 (br d, 1H), 8.55 (s, 1H), 8.46 (s, 1H), 7.97 (br d, 1H), 7.87-7.95 (m, 2H), 7.39 (br d, 1H), 6.71 (br d, 1H), 4.50 (br d, 2H), 3.89 (br d, 1H), 3.59-3.71 (m, 3H), 3.51 (br d, 1H), 2.70 (br dd, 2H), 2.44 (s, 3H), 2.34-2.37 (m, 1H), 1.37 (s, 9H), 1.15 (br d, 3H).

Example 30, Peak 2; (R)-5-(tert-butyl)-N-(2-methyl-4-(6-(2-methylmorpholino)pyrrolo[2,1-f][1,2,4]triazin-4-yl)benzyl)-1,2,4-oxadiazole-3-carboxamide (12 mg). LCMS m/z=490.2 [M+H]+; 1H NMR (500 MHz, DMSO-d6) δ: 9.51 (t, 1H), 8.47 (s, 1H), 7.98 (d, 1H), 7.88-7.95 (m, 2H), 7.42 (d, 1H), 6.72 (d, 1H), 4.54 (d, 2H), 3.90 (br d, 1H), 3.59-3.72 (m, 3H), 3.52 (br d, 1H), 2.65-2.76 (m, 1H), 2.45 (s, 3H), 2.38-2.43 (m, 1H), 1.44 (s, 9H), 1.15 (d, 3H)

Example 31. (R)-5-(tert-butyl)-N-(1-(3-fluoro-2-methyl-4-(6-morpholinopyrrolo[2,1-f][1,2,4]triazin-4-yl)phenyl)ethyl)-1,2,4-oxadiazole-3-carboxamide

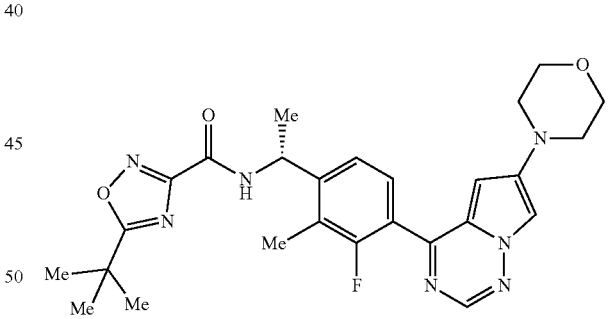

1. Synthesis of (S,E)-N-(1-(4-bromo-3-fluoro-2-methylphenyl)ethylidene)-2-methylpropane-2-sulfinamide

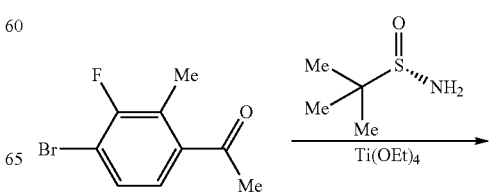

-continued

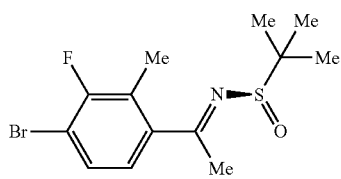

(S)-2-Methylpropane-2-sulfinamide (22.6 g, 186 mmol) and Ti(OEt)₄ (46.8 g, 205 mmol) was added to a solution of 1-(4-bromo-3-fluoro-2-methylphenyl)ethan-1-one (WO2015124877, 21.6 g, 93 mmol) in THF (400 mL) and the reaction was stirred at 75° C. for 24 h. The cooled reaction mixture was concentrated in vacuo, to reduce the volume to 1/3, then the mixture was filtered through a short pad of silica, eluting with Hept/EtOAc (4:1 to 1:1) to provide the title compound as a beige oil (28.0 g, 89%), which was used without further purification.

2. Synthesis of (S)—N—((R)-1-(4-bromo-3-fluoro-2-methylphenyl)ethyl)-2-methylpropane-2-sulfinamide

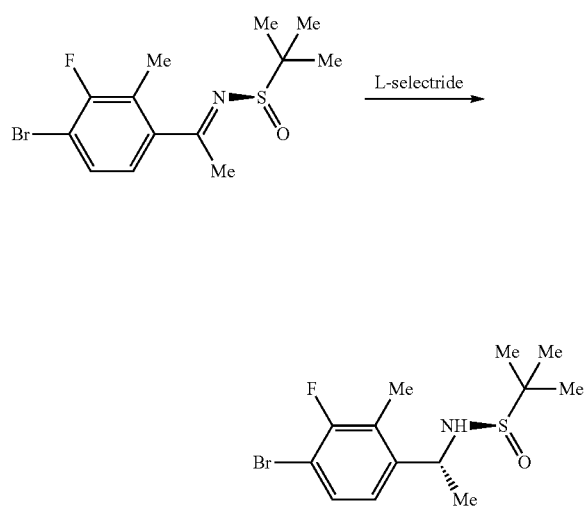

L-Selectride (251 mL, 251 mmol) was slowly added to a solution of (S,E)-N-(1-(4-bromo-3-fluoro-2-methylphenyl)ethylidene)-2-methylpropane-2-sulfinamide (28.0 g, 84 mmol) in THF (575 mL) cooled to −60° C. under N₂, so as to maintain the internal temperature below −55° C. The reaction mixture was warmed to RT over 3.5 h, MeOH (70 mL) was added slowly, and the mixture was stirred for 15 min. The reaction was cooled to −30° C., hydrogen peroxide (66.0 mL, 754 mmol) and NaOH (30.1 g, 754 mmol) in H₂O (100 mL) were added slowly. The mixture was then stirred at RT for 3 d. The mixture was diluted with EtOAc (1 L), washed with sat. aq. Na₂SO₃ (3×500 mL), dried (Na₂SO₄), filtered, and concentrated in vacuo. The crude product was purified by silica gel column chromatography (30% EtOAc/DCM) to afford the title product as a white solid (22 g, 78%). ¹H NMR (300 MHz, DMSO-d₆) δ: 7.51 (dd, 1H), 7.16 (dd, 1H), 5.40 (d, 1H), 4.59-4.55 (m, 1H), 2.24 (d, 3H), 1.40 (d, 3H), 1.07 (s, 9H)

3. Synthesis of (R)-1-(4-bromo-3-fluoro-2-methylphenyl)ethan-1-amine hydrochloride

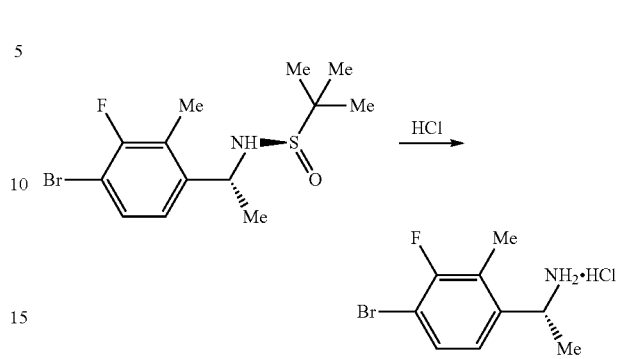

To a solution of (S)—N—((R)-1-(4-bromo-3-fluoro-2-methylphenyl)ethyl)-2-methylpropane-2-sulfinamide (20.9 g, 62.2 mmol) in dioxane (125 mL) was added 4 N HCl in dioxane (0.2 L, 622 mmol) and the reaction was stirred at RT for 1 h. The reaction mixture was concentrated in vacuo and azeotroped with toluene. The residue was triturated with Et₂O, the resulting suspension was filtered, and the solid was dried in vacuo to afford the title compound as a white solid (16.5 g, 99%). ¹H NMR (300 MHz, DMSO-d₆) δ: 8.65 (br s, 3H), 7.63 (dd, 1H), 7.39 (dd, 1H), 4.54-4.52 (m, 1H), 2.28 (d, 3H), 1.45 (d, 3H).

4. Synthesis of tert-butyl (R)-1-(4-bromo-3-fluoro-2-methylphenyl)ethyl)carbamate

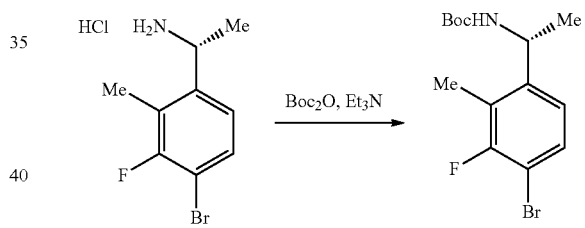

Et₃N (12.4 g, 123 mmol) and Boc₂O (16.1 g, 92.2 mmol) were added to an ice-cooled solution of (R)-1-(4-bromo-3-fluoro-2-methylphenyl)ethan-1-amine hydrochloride (16.5 g, 61.4 mmol) in DCM (275 mL) and the reaction was stirred at RT for 3 d. The reaction mixture was diluted with DCM (500 mL) and washed with water (300 mL). The organic layer was dried (Na₂SO₄), filtered and concentrated in vacuo. The residue was purified by silica gel chromatography (20% EtOAc/Hept) to afford the title product as a white-beige solid (18.9 g, 92%). ¹H NMR (300 MHz, DMSO-d₆) δ: 7.49 (dd, 1H), 7.10 (dd, 1H), 4.77-4.72 (m, 1H), 2.24 (d, 3H), 1.32 (s, 9H).

5. Synthesis of tert-butyl (R)-1-(3-fluoro-2-methyl-4-(4,4,5,5-tetramethyl-1,3,2-dioxaborolan-2-yl)phenyl)ethyl)carbamate

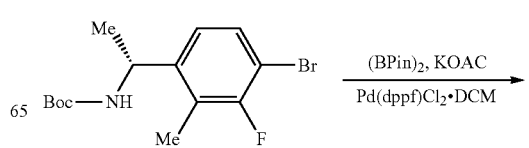

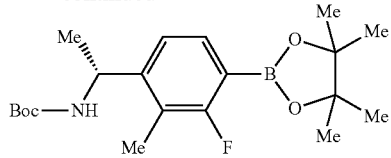

To a solution of tert-butyl (R)-1-(4-bromo-3-fluoro-2-methylphenyl)ethyl)carbamate (18.9 g, 57 mmol) and (bispinacolato)diboron (20.2 g, 80 mmol) in DMSO (220 mL) was added KOAc (16.7 g, 171 mmol) and Pd(dppf)Cl$_2$·DCM (2.32 g, 2.8 mmol). The reaction was degassed with N$_2$ for 10 min, and then stirred at 90° C. overnight. The cooled reaction was diluted with TBME (1 L) and filtered through Celite®. The filtrate was washed with water (3×500 mL), then dried (Na$_2$SO$_4$), filtered, and concentrated in vacuo. The residue was purified by silica gel column chromatography (20% EtOAc/Hept) to afford the title product as a beige oil (16.4 g, 76%). $^1$H NMR (300 MHz, DMSO-d$_6$) δ: 7.41 (dd, 1H), 7.16 (dd, 1H), 4.80-4.75 (m, 1H), 2.16 (s, 3H), 1.32-1.20 (m, 15H).

6. Synthesis of tert-butyl (R)-(1-(4-(6-bromopyrrolo[2,1-f][1,2,4]triazin-4-yl)-3-fluoro-2-methylphenyl)ethyl)carbamate

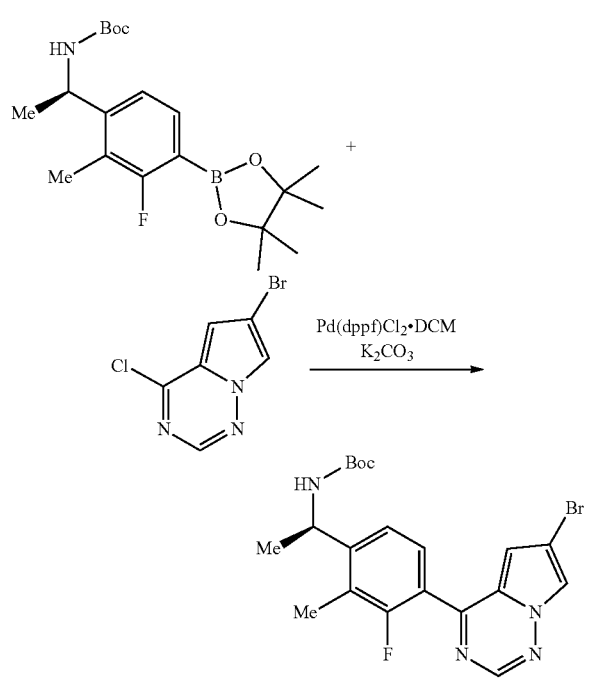

A mixture of tert-butyl (R)-1-(3-fluoro-2-methyl-4-(4,4,5,5-tetramethyl-1,3,2-dioxaborolan-2-yl)phenyl)ethyl)carbamate (569 mg, 1.5 mmol), 6-bromo-4-chloro-pyrrolo[2,1-f][1,2,4]triazine (384 mg, 1.7 mmol), Pd(dppf)Cl$_2$·DCM (123 mg, 0.15 mmol) and K$_2$CO$_3$ (415 mg, 3.0 mmol) in dioxane (12.8 mL) and water (3.0 mL) was purged with N$_2$ for 5 min. The reaction mixture was stirred at 100° C. under N$_2$ for 1 h. The cooled reaction was concentrated in vacuo, the residue partitioned between water (100 mL) and EtOAc (100 mL) and the layers were separated. The aqueous phase was extracted with EtOAc (2×50 mL), the combined organic layers were washed with brine (150 mL), dried (Na$_2$SO$_4$), filtered, and concentrated in vacuo. The residue was purified by silica gel column chromatography (0-100% EtOAc/Hept), then again (10% EtOAc/Hept) to afford the title compound as a yellow foam (117 mg, 17%). LCMS m/z=450.9 [M+H]$^+$ 7. Synthesis of tert-butyl (R)-(1-(3-fluoro-2-methyl-4-(6-morpholinopyrrolo[2,1-f][1,2,4]triazin-4-yl)phenyl)ethyl)carbamate

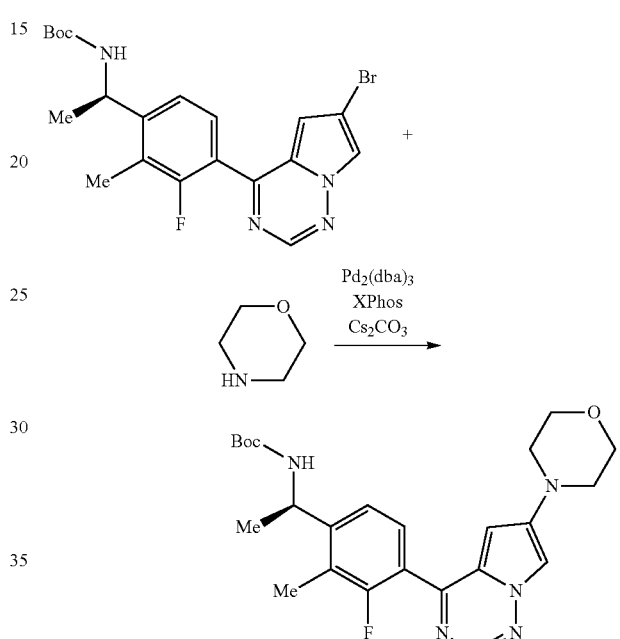

The title compound (44 mg, 37%) was obtained from tert-butyl (R)-(1-(4-(6-bromopyrrolo[2,1-f][1,2,4]triazin-4-yl)-3-fluoro-2-methylphenyl)ethyl)carbamate and morpholine following the procedure described in Example 2, Step 1. LCMS m/z=456.0 [M+H]$^+$; $^1$H NMR (500 MHz, MeOH-d$_4$) δ: 8.35 (s, 1H), 7.85 (d, 1H), 7.53 (br t, 1H), 7.35 (d, 1H), 6.33 (br s, 1H), 5.04-4.95 (m, 1H), 3.87-3.78 (m, 4H), 3.20-3.12 (m, 4H), 2.39 (d, 3H), 1.52-1.35 (m, 9H)

8. Synthesis of (R)-1-(3-fluoro-2-methyl-4-(6-morpholinopyrrolo[2,1-f][1,2,4]triazin-4-yl)phenyl)ethan-1-amine hydrochloride

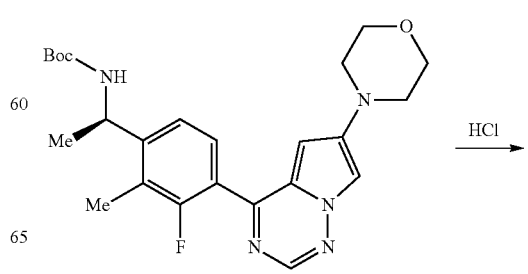

-continued

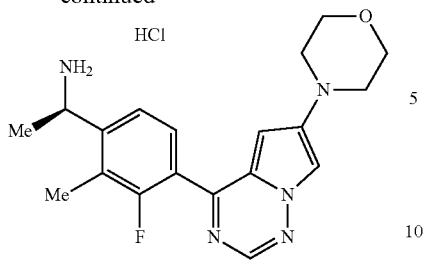

An HCl solution (0.1 mL, 1 M in EtOAc) was added to a solution of tert-butyl (R)-(1-(3-fluoro-2-methyl-4-(6-morpholinopyrrolo[2,1-f][1,2,4]triazin-4-yl)phenyl)ethyl)carbamate (44 mg, 0.1 mmol) in EtOAc (1 mL) and the reaction was stirred at RT for 24 h. Additional 1 M HCl in EtOAc (0.1 mL) was added and the reaction stirred for a further 18 h. The mixture was concentrated in vacuo to afford the title compound, which was carried forward without further purification. LCMS m/z=356.1 [M+H]$^+$ 9. Synthesis of (R)-5-(tert-butyl)-N-(1-(3-fluoro-2-methyl-4-(6-morpholinopyrrolo[2,1-f][1,2,4]triazin-4-yl)phenyl)ethyl)-1,2,4-oxadiazole-3-carboxamide

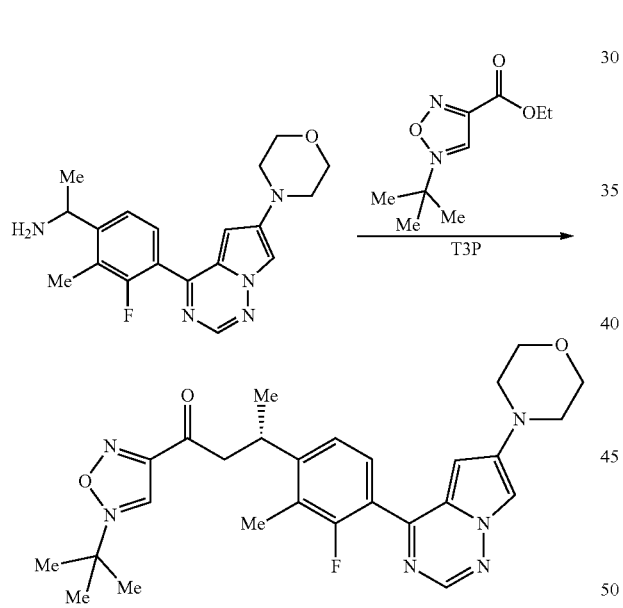

T3P® (37 mg, 0.14 mmol) was added to a mixture of (R)-1-(3-fluoro-2-methyl-4-(6-morpholinopyrrolo[2,1-f][1,2,4]triazin-4-yl)phenyl)ethan-1-amine hydrochloride (41 mg, 0.1 mmol) and ethyl 5-(tert-butyl)-1,2,4-oxadiazole-3-carboxylate (29 mg, 0.14 mmol) in THF (1.5 mL) at RT and the mixture was heated at 45° C. for 18 h. The reaction mixture was diluted with MeOH and filtered. The filtrate was concentrated in vacuo and the residue purified by prep-HPLC (Method C, 10-90%) to afford the title compound as a yellow solid (16.8 mg, 34%). LCMS m/z=508.0 [M+H]$^+$. $^1$H NMR (500 MHz, DMSO-$d_6$) δ: 9.60 (d, 1H), 8.50-8.47 (m, 1H), 8.04-8.01 (m, 1H), 7.59 (t, 1H), 7.46 (d, 1H), 6.35-6.32 (m, 1H), 5.38 (t, 1H), 3.76-3.69 (m, 4H), 3.17-3.08 (m, 4H), 2.41-2.31 (m, 3H), 1.56-1.46 (m, 3H), 1.46-1.36 (m, 9H).

Example 32. 5-(tert-butyl)-N-(2-methyl-4-(6-(4-(oxetan-3-yl)piperazin-1-yl)pyrrolo[2,1-f][1,2,4]triazin-4-yl)benzyl)-1,2,4-oxadiazole-3-carboxamide trifluoroacetate

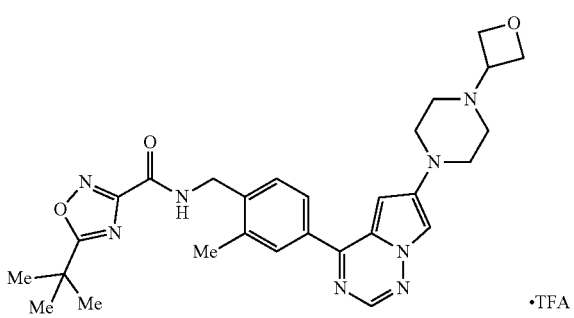 [SMILES: Cc1cc(-c2ncnn3cc(N4CCN(C5COC5)CC4)cc23)ccc1CNC(=O)c1noc(C(C)(C)C)n1]

1. Synthesis of benzyl 4-(4-(4-(((tert-butoxycarbonyl)amino)methyl)-3-methylphenyl)pyrrolo[2,1-f][1,2,4]triazin-6-yl)piperazine-1-carboxylate

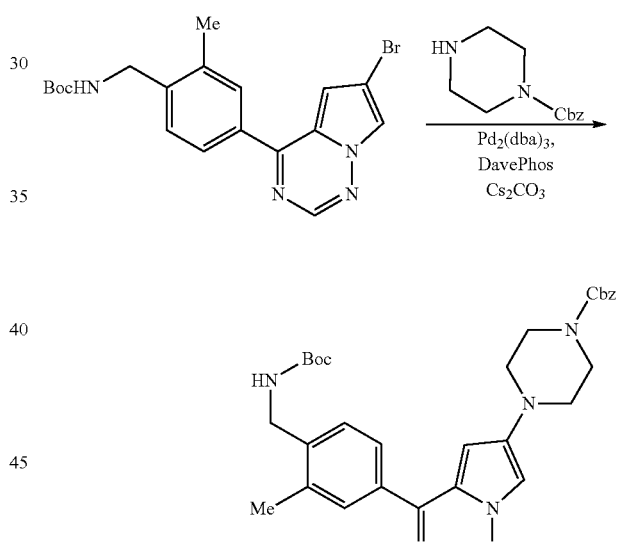

A mixture of tert-butyl (4-(6-bromopyrrolo[2,1-f][1,2,4]triazin-4-yl)-2-methylbenzyl)carbamate (300 mg, 0.72 mmol), benzyl piperazine-1-carboxylate (157 mg, 0.72 mmol), Pd$_2$(dba)$_3$ (66 mg, 0.07 mmol), DavePhos (57 mg, 0.14 mmol) and Cs$_2$CO$_3$ (703 mg, 2.2 mmol) in dioxane (12 mL) was purged with N$_2$ for 5 mins and then was stirred at 100° C. for 16 h. Additional benzyl piperazine-1-carboxylate (157 mg, 0.72 mmol), Pd$_2$(dba)$_3$ (55 mg, 0.06 mmol), DavePhos (47 mg, 0.12 mmol) and Cs$_2$CO$_3$ (782 mg, 2.4 mmol) were added and the reaction was stirred for a further 24 h at 110° C. The cooled reaction was filtered through Celite® and washed with EtOAc. The combined filtrates were concentrated in vacuo and the crude product purified by column chromatography (0-100% EtOAc/Hept) to afford the title compound as a yellow solid (277 mg, 69%). LCMS m/z=557.2 [M+H]$^+$

127

2. Synthesis of benzyl 4-(4-(4-(((tert-butoxycarbonyl)amino)methyl)-3-methylphenyl)pyrrolo[2,1-f][1,2,4]triazin-6-yl)piperazine-1-carboxylate

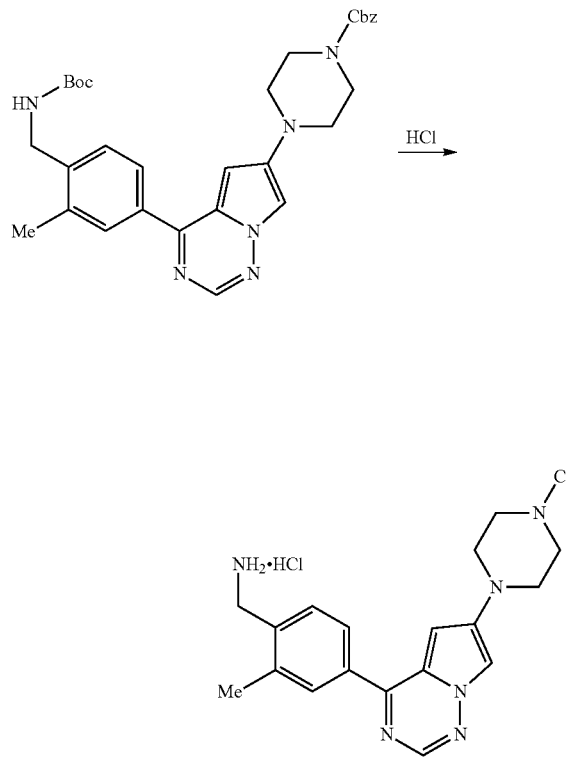

An HCl solution (0.5 mL, 4 M in MeOH) was added to benzyl 4-(4-(4-(((tert-butoxycarbonyl)amino)methyl)-3-methylphenyl)pyrrolo[2,1-f][1,2,4]triazin-6-yl)piperazine-1-carboxylate (277 mg, 0.5 mmol) in MeOH (2 mL) and the reaction was stirred overnight at RT. The mixture was concentrated in vacuo to afford the title compound (230 mg, 94%) which was used in the next step without further purification. LCMS m/z=457.1 [M+H]+

128

3. Synthesis of benzyl 4-(4-(4-((5-(tert-butyl)-1,2,4-oxadiazole-3-carboxamido)methyl)-3-methylphenyl)pyrrolo[2,1-f][1,2,4]triazin-6-yl)piperazine-1-carboxylate

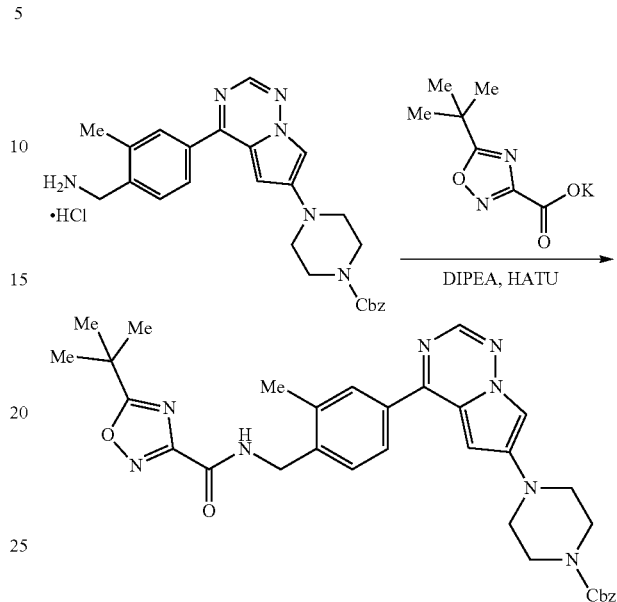

A vial was charged with benzyl 4-(4-(4-(((tert-butoxycarbonyl)amino)methyl)-3-methylphenyl)pyrrolo[2,1-f][1,2,4]triazin-6-yl)piperazine-1-carboxylate (217 mg, 0.4 mmol), potassium 5-tert-butyl-1,2,4-oxadiazole-3-carboxylate (138 mg, 0.7 mmol) and DCM (4 mL). DIPEA (170 mg, 1.3 mmol) was added and the reaction cooled to 0° C. before HATU (252 mg, 0.7 mmol) was added in a single portion. The reaction was stirred overnight at RT. The reaction was concentrated in vacuo and the residue purified by silica gel column chromatography (0-100% EtOAc:Hept) to afford the title compound as a light yellow solid (236 mg, 88%). LCMS m/z=609.2 [M+H]+, 4. Synthesis of 5-(tert-butyl)-N-(2-methyl-4-(6-(4-(oxetan-3-yl)piperazin-1-yl)pyrrolo[2,1-f][1,2,4]triazin-4-yl)benzyl)-1,2,4-oxadiazole-3-carboxamide trifluoroacetate

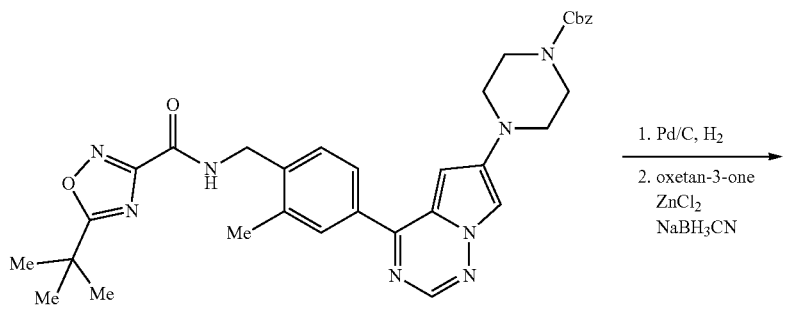

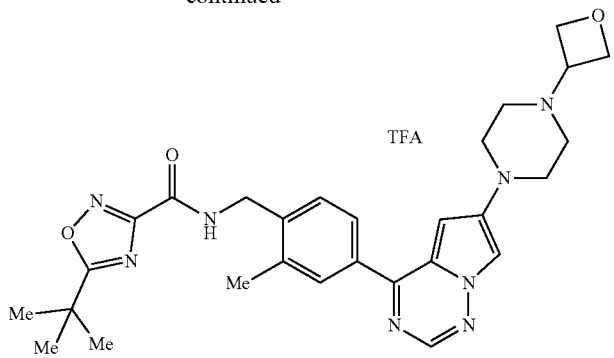

Pd/C (4 mg, 0.04 mmol) was added to a solution of benzyl 4-(4-(4-((5-(tert-butyl)-1,2,4-oxadiazole-3-carboxamido)methyl)-3-methylphenyl)pyrrolo[2,1-f][1,2,4]triazin-6-yl)piperazine-1-carboxylate (236 mg, 0.4 mmol) in MeOH (4 mL) and the reaction was stirred under $H_2$ for 16 h. The mixture was filtered through Celite®, and the filtrate concentrated in vacuo to provide a residue that was used without further purification. The residue was re-dissolved in MeOH (3 mL) and oxetan-3-one (43 mg, 0.6 mmol), $ZnCl_2$ (0.3 mL, 1.9 M in MeTHF) and $NaBH_3CN$ (38 mg, 0.6 mmol) were added and the mixture was heated at 50° C. for 4 h. The reaction mixture was concentrated in vacuo and the residue purified by prep-HPLC (Method B; 10-90%) to afford the title compound (57 mg, 34%). LCMS m/z=531.2 [M+H]$^+$; $^1$H NMR (400 MHz, $CDCl_3$) δ: 8.46-8.32 (m, 1H), 7.88-7.79 (m, 1H), 7.76-7.59 (m, 2H), 7.51-7.26 (m, 2H), 6.61-6.561 (m, 1H), 5.06-4.94 (m, 2H), 4.80-4.73 (m, 2H), 4.71-4.60 (m, 2H), 4.25-4.12 (m, 1H), 3.80-3.69 (m, 4H), 3.67-3.58 (m, 2H), 3.28-3.19 (m, 2H), 2.40 (s, 3H), 1.46-1.34 (s, 9H).

Example 33. N-(3-fluoro-2-methyl-4-(6-(1-methyl-1H-pyrazol-4-yl)pyrrolo[2,1-f][1,2,4]triazin-4-yl)benzyl)-5-(1-fluoro-2-methylpropan-2-yl)-1,2,4-oxadiazole-3-carboxamide 1. Synthesis of tert-butyl (4-(6-(1-methyl-1H-pyrazol-4-yl)pyrrolo[2,1-f][1,2,4]triazin-4-yl)-3-fluoro-2-methylbenzyl)carbamate

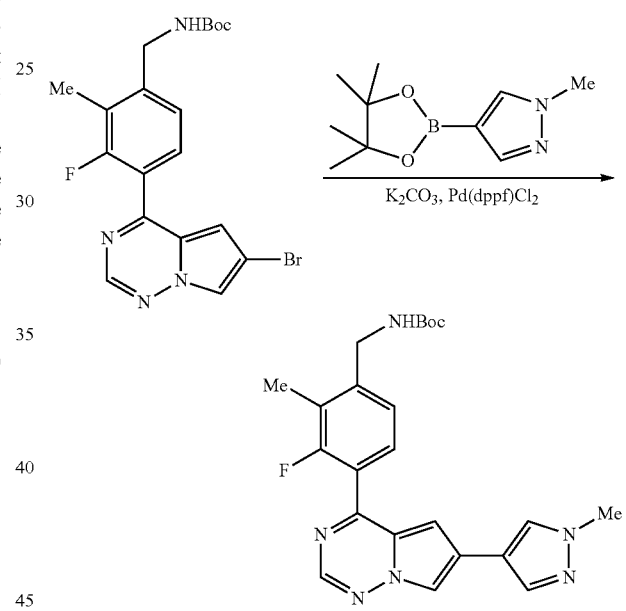

The crude compound was obtained from tert-butyl (4-(6-bromopyrrolo[2,1-f][1,2,4]triazin-4-yl)-3-fluoro-2-methylbenzyl)carbamate and 1-methylpyrazole-4-boronic acid pinacol ester following the procedure described in Example 10, Step 1. The crude was purified by silica gel column chromatography (0-50% EtOAc/petroleum ether) to afford the title compound as a yellow solid (290 mg, 72%). LCMS m/z=437.2 [M+H]$^+$ 2. Synthesis of ethyl (E)-2-amino-2-(hydroxyimino)acetate

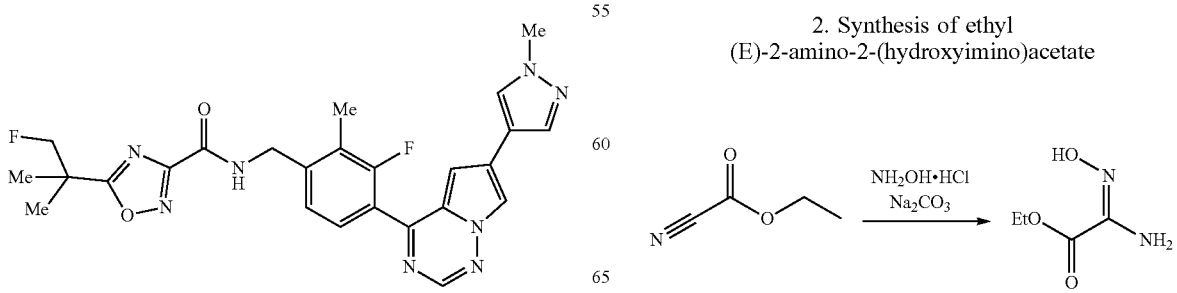

To a solution of ethyl carbonocyanidate (10 g, 101 mmol) in EtOH (75 mL) and H₂O (25 mL) was added Na₂CO₃ (10.7 g, 101 mmol) and hydroxylamine hydrochloride (7.0 g, 101 mmol) and the reaction was stirred at 25° C. for 12 h. The reaction mixture was poured into EtOAc (100 mL), filtered, and the filtrate concentrated in vacuo. The residue was re-dissolved in EtOAc (100 mL), filtered, and the filtrate concentrated in vacuo to give the title compound as a yellow solid (10 g, crude). ¹H NMR (400 MHz, CDCl₃) δ: 4.37-4.32 (m, 2H), 1.38-1.30 (m, 3H).

3. Synthesis of ethyl (E)-2-(3-hydroxy-2,2-dimethylpropanamido)-2-(hydroxyimino)acetate

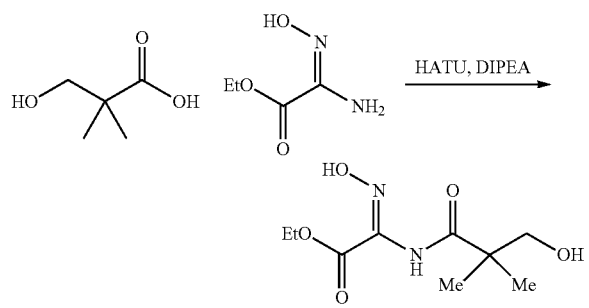

A mixture of ethyl (E)-2-amino-2-(hydroxyimino)acetate (500 mg, 3.8 mmol), 3-hydroxy-2,2-dimethylpropanoic acid (447 mg, 3.8 mmol), HATU (2.9 g, 7.6 mmol), and DIPEA (977 mg, 7.6 mmol) in DCM (10 mL) was stirred at 25° C. for 1 h. An additional portion of DCM (30 mL) was added and the organic phase was washed with H₂O (3×10 mL). The organic phase was dried (Na₂SO₄), filtered, and concentrated in vacuo. The crude product was purified by silica gel column chromatography (16-100% EtOAc/petroleum ether) to afford the title compound as a white solid (500 mg, 57%). LCMS m/z=233.1 [M+H]⁺. ¹H NMR (500 MHz, MeOH-d₄) δ: 4.37 (q, 2H), 3.66 (s, 2H), 1.38 (t, 3H), 1.28 (s, 6H).

4. Synthesis of ethyl 5-(1-hydroxy-2-methylpropan-2-yl)-1,2,4-oxadiazole-3-carboxylate

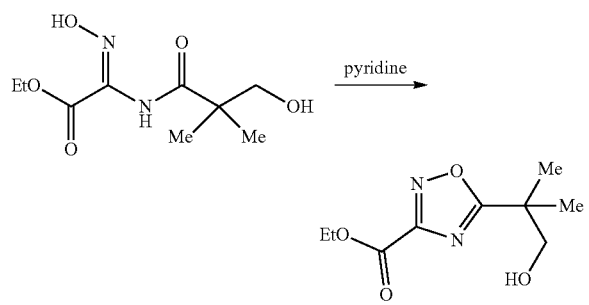

A solution of ethyl (E)-2-(3-hydroxy-2,2-dimethylpropanamido)-2-(hydroxyimino)acetate (500 mg, 2.2 mmol) in pyridine (10 mL) was heated to 80° C. and stirred at that temperature for 12 h. The reaction mixture was concentrated in vacuo and the residue purified by silica gel column chromatography (9-50% EtOAc/petroleum ether) to afford the title compound as a colorless oil (250 mg, 54%). LCMS m/z=215.1 [M+H]⁺. ¹H NMR (500 MHz, CDCl₃) δ: 4.50 (q, 2H), 3.81 (s, 2H), 1.46 (s, 6H), 1.28-1.14 (m, 3H).

5. ethyl 5-(2-methyl-1-(((trifluoromethyl)sulfonyl)oxy)propan-2-yl)-1,2,4-oxadiazole-3-carboxylate

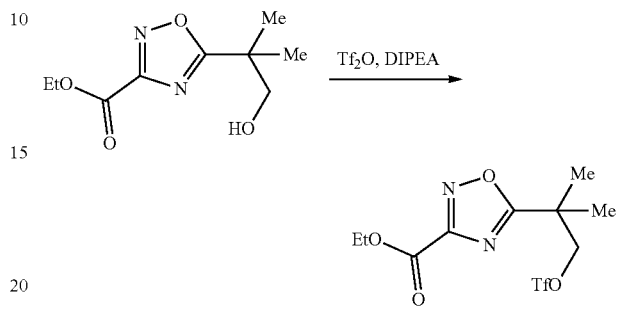

To a solution of ethyl 5-(1-hydroxy-2-methylpropan-2-yl)-1,2,4-oxadiazole-3-carboxylate (430 mg, 2.0 mmol) and DIPEA (390 mg, 3.0 mmol) in DCM (10 mL) at 0° C. was added Tf₂O (566 mg, 4.0 mmol). The reaction mixture was stirred at 25° C. for 2 h. An additional portion of DCM (40 mL) was added and the organic phase washed with H₂O (3×20 mL). The organic phase was dried (Na₂SO₄), filtered, and concentrated in vacuo. The crude product was purified by silica gel column chromatography (9-50% EtOAc/petroleum ether) to afford the title compound as a colorless oil (600 mg, 86%). LCMS m/z=347.1 [M+H]⁺

6. Synthesis of 5-(2-methyl-1-(((trifluoromethyl)sulfonyl)oxy)propan-2-yl)-1,2,4-oxadiazole-3-carboxylic Acid

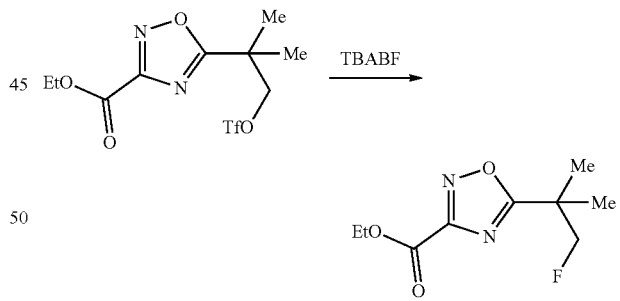

A solution of ethyl 5-(2-methyl-1-(((trifluoromethyl)sulfonyl)oxy)propan-2-yl)-1,2,4-oxadiazole-3-carboxylate (600 mg, 1.7 mmol) and tetrabutylammonium bifluoride (536 mg, 1.9 mmol) in THF (30 mL) was heated to 40° C. and stirred at that temperature for 12 h. The cooled reaction mixture was concentrated in vacuo and the crude product purified by silica gel column chromatography (9-25% EtOAc/petroleum ether) to afford the title compound as a colorless oil (330 mg, 88%). LCMS m/z=217.1 [M+H]⁺. ¹H NMR (500 MHz, CDCl₃) δ: 4.63 (s, 1H), 4.53-4.51 (m, 3H), 1.52 (s, 6H), 1.44 (t, 3H).

7. Synthesis of 5-(1-fluoro-2-methylpropan-2-yl)-1,2,4-oxadiazole-3-carboxylic Acid

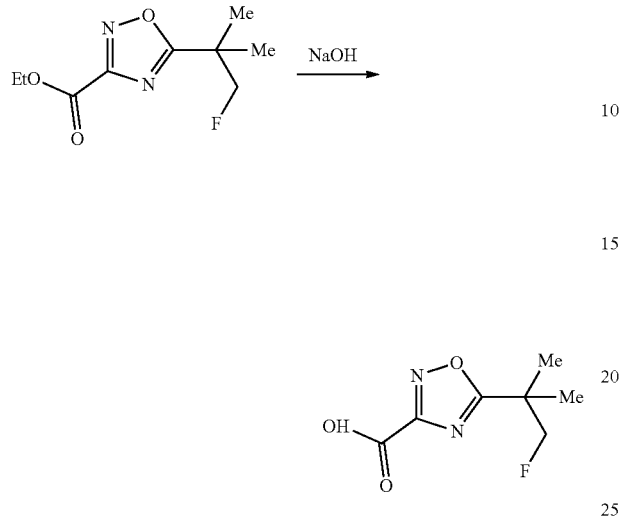

To a solution of ethyl 5-(1-fluoro-2-methylpropan-2-yl)-1,2,4-oxadiazole-3-carboxylate (300 mg, 1.4 mmol) in MeOH (20 mL) was added a solution of NaOH (111 mg, 2.8 mmol) in $H_2O$ (10 mL) and the reaction was stirred at RT for 2 h. The pH of the reaction was adjusted to 6 with the addition of 1 M HCl solution. The reaction mixture was concentrated in vacuo to remove MeOH and the aqueous phase was lyophilized to give the title compound as a white solid (300 mg, crude) that was used without further purification.

8. Synthesis of 5-(1-fluoro-2-methylpropan-2-yl)-1,2,4-oxadiazole-3-carbonyl chloride

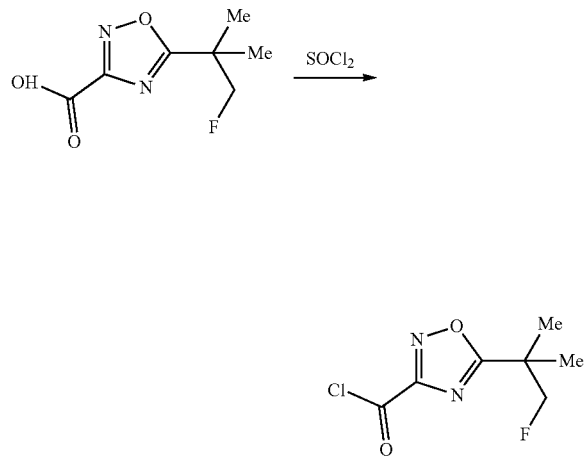

The title compound was obtained from 5-(1-fluoro-2-methylpropan-2-yl)-1,2,4-oxadiazole-3-carboxylic acid, following the procedure described in Example 34, Step 7. The crude material was carried forward without further purification (Example 33, Step 10).

9. Synthesis of (3-fluoro-2-methyl-4-(6-(1-methyl-1H-pyrazol-4-yl)pyrrolo[2,1-f][1,2,4]triazin-4-yl)phenyl)methanamine hydrochloride

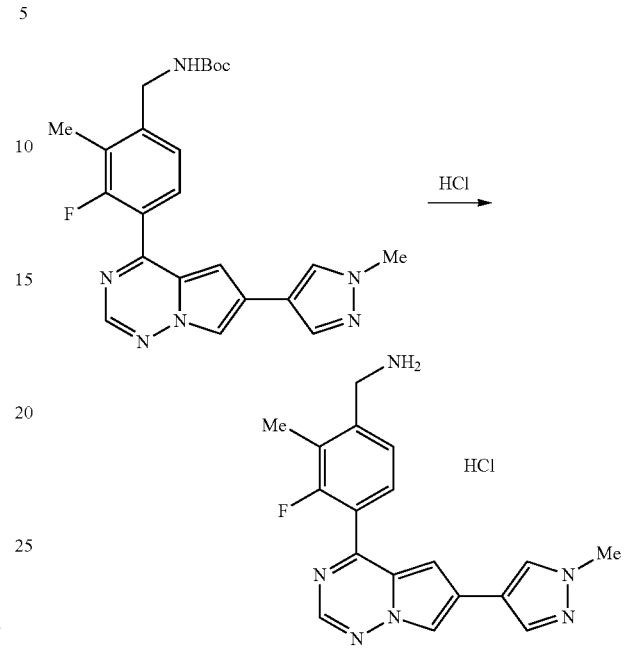

To tert-butyl (4-(6-(1-methyl-1H-pyrazol-4-yl)pyrrolo[2,1-f][1,2,4]triazin-4-yl)-3-fluoro-2-methylbenzyl)carbamate (290 mg, 0.7 mmol) was added an HCl solution (10 mL, 4 M in EtOAc). The reaction was stirred at 20° C. for 1 h. The mixture was concentrated in vacuo to afford the title compound as a yellow solid (240 mg, crude), which was used in next step without further purification. LCMS m/z=337.1 $[M+H]^+$

10. Synthesis of N-(3-fluoro-2-methyl-4-(6-(1-methyl-1H-pyrazol-4-yl)pyrrolo[2,1-f][1,2,4]triazin-4-yl)benzyl)-5-(1-fluoro-2-methylpropan-2-yl)-1,2,4-oxadiazole-3-carboxamide

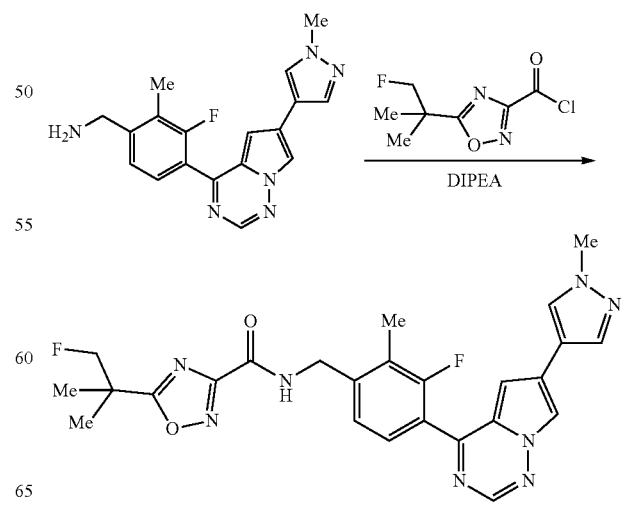

5-(1-fluoro-2-methylpropan-2-yl)-1,2,4-oxadiazole-3-carbonyl chloride (117 mg, 0.6 mmol) was added slowly to a solution of (3-fluoro-2-methyl-4-(6-(1-methyl-1H-pyrazol-4-yl)pyrrolo[2,1-f][1,2,4]triazin-4-yl)phenyl)methanamine hydrochloride (95 mg, 0.3 mmol) and DIPEA (73 mg, 0.6 mmol) in DCM (35 mL) and the mixture was stirred at 20° C. for 1 h. The mixture was concentrated in vacuo and the residue purified by prep-HPLC (Method E 48-75%) to give the title compound as a yellow solid (33 mg, 23%). LCMS m/z=507.0 [M+H]$^+$; $^1$H NMR (500 MHz, DMSO-d$_6$) δ: 9.64 (t, 1H), 8.60 (s, 1H), 8.50 (d, 1H), 8.19 (s, 1H), 7.92 (s, 1H), 7.62 (t, 1H), 7.31 (d, 1H), 7.02 (s, 1H), 4.70-4.59 (m, 4H), 3.86 (s, 3H), 2.38-2.37 (m, 3H), 1.47 (d, 6H).

Example 34. 5-(tert-butyl)-N-(4-(6-morpholinopyrrolo[2,1-f][1,2,4]triazin-4-yl)-2-(trifluoromethyl)benzyl)-1,2,4-oxadiazole-3-carboxamide hydrochloride

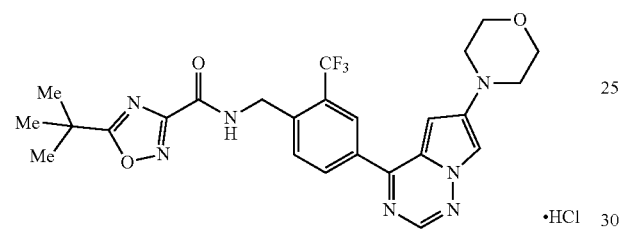

1. Synthesis of tert-butyl (4-(6-bromopyrrolo[2,1-f][1,2,4]triazin-4-yl)-2-(trifluoromethyl)benzyl)carbamate

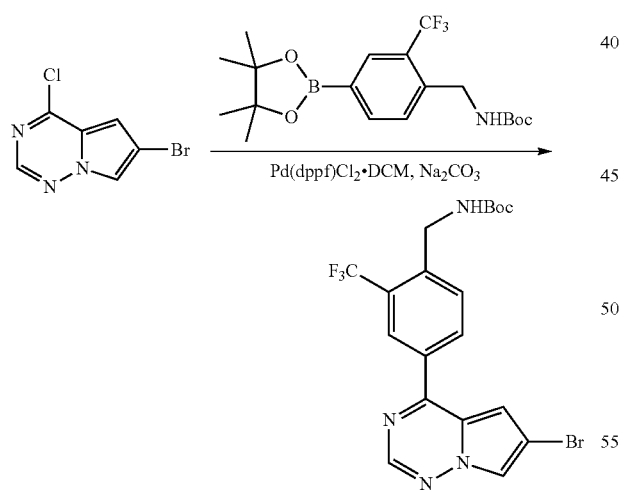

To a solution of tert-butyl (2-(trifluoromethyl)-4-(4,4,5,5-tetramethyl-1,3,2-dioxaborolan-2-yl)benzyl)carbamate (WO2015089327 Example 114, 400 mg, 1.0 mmol) and 6-bromo-4-chloropyrrolo[2,1-f][1,2,4]triazine (580 mg, 2.5 mmol) in a mixture of dioxane (4 mL) and water (1 mL) was added Na$_2$CO$_3$ (211 mg, 2.0 mmol) and Pd(dppf)Cl$_2$·DCM (122 mg, 0.15 mmol) at 25° C. The reaction mixture was stirred at 90° C. under N$_2$ for 5 h. The reaction mixture was concentrated in vacuo and the residue was purified by silica gel chromatography (petroleum ether/EtOAc=12:1 to 5:1) to give the title compound as a grey solid (250 mg, 53%). LCMS m/z=471.1 [M+H]$^+$ 2. Synthesis of tert-butyl (4-(6-morpholinopyrrolo[2,1-f][1,2,4]triazin-4-yl-2-trifluoromethyl)benzyl)carbamate

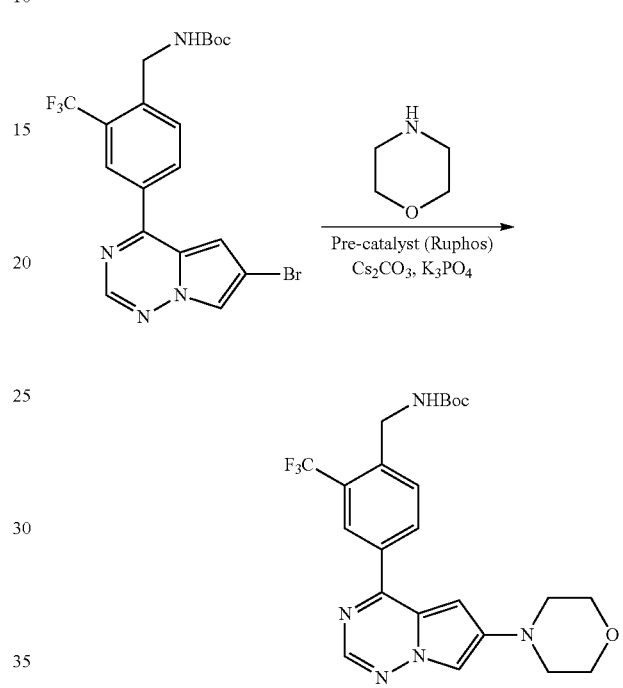

To a solution of morpholine (479 mg, 5.5 mmol) and tert-butyl (4-(6-bromopyrrolo[2,1-f][1,2,4]triazin-4-yl)-2-(trifluoromethyl)benzyl)carbamate (520 mg, 1.1 mmol) in dioxane (15 mL) was added K$_3$PO$_4$ (467 mg, 2.2 mmol), Cs$_2$CO$_3$ (717 mg, 2.2 mmol) and RuPhos-Pd G1 methyl t-butyl ether adduct (90 mg, 0.11 mmol) at 20° C. The reaction mixture was stirred at 100° C. under N$_2$ for 12 h. The reaction mixture was concentrated in vacuo and the residue was purified by silica gel chromatography (petroleum ether/EtOAc=10:1 to 2:1) to give the title compound as a yellow solid (180 mg, 34%). LCMS m/z=478.2 [M+H]$^+$ 3. Synthesis of (4-(6-morpholinopyrrolo[2,1-f][1,2,4]triazin-4-yl)-2-(trifluoromethyl)phenyl)methanamine hydrochloride

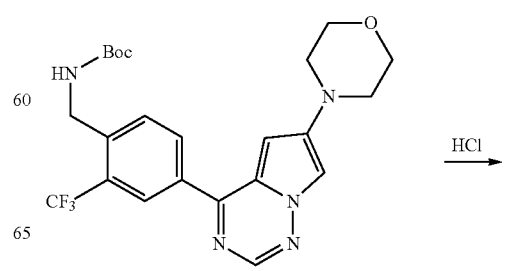

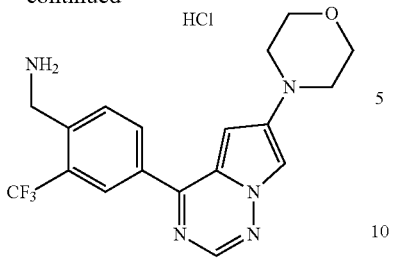

tert-butyl (4-(6-morpholinopyrrolo[2,1-f][1,2,4]triazin-4-yl-2-trifluoromethyl)benzyl)carbamate (60 mg, 0.13 mmol) was added into an HCl solution (12 mL, 1M in EtOAc) at 20° C. The reaction mixture was stirred at 20° C. for 1 h and then concentrated in vacuo to afford the title compound as a yellow solid (40 mg) which was used for the next step without further purification (Example 34, Step 8). LCMS m/z=361.1 [M−NH$_2$]$^+$ 4. Synthesis of ethyl (Z)-2-amino-2-((pivaloyloxy)imino)acetate

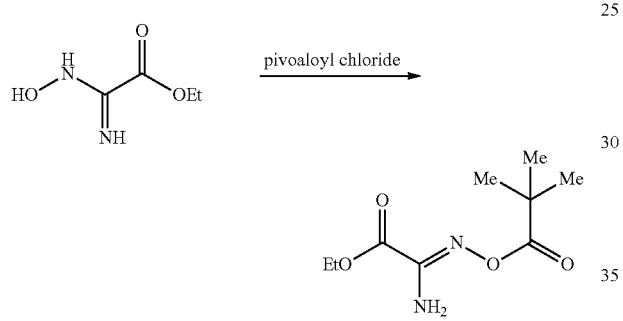

Pivaloyl chloride (33.5 mL, 272 mmol) was added dropwise over a period of 15 min to an ice cooled suspension of ethyl 2-(hydroxyamino)-2-iminoacetate (30.0 g, 227 mmol) in DCM (500 mL) and the reaction was stirred at RT for 4 h. Additional pivaloyl chloride (16.5 mL, 136 mmol) was added and the reaction stirred for a further 18 h. Additional pivaloyl chloride (16.5 mL, 136 mmol) was added and the reaction stirred for a further 24 h. The mixture was diluted with DCM (200 mL) and washed with water (200 mL). The aqueous layer was extracted with DCM (3×200 mL). The combined organic layers were dried (Na$_2$SO$_4$), filtered, and the filtrate concentrated in vacuo. The residue was suspended in Et$_2$O (100 mL), the resulting solid filtered off, washed with Et$_2$O and dried in air to afford the title compound as white crystals (24.5 g, 50%). $^1$H NMR (300 MHz, CDCl$_3$) δ: 5.38 (br s, 2H), 4.36 (q, 2H), 1.36 (t, 3H), 1.28 (s, 9H).

5. Synthesis of ethyl 5-(tert-butyl)-1,2,4-oxadiazole-3-carboxylate

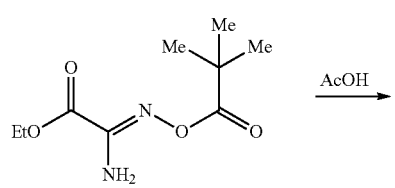

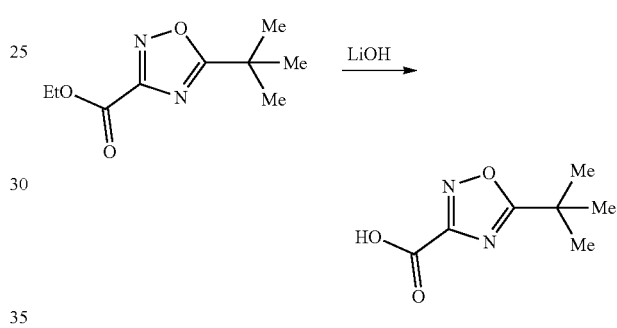

Ethyl (Z)-2-amino-2-((pivaloyloxy)imino)acetate (24.5 g, 113 mmol) was suspended in AcOH (50 ml) and the reaction was heated to 120° C. (external temperature) for 20 h. The cooled mixture was concentrated in vacuo and then azeotroped with toluene. The residue was dissolved in EtOAc (100 mL) and the solution was washed with water (50 mL) and brine (50 mL). The organic solution was dried (Na$_2$SO$_4$), filtered, and concentrated in vacuo to afford the title compound as a colorless oil (19.8 g, 88%). $^1$H NMR (300 MHz, CDCl$_3$) δ: 4.51 (q, 2H), 1.48 (s, 9H), 1.41 (t, 3H).

6. Synthesis of 5-(tert-butyl)-1,2,4-oxadiazole-3-carboxylic Acid

To a solution of ethyl 5-(tert-butyl)-1,2,4-oxadiazole-3-carboxylate (34.5 g, 174 mmol) in MeOH (350 mL) was added (in one portion), a solution of LiOH·H$_2$O (14.6 g, 348 mmol) in water (35 mL) and the reaction was stirred for 2 h at RT. The reaction was concentrated in vacuo and the aqueous residue was acidified with conc. HCl until pH=2-3. The mixture was concentrated in vacuo and the oily residue was azeotroped with toluene (3×50 mL). 5% MeOH in DCM (500 mL) was added, the mixture was filtered, and the solid washed with 5% MeOH in DCM (3×100 mL). The filtrates were combined, dried (Na$_2$SO$_4$), filtered, and concentrated in vacuo to give the title compound as white solid (29.2 g, 89%). H NMR (300 MHz, DMSO-d$_6$) δ: 0.96 (s, 9H).

7. Synthesis of 5-(tert-butyl)-1,2,4-oxadiazole-3-carbonyl chloride

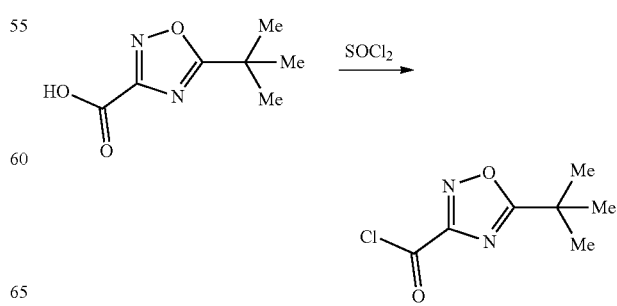

To a solution of 5-(tert-butyl)-1,2,4-oxadiazole-3-carboxylic acid (200 mg, 1.2 mmol) in DCM (10 mL) was added thionyl chloride (140 mg, 1.2 mmol) and DMF (200 μL) and the reaction was stirred at RT for 1 h. The reaction mixture was concentrated in vacuo to give the title compound (230 mg, crude), which was used directly without further purification.

8. Synthesis of 5-(tert-butyl)-N-(4-(6-morpholinopyrrolo[2,1-f][1,2,4]triazin-4-yl)-2-(trifluoromethyl)benzyl)-1,2,4-oxadiazole-3-carboxamide hydrochloride

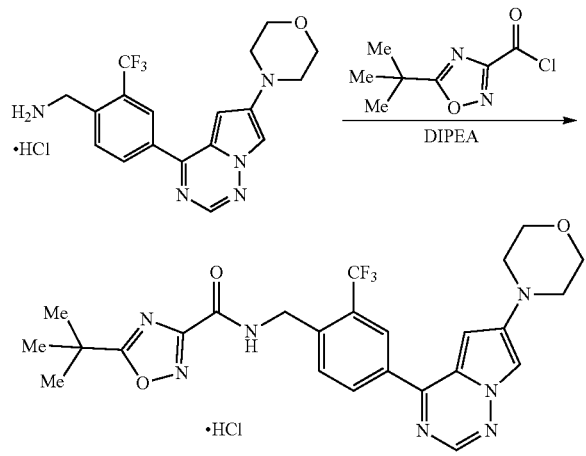

To a solution of (4-(6-morpholinopyrrolo[2,1-f][1,2,4]triazin-4-yl)-2-(trifluoromethyl)phenyl)methanamine hydrochloride (40 mg, 0.1 mmol) and DIPEA (50 mg, 0.4 mmol) in DCM (15 mL) was added 5-(tert-butyl)-1,2,4-oxadiazole-3-carbonyl chloride (55 mg, 0.3 mmol) at 20° C. The reaction mixture was stirred at 20° C. for 2 h. The reaction mixture was concentrated in vacuo and the residue purified by prep-HPLC (Method A, 54-74%) to give the title compound as a red solid (20 mg, 36%). LCMS m/z=530.3 [M+H]⁺. ¹H NMR (400 MHz, DMSO-$d_6$) δ: 9.68 (t, 1H), 8.53 (s, 1H), 8.42-8.37 (m, 2H), 8.12 (s, 1H), 7.68 (d, 1H), 6.80 (s, 1H), 4.72 (d, 2H), 3.74-3.72 (m, 4H), 3.18-3.16 (m, 4H), 1.43 (m, 9H).

Example 35. 5-(tert-butyl)-N-(2-methoxy-4-(6-(1-methyl-1H-pyrazol-4-yl)pyrrolo[2,1-f][1,2,4]triazin-4-yl)benzyl)-1,2,4-oxadiazole-3-carboxamide hydrochloride

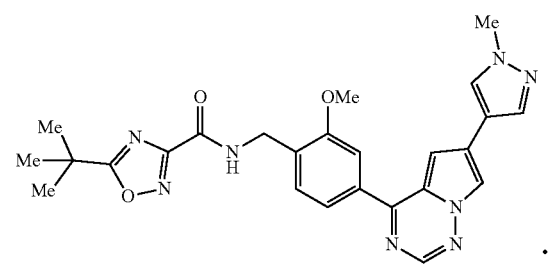

1. Synthesis of tert-butyl (4-bromo-2-methoxybenzyl)carbamate

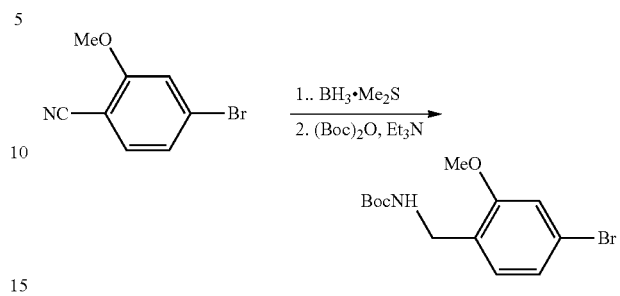

BH$_3$·Me$_2$S (17 mL, 10 M, 170 mmol) was added dropwise to a solution of 4-bromo-2-methoxybenzonitrile (18 g, 85 mmol) in THF (300 mL) and the reaction was stirred at 65° C. for 5 h. The cooled mixture was carefully quenched with MeOH (60 mL), followed by the addition of HCl (2 M, 50 mL) and the mixture was concentrated in vacuo. The residue was diluted with DCM (300 mL), extracted with H$_2$O (3×300 mL), the combined aqueous phase was basified to pH=9-10 with NaOH (aq.), and extracted with DCM (3×200 mL). The combined organic layers were concentrated to give (4-bromo-2-methoxyphenyl)methanamine (11 g, crude). Boc$_2$O (12.2 g, 56 mmol) was added dropwise to a solution of this solid in DCM (200 mL) and Et$_3$N (10.3 g, 102 mmol) and the reaction was stirred at 20° C. for 17 h. The mixture was concentrated in vacuo and the residue purified by silica gel column chromatography (petroleum ether/EtOAc=99.5:0.5 to 98:2) to afford the title compound as a pale-yellow solid (15 g, 93%). ¹H NMR (CDCl$_3$, 400 MHz) δ: 7.14-7.11 (m, 1H), 7.06-7.03 (m, 1H), 6.98-6.97 (m, 1H), 4.97 (br s, 1H), 4.23 (d, 2H), 3.83 (s, 3H), 1.43 (s, 9H).

2. Synthesis of tert-butyl (2-methoxy-4-(4,4,5,5-tetramethyl-1,3,2-dioxaborolan-2-yl)benzyl)carbamate

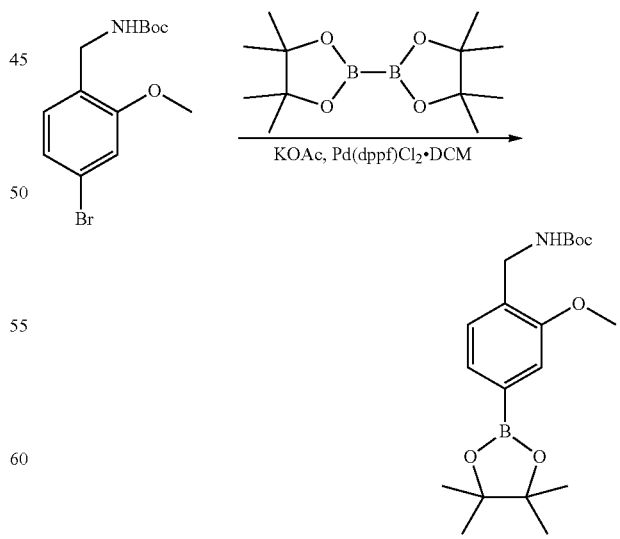

The title compound was prepared as a white solid (16 g, 93%) from tert-butyl (4-bromo-2-methoxybenzyl)carbamate following an analogous procedure to that described in Example 1, Step 1. LCMS m/z=364.1 [M+H]+; 1H NMR (CDCl3, 400 MHz) δ: 7.37-7.35 (m, 1H), 7.26-7.24 (m, 2H), 5.00 (br s, 1H), 4.29 (d, 2H), 3.86 (s, 3H), 1.41 (s, 9H), 1.32 (s, 12H).

3. Synthesis of tert-butyl (4-(6-bromopyrrolo[2,1-f][1,2,4]triazin-4-yl)-2-methoxybenzyl)carbamate

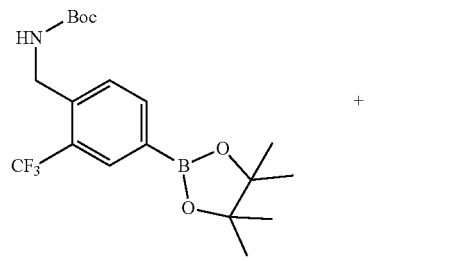

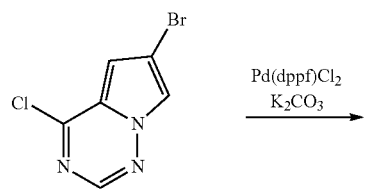

The title compound was obtained as a yellow solid (240 mg, 92%) from tert-butyl (2-methoxy-4-(4,4,5,5-tetramethyl-1,3,2-dioxaborolan-2-yl)benzyl)carbamate and 6-bromo-4-chloro-pyrrolo[2,1-f][1,2,4]triazine following the procedure described in Example 25, Step 6. LCMS m/z=433.2 [M+H]+

4. Synthesis of tert-butyl (2-methoxy-4-(6-(1-methyl-1H-pyrazol-4-yl)pyrrolo[2,1-f][1,2,4]triazin-4-yl)benzyl)carbamate

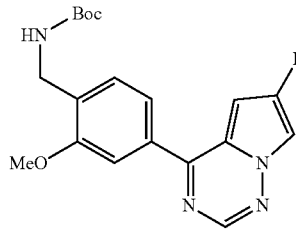

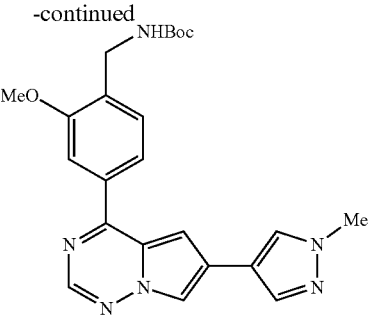

The crude product was obtained from tert-butyl (4-(6-bromopyrrolo[2,1-f][1,2,4]triazin-4-yl)-2-methoxybenzyl) carbamate and 1-methylpyrazole-4-boronic acid pinacol ester following the procedure described in Example 10, Step 1. The crude product was purified by silica gel column chromatography (petroleum ether/EtOAc=1:9) to afford the title compound as an orange solid (110 mg, 65%). LCMS m/z=435.2 [M+H]+

5. Synthesis of (2-methoxy-4-(6-(1-methyl-1H-pyrazol-4-yl)pyrrolo[2,1-f][1,2,4]triazin-4-yl)phenyl)methanamine hydrochloride

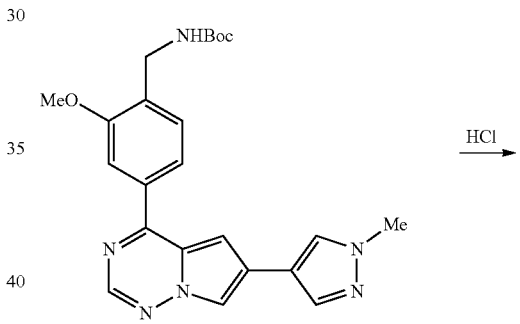

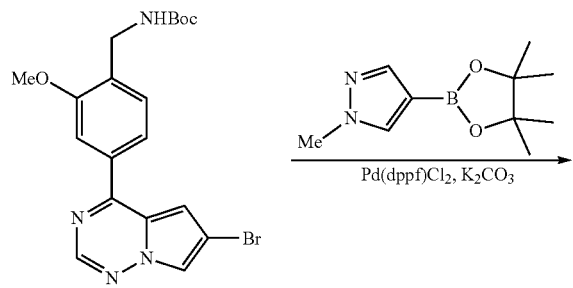

To a solution of tert-butyl (2-methoxy-4-(6-(1-methyl-1H-pyrazol-4-yl)pyrrolo[2,1-f][1,2,4]triazin-4-yl)benzyl) carbamate (110 mg, 0.25 mmol) in DCM (30 mL) was added an HCl solution (7 mL, 4 M in EtOAc) at 30° C. and the reaction was stirred for 2 h. The mixture was concentrated in vacuo to afford the title compound as an orange solid, which was used for the next step. LCMS m/z=335.1 [M+H]+

6. Synthesis of 5-(tert-butyl)-N-(2-methoxy-4-(6-(1-methyl-1H-pyrazol-4-yl)pyrrolo[2,1-f][1,2,4]triazin-4-yl)benzyl)-1,2,4-oxadiazole-3-carboxamide hydrochloride

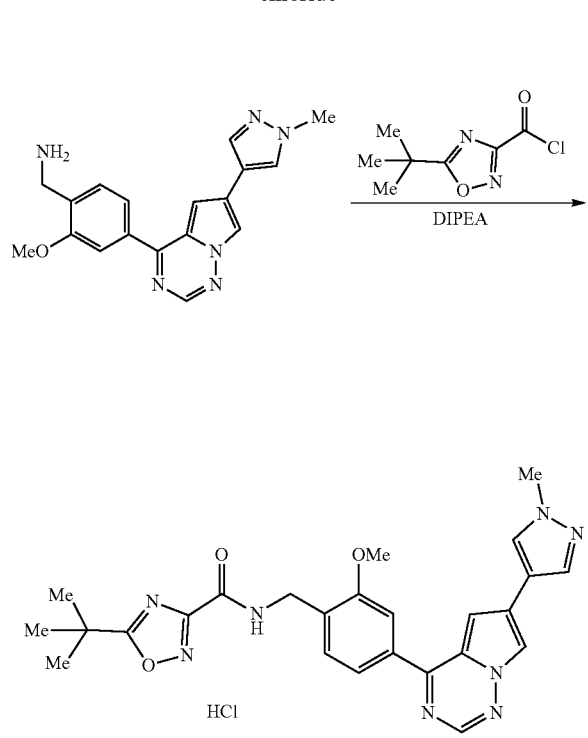

The compound was obtained from (2-methoxy-4-(6-(1-methyl-1H-pyrazol-4-yl)pyrrolo[2,1-f][1,2,4]triazin-4-yl)phenyl)methanamine hydrochloride and 5-(tert-butyl)-1,2,4-oxadiazole-3-carbonyl chloride following the procedure described in Example 34, Step 8. The crude product was purified by prep-HPLC (Method A, 44-64%) to afford the title compound as an orange solid (15.7 mg, 26%). LCMS m/z=487.1 [M+H]+; $^1$H NMR (400 MHz, DMSO-$d_6$) δ: 9.44 (t, 1H), 8.58 (s, 1H), 8.48 (s, 1H), 8.20 (s, 1H), 7.95 (s, 1H), 7.77-7.68 (m, 2H), 7.42-7.37 (m, 2H), 4.54 (d, 2H), 3.97 (s, 3H), 3.86 (s, 3H), 1.44 (s, 9H).

Example 36. 5-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,2,4-oxadiazole-3-carboxamide hydrochloride

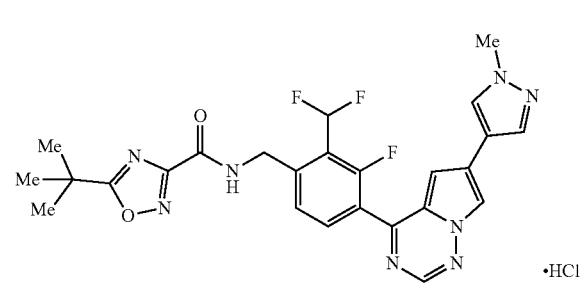 [SMILES: Cn1cc(-c2cc3c(-c4ccc(CNC(=O)c5noc(C(C)(C)C)n5)c(C(F)F)c4F)ncnn3c2)cn1 ; Cl]

1. Synthesis of 2-fluoro-3-nitrobenzaldehyde

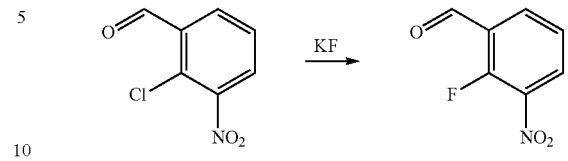

To a solution of 2-chloro-3-nitrobenzaldehyde (9.5 g, 51 mmol) in DMF (100 mL) was added KF (8.9 g, 154 mmol) and the reaction was stirred at 150° C. for 5 h. The cooled reaction mixture was concentrated in vacuo, the residue poured into H$_2$O (400 mL) and extracted with DCM (4×100 mL). The combined organic extracts were concentrated in vacuo and the crude material purified by silica gel column chromatography (petroleum ether/EtOAc=20:1) to give the title compound as a yellow oil (6.7 g, 77%). $^1$H NMR (400 MHz, CDCl$_3$) δ: 10.44 (s, 1H), 8.36-8.30 (m, 1H), 8.22-8.16 (m, 1H), 7.47 (dd, 1H).

2. Synthesis of 1-(difluoromethyl)-2-fluoro-3-nitrobenzene

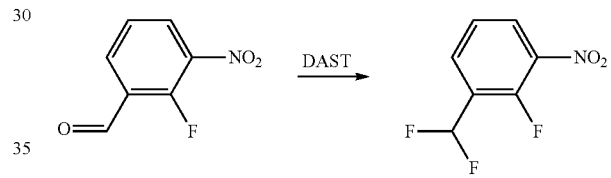

The title compound was obtained as an orange oil (6.6 g, 87%) from 2-fluoro-3-nitrobenzaldehyde following a similar procedure to that described in Example 65, Step 3. $^1$H NMR (400 MHz, CDCl$_3$) δ: 8.20 (t, 1H), 7.92 (t, 1H), 7.44 (t, 1H), 6.97 (t, 1H).

3. Synthesis of 3-(difluoromethyl)-2-fluoroaniline

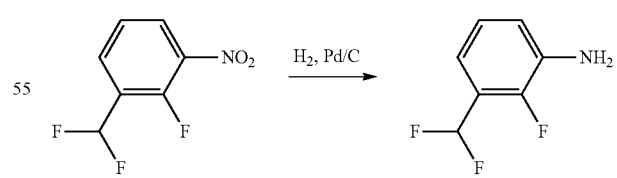

To a solution of 1-(difluoromethyl)-2-fluoro-3-nitrobenzene (6.6 g, 35 mmol) in MeOH (100 mL) was added Pd/C (1.4 g) and the reaction was stirred at 28° C. under an atmosphere of H$_2$ (15 psi) for 17 h. The mixture was filtered, and the filtrate concentrated in vacuo to give the title compound as a yellow oil (4.7 g, 83%). LCMS m/z=162.0 [M+H]+

4. Synthesis of 4-bromo-3-(difluoromethyl)-2-fluoroaniline

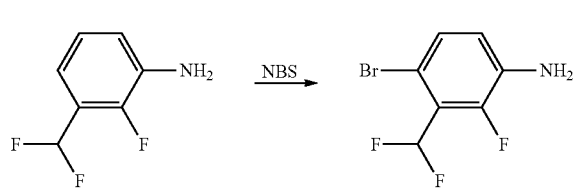

To a solution of 3-(difluoromethyl)-2-fluoroaniline (4.7 g, 29 mmol) in DCM (100 mL) was slowly added NBS (5.1 g, 29 mmol) and the reaction was stirred at 15° C. for 17 h. The reaction mixture was concentrated in vacuo and the crude material was purified by silica gel column chromatography (petroleum ether/EtOAc=98:2 to 91:9) to give the title compound as a brown solid (3.3 g, 47%). $^1$H NMR (400 MHz, CDCl$_3$) δ: 7.16 (dd, 1H), 6.99 (td, 1H), 6.79-6.73 (m, 1H), 3.87 (s, 2H).

5. Synthesis of Methyl 4-amino-2-(difluoromethyl)-3-fluorobenzoate

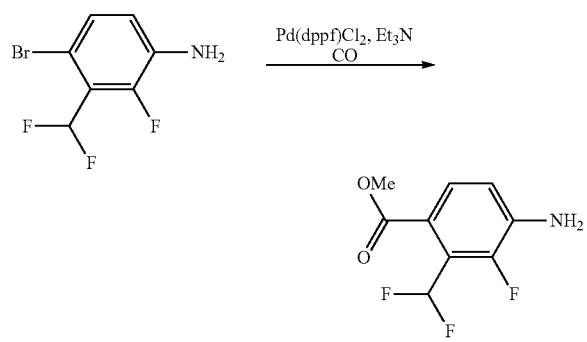

A solution of 4-bromo-3-(difluoromethyl)-2-fluoroaniline (3.1 g, 13 mmol), Pd(dppf)Cl$_2$ (945 mg, 1.3 mmol), and Et$_3$N (6.5 g, 65 mmol) in MeOH (100 mL) was stirred for 40 h at 80° C. under an atmosphere of CO (50 psi). The cooled reaction mixture was filtered, and the filtrate was concentrated in vacuo. The crude material was purified by silica gel column chromatography (petroleum ether/EtOAc=20:1) to give the title compound as an orange solid (2.2 g, 75%). LCMS m/z=220.0 [M+H]$^+$

6. Synthesis of Methyl 4-bromo-2-(difluoromethyl)-3-fluorobenzoate

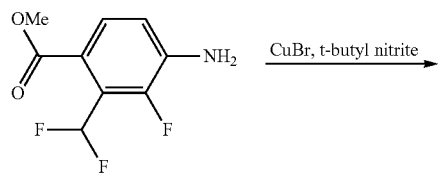

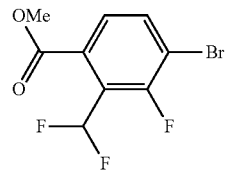

To a suspension of CuBr (2.55 g, 17.8 mmol) in MeCN (40 mL) was added tert-butyl nitrite (1.83 g, 17.8 mmol) at 15° C. A solution of methyl 4-bromo-2-(difluoromethyl)-3-fluorobenzoate (2.00 g, 8.9 mmol) in MeCN (20 mL) was added dropwise at 65° C. and the reaction was then stirred at that temperature for 17 h. The cooled mixture was concentrated in vacuo and the crude material was purified by silica gel column chromatography (petroleum ether/EtOAc=20:1) to give the title compound as a pale, yellow solid (1.7 g, 68%). $^1$H NMR (400 MHz, CDCl$_3$) δ: 7.77-7.73 (m, 1H), 7.64-7.61 (m, 1H), 7.62-7.42 (m, 1H), 3.95 (s, 3H).

7. Synthesis of (4-bromo-2-(difluoromethyl)-3-fluorophenyl)methanamine

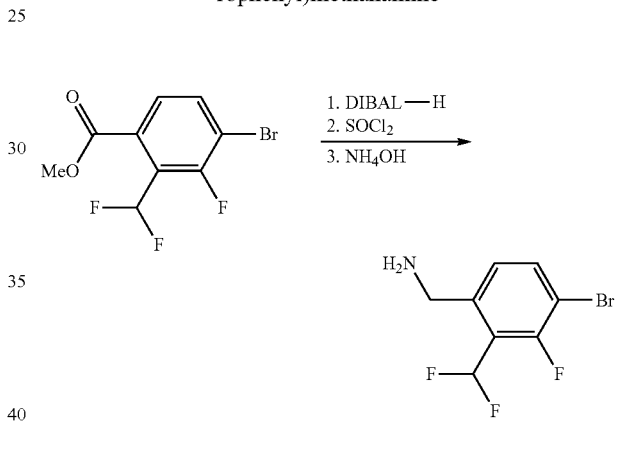

To a solution of methyl 4-bromo-2-(difluoromethyl)-3-fluorobenzoate (1.2 g, 4.2 mmol) in DCM (60 mL) in an EtOH-dry ice bath was slowly added DIBAL-H (1.0 M, 10.6 mL) and the reaction mixture was stirred at 10° C. for 17 h. H$_2$O (1 mL) was added, followed by a 10% NaOH solution (1 mL), more H$_2$O (1 mL) and Na$_2$SO$_4$. The reaction mixture was filtered and the filtrate was concentrated in vacuo to give (4-bromo-2-(difluoromethyl)-3-fluorophenyl)methanol (1.1 g, crude). SOCl$_2$ (2.5 g, 22 mmol) was added dropwise to a solution of this product (1.1 g, 4.3 mmol) in DCM (50 mL) and DMF (1 mL) and the reaction was stirred at 20° C. for 2 h. The reaction mixture was poured into H$_2$O (100 mL) and extracted with DCM (3×50 mL). The combined organic extracts were dried (Na$_2$SO$_4$), filtered, and concentrated in vacuo to give 1-bromo-4-(chloromethyl)-3-(difluoromethyl)-2-fluorobenzene (1.1 g, crude), which was carried forward without further purification. To a solution of 1-bromo-4-(chloromethyl)-3-(difluoromethyl)-2-fluorobenzene, (1.1 g, 4.0 mmol) in i-PrOH (60 mL) was added NH$_4$OH (100 mL) and the reaction stirred at 65° C. for 17 h. The cooled reaction mixture was concentrated in vacuo and the residue dissolved in DCM (100 mL). The organic phase was washed with H$_2$O (100 mL), dried (Na$_2$SO$_4$), filtered, and concentrated in vacuo to give the title compound (1.0 g, crude). LCMS m/z=236.9 [M−NH$_2$]$^+$

8. Synthesis of tert-butyl (4-bromo-2-(difluoromethyl)-3-fluorobenzyl)carbamate

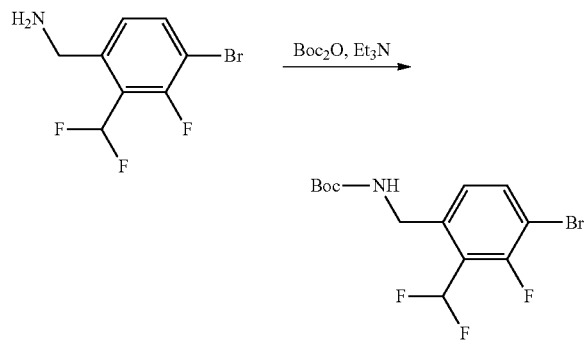

To a solution of (4-bromo-2-(difluoromethyl)-3-fluorophenyl)methanamine (1.0 g, 3.9 mmol) in DCM (30 mL) was added Et$_3$N (797 mg, 7.9 mmol), followed by Boc$_2$O (902 mg, 4.1 mmol) and the reaction was stirred at RT for 2 h. The mixture was poured into H$_2$O (100 mL), the layers separated, and the aqueous phase extracted with DCM (3×50 mL). The combined organic extracts were concentrated in vacuo and the crude material was purified by silica gel column chromatography (petroleum ether/EtOAc=20:1 to 10:1) to give the title compound as a yellow oil (900 mg, 78%). LCMS m/z=297.9 [M+H−t-Bu]$^+$

9. Synthesis of tert-butyl (3-fluoro-2-(difluoromethyl)-4-(4,4,5,5-tetramethyl-1,3,2-dioxaborolan-2-yl)benzyl)carbamate

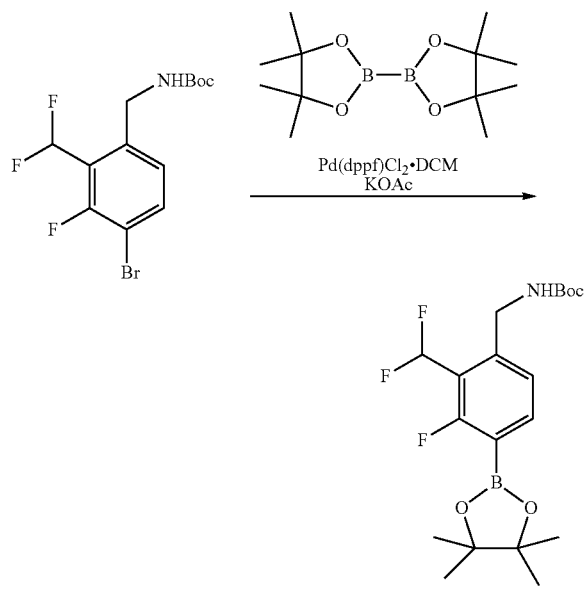

The title compound was prepared as a white solid (700 mg, 80%) from tert-butyl (4-bromo-2-(difluoromethyl)-3-fluorobenzyl)carbamate following the procedure described in Example 1, Step 1. $^1$H NMR (500 MHz, CDCl$_3$) δ: 7.81 (dd, 1H), 7.32 (d, 1H), 7.09 (t, 1H), 4.96 (t, 1H), 4.56 (d, 2H), 1.44 (s, 9H), 1.35 (s, 12H).

10. Synthesis of tert-butyl (4-(6-bromopyrrolo[2,1-f][1,2,4]triazin-4-yl)-2-(difluoromethyl)-3-fluorobenzyl)carbamate

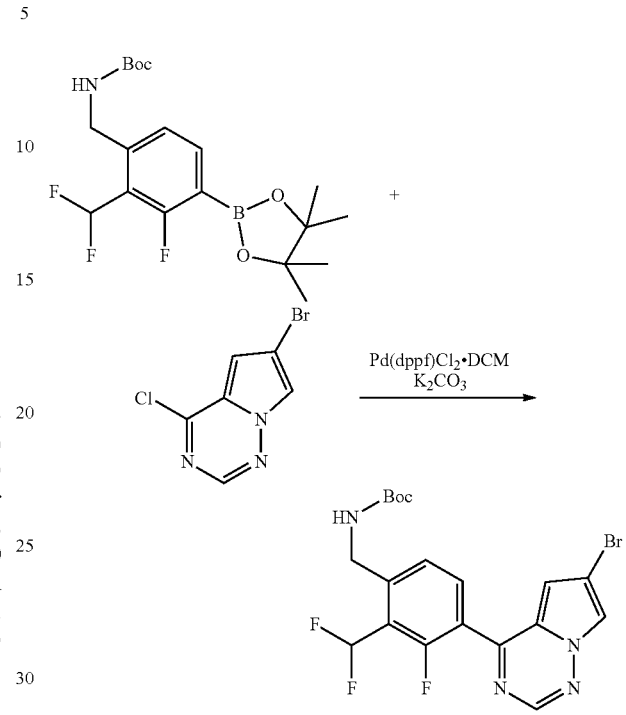

To a solution of tert-butyl (3-fluoro-2-(difluoromethyl)-4-(4,4,5,5-tetramethyl-1,3,2-dioxaborolan-2-yl)benzyl)carbamate (923 mg, 4.0 mmol) and 6-bromo-4-chloro-pyrrolo[2,1-f][1,2,4]triazine (760 mg, 1.9 mmol) in a mixture of dioxane (9 mL) and H$_2$O (1 mL) was added K$_2$CO$_3$ (524 mg, 3.8 mmol) and Pd(dppf)Cl$_2$·DCM (155 mg, 0.19 mmol) and the reaction mixture was stirred at 95° C. under N$_2$ for 4 h. The cooled reaction mixture was concentrated in vacuo and the crude product was purified by silica gel chromatography (petroleum ether/EtOAc=15:1 to 4:1) to afford the title compound (470 mg, 53% yield) as a yellow solid. LCMS m/z=471.1 [M+H]$^+$

11. Synthesis of tert-butyl (2-(difluoromethyl)-3-fluoro-4-(6-(1-methyl-1H-pyrazol-4-yl)pyrrolo[2,1-f][1,2,4]triazin-4-yl)benzyl)carbamate

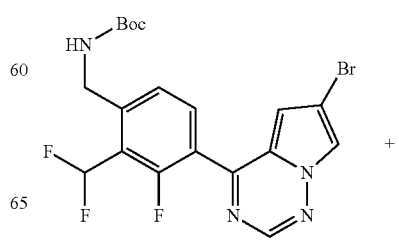

13. Synthesis of 5-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,2,4-oxadiazole-3-carboxamide hydrochloride

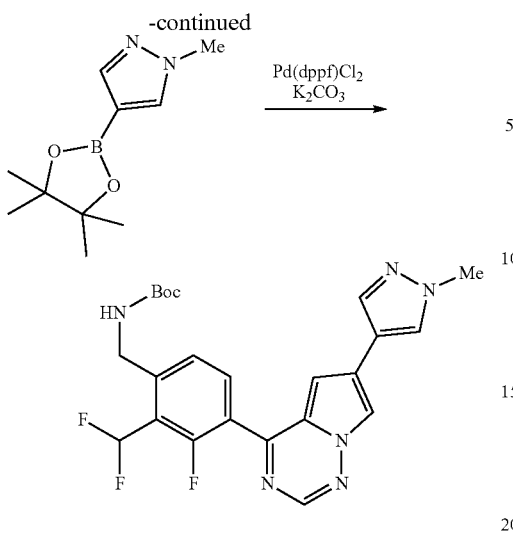

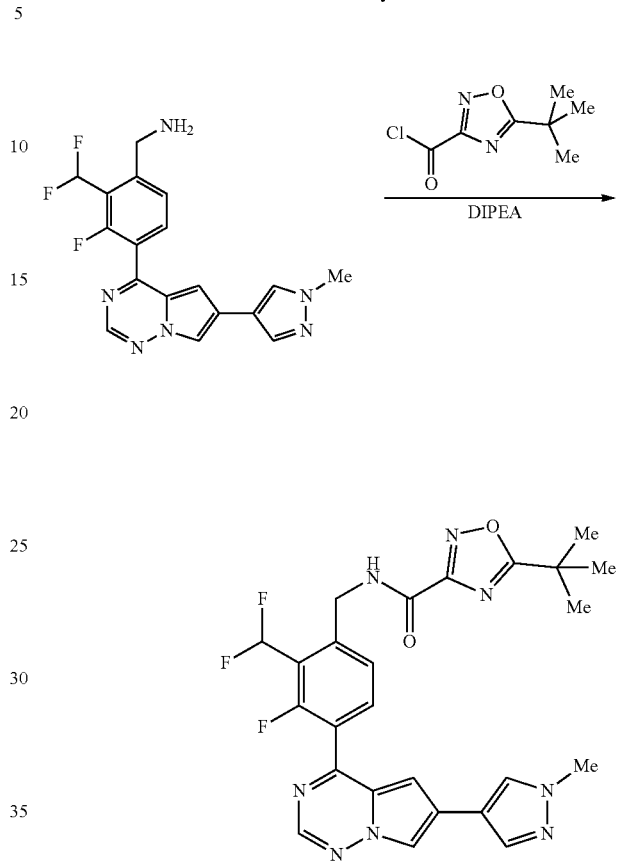

The crude product was obtained from 1-methylpyrazole-4-boronic acid pinacol ester and tert-butyl (4-(6-bromopyrrolo[2,1-f][1,2,4]triazin-4-yl)-2-(difluoromethyl)-3-fluorobenzyl)carbamate following the procedure described in Example 10, Step 1. The crude product was purified by silica gel chromatography (petroleum ether/EtOAc=10:1 to 1:1) to afford the title compound as a light yellow solid (165 mg, 82%). LCMS m/z=473.2 [M+H]$^+$

12. Synthesis of (2-(difluoromethyl)-3-fluoro-4-(6-(1-methyl-1H-pyrazol-4-yl)pyrrolo[2,1-f][1,2,4]triazin-4-yl)phenyl)methanamine hydrochloride

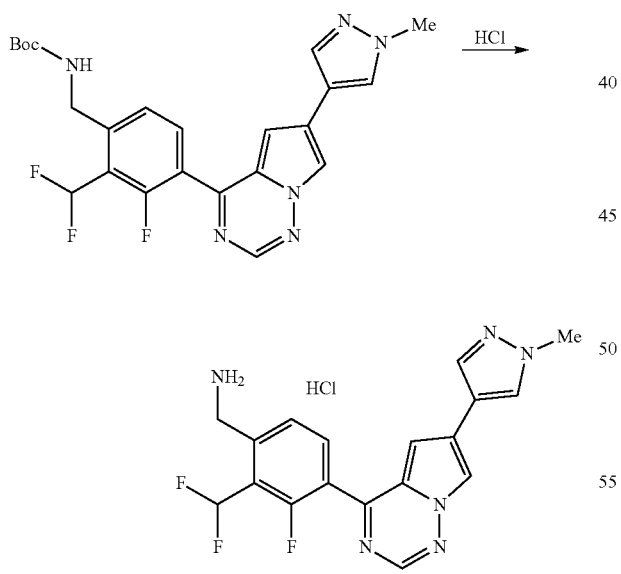

A solution of tert-butyl (2-(difluoromethyl)-3-fluoro-4-(6-(1-methyl-1H-pyrazol-4-yl)pyrrolo[2,1-f][1,2,4]triazin-4-yl)benzyl)carbamate (165 mg, 0.349 mmol) in an HCl solution (20 mL, 1 M in EtOAc) was stirred at RT for 2 h. The mixture was concentrated in vacuo to afford the title compound, as a grey solid (140 mg, crude). LCMS m/z=373.1 [M+H]$^+$ The crude product was obtained from (2-(difluoromethyl)-3-fluoro-4-(6-(1-methyl-1H-pyrazol-4-yl)pyrrolo[2,1-f][1,2,4]triazin-4-yl)phenyl)methanamine hydrochloride and 5-(tert-butyl)-1,2,4-oxadiazole-3-carbonyl chloride following the procedure described in Example 34, Step 7. The crude product was purified by prep-HPLC Method A; 44-74% to afford the title compound as a white solid (30.2 mg, 47%). LCMS m/z=525.1 [M+H]$^+$; $^1$H NMR (400 MHz, DMSO-d$_6$) δ: 9.69-9.65 (m, 1H), 8.60 (s, 1H), 8.53 (d, 1H), 8.16 (s, 1H), 7.97-7.94 (m, 1H), 7.89 (s, 1H), 7.65-7.44 (m, 2H), 7.04 (s, 1H), 4.77 (d, 2H), 3.82 (s, 3H), 1.41 (s, 9H).

Example 37. 5-(tert-butyl)-N-(2-cyclopropyl-4-(6-morpholinopyrrolo[2,1-f][1,2,4]triazin-4-yl)benzyl)-1,2,4-oxadiazole-3-carboxamide

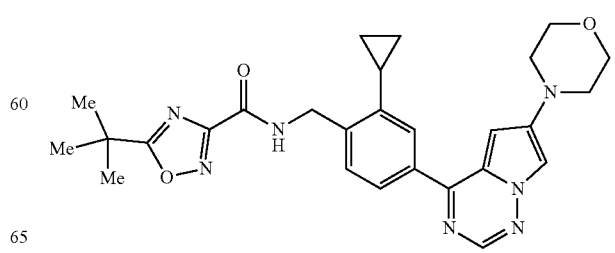

1. Synthesis of tert-butyl (4-chloro-2-cyclopropylphenyl)carbamate

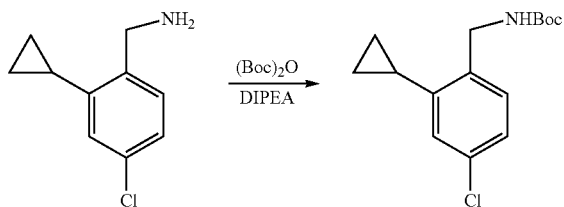 [SMILES: "(Boc)2O" ; NCc1ccc(Cl)cc1C1CC1 ; "DIPEA" ; CC(C)(C)OC(=O)NCc1ccc(Cl)cc1C1CC1]

To a solution of (4-chloro-2-cyclopropylphenyl)methanamine (1 g, 5.5 mmol) and DIPEA (2.13 g, 16.5 mmol) in DCM (30 mL) was added (Boc)$_2$O (1.56 g, 7.2 mmol) and the reaction was stirred at 20° C. for 1 h. The mixture was concentrated in vacuo and the crude product purified by silica gel column chromatography (petroleum ether/EtOAc=95:5) to afford the title compound as a clear oil (1.10 g, 71%). LCMS m/z=226.0 [M−tBu+H$^+$]

2. Synthesis of tert-butyl (2-cyclopropyl-4-(4,4,5,5-tetramethyl-1,3,2-dioxaborolan-2-yl)benzyl)carbamate

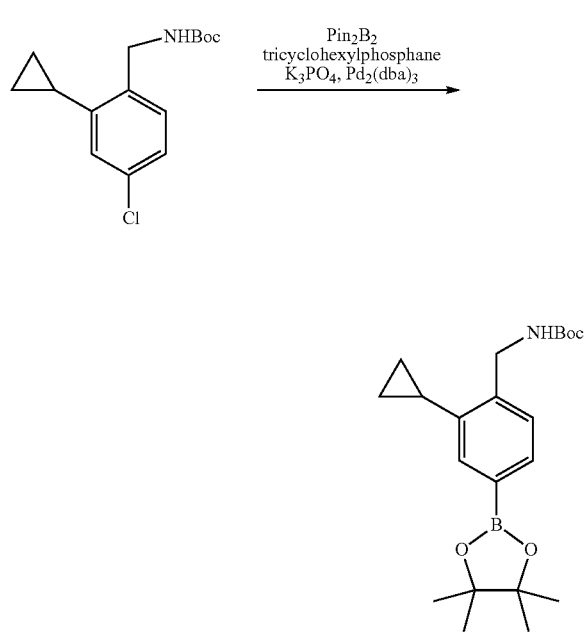

To a solution of tert-butyl (4-chloro-2-cyclopropylphenyl)carbamate (1.10 g, 3.9 mmol) and (bispinacolato)diboron (1.98 g, 7.8 mmol) in toluene (40 mL) was added P(Cy)$_3$ (328 mg, 1.2 mmol) and K$_3$PO$_4$ (2.49 g, 11.7 mmol) at 20° C. Pd$_2$(dba)$_3$ (358 mg, 0.39 mmol) was added and the reaction was stirred at 90° C. under N$_2$ for 12 h. The cooled mixture was concentrated in vacuo and azeotroped with EtOAc. The crude product was purified by silica gel column chromatography (petroleum ether/EtOAc=9:1) to afford the title compound as an orange oil (2.0 g, crude). LCMS m/z=318.2 [M−tBu+H]$^+$

3. Synthesis of tert-butyl (2-cyclopropyl-4-(6-morpholinopyrrolo[2,1-f][1,2,4]triazin-4-yl)benzyl)carbamate

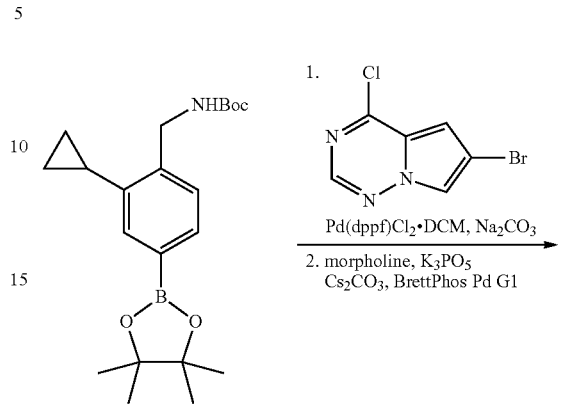

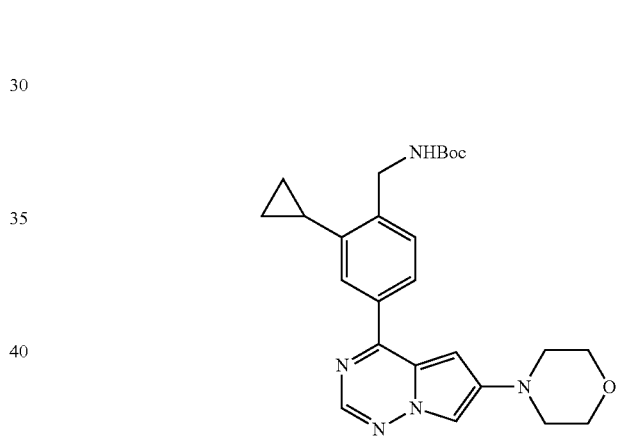

To a solution of tert-butyl (2-cyclopropyl-4-(4,4,5,5-tetramethyl-1,3,2-dioxaborolan-2-yl)benzyl)carbamate (1.0 g, 2.7 mmol) in dioxane (30 mL) and H$_2$O (3 mL) was added 6-bromo-4-chloro-pyrrolo[2,1-f][1,2,4]triazine (623 mg, 2.7 mmol). Na$_2$CO$_3$ (852 mg, 8.0 mmol) and Pd(dppf)Cl$_2$·DCM (219 mg, 0.27 mmol) were added and the reaction mixture was stirred at 95° C. for 6 h under N$_2$. The cooled mixture was concentrated in vacuo and the crude purified by silica gel column chromatography (petroleum ether/EtOAc=5:1) to give tert-butyl (4-(6-bromopyrrolo[2,1-f][1,2,4]triazin-4-yl)-2-cyclopropylbenzyl)carbamate as an orange solid (410 mg, 35%).

To a solution of this solid (410 mg, 0.93 mmol) and morpholine (403 mg, 5.3 mmol) in dioxane (20 mL) were added K$_3$PO$_4$ (393 mg, 1.9 mmol), Cs$_2$CO$_3$ (603 mg, 1.9 mmol) and BrettPhos Pd G1 methyl t-butyl ether adduct (76 mg, 0.09 mmol) under N$_2$ and the reaction was stirred at 95° C. for 12 h. The cooled mixture was concentrated in vacuo and the crude purified by silica gel column chromatography (petroleum ether/EtOAc=7:3) to afford the title compound as a yellow oil (52 mg, 22%). LCMS m/z=450.3 [M+H]$^+$

4. Synthesis of (2-cyclopropyl-4-(6-morpholinopyrrolo[2,1-f][1,2,4]triazin-4-yl)phenyl)methanamine hydrochloride

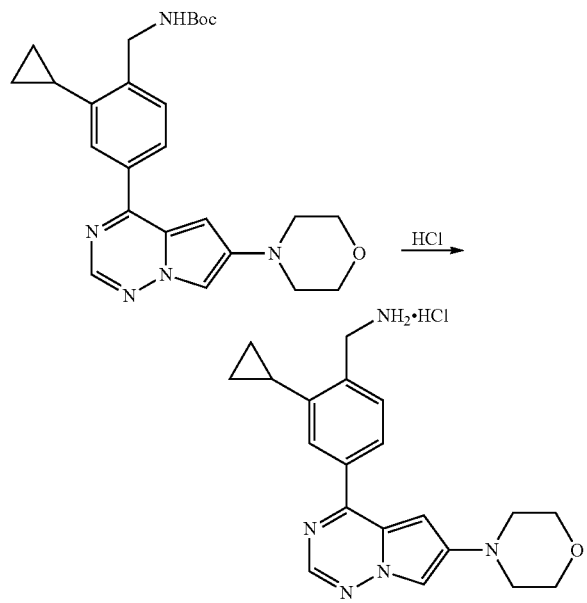

The title compound was obtained as an orange solid (54 mg, crude) from tert-butyl (2-cyclopropyl-4-(6-morpholinopyrrolo[2,1-f][1,2,4]triazin-4-yl)benzyl) following the procedure described in Example 35, Step 5. LCMS m/z=333.1 [M−NH$_2$]$^+$

5. Synthesis of 5-(tert-butyl)-N-(2-cyclopropyl-4-(6-morpholinopyrrolo[2,1-f][1,2,4]triazin-4-yl)benzyl)-1,2,4-oxadiazole-3-carboxamide

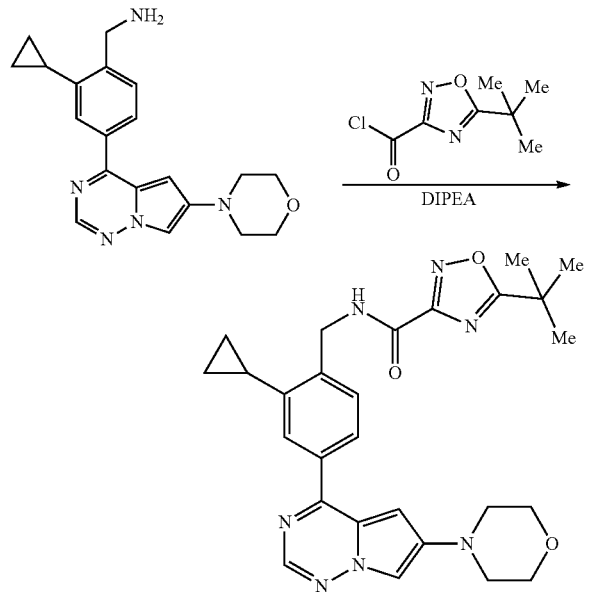

To a solution of (2-cyclopropyl-4-(6-morpholinopyrrolo[2,1-f][1,2,4]triazin-4-yl)phenyl)methanamine hydrochloride (40 mg, 0.10 mmol) in DCM (20 mL) was added DIPEA (27 mg, 0.21 mmol). Then 5-(tert-butyl)-1,2,4-oxadiazole-3-carbonyl chloride (39 mg, 0.21 mmol) was added slowly to the mixture and the mixture was stirred at 20° C. for 2 h. The mixture was poured into water (50 mL) and extracted into DCM (3×50 mL). The combined extracts were washed with brine, dried (Na$_2$SO$_4$), and concentrated in vacuo. The residue was purified by prep-HPLC (Method E, 56-75%) to give the title compound as a red solid (14 mg, 26%). LCMS m/z=502.2 [M+H]$^+$; $^1$H NMR (400 MHz, DMSO-d$_6$) δ: 9.51-9.48 (m, 1H), 8.45 (s, 1H), 7.96 (s, 1H), 7.89 (d, 1H), 7.67 (s, 1H), 7.39 (d, 1H), 6.61 (s, 1H), 4.72 (d, 2H), 3.73-3.70 (m, 4H), 3.13-3.10 (m, 4H), 2.13-2.08 (m, 1H), 1.41 (s, 9H), 1.02-0.97 (m, 2H), 0.71-0.68 (m, 2H).

Example 38. 5-(tert-butyl)-N-(2-methyl-4-(6-(pyridin-4-yl)pyrrolo[2,1-f][1,2,4]triazin-4-yl)benzyl)-1,2,4-oxadiazole-3-carboxamide

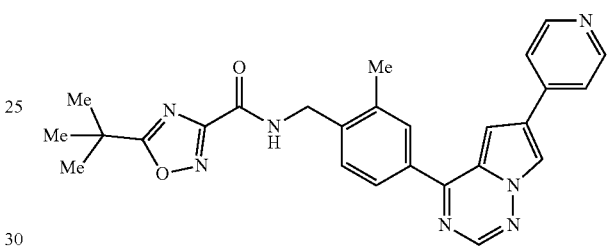

1. Synthesis of tert-butyl (2-methyl-4-(6-(pyridin-4-yl)pyrrolo[2,1-f][1,2,4]triazin-4-yl)benzyl)carbamate

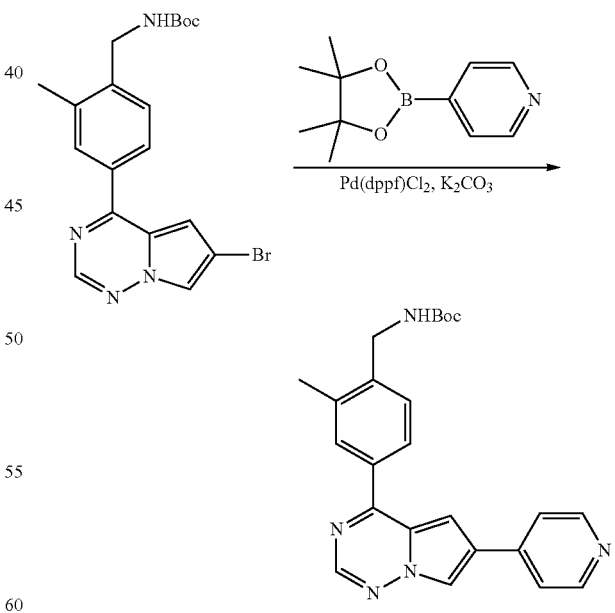

A mixture of tert-butyl (4-(6-bromopyrrolo[2,1-f][1,2,4]triazin-4-yl)-2-methylbenzyl)carbamate (180 mg, 0.43 mmol), 4-(4,4,5,5-tetramethyl-1,3,2-dioxaborolan-2-yl)pyridine (106 mg, 0.52 mol), K$_2$CO$_3$ (119 mg, 0.86 mmol) and Pd(dppf)Cl$_2$ (32 mg, 0.04 mmol) in dioxane (30 mL) and water (3 mL) was stirred at 90° C. for 2 h under N$_2$. The mixture was concentrated in vacuo and the crude product was purified by silica gel column chromatography (petroleum ether/EtOAc=100:0 to 0:100) to afford the title compound as a white solid (150 mg, 84%), which was carried forward without further purification.

2. Synthesis of (2-methyl-4-(6-(pyridin-4-yl)pyrrolo[2,1-f][1,2,4]triazin-4-yl)phenyl)methanamine hydrochloride

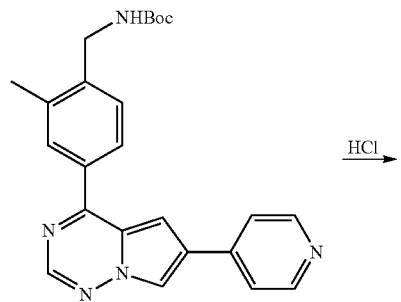

The title compound was obtained (113 mg, crude) from tert-butyl (2-methyl-4-(6-(pyridin-4-yl)pyrrolo[2,1-f][1,2,4]triazin-4-yl)benzyl)carbamate following the procedure described in Example 36, Step 12 and was used without further purification. LCMS m/z=316.2 [M+H]+

3. Synthesis of 5-(tert-butyl)-N-(2-methyl-4-(6-(pyridin-4-yl)pyrrolo[2,1-f][1,2,4]triazin-4-yl)benzyl)-1,2,4-oxadiazole-3-carboxamide

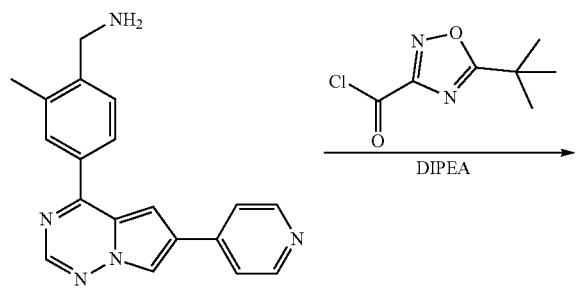

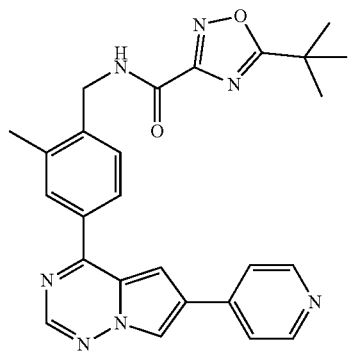

To a mixture of (2-methyl-4-(6-(pyridin-4-yl)pyrrolo[2,1-f][1,2,4]triazin-4-yl)phenyl)methanamine hydrochloride (80 mg, 0.23 mmol) in DCM (40 mL) was added DIPEA (88 mg, 0.68 mmol). 5-(tert-Butyl)-1,2,4-oxadiazole-3-carbonyl chloride (86 mg, 0.46 mmol) was added and the reaction was stirred at 20° C. for 1 h. The mixture was concentrated in vacuo to give a crude, which was purified by prep-HPLC, Method D 45-75%, to afford the title compound as a brown solid (46 mg, 43%). LCMS m/z=468.1 [M+H]+; $^1$H NMR (500 MHz, DMSO-d$_6$) δ: 9.57 (t, 1H), 8.93 (d, 1H), 8.67 (s, 1H), 8.63-8.61 (m, 2H), 8.08 (d, 1H), 8.04 (s, 1H), 8.00-7.94 (m, 2H), 7.83 (d, 1H), 7.50 (d, 1H), 4.59 (d, 2H), 2.53 (s, 3H), 1.46 (s, 9H).

Example 39. 5-(tert-butyl)-N-(4-(6-((2,6-syn)-2,6-dimethylmorpholino)pyrrolo[2,1-f][1,2,4]triazin-4-yl)-2-methylbenzyl)-1,2,4-oxadiazole-3-carboxamide

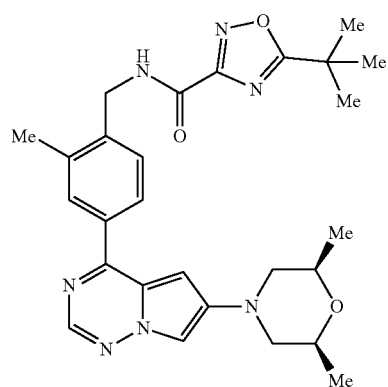 [SMILES: Cc1cc(-c2ncnn3cc(N4C[C@@H](C)O[C@@H](C)C4)cc23)ccc1CNC(=O)c1noc(C(C)(C)C)n1]

157

Relative Stereochemical Configuration Shown

1. Synthesis of racemic tert-butyl (4-(6-((2,6-syn)-2,6-dimethylmorpholino)pyrrolo[2,1-f][1,2,4]triazin-4-yl)-2-methylbenzyl)carbamate

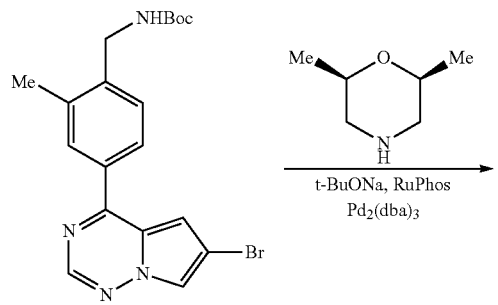

A mixture of tert-butyl (4-(6-bromopyrrolo[2,1-f][1,2,4]triazin-4-yl)-2-methylbenzyl)carbamate (160 mg, 0.38 mmol), cis-2,6-dimethylmorpholine (221 mg, 1.9 mmol), t-BuONa (74 mg, 0.77 mmol), RuPhos (36 mg, 0.08 mmol) and Pd$_2$(dba)$_3$ (35 mg, 0.04 mmol) in dioxane (10 mL) and THF (10 mL) was stirred at 100° C. for 4 h under N$_2$. The mixture was concentrated in vacuo and the residue was purified by silica gel column chromatography (EtOAc/petroleum ether=0:100 to 3:7) to afford the title compound as a yellow oil (160 mg, 78%). LCMS m/z=452.2 [M+H]$^+$

2. Synthesis of racemic (4-(6-((2,6-syn)-2,6-dimethylmorpholino)pyrrolo[2,1-f][1,2,4]triazin-4-yl)-2-methylphenyl)methanamine hydrochloride

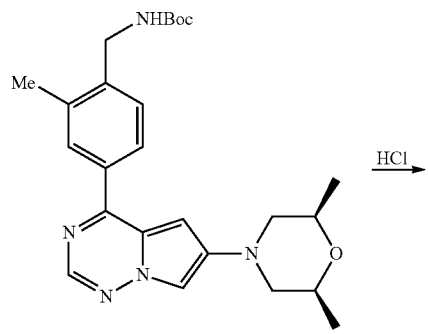

158

-continued

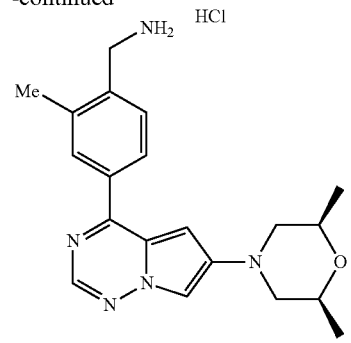

A mixture of racemic tert-butyl (4-(6-((2,6-syn)-2,6-dimethylmorpholino)pyrrolo[2,1-f][1,2,4]triazin-4-yl)-2-methylbenzyl)carbamate (160 mg, 0.35 mmol) in an HCl solution (10 mL, 4 M in EtOAc) was stirred at RT for 1 h. The mixture was concentrated in vacuo to afford the title compound as a yellow solid (120 mg, crude). LCMS m/z=352.2 [M+H]$^+$

3. Synthesis of 5-(tert-butyl)-N-(4-(6-((2,6-syn)-2,6-dimethylmorpholino)pyrrolo[2,1-f][1,2,4]triazin-4-yl)-2-methylbenzyl)-1,2,4-oxadiazole-3-carboxamide

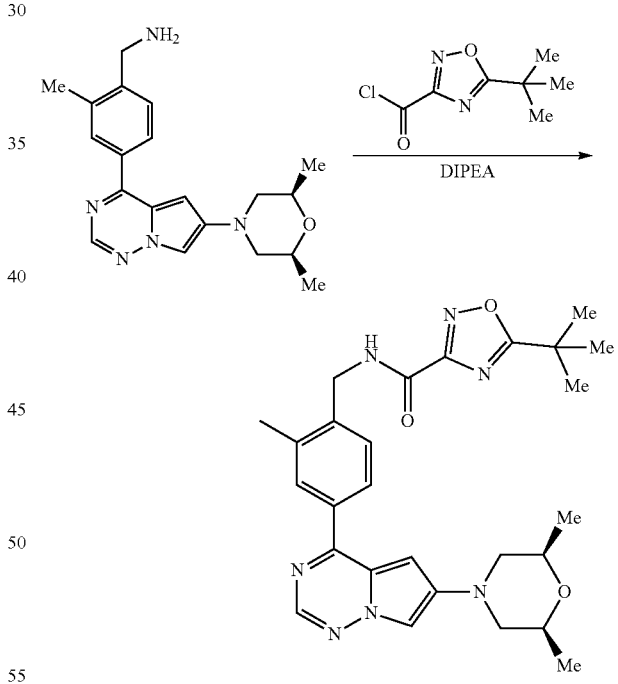

The compound was obtained from (4-(6-((2,6-syn)-2,6-dimethylmorpholino)pyrrolo[2,1-f][1,2,4]triazin-4-yl)-2-methylphenyl)methanamine hydrochloride and 5-(tert-butyl)-1,2,4-oxadiazole-3-carbonyl chloride, following the method described in Example 34, Step 8. The crude product was purified by prep HPLC Method A, 46-66% to afford the title compound, (65 mg, 43%). LCMS m/z=526.1 [M+Na]$^+$; $^1$H NMR (500 MHz, DMSO-d$_6$) δ: 9.54 (t, 1H), 8.53 (s, 1H), 8.12 (s, 1H), 7.97-7.90 (m, 2H), 7.45 (d, 1H), 6.78-6.77 (m, 1H), 4.55 (d, 2H), 3.75-3.71 (m, 2H), 3.65 (d, 2H), 2.47 (s, 3H), 2.39-2.33 (m, 2H), 1.45 (s, 9H), 1.16 (d, 6H).

Example 40. N-(2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide

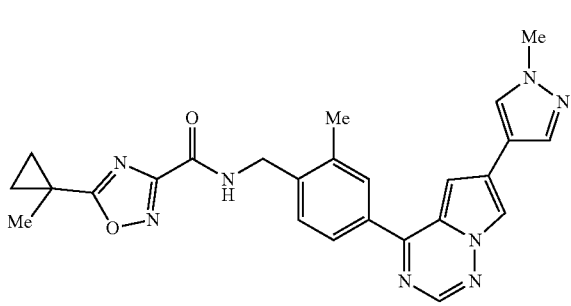 [SMILES: Cc1cc(-c2ncnn3cc(-c4cnn(C)c4)cc23)ccc1CNC(=O)c1noc(C2(C)CC2)n1]

1. Synthesis of tert-butyl (4-(6-(1-methyl-1H-pyrazol-4-yl)pyrrolo[2,1-f][1,2,4]triazin-4-yl)-2-methylbenzyl)carbamate

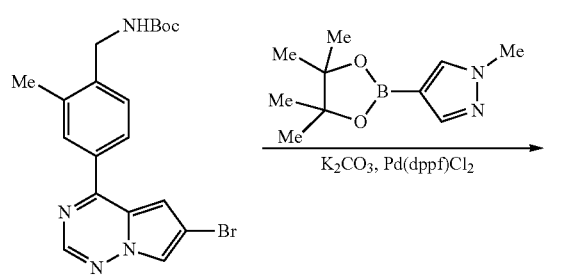

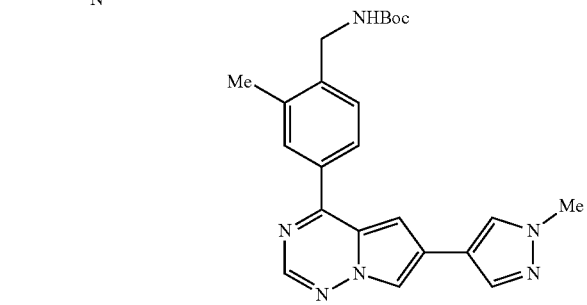

To a solution of tert-butyl (4-(6-bromopyrrolo[2,1-f][1,2,4]triazin-4-yl)-2-methylbenzyl)carbamate (336 mg, 0.81 mmol) in dioxane (6 mL) and H$_2$O (2 mL) was added 1-methyl-1H-pyrazole-4-boronic acid pinacol ester (168 mg, 0.81 mmol), K$_2$CO$_3$ (223 mg, 1.6 mmol) and Pd(dppf)Cl$_2$ (66 mg, 0.081 mmol) and the reaction was stirred at 80° C. under N$_2$ for 1 h. The cooled mixture was concentrated in vacuo, the residue was dissolved in EtOAc, the mixture was washed with water (20 mL), and extracted with EtOAc (3×20 mL). The combined organic layers were dried (Na$_2$SO$_4$), filtered, and concentrated in vacuo. The residue was purified by silica gel column chromatography (petroleum ether/EtOAc=100:0 to 0:100) to afford the title compound as a yellow solid (300 mg, 89%). LCMS m/z=419.2 [M+H]$^+$; $^1$H NMR (400 MHz, DMSO-d$_6$) δ: 8.55 (s, 1H), 8.46 (d, 1H), 8.21 (s, 1H), 7.99 (br d, 1H), 7.97-7.93 (m, 2H), 7.49 (br t, 1H), 7.43-7.39 (m, 2H), 4.22 (br d, 2H), 3.87 (s, 3H), 2.41 (s, 3H), 1.42 (s, 9H)

2. Synthesis of (2-methyl-4-(6-(1-methyl-1H-pyrazol-4-yl)pyrrolo[2,1-f][1,2,4]triazin-4-yl)phenyl)methanamine hydrochloride

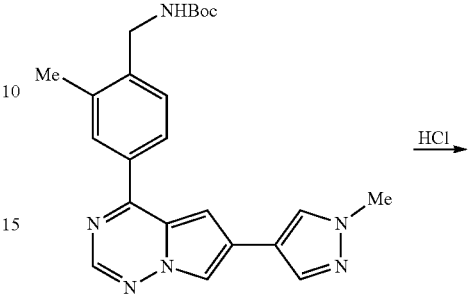

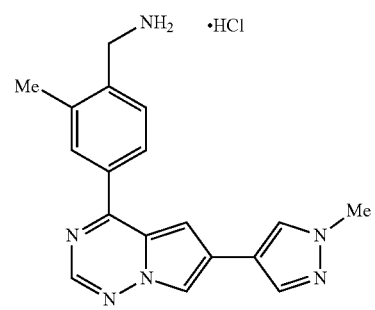

A solution of tert-butyl (4-(6-(1-methyl-1H-pyrazol-4-yl)pyrrolo[2,1-f][1,2,4]triazin-4-yl)-2-methylbenzyl)carbamate (300 mg, 0.72 mmol) in an HCl solution (30 mL, 1 M in EtOAc) was stirred at 20° C. for 1 h. The mixture was concentrated in vacuo to afford the title compound as a white solid (200 mg, 88%). $^1$H NMR (400 MHz, DMSO-d$_6$) δ: 8.61-8.52 (m, 3H), 8.23 (s, 1H), 8.08-8.02 (m, 2H), 7.97 (s, 1H), 7.67 (br d, 1H), 7.42 (s, 1H), 5.76 (s, 1H), 4.14 (br d, 2H), 3.88 (s, 3H), 1.98 (s, 3H).

3. Synthesis of 5-(1-methylcyclopropyl)-1,2,4-oxadiazole-3-carbonyl chloride

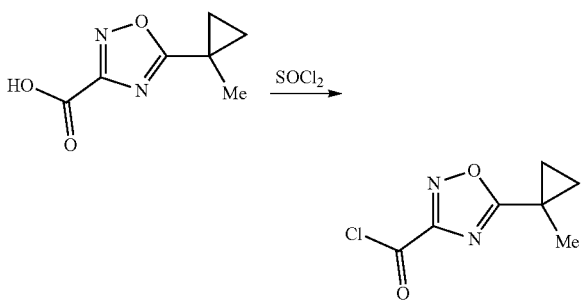

The title compound was obtained from 5-(1-methylcyclopropyl)-1,2,4-oxadiazole-3-carboxylic acid following the procedure described in Example 34, Step 7. The crude material was carried used directly.

4. Synthesis of N-(2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide

1. Synthesis of 5-(1-fluoro-2-methylpropan-2-yl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide

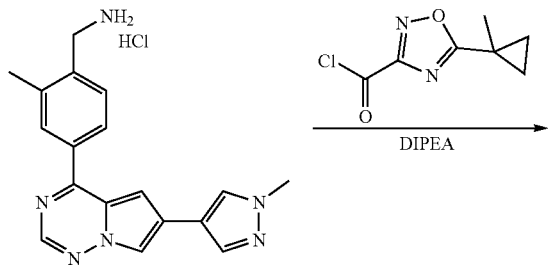
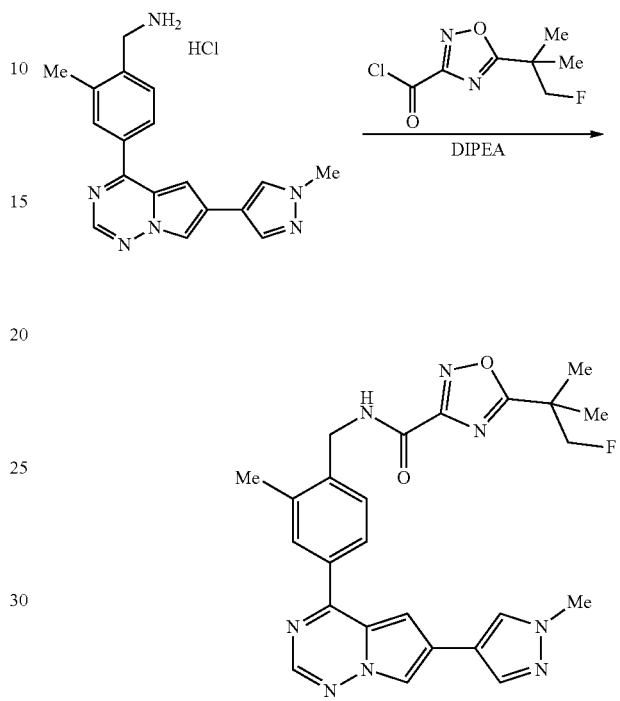

The product was prepared from (2-methyl-4-(6-(1-methyl-1H-pyrazol-4-yl)pyrrolo[2,1-f][1,2,4]triazin-4-yl)phenyl)methanamine hydrochloride and 5-(1-methylcyclopropyl)-1,2,4-oxadiazole-3-carbonyl chloride, following the procedure described in Example 34, Step 8. The crude product was purified by prep HPLC using Method E, to afford the title compound as a yellow solid (19 mg, 22%). LCMS m/z=469.1 [M+H]$^+$; $^1$H NMR (400 MHz, DMSO-$d_6$) δ: 9.48 (t, 1H), 8.55 (s, 1H), 8.45 (s, 1H), 8.20 (s, 1H), 8.01-7.92 (m, 3H), 7.45 (d, 1H), 7.39 (s, 1H), 4.54 (d, 2H), 3.87 (s, 3H), 2.47 (br s, 3H), 1.55 (s, 3H), 1.41-1.38 (m, 2H), 1.20-1.16 (m, 2H).

The compound was prepared using an analogous method to that described for Example 33, Step 10, using (2-methyl-4-(6-(1-methyl-1H-pyrazol-4-yl)pyrrolo[2,1-f][1,2,4]triazin-4-yl)phenyl)methanamine hydrochloride and 5-(1-fluoro-2-methylpropan-2-yl)-1,2,4-oxadiazole-3-carbonyl chloride. The crude product was purified by prep-HPLC (Method E 50-72%) as a yellow solid (14 mg, 17%). LCMS m/z=489.2 [M+H]$^+$; $^1$H NMR (400 MHz, DMSO-$d_6$) δ: 9.58-9.54 (m, 1H), 8.60-8.42 (m, 2H), 8.17 (s, 1H), 7.98-7.91 (m, 3H), 7.43 (d, 1H), 7.37 (s, 1H), 4.68-4.53 (m, 4H), 3.84 (s, 3H), 2.45 (s, 3H), 1.43 (d, 6H).

Example 41. 5-(1-fluoro-2-methylpropan-2-yl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide Example 42. N-(3-fluoro-2-methyl-4-(6-(1-methyl-1H-pyrazol-4-yl)pyrrolo[2,1-f][1,2,4]triazin-4-yl)benzyl)-5-(1-methylcyclopropyl)-1,24-oxadiazole-3-carboxamide hydrochloride

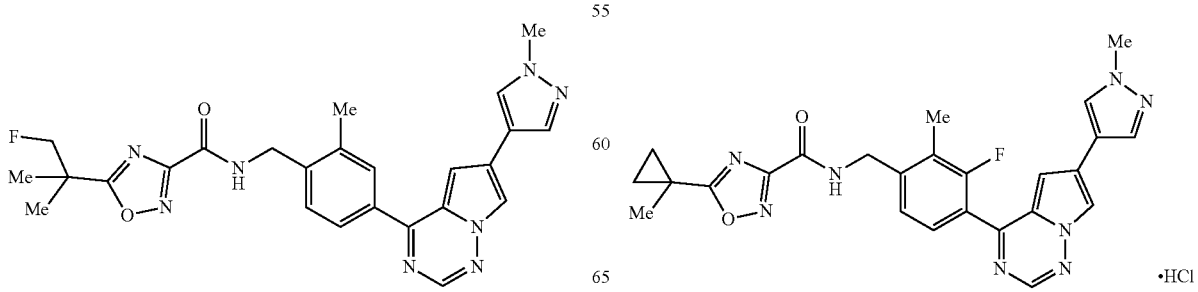

1. Synthesis of N-(3-fluoro-2-methyl-4-(6-(1-methyl-1H-pyrazol-4-yl)pyrrolo[2,1-f][1,2,4]triazin-4-yl)benzyl)-5-(1-methylcyclopropyl)-1,2,4-oxadiazole-3-carboxamide hydrochloride

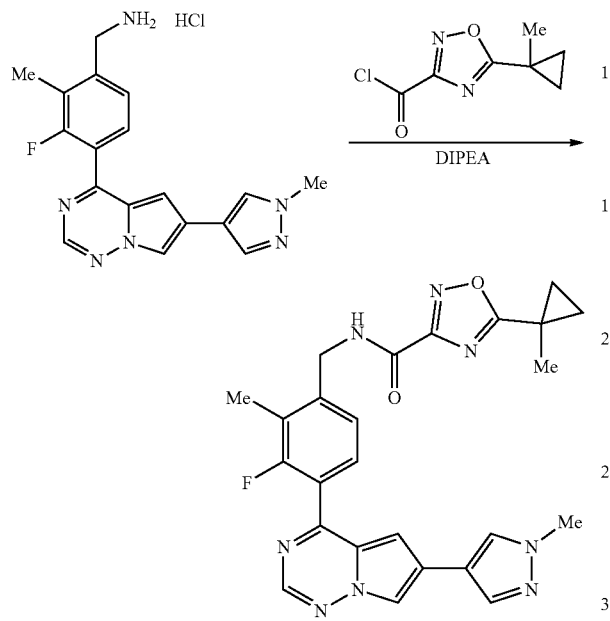

The title compound was prepared using an analogous method to that described for Example 33, Step 10 using (3-fluoro-2-methyl-4-(6-(1-methyl-1H-pyrazol-4-yl)pyrrolo[2,1-f][1,2,4]triazin-4-yl)phenyl)methanamine hydrochloride and 5-(1-methylcyclopropyl)-1,2,4-oxadiazole-3-carbonyl chloride. The product was purified by prep-HPLC (Method A; 49-69%) as a yellow solid (47 mg, 97%). LCMS m/z=487.1 [M+H]$^+$; $^1$H NMR (500 MHz, DMSO-d$_6$) δ: 9.56-9.53 (m, 1H), 8.60 (s, 1H), 8.51 (s, 1H), 8.19 (s, 1H), 7.92 (s, 1H), 7.62 (t, 1H), 7.30 (d, 1H), 7.03 (s, 1H), 4.58 (d, 2H), 3.86 (s, 3H), 2.37-2.36 (m, 3H), 1.58 (s, 3H), 1.41-1.40 (m, 2H), 1.19-1.18 (m, 2H).

Example 43 and Example 44. 5-(tert-butyl)-N-(4-(6-((2R,6R)-2,6-dimethylmorpholino)pyrrolo[2,1-f][1,2,4]triazin-4-yl)-2-methylbenzyl)-1,2,4-oxadiazole-3-carboxamide and 5-(tert-butyl)-N-(4-(6-((2S,6S)-2,6-dimethylmorpholino)pyrrolo[2,1-f][1,2,4]triazin-4-yl)-2-methylbenzyl)-1,2,4-oxadiazole-3-carboxamide hydrochloride

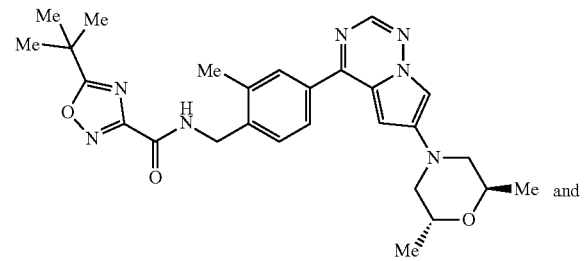

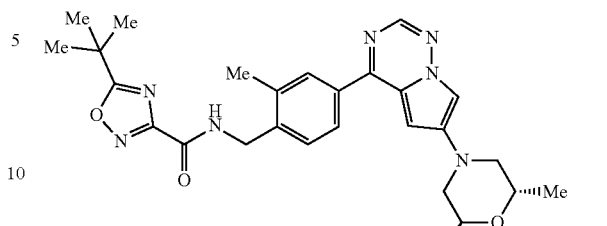

(absolute stereochemistry arbitrarily assigned)

1. Synthesis of racemic tert-butyl (4-(6-((2,6-trans)-2,6-dimethylmorpholino)pyrrolo[2,1-f][1,2,4]triazin-4-yl)-2-methylbenzyl)carbamate

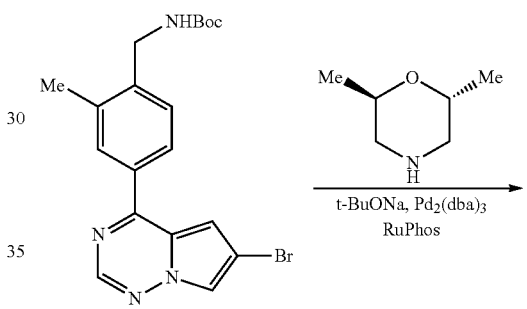

The title compound was obtained as a yellow solid (150 mg, 31%) from tert-butyl (4-(6-bromopyrrolo[2,1-f][1,2,4]triazin-4-yl)-2-methylbenzyl)carbamate and racemic (2,6-trans)-2,6-dimethylmorpholine, following the procedure described in Example 39, Step 1. LCMS m/z=452.3 [M+H]$^+$ 2. Synthesis of racemic (4-(6-((2R,6R)-2,6-dimethylmorpholino)pyrrolo[2,1-f][1,2,4]triazin-4-yl)phenyl)methanamine hydrochloride

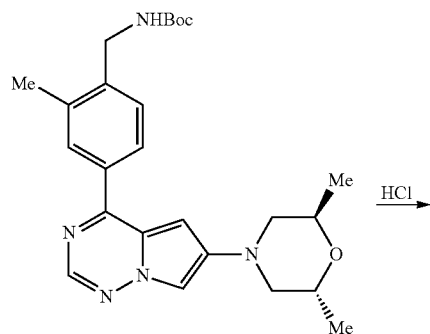

The title compound was obtained as a yellow solid (100 mg, 95%) from racemic tert-butyl (4-(6-((2,6-trans)-2,6-dimethylmorpholino)pyrrolo[2,1-f][1,2,4]triazin-4-yl)-2-methylbenzyl)carbamate, following the procedure described in Example 36, Step 12. LCMS m/z=352.2 [M+H]+

3. Synthesis of rac-5-(tert-butyl)-N-(4-(6-((2R,6R)-2,6-dimethylmorpholino)pyrrolo[2,1-f][1,2,4]triazin-4-yl)-2-methylbenzyl)-1,2,4-oxadiazole-3-carboxamide hydrochloride

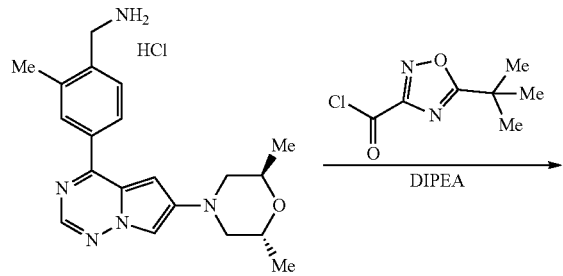

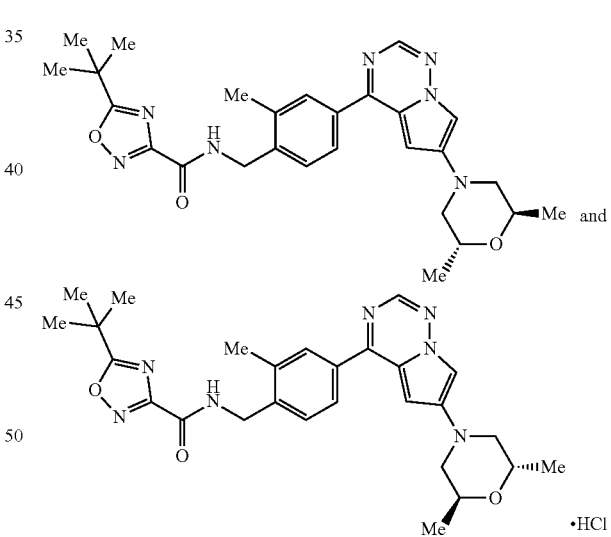

The product was obtained as a yellow solid from racemic (4-(6-((2,6-trans)-2,6-dimethylmorpholino)pyrrolo[2,1-f][1,2,4]triazin-4-yl)phenyl)methanamine hydrochloride, following the procedure described in Example 38, Step 8. The crude product was purified by prep HPLC, method A, 45-65%. LCMS m/z=504.3 [M+H]+

4. Synthesis of 5-(tert-butyl)-N-(4-(6-((2R,6R)-2,6-dimethylmorpholino)pyrrolo[2,1-f][1,2,4]triazin-4-yl)-2-methylbenzyl)-1,2,4-oxadiazole-3-carboxamide and 5-(tert-butyl)-N-(4-(6-((2S,6S)-2,6-dimethylmorpholino)pyrrolo[2,1-f][1,2,4]triazin-4-yl)-2-methylbenzyl)-1,2,4-oxadiazole-3-carboxamide hydrochloride (absolute stereochemistry arbitrarily assigned)

The title compounds were prepared by SFC separation (Diacel Chiralcel OJ-H, 250×30 mm, 5 mm, 0.1% NH4OH/EtOH) of rac-5-(tert-butyl)-N-(4-(6-((2,6-trans)-2,6-dimethylmorpholino)pyrrolo[2,1-f][1,2,4]triazin-4-yl)-2-methylbenzyl)-1,2,4-oxadiazole-3-carboxamide hydrochloride.

Example 43. Peak 1: 5-(tert-butyl)-N-(4-(6-((2R,6R)-2,6-dimethylmorpholino)pyrrolo[2,1-f][1,2,4]triazin-4-yl)-2-methylbenzyl)-1,2,4-oxadiazole-3-carboxamide (absolute stereochemistry arbitrarily assigned). yellow solid; 21 mg. LCMS m/z=504.2 [M+H]+. 1H NMR (400 MHz, DMSO-d6) δ: 9.51 (br t, 1H), 8.46 (s, 1H), 8.05-7.87 (m, 3H), 7.42 (d, 1H), 6.71 (d, 1H), 4.54 (d, 2H), 4.07 (br dd, 2H), 3.23 (dd, 2H), 2.88 (dd, 2H), 2.45 (s, 3H), 1.44 (s, 9H), 1.21 (d, 6H). Example 44. Peak 2 was further purified by prep-HPLC (Method A; 52-72%) to afford 5-(tert-butyl)-N-(4-(6-((2S,6S)-2,6-dimethylmorpholino)pyrrolo[2,1-f][1,2,4]triazin-4-yl)-2-methylbenzyl)-1,2,4-oxadiazole-3-carboxamide hydrochloride (absolute stereochemistry arbitrarily assigned). red solid; 15 mg. LCMS m/z=504.2 [M+H]+. 1H NMR (400 MHz, DMSO-d6) δ: 9.51 (br t, 1H), 8.46 (s, 1H), 8.05-7.87 (m, 3H), 7.42 (d, 1H), 6.71 (d, 1H), 4.54 (d, 2H), 4.07 (br dd, 2H), 3.23 (dd, 2H), 2.88 (dd, 2H), 2.45 (s, 3H), 1.44 (s, 9H), 1.21 (d, 6H).

Example 45. 3-(tert-butyl)-N-(3-fluoro-2-methoxy-4-(6-(1-methyl-1H-pyrazol-4-yl)pyrrolo[2,1-f][1,2,4]triazin-4-yl)benzyl)-1,2,4-oxadiazole-5-carboxamide

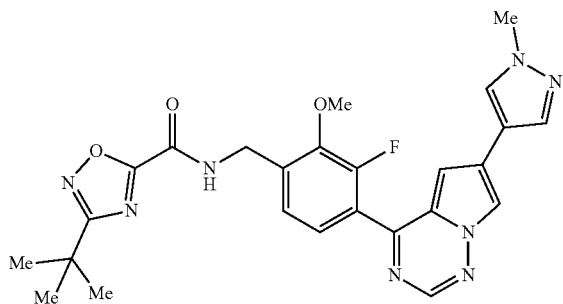 [SMILES: COc1c(CNC(=O)c2nc(C(C)(C)C)no2)ccc(-c2ncnn3cc(-c4cnn(C)c4)cc23)c1F]

1. Synthesis of 4-bromo-3-fluoro-2-methoxybenzonitrile

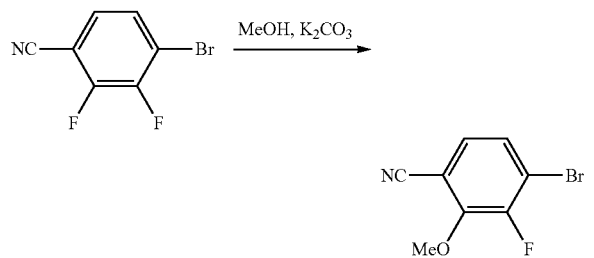

To a solution of 4-bromo-2,3-difluorobenzonitrile (9.50 g, 43.6 mmol) in DMF (30 mL) was added K2CO3 (18.1 g, 131 mmol) and MeOH (7.1 mL, 174 mmol) and the reaction was stirred at 55° C. for 16 h. The reaction mixture was diluted with H2O (300 mL) and the resulting solid was filtered off and washed with H2O (200 mL). The solid was dried in vacuo to afford the title compound as a white solid (12.0 g, crude). 1H NMR (400 MHz, CDCl3) δ: 7.30-7.20 (m, 2H), 4.16 (s, 3H).

2. Synthesis of tert-butyl (4-bromo-3-fluoro-2-methoxybenzyl)carbamate

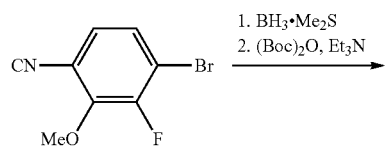

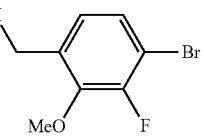

The title compound was obtained as an oil (5.7 g, 50%) from 4-bromo-3-fluoro-2-methoxybenzonitrile, following a similar procedure to that described in Example 35, Step 1. LCMS m/z=277.9 [M−tBu+H]+

3. Synthesis of tert-butyl (3-fluoro-2-methoxy-4-(4,4,5,5-tetramethyl-1,3,2-dioxaborolan-2-yl)benzyl)carbamate

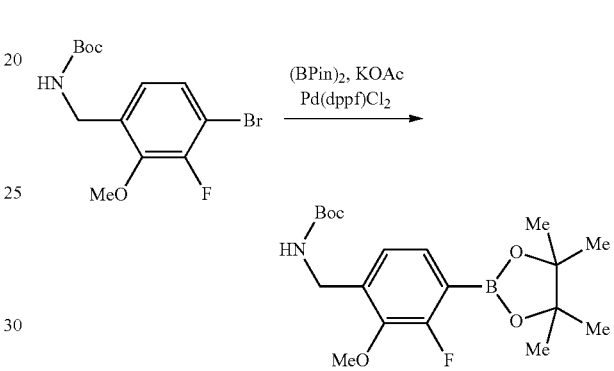

The title compound was prepared from tert-butyl (4-bromo-3-fluoro-2-methoxybenzyl)carbamate, following a similar procedure to that described in Example 25, Step 5. LCMS m/z=326.1 [M−tBu+H]+

4. Synthesis of tert-butyl (4-(6-bromopyrrolo[2,1-f][1,2,4]triazin-4-yl)-3-fluoro-2-methoxybenzyl)carbamate

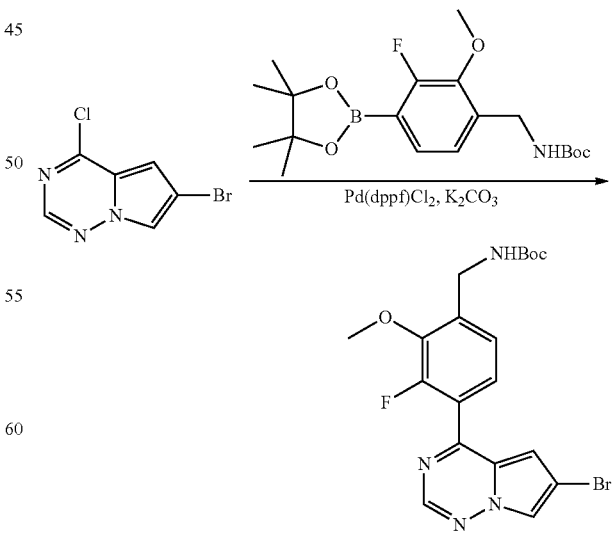

To a solution of 6-bromo-4-chloro-pyrrolo[2,1-f][1,2,4]triazine (350 mg, 0.92 mmol) in dioxane (30 mL) and water (3 mL) was added tert-butyl (3-fluoro-2-methoxy-4-(4,4,5,5-tetramethyl-1,3,2-dioxaborolan-2-yl)benzyl)carbamate (470 mg, 2.0 mmol) and K₂CO₃ (381 mg, 2.8 mmol). Pd(dppf)Cl₂ (34 mg, 0.05 mmol) was added and the reaction was stirred at 85° C. for 16 h under N₂. The solvents were concentrated in vacuo to give a residue which was purified by silica gel chromatography (petroleum ether/EtOAc=100:0 to 75:25) to afford the title compound as a yellow oil (450 mg, crude). LCMS m/z=453.1 [M+H]⁺

5. Synthesis of tert-butyl (3-fluoro-2-methoxy-4-(6-(1-methyl-1H-pyrazol-4-yl)pyrrolo[2,1-f][1,2,4]triazin-4-yl)benzyl)carbamate

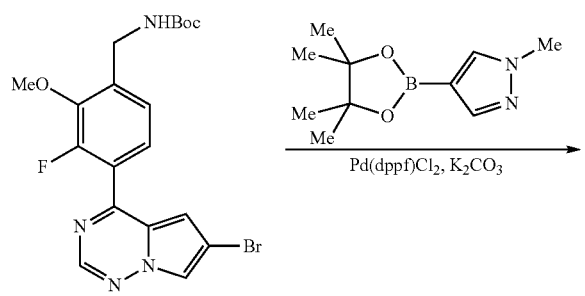

The title compound was obtained as a yellow oil (170 mg, 81% over 3 steps) from tert-butyl (4-(6-bromopyrrolo[2,1-f][1,2,4]triazin-4-yl)-3-fluoro-2-methoxybenzyl)carbamate and 1-methylpyrazole-4-boronic acid pinacol ester following the procedure described in Example 38, Step 1. LCMS m/z=453.2 [M+H]⁺

6. Synthesis of (3-fluoro-2-methoxy-4-(6-(1-methyl-1H-pyrazol-4-yl)pyrrolo[2,1-f][1,2,4]triazin-4-yl)phenyl)methanamine hydrochloride

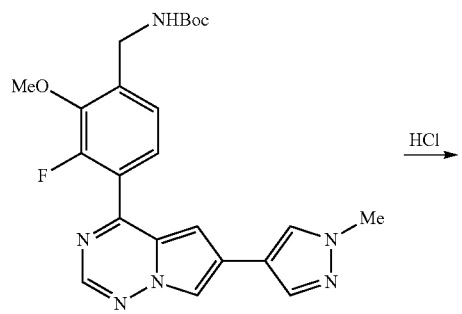

The title compound was obtained as a white solid from tert-butyl (3-fluoro-2-methoxy-4-(6-(1-methyl-1H-pyrazol-4-yl)pyrrolo[2,1-f][1,2,4]triazin-4-yl)benzyl)carbamate following the procedure described in Example 35, Step 5. LCMS m/z=353.1 [M+H]⁺

7. Synthesis of 3-(tert-butyl)-N-(3-fluoro-2-methoxy-4-(6-(1-methyl-1H-pyrazol-4-yl)pyrrolo[2,1-f][1,2,4]triazin-4-yl)benzyl)-1,2,4-oxadiazole-5-carboxamide]

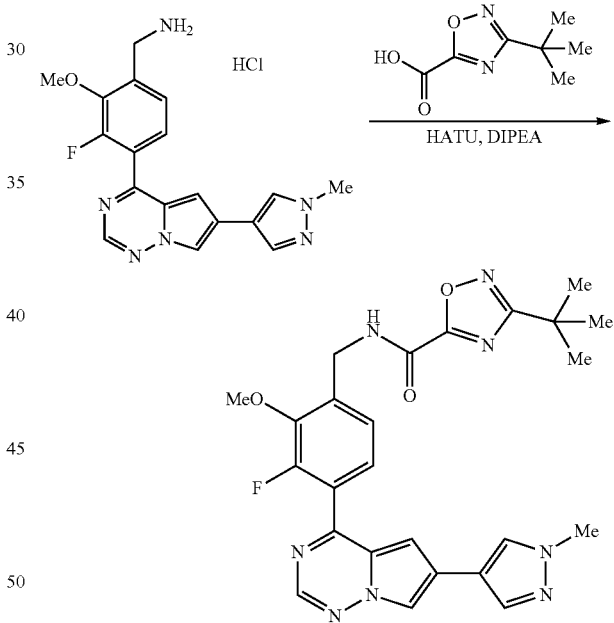

To a solution of (3-fluoro-2-methoxy-4-(6-(1-methyl-1H-pyrazol-4-yl)pyrrolo[2,1-f][1,2,4]triazin-4-yl)phenyl)methanamine hydrochloride (40 mg, 0.11 mmol) in DCM (30 mL) and DMF (3 mL) was added 3-(tert-butyl)-1,2,4-oxadiazole-5-carboxylic acid (39 mg, 0.23 mmol), HATU (43 mg, 0.11 mmol) and DIPEA (44 mg, 0.34 mmol) and the reaction was stirred at 20° C. for 4 h. The reaction was concentrated in vacuo and residue purified by prep-HPLC (Method E, 50-73%) to afford the title compound as a yellow solid (15 mg, 26% over 2 steps). LCMS m/z=505.1 [M+H]⁺; ¹H NMR (400 MHz, DMSO-d₆) δ: 9.92 (t, 1H), 8.59 (s, 1H), 8.51 (s, 1H), 8.18 (s, 1H), 7.92 (s, 1H), 7.50 (t, 1H), 7.33 (d, 1H), 7.05 (s, 1H), 4.61 (d, 2H), 4.00 (s, 3H), 3.85 (s, 3H), 1.37 (s, 9H).

Examples 46-55

The title compounds were prepared in parallel using the general protocol below:

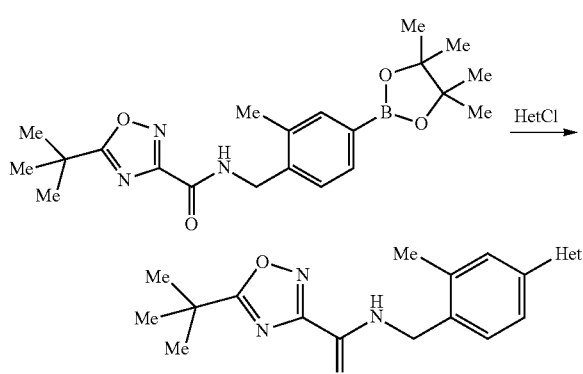

1. Synthesis of (2-methyl-4-(4,4,5,5-tetramethyl-1,3,2-dioxaborolan-2-yl)phenyl)methanamine hydrochloride

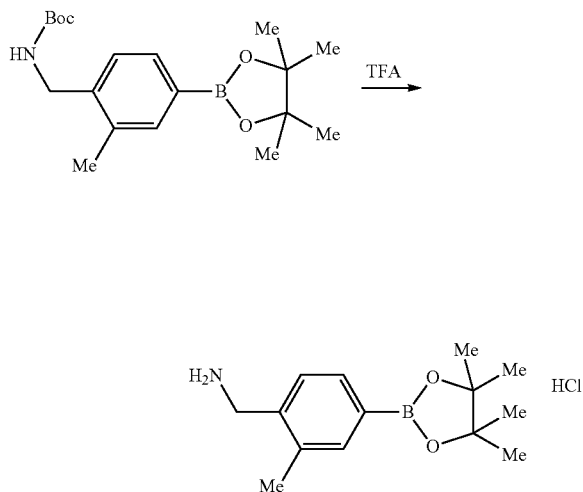

A solution of tert-butyl N-[[2-methyl-4-(4,4,5,5-tetramethyl-1,3,2-dioxaborolan-2-yl)phenyl]methyl]carbamate (WO 2015089327 A1, 35.7 g, 103 mmol) in DCM, was treated with TFA (85 mL, 1110 mmol) and the reaction was stirred at RT for 2 h. The mixture was concentrated in vacuo, and the residue was azeotroped with toluene. The residue was suspended in saturated aqueous NaHCO$_3$ solution and extracted with EtOAc (2×100 mL). The combined organic extracts were washed with brine, dried (Na$_2$SO$_4$), and filtered. 4M HCl in dioxane (30 mL) was added and the solution concentrated in vacuo. Diethyl ether (500 mL) was added and the suspension was stirred and filtered. The solid was dried in vacuo to afford the title compound as an off-white solid (23.5 g, 84%). $^1$H NMR (300 MHz, DMSO-d$_6$) δ: 8.56 (br s, 3H), 7.49-7.52 (m, 2H), 7.41 (dd, 1H), 4.01-4.04 (m, 2H), 2.34 (s, 3H), 1.27 (s, 12H).

2. Synthesis of 5-(tert-butyl)-N-(2-methyl-4-(4,4,5,5-tetramethyl-1,3,2-dioxaborolan-2-yl)benzyl)-1,2,4-oxadiazole-3-carboxamide

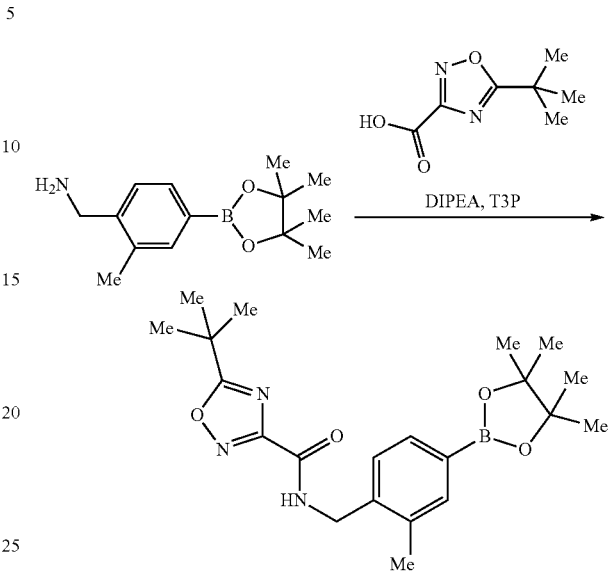

To a suspension of (2-methyl-4-(4,4,5,5-tetramethyl-1,3,2-dioxaborolan-2-yl)phenyl)methanamine hydrochloride (34 g, 0.12 mol) and 5-(tert-butyl)-1,2,4-oxadiazole-3-carboxylic acid (29.2 g, 0.15 mol) in anhydrous DMF (500 mL) was added, DIPEA (62 mL, 0.36 mol). The resulting mixture was cooled to 0° C., T3P® (50% in DMF, 90 mL, 0.15 mol) was added, and the reaction was warmed to RT and was stirred for 2 h. The reaction mixture was partitioned between water (300 mL) and EtOAc (300 mL) and the layers were separated. The aqueous phase was extracted with EtOAc (3×100 mL), the combined organic extracts were washed with water (3×50 mL), saturated aqueous NaHCO$_3$ solution (50 mL), and brine (50 mL). The organic layer was dried (Na$_2$SO$_4$), filtered, and concentrated in vacuo to give a beige oil. The crude oil was purified by silica gel column chromatography (0-30% EtOAc/Hept) to give the title compound as a thick, pale yellow oil which slowly solidified on standing (29.0 g, 60%). LCMS m/z=400.2 [M+H]$^+$; $^1$H NMR (500 MHz, CDCl$_3$) δ: 7.70-7.62 (m, 2H), 7.31 (d, 1H), 7.09 (br s, 1H), 4.68 (d, 2H), 2.39 (s, 3H), 1.45 (s, 9H), 1.36 (s, 12H).

3. Synthesis of Examples 46-55 Using Parallel Chemistry Protocol

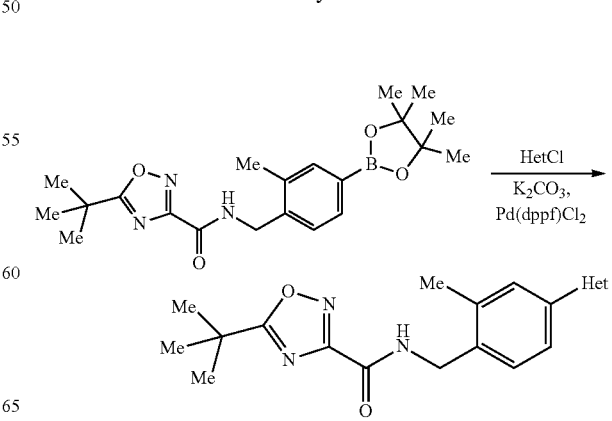

2 dram vials were charged with 5-(tert-butyl)-N-(2-methyl-4-(4,4,5,5-tetramethyl-1,3,2-dioxaborolan-2-yl)benzyl)-1,2,4-oxadiazole-3-carboxamide, the appropriate chloride (HetCl), Pd(dppf)Cl₂·DCM and K₂CO₃. Dioxane (1 mL) and H₂O (1 mL) were added and each reaction mixture was purged with a stream of N₂ for about 1 min. The reactions were heated at 90-100° C. for 16 h. The cooled reaction mixtures were concentrated in vacuo to yield black solids/oils and the residues were taken up in MeCN, filtered through a silica plug, and purified by prep-HPLC (Method B or Method C; optimized gradients per compound).

| Example Number | Name/Structure/HetCl | HPLC Method/Yield/Data |
|---|---|---|
| Example 46 | 5-(tert-butyl)-N-(2-methyl-4-(2-methylpyrazolo[1,5-a]pyrimidin-7-yl)benzyl)-1,2,4-oxadiazole-3-carboxamide trifluoroacetate<br />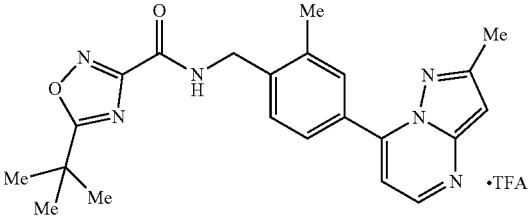<br />HetCl: 7-chloro-2-methylpyrazolo[1,5-a]pyrimidine | Method B.<br />Amber solid: 25.8 mg (40%)<br />LCMS m/z = 405.2 [M + H]⁺<br />¹H NMR (500 MHz, MeOH-d₄) δ: 8.76 (d, 1H), 7.99 (s, 1H), 7.94 (dd, 1H), 7.49-7.40 (m, 2H), 6.49 (s, 1H), 4.66 (s, 2H), 2.49 (d, 5H), 1.54-1.43 (m, 9H). |
| Example 47 | N-(4-([1,2,4]triazolo[4,3-b]pyridazin-8-yl)-2-methylbenzyl)-5-(tert-butyl)-1,2,4-oxadiazole-3-carboxamide<br />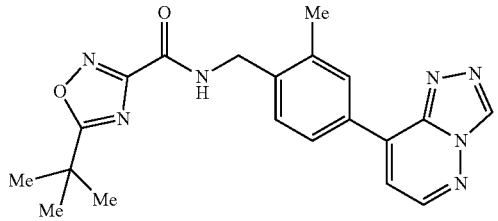<br />HetCl: 8-chloro-[1,2,4]triazolo[4,3-b]pyridazine | Method C.<br />Grey solid: 18.7 mg (38%)<br />LCMS m/z = 392.2 [M + H]⁺<br />¹H NMR (500 MHz, MeOH-d₄) δ: 9.50 (s, 1H), 8.62-8.55 (m, 1H), 8.17-8.04 (m, 2H), 7.60-7.47 (m, 2H), 4.73-4.66 (m, 2H), 2.52 (s, 3H), 1.54-1.44 (m, 1H), 1.54-1.44 (m, 9H) |
| Example 48 | 5-(tert-butyl)-N-(2-methyl-4-(5-methylimidazo[5,1-f][1,2,4]triazin-4-yl)benzyl)-1,2,4-oxadiazole-3-carboxamide<br />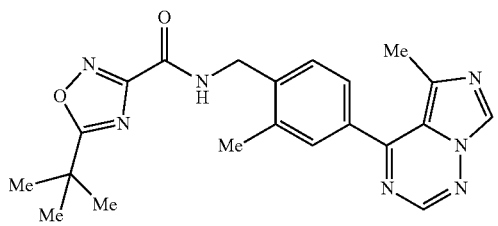<br />HetCl: 4-chloro-5-methylimidazo[5,1-f][1,2,4]triazine | Method C.<br />Green solid: 8.4 mg (16.5%)<br />LCMS m/z = 406.2 [M + H]⁺<br />¹H NMR (500 MHz, MeOH-d₄) δ: 8.68 (s, 1H), 8.47-8.40 (m, 1H), 7.67-7.57 (m, 2H), 7.56-7.50 (m, 1H), 4.71 (s, 2H), 2.56-2.46 (m, 3H), 2.42-2.31 (m, 3H), 1.54-1.47 (m, 9H). |

| Example Number | Name/Structure/HetCl | HPLC Method/Yield/Data |
|---|---|---|
| Example 49 | 5-(tert-butyl)-N-(2-methyl-4-(5-methylpyrrolo[2,1-f][1,2,4]triazin-4-yl)benzyl)-1,2,4-oxadiazole-3-carboxamide trifluoroacetate<br>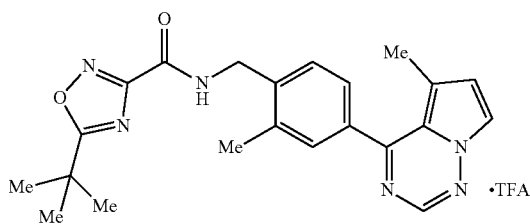<br>HctCl: 4-chloro-5-methylimidazo[2,1-f][1,2,4]triazine | Method B; 5-60%<br>Yield: 8.9 mg<br>LCMS m/z = 405.1 [M + H]$^+$<br>$^1$H NMR (500 MHz, MeOH-d$_4$) δ: 9.42 (br s, 1H), 8.41-8.31 (m, 1H), 8.17-8.07 (m, 1H), 7.59-7.46 (m, 3H), 6.98 (br d, 1H), 4.75-4.67 (m, 2H), 2.55-2.46 (m, 3H), 2.15-2.08 (m, 3H), 1.55-1.45 (m, 9H). |
| Example 50 | 5-(tert-butyl)-N-(2-methyl-4-(pyrazolo[1,5-a]pyrimidin-7-yl)benzyl)-1,2,4-oxadiazole-3-carboxamide trifluoroacetate<br>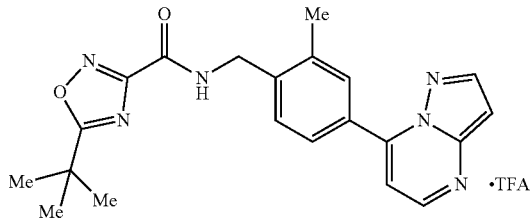<br>HetCl: 7-chloropyrazolo[1,5-a]pyrimidine | Method B; 18 mg<br>LCMS m/z = 391.0 [M + H]$^+$<br>$^1$H NMR (500 MHz, MeOH-d$_4$) δ: 9.48-9.28 (m, 1H), 8.55 (d, 1H), 8.19 (d, 1H), 7.97-7.86 (m, 2H), 7.52 (d, 1H), 7.12 (d, 1H), 6.77 (d, 1H), 4.70 (d, 2H), 2.56-2.46 (m, 3H), 1.54-1.45 (m, 9H) |
| Example 51 | N-(4-(6-bromopyrrolo[2,1-f][1,2,4]triazin-4-yl)-2-methylbenzyl)-5-(tert-butyl)-1,2,4-oxadiazole-3-carboxamide trifluoroacetate<br>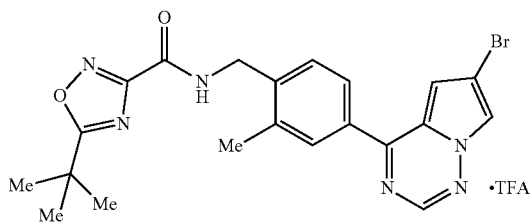<br>HetCl: 6-bromo-4-chloropyrrolo[2,1-f][1,2,4]triazine | Method B; 20-80%; 15 mg<br>LCMS m/z = 490.7 [M + Na]$^+$<br>$^1$H NMR (500 MHz, MeOH-d$_4$) δ: 8.49 (s, 1H), 8.10 (s, 1H), 7.93-7.86 (m, 2H), 7.53 (d, 1H), 7.24 (s, 1H), 4.83-4.68 (m, 2H), 2.52 (s, 3H), 1.49 (s, 9H). |
| Example 52 | 5-tert-butyl-N-[(4-imidazo[2,1-f][1,2,4]triazin-4-yl-2-methyl-phenyl)methyl]-1,2,4-oxadiazole-3-carboxamide trifluoroacetate<br>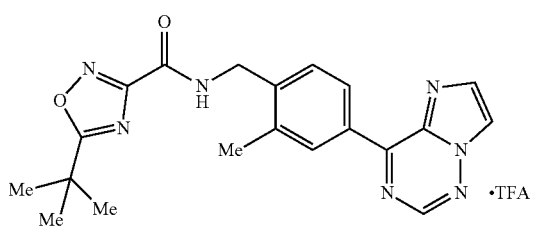<br>HetCl: 4-chloroimidazo[2,1-f][1,2,4]triazine | Method B; 5-65%; 8.9 mg, 18%<br>LCMS m/z = 392.1 [M + H]$^+$<br>$^1$H NMR (500 MHz, MeOH-d$_4$) δ: 8.87-8.79 (m, 1H), 8.72-8.61 (m, 2H), 8.29 (d, 1H), 8.01-7.98 (m, 1H), 7.53 (d, 1H), 4.75-4.68 (m, 2H), 2.56-2.50 (m, 3H), 1.53-1.44 (m, 9H). |

| Example Number | Name/Structure/HetCl | HPLC Method/Yield/Data |
|---|---|---|
| Example 53 | 5-tert-butyl-N-[[4-(3-cyanopyrrolo[1,2-b]pyridazin-4-yl)-2-methyl-phenyl]methyl]-1,2,4-oxadiazole-3-carboxamide trifluoroacetate 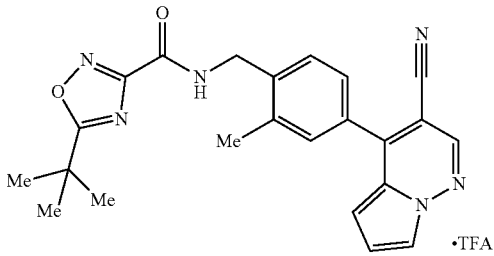 HetCl: 4-chloropyrrolo[1,2-b]pyridazine-3-carbonitrile | Method B 5-55%, 0.8 mg, 1.5% LCMS m/z = 415.2 [M + H]$^+$ |
| Example 54 | 5-tert-butyl-N-[(4-imidazo[5,1-f][1,2,4]triazin-4-yl-2-methyl-phenyl)methyl]-1,2,4-oxadiazole-3-carboxamide triacetate 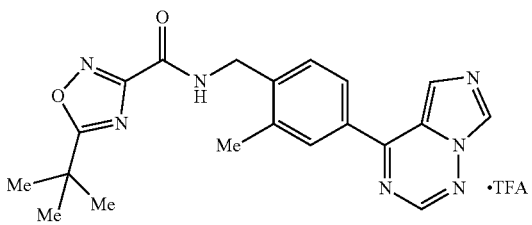 HetCl: 4-chloroimidazo[5,1-f][1,2,4]triazine | Method B 5-55%, 1.3 mg, 2.6% LCMS m/z = 392.1 [M + H]$^+$ |
| Example 55 | 5-(tert-butyl)-N-(2-methyl-4-(6-methylpyrrolo[2,1-f][1,2,4]triazin-4-yl)benzyl)-1,2,4-oxadiazole-3-carboxamide trifluoroacetate 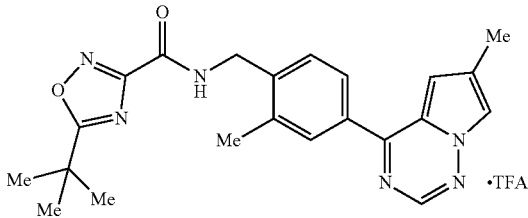 HetCl: 4-chloro-6-methylpyrrolo[2,1-f][1,2,4]triazine | Method B; 5-95% Yellow solid: 34.5 mg, 36% LCMS m/z = 405.5 [M + H]$^+$ $^1$H NMR (500 MHz, CDCl$_3$) δ: 8.46-8.44 (m, 1H), 7.94-7.89 (m, 2H), 7.73 (s, 1H), 7.48 (d, 1H), 7.20 (br s, 1H), 6.86 (s, 1H), 4.76 (d, 2H), 2.49 (s, 3H), 2.41 (s, 3H), 1.48 (s, 9H). |

Example 56. (R)-5-(tert-butyl)-N-(1-fluoro-2-(pyrrolo[2,1-f][1,2,4]triazin-4-yl)-6,7,8,9-tetrahydro-5H-benzo[7]annulen-5-yl)-1,2,4-oxadiazole-3-carboxamide

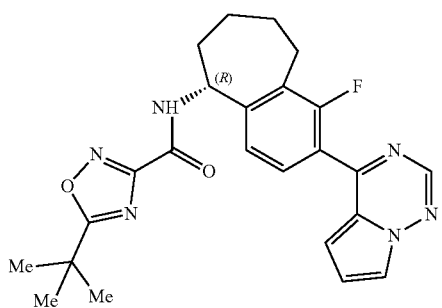

1. Synthesis of 5-(2-fluoro-3-methoxyphenyl)pent-4-enoic Acid

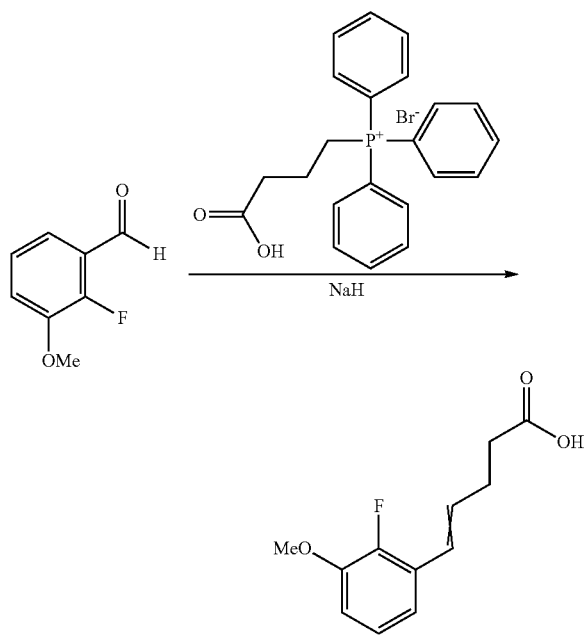

NaH (13.0 g, 324 mmol, 60% in mineral oil) was added to a solution of (3-carboxypropyl)triphenylphosphonium bromide (55.6 g, 129 mmol) in DMSO (500 mL) at 0° C. and the mixture was stirred at 0° C. for 30 min. 2-fluoro-3-methoxybenzaldehyde (20.0 g, 129 mmol) in DMSO (50 mL) was added and the mixture was stirred at RT for 14 h. The reaction mixture was quenched with water (500 mL) and extracted with EtOAc (500 mL). The aqueous layer was acidified to pH 3 with HCl aq. (1 N) and extracted with EtOAc (500 mL). The combined extracts were washed with water (500 mL), brine (2×500 mL), dried (Na$_2$SO$_4$), and concentrated in vacuo. The residue was purified by silica gel column chromatography (petroleum ether/EtOAc=5:1 to 1:1) to afford the title compound as a mixture of cis/trans isomers as a yellow oil (22 g, 76%). $^1$H NMR (400 MHz, CDCl$_3$) δ: 11.27 (brs, 1H), 7.00-7.10 (m, 1.5H), 6.80-6.90 (m, 1.5H), 6.60-6.70 (m, 0.5H), 6.40-6.50 (m, 0.5H), 6.30-6.40 (m, 0.5H), 5.70-5.80 (m, 0.5H), 3.85-3.90 (m, 3H), 2.40-2.60 (m, 4H).

2. Synthesis of 5-(2-fluoro-3-methoxyphenyl)pentanoic Acid

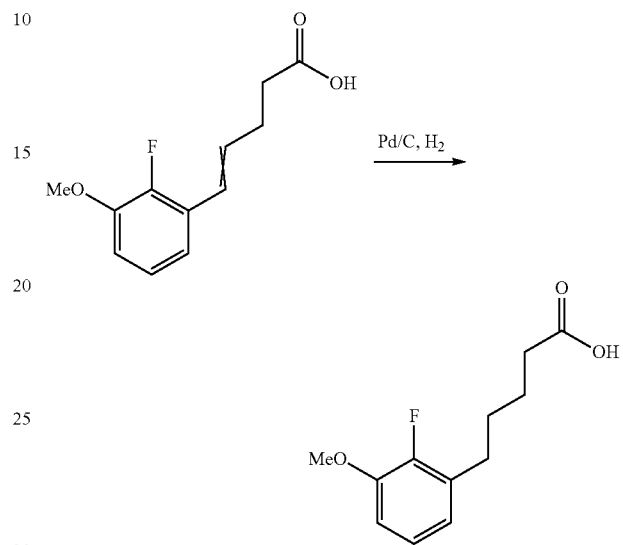

To a mixture of 5-(2-fluoro-3-methoxyphenyl)pent-4-enoic acid (22 g, 98 mmol) in EtOH (50 mL) was added Pd/C (4.00 g, 10% w/w, wet) and the mixture was stirred at 20° C. under H$_2$ (15 psi) for 1 h. The reaction mixture was filtered through Celite® and the filtrate concentrated in vacuo to give the title compound as an off-white solid (22 g, 99%). $^1$H NMR: (400 MHz, DMSO-d$_6$) δ: 12.04 (br s, 1H), 6.90-7.10 (m, 2H), 6.70-6.80 (m, 1H), 3.80 (s, 3H), 2.58 (t, 2H), 2.22 (t, 2H), 0.90-1.10 (m, 4H).

3. Synthesis of 1-fluoro-2-methoxy-6,7,8,9-tetrahydro-5H-benzo[7]annulen-5-one

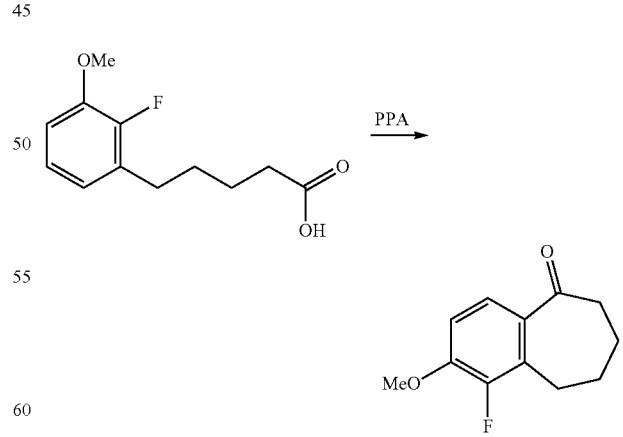

A solution of 5-(2-fluoro-3-methoxyphenyl)pentanoic acid (22.0 g, 97.2 mmol) in PPA (100 mL) was stirred at 100° C. for 30 min. The mixture was cooled to 15° C., diluted with NaOH aq. (1N, 300 mL), and extracted with EtOAc (2×300 mL). The combined organics were washed with brine (500 mL), dried (Na$_2$SO$_4$), and concentrated in vacuo. The residue was purified by silica gel column chromatography (petroleum ether/EtOAc=3:1) to give the title compound as a yellow oil (15 g, 74%). $^1$H NMR: (400 MHz, CDCl$_3$) δ: 7.58 (dd, 1H), 6.89 (t, 1H), 3.94 (s, 3H), 3.01 (t, 2H), 2.73 (t, 2H), 1.60-1.90 (m, 4H).

4. Synthesis of 1-fluoro-2-hydroxy-6,7,8,9-tetrahydro-5H-benzo[7]annulen-5-one

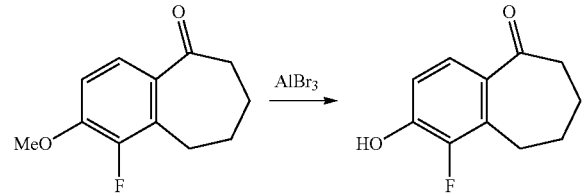

AlBr$_3$ (28.8 mL, 29 mmol, 1 M in CH$_2$Br$_2$) was added to a solution of 1-fluoro-2-methoxy-6,7,8,9-tetrahydro-5H-benzo[7]annulen-5-one (5.0 g, 24 mmol) in toluene (50 mL) under N$_2$. The mixture was stirred at 95° C. under N$_2$ for 2 h. The reaction mixture was poured into aqueous HCl solution (100 mL, 1 M) and extracted with EtOAc (2×100 mL). The combined organics were washed with brine (100 mL), dried (Na$_2$SO$_4$) and concentrated in vacuo. The residue was purified by silica gel column chromatography (petroleum ether/EtOAc=5:1) to give the title compound as a brown solid (5.4 g, 96%). $^1$H NMR (400 MHz, CDCl$_3$) δ: 7.53 (dd, 1H), 6.92 (t, 1H), 5.88-5.87 (m, 1H), 2.99 (t, 2H), 2.73 (t, 2H), 1.92-1.79 (m, 4H).

5. Synthesis of (R,Z)—N-(1-fluoro-2-hydroxy-6,7,8,9-tetrahydro-5H-benzo[7]annulen-5-ylidene)-2-methylpropane-2-sulfinamide

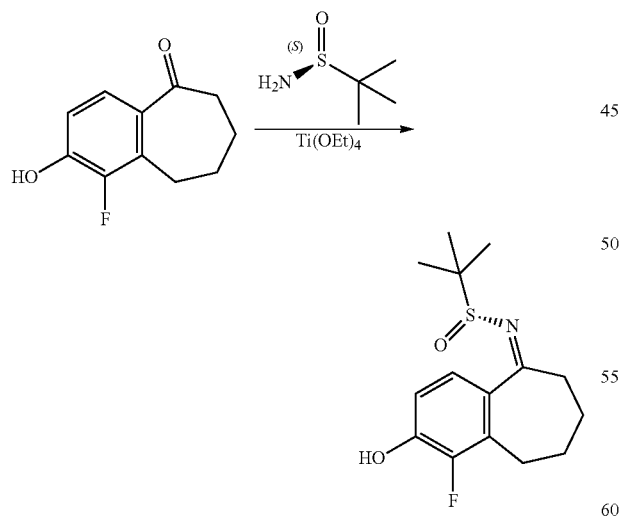

To a solution of 1-fluoro-2-hydroxy-6,7,8,9-tetrahydro-5H-benzo[7]annulen-5-one (5.0 g, 25.8 mmol) in THF (300 mL) was added (S)-2-methylpropane-2-sulfinamide (25 g, 206 mmol) and titanium ethoxide (47 g, 206 mmol) and the mixture was stirred at 80° C. for 17 h. The reaction mixture was poured into H$_2$O (1 L) and extracted with EtOAc (3×500 mL). The combined organics were dried (Na$_2$SO$_4$) and concentrated in vacuo. The residue was purified by silica gel column chromatography (petroleum ether/EtOAc=5:1) to give the title compound as a yellow solid (6.0 g, 78%). $^1$H NMR: (400 MHz, DMSO-d$_6$) δ: 10.30 (s, 1H), 7.23 (d, 1H), 6.84 (t, 1H), 3.13-2.77 (m, 4H), 1.74-1.69 (m, 4H), 1.18 (s, 9H).

6. Synthesis of (S)—N—((R)-1-fluoro-2-hydroxy-6,7,8,9-tetrahydro-5H-benzo[7]annulen-5-yl)-2-methylpropane-2-sulfinamide

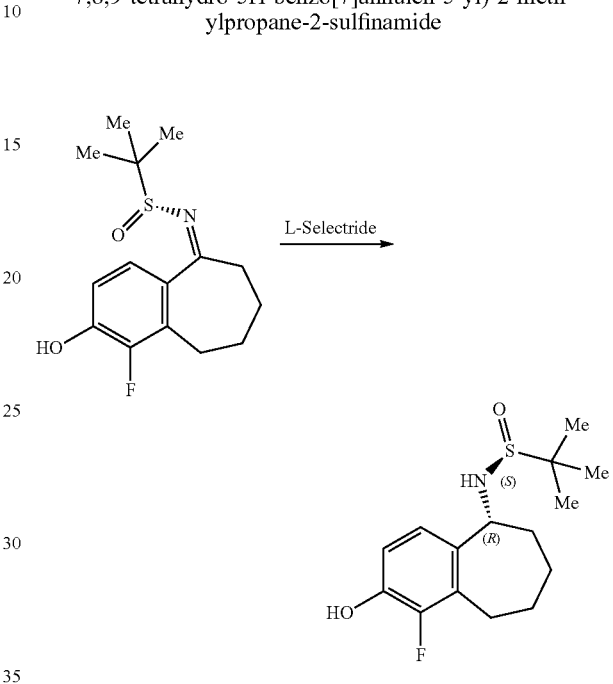

L-selectride (26.9 mL, 26.9 mmol) was added slowly to a solution of (R,Z)—N-(1-fluoro-2-hydroxy-6,7,8,9-tetrahydro-5H-benzo[7]annulen-5-ylidene)-2-methylpropane-2-sulfinamide (2.0 g, 6.7 mmol) in THF (40 mL) at 20° C. and stirred for 2 h. The reaction was quenched with saturated aqueous NH$_4$Cl solution (30 mL), poured into H$_2$O (100 mL) and extracted with EtOAc (2×100 mL). The combined organics were washed with brine (100 mL), dried (Na$_2$SO$_4$), and concentrated in vacuo. The residue was purified by pre-HPLC (Waters Xbridge Prep OBD C18 150×30 mm, 5 μm, water (0.05% NH$_4$OH)-MeCN; 26-56%) to afford the title compound as a white solid (500 mg, 25%). $^1$H NMR: (400 MHz, DMSO-d$_6$) δ: 9.56 (s, 1H), 6.86 (d, 1H), 6.65 (t, 1H), 5.14 (d, J=3.6 Hz, 1H), 4.34 (s, 1H), 2.87-2.65 (m, 2H), 1.92-1.48 (m, 6H), 1.11 (s, 9H).

7. Synthesis of (R)-5-amino-1-fluoro-6,7,8,9-tetrahydro-5H-benzo[7]annulen-2-ol

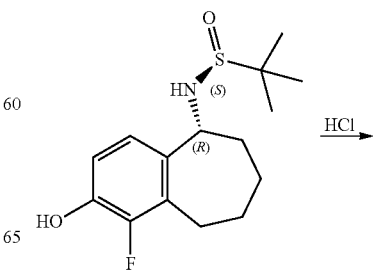

-continued

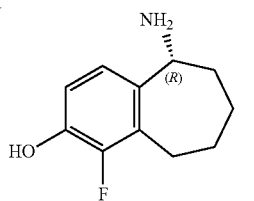

An HCl solution (5 mL, 4 M in EtOAc) was added to a solution of (S)—N—((R)-1-fluoro-2-hydroxy-6,7,8,9-tetrahydro-5H-benzo[7]annulen-5-yl)-2-methylpropane-2-sulfinamide (550 mg, 1.8 mmol) in EtOAc (1 mL) and the mixture was stirred at 10° C. for 1 h. The reaction mixture was concentrated in vacuo and the residue was used for the next step directly without further purification. LCMS m/z=179.0 [M−OH]$^+$ 8. Synthesis of tert-butyl (R)-(1-fluoro-2-hydroxy-6,7,8,9-tetrahydro-5H-benzo[7]annulen-5-yl)carbamate

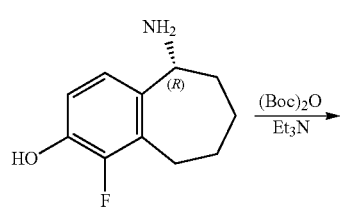

Boc$_2$O (402 mg, 1.84 mmol) was added to a solution of (R)-5-amino-1-fluoro-6,7,8,9-tetrahydro-5H-benzo[7]annulen-2-ol (360 mg, 1.8 mmol) and Et$_3$N (373 mg, 3.7 mmol) in DCM (5 mL) and the mixture was stirred at 20° C. for 2 h. The reaction mixture was concentrated in vacuo and the residue was purified by silica gel column chromatography (petroleum ether/EtOAc=20:1) to afford the title compound as a white solid (250 mg, 46%). $^1$H NMR: (400 MHz, DMSO-d$_6$) δ: 9.46 (s, 1H), 7.37 (d, 1H), 6.75 (d, 1H), 6.66 (t, 1H), 4.59 (t, 1H), 3.07-3.03 (m, 1H), 2.45-2.42 (m, 1H), 1.77-1.64 (m, 4H), 1.47-1.45 (m, 1H), 1.37 (s, 9H), 1.28-1.16 (m, 1H).

9. Synthesis of (R)-5-((tert-butoxycarbonyl)amino)-1-fluoro-6,7,8,9-tetrahydro-5H-benzo[7]annulen-2-yl trifluoromethanesulfonate

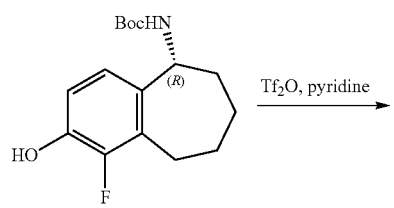

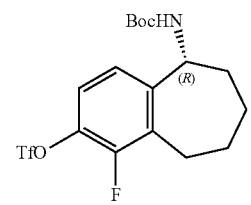

To a solution of tert-butyl (R)-(1-fluoro-2-hydroxy-6,7,8,9-tetrahydro-5H-benzo[7]annulen-5-yl)carbamate (250 mg, 0.85 mmol) in DCM (5 mL) was added Tf$_2$O (263 mg, 0.93 mmol) and pyridine (134 mg, 1.7 mmol) at 10° C. and the resulting mixture was stirred at 10° C. for 1 h. The reaction mixture was poured into water (20 mL) and extracted with DCM (2×2 mL). The combined organics were washed with brine (60 mL), dried (Na$_2$SO$_4$), and concentrated in vacuo.

The residue was purified by silica gel column chromatography (petroleum ether/EtOAc=10:1) to afford the title compound as a yellow solid (380 mg, quantitative). $^1$H NMR: (400 MHz, DMSO-d$_6$) δ: 7.64 (d, 1H), 7.47 (t, 1H), 7.12 (d, 1H), 4.73 (t, 1H), 3.16-3.11 (m, 1H), 2.65-2.58 (m, 1H), 1.81-1.74 (m, 4H), 1.54-1.45 (m, 1H), 1.38 (s, 9H), 1.22-1.20 (m, 1H).

10. Synthesis of tert-butyl (R)-(1-fluoro-2-(4,4,5,5-tetramethyl-1,3,2-dioxaborolan-2-yl)-6,7,8,9-tetrahydro-5H-benzo[7]annulen-5-yl)carbamate

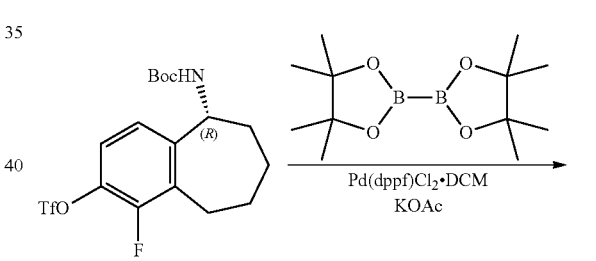

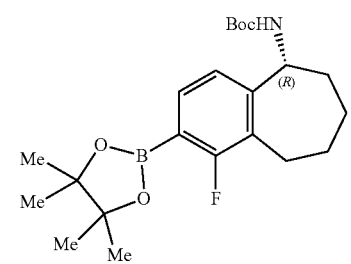

To a solution of (R)-5-((tert-butoxycarbonyl)amino)-1-fluoro-6,7,8,9-tetrahydro-5H-benzo[7]annulen-2-yl trifluoromethanesulfonate (380 mg, 0.9 mmol) in dioxane (5 mL) were added bis(pinacolato)diboron (339 mg, 1.3 mmol), Pd(dppf)Cl$_2$·DCM (73 mg, 0.09 mmol) and KOAc (175 mg, 1.8 mmol). The mixture was stirred at 85° C. under N$_2$ for 17 h. The mixture was concentrated under reduced pressure and the residue purified by silica gel column chromatography (petroleum ether/EtOAc=10:1) to afford the title compound as a yellow solid (350 mg, crude). LCMS m/z=268.0 [M−(C$_6$H$_{10}$)−tBu+H]$^+$

11. Synthesis of tert-butyl (R)-(1-fluoro-2-(pyrrolo[2,1-f][1,2,4]triazin-4-yl)-6,7,8,9-tetrahydro-5H-benzo[7]annulen-5-yl)carbamate

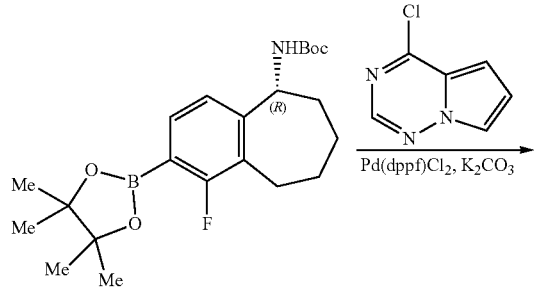

To a solution of tert-butyl (R)-(1-fluoro-2-(4,4,5,5-tetramethyl-1,3,2-dioxaborolan-2-yl)-6,7,8,9-tetrahydro-5H-benzo[7]annulen-5-yl)carbamate (250 mg, 0.62 mmol) in dioxane (30 mL) and H$_2$O (5 mL) were added 4-chloropyrrolo[2,1-f][1,2,4]triazine (104 mg, 0.68 mmol) and K$_2$CO$_3$ (171 mg, 1.2 mmol) at 20° C. Pd(dppf)Cl$_2$ (45 mg, 0.06 mmol) was added under a N$_2$ atmosphere at 20° C. and the mixture stirred at 85° C. for 4 h under N$_2$. The cooled reaction mixture was filtered and concentrated in vacuo and the residue was purified by silica gel column chromatography (petroleum ether/EtOAc=5:1) to afford the title compound as a yellow solid (180 mg, 74%). LCMS m/z=397.1 [M+H]$^+$

12. Synthesis of (R)-1-fluoro-2-(pyrrolo[2,1-f][1,2,4]triazin-4-yl)-6,7,8,9-tetrahydro-5H-benzo[7]annulen-5-amine hydrochloride

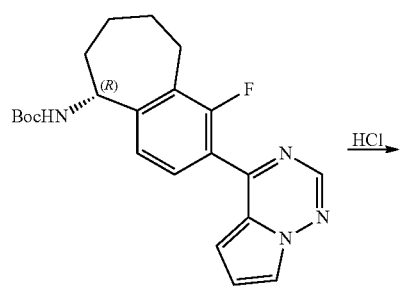

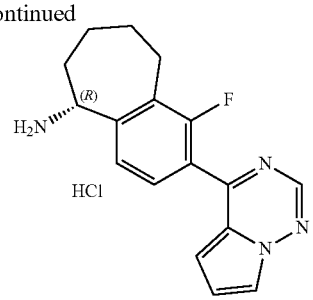

A solution of tert-butyl (R)-(1-fluoro-2-(pyrrolo[2,1-f][1,2,4]triazin-4-yl)-6,7,8,9-tetrahydro-5H-benzo[7]annulen-5-yl)carbamate (180 mg, 0.45 mmol) in an HCl solution (30 mL, 4 M in EtOAc) was stirred at 20° C. for 1 h. The mixture was concentrated in vacuo to afford the title compound as a yellow solid (150 mg, crude) which was used in the next step without further purification. LCMS m/z=297.1 [M+H]$^+$

13. Synthesis of (R)-5-(tert-butyl)-N-(1-fluoro-2-(pyrrolo[2,1-f][1,2,4]triazin-4-yl)-6,7,8,9-tetrahydro-5H-benzo[7]annulen-5-yl)-1,2,4-oxadiazole-3-carboxamide hydrochloride To a solution of (R)-1-fluoro-2-(pyrrolo[2,1-f][1,2,4]triazin-4-yl)-6,7,8,9-tetrahydro-5H-benzo[7]annulen-5-amine hydrochloride (100 mg, 0.3 mmol) in DCM (30 mL) was added DIPEA (78 mg, 0.6 mmol) at 20° C. 5-(tert-butyl)-1,2,4-oxadiazole-3-carboxylic acid (77 mg, 0.5 mmol) and HATU (172 mg, 0.5 mmol) were added slowly at 20° C. and the mixture was stirred at 20° C. for 1 h. The reaction mixture was poured into H$_2$O (50 mL) and extracted with DCM (3×50 mL). The combined organics were washed with brine (100 mL), dried (Na$_2$SO$_4$), and concentrated in vacuo. The residue was purified by prep-HPLC (Method A; 50-70%) to afford the title compound as a white solid (90 mg, 67%). LCMS m/z=449.1 [M+H]$^+$. $^1$H NMR: (400 MHz, DMSO-d$_6$) δ: 9.67 (d, 1H), 8.62 (s, 1H), 8.18 (s, 1H), 7.61-7.56 (m, 1H), 7.22 (d, 1H), 7.08-7.05 (m, 1H), 6.86 (s, 1H), 5.32 (t, 1H), 3.28 (d, 1H), 2.66 (d, 1H), 1.93-1.81 (m, 5H), 1.44 (s, 9H), 1.29 (d, 1H).

Example 57. (R)-3-(tert-butyl)-N-(1-(2-methyl-4-(6-(1-methyl-1H-pyrazol-4-yl)pyrrolo[2,1-f][1,2,4]triazin-4-yl)phenyl)ethyl)-1,2,4-oxadiazole-5-carboxamide

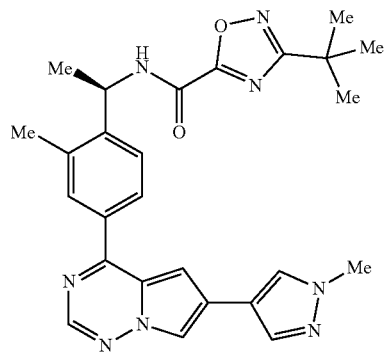 [SMILES: Cc1cc(-c2ncnn3cc(-c4cnn(C)c4)cc23)ccc1[C@@H](C)NC(=O)c1nc(C(C)(C)C)no1]

1. Synthesis of 1-(4-bromo-2-methylphenyl)ethan-1-one

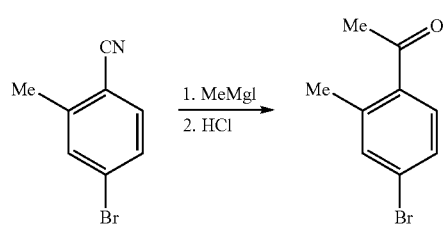 [SMILES: Cc1cc(Br)ccc1C#N ; CC(=O)c1ccc(Br)cc1C]

Methylmagnesium iodide (3M, 10.2 mL) was added dropwise to a solution of 4-bromo-2-methyl-benzonitrile (4.0 g, 20 mmol) in THF (20 mL) at RT. The reaction mixture was heated under reflux for 2 h, cooled to RT, and stirred for a further 72 h. The reaction mixture was cooled to 0° C. and quenched with saturated aqueous NH$_4$Cl solution (100 mL) and extracted into EtOAc (2×100 mL). The combined organics were concentrated in vacuo and the residue treated with aqueous HCl solution (4 N, 20 mL) at 0° C. and the mixture was then stirred at RT for 18 h. The reaction mixture was extracted with EtOAc (50 mL), washed with H$_2$O (50 mL), dried (Na$_2$SO$_4$), and concentrated in vacuo to give the title compound as a pale orange oil (3.0 g, 70%). LCMS m/z=213.0 [M+H]$^+$ 2. Synthesis of (R,E)-N-(1-(4-bromo-2-methylphenyl)ethylidene)-2-methylpropane-2-sulfinamide

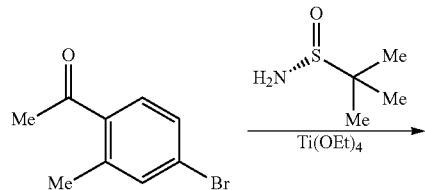

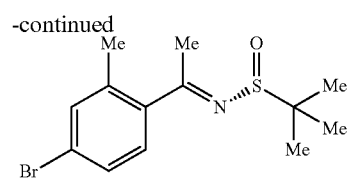

To a solution of 1-(4-bromo-2-methylphenyl)ethan-1-one (3.0 g, 14 mmol) in THF (48 mL) was added (R)-(+)-2-methyl-2-propanesulfinamide (1.7 g, 14 mmol) and Ti(OEt)$_4$ (6.5 g, 28 mmol) and the mixture heated at 70° C. for 20 h. The cooled reaction mixture was quenched with brine (100 mL) and diluted with EtOAc (100 mL) to afford a biphasic mixture with a thick white precipitate. The solid was removed by filtration and the layers were separated, and the combined organics were dried (Na$_2$SO$_4$) and concentrated in vacuo. The residue was purified by silica gel column chromatography (0-50% EtOAc/Hept) to afford the title compound as a yellow oil (2.96 g, 66%). LCMS m/z=318.0 [M+H]$^+$ 3. Synthesis of (R)—N—((R)-1-(4-bromo-2-methylphenyl)ethyl)-2-methylpropane-2-sulfinamide

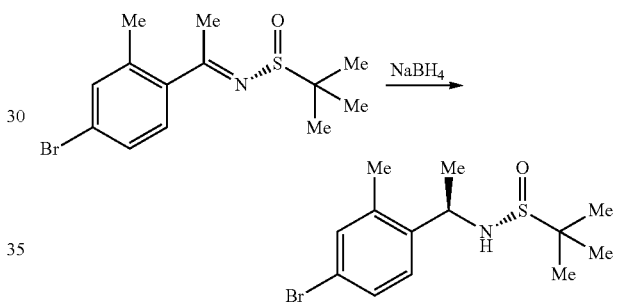

NaBH$_4$ (1.06 g, 28 mmol) was slowly added portion-wise to a solution of (R,E)-N-(1-(4-bromo-2-methylphenyl)ethylidene)-2-methylpropane-2-sulfinamide (2.96 g, 9.4 mmol) in THF/H$_2$O (98/2, 62.4 mL) at −50° C. The mixture was stirred for 7 h at −50° C. and then was warmed to RT over 18 h. The reaction was quenched with H$_2$O (20 mL) and extracted with EtOAc (100 mL). The combined organics were dried (Na$_2$SO$_4$) and concentrated in vacuo. The residue was purified by silica gel column chromatography (20-100% EtOAc/Hept) to afford the title compound as a colorless oil (1.6 g, yield: 55%). LCMS m/z=320.1 [M+H]$^+$ 4. Synthesis of (R)-1-(4-bromo-2-methylphenyl)ethan-1-amine hydrochloride

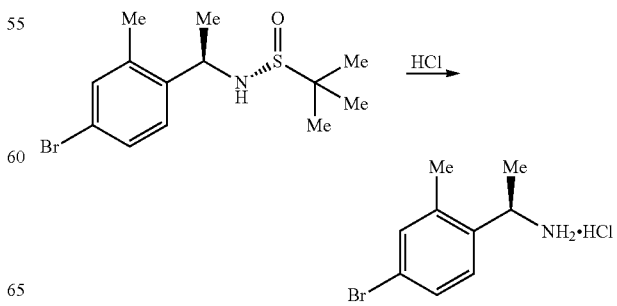

An HCl solution (30 mL, 4 M in EtOAc) was added to a solution of (R)—N—((R)-1-(4-bromo-2-methylphenyl)ethyl)-2-methylpropane-2-sulfinamide (4.5 g, 14 mmol) in EtOAc (5 mL) at 15° C. and the reaction mixture was stirred for 2 h. The mixture was filtered, and the filter cake was dried in vacuo to give the title compound as a white solid (3.3 g, 93%) which was used in the next step without further purification. LCMS m/z=198.9 [M–NH$_2$]$^+$

5. Synthesis of tert-butyl (R)-(1-(4-bromo-2-methylphenyl)ethyl)carbamate

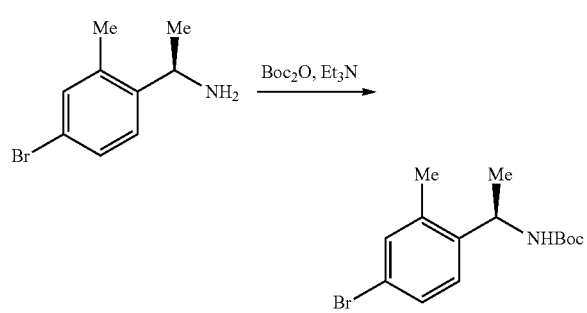

To a solution of (R)-1-(4-bromo-2-methylphenyl)ethan-1-amine hydrochloride (3.3 g, 13.2 mmol) in DCM (40 mL) at 15° C. was added Et$_3$N (2.67 g, 26.3 mmol) and Boc$_2$O (3.7 g, 17.1 mmol) and the mixture was stirred at 15° C. for 17 h. The reaction mixture was concentrated in vacuo and the residue purified by silica gel column chromatography (petroleum ether/EtOAc=20:1) to give the title compound as a white solid (3.8 g, 92%). LCMS m/z=198.8 [M-Boc-NH$_2$]$^+$

6. Synthesis of tert-butyl (R)-(1-(2-methyl-4-(4,4,5,5-tetramethyl-1,3,2-dioxaborolan-2-yl)phenyl)ethyl)carbamate

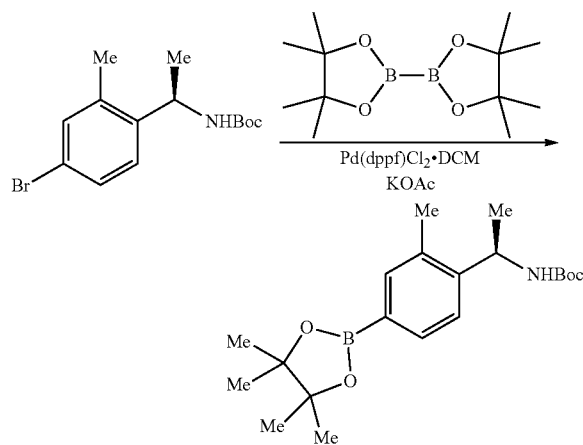

To a solution of tert-butyl (R)-(1-(4-bromo-2-methylphenyl)ethyl)carbamate (3.8 g, 12.1 mmol) in 1,4-dioxane (30 mL) under N$_2$ were added bis(pinacolato)diboron (3.7 g, 14.5 mmol), Pd(dppf)Cl$_2$·DCM (987 mg, 1.2 mmol) and KOAc (2.4 g, 24.2 mmol). The reaction mixture was heated at 85° C. under N$_2$ for 17 h. The reaction mixture was concentrated in vacuo and the residue purified by silica gel column chromatography (petroleum ether/EtOAc=20:1) to give the title compound as a yellow oil (4.0 g, 87%). $^1$H NMR: (400 MHz, MeOH-d$_4$) δ: 7.53 (d, 1H), 7.50 (s, 1H), 7.30 (d, 1H), 3.65 (s, 1H), 2.37 (s, 3H), 1.41 (s, 9H), 1.33 (s, 12H), 1.25-1.22 (m, 3H).

7. Synthesis of tert-butyl (R)-(1-(4-(6-bromopyrrolo[2,1-f][1,2,4]triazin-4-yl)-2-methylphenyl)ethyl)carbamate

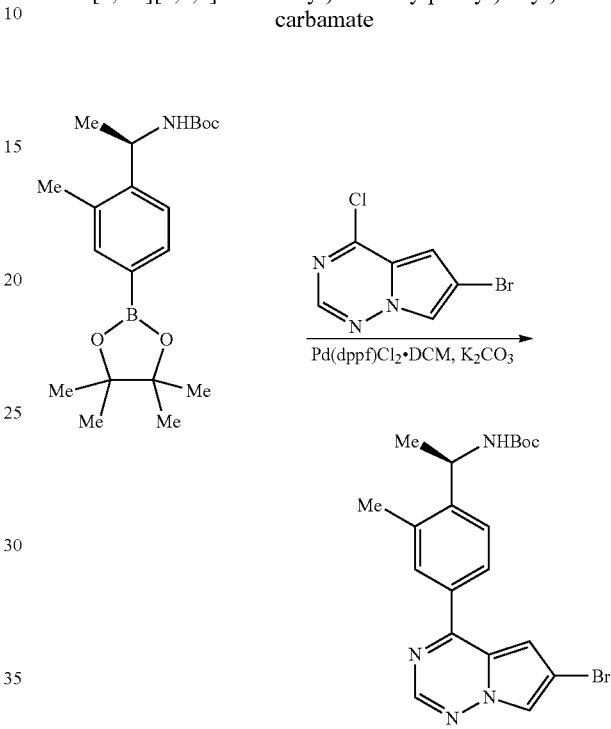

A mixture of tert-butyl (R)-(1-(2-methyl-4-(4,4,5,5-tetramethyl-1,3,2-dioxaborolan-2-yl)phenyl)ethyl)carbamate (405 mg, 1.1 mmol), 6-bromo-4-chloropyrrolo[2,1-f][1,2,4]triazine (520 mg, 2.2 mmol), Pd(dppf)Cl$_2$·DCM (82 mg, 0.11 mmol) and K$_2$CO$_3$ (310 mg, 2.2 mmol) in dioxane (10 mL) and water (0.1 mL) was stirred at 100° C. for 12 h under N$_2$. The mixture was concentrated in vacuo and the residue was purified by silica gel column chromatography (0-33% EtOAc/petroleum ether) to give the title compound as a red solid (380 mg, 79%). LCMS m/z=433.1 [M+H]$^+$

8. Synthesis of tert-butyl (R)-(1-(2-methyl-4-(6-(1-methyl-1H-pyrazol-4-yl)pyrrolo[2,1-f][1,2,4]triazin-4-yl)phenyl)ethyl)carbamate

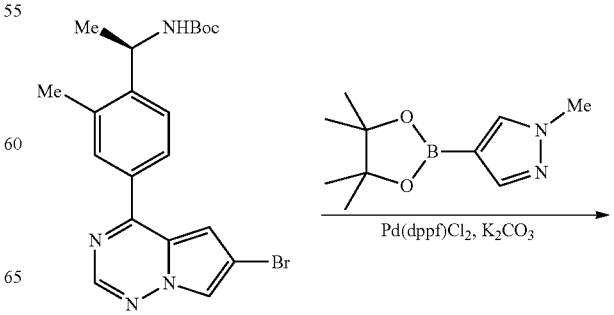

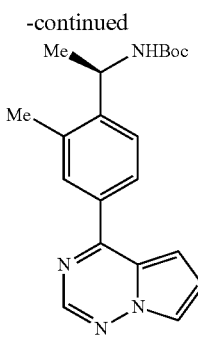

A mixture of tert-butyl (R)-(1-(4-(6-bromopyrrolo[2,1-f][1,2,4]triazin-4-yl)-2-methylphenyl)ethyl)carbamate (380 mg, 0.88 mmol), 1-methyl-4-(4,4,5,5-tetramethyl-1,3,2-dioxaborolan-2-yl)-1H-pyrazole (183 mg, 0.88 mmol), Pd(dppf)Cl$_2$ (64 mg, 0.09 mmol) and K$_2$CO$_3$ (244 mg, 1.76 mmol) in a mixture of dioxane (10 mL) and water (1 mL) was stirred at 90° C. for 12 hours under N$_2$. The mixture was concentrated in vacuo and the residue purified by silica gel column chromatography (0-50% EtOAc/petroleum ether) to give the title compound as a yellow oil (260 mg, 68%). LCMS m/z=433.1 [M+H]$^+$

9. Synthesis of (R)-1-(2-methyl-4-(6-(1-methyl-1H-pyrazol-4-yl)pyrrolo[2,1-f][1,2,4]triazin-4-yl)phenyl)ethan-1-amine hydrochloride

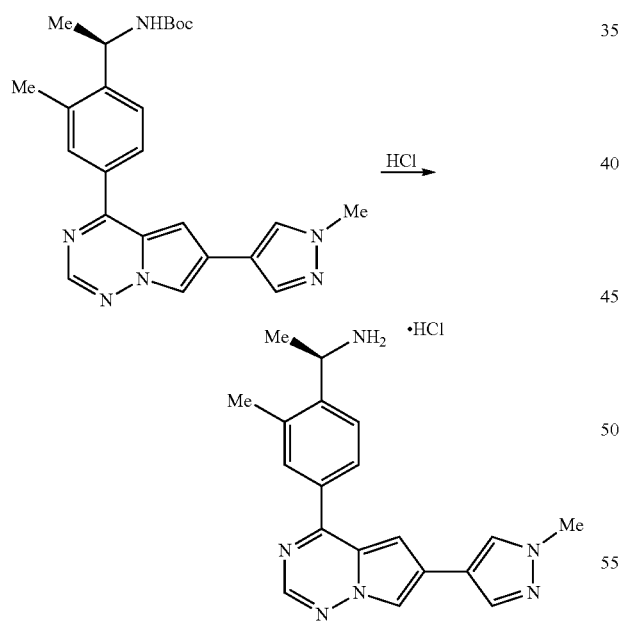

An HCl solution (10 mL, 4 M in EtOAc) was added to tert-butyl (R)-(1-(2-methyl-4-(6-(1-methyl-1H-pyrazol-4-yl)pyrrolo[2,1-f][1,2,4]triazin-4-yl)phenyl)ethyl)carbamate (260 mg, 0.6 mmol) and the mixture was stirred at 20° C. for 1 h. The mixture was concentrated in vacuo to give the title compound as a yellow solid (220 mg, crude) which was used in next step without further purification. LCMS m/z=333.3 [M+H]$^+$

10. Synthesis of (R)-3-(tert-butyl)-N-(1-(2-methyl-4-(6-(1-methyl-1H-pyrazol-4-yl)pyrrolo[2,1-f][1,2,4]triazin-4-yl)phenyl)ethyl)-1,2,4-oxadiazole-5-carboxamide

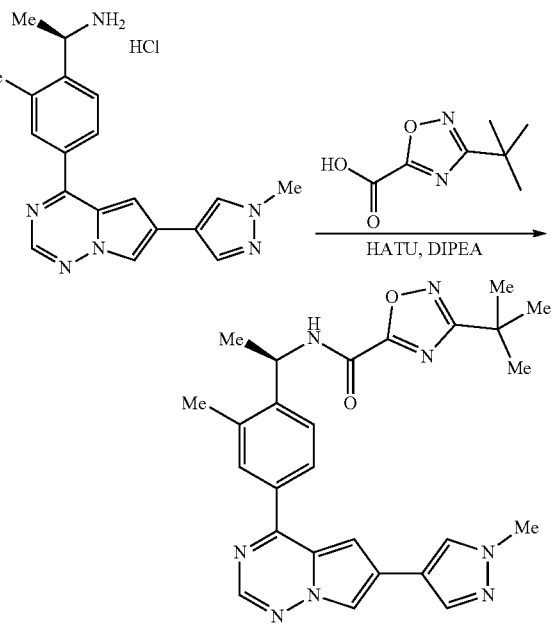

To a solution of (R)-1-(2-methyl-4-(6-(1-methyl-1H-pyrazol-4-yl)pyrrolo[2,1-f][1,2,4]triazin-4-yl)phenyl)ethan-1-amine hydrochloride (80 mg, 0.22 mmol) and 3-(tert-butyl)-1,2,4-oxadiazole-5-carboxylic acid (74 mg, 0.44 mmol) in DCM (45 mL) was added DIPEA (84 mg, 0.65 mmol), followed by slow addition of HATU (99 mg, 0.26 mmol). The reaction mixture was stirred at 20° C. for 1 h and concentrated in vacuo. The residue was purified by prep-HPLC (Method A; 51-71%) to give the title compound as a yellow solid (55.6 mg, 52%). LCMS m/z=485.2 [M+H]$^+$; $^1$H NMR: (500 MHz, DMSO-d$_6$) δ: 10.01 (d, 1H), 8.59 (s, 1H), 8.50 (d, 1H), 8.22 (s, 1H), 8.03-8.01 (m, 1H), 7.98-7.96 (m, 2H), 7.70 (d, 1H), 7.45 (d, 1H), 5.42-5.35 (m, 1H), 3.88 (s, 3H), 2.55 (s, 3H), 1.56 (d, 3H), 1.38 (s, 9H).

Example 58. 5-(tert-butyl)-N-(4-(6-(2-methoxyethoxy)pyrrolo[2,1-f][1,2,4]triazin-4-yl)-2-methylbenzyl)-1,2,4-oxadiazole-3-carboxamide

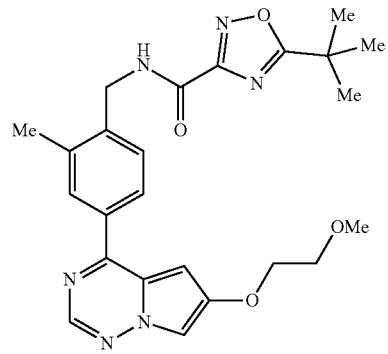 [SMILES: COCCOc1cc2c(-c3ccc(CNC(=O)c4noc(C(C)(C)C)n4)c(C)c3)ncnn2c1]

1. Synthesis of tert-butyl (2-methyl-4-(6-(4,4,5,5-tetramethyl-1,3,2-dioxaborolan-2-yl)pyrrolo[2,1-f][1,2,4]triazin-4-yl)benzyl)carbamate

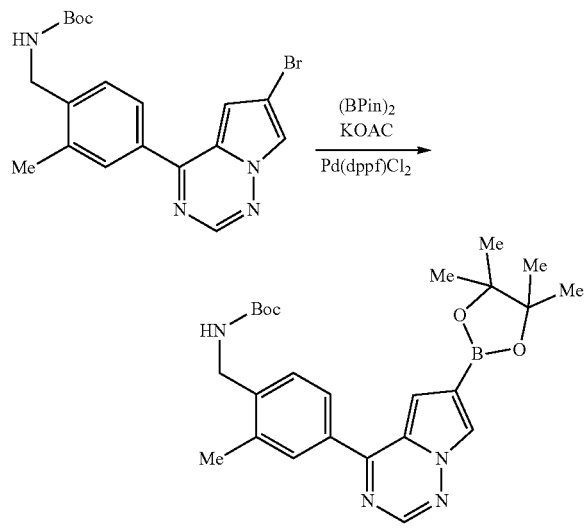

(Bispinacolato)diboron (183 mg, 0.72 mmol), KOAc (71 mg, 0.72 mmol) and Pd(dppf)Cl$_2$ (29 mg, 0.036 mmol) were added to a solution of tert-butyl (4-(6-bromopyrrolo[2,1-f][1,2,4]triazin-4-yl)-2-methylbenzyl)carbamate (150 mg, 0.36 mmol) in dioxane (15 mL) and the reaction stirred at 80° C. under N$_2$ for 16 h. The cooled mixture was concentrated in vacuo to afford the title compound which was carried forward without further purification. LCMS m/z=465.3 [M+H]$^+$

2. Synthesis of tert-butyl (4-(6-hydroxypyrrolo[2,1-f][1,2,4]triazin-4-yl)-2-methylbenzyl)carbamate

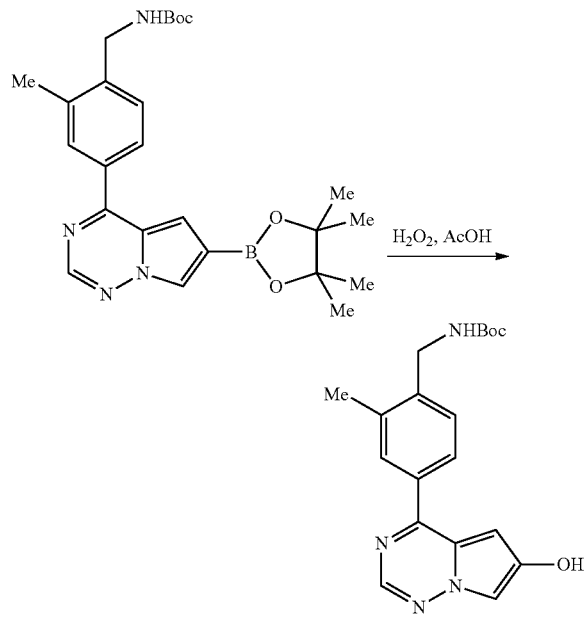

To a solution of tert-butyl (2-methyl-4-(6-(4,4,5,5-tetramethyl-1,3,2-dioxaborolan-2-yl)pyrrolo[2,1-f][1,2,4]triazin-4-yl)benzyl)carbamate (680 mg, 1.5 mmol) in THF (20 mL) was added H$_2$O$_2$ (498 mg, 4.4 mmol, 30% purity) and AcOH (264 mg, 4.4 mmol) and the mixture was stirred at 50° C. for 2 h. The reaction was poured into H$_2$O (20 mL) and extracted with DCM (3×10 mL). The combined organics were treated with Na$_2$SO$_3$ and the mixture was concentrated in vacuo. The residue was purified by silica gel column chromatography (0-100% petroleum ether/EtOAc) to afford the title compound as a yellow oil (350 mg, 68%). LCMS m/z=355.1 [M+H]$^+$

3. Synthesis of tert-butyl (4-(6-(2-methoxyethoxy)pyrrolo[2,1-f][1,2,4]triazin-4-yl)-2-methylbenzyl)carbamate

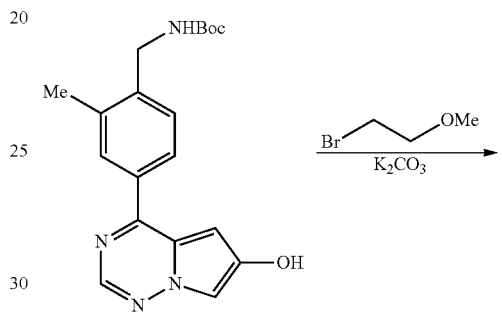

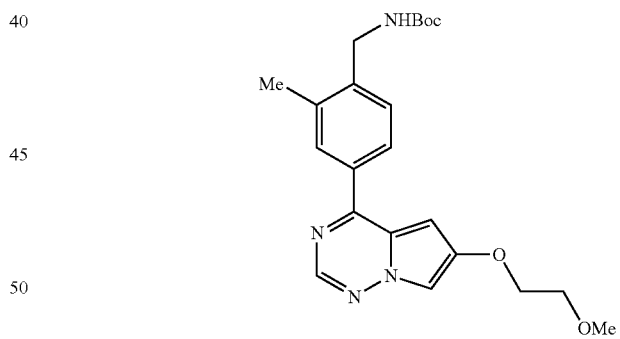

To a solution of tert-butyl (4-(6-hydroxypyrrolo[2,1-f][1,2,4]triazin-4-yl)-2-methylbenzyl)carbamate (130 mg, 0.37 mmol) in DMF (3 mL) was added 1-bromo-2-methoxyethane (153 mg, 1.1 mmol) and K$_2$CO$_3$ (152 mg, 1.1 mmol) and the mixture was stirred at 100° C. for 5 h. The reaction was diluted with brine (20 mL) and extracted with EtOAc (3×10 mL). The combined organics were dried (Na$_2$SO$_4$) and concentrated in vacuo. The residue was purified by prep-TLC (50% petroleum ether/EtOAc) to afford the title compound as a yellow oil (120 mg, 79%). $^1$H NMR (400 MHz, CDCl$_3$) δ: 8.46 (s, 1H), 7.82 (s, 2H), 7.62 (d, 1H), 7.41-7.37 (m, 1H), 6.58 (d, 1H), 4.84 (s, 1H), 4.38 (d, 2H), 4.20-4.17 (m, 2H), 3.77-3.74 (m, 2H), 3.44 (s, 3H), 2.40 (s, 3H), 1.46 (s, 9H).

4. Synthesis of (4-(6-(2-methoxyethoxy)pyrrolo[2,1-f][1,2,4]triazin-4-yl)-2-methylphenyl)methanamine hydrochloride

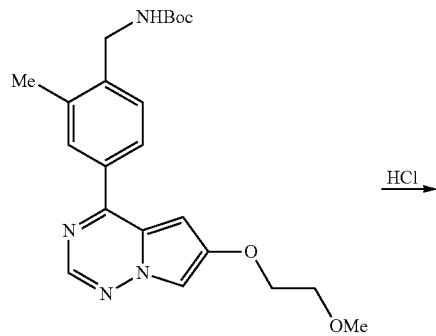

HCl →

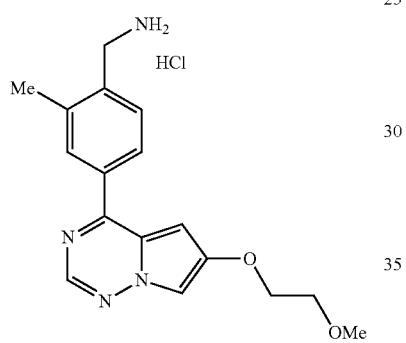

tert-Butyl (4-(6-(2-methoxyethoxy)pyrrolo[2,1-f][1,2,4]triazin-4-yl)-2-methylbenzyl)carbamate (110 mg, 0.27 mmol) was dissolved in an HCl solution (25 mL, 4 M in EtOAc) and the mixture was stirred at 20° C. for 1 h. The resulting solid was collected by filtration to give the title compound as a yellow solid (100 mg, crude) which was used in the next step without further purification. LCMS m/z=312.7 [M+H]+

5. Synthesis of 5-(tert-butyl)-N-(4-(6-(2-methoxyethoxy)pyrrolo[2,1-f][1,2,4]triazin-4-yl)-2-methylbenzyl)-1,2,4-oxadiazole-3-carboxamide

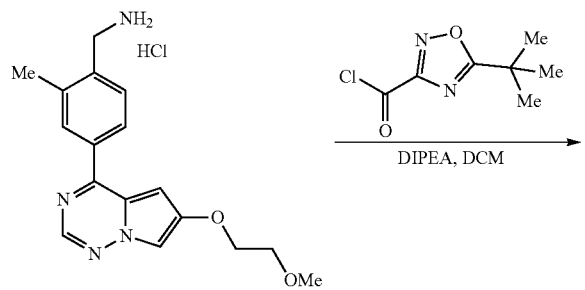

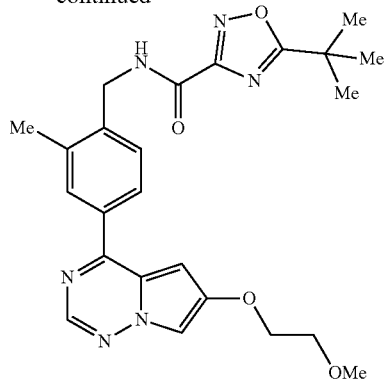

To a solution of (4-(6-(2-methoxyethoxy)pyrrolo[2,1-f][1,2,4]triazin-4-yl)-2-methylphenyl)methanamine hydrochloride (100 mg, 0.29 mmol) in DCM (30 mL) was added DIPEA (74 mg, 0.57 mmol) and 5-(tert-butyl)-1,2,4-oxadiazole-3-carbonyl chloride (54 mg, 0.29 mmol) and the mixture was stirred at 20° C. for 10 minutes. The mixture was diluted with water (30 mL) and extracted with DCM (3×15 mL). The combined organics were concentrated in vacuo and the residue purified by prep-HPLC (Method D; 43-73%) to afford the title compound as a yellow solid (70.5 mg, 53%). LCMS m/z=465.1 [M+H]+. $^1$H NMR: (400 MHz, DMSO-$d_6$) δ: 9.52 (t, 1H), 8.57 (s, 1H), 8.05 (d, 1H), 7.95-7.92 (m, 2H), 7.43 (d, 1H), 6.84 (d, 1H), 4.54 (d, 2H), 4.24-4.21 (m, 2H), 3.69-3.66 (m, 2H), 3.31 (s, 3H), 2.45 (s, 3H), 1.44 (s, 9H).

Example 59. N-(4-(6-(1-acryloyl-1H-pyrazol-4-yl)pyrrolo[2,1-f][1,2,4]triazin-4-yl)-2-methylbenzyl)-5-(tert-butyl)-1,2,4-oxadiazole-3-carboxamide

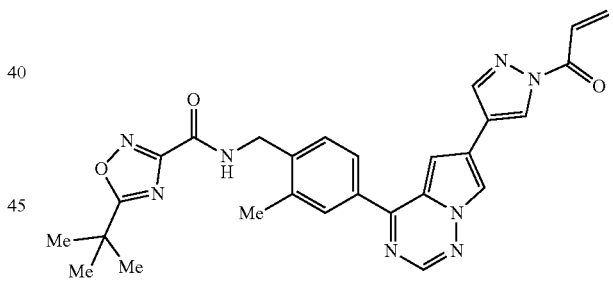

1. Synthesis of tert-butyl (4-(6-(1H-pyrazol-4-yl)pyrrolo[2,1-f][1,2,4]triazin-4-yl)-2-methylbenzyl)carbamate

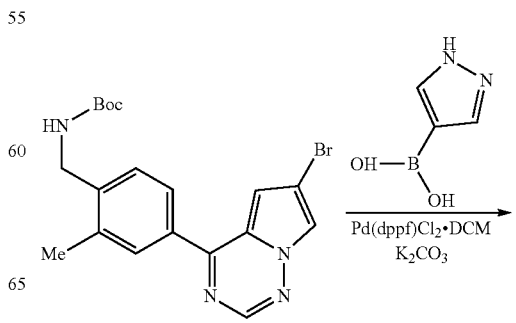

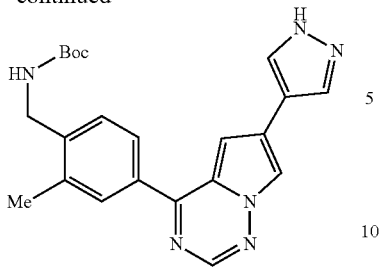

A mixture of tert-butyl (4-(6-bromopyrrolo[2,1-f][1,2,4]triazin-4-yl)-2-methylbenzyl)carbamate (500 mg, 1.2 mmol), 1H-pyrazol-4-ylboronic acid (168 mg, 1.5 mmol), Pd(dppf)Cl₂·DCM (98 mg, 0.12 mmol) and K₂CO₃ (332 mg, 2.4 mmol) in dioxane (10.3 mL) and water (2.4 mL) was purged with N₂ for 5 min. The reaction mixture was stirred at 100° C. under N₂ for 24 h. The cooled reaction was concentrated in vacuo and the residue was partitioned between water (100 mL) and EtOAc (100 mL). The layers were separated, the aqueous phase extracted with EtOAc (2×50 mL) and the combined organic layers were washed with brine (150 mL). The organic phase was dried (Na₂SO₄), filtered, and concentrated and the residue purified by silica gel column chromatography (0-100% EtOA/Hept) to afford the title compound as a yellow solid (96 mg, 20%). LCMS m/z=405.0 [M+H]⁺ ¹H NMR (500 MHz, MeOH-d₄) δ: 8.41 (s, 1H), 8.28 (d, 1H), 8.12 (br s, 1H), 8.02-7.88 (m, 3H), 7.49 (d, 1H), 7.32 (d, 1H), 7.17 (br d, 1H), 4.39-4.31 (m, 2H), 2.47 (s, 3H), 1.49 (s, 9H)

2. Synthesis of (4-(6-(1H-pyrazol-4-yl)pyrrolo[2,1-f][1,2,4]triazin-4-yl)-2-methylphenyl)methanamine hydrochloride

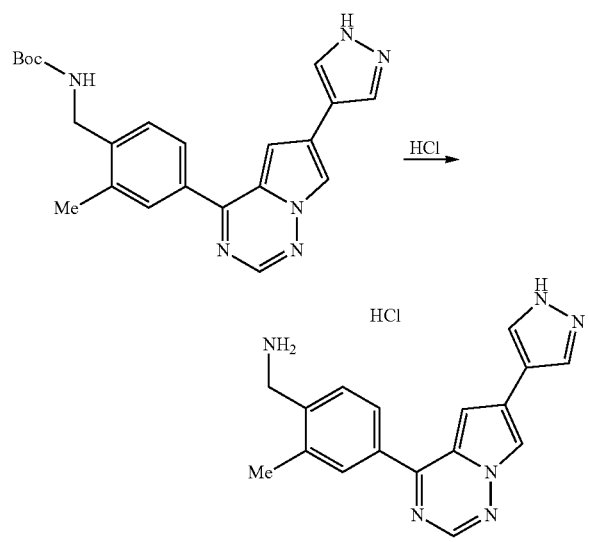

An HCl solution (0.2 mL, 1 M in EtOAc) was added to a solution of tert-butyl (4-(6-(1H-pyrazol-4-yl)pyrrolo[2,1-f][1,2,4]triazin-4-yl)-2-methylbenzyl)carbamate (96 mg, 0.24 mmol) in EtOAc (2.3 mL) and the reaction was stirred at RT for 5 days. The mixture was concentrated in vacuo to afford the title compound (72 mg, crude), which was carried forward without further purification. LCMS m/z=305.0 [M+H]⁺

3. Synthesis of N-(4-(6-(1-acryloyl-1H-pyrazol-4-yl)pyrrolo[2,1-f][1,2,4]triazin-4-yl)-2-methylbenzyl)-5-(tert-butyl)-1,2,4-oxadiazole-3-carboxamide

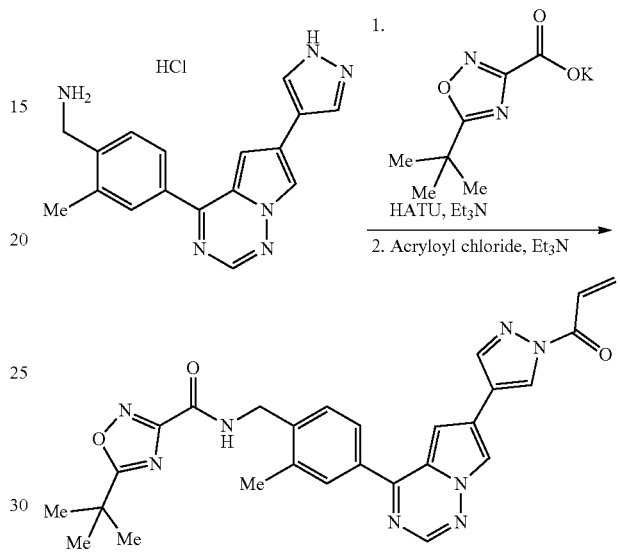

Part A: Et₃N (0.13 mL, 0.95 mmol) and HATU (140 mg, 0.36 mmol) were added to a solution of potassium 5-(tert-butyl)-1,2,4-oxadiazole-3-carboxylate (54 mg, 0.26 mmol) in THF (3.9 mL) in an ice water cooling bath and the reaction mixture stirred at 0° C. for 10 min before (4-(6-(1H-pyrazol-4-yl)pyrrolo[2,1-f][1,2,4]triazin-4-yl)-2-methylphenyl)methanamine hydrochloride (72 mg, 0.24 mmol) was added. The reaction was warmed to RT and was stirred for 24 h. The reaction was quenched with H₂O (5 mL) and extracted with EtOAc (3×5 mL). The combined organics were washed with brine, dried (Na₂SO₄), and concentrated in vacuo. The crude was purified by silica gel column chromatography (2-100% EtOAc/Hept) to afford N-(4-(6-(1H-pyrazol-4-yl)pyrrolo[2,1-f][1,2,4]triazin-4-yl)-2-methylbenzyl)-5-(tert-butyl)-1,2,4-oxadiazole-3-carboxamide as a yellow solid (72 mg, crude). LCMS m/z=457.0 [M+H]⁺

Part B: To a solution of N-(4-(6-(1H-pyrazol-4-yl)pyrrolo[2,1-f][1,2,4]triazin-4-yl)-2-methylbenzyl)-5-(tert-butyl)-1,2,4-oxadiazole-3-carboxamide (Part A, 33 mg, 0.07 mmol) in DCM (1.7 mL) at 0° C. was added Et₃N (22 mg, 0.22 mmol) and acryloyl chloride (8 mg, 0.09 mmol). The reaction mixture was warmed to RT and stirred for 0.5 h before an additional portion of acryloyl chloride was added (8 mg, 0.09 mmol). The reaction was concentrated in vacuo and the residue purified by silica gel column chromatography (0-100% EtOAc/Hept) to afford the title compound as a light-yellow solid (12 mg, 31%). LCMS m/z=511.0 [M+H]⁺; ¹H NMR (500 MHz, DMSO-d₆) δ: 9.55 (t, 1H), 9.13 (s, 1H), 8.71 (d, 1H), 8.61 (s, 1H), 8.56 (s, 1H), 8.07-7.98 (m, 2H), 7.73 (d, 1H), 7.57-7.46 (m, 2H), 6.68 (dd, 1H), 6.28-6.20 (m, 1H), 4.57 (d, 2H), 1.44 (s, 9H).

Example 60. 5-(tert-butyl)-N-(2-methyl-4-(6-(1-methylazetidin-3-yl)pyrrolo[2,1-f][1,2,4]triazin-4-yl)benzyl)-1,2,4-oxadiazole-3-carboxamide trifluoroacetate

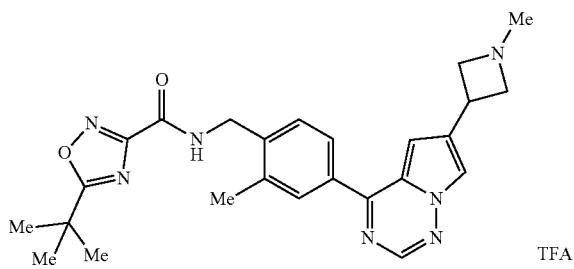 [SMILES: Cc1cc(-c2ncnn3cc(C4CN(C)C4)cc23)ccc1CNC(=O)c1noc(C(C)(C)C)n1]

1. Synthesis of (4-(6-bromopyrrolo[2,1-f][1,2,4]triazin-4-yl)-2-methylphenyl)methanamine hydrochloride

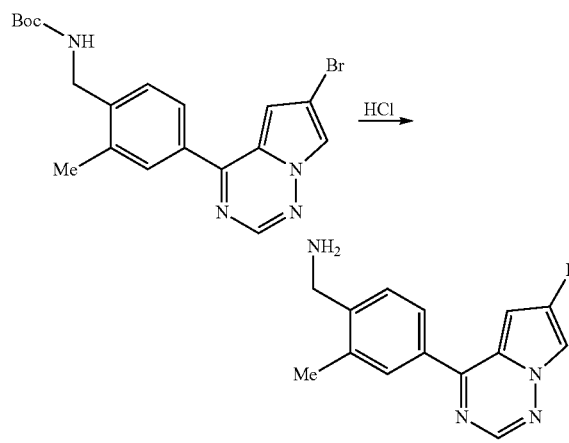

An HCl solution (0.2 mL, 4 M in dioxane) was added to a solution of tert-butyl (4-(6-bromopyrrolo[2,1-f][1,2,4]triazin-4-yl)-2-methylbenzyl)carbamate (186 mg, 0.45 mmol) in MeOH (2 mL) and the reaction was stirred at RT for 18 h. The reaction mixture was concentrated in vacuo to afford the title compound (185 mg, crude). LCMS m/z=319.0 [M+H]+

2. Synthesis of benzyl (4-(6-bromopyrrolo[2,1-f][1,2,4]triazine-4-yl)-2-methylbenzyl)carbamate

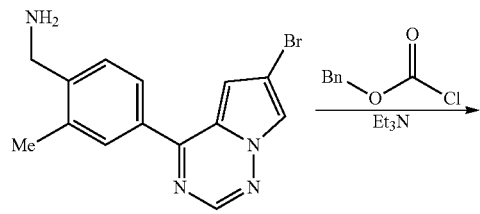

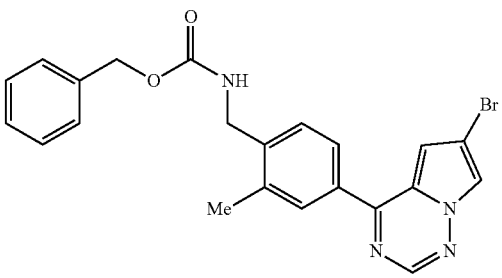

To a solution of (4-(6-bromopyrrolo[2,1-f][1,2,4]triazine-4-yl)-2-methylphenyl)methanamine hydrochloride (185 mg, 0.52 mmol) in DCM (4 mL), was added Et₃N (0.2 mL, 1.6 mmol) and benzyl chloroformate (89 μL, 0.63 mmol) and the reaction was stirred at RT for 18 h. The mixture was concentrated in vacuo and the crude product was purified by silica gel column chromatography (0-100% EtOAc/Hept) to afford the title compound (163 mg, 69%). LCMS m/z=451.1 [M+H]+

3. Synthesis of tert-butyl 3-(4-(4-((((benzyloxy)carbonyl)amino)methyl)-3-methylphenyl)pyrrolo[2,1-f][1,2,4]159riazine-6-yl)azetidine-1-carboxylate

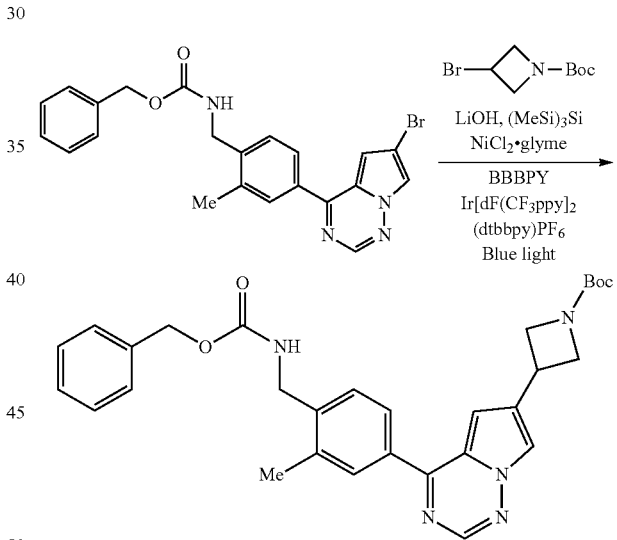

A mixture of benzyl (4-(6-bromopyrrolo[2,1-f][1,2,4]triazin-4-yl)-2-methylbenzyl)carbamate (163 mg, 0.36 mmol), tert-butyl 3-bromoazetidine-1-carboxylate (128 mg, 0.54 mmol), tris(trimethylsilyl)silane (0.22 mL, 0.72 mmol) and LiOH (35 mg, 1.4 mmol) in DME (4 mL) was degassed (Mixture 1). A mixture of NiCl₂·glyme (8 mg, 0.04 mmol), BBBPY (10 mg, 0.04 mmol) and Ir[dF(CF₃)ppy]₂(dtbbpy)PF₆ (4 mg, 3.6 μmol) in DME (4 mL) was degassed and transferred into Mixture 1. The combined reaction mixture was degassed, then was irradiated with 30W CREE 450 nm EvoluChem lamp (blue light) at RT for 18 h and the was mixture filtered. The filtrate was concentrated in vacuo and the residue purified by silica gel column chromatography (0-100% EtOAc/Hept) to afford the title compound (46 mg, 24%). LCMS m/z=528.2 [M+H]+

4. Synthesis of tert-butyl 3-(4-(4-(aminomethyl)-3-methylphenyl)pyrrolo[2,1-f][1,2,4]triazin-6-yl)azetidine-1-carboxylate

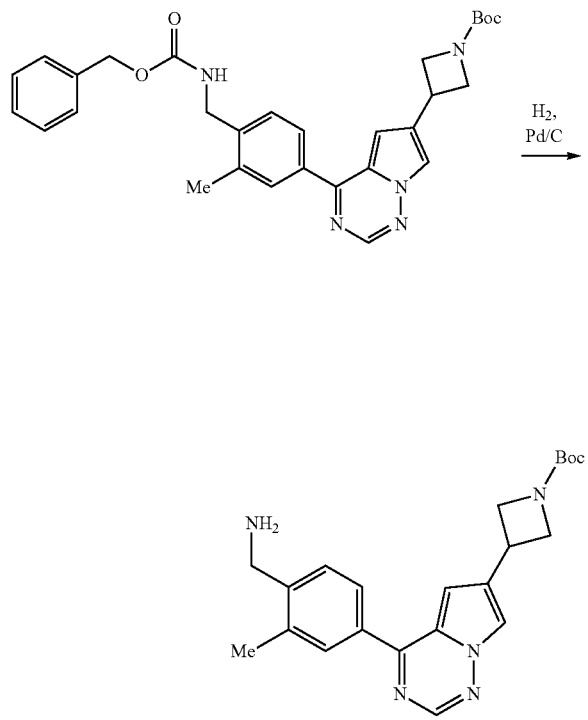

A mixture of tert-butyl 3-(4-(4-(((((benzyloxy)carbonyl)amino)methyl)-3-methylphenyl)pyrrolo[2,1-f][1,2,4]triazin-6-yl)azetidine-1-carboxylate (46 mg, 0.09 mmol) and Pd/C (5 mg, 0.04 mmol) in MeOH (2 mL) was stirred under H₂ for 6 h. The mixture was filtered through Celite® and the filtrate concentrated in vacuo to afford the title compound, which was carried forward without further purification. LCMS m/z=394.4 [M+H]⁺

5. Synthesis of potassium 5-tert-butyl-1,2,4-oxadiazole-3-carboxylate

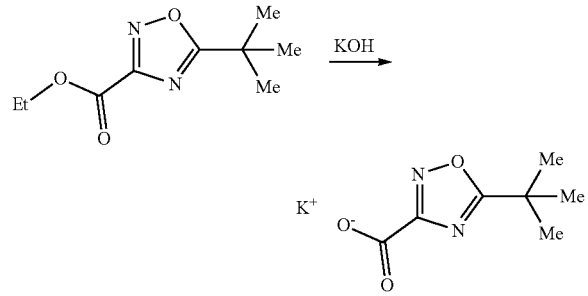

The title compound was obtained from ethyl 5-tert-butyl-1,2,4-oxadiazole-3-carboxylate, following an analogous procedure to that described in Example 2, Step 3. The crude material was carried forward without further purification.

6. Synthesis of tert-butyl 3-(4-(4-((5-(tert-butyl)-1,2,4-oxadiazole-3-carboxamido)methyl)-3-methylphenyl)pyrrolo[2,1-f][1,2,4]triazin-6-yl)azetidine-1-carboxylate

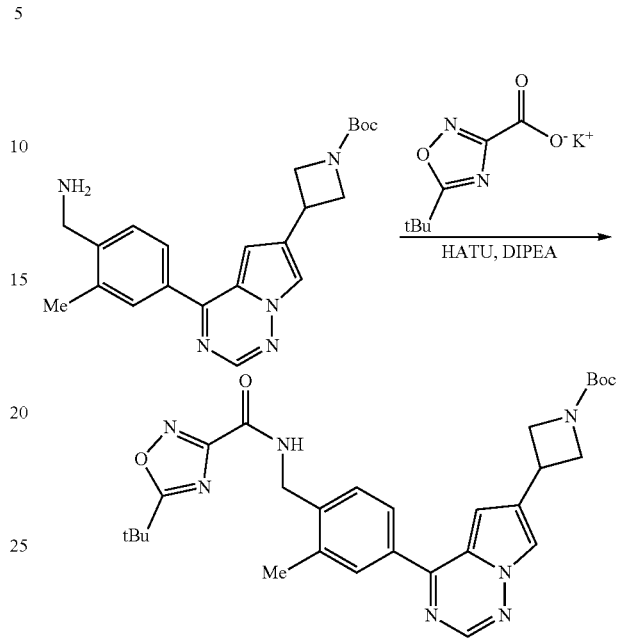

A mixture of tert-butyl 3-(4-(4-(aminomethyl)-3-methylphenyl)pyrrolo[2,1-f][1,2,4]triazin-6-yl)azetidine-1-carboxylate (40 mg, 0.1 mmol), potassium 5-tert-butyl-1,2,4-oxadiazole-3-carboxylate (42 mg, 0.2 mmol), HATU (78 mg, 0.2 mmol) and DIPEA (53 μL, 0.3 mmol) in DCM (2 mL) was stirred at RT for 18 h. The reaction mixture was concentrated in vacuo and the crude product was purified by silica gel column chromatography (0-100% EtOAc/Hept) to afford the title compound (10 mg, 18%). LCMS m/z=546.3 [M+H]⁺

7. Synthesis of 5-(tert-butyl)-N-(2-methyl-4-(6-(1-methylazetidin-3-yl)pyrrolo[2,1-f][1,2,4]triazin-4-yl)benzyl)-1,2,4-oxadiazole-3-carboxamide trifluoroacetate

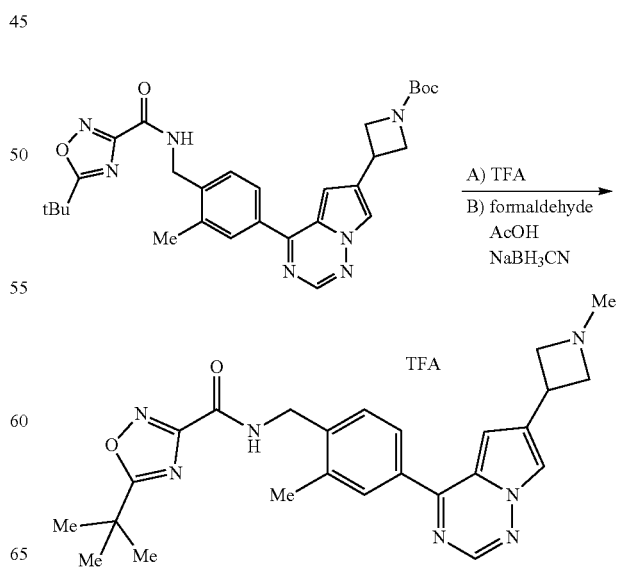

Part A: A solution of tert-butyl 3-(4-(4-((5-(tert-butyl)-1,2,4-oxadiazole-3-carboxamido)methyl)-3-methylphenyl)pyrrolo[2,1-f][1,2,4]triazin-6-yl)azetidine-1-carboxylate (10 mg, 0.02 mmol) in DCM (2 mL) and TFA (0.5 mL) was stirred at RT for 16 h. The mixture was concentrated in vacuo and the residue was used in Part B (9 mg, crude). LCMS m/z=446.3 [M+H]+

Part B: AcOH (1 mg, 0.02 mmol) and formaldehyde (8 mg, 0.1 mmol, 37% purity) were added to a solution of N-(4-(6-(azetidin-3-yl)pyrrolo[2,1-f][1,2,4]triazin-4-yl)-2-methylbenzyl)-5-(tert-butyl)-1,2,4-oxadiazole-3-carboxamide trifluoroacetate (Part A, 9 mg, 0.02 mmol) in MeOH (2 mL). NaBH$_3$CN (4 mg, 0.06 mmol) was added and the reaction was mixture stirred at RT for 1 h.

The mixture was concentrated in vacuo and the residue purified by prep-HPLC (Method B; 10-90%) to give the title compound (5 mg, 41%). LCMS m/z=460.3 [M+H]+; $^1$H NMR (400 MHz, MeOH-d$_4$) δ: 9.19-9.28 (m, 1H), 7.92-7.98 (m, 1H), 7.28-7.34 (m, 1H), 7.13-7.21 (m, 3H), 6.78-6.82 (m, 1H), 5.68-5.74 (m, 2H), 4.55-4.61 (m, 2H), 4.41-4.48 (m, 1H), 4.15-4.27 (m, 2H), 3.95-4.05 (m, 1H), 2.88-2.98 (m, 3H), 2.37-2.42 (m, 3H), 1.47-1.50 (m, 9H).

Example 61. 1-(tert-butyl)-N-(4-(6-(1-methyl-1H-pyrazol-4-yl)pyrrolo[2,1-f][1,2,4]triazin-4-yl)-2-(trifluoromethyl)benzyl)-1H-pyrazole-4-carboxamide

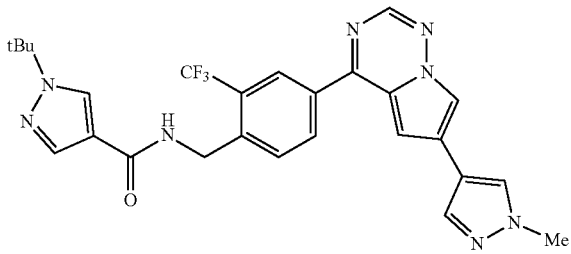 [SMILES: Cn1cc(-c2cc3c(-c4ccc(CNC(=O)c5cnn(C(C)(C)C)c5)c(C(F)(F)F)c4)ncnn3c2)cn1]

1. Synthesis of (4-(6-bromopyrrolo[2,1-f][1,2,4]triazin-4-yl)-2-(trifluoromethyl)phenyl)methanamine hydrochloride

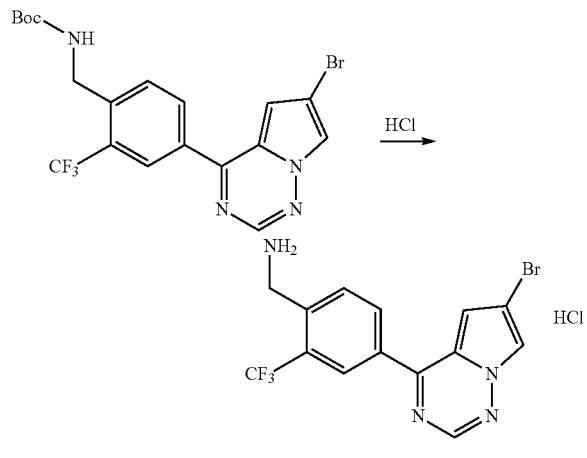

The title compound was obtained as an orange solid from tert-butyl (4-(6-bromopyrrolo[2,1-f][1,2,4]triazin-4-yl)-2-(trifluoromethyl)benzyl)carbamate following the procedure described in Example 60, Step 1. LCMS m/z=371.0 [M+H]+

2. Synthesis of N-(4-(6-bromopyrrolo[2,1-f][1,2,4]triazin-4-yl)-2-(trifluoromethyl)benzyl)-1-(tert-butyl)-1H-pyrazole-4-carboxamide

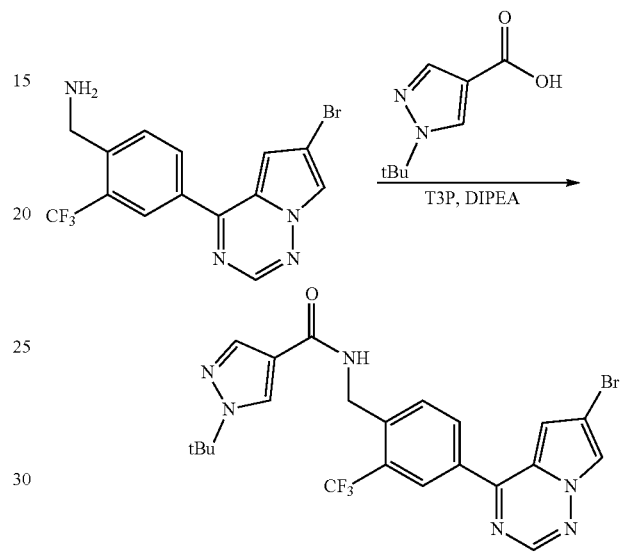

To a solution of (4-(6-bromopyrrolo[2,1-f][1,2,4]triazin-4-yl)-2-(trifluoromethyl)phenyl)methanamine hydrochloride (430 mg, 1.1 mmol), 1-tert-butylpyrazole-4-carboxylic acid (353 mg, 2.1 mmol) and DIPEA (0.92 mL, 5.3 mmol) in dry DMF (5 mL) was added T3P® (2.1 mL 3.2 mmol, 50% purity) and the reaction was stirred at RT for 17 h. The reaction was quenched with saturated aqueous NaHCO$_3$ solution, diluted with EtOAc, the layers were separated, and the aqueous phase extracted with EtOAc. The combined organic layers were dried (MgSO$_4$), filtered, and concentrated in vacuo. The residue was purified by silica gel column chromatography (0-100% EtOAc/Hept) to afford the title compound as a yellow solid (226 mg, 41%). LCMS m/z=521.1 [M+H]+

3. Synthesis of 1-(tert-butyl)-N-(4-(6-(1-methyl-1H-pyrazol-4-yl)pyrrolo[2,1-f][1,2,4]triazin-4-yl)-2-(trifluoromethyl)benzyl)-1H-pyrazole-4-carboxamide

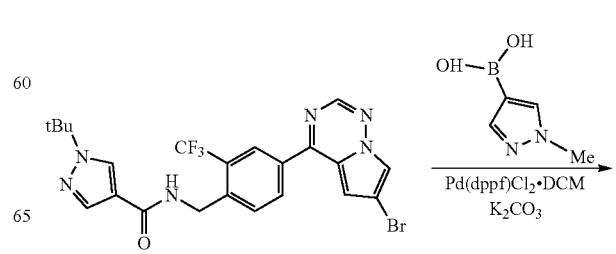

205

-continued

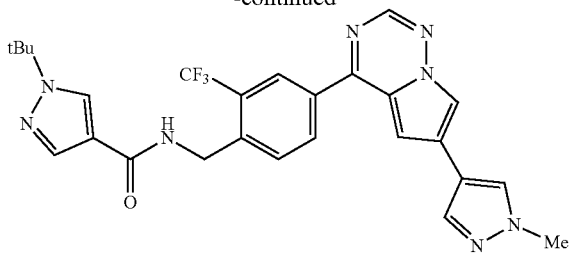

A mixture of N-(4-(6-bromopyrrolo[2,1-f][1,2,4]triazin-4-yl)-2-(trifluoromethyl)benzyl)-1-(tert-butyl)-1H-pyrazole-4-carboxamide (100 mg, 0.19 mmol), (1-methylpyrazol-4-yl)boronic acid (27 mg, 0.21 mmol) and K$_2$CO$_3$ (80 mg, 0.58 mmol) in dioxane (2 mL) and H$_2$O (0.5 mL) was degassed with N$_2$ for 5 min. Pd(dppf)Cl$_2$·DCM (151 mg, 0.19 mmol) was added and the resulting mixture was heated to 100° C. overnight. The cooled reaction mixture was filtered through Celite® with aid of EtOAc and H$_2$O. The layers were separated, and the aqueous phase was extracted with EtOAc. The combined extracts were dried (MgSO$_4$), filtered, and concentrated in vacuo. The residue was purified by prep HPLC (Method B; 10-90%) to afford the title compound as a yellow solid (5.9 mg, 5.3%). LCMS m/z=523.2 [M+H]$^+$, $^1$H NMR (500 MHz, CDCl$_3$) δ: 8.49-8.58 (m, 1H), 8.41 (s, 1H), 8.26 (br d, 1H), 8.06 (br d, 2H), 7.87 (br d, 1H), 7.85-7.77 (m, 2H), 7.74-7.63 (m, 1H), 7.06 (s, 1H), 6.37-6.20 (m, 1H), 4.90 (br d, 2H), 3.99 (s, 3H), 1.62 (s, 9H).

Example 62. 5-(tert-butyl)-N-(2-cyclopropyl-3-fluoro-4-(pyrrolo[2,1-f][1,2,4]triazin-4-yl)benzyl)-1,2,4-oxadiazole-3-carboxamide trifluoroacetate

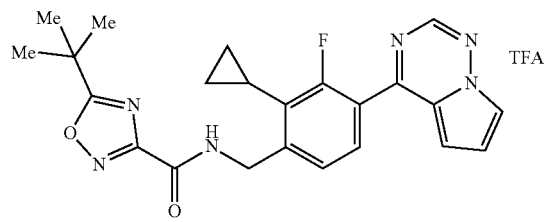 [SMILES: CC(C)(C)c1nc(C(=O)NCc2ccc(-c3ncnn4cccc34)c(F)c2C2CC2)no1]

1. Synthesis of (E)-N-(2-bromo-4-chloro-3-fluorobenzylidene)-2-methylpropane-2-sulfinamide

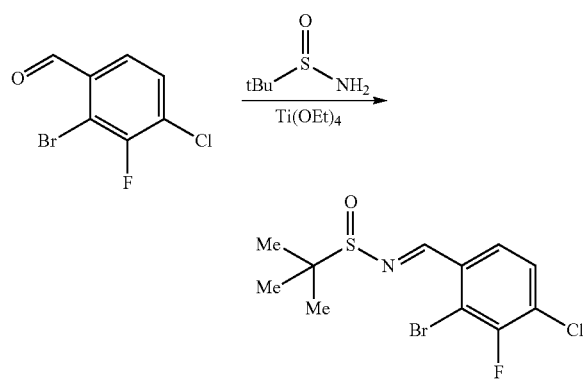

206

To a solution of 2-bromo-4-chloro-3-fluorobenzaldehyde (131 g, 0.55 mol) in THF (1 L) was added tert-butylsulfinamide (73 g, 0.60 mol) and Ti(OEt)$_4$ (232 mL, 1.1 mol) and the reaction was stirred at RT for 12 h. H$_2$O was added, the resulting solid was filtered off and washed with EtOAc (2×), and the layers were separated. The filtrate was extracted with EtOAc (2×), the combined organic layers were washed sequentially with 2 M HCl solution, water, and brine, dried (Na$_2$SO$_4$), filtered, and concentrated in vacuo to afford the title compound as a beige solid (144 g, 77%). $^1$H NMR (300 MHz, CDCl$_3$) δ: 8.89 (s, 1H), 7.81 (dd, 1H), 7.45 (dd, 1H), 1.35 (s, 9H).

2. Synthesis of (2-bromo-4-chloro-3-fluorobenzyl)methanamine hydrochloride

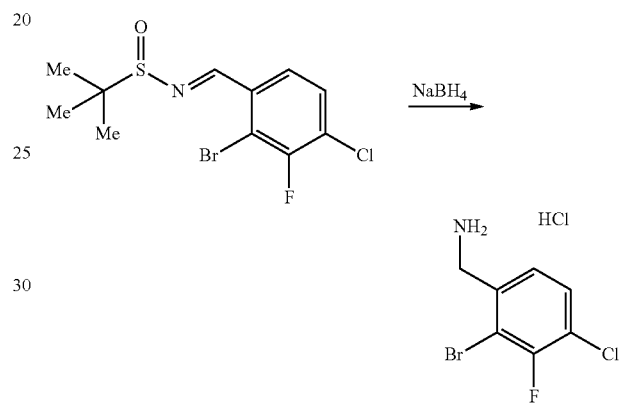

To a solution of (E)-N-(2-bromo-4-chloro-3-fluorobenzylidene)-2-methylpropane-2-sulfinamide (144 g, 0.42 mol) in MeOH (1.5 L) was added NaBH$_4$ (19.2 g, 0.51 mol) and the reaction was stirred at RT for 1 h. The reaction mixture was concentrated to approx. 150 mL, the mixture diluted with water and the solution was extracted with EtOAc (3×). The organic layers were dried (Na$_2$SO$_4$), filtered, and concentrated in vacuo. The residue was dissolved in 2 M HCl in Et$_2$O and stirred at RT for 10 min. The resulting solid was filtered off, washed with heptanes, and dried in vacuo to afford the title compound as a white solid (92 g, 80%). $^1$H NMR (300 MHz, DMSO-d$_6$) δ: 8.75 (br s, 3H), 7.80 (dd, 1H), 7.57 (dd, 1H).

3. Synthesis of tert-butyl (2-bromo-4-chloro-3-fluorobenzyl)carbamate

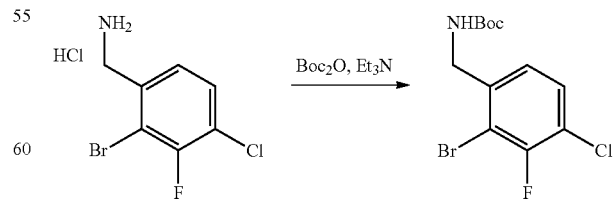

Boc$_2$O (80 g, 0.37 mol) was added to a solution of (2-bromo-4-chloro-3-fluorobenzyl)methanamine hydrochloride (92 g, 0.33 mol) and Et$_3$N (233 mL, 1.7 mol) in DCM (1.5 L) and the reaction was stirred at RT for 16 h. The mixture was diluted with water and extracted with DCM (2×). The combined organic layers were washed with water, 1 M aq. HCl and brine, dried (Na$_2$SO$_4$), filtered, and concentrated in vacuo to afford the title compound as a white solid (95 g, 84%). $^1$H NMR (300 MHz, CDCl$_3$) δ: 7.33 (dd, 1H), 7.15 (dd, 1H), 4.36 (br s, 1H), 5.14 (s, 2H), 1.49 (s, 9H).

4. Synthesis of tert-butyl (4-chloro-2-cyclopropyl-3-fluorobenzyl)carbamate

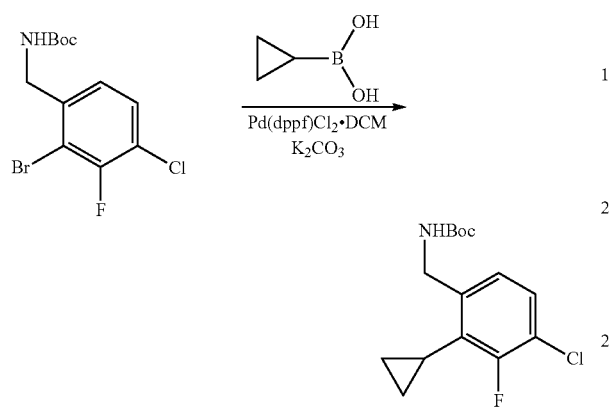

To a solution of tert-butyl (2-bromo-4-chloro-3-fluorobenzyl)carbamate (72 g, 0.21 mol) in dioxane (1 L), cyclopropylboronic acid (23 g, 0.27 mol), K$_2$CO$_3$ (58 g, 0.42 mol), Pd(dppf)Cl$_2$·DCM (26 g, 32 mmol) and H$_2$O (200 mL) were added and the reaction was stirred at 90° C. for 16 h under N$_2$. The cooled mixture was concentrated in vacuo, diluted with EtOAc, and filtered through Celite®. The filtrate was washed with H$_2$O, 1 M aqueous HCl and brine, then dried (Na$_2$SO$_4$), filtered, and concentrated in vacuo. The residue was purified by silica gel column chromatography (0-5% EtOAc/Hept) to afford the title compound as a white solid (48 g, 76%). LCMS m/z=244.0 [M-tBu+H]$^+$ 5. Synthesis of tert-butyl (2-cyclopropyl-3-fluoro-4-(4,4,5,5-tetramethyl-1,3,2-dioxaborolan-2-yl)benzyl) carbamate

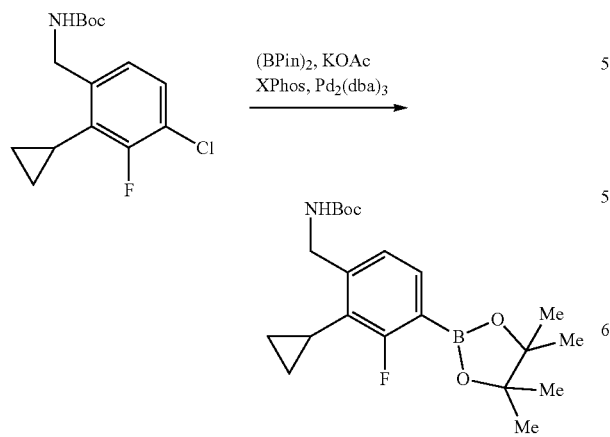

KOAc (16 g, 170 mmol), tert-butyl (4-chloro-2-cyclopropyl-3-fluorobenzyl)carbamate (25 g, 83 mmol) and (bispinacolato)diboron (32 g, 125 mmol) were added to a mixture of Pd$_2$(dba)$_3$ (2.4 g, 4.2 mmol) and XPhos (4 g, 8.3 mmol) in dioxane (500 mL) and the reaction was stirred at 100° C. for 12 h. The cooled reaction mixture was filtered through Celite® and concentrated. The residue was diluted with EtOAc and washed with water and brine. The organic layer was dried (Na$_2$SO$_4$), filtered, and concentrated. The crude product was purified by silica gel column chromatography (0-10% EtOAc/Hept) to give a brown oil. This was dissolved in EtOAc, activated charcoal was added and the mixture was stirred for 30 mins. The mixture was filtered, the filtrate was concentrated in vacuo and the residue purified by silica gel column chromatography (0-10% EtOAc/Hept) to afford the title compound as a yellow oil which solidified upon standing to a white solid (35.6 g, 68%). LCMS m/z=336.2 [M+H]$^+$ 6. Synthesis of tert-butyl (2-cyclopropyl-3-fluoro-4-(pyrrolo[2,1-f][1,2,4]triazin-4-yl)benzyl)carbamate

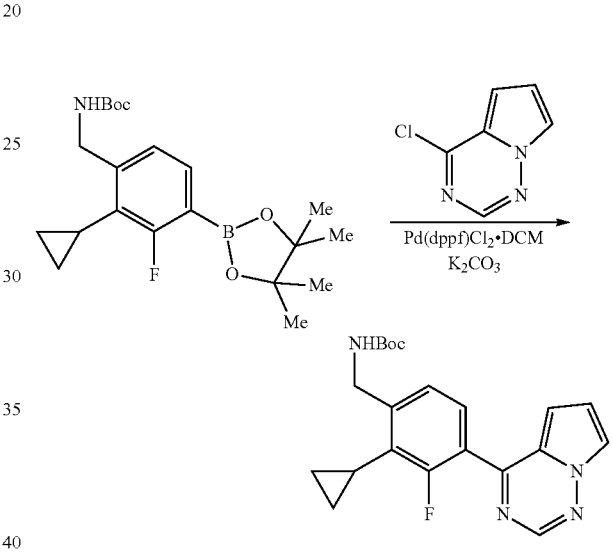

A mixture of 4-chloropyrrolo[2,1-f][1,2,4]triazine (110 mg, 0.72 mmol), tert-butyl (2-cyclopropyl-3-fluoro-4-(4,4,5,5-tetramethyl-1,3,2-dioxaborolan-2-yl)benzyl)carbamate (561 mg, 1.4 mmol), K$_2$CO$_3$ (297 mg, 2.2 mmol) and Pd(dppf)Cl$_2$·DCM (58 mg, 0.07 mmol) in dioxane (3 mL) and water (1 mL) was purged with N$_2$. The mixture was stirred at RT for 5 mins and then at 95° C. for 18 h. The cooled mixture was diluted with EtOAc and filtered, washing through with additional EtOAc. The filtrate was concentrated in vacuo and the crude purified by silica gel column chromatography (Hept/EtOAc=5:1) to afford the title compound as a yellow foam (300 mg, 98%). LCMS m/z=383.5 [M+H]$^+$ 7. Synthesis of (2-cyclopropyl-3-fluoro-4-(pyrrolo[2,1-f][1,2,4]triazin-4-yl)phenyl)methanamine

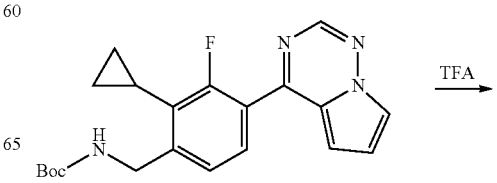

-continued

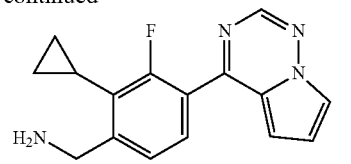

The title compound was obtained as a pale yellow solid (200 mg, 37%), from tert-butyl (2-cyclopropyl-3-fluoro-4-(pyrrolo[2,1-f][1,2,4]triazin-4-yl)benzyl)carbamate, following the procedure described in Example 14, Step 7 and was used without further purification.

8. Synthesis of 5-(tert-butyl)-N-(2-cyclopropyl-3-fluoro-4-(pyrrolo[2,1-f][1,2,4]triazin-4-yl)benzyl)-1,2,4-oxadiazole-3-carboxamide trifluoroacetate

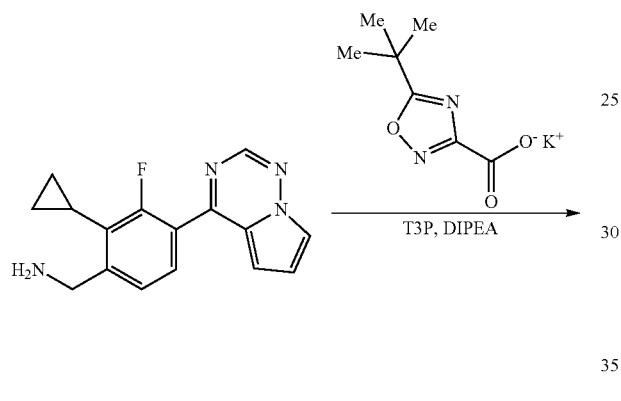

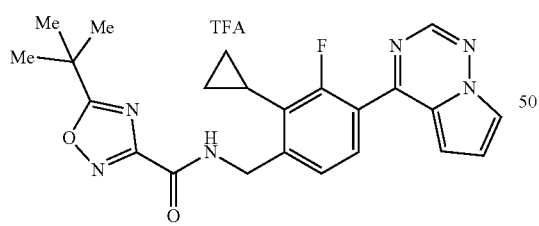

The crude compound was obtained from (2-cyclopropyl-3-fluoro-4-(pyrrolo[2,1-f][1,2,4]triazin-4-yl)phenyl)methanamine and potassium 5-(tert-butyl)-1,2,4-oxadiazole-3-carboxylate, following the procedure described in Example 14, Step 8. The crude product was purified by prep HPLC using Method B (20-80%) to afford the title compound as a yellow solid (26 mg, 18%). LCMS m/z=435.6 [M+H]$^+$. $^1$H NMR (400 MHz, CDCl$_3$) δ: 8.67 (s, 1H), 8.15 (dd, 1H), 7.63-7.57 (m, 1H), 7.56-7.49 (m, 1H), 7.36 (d, 1H), 7.24-7.20 (m, 1H), 7.17-7.13 (m, 1H), 5.00 (d, 2H), 1.84-1.75 (m, 1H), 1.49 (s, 9H), 1.19-1.12 (m, 2H), 0.91-0.86 (m, 2H).

Example 63. 5-(tert-butyl)-N-(3,5-difluoro-2-methyl-4-(pyrrolo[2,1-f][1,2,4]triazin-4-yl)benzyl)-1,2,4-oxadiazole-3-carboxamide hydrochloride

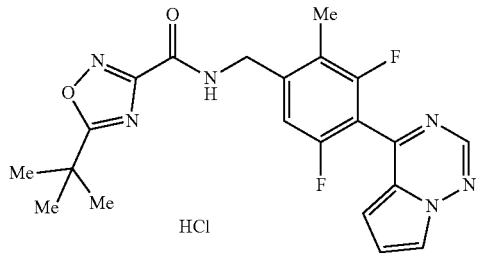 [SMILES: Cc1c(CNC(=O)c2noc(C(C)(C)C)n2)cc(F)c(-c2ncnn3cccc23)c1F ; Cl]

1. Synthesis of 3,5-difluoro-4-hydroxy-2-methylbenzonitrile

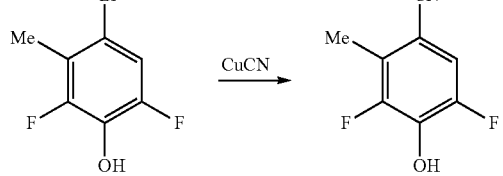

To a solution of 4-bromo-2,6-difluoro-3-methyl-phenol (5.5 g, 24.7 mmol) in DMF (100 mL) was added CuCN (4.4 g, 49.3 mmol) and the reaction was stirred at 125° C. for 12 h. The cooled mixture was concentrated in vacuo and the residue purified by silica gel column chromatography (petroleum ether/EtOAc=16:1 to 2:1) to afford the title compound as a grey solid (2.3 g, 55%). $^1$H NMR (400 MHz, CDCl$_3$) δ: 7.22-7.19 (m, 1H), 6.02 (br s, 1H), 2.44 (d, 3H).

2. Synthesis of 4-(aminomethyl)-2,6-difluoro-3-methylphenol

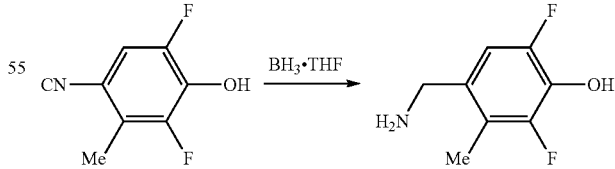

To a solution of 3,5-difluoro-4-hydroxy-2-methylbenzonitrile (1.5 g, 8.9 mmol) in THF (35 mL) was added BH$_3$·THF (28 mmol, 1 M, 28 mL) and the reaction was stirred at 60° C. under N$_2$ for 12 h. The cooled reaction was quenched with MeOH (5 mL) and the mixture was concentrated in vacuo to afford the title compound as a white solid (1.3 g, crude). LCMS m/z=174.1 [M+H]$^+$

3. Synthesis of tert-butyl (3,5-difluoro-4-hydroxy-2-methylbenzyl)carbamate

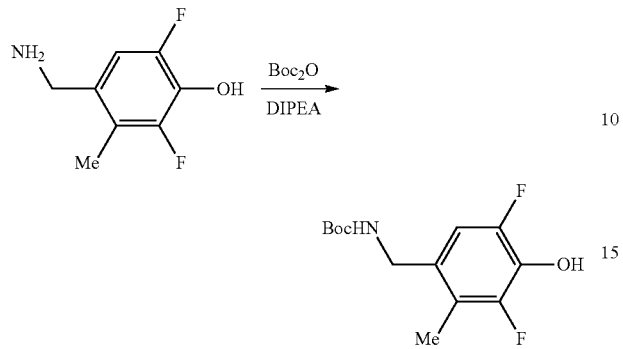

To a solution of 4-(aminomethyl)-2,6-difluoro-3-methylphenol (750 mg, crude) and DIPEA (1.68 g, 13 mmol) in DCM (65 mL) was added (Boc)$_2$O (1.04 g, 4.8 mmol) and the reaction mixture was stirred at 25° C. for 2 h. The reaction mixture was concentrated in vacuo and the crude product was purified by silica gel chromatography (petroleum ether/EtOAc=10:1 to 3:1) to afford the title compound as a light grey solid (550 mg, 46%). LCMS m/z=218.0 [M+H]$^+$

4. Synthesis of 4-(((tert-butoxycarbonyl)amino)methyl)-2,6-difluoro-3-methylphenyl trifluoromethanesulfonate

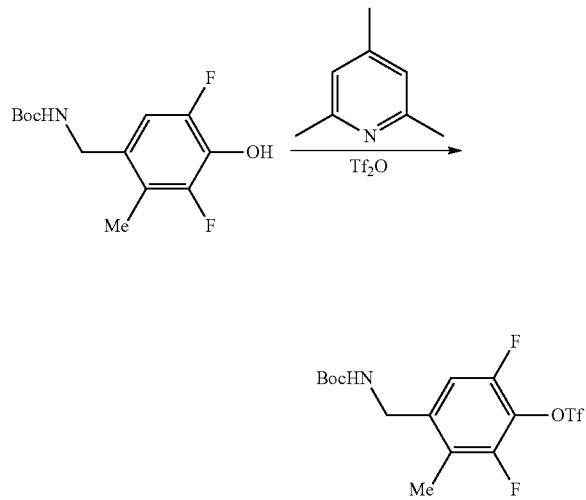

Tf$_2$O (851 mg, 3.0 mmol) was added to a solution of tert-butyl (3,5-difluoro-4-hydroxy-2-methylbenzyl)carbamate (550 mg, 2.0 mmol) and 2,4,6-trimethylpyridine (731 mg, 6.0 mmol) in DCM (45 mL) and the reaction was stirred at 25° C. for 2 h. The reaction mixture was quenched with MeOH (5 mL), then was concentrated in vacuo. The crude product was purified by silica gel column chromatography (3-6% EtOAc/petroleum ether) to afford the title compound as a white solid (490 mg, 60%). LCMS m/z=447.2 [M+H]$^+$

5. Synthesis of tert-butyl (3,5-difluoro-2-methyl-4-(4,4,5,5-tetramethyl-1,3,2-dioxaboralan-2-yl)benzyl)carbamate

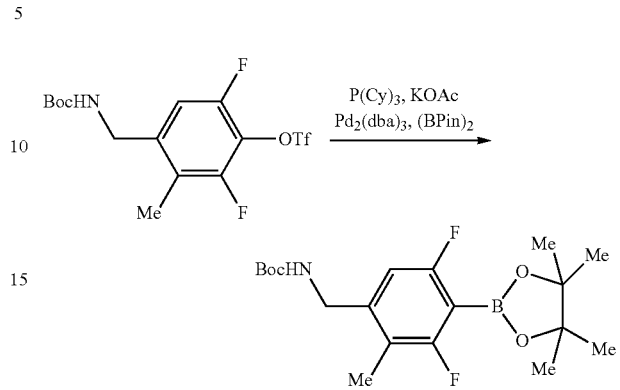

Pd$_2$(dba)$_3$ (166 mg, 0.18 mmol), P(Cy)$_3$ (85 mg, 0.30 mmol) and KOAc (238 mg, 2.4 mmol) were added to a solution of 4-(((tert-butoxycarbonyl)amino)methyl)-2,6-difluoro-3-methylphenyl trifluoromethanesulfonate (490 mg, 1.2 mmol) and (bispinacolato)diboron (615 mg, 2.4 mmol) in dioxane (25 mL) and the reaction was stirred at 85° C. under N$_2$ for 12 h. The reaction mixture was concentrated in vacuo and the crude product was purified by silica gel chromatography (3-11% EtOAc/petroleum ether) to afford the title compound as a white solid (240 mg, crude) which was carried forward without further purification. LCMS m/z=328.1 [M−tBu+H]$^+$

6. Synthesis of tert-butyl (3,5-difluoro-2-methyl-4-(pyrrolo[2,1-f][1,2,4]triazin-4-yl)benzyl)carbamate

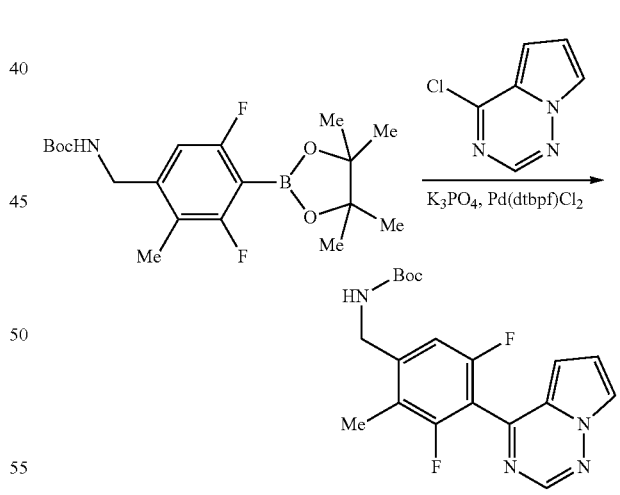

K$_3$PO$_4$ (266 mg, 1.3 mmol) and Pd(dtbpf)Cl$_2$ (61 mg, 0.09 mmol) were added to a solution of 4-chloropyrrolo[1,2-f][1,2,4]triazine (96 mg, 0.63 mmol) and tert-butyl (3,5-difluoro-2-methyl-4-(4,4,5,5-tetramethyl-1,3,2-dioxaboralan-2-yl)benzyl)carbamate (240 mg, 0.63 mmol) in dioxane (8 mL) and H$_2$O (2 mL) and the reaction was stirred at 90° C. under N$_2$ for 3 h. The cooled reaction mixture was concentrated in vacuo and the crude product purified by silica gel chromatography (petroleum ether/EtOAc=10:1 to 2:1) to afford the title compound as a light brown solid (100 mg, 42%). ¹H NMR (500 MHz, CDCl₃) δ: 8.54 (s, 1H), 7.90 (s, 1H), 7.02 (d, 1H), 6.98-6.97 (m, 1H), 6.69 (d, 1H), 4.95 (br s, 1H), 4.39 (d, 2H), 2.25 (s, 3H), 1.49 (s, 9H).

7. Synthesis of 3,5-difluoro-2-methyl-4-(pyrrolo[2,1-f][1,2,4]triazin-4-yl)phenyl)methanamine hydrochloride

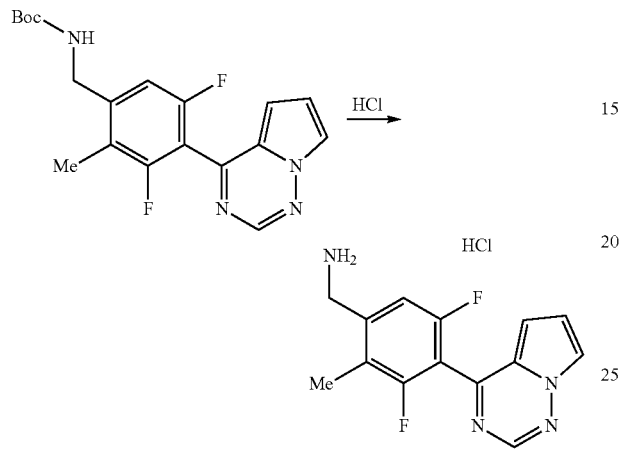

The title compound was obtained as a light brown solid (80 mg, crude) from tert-butyl (3,5-difluoro-2-methyl-4-(pyrrolo[2,1-f][1,2,4]triazin-4-yl)benzyl)carbamate, following the procedure described in Example 35, Step 5. LCMS m/z=316.0 [M+H]⁺

8. Synthesis of 5-(tert-butyl)-1,2,4-oxadiazole-3-carboxylic Acid

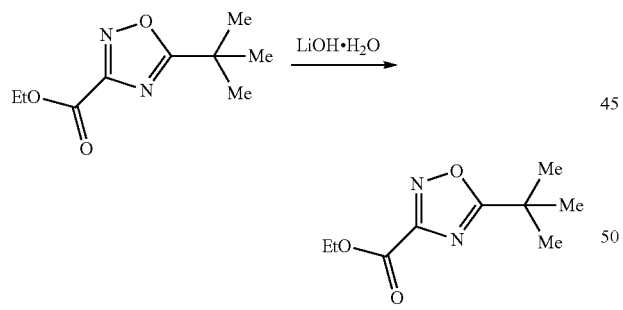

To a solution of ethyl 5-(tert-butyl)-1,2,4-oxadiazole-3-carboxylate (34 g, 174 mmol) in MeOH (350 mL) was added (in one portion), a solution of LiOH·H₂O (14.6 g, 348 mmol) in water (35 mL) and the reaction was stirred for 2 h at RT. The reaction was concentrated in vacuo and the aqueous residue was acidified with concentrated HCl until pH=2-3. The mixture was concentrated in vacuo and the oily residue was azeotroped with toluene (3×50 mL). 5% MeOH in DCM (500 mL) was added, the mixture was filtered and the solid washed with 5% MeOH in DCM (3×100 mL). The filtrates were combined, dried (Na₂SO₄), filtered, and concentrated in vacuo to give the title compound as white solid (29.2 g, 89%). ¹H NMR (300 MHz, DMSO-d₆) δ: 0.96 (s, 9H).

9. Synthesis of 5-(tert-butyl)-N-(3,5-difluoro-2-methyl-4-(pyrrolo[2,1-f][1,2,4]triazin-4-yl)benzyl)-1,2,4-oxadiazole-3-carboxamide hydrochloride

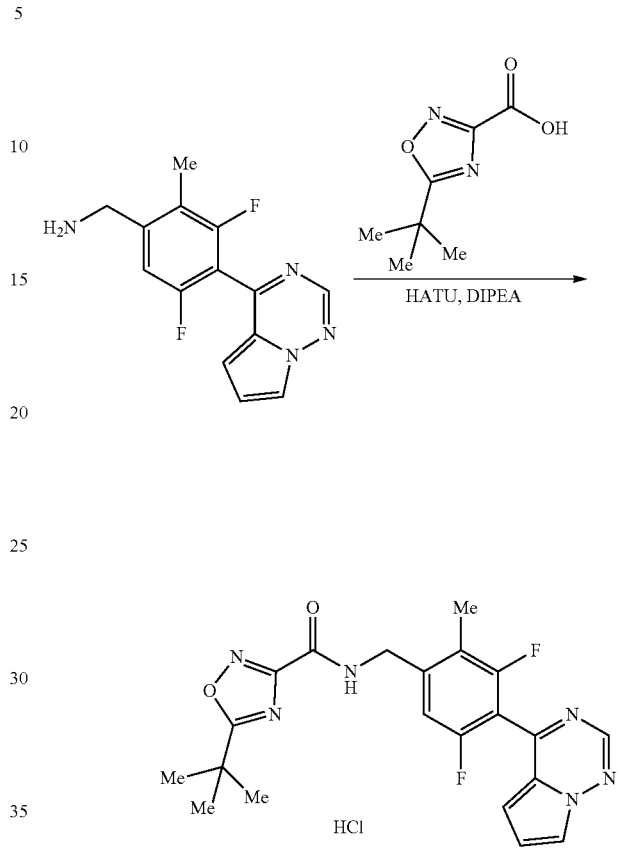

Crude product was obtained from (3,5-difluoro-2-methyl-4-(pyrrolo[2,1-f][1,2,4]triazin-4-yl)phenyl)methanamine hydrochloride and 5-(tert-butyl)-1,2,4-oxadiazole-3-carboxylic acid following the procedure described in Example 45, Step 7. The crude product was purified by prep-HPLC Method A, 42-62% to afford the title compound as a light brown solid (73 mg, 61%). LCMS m/z=427.0 [M+H]⁺; ¹H NMR (400 MHz, DMSO-d₆) δ: 9.59 (t, 1H), 8.70 (s, 1H), 8.27-8.26 (m, 1H), 7.21 (d, 1H), 7.13-7.11 (m, 1H), 6.80 (d, 1H), 4.59 (d, 2H), 2.30 (s, 3H), 1.45 (s, 9H).

Example 64. 1-(tert-butyl)-N-(2-(difluoromethyl)-4-(6-(1-methyl-1H-pyrazol-4-yl)pyrrolo[2,1-f][1,2,4]triazin-4-yl)benzyl)-1H-1,2,3-triazole-4-carboxamide hydrochloride

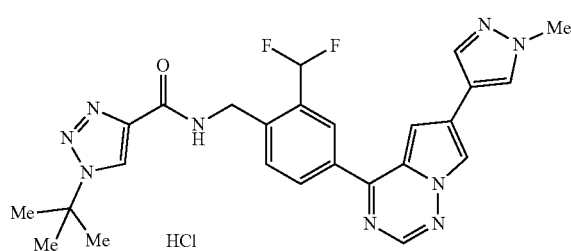 [SMILES: Cn1cc(-c2cc3c(-c4ccc(CNC(=O)c5cn(C(C)(C)C)nn5)c(C(F)F)c4)ncnn3c2)cn1 ; Cl]

1. Synthesis of 4-bromo-2-(dibromomethyl)benzonitrile

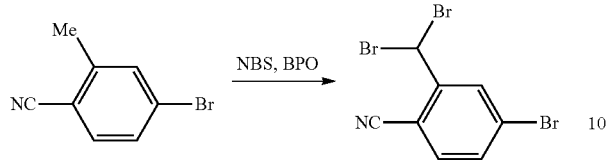

To a solution of 4-bromo-2-methylbenzonitrile (15 g, 76.5 mmol) in CCl$_4$ (500 mL) was added NBS (40.9 g, 229 mmol) and BPO (1.85 g, 7.65 mmol) and the reaction was heated under reflux for 64 h. The cooled mixture was filtered and the solid was washed with EtOAc (500 mL). The filtrate was concentrated in vacuo and the residue was purified by silica gel column chromatography (petroleum ether/EtOAc=40:1) to afford the title compound as a white solid (28 g, crude). $^1$H NMR (400 MHz, CDCl$_3$) δ: 8.16 (s, 1H), 7.59 (dd, 1H), 7.47 (d, 1H), 6.90 (s, 1H).

2. Synthesis of 4-bromo-2-formylbenzonitrile

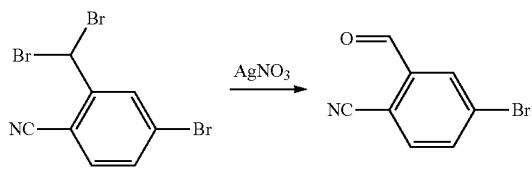 [SMILES: N#Cc1ccc(Br)cc1C(Br)Br ; "AgNO3" ; N#Cc1ccc(Br)cc1C=O]

To a solution of 4-bromo-2-(dibromomethyl)benzonitrile (28 g, 79.3 mmol) in MeCN (105 mL) was added a solution of AgNO$_3$ (54 g, 317 mmol) in H$_2$O (35 mL) and the reaction was stirred at 90° C. for 30 h. The cooled mixture was filtered, and the filter cake washed with DCM. The filtrate was washed with brine (200 mL), dried (Na$_2$SO$_4$), filtered, and concentrated in vacuo and the crude was purified by silica gel column chromatography (3-16% EtOAc/petroleum ether) to give the title compound as a white solid (11 g, 66%). $^1$H NMR (400 MHz, CDCl$_3$) δ: 10.29 (s, 1H), 8.16 (d, 1H), 7.87 (dd, 1H), 7.68 (d, 1H).

3. Synthesis of 4-bromo-2-(difluoromethyl)benzonitrile

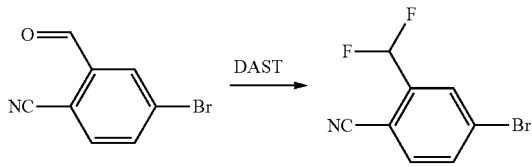

A solution of DAST (21 g, 131 mmol) in DCM (100 mL) was added dropwise to an ice-cooled solution of 4-bromo-2-formylbenzonitrile (11 g, 52 mmol) in DCM (10 mL) and the reaction was stirred at RT for 30 mins. The mixture was concentrated in vacuo and the crude product purified by silica gel column chromatography (petroleum ether/EtOAc=20:1 to 5:1) to give the title compound as a yellow solid (10.4 g, 86%). $^1$H NMR (400 MHz, CDCl$_3$) δ: 7.92 (s, 1H), 7.75 (dd, 1H), 7.62 (d, 1H), 6.89 (t, 1H).

4. Synthesis of tert-butyl (4-bromo-2-(difluoromethyl)benzyl)carbamate

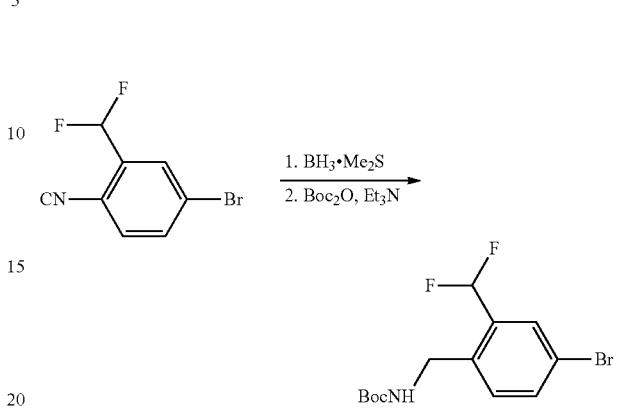

To a solution of 4-bromo-2-(difluoromethyl)benzonitrile (10.4 g, 45 mmol) in THF (100 mL) was added BH$_3$·Me$_2$S (13.4 mL, 10 M, 134 mmol) and the reaction was stirred at 80° C. for 18 h. The cooled mixture was quenched with MeOH (100 mL), Boc$_2$O (19.5 g, 90 mmol) and Et$_3$N (18 g, 179 mmol) were added, and the reaction was stirred at RT for 3 h. The mixture was concentrated in vacuo and the crude was purified by silica gel column chromatography (2-5% EtOAc/petroleum ether) to give the title compound as a yellow oil (8.6 g, 57%, two steps). $^1$H NMR (400 MHz, CDCl$_3$) δ: 7.65 (s, 1H), 7.55 (d, 1H), 7.30 (d, 1H), 6.70 (dd, 1H), 4.90 (br, 1H), 4.36 (d, 2H), 1.42 (s, 9H).

5. Synthesis of tert-butyl (2-(difluoromethyl)-4-(4,4,5,5-tetramethyl-1,3,2-dioxaborolan-2-yl)benzyl)carbamate

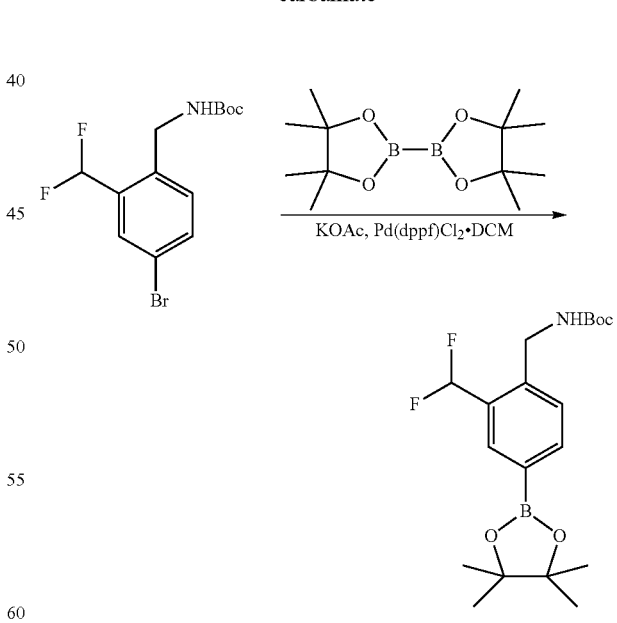

The title compound was prepared as a yellow oil (3.2 g, 94%) from tert-butyl (4-bromo-2-(difluoromethyl)benzyl) carbamate, following the procedure described in Example 1, Step 1. $^1$H NMR (400 MHz, CDCl$_3$) δ: 7.90-7.79 (m, 2H), 7.44 (d, 1H), 6.79 (t, 1H), 4.89 (br s, 1H), 4.46 (d, 2H), 1.42 (s, 9H), 1.35-1.32 (m, 12H).

6. Synthesis of tert-butyl (4-(6-bromopyrrolo[2,1-f][1,2,4]triazin-4-yl)-2-(difluoromethyl)benzyl)carbamate

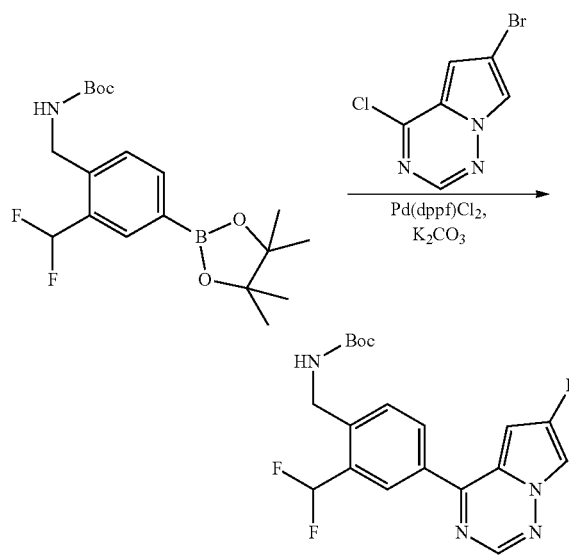

The title compound was obtained as a yellow solid (1.3 g, crude) from tert-butyl (2-(difluoromethyl)-4-(4,4,5,5-tetramethyl-1,3,2-dioxaborolan-2-yl)benzyl)carbamate and 6-bromo-4-chloro-pyrrolo[2,1-f][1,2,4]triazine, following an analogous procedure to that described in Example 35, Step 3. LCMS m/z=454.5 [M+H]$^+$

7. Synthesis of tert-butyl (2-(difluoromethyl)-4-(6-(1-methyl-1H-pyrazol-4-yl)pyrrolo[2,1-f][1,2,4]triazin-4-yl)benzyl)carbamate

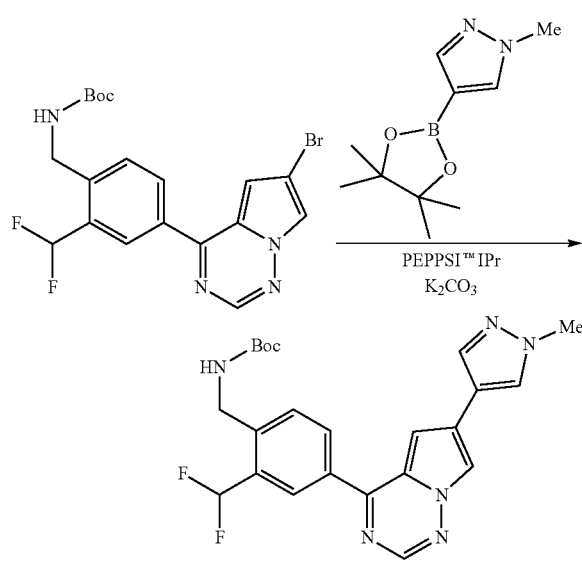

A mixture of tert-butyl (4-(6-bromopyrrolo[2,1-f][1,2,4]triazin-4-yl)-2-(difluoromethyl)benzyl)carbamate (260 mg, 0.57 mmol), 1-methylpyrazole-4-boronic acid pinacol ester (119 mg, 0.57 mmol), PEPPSI™-IPr catalyst (39 mg, 0.06 mmol) and K$_2$CO$_3$ (159 mg, 1.2 mmol) in EtOH (20 mL) and water (2 mL) was stirred at 90° C. for 4 h under N$_2$. The cooled mixture was concentrated in vacuo and the crude product was purified by silica gel column chromatography (0-50% EtOAc/petroleum ether) to afford the title compound as a yellow solid (175 mg, 67%). LCMS m/z=455.4 [M+H]$^+$

8. Synthesis of (2-(difluoromethyl)-4-(6-(1-methyl-1H-pyrazol-4-yl)pyrrolo[2,1-f][1,2,4]triazin-4-yl)phenyl)methanamine hydrochloride

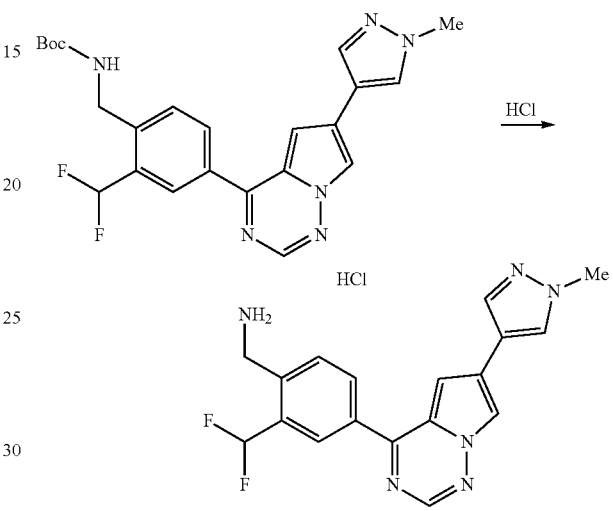

The title compound was obtained (200 mg, crude) from tert-butyl (2-(difluoromethyl)-4-(6-(1-methyl-1H-pyrazol-4-yl)pyrrolo[2,1-f][1,2,4]triazin-4-yl)benzyl)carbamate, following the procedure described in Example 35, Step 5. LCMS m/z=355.1 [M+H]$^+$

9. Synthesis of 1-(tert-butyl)-N-(2-(difluoromethyl)-4-(6-(1-methyl-1H-pyrazol-4-yl)pyrrolo[2,1-f][1,2,4]triazin-4-yl)benzyl)-1H-1,2,3-triazole-4-carboxamide hydrochloride

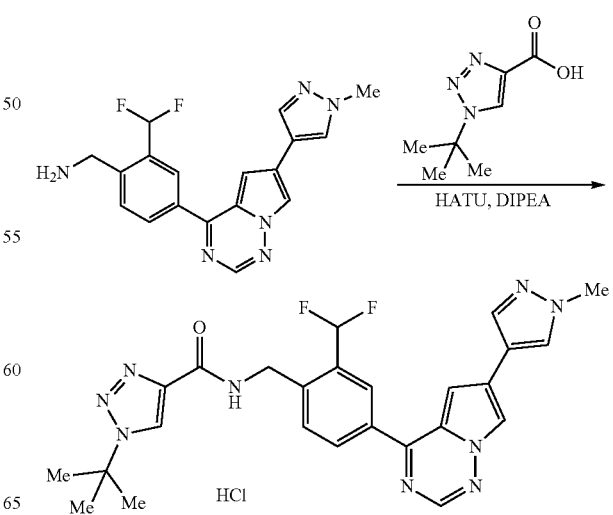

The crude was obtained from (2-(difluoromethyl)-4-(6-(1-methyl-1H-pyrazol-4-yl)pyrrolo[2,1-f][1,2,4]triazin-4-yl)phenyl)methanamine hydrochloride and 1-(tert-butyl)-1H-1,2,3-triazole-4-carboxylic acid, following the procedure described in Example 45, Step 7. The crude product was purified by prep HPLC using method A, 42-62% to afford the title compound as a yellow solid (48 mg, 62%). LCMS m/z=528.1 [M+Na]$^+$; $^1$H NMR (400 MHz, DMSO-d$_6$) δ: 9.25 (t, 1H), 8.72 (s, 1H), 8.58 (s, 1H), 8.48 (d, 1H), 8.33-8.31 (m, 2H), 8.16 (s, 1H), 7.91 (d, 1H), 7.66-7.63 (m, 1H), 7.40-7.35 (m, 2H), 4.71 (d, 2H), 3.84 (s, 3H), 1.63-1.61 (m, 9H).

Example 65. 3-(tert-butyl)-N-(2-(2,2-difluoroethyl)-4-(6-morpholinopyrrolo[2,1-f][1,2,4]triazin-4-yl)benzyl)-1,2,4-oxadiazole-5-carboxamide hydrochloride

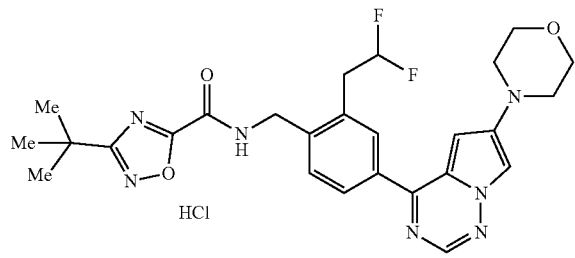 [SMILES: CC(C)(C)c1noc(C(=O)NCc2ccc(-c3ncnn4cc(N5CCOCC5)cc34)cc2CC(F)F)n1 ; Cl]

1. Synthesis of (E)-4-bromo-2-(2-(dimethylamino)vinyl)benzonitrile

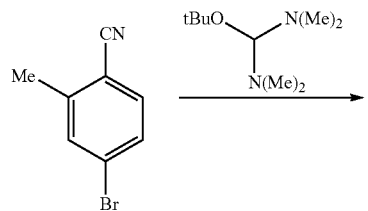

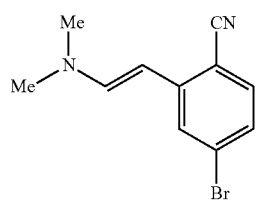

A solution of 4-bromo-2-methylbenzonitrile (20 g, 102 mmol) in tert-butoxy bis(dimethylamino)methane (53 g, 306 mmol) was stirred at 140° C. for 8 h. The cooled reaction mixture was filtered, the filter cake was washed with petroleum ether (100 mL), and the solids were dried in vacuo to give the title compound (15 g, 53%). H NMR (500 MHz, CDCl$_3$) δ: 7.73 (d, 1H), 7.56-7.49 (m, 1H), 7.28-7.21 (m, 2H), 5.53 (d, 1H), 3.18 (s, 6H).

2. Synthesis of 4-bromo-2-(2-oxoethyl)benzonitrile

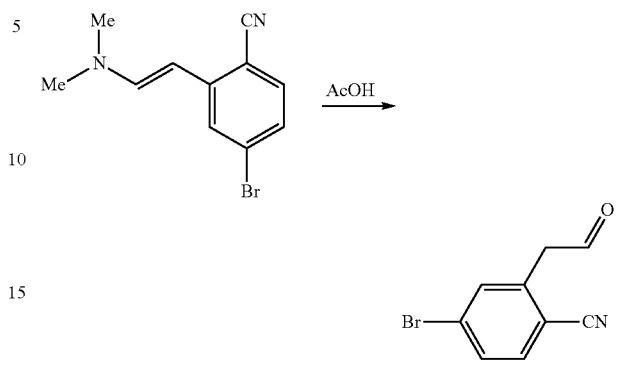

A solution of (E)-4-bromo-2-(2-(dimethylamino)vinyl)benzonitrile (15 g, 54 mmol) in aqueous AcOH (250 mL, 4 M) was stirred at RT for 1 h. The reaction mixture was filtered, and the filter cake washed with H$_2$O (100 mL). The crude material was dried in vacuo to give the title compound as a yellow solid (10 g, crude). $^1$H NMR (400 MHz, CDCl$_3$) δ: 9.84 (s, 1H), 7.58-7.56 (m, 2H), 7.52 (s, 1H), 4.01 (s, 2H).

3. Synthesis of 4-bromo-2-(2,2-difluoroethyl)benzonitrile

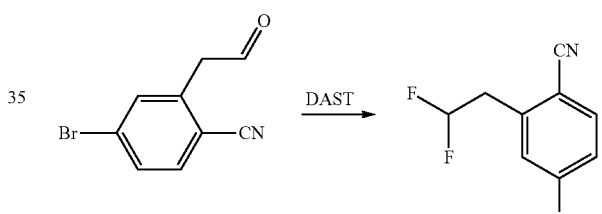

To a solution of 4-bromo-2-(2-oxoethyl)benzonitrile (10 g, 40 mmol) in DCM (100 mL) at 0° C. was slowly added DAST (19.4 g, 121 mmol) and the reaction was warmed to RT over 30 min. MeOH (50 mL) was added and the reaction mixture was concentrated in vacuo. The residue was poured into H$_2$O (200 mL) and extracted with EtOAc (3×200 mL). The combined organic layers were washed with brine (200 mL), dried (Na$_2$SO$_4$), filtered, and concentrated in vacuo. The crude material was purified by silica-gel column chromatography (petroleum ether/EtOAc=5:1) to give the title compound as a yellow solid (9.5 g, 97%). $^1$H NMR (400 MHz, CDCl$_3$) δ: 7.66-7.51 (m, 3H), 6.28-5.79 (m, 1H), 3.41-3.31 (m, 2H).

4. Synthesis of tert-butyl (4-bromo-2-(2,2-difluoroethyl)benzyl)carbamate

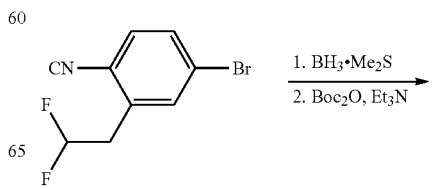

221

-continued

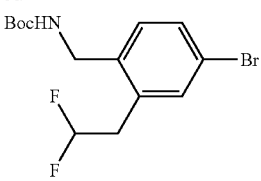

The title compound was obtained as a colorless oil (3.8 g, 90%), from 4-bromo-2-(2,2-difluoroethyl)benzonitrile, following a similar procedure to that described in Example 35, Step 1. LCMS m/z=295.9 [M−tBu+H]$^+$ 5. Synthesis of tert-butyl (2-(2,2-difluoroethyl)-4-(4,4,5,5-tetramethyl-1,3,2-dioxaborolan-2-yl)benzyl) carbamate

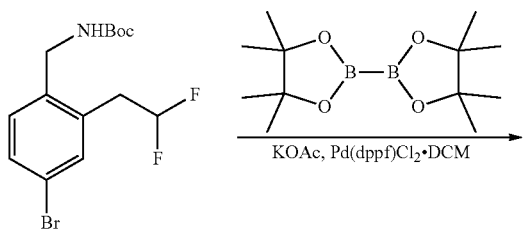

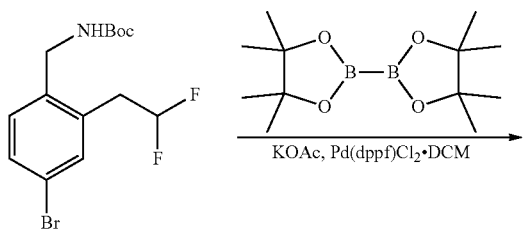

The title compound was obtained as a yellow solid (4.0 g, 86%) from tert-butyl (4-bromo-2-(2,2-difluoroethyl)benzyl) carbamate, following the procedure described in Example 1, Step 1. LCMS m/z=342.1 [M+H−tBu]$^+$ 6. Synthesis of tert-butyl (4-(6-bromopyrrolo[2,1-f][1,2,4]triazin-4-yl)-2-(2,2-difluoroethyl)benzyl)carbamate

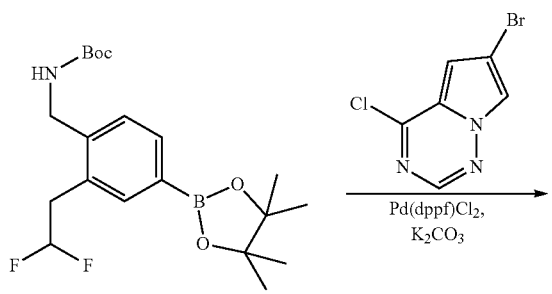

222

-continued

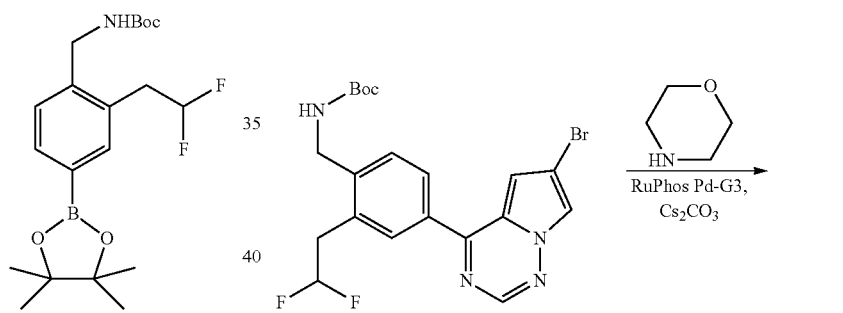

To a solution of tert-butyl (2-(2,2-difluoroethyl)-4-(4,4,5,5-tetramethyl-1,3,2-dioxaborolan-2-yl)benzyl)carbamate (1.10 g, 2.8 mmol) in dioxane (30 mL) and water (2 mL) was added 6-bromo-4-chloro-pyrrolo[2,1-f][1,2,4]triazine (1.35 g, 5.8 mmol), K$_2$CO$_3$ (765 mg, 5.5 mmol) and Pd(dppf)Cl$_2$ (203 mg, 0.28 mmol) and the reaction stirred at 90° C. under N$_2$ for 1 h. The cooled mixture was concentrated in vacuo and the residue was dissolved in EtOAc. The mixture was washed with water (20 mL) and extracted with EtOAc (3×10 mL). The combined organic layers were dried (Na$_2$SO$_4$), filtered and concentrated in vacuo. The residue was purified by silica gel column chromatography (petroleum ether/EtOAc=2:1) to afford the title compound as a yellow solid (1.1 g, 85%). LCMS m/z=467.0 [M+H]$^+$ 7. Synthesis of tert-butyl (2-(2,2-difluoroethyl)-4-(6-morpholinopyrrolo[2,1-f][1,2,4]triazin-4-yl)benzyl)carbamate To a solution of tert-butyl (4-(6-bromopyrrolo[2,1-f][1,2,4]triazin-4-yl)-2-(2,2-difluoroethyl)benzyl)carbamate (800 mg, 1.7 mmol) in toluene (30 mL) was added morpholine (447 mg, 5.1 mmol), Cs$_2$CO$_3$ (1.67 g, 5.1 mmol) and Ruphos Pd G3 (286 mg, 0.34 mmol) and the mixture was stirred at 90° C. under N$_2$ for 16 h. The cooled mixture was concentrated in vacuo and the residue was dissolved in EtOAc. The mixture was washed with water (20 mL), extracted with EtOAc (3×10 mL) and the combined organic layers were dried (Na$_2$SO$_4$), filtered, and concentrated in vacuo. The residue was purified by silica gel column chromatography (0-50% EtOAc/petroleum ether/EtOAc) to afford the title compound as a yellow solid (250 mg, 25%). LCMS m/z=474.3 [M+H]$^+$

8. Synthesis of (2-(2,2-difluoroethyl)-4-(6-morpholinopyrrolo[2,1-f][1,2,4]triazin-4-yl)phenyl)methanamine hydrochloride

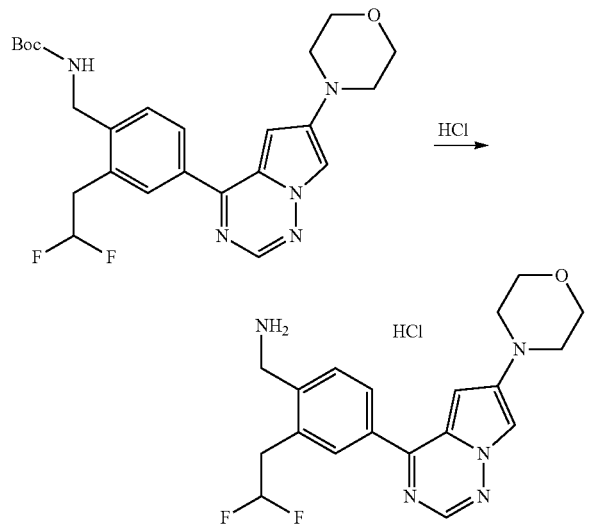

The title compound was obtained as a red solid (180 mg, crude) from tert-butyl (2-(2,2-difluoroethyl)-4-(6-morpholinopyrrolo[2,1-f][1,2,4]triazin-4-yl)benzyl)carbamate following the procedure described in Example 35, Step 5 and was used without further purification.

9. Synthesis of 3-(tert-butyl)-N-(2-(2,2-difluoroethyl)-4-(6-morpholinopyrrolo[2,1-f][1,2,4]triazin-4-yl)benzyl)-1,2,4-oxadiazole-5-carboxamide hydrochloride

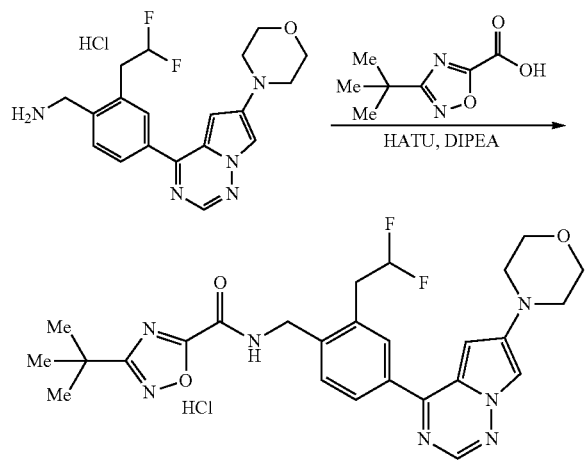

The crude product was obtained from (2-(2,2-difluoroethyl)-4-(6-morpholinopyrrolo[2,1-f][1,2,4]triazin-4-yl)phenyl)methanamine hydrochloride and 3-(tert-butyl)-1,2,4-oxadiazole-5-carboxylic acid following an analogous procedure to that described in Example 45, Step 7. The crude was purified by prep HPLC, Method A; 45-65%, to afford the title compound as a red solid (30 mg, 26%). LCMS m/z=526.2 [M+H]$^+$; $^1$H NMR (400 MHz, DMSO-d$_6$) δ: 9.96 (br t, 1H), 8.52 (s, 1H), 8.10-7.99 (m, 3H), 7.59 (d, 1H), 6.75 (s, 1H), 6.57-6.21 (m, 1H), 4.61 (br d, 2H), 3.80-3.72 (m, 4H), 3.53 (dt, 2H), 3.20-3.13 (m, 4H), 1.36 (s, 9H).

Example 66. 3-(tert-butyl)-N-(2-(2,2-difluoroethyl)-3-fluoro-4-(6-(1-methyl-1H-pyrazol-4-yl)pyrrolo[2,1-f][1,2,4]triazin-4-yl)benzyl)-1,2,4-oxadiazole-5-carboxamide hydrochloride

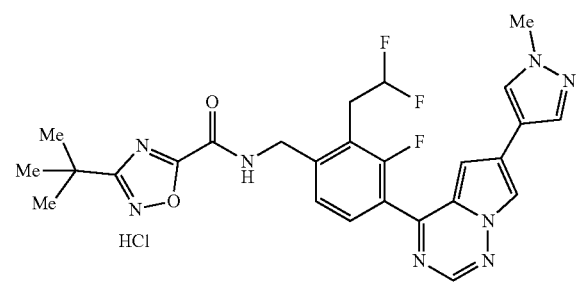 [SMILES: Cn1cc(-c2cc3c(-c4ccc(CNC(=O)c5nc(C(C)(C)C)no5)c(CC(F)F)c4F)ncnn3c2)cn1 ; Cl]

1. Synthesis of (E)-4-bromo-2-(2-(dimethylamino)vinyl)-3-fluorobenzonitrile

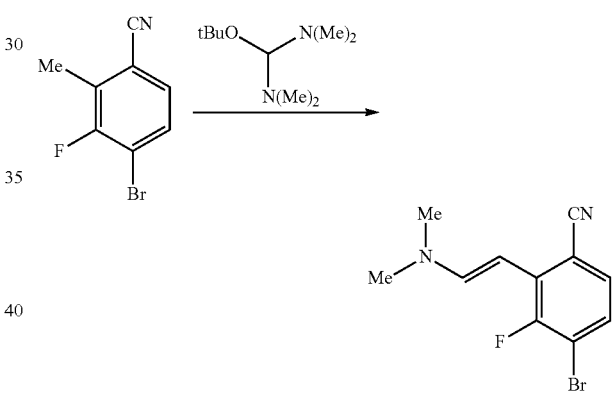

A solution of 4-bromo-3-fluoro-2-methylbenzonitrile (11.5 g, 54 mmol) in tert-butoxy bis(dimethylamino)methane (100 mL) was stirred at 135° C. for 6 h. The cooled reaction was concentrated in vacuo and the crude was purified by silica gel column chromatography (petroleum ether/EtOAc=5:1) to afford the title compound as a yellow solid (10.0 g, crude). $^1$H NMR (400 MHz, CDCl$_3$) δ: 7.46 (d, 1H), 7.13 (d, 1H), 7.05 (t, 1H), 5.15 (d, 1H), 2.95 (s, 6H).

2. Synthesis of 4-bromo-3-fluoro-2-(2-oxoethyl)benzonitrile

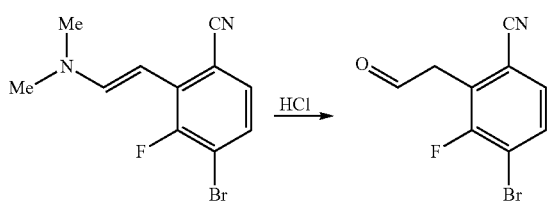 [SMILES: CN(C)/C=C/c1c(C#N)ccc(Br)c1F ; Cl ; N#Cc1ccc(Br)c(F)c1CC=O]

To a solution of (E)-4-bromo-2-(2-(dimethylamino)vinyl)-3-fluorobenzonitrile (5 g, 19 mmol) in MeCN (30 mL) was added an HCl solution (20 mL, 6 M) and the reaction was stirred at 50° C. for 5 h. The mixture was cooled, H$_2$O (20 mL) added, and the mixture was dried by lyophilization to afford the title compound as a red solid (5.0 g, crude). H NMR (400 MHz, CDCl$_3$) δ: 9.82 (s, 1H), 7.65 (dd, 1H), 7.38 (d, 1H), 4.09 (s, 2H).

3. Synthesis of 4-bromo-2-(2,2-difluoroethyl)-3-fluorobenzonitrile

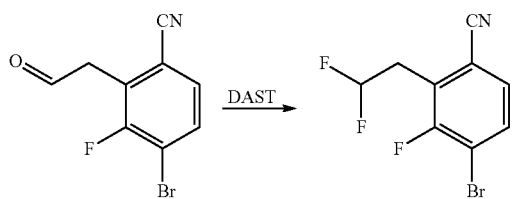

The title compound was obtained as a brown oil (3.0 g, 50%) from 4-bromo-3-fluoro-2-(2-oxoethyl)benzonitrile, following the procedure described in Example 65, Step 3. $^1$H NMR (400 MHz, CDCl$_3$) δ: 7.67 (dd, 1H), 7.39 (d, 1H), 6.09 (dd, 1H), 3.49 (dd, 2H).

4. Synthesis of (4-bromo-2-(2,2-difluoroethyl)-3-fluorophenyl)methanamine

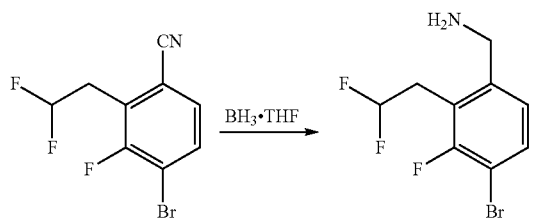 [SMILES: N#Cc1ccc(Br)c(F)c1CC(F)F ; NCc1ccc(Br)c(F)c1CC(F)F ; "BH3·THF"]

BH$_3$·THF (1 M, 17.7 mL, 17.7 mmol) was added dropwise to a solution of 4-bromo-2-(2,2-difluoroethyl)-3-fluorobenzonitrile (2.34 g, 8.9 mmol) in THF (100 mL) and the reaction stirred at 60° C. for 12 h. The mixture was quenched by the dropwise addition of MeOH (50 mL), the pH was adjusted to 4 with HCl (3 M), and the mixture was stirred at 60° C. for 1 h. The mixture was concentrated in vacuo, the residue was diluted with water (100 mL) and extracted with DCM (2×50 mL). The combined organic layers were washed with water (50 mL). The combined water layers were dried by lyophilization to give the title compound as a white solid (2.4 g, crude). LCMS m/z=268.0 [M+H]$^+$

5. Synthesis of tert-butyl (4-bromo-2-(2,2-difluoroethyl)-3-fluorobenzyl)carbamate

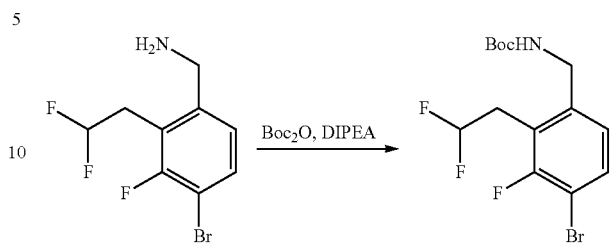

Boc$_2$O (2.3 g, 10.5 mmol) was added to a solution of (4-bromo-2-(2,2-difluoroethyl)-3-fluorophenyl)methanamine (2.4 g, 8.8 mmol) in H$_2$O (100 mL) and DIPEA (4.6 mL, 26.3 mmol) and the reaction was stirred at 20° C. for 2 h. The mixture was extracted with EtOAc (2×100 mL), the combined organic layers were washed with water (100 mL), dried (Na$_2$SO$_4$), filtered, and concentrated in vacuo. The crude product was purified by silica gel column chromatography (petroleum ether/EtOAc=10:1) to give the title compound as a white solid (2.9 g, 84%). 6. Synthesis of tert-butyl (2-(2,2-difluoroethyl)-3-fluoro-4-(4,4,5,5-tetramethyl-1,3,2-dioxaborolan-2-yl)benzyl)carbamate

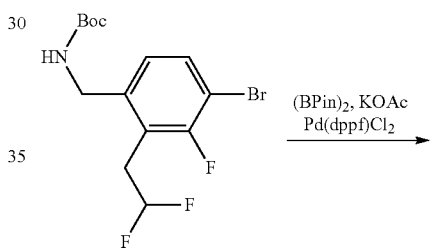

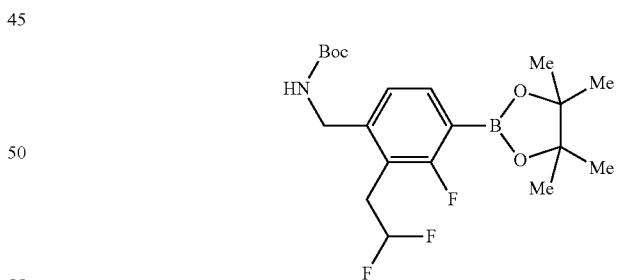

To a solution of tert-butyl (4-bromo-2-(2,2-difluoroethyl)-3-fluorobenzyl)carbamate (280 mg, 0.76 mmol) and (bispinacolato)diboron (386 mg, 1.52 mmol) in dioxane (20 mL) was added KOAc (224 mg, 2.28 mmol). Pd(dppf)Cl$_2$ (56 mg, 0.076 mmol) was added and the reaction stirred at 90° C. under N$_2$ for 12 h. The cooled mixture was poured into H$_2$O (30 mL) and extracted with EtOAc (2×20 mL). The combined organic layers were washed with water (20 mL), dried (Na$_2$SO$_4$), filtered, and concentrated in vacuo to afford the title compound as a black solid (300 mg, crude), which was used without further purification.

7. Synthesis of tert-butyl (4-(6-bromopyrrolo[2,1-f][1,2,4]triazin-4-yl)-2-(2,2-difluoroethyl)-3-fluorobenzyl)carbamate

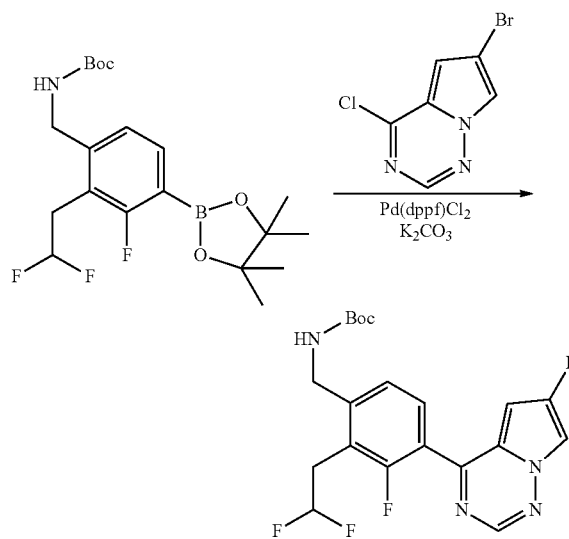

The title compound was obtained as a brown solid (84 mg, 35%) from tert-butyl (2-(2,2-difluoroethyl)-3-fluoro-4-(4,4,5,5-tetramethyl-1,3,2-dioxaborolan-2-yl)benzyl)carbamate and 6-bromo-4-chloro-pyrrolo[2,1-f][1,2,4]triazine, following an analogous procedure to that described in Example 34, Step 1. LCMS m/z=485.1 [M+H]+

8. Synthesis of tert-butyl (2-(2,2-difluoroethyl)-3-fluoro-4-(6-(1-methyl-1H-pyrazol-4-yl)pyrrolo[2,1-f][1,2,4]triazin-4-yl)benzyl)carbamate

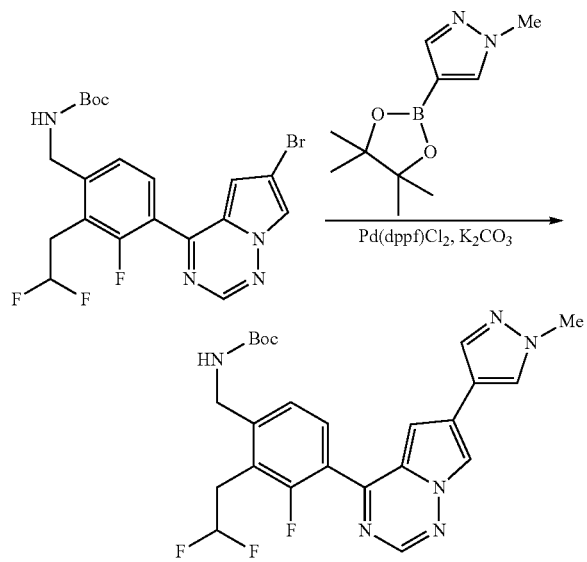

The title compound was obtained as an orange solid (70 mg, 83%) from tert-butyl (4-(6-bromopyrrolo[2,1-f][1,2,4]triazin-4-yl)-2-(2,2-difluoroethyl)-3-fluorobenzyl)carbamate and 1-methylpyrazole-4-boronic acid pinacol ester, following the procedure described in Example 33, Step 1. LCMS m/z=487.2 [M+H]+

9. Synthesis of (2-(2,2-difluoroethyl)-3-fluoro-4-(6-(1-methyl-1H-pyrazol-4-yl)pyrrolo[2,1-f][1,2,4]triazin-4-yl)phenyl)methanamine hydrochloride

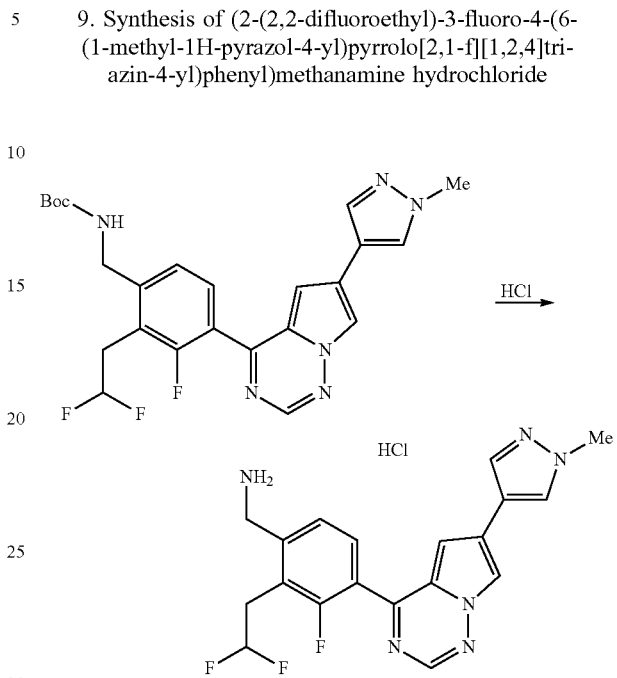

The title compound was obtained as an orange solid (70 mg, crude), from tert-butyl (2-(2,2-difluoroethyl)-3-fluoro-4-(6-(1-methyl-1H-pyrazol-4-yl)pyrrolo[2,1-f][1,2,4]triazin-4-yl)benzyl)carbamate following the procedure described in Example 35, Step 5. LCMS m/z=370.1 [M+H]+

10. Synthesis of 3-(tert-butyl)-N-(2-(2,2-difluoroethyl)-3-fluoro-4-(6-(1-methyl-1H-pyrazol-4-yl)pyrrolo[2,1-f][1,2,4]triazin-4-yl)benzyl)-1,2,4-oxadiazole-5-carboxamide hydrochloride

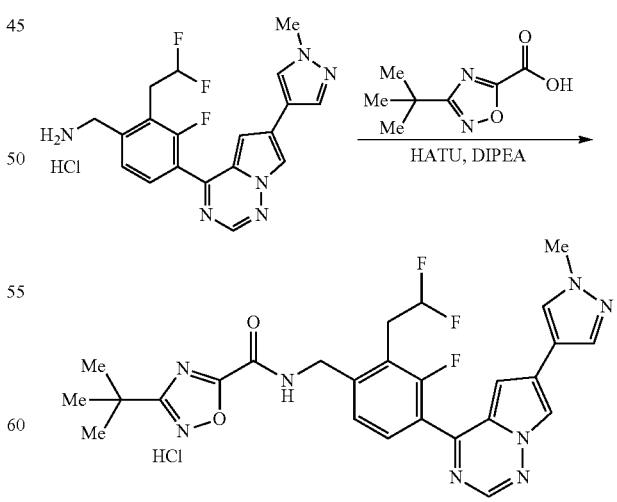

The product was prepared from (2-(2,2-difluoroethyl)-3-fluoro-4-(6-(1-methyl-1H-pyrazol-4-yl)pyrrolo[2,1-f][1,2,4]triazin-4-yl)phenyl)methanamine hydrochloride and 3-(tert-butyl)-1,2,4-oxadiazole-5-carboxylic acid, following the procedure described in Example 45, Step 7. It was then purified by prep HPLC using Method A (55-75%) to afford the title compound as a yellow solid (29 mg, 32%). LCMS m/z=539.1 [M+H]⁺; ¹H NMR (400 MHz, DMSO-d₆) δ: 10.01 (t, 1H), 8.60 (s, 1H), 8.51 (s, 1H), 8.15 (s, 1H), 7.90 (s, 1H), 7.77 (t, 1H), 7.46 (d, 1H), 7.03 (s, 1H), 6.42 (t, 1H), 4.64 (d, 2H), 3.85 (s, 3H), 3.55 (t, 2H), 1.36 (s, 9H).

Example 67. 5-(tert-butyl)-N-(4-(6-(dimethylcarbamoyl)pyrrolo[2,1-f][1,2,4]triazin-4-yl)-2-methylbenzyl)-1,2,4-oxadiazole-3-carboxamide hydrochloride

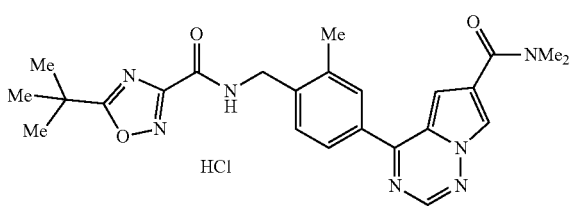 [SMILES: Cc1cc(-c2ncnn3cc(C(=O)N(C)C)cc23)ccc1CNC(=O)c1noc(C(C)(C)C)n1 ; Cl]

1. Synthesis of methyl 4-(4-(((tert-butoxycarbonyl)amino)methyl)-3-methylphenyl)pyrrolo[2,1-f][1,2,4]triazine-6-carboxylate

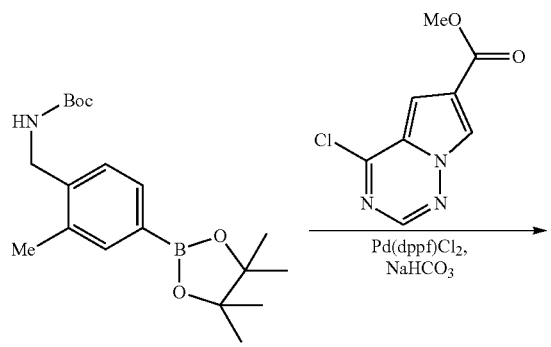

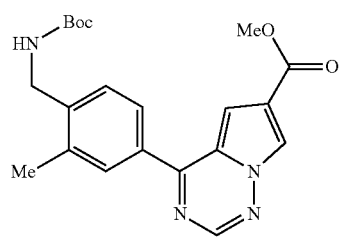

The title compound was obtained as a yellow solid (200 mg, 27%) from tert-butyl (2-methyl-4-(4,4,5,5-tetramethyl-1,3,2-dioxaborolan-2-yl)benzyl)carbamate and methyl 4-chloropyrrolo[1,2-f][1,2,4]triazine-6-carboxylate, following the procedure described in Example 34, Step 1. LCMS m/z=397.1 [M+H]⁺

2. Synthesis of methyl 4-(4-(aminomethyl)-3-methylphenyl)pyrrolo[2,1-f]triazine-6-carboxylate hydrochloride

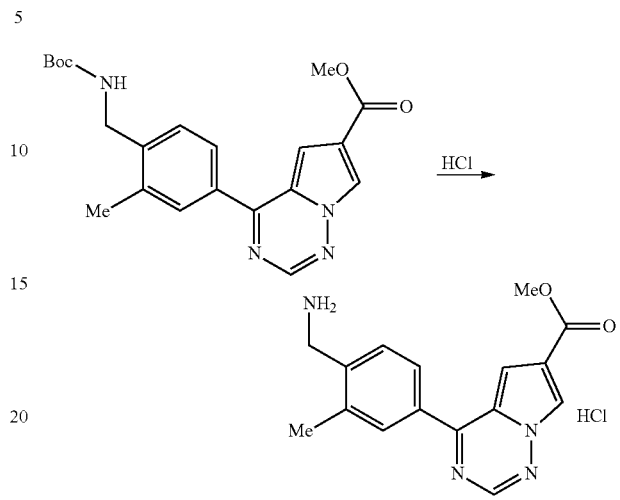

The title compound was obtained as a yellow solid from methyl 4-(4-(((tert-butoxycarbonyl)amino)methyl)-3-methylphenyl)pyrrolo[2,1-f][1,2,4]triazine-6-carboxylate, following the procedure described in Example 35, Step 5. The crude material was carried forward without further purification. LCMS m/z=297.2 [M+H]⁺

3. Synthesis of 5-(tert-butyl)-1,2,4-oxadiazole-3-carbonyl chloride

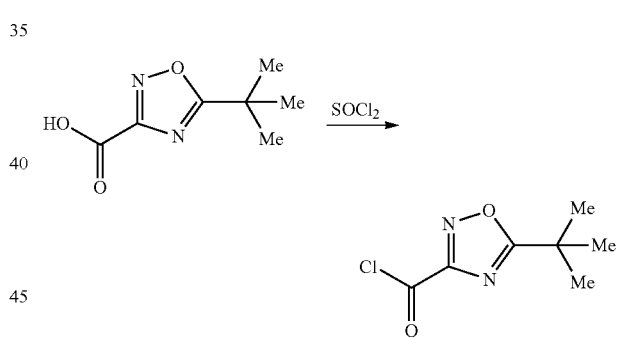

The title compound was obtained from 5-(tert-butyl)-1,2,4-oxadiazole-3-carboxylic acid, following the procedure described in Example 34, Step 7. The crude material was carried forward without further purification.

4. Synthesis of 5-(tert-butyl)-N-(4-(6-(dimethylcarbamoyl)pyrrolo[2,1-f][1,2,4]triazin-4-yl)-2-methylbenzyl)-1,2,4-oxadiazole-3-carboxamide hydrochloride

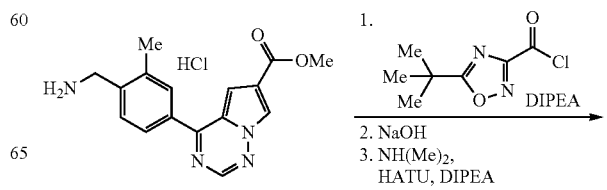

231
-continued

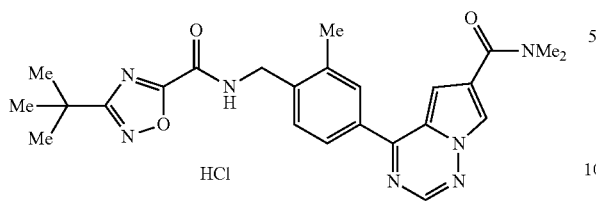

The title compound was prepared using a 3-step procedure as described below.

Part A: 5-(tert-butyl)-1,2,4-oxadiazole-3-carbonyl chloride (107 mg, 0.57 mmol) was slowly added to a solution of methyl 4-(4-(aminomethyl)-3-methylphenyl)pyrrolo[2,1-f]triazine-6-carboxylate hydrochloride (140 mg, 0.47 mmol) and DIPEA (122 mg, 0.95 mmol) in DCM (30 mL) and the reaction was stirred at 20° C. for 1 h. The mixture was poured into water (50 mL) and extracted with DCM (3×50 mL). The combined organic layers were washed with brine (100 mL), dried ($Na_2SO_4$), filtered, and concentrated in vacuo. The residue was purified by silica gel column chromatography (petroleum ether/EtOAc=1:1) to give methyl 4-(4-((5-(tert-butyl)-1,2,4-oxadiazole-3-carboxamido)methyl)-3-methylphenyl)pyrrolo[2,1-f][1,2,4]triazine-6-carboxylate as a yellow solid (120 mg, 57%). LCMS m/z=449.2 [M+H]$^+$ Part B: To a solution of methyl 4-(4-((5-(tert-butyl)-1,2,4-oxadiazole-3-carboxamido)methyl)-3-methylphenyl)pyrrolo[2,1-f][1,2,4]triazine-6-carboxylate (Part A, 120 mg, 0.27 mmol) in MeOH (10 mL) and $H_2O$ (2 mL) was added NaOH (21 mg, 0.54 mmol) and the reaction was stirred at 20° C. for 3 h. The reaction mixture was concentrated in vacuo and the residue dissolved in $H_2O$ (10 mL) and acidified to pH=5~6 using 2 M HCl. The mixture was freeze-dried to provide 4-(4-((5-(tert-butyl)-1,2,4-oxadiazole-3-carboxamido)methyl)-3-methylphenyl)pyrrolo[2,1-f][1,2,4]triazine-6-carboxylic acid as a yellow solid (120 mg, crude). LCMS m/z=435.1 [M+H]$^+$ Part C: To a solution of dimethylamine hydrochloride (11 mg, 0.14 mmol) in DCM (30 mL) at 20° C. was added DIPEA (36 mg, 0.14 mmol), 4-(4-((5-(tert-butyl)-1,2,4-oxadiazole-3-carboxamido)methyl)-3-methylphenyl)pyrrolo[2,1-f][1,2,4]triazine-6-carboxylic acid (Part B, 60 mg, 0.14 mmol) and HATU (53 mg, 0.14 mmol) and the mixture was stirred at 20° C. for 30 min.

The reaction was poured into $H_2O$ (50 mL) and extracted with DCM (3×50 mL). The combined organics were washed with brine (100 mL), dried ($Na_2SO_4$), and concentrated in vacuo. The residue was purified by pre-HPLC (Method A 35-55%) to give the title compound as a yellow solid (43 mg, 67%). LCMS m/z=484.2 [M+Na]$^+$, $^1$H NMR (400 MHz, DMSO-$d_6$) δ: 9.52-9.49 (m, 1H), 8.67 (s, 1H), 8.39 (d, 1H), 7.98-7.94 (m, 2H), 7.44 (d, 1H), 7.33 (s, 1H), 4.54 (d, 2H), 3.14-3.09 (m, 3H), 3.00 (s, 3H), 2.44 (s, 3H), 1.42 (s, 9H).

232

Example 68. 5-(tert-butyl)-N-(2-methyl-4-(6-(pyrimidin-2-yl)pyrrolo[2,1-f][1,2,4]triazin-4-yl)benzyl)-1,2,4-oxadiazole-3-carboxamide hydrochloride

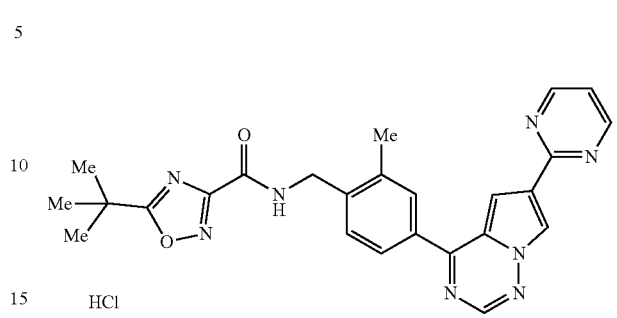

1. Synthesis of tert-butyl (2-methyl-4-(6-(4,4,5,5-tetramethyl-1,3,2-dioxaborolan-2-yl)pyrrolo[2,1-f][1,2,4]triazin-4-yl)benzyl)carbamate

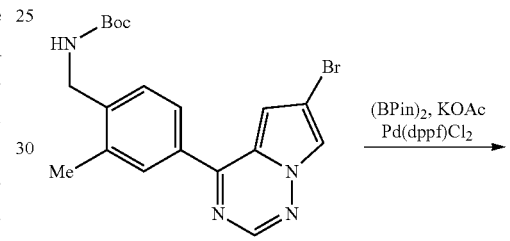

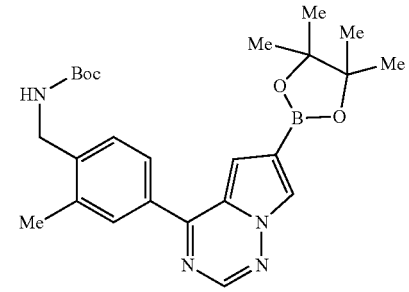

(Bispinacolato)diboron (183 mg, 0.72 mmol), KOAc (71 mg, 0.72 mmol) and Pd(dppf)$Cl_2$ (29 mg, 0.036 mmol) were added to a solution of tert-butyl (4-(6-bromopyrrolo[2,1-f][1,2,4]triazin-4-yl)-2-methylbenzyl)carbamate (150 mg, 0.36 mmol) in dioxane (15 mL) and the reaction stirred at 80° C. under $N_2$ for 16 h. The cooled mixture was concentrated in vacuo to afford the title compound (150 mg, crude), which was carried forward without further purification. LCMS m/z=465.3 [M+H]$^+$

2. Synthesis of tert-butyl (2-methyl-4-(6-(pyrimidin-2-yl)pyrrolo[2,1-f][1,2,4]triazin-4-yl)benzyl)carbamate

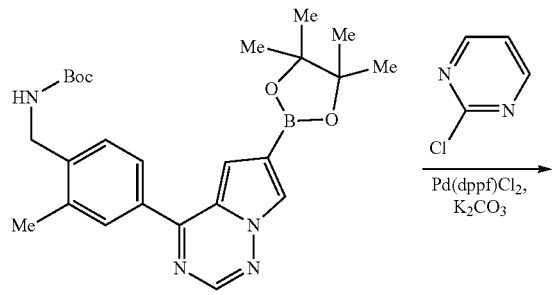

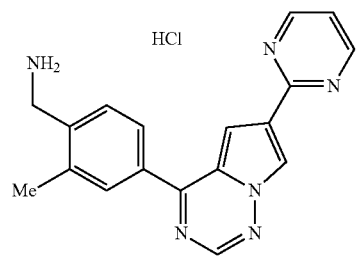

To a solution of tert-butyl (2-methyl-4-(6-(4,4,5,5-tetramethyl-1,3,2-dioxaborolan-2-yl)pyrrolo[2,1-f][1,2,4]triazin-4-yl)benzyl)carbamate (150 mg, 0.32 mmol) in dioxane (15 mL) and H$_2$O (2 mL) were added 2-chloropyrimidine (55 mg, 0.49 mmol), K$_2$CO$_3$ (89 mg, 0.65 mmol) and Pd(dppf)Cl$_2$ (24 mg, 0.032 mmol) and the reaction was stirred at 80° C. under N$_2$ for 1 h. The cooled mixture was concentrated in vacuo, the residue was dissolved in EtOAc, was washed with H$_2$O (20 mL), and was extracted with EtOAc (3×20 mL). The combined organic layers were dried (Na$_2$SO$_4$), filtered, and concentrated in vacuo. The residue was purified by silica gel column chromatography (0-50% EtOAc/petroleum ether) to afford the title compound as a yellow solid (100 mg, 74%). LCMS m/z=417.4 [M+H]$^+$

3. Synthesis of (2-methyl-4-(6-(pyrimidin-2-yl)pyrrolo[2,1-f][1,2,4]triazin-4-yl)phenyl)methanamine hydrochloride

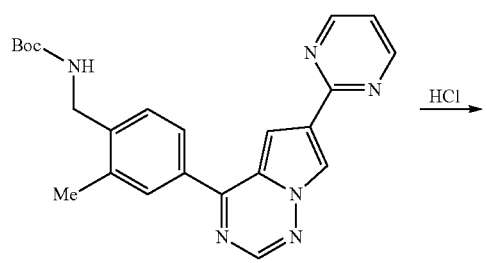

The title compound was obtained as a yellow solid (60 mg, crude) from tert-butyl (2-methyl-4-(6-(pyrimidin-2-yl)pyrrolo[2,1-f][1,2,4]triazin-4-yl)benzyl)carbamate following the procedure described in Example 35, Step 5. LCMS m/z=358.3 [M+H]$^+$

4. Synthesis of 5-(tert-butyl)-N-(2-methyl-4-(6-(pyrimidin-2-yl)pyrrolo[2,1-f][1,2,4]triazin-4-yl)benzyl)-1,2,4-oxadiazole-3-carboxamide hydrochloride

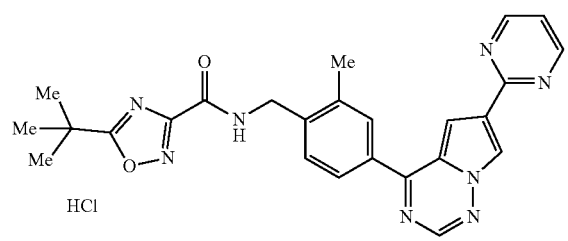 [SMILES: Cc1cc(-c2ncnn3cc(-c4ncccn4)cc23)ccc1CNC(=O)c1noc(C(C)(C)C)n1 ; Cl]

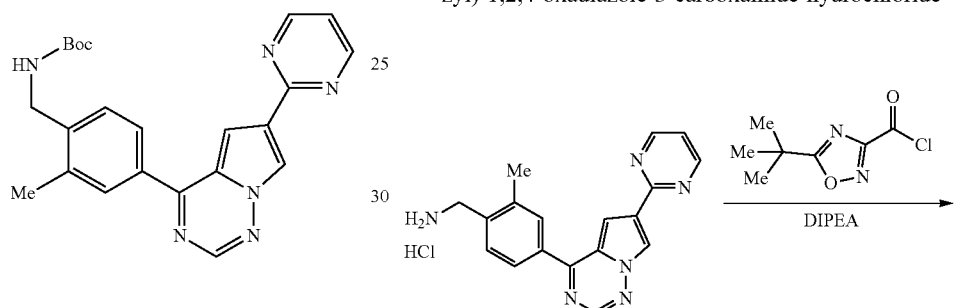

The product was obtained from (2-methyl-4-(6-(pyrimidin-2-yl)pyrrolo[2,1-f][1,2,4]triazin-4-yl)phenyl)methanamine hydrochloride and 5-(tert-butyl)-1,2,4-oxadiazole-3-carbonyl chloride following the procedure described in Example 33, Step 9. The residue was purified by prep-HPLC Method A (45-65%) to afford the title compound as a yellow solid (50 mg, 56%). LCMS m/z=469.2 [M+H]$^+$; $^1$H NMR (400 MHz, DMSO-d$_6$) δ: 9.54 (t, 1H), 8.88 (d, 2H), 8.70 (s, 2H), 8.03-7.97 (m, 2H), 7.51 (d, 1H), 7.43 (t, 1H), 4.57 (d, 2H), 2.50 (s, 3H), 1.44 (s, 9H).

Example 69. 3-(tert-butyl)-N-(2-methyl-4-(6-(4-methylpiperazin-1-yl)pyrrolo[2,1-f][1,2,4]triazin-4-yl)benzyl)-1,2,4-oxadiazole-5-carboxamide

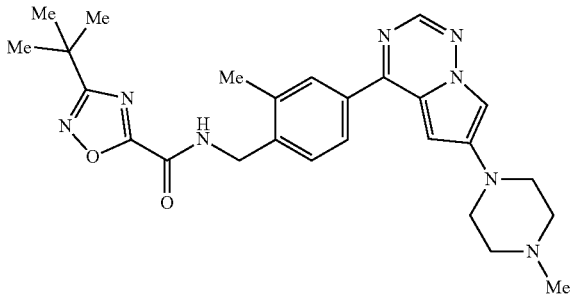 [SMILES: Cc1cc(-c2ncnn3cc(N4CCN(C)CC4)cc23)ccc1CNC(=O)c1nc(C(C)(C)C)no1]

1. Synthesis of tert-butyl (2-methyl-4-(6-(4-methylpiperazin-1-yl)pyrrolo[2,1-f][1,2,4]triazin-4-yl)benzyl)carbamate

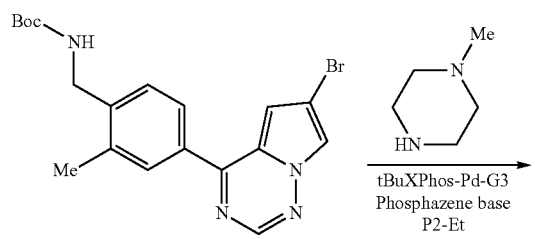

N₂ was bubbled through a mixture of tert-butyl (4-(6-bromopyrrolo[2,1-f][1,2,4]triazin-4-yl)-2-methylbenzyl)carbamate (350 mg, 0.84 mmol) and tBuXPhos-Pd-G3 (67 mg, 0.084 mmol) in t-amyl alcohol (4.2 mL) for 5 mins. Phosphazene base P2-Et (569 mg, 1.7 mmol) and 1-methylpiperazine (126 mg, 1.3 mmol) were added and the reaction was stirred for 4 h at RT. The reaction was diluted with saturated aqueous NH₄Cl solution and extracted with EtOAc (2×). The combined organic layers were washed with brine, dried (Na₂SO₄), filtered, and concentrated in vacuo. The crude was purified by silica gel column chromatography (0-10% MeOH/DCM with 1% NH₄OH modifier) to afford the title compound as a bright yellow solid (75 mg, 20%). LCMS m/z=437.3 [M+H]⁺

2. Synthesis of (2-methyl-4-(6-(4-methylpiperazin-1-yl)pyrrolo[2,1-f][1,2,4]triazin-4-yl)phenyl)methanamine hydrochloride

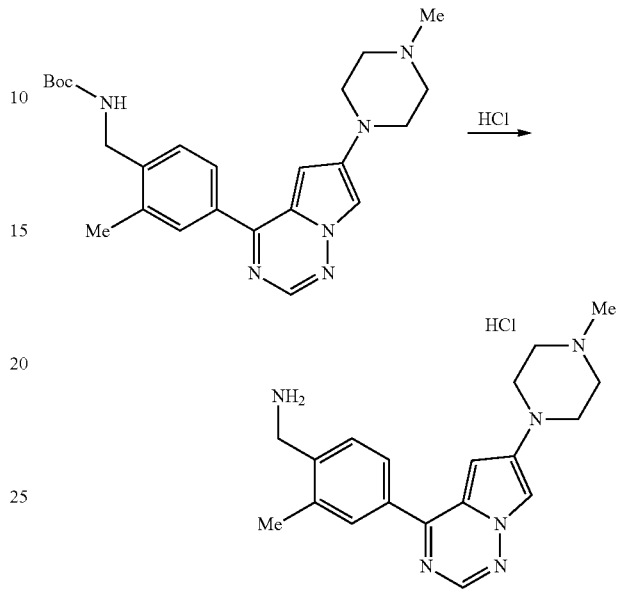

An HCl solution (9 μL, 4 M in MeOH) was added to a solution of tert-butyl (2-methyl-4-(6-(4-methylpiperazin-1-yl)pyrrolo[2,1-f][1,2,4]triazin-4-yl)benzyl)carbamate (3.9 mg, 9 μmol) in MeOH (1 mL) and the reaction was stirred at RT for 18 h. The mixture was concentrated in vacuo to afford the title compound (4.3 mg, crude). LCMS m/z=337.0 [M+H]⁺

3. Synthesis of 3-(tert-butyl)-N-(2-methyl-4-(6-(4-methylpiperazin-1-yl)pyrrolo[2,1-f][1,2,4]triazin-4-yl)benzyl)-1,2,4-oxadiazole-5-carboxamide

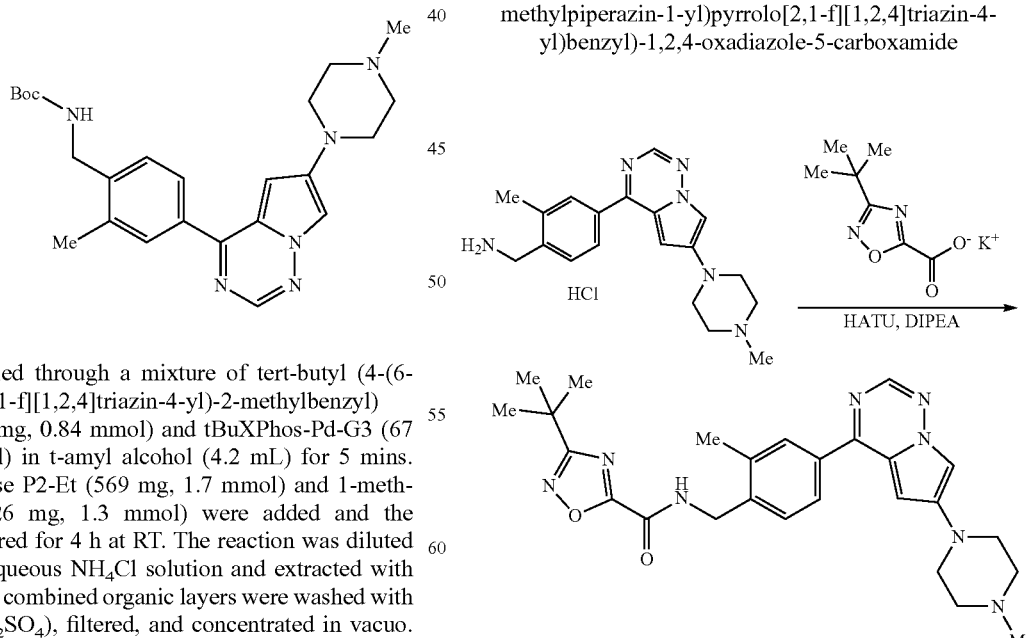

A mixture of (2-methyl-4-(6-(4-methylpiperazin-1-yl)pyrrolo[2,1-f][1,2,4]triazin-4-yl)phenyl)methanamine hydrochloride (4.3 mg, 0.013 mmol), potassium 3-(tert-butyl)-1,2,4-oxadiazole-5-carboxylate (5.3 mg, 0.026 mmol), HATU (9.7 mg, 0.026 mmol) and DIPEA (6.6 mg, 0.051 mmol) in DCM (2 mL) was stirred at RT overnight. The mixture was concentrated in vacuo and the residue purified by silica gel column chromatography (0-100% MeOH/DCM) to afford the title compound (4.9 mg, 75%). LCMS m/z=489.3 [M+H]$^+$; $^1$H NMR (500 MHz, CDCl$_3$) δ: 8.42-8.45 (m, 1H), 7.83-7.89 (m, 2H), 7.44-7.51 (m, 3H), 6.44-6.50 (m, 1H), 4.71-4.78 (m, 2H), 2.77-3.80 (m, 11H) 2.54 (s, 3H), 1.37-1.41 (m, 9H).

Example 70. (R)-5-(tert-butyl)-N-(4-(6-(2,4-dimethylpiperazin-1-yl)pyrrolo[2,1-f][1,2,4]triazin-4-yl)-2-methylbenzyl)-1,2,4-oxadiazole-3-carboxamide trifluoroacetate

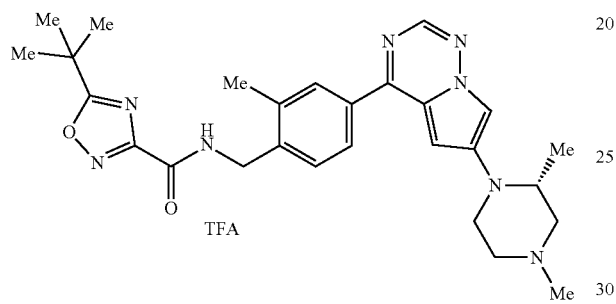

1. Synthesis of tert-butyl (R)-(4-(6-(2,4-dimethylpiperazin-1-yl)pyrrolo[2,1-f][1,2,4]triazin-4-yl)-2-methylbenzyl)carbamate

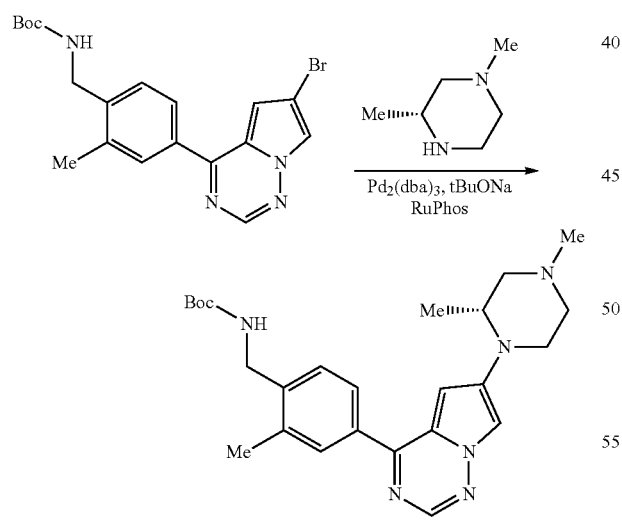

A mixture of tert-butyl (4-(6-bromopyrrolo[2,1-f][1,2,4]triazin-4-yl)-2-methylbenzyl)carbamate (50 mg, 0.12 mmol), (3R)-1,3-dimethylpiperazine (14 mg, 0.12 mmol), Pd$_2$(dba)$_3$ (11 mg, 0.012 mmol), tBuONa (23 mg, 0.24 mmol) and RuPhos (11 mg, 0.024 mmol) in toluene (2 mL) was degassed and stirred at 110° C. for 16 h. The cooled mixture was filtered through Celite®, washing through with DCM. The filtrate was concentrated in vacuo and the residue purified by silica gel column chromatography (0-100% MeOH/DCM) to afford the title compound (29 mg, 54%). LCMS m/z=451.4 [M+H]$^+$ 2. Synthesis of (R)-(4-(6-(2,4-dimethylpiperazin-1-yl)pyrrolo[2,1-f][1,2,4]triazin-4-yl)-2-methylphenyl)methanamine hydrochloride

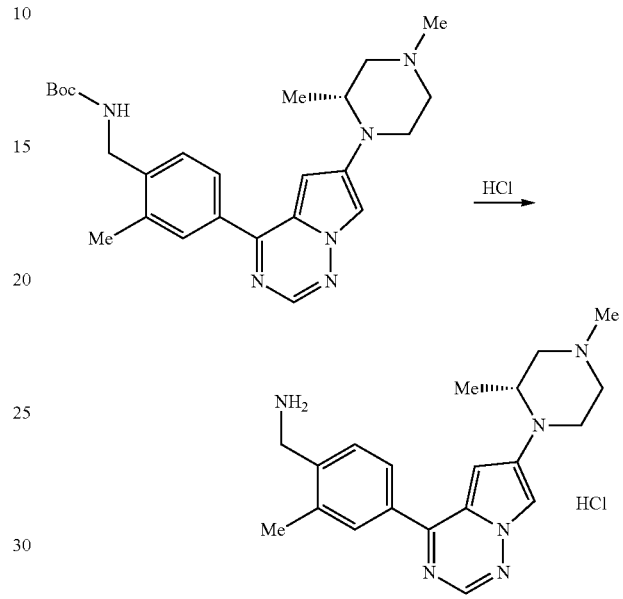

The title compound was obtained (35 mg, crude) from tert-butyl (R)-(4-(6-(2,4-dimethylpiperazin-1-yl)pyrrolo[2,1-f][1,2,4]triazin-4-yl)-2-methylbenzyl)carbamate, following the procedure described in Example 60, Step 1. LCMS m/z=351.4 [M+H]$^+$ 3. Synthesis of (R)-5-(tert-butyl)-N-(4-(6-(2,4-dimethylpiperazin-1-yl)pyrrolo[2,1-f][1,2,4]triazin-4-yl)-2-methylbenzyl)-1,2,4-oxadiazole-3-carboxamide trifluoroacetate

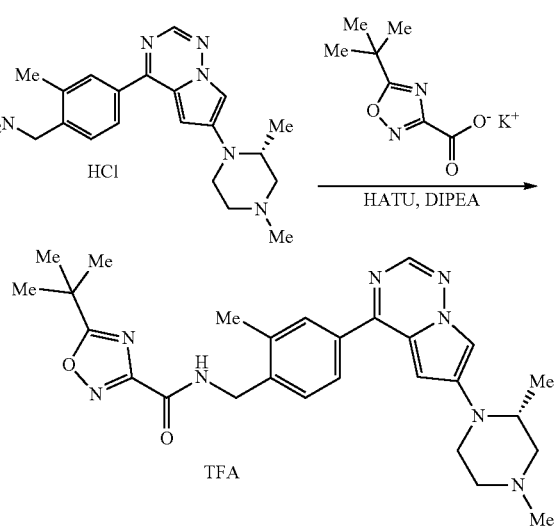

Crude product was obtained from (R)-(4-(6-(2,4-dimethylpiperazin-1-yl)pyrrolo[2,1-f][1,2,4]triazin-4-yl)-2-methylphenyl)methanamine hydrochloride and potassium 5-(tert-butyl)-1,2,4-oxadiazole-3-carboxylate following the procedure described in Example 69, Step 3. The crude was purified by prep HPLC (Method B, 10-90%) to afford the title compound (9.2 mg, 15%). LCMS m/z=503.2 [M+H]+; 1H NMR (400 MHz, MeOH-d4) δ: 9.28-9.55 (m, 1H), 8.47 (s, 1H), 8.10 (br s, 1H), 7.86 (br s, 2H), 7.57 (br d, 1H), 6.82 (br s, 1H), 4.61-4.79 (m, 2H), 4.35 (br d, 1H), 3.71-3.86 (m, 1H), 3.51-3.69 (m, 2H), 3.35-3.49 (m, 2H), 3.26 (br dd, 1H), 2.99 (s, 3H), 2.54 (s, 3H), 1.50 (s, 9H), 1.31 (br d, 3H).

Example 71. 5-(tert-butyl)-N-(2-methyl-4-(6-(oxetan-3-yl)pyrrolo[2,1-f][1,2,4]triazin-4-yl)benzyl)-1,2,4-oxadiazole-3-carboxamide trifluoroacetate

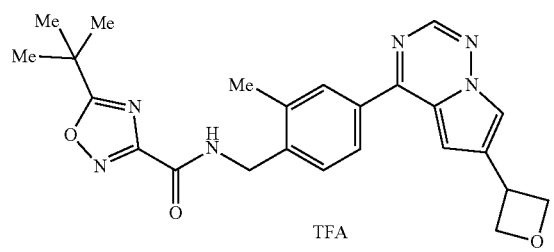 [SMILES: Cc1cc(-c2ncnn3cc(C4COC4)cc23)ccc1CNC(=O)c1noc(C(C)(C)C)n1]

1. Synthesis of tert-butyl (2-methyl-4-(6-oxetan-3-yl)pyrrolo[2,1-f][1,2,4]triazin-4-yl)benzyl)carbamate

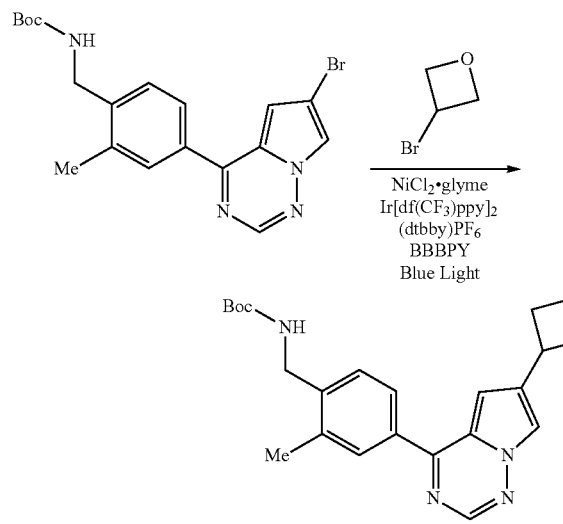

A mixture of NiCl2·glyme (2.6 mg, 12 μmol), Ir[dF(CF3)ppy]2(dtbbpy)PF6 (1.3 mg, 1.2 μmol) and BBBPY (3.2 mg, 12 μmol) in DME (1 mL) was purged with N2 for 10 min.

A mixture of tert-butyl (4-(6-bromopyrrolo[2,1-f][1,2,4]triazin-4-yl)-2-methylbenzyl)carbamate (50 mg, 120 μmol) and 3-bromooxetane (25 mg, 180 μmol) in DME (1 ml) was purged with N2 for 10 min. The first solution was added to the 2nd solution under N2. The reaction was irradiated with 30W CREE 450 nm EvoluChem lamp (blue light) at RT for 18 h. The reaction was filtered, the filtrate concentrated in vacuo, and the crude purified by silica gel column chromatography (0-100% EtOAc/Hept) to afford the title compound (21 mg, 43%). LCMS m/z=395.1 [M+H]+

2. Synthesis of (2-methyl-4-(6-(oxetan-3-yl)pyrrolo[2,1-f][1,2,4]triazin-4-yl)phenyl)methanamine

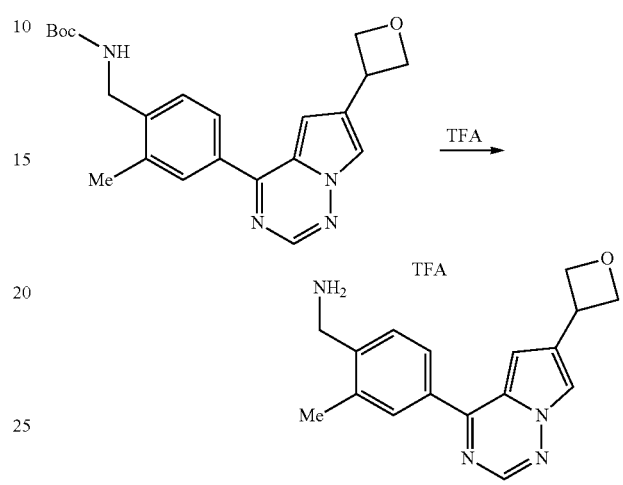

TFA (0.5 mL) was added to a solution of tert-butyl (2-methyl-4-(6-oxetan-3-yl)pyrrolo[2,1-f][1,2,4]triazin-4-yl)benzyl)carbamate (21 mg, 0.05 mmol) in DCM (2 mL) and the reaction was stirred at RT for 18 h. The mixture was concentrated in vacuo to afford the title compound, which was carried forward without further purification. LCMS m/z=295.2 [M+H]+

3. Synthesis of 5-(tert-butyl)-N-(2-methyl-4-(6-(oxetan-3-yl)pyrrolo[2,1-f][1,2,4]triazin-4-yl)benzyl)-1,2,4-oxadiazole-3-carboxamide trifluoroacetate

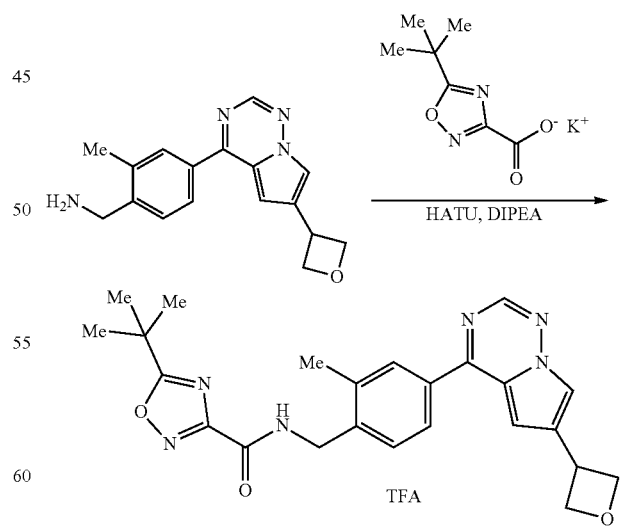

The crude product was obtained from (2-methyl-4-(6-(oxetan-3-yl)pyrrolo[2,1-f][1,2,4]triazin-4-yl)phenyl)methanamine trifluoroacetate and potassium 5-(tert-butyl)-1,2,4-oxadiazole-3-carboxylate, following the procedure described in Example 69, Step 3. The crude was purified by prep HPLC (Method B, 10-90%) to afford the title compound (5 mg, 9%). LCMS m/z=447.1 [M+H]⁺; ¹H NMR (400 MHz, CDCl₃) δ: 10.05 (br s, 1H), 8.56 (s, 1H), 7.84-7.99 (m, 3H), 7.44-7.62 (m, 1H), 7.15 (d, 1H), 5.09-5.31 (m, 2H), 4.67-4.88 (m, 4H), 4.37-4.47 (m, 1H), 2.48-2.55 (m, 3H), 1.48 (s, 9H).

Example 72. 3-(tert-butyl)-N-(2-methyl-4-(6-(tetrahydro-2H-pyran-4-yl)pyrrolo[2,1-f][1,2,4]triazin-4-yl)benzyl)-1,2,4-oxadiazole-5-carboxamide trifluoroacetate

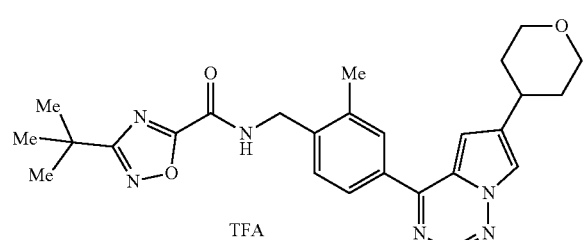

1. Synthesis of benzyl (4-(6-bromopyrrolo[2,1-f][1,2,4]triazin-4-yl)-2-methylbenzyl)carbamate

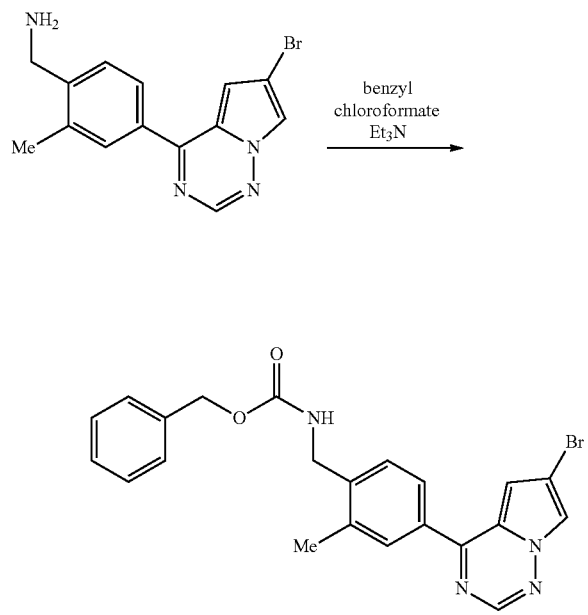 [SMILES: Cc1cc(-c2ncnn3cc(Br)cc23)ccc1CN ; Cc1cc(-c2ncnn3cc(Br)cc23)ccc1CNC(=O)OCc1ccccc1]

To a solution of (4-(6-bromopyrrolo[2,1-f][1,2,4]triazin-4-yl)-2-methylphenyl)methanamine hydrochloride (185 mg, 0.52 mmol) in DCM (4 mL), was added Et₃N (0.22 mL, 1.6 mmol) and benzyl chloroformate (0.9 mL, 0.63 mmol) and the reaction was stirred at RT for 18 h. The mixture was concentrated in vacuo and the crude product was purified by silica gel column chromatography (0-100% EtOAc/Hept) to afford the title compound (163 mg, 69%). LCMS m/z=451.1 [M+H]⁺

2. Synthesis of benzyl (2-methyl-4-(6-(tetrahydro-2H-pyran-4-yl)pyrrolo[2,1-f][1,2,4]triazin-4-yl)benzyl)carbamate

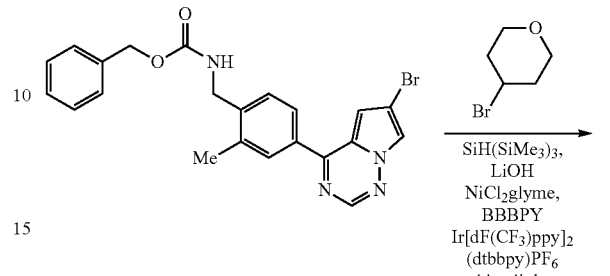

Benzyl (4-(6-bromopyrrolo[2,1-f][1,2,4]triazin-4-yl)-2-methylbenzyl)carbamate (133 mg, 0.30 mmol), 4-bromotetrahydropyran (73 mg, 0.44 mmol), tris(trimethylsilyl)silane (147 mg, 0.59 mmol), LiOH (28 mg, 1.2 mmol) in DME (4 mL) was degassed (Mixture 1). NiCl₂·glyme (6.5 mg, 0.03 mmol), BBBPY (7.9 mg, 0.03 mmol) and Ir[dF(CF₃)ppy]₂(dtbbpy)PF₆ (3.3 mg, 0.003 mmol) in DME (4 mL) was degassed for 10 min and was transferred to mixture 1 and the combined reaction mixture was degassed again for 10 min. The reaction was irradiated under a 30W CREE 450 nm EvoluChem lamp (blue light) at RT overnight. The reaction was filtered, and the filtrate was concentrated in vacuo. The crude product was purified by silica gel column chromatography (0-100% EtOAc/Hept) to afford the title compound, which was used without further purification (63 mg, 47%).

3. Synthesis of (2-methyl-4-(6-(tetrahydro-2H-pyran-4-yl)pyrrolo[2,1-f][1,2,4]triazin-4-yl)phenyl)methanamine

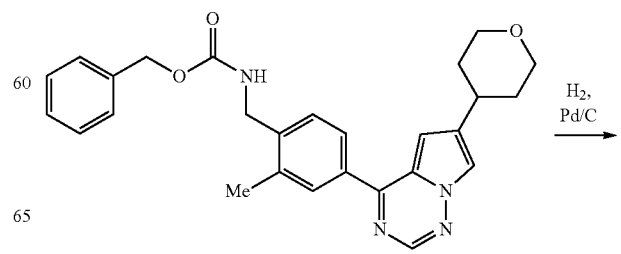

-continued

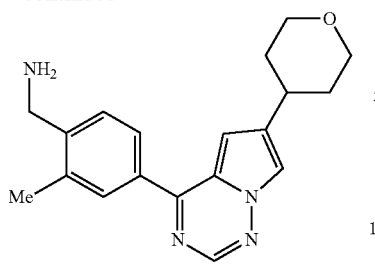

The title compound was prepared from benzyl (2-methyl-4-(6-(tetrahydro-2H-pyran-4-yl)pyrrolo[2,1-f][1,2,4]triazin-4-yl)benzyl)carbamate, following a similar procedure to that described in Example 60, Step 4. The crude material was carried forward without further purification. LCMS m/z=323.1 [M+H]$^+$ 4. Synthesis of 3-(tert-butyl)-N-(2-methyl-4-(6-(tetrahydro-2H-pyran-4-yl)pyrrolo[2,1-f][1,2,4]triazin-4-yl)benzyl)-1,2,4-oxadiazole-5-carboxamide trifluoroacetate

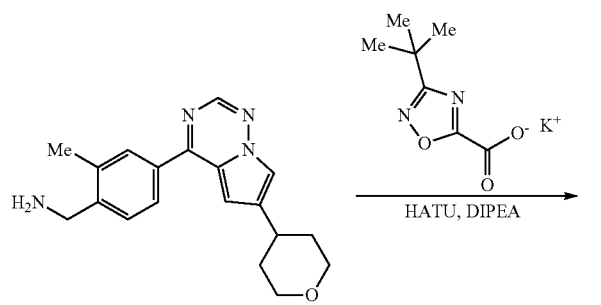

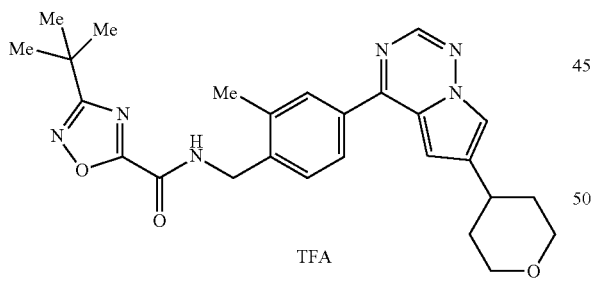

Crude product was obtained from (2-methyl-4-(6-(tetrahydro-2H-pyran-4-yl)pyrrolo[2,1-f][1,2,4]triazin-4-yl)phenyl)methanamine and potassium 3-(tert-butyl)-1,2,4-oxadiazole-5-carboxylate following the procedure described in Example 69, Step 3. The crude was purified by prep HPLC (Method B, 10-90%) to afford the title compound (8 mg, 10% over 2 steps). LCMS m/z=475.2 [M+H]$^+$; $^1$H NMR (400 MHz, MeOH-d$_4$) δ: 8.41-8.53 (m, 1H), 8.05-8.18 (m, 1H), 7.85-7.93 (m, 2H), 7.54-7.62 (m, 1H), 7.19 (s, 1H), 4.68-4.73 (m, 2H), 4.00-4.08 (m, 2H), 3.54-3.65 (m, 2H), 3.08 (tt, 1H), 2.48-2.59 (m, 3H), 1.93-2.02 (m, 2H), 1.73-1.88 (m, 2H), 1.43 (s, 9H).

Example 73. N-(4-(6-(3,3-bis(hydroxymethyl)azetidin-1-yl)pyrrolo[2,1-f][1,2,4]triazin-4-yl)-2-methylbenzyl)-5-(tert-butyl)-1,2,4-oxadiazole-3-carboxamide

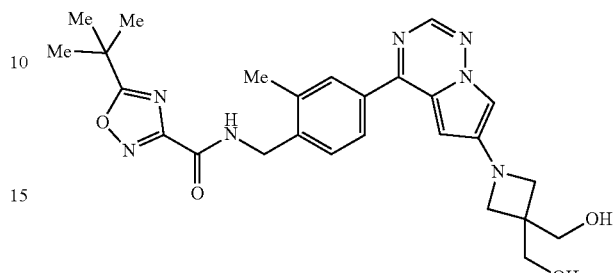

1. Synthesis of tert-butyl (4-(6-(2-oxa-6-azaspiro[3.3]heptan-6-yl)pyrrolo[2,1-f][1.2.4]triazin-4-yl)-2-methylbenzyl)carbamate

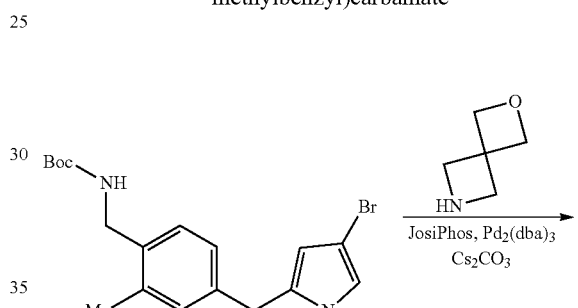

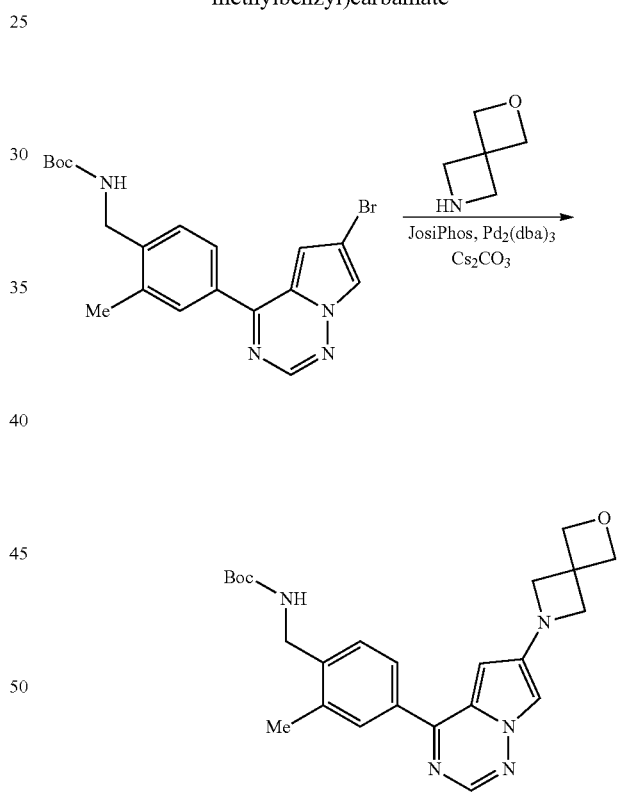

A mixture of tert-butyl (4-(6-bromopyrrolo[2,1-f][1,2,4]triazin-4-yl)-2-methylbenzyl)carbamate (50 mg, 0.12 mmol), Pd$_2$(dba)$_3$ (11 mg, 0.012 mmol), JosiPhos (13 mg, 0.024 mmol) and Cs$_2$CO$_3$ (78 mg, 0.24 mmol) in dioxane (1.2 mL) was purged with N$_2$ for 5 mins. 2-Oxa-6-azaspiro[3.3]heptane (18 mg, 0.18 mmol) was added and the reaction was heated at 85° C. for 18 h. The cooled reaction was concentrated in vacuo and the residue was purified by silica gel column chromatography (0-100% EtOAc/Hept) to afford the title compound as a yellow film (41 mg, 79%). LCMS m/z=436.2 [M+H]$^+$ 2. Synthesis of (1-(4-(4-(aminomethyl)-3-methylphenyl)pyrrolo[2,1-f][1,2,4]triazin-6-yl)azetidine-3,3-diyl)dimethanol

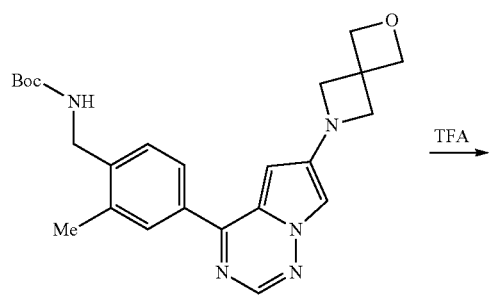

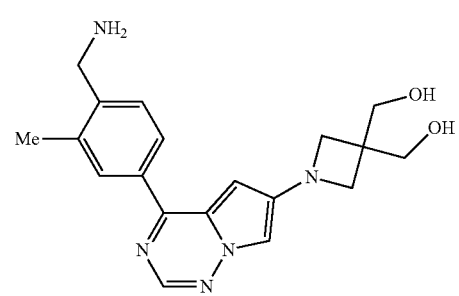

A solution of tert-butyl (4-(6-(2-oxa-6-azaspiro[3.3]heptan-6-yl)pyrrolo[2,1-f][1.2.4]triazin-4-yl)-2-methylbenzyl)carbamate (45 mg, 0.1 mmol) and TFA (79 μL, 1.0 mmol) in DCM (1 mL) was stirred at RT for 18 h. The reaction was concentrated in vacuo, the residue dissolved in MeOH, and passed through an SCX ion exchange column flushing through with MeOH followed by 2M methanolic $NH_3$. The combined organic phases were concentrated in vacuo to afford the title compound (41 mg, crude), which was carried forward without further purification. LCMS m/z=354.2 $[M+H]^+$ 3. Synthesis of N-(4-(6-(3,3-bis(hydroxymethyl)azetidin-1-yl)pyrrolo[2,1-f][1,2,4]triazin-4-yl)-2-methylbenzyl)-5-(tert-butyl)-1,2,4-oxadiazole-3-carboxamide

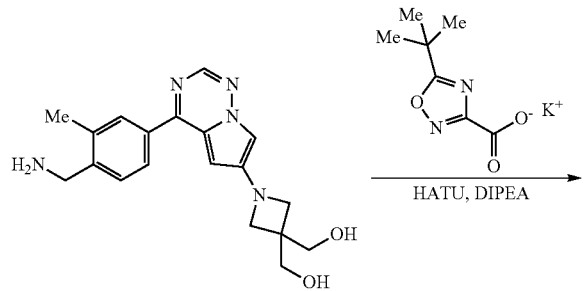

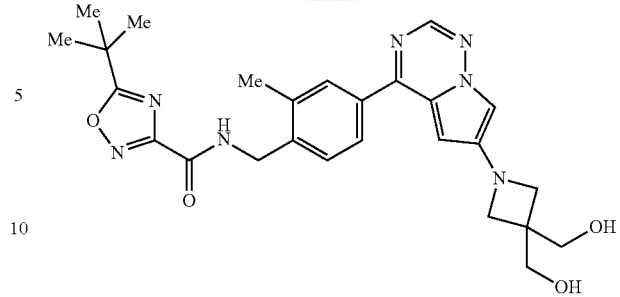

Crude product was obtained by reaction of (1-(4-(4-(aminomethyl)-3-methylphenyl)pyrrolo[2,1-f][1,2,4]triazin-6-yl)azetidine-3,3-diyl)dimethanol and potassium 5-(tert-butyl)-1,2,4-oxadiazole-3-carboxylate following the procedure described in Example 69, Step 3. The crude product was purified by silica gel column chromatography (0-100% [3:1 EtOAc/EtOH]/Hept) to afford the title compound as an orange solid (24 mg, 93%). LCMS m/z=506.4 $[M+H]^+$; $^1H$ NMR (500 MHz, DMSO-$d_6$) δ: 9.49 (br t, 1H), 8.43 (s, 1H), 7.88-7.94 (m, 2H), 7.69 (d, 1H), 7.42 (d, 1H), 6.38 (d, 1H), 4.75 (t, 2H), 4.54 (d, 2H), 3.60 (s, 4H), 3.55 (d, 4H), 2.44 (s, 3H), 1.44 (s, 9H).

Example 74. 5-(tert-butyl)-N-(4-(6-cyclopropylpyrrolo[2,1-f][1,2,4]triazin-4-yl)-2-methylbenzyl)-1,2,4-oxadiazole-3-carboxamide trifluoroacetate

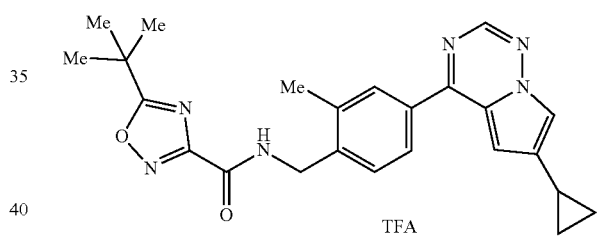

1. Synthesis of tert-butyl (4-(6-cyclopropylpyrrolo[2,1-f][1,2,4]triazin-4-yl)-2-methylbenzyl)carbamate

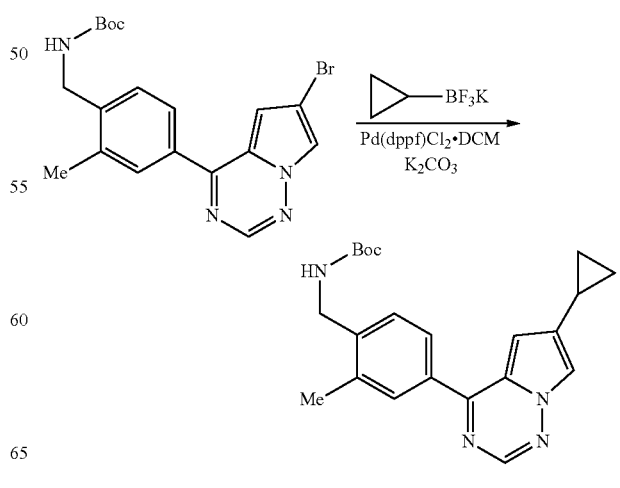

A mixture of tert-butyl (4-(6-bromopyrrolo[2,1-f][1,2,4]triazin-4-yl)-2-methylbenzyl)carbamate (80 mg, 0.19 mmol), potassium cyclopropyltrifluoroborate (57 mg, 0.38 mmol), Pd(dppf)Cl$_2$·DCM (16 mg, 0.019 mmol) and K$_2$CO$_3$ (79 mg, 0.57 mmol) in dioxane (1.3 mL) and H$_2$O (0.6 mL) was purged with N$_2$ and the reaction was stirred at 100° C. overnight. The cooled reaction mixture was concentrated in vacuo and the crude material was purified by silica gel column chromatography (0-100% EtOAc/Hept) to afford the title compound as a light-yellow solid (39 mg, 54%). LCMS m/z=379.2 [M+H]$^+$ 2. Synthesis of (4-(6-cyclopropylpyrrolo[2,1-f][1,2,4]triazin-4-yl)-2-methylphenyl)methanamine hydrochloride

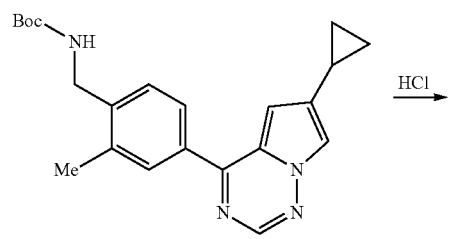

A solution of tert-butyl (4-(6-cyclopropylpyrrolo[2,1-f][1,2,4]triazin-4-yl)-2-methylbenzyl)carbamate (39 mg, 0.1 mmol) and an HCl solution (0.8 mL, 1.25 M in MeOH) in MeOH (1 mL) was stirred at 50° C. for 18 h. The reaction was concentrated in vacuo to afford the title compound as a yellow solid (36 mg, crude). LCMS m/z=279.1 [M+H]$^+$ 3. Synthesis of 5-(tert-butyl)-N-(4-(6-cyclopropylpyrrolo[2,1-f][1,2,4]triazin-4-yl)-2-methylbenzyl)-1,2,4-oxadiazole-3-carboxamide trifluoroacetate

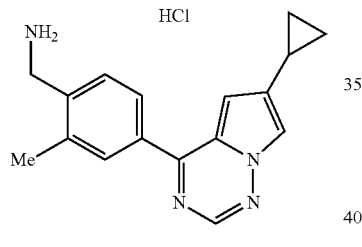

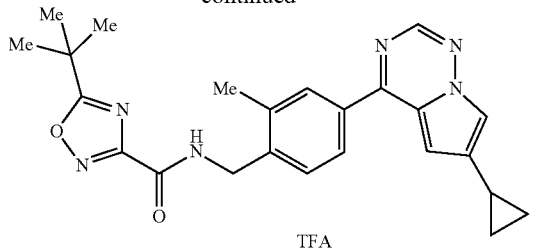

Crude product was prepared from (4-(6-cyclopropylpyrrolo[2,1-f][1,2,4]triazin-4-yl)-2-methylphenyl)methanamine hydrochloride and potassium 5-(tert-butyl)-1,2,4-oxadiazole-3-carboxylate following the procedure described in Example 69, Step 3. The crude product was purified by silica gel column chromatography (0-100% [3:1 EtOAc/EtOH]/Hept) and further purified by prep HPLC (Method B, 10-90%), to afford the title compound as a yellow solid (17 mg, 18%). LCMS m/z=431.2 [M+H]$^+$; $^1$H NMR (400 MHz, DMSO-d$_6$) δ: 9.51 (t, 1H), 8.52 (s, 1H), 8.04 (d, 1H), 7.89-7.97 (m, 2H), 7.43 (d, 1H), 6.96 (d, 1H), 4.54 (d, 2H), 2.45 (s, 3H), 1.96-2.08 (m, 1H), 1.44 (s, 9H), 0.94-1.04 (m, 2H), 0.69-0.81 (m, 2H).

Example 75. (S)-5-(tert-butyl)-N-(2-methyl-4-(6-(2-methyl-4-(oxetan-3-yl)piperazin-1-yl)pyrrolo[2,1-f][1,2,4]triazin-4-yl)benzyl)-1,2,4-oxadiazole-3-carboxamide

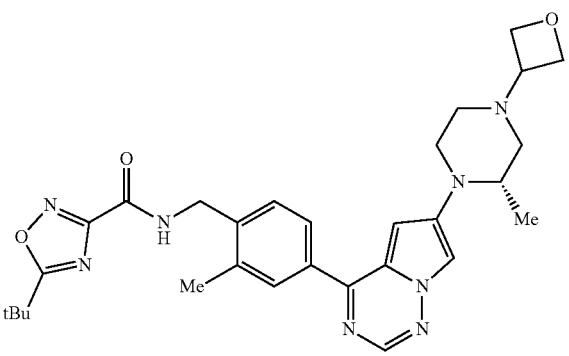 [SMILES: Cc1cc(-c2ncnn3cc(N4CCN(C5COC5)C[C@@H]4C)cc23)ccc1CNC(=O)c1noc(C(C)(C)C)n1]

1. Synthesis of benzyl (S)-4-(4-(4-(((tert-butoxycarbonyl)amino)methyl)-3-methylphenyl)pyrrolo[2,1-f][1,2,4]triazin-6-yl)-3-methylpiperazine-1-carboxylate

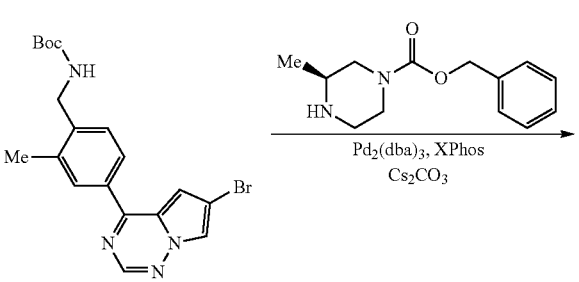

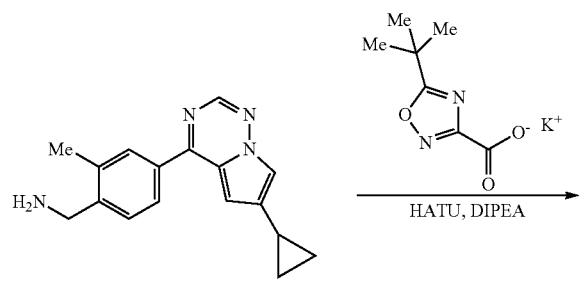

249

-continued

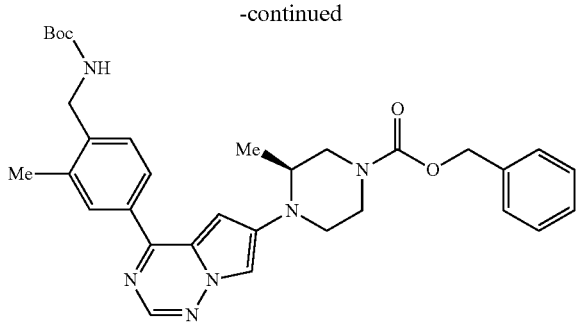

The title compound (123 mg, 29%) was prepared from benzyl (3S)-3-methylpiperazine-1-carboxylate and tert-butyl (4-(6-bromopyrrolo[2,1-f][1,2,4]triazin-4-yl)-2-methylbenzyl)carbamate following the procedure described in Example 11, Step 1. LCMS m/z=571.3 [M+H]⁺

2. Synthesis of benzyl (S)-4-(4-(4-(aminomethyl)-3-methylphenyl)pyrrolo[2,1-f][1,2,4]triazin-6-yl)-3-methylpiperazine-1-carboxylate hydrochloride

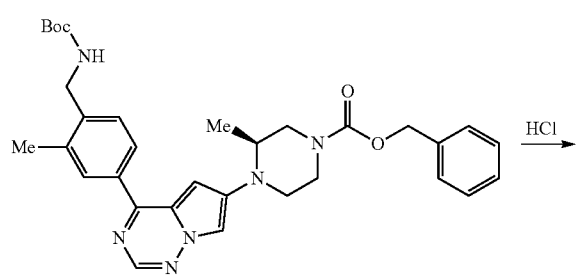

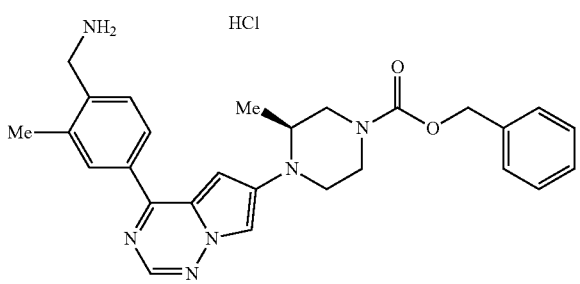

The title compound was obtained (84 mg, crude) from benzyl (S)-4-(4-(4-(((tert-butoxycarbonyl)amino)methyl)-3-methylphenyl)pyrrolo[2,1-f][1,2,4]triazin-6-yl)-3-methylpiperazine-1-carboxylate following the procedure described in Example 27, Step 2. LCMS m/z=471.3 [M+H]⁺

250

3. Synthesis of benzyl (S)-4-(4-(4-((5-(tert-butyl)-1,2,4-oxadiazole-3-carboxamido)methyl)-3-methylphenyl)pyrrolo[2,1-f][1,2,4]triazin-6-yl)-3-methylpiperazine-1-carboxylate

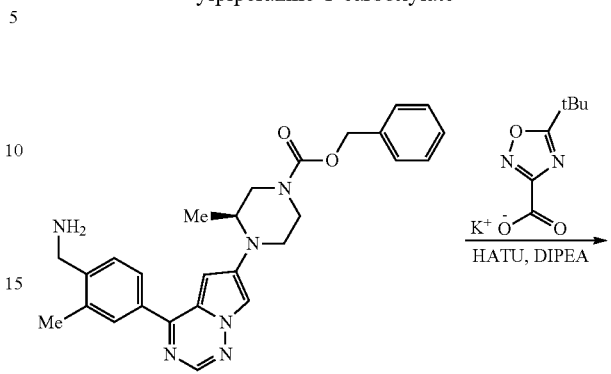

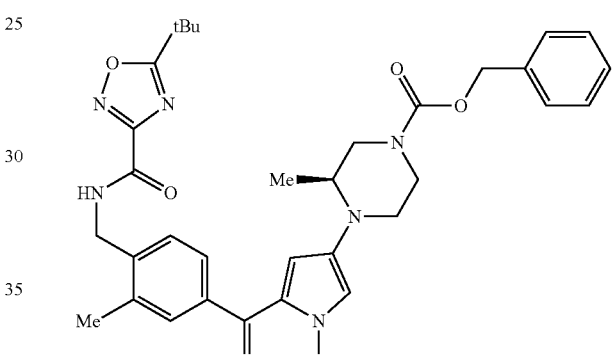

The title compound was obtained (43 mg, 41% over 2 steps) from benzyl (S)-4-(4-(4-(aminomethyl)-3-methylphenyl)pyrrolo[2,1-f][1,2,4]triazin-6-yl)-3-methylpiperazine-1-carboxylate hydrochloride and potassium 5-tert-butyl-1,2,4-oxadiazole-3-carboxylate, following the procedure described in Example 60, Step 6. LCMS m/z=623.5 [M+H]⁺

4. Synthesis of (S)-5-(tert-butyl)-N-(2-methyl-4-(6-(2-methyl-4-(oxetan-3-yl)piperazin-1-yl)pyrrolo[2,1-f][1,2,4]triazin-4-yl)benzyl)-1,2,4-oxadiazole-3-carboxamide trifluoroacetate

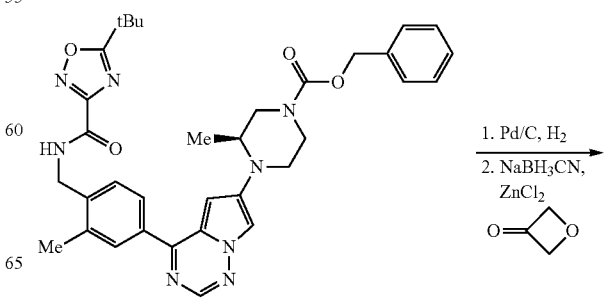

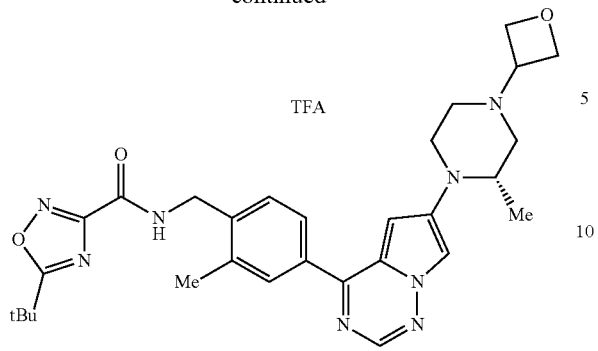

Pd/C (7 mg, 0.07 mmol) was added to a solution of benzyl (S)-4-(4-(4-((5-(tert-butyl)-1,2,4-oxadiazole-3-carboxamido)methyl)-3-methylphenyl)pyrrolo[2,1-f][1,2,4]triazin-6-yl)-3-methylpiperazine-1-carboxylate (43 mg, 0.07 mmol) in MeOH (2 mL) and the reaction was stirred under a balloon of H$_2$ overnight. The reaction mixture was filtered through Celite® and concentrated in vacuo to a residue which was used without further purification. The residue was re-dissolved in MeOH (2 mL) and oxetan-3-one (6.5 mg, 0.09 mmol), ZnCl$_2$ (0.05 mL, 1.9 M in MeTHF) and NaBH$_3$CN (6 mg, 0.09 mmol) were added. The reaction mixture was heated at 50° C. for 4 h. The reaction mixture was concentrated in vacuo and the residue was purified by prep-HPLC (Method B; 10-90%) to afford the title compound (4.6 mg, 17%). LCMS m/z=545.4 [M+H]$^+$; $^1$H NMR (400 MHz, CHLOROFORM-d) δ 8.46-8.54 (m, 1H), 8.01 (br s, 1H), 7.75-7.90 (m, 2H), 7.52-7.61 (m, 1H), 7.36-7.45 (m, 1H), 6.82 (br s, 1H), 5.07-5.25 (m, 2H), 4.87 (m, 2H), 4.75 (m, 2H), 4.26-4.35 (m, 1H), 3.10-3.93 (m, 7H), 2.50-2.53 (m, 3H), 1.49 (brs, 9H), 1.45 (m, 3H).

Example 76. 5-(tert-butyl)-N-(4-(6-ethynylpyrrolo[2,1-f][1,2,4]triazin-4-yl)-2-methylbenzyl)-1,2,4-oxadiazole-3-carboxamide trifluoroacetate

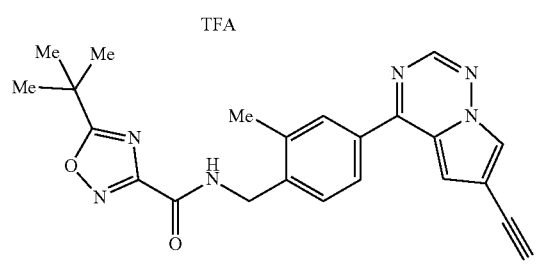 [SMILES: C#Cc1cc2c(-c3ccc(CNC(=O)c4noc(C(C)(C)C)n4)c(C)c3)ncnn2c1]

1. Synthesis of (4-(6-ethynylpyrrolo[2,1-f][1,2,4]triazin-4-yl)-2-methylphenyl)methanamine

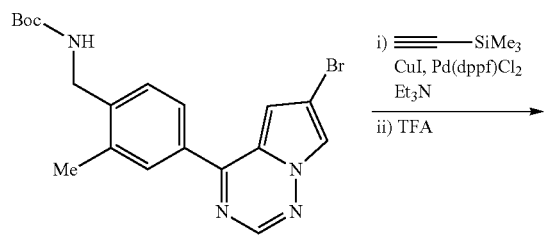

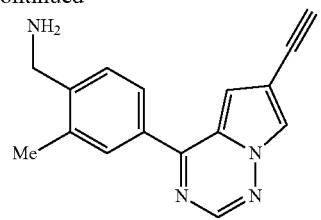

A mixture of tert-butyl (4-(6-bromopyrrolo[2,1-f][1,2,4]triazin-4-yl)-2-methylbenzyl)carbamate (100 mg, 0.24 mmol), ethynyl(trimethyl)silane (31 mg, 0.31 mmol), CuI (4.6 mg, 0.024 mmol) and Pd(dppf)Cl$_2$ (8.4 mg, 0.012 mmol) was purged with N$_2$·Et$_3$N (364 mg, 3.6 mmol) was added and the reaction was stirred at RT for 18 h. The mixture was diluted with EtOAc, filtered, washing through with EtOAc. The filtrate was concentrated in vacuo and the residue was purified by silica gel column chromatography (EtOAc/Hept=1:5) and then further purified by prep HPLC Method B (20-80%). The product was dissolved in DCM (1 mL), TFA (0.5 mL) was added dropwise, and the reaction was stirred at RT for 18 h. The reaction was concentrated in vacuo, the residue dissolved in MeOH, and passed through an SCX ion exchange column flushing through with MeOH followed by 2M methanolic NH$_3$. The combined organic phases were concentrated in vacuo to afford the title compound as a yellow gum (8 mg, 13%). LCMS m/z=263.4 [M+H]$^+$ 2. Synthesis of 5-(tert-butyl)-N-(4-(6-ethynylpyrrolo[2,1-f][1,2,4]triazin-4-yl)-2-methylbenzyl)-1,2,4-oxadiazole-3-carboxamide trifluoroacetate

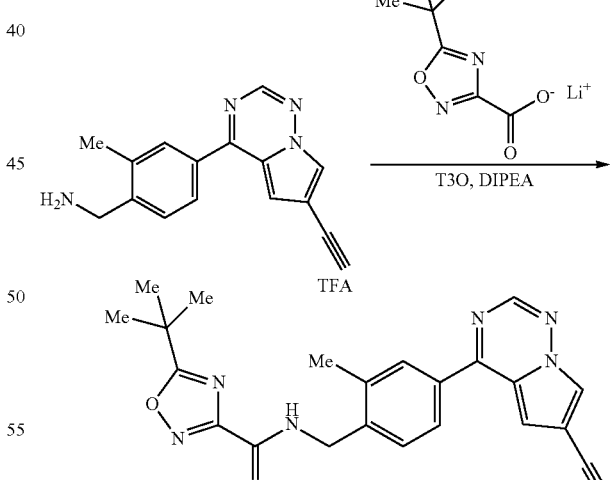

A mixture of (4-(6-ethynylpyrrolo[2,1-f][1,2,4]triazin-4-yl)-2-methylphenyl)methanamine (8 mg, 0.03 mmol) and lithium 5-(tert-butyl)-1,2,4-oxadiazole-3-carboxylate (11 mg, 0.06 mmol) in DMF (0.5 mL) was cooled in an ice bath. DIPEA (8 mg, 0.06 mmol) was added dropwise, followed by T3P® (39 mg, 0.06 mmol) and the reaction was stirred at RT for 18 h. The mixture was diluted with EtOAc, washed with water, and the aqueous phase was extracted with EtOAc.

The combined organic extracts were dried (Na₂SO₄), filtered, and the filtrate was concentrated in vacuo. The crude product was purified by acidic prep HPLC (Method B, 10-95%) to afford the title compound as a yellow solid (3 mg, 68%). LCMS m/z=415.6 [M+H]⁺; ¹H NMR (500 MHz, CDCl₃) δ: 8.61 (s, 1H), 8.10 (d, 1H), 7.89-7.84 (m, 2H), 7.54 (d, 1H), 7.33-7.28 (m, 2H), 4.78 (d, 2H), 3.24 (s, 1H), 2.51 (s, 3H), 1.49 (s, 9H).

Example 77. 5-(tert-butyl)-N-(4-(6-(methoxymethyl)pyrrolo[2,1-f][1,2,4]triazin-4-yl)-2-methylbenzyl)-1,2,4-oxadiazole-3-carboxamide hydrochloride

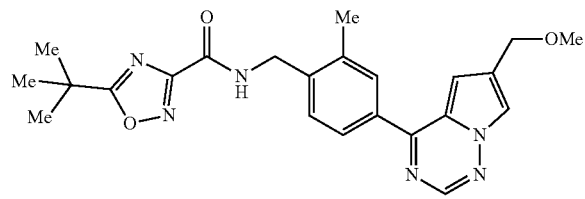 [SMILES: COCc1cc2c(-c3ccc(CNC(=O)c4noc(C(C)(C)C)n4)c(C)c3)ncnn2c1]

1. Synthesis of tert-butyl (4-(6-(hydroxymethyl)pyrrolo[2,1-f]triazin-4-yl)-2-methylbenzyl)carbamate

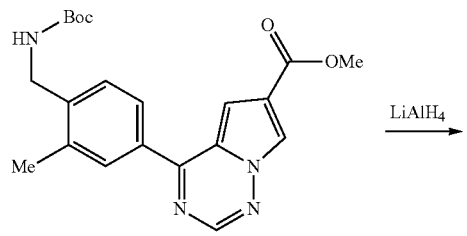

LiALH₄ (16 mg, 0.42 mmol) was added to a solution of methyl 4-(4-(((tert-butoxycarbonyl)amino)methyl)-3-methylphenyl)pyrrolo[2,1-f][1,2,4]triazine-6-carboxylate 150 mg, 0.38 mmol) in THF (15 mL) cooled to 0° C. and the mixture was stirred for 10 min. The reaction was quenched with H₂O (1 mL), the mixture was filtered and concentrated in vacuo. The crude product was purified by silica gel column chromatography (petroleum ether/EtOAc=1:2) to afford the title compound as a yellow solid (110 mg, crude). LCMS m/z=369.1 [M+H]⁺

2. Synthesis of tert-butyl (4-(6-(methoxymethyl)pyrrolo[2,1-f][1,2,4]triazin-4-yl)-2-methylbenzyl)carbamate

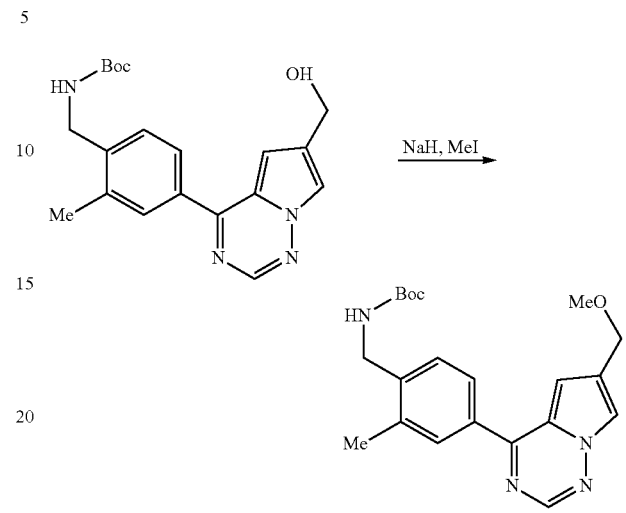

NaH (500 mg, 60% purity, 12.5 mmol) was added to a solution of tert-butyl (4-(6-(hydroxymethyl)pyrrolo[2,1-f]triazin-4-yl)-2-methylbenzyl)carbamate (110 mg, 0.30 mmol) in THF (5 mL) and the mixture stirred at 20° C. for 30 mins. Iodomethane (1.2 g, 8.4 mmol) was added and the reaction was stirred for 1 h. The reaction was quenched with MeOH and H₂O and the mixture was concentrated in vacuo. The mixture was diluted with H₂O (50 mL) and extracted with EtOAc (3×50 mL). The combined organic layers were washed with brine (50 mL), dried (Na₂SO₄), filtered, and concentrated in vacuo. The crude product was purified by silica gel column chromatography (petroleum ether/EtOAc=3:1) to afford the title compound as a yellow solid (100 mg, 83%). LCMS m/z=383.2 [M+H]⁺

3. Synthesis of (4-(6-methoxymethyl)pyrrolo[2,1-f][1,2,4]triazin-4-yl)-2-methylphenyl)methanamine hydrochloride

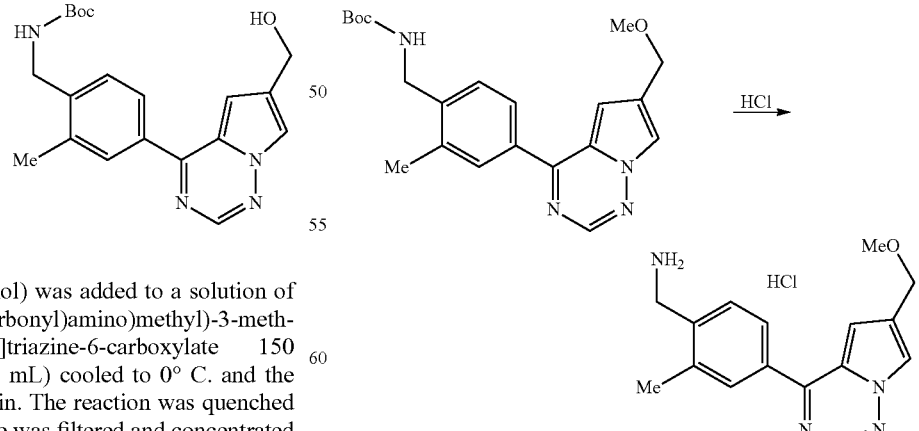

The title compound was obtained as a yellow solid from tert-butyl (4-(6-(methoxymethyl)pyrrolo[2,1-f][1,2,4]triazin-4-yl)-2-methylbenzyl)carbamate following the procedure described in Example 35, Step 5, and was used without further purification.

4. Synthesis of 5-(tert-butyl)-N-(4-(6-(methoxymethyl)pyrrolo[2,1-f][1,2,4]triazin-4-yl)-2-methylbenzyl)-1,2,4-oxadiazole-3-carboxamide hydrochloride

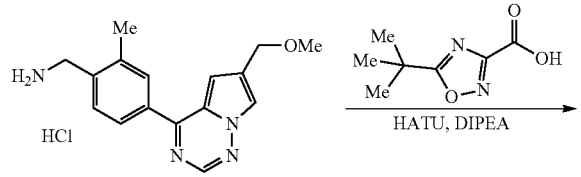

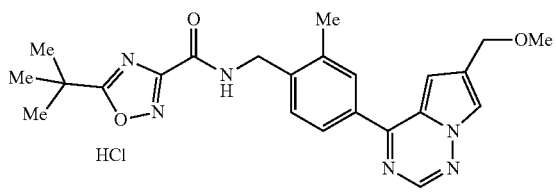

The crude product was prepared from (4-(6-(methoxymethyl)pyrrolo[2,1-f][1,2,4]triazin-4-yl)-2-methylphenyl)methanamine hydrochloride and 5-(tert-butyl)-1,2,4-oxadiazole-3-carboxylic acid, following the procedure described in Example 45, Step 7. The crude product was purified by prep HPLC (Method A, 52-72%) to afford the title compound as a white solid (50 mg, 52% over 2 steps). LCMS m/z=435.1 [M+H]$^+$; $^1$H NMR (400 MHz, DMSO-d$_6$) δ: 9.51-9.47 (m, 1H), 8.60-8.53 (m, 1H), 8.12 (d, 1H), 7.93-7.90 (m, 2H), 7.42 (d, 1H), 7.15 (s, 1H), 4.54 (s, 2H), 4.52 (s, 2H), 3.28 (s, 3H), 2.42 (s, 3H), 1.40 (s, 9H).

Example 78. 5-(tert-butyl)-N-(4-(6-(2,2-dimethylmorpholino)pyrrolo[2,1-f][1,2,4]triazin-4-yl)-2-methylbenzyl)-1,2,4-oxadiazole-3-carboxamide hydrochloride

1. Synthesis of tert-butyl (4-(6-(2,2-dimethylmorpholino)pyrrolo[2,1-f][1,2,4]triazin-4-yl)-2-methylbenzyl)carbamate

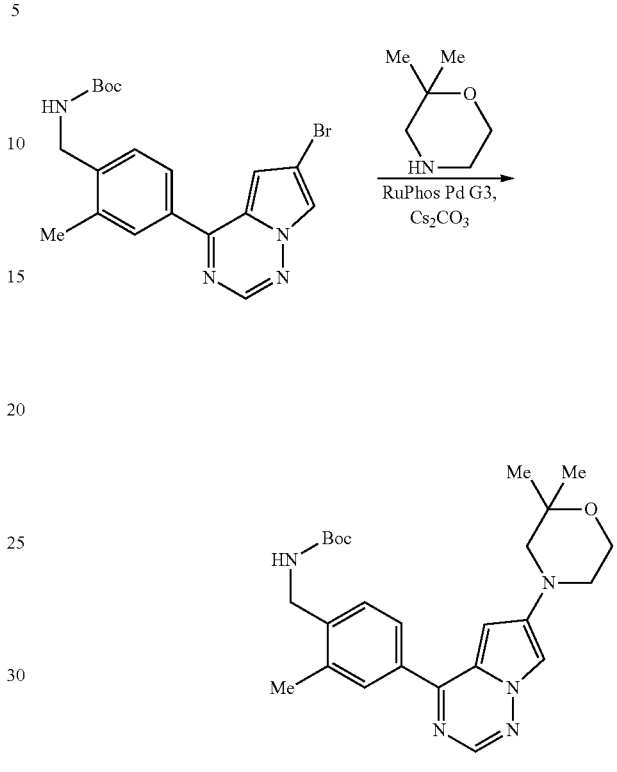

To a solution of tert-butyl (4-(6-bromopyrrolo[2,1-f][1,2,4]triazin-4-yl)-2-methylbenzyl)carbamate (250 mg, 0.60 mmol) in toluene (15 mL) was added 2,2-dimethylmorpholine (207 mg, 1.8 mmol), Cs$_2$CO$_3$ (586 mg, 1.8 mmol) and RuPhos Pd G3 (50 mg, 0.06 mmol) and the reaction was stirred at 90° C. under N$_2$ for 16 h. The cooled mixture was concentrated in vacuo, the residue partitioned between water (20 mL) and EtOAc (20 mL) and the layers were separated. The aqueous phase was extracted with EtOAc (3×10 mL), the combined organic layers were dried (Na$_2$SO$_4$), filtered, and concentrated in vacuo. The residue was purified by silica gel column chromatography (0-50% EtOAc/petroleum ether/EtOAc) to afford the title compound as a yellow oil (30 mg, 11%). LCMS m/z=452.2 [M+H]$^+$

2. Synthesis of (4-(6-(2,2-dimethylmorpholino)pyrrolo[2,1-f][1,2,4]triazin-4-yl)-2-methylphenyl)methanamine hydrochloride

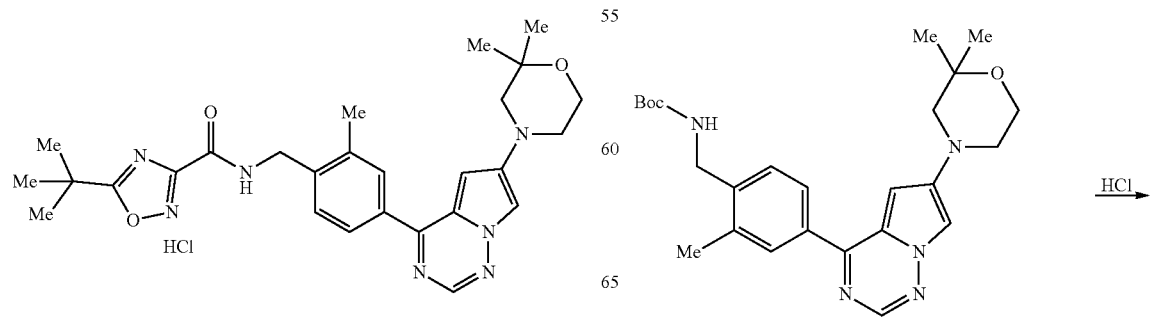

-continued

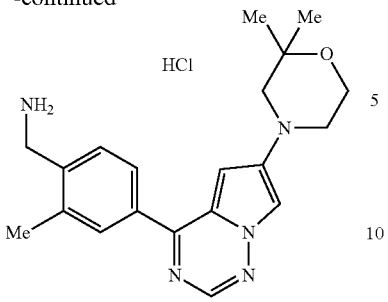

The title compound was obtained as a red solid (70 mg, crude) from tert-butyl (4-(6-(2,2-dimethylmorpholino)pyrrolo[2,1-f][1,2,4]triazin-4-yl)-2-methylbenzyl)carbamate following the procedure described in Example 35, Step 5. LCMS m/z=352.2 [M+H]+

3. Synthesis of 5-(tert-butyl)-N-(4-(6-(2,2-dimethyl-morpholino)pyrrolo[2,1-f][1,2,4]triazin-4-yl)-2-methylbenzyl)-1,2,4-oxadiazole-3-carboxamide hydrochloride

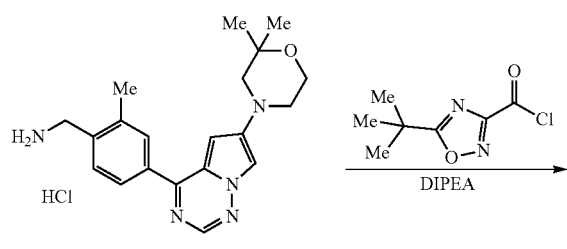

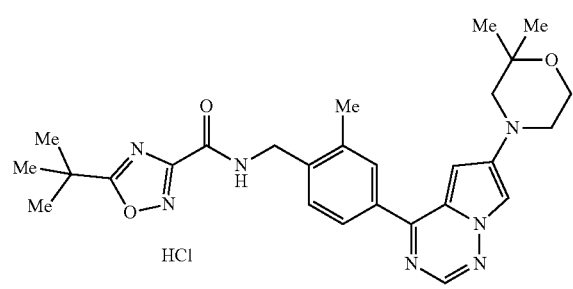

The compound was obtained from (4-(6-(2,2-dimethylmorpholino)pyrrolo[2,1-f][1,2,4]triazin-4-yl)-2-methylphenyl)methanamine hydrochloride and 5-(tert-butyl)-1,2,4-oxadiazole-3-carbonyl chloride following the procedure described in Example 34, Step 8. The crude product was purified by prep HPLC Method A, 45-65%, to afford the title compound as a red solid (37 mg, 37%). LCMS m/z=504.2 [M+H]+; 1H NMR (400 MHz, DMSO-$d_6$) δ: 9.53 (t, 1H), 8.50 (s, 1H), 8.09 (s, 1H), 7.95-7.85 (m, 2H), 7.43 (d, 1H), 6.75 (s, 1H), 4.54 (d, 2H), 3.76 (br d, 2H), 3.14-3.11 (m, 2H), 3.01 (s, 2H), 2.47-2.44 (m, 3H), 1.44 (s, 9H), 1.23 (s, 6H).

Example 79. 5-(tert-butyl)-N-(2-methyl-4-(6-((tetrahydro-2H-pyran-4-yl)oxy)pyrrolo[2,1-f][1,2,4]triazin-4-yl)benzyl)-1,2,4-oxadiazole-3-carboxamide

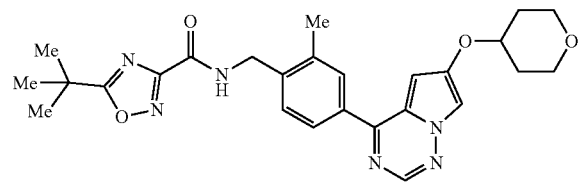 [SMILES: Cc1cc(-c2ncnn3cc(OC4CCOCC4)cc23)ccc1CNC(=O)c1noc(C(C)(C)C)n1]

1. Synthesis of tert-butyl (4-(6-hydroxypyrrolo[2,1-f]triazin-4-yl)-2-methylbenzyl)carbamate

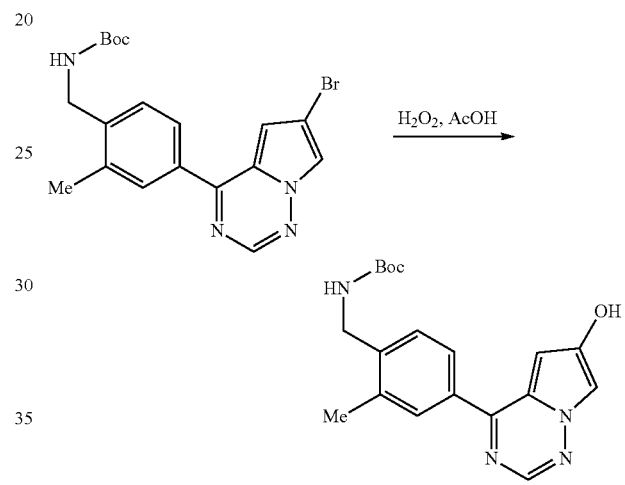

To a solution of tert-butyl (4-(6-bromopyrrolo[2,1-f][1,2,4]triazin-4-yl)-2-methylbenzyl)carbamate (680 mg, 1.46 mmol) in THF (20 mL) was added hydrogen peroxide (498 mg, 4.38 mmol, 30% purity) and AcOH (264 mg, 4.38 mmol) and the reaction was stirred at 50° C. for 2 h. The mixture was washed with water (20 mL) and extracted with DCM (3×10 mL). The combined organic layers were quenched with aqueous $Na_2SO_3$ then were concentrated in vacuo. The residue was purified by silica gel column chromatography (0-100% EtOAc/petroleum ether) to afford the title compound as a yellow oil (350 mg, 67%). LCMS m/z=355.1 [M+H]+

2. Synthesis of tert-butyl (2-methyl-4-(6-((tetrahydro-2H-pyran-4-yl)oxy)pyrrolo[2,1-f]triazin-4-yl)benzyl)carbamate

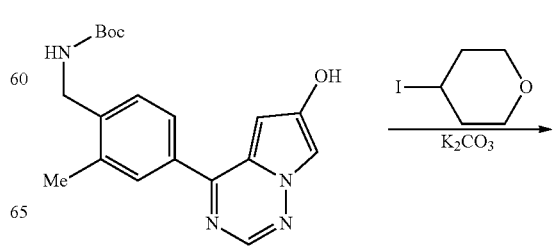

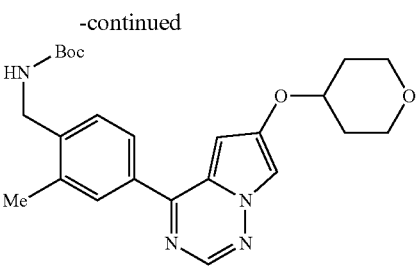

To a solution of 4-iodotetrahydropyran (90 mg, 0.25 mmol) in DMF (3 mL) was added tert-butyl (4-(6-hydroxypyrrolo[2,1-f]triazin-4-yl)-2-methylbenzyl)carbamate (108 mg, 0.51 mmol) and $K_2CO_3$ (105 mg, 0.76 mmol) and the reaction was stirred at 100° C. for 5 h. The cooled mixture was washed with brine (3×20 mL) and extracted with EtOAc (3×10 mL). The combined organic layers were dried ($Na_2SO_4$), filtered, and concentrated in vacuo. The residue was purified by prep-TLC (petroleum ether/EtOAc=1:1) to afford the title compound as a yellow oil (90 mg, 81%). LCMS m/z=439.1 [M+H]$^+$. $^1$H NMR (400 MHz, CDCl$_3$) δ: 8.47 (s, 1H), 8.00 (s, 1H), 7.82 (br s, 2H), 7.62 (d 1H), 7.42 (br d, 1H), 6.57 (d, 1H), 4.94 (br s, 1H), 4.47-4.38 (m, 3H), 4.02-3.96 (m, 2H), 3.62-3.56 (m, 2H), 2.44-2.41 (m, 3H), 2.11-2.05 (m, 2H), 1.88-1.79 (m, 2H), 1.48 (s, 9H).

3. Synthesis of (2-methyl-4-(6-((tetrahydro-2H-pyran-4-yl)oxy)pyrrolo[2,1-f][1,2,4]triazin-4-yl)phenyl)methanamine hydrochloride

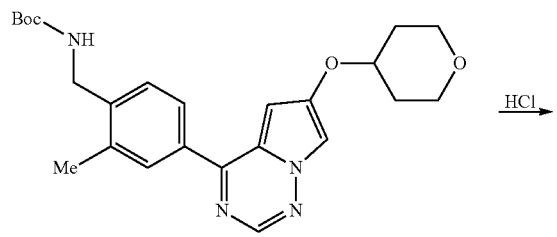

The title compound was obtained as a red solid (75 mg, crude) from tert-butyl (2-methyl-4-(6-((tetrahydro-2H-pyran-4-yl)oxy)pyrrolo[2,1-f]triazin-4-yl)benzyl)carbamate, following the procedure described in Example 35, Step 5. LCMS m/z=379.8 [M+H]$^+$ 4. Synthesis of 5-(tert-butyl)-N-(2-methyl-4-(6-((tetrahydro-2H-pyran-4-yl)oxy)pyrrolo[2,1-f][1,2,4]triazin-4-yl)benzyl)-1,2,4-oxadiazole-3-carboxamide

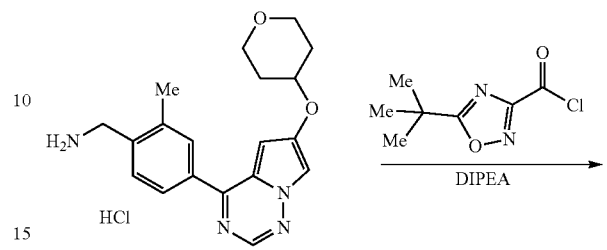

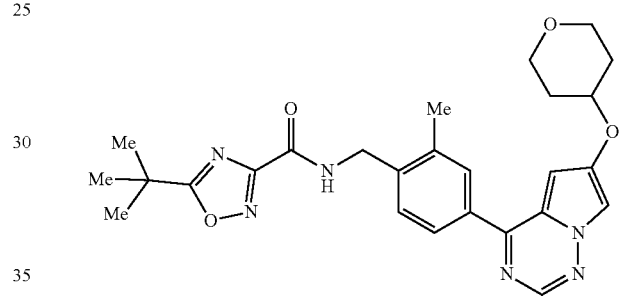

Crude product was obtained from (2-methyl-4-(6-((tetrahydro-2H-pyran-4-yl)oxy)pyrrolo[2,1-f][1,2,4]triazin-4-yl)phenyl)methanamine hydrochloride and 5-(tert-butyl)-1,2,4-oxadiazole-3-carbonyl chloride, following the procedure described in Example 34, Step 8. The crude was purified by HPLC using Method D to afford the title compound as a yellow solid (30 mg, 30%). LCMS m/z=504.2 [M+H]$^+$; $^1$H NMR (400 MHz, DMSO-d$_6$) δ: 9.52 (t, 1H), 8.56 (s, 1H), 8.09 (d, 1H), 7.98-7.89 (m, 2H), 7.43 (d, 1H), 6.85 (d, 1H), 4.65-4.51 (m, 3H), 3.86 (td, 2H), 3.53-3.44 (m, 2H), 2.45 (s, 3H), 2.06-2.00 (m, 2H), 1.66-1.56 (m, 2H), 1.44 (s, 9H).

Example 80. 5-(tert-butyl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide

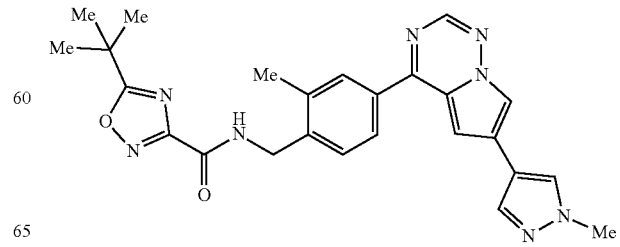

1. Synthesis of 5-(tert-butyl)-N-(2-methyl-4-(6-(1-methyl-1H-pyrazol-4-yl)pyrrolo[2,1-f][1,2,4]triazin-4-yl)benzyl)-1,2,4-oxadiazole-3-carboxamide

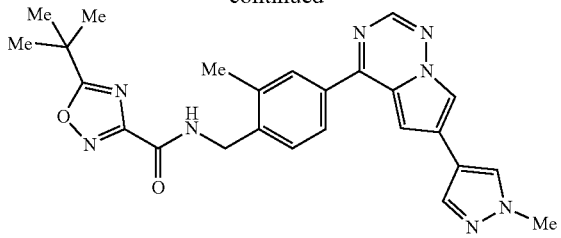

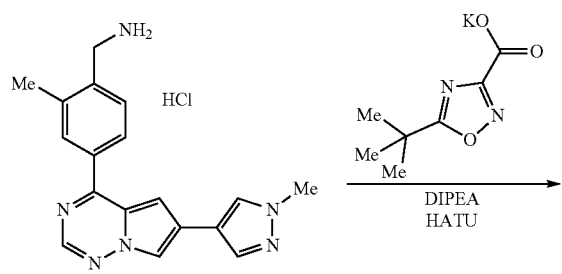

The title compound was prepared (87 mg, 72%) using an analogous method to that described for Example 1, Step 5 using (2-methyl-4-(6-(1-methyl-1H-pyrazol-4-yl)pyrrolo[2,1-f][1,2,4]triazin-4-yl)phenyl)methanamine hydrochloride and potassium 5-(tert-butyl)-1,2,4-oxadiazole-3-carboxylate with DIPEA as base and DCM as solvent. LCMS m/z=471.3 [M+H]$^+$; $^1$H NMR (500 MHz, DMSO-d$_6$) δ: 9.53 (t, 1H), 8.56 (s, 1H), 8.45 (d, 1H), 8.20 (s, 1H), 7.99 (d, 1H), 7.97 (s, 1H), 7.95 (s, 1H), 7.46 (d, 1H), 7.39 (d, 1H), 4.56 (d, 2H), 3.87 (s, 3H), 2.48 (s, 3H), 1.44 (s, 9H).

| Example Number | Name Structure | HPLC Method/Yield/Data |
|---|---|---|
| Example 81 | 5-tert-butyl-N-[[3-fluoro-2-methyl-4-(6 morpholinopyrrolo[2,1-f][1,2,4]triazin-4yl)phenyl]methyl]-1,3,4-oxadiazole2--carboxamide<br>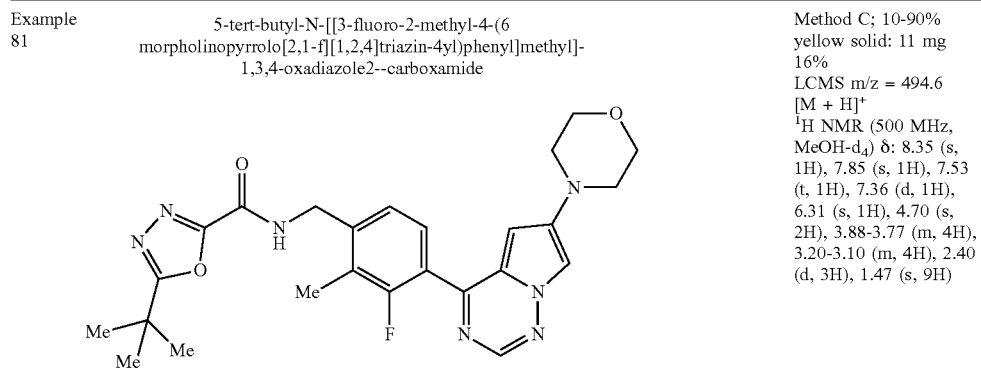 | Method C; 10-90% yellow solid: 11 mg 16%<br>LCMS m/z = 494.6 [M + H]$^+$<br>$^1$H NMR (500 MHz, MeOH-d$_4$) δ: 8.35 (s, 1H), 7.85 (s, 1H), 7.53 (t, 1H), 7.36 (d, 1H), 6.31 (s, 1H), 4.70 (s, 2H), 3.88-3.77 (m, 4H), 3.20-3.10 (m, 4H), 2.40 (d, 3H), 1.47 (s, 9H) |
| Example 82 | 5-tert-butyl-N-[[3-fluoro-2-methyl-4-[2-(1-methylpyrazol-4-yl)pyrazolo[1,5-a]pyrimidin-7-yl]phenyl]methyl]-1,2,4-oxadiazole-3-carboxamide<br>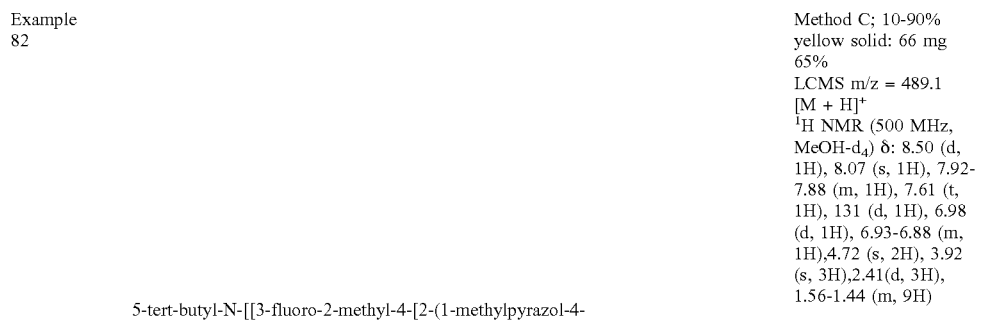 | Method C; 10-90% yellow solid: 66 mg 65%<br>LCMS m/z = 489.1 [M + H]$^+$<br>$^1$H NMR (500 MHz, MeOH-d$_4$) δ: 8.50 (d, 1H), 8.07 (s, 1H), 7.92-7.88 (m, 1H), 7.61 (t, 1H), 131 (d, 1H), 6.98 (d, 1H), 6.93-6.88 (m, 1H), 4.72 (s, 2H), 3.92 (s, 3H), 2.41(d, 3H), 1.56-1.44 (m, 9H) |

| Example Number | Name Structure | HPLC Method/Yield/Data |
|---|---|---|
| Example 83 | 3-tert-butyl-N-[[3-fluoro-2-methyl-4-[2-(1-methylpyrazol-4-yl)pyrazolo[1,5-a]pyrimidin-7-yl]phenyl]methyl]-1,2,4-oxadiazole-5-carboxamide | Method C; 5-65% yellow solid: 20 mg 20% LCMS m/z = 489.1 [M + H]+ $^1$H NMR (500 MHz, MeOH-d$_4$) δ: 9.97 (br s, 1H), 8.54 (d, 1H), 8.16 (s, 1H), 7.86 (s, 1H), 7.61 (t, 1H), 7.34 (d, 1H), 7.04 (d, 1H), 7.00 (s, 1H), 4.59 (s, 2H), 3.86 (s, 3H), 2.42-2.29 (m, 3H), 1.38 (s, 9H) |
| Example 84 | 5-(tert-butyl)-N-(3-fluoro-2-methyl-4-(2-morpholinopyrazolo[1,5-a]pyrimidin-7-yl)benzyl)-1,2,4-oxadiazole-3-carboxamide | Method C; 5-65% yellow solid: 38 mg 35% LCMS m/z = 494.2 [M + H]+ $^1$H NMR (500 MHz, MeOH-d$_4$) δ: 9.56 (br t, 1H), 8.46-8.30 (m, 1H), 7.57 (t, 1H), 7.25 (d, 1H), 6.83 (d, 1H), 6.23 (s, 1H), 4.55 (d, 2H), 3.75-3.63 (m, 5H), 3.27-3.16 (m, 2H), 2.31 (d, 3H), 1.51-1.34 (m, 9H). |
| Example 85 | 5-tert-butyl-N-[[2-methyl-4-[6-(1H-pyrazol-4-yl)pyrrolo[2,1-f][1,2,4]triazin-4-yl]phenyl]methyl]-1,2,4-oxadiazole-3-carboxamide | SiO$_2$; 2-100% EtOAc/Hept yellow solid: 72 mg 66% LCMS m/z = 457.0 [M + H]+ $^1$H NMR (500 MHz, MeOH-d$_4$) δ: 8.45-8.39 (m, 1H), 8.32-8.24 (m, 1H), 8.17-7.98 (m, 2H), 7.94 (dd, 2H), 7.58-7.50 (m, 1H), 7.32 (d, 1H), 4.71 (s, 2H), 2.53 (s, 3H), 1.49 (s, 10H) |
| Example 86 | 5-(tert-butyl)-N-(3-fluoro-2-methyl-4-(6-morpholinopyrrolo[2,1-f][1,2,4]triazin-4-yl)benzyl)-1,2,4-oxadiazole-3-carboxamide | Method C; 10-90% yellow solid: 92 mg 55% LCMS m/z = 494.6 [M + H]+ $^1$H NMR (400 MHz, MeOH-d$_4$) δ: 8.35 (s, 1H), 7.83 (d, 1H), 7.52 (t, 1H), 7.33 (d, 1H), 6.30 (t, 1H), 4.69 (s, 2H), 3.86-3.77 (m, 4H), 3.20-3.10 (m, 4H), 2.39 (d, 3H), 1.48 (s, 9H). |

| Example Number | Name Structure | HPLC Method/Yield/Data |
|---|---|---|
| Example 87 | 1-(tert-butyl)-N-(3-fluoro-2-methyl-4-(6-morpholinopyrrolo[2,1-f][1,2,4]triazin-4-yl)benzyl)-1H-1,2,3-triazole-4-carboxamide 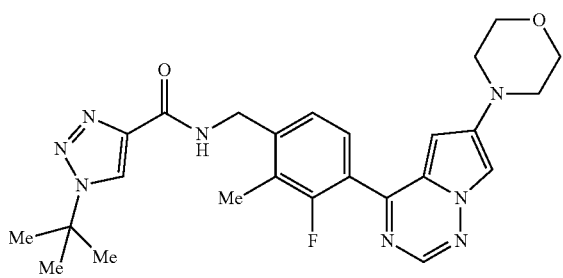 | Method C; 20-80% yellow solid: 14 mg, 20% LCMS m/z = 493.6 [M + H]+ $^1$H NMR (500 MHz, MeOH-d$_4$) δ: 8.48 (s, 1H), 8.35 (s, 1H), 7.87-7.81 (m, 1H), 7.51 (br t, 1H), 7.33 (d, 1H), 6.30 (s, 1H), 4.70 (s, 2H), 3.82 (t, 4H), 3.16-3.11 (m, 4H), 2.40 (s, 3H), 1.71 (s, 9H). |
| Example 88 | 1-(tert-butyl)-N-(3-fluoro-2-methyl-4-(6-morpholinopyrrolo[2,1-f][1,2,4]triazin-4-yl)benzyl)-1H-pyrazole-4-carboxamide 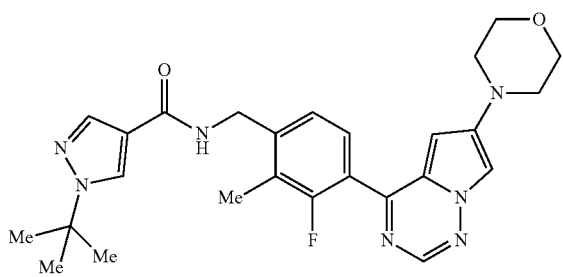 | Method C; 10-90% yellow solid: 15 mg 21% LCMS m/z = 492.6 [M + H]+ $^1$H NMR (500 MHz, MeOH-d$_4$) δ: 8.35 (s, 1H), 8.27 (s, 1H), 7.97 (s, 1H), 7.85 (d, 1H), 7.52 (t, 1H), 7.31 (d, 1H), 6.30 (t, 1H), 4.64 (s, 2H), 3.88-3.79 (m, 4H), 3.19-3.10 (m, 4H), 2.39 (d, 3H), 1.64-1.56 (m, 9H). |
| Example 89 | 1-(tert-butyl)-N-(3-fluoro-2-methyl-4-(6-morpholinopyrrolo[2,1-f][1,2,4]triazin-4-yl)benzyl)-1H-pyrazole-3-carboxamide 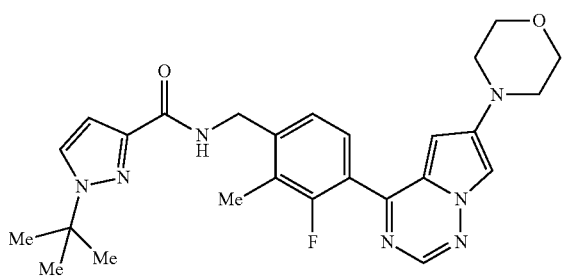 | Method C; 5-95% yellow solid: 13 mg 27% LCMS m/z = 492.6 [M + H]+ $^1$H NMR (400 MHz, MeOH-d$_4$) δ: 8.34 (s, 1H), 7.82 (dd, 2H), 7.51 (t, 1H), 7.32 (d, 1H), 6.74 (d, 1H), 6.31 (t, 1H), 4.67 (s, 2H), 3.87-3.76 (m, 4H), 3.20-3.08 (m, 4H), 2.39 (d, 3H), 1.63 (s, 9H). |
| Example 90 | 2-(tert-butyl)-N-(2-methyl-4-(6-(2-methylmorpholino)pyrrolo[2,1-f][1,2,4]triazin-4-yl)benzyl)-2H-tetrazole-5-carboxamide 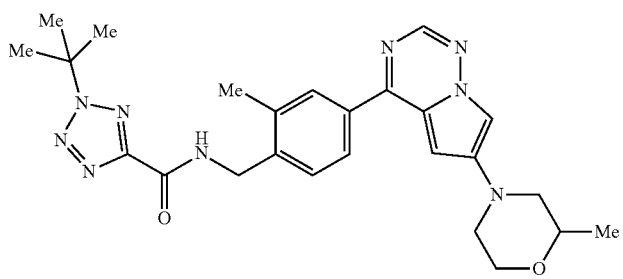 | SiO$_2$; 0-100% EtOAc/Hept yellow film: 28 mg, 59% LCMS m/z = 490.2 [M + H]+ |

| Example Number | Name Structure | HPLC Method/Yield/Data |
|---|---|---|
| Example 91 | 2-(tert-butyl)-N-(2-methyl-4-(6-(2-methylmorpholino)pyrrolo[2,1-f][1,2,4]triazin-4-yl)benzyl)-oxaxole-4-carboxamide | SiO$_2$; 0-100% EtOAc/Hept yellow film: 34 mg, 71% LCMS m/z = 489.2 [M + H]$^+$ |
| Example 92 | (S)-5-(tert-butyl)-N-(4-(6-(2,4-dimethylpiperazin-1-yl)pyrrolo[2,1-f][1,2,4]triazin-4-yl)-2-methylbenzyl)-1,2,4-oxadiazole-3-carboxamide trifluoroacetate | SiO$_2$; 0-40% MeOH/DCM then Method B; 10-90% 2.5 mg (12%) LCMS m/z = 503.3 [M + H]$^+$ $^1$H NMR (400 MHz, MeOH-d$_4$) δ: 9.28-9.55 (m, 1H), 8.47 (s, 1H), 8.10 (br s, 1H), 7.86 (br s, 2H), 7.57 (br d, 1H), 6.82 (br s, 1H), 4.61-4.79 (m, 2H), 4.35 (br d, 1H), 3.71-3.86 (m, 1H), 3.51-3.69 (m, 2H), 3.35-3.49 (m, 2H), 3.26 (br dd, 1H), 2.99 (s, 3H), 2.54 (s, 3H), 1.50-1.51 (m, 9H), 1.31 (br d, 3H). |
| Example 93 | 5-(tert-butyl)-N-(2-methyl-4-(6-((1S,4S)-5-methyl-2,5-diazabicyclo[2.2.1]heptan-2-yl)pyrrolo[2,1-f][1,2,4]triazin-4-yl)benzyl)-1,2,4-oxadiazole-3-carboxamide | SiO$_2$; 0-40% MeOH/DCM 2.5 mg (12%) LCMS m/z = 501.3 [M + H]$^+$ $^1$H NMR (400 MHz, MeOH-d$_4$) δ: 9.44 (br s, 1H), 8.43 (br s, 1H), 7.80-8.01 (m, 3H), 7.55 (br d, 1H), 6.65 (br s, 1H), 4.54-4.77 (m, 3H), 4.30-4.48 (m, 1H), 3.62-3.94 (m, 2H), 3.13-3.25 (m, 1H), 2.98 (br s, 3H), 2.53 (br s, 3H), 2.22-2.46 (m, 1H), 1.82-2.13 (m, 1H), 1.48-1.49 (m, 9H), 1.29-1.41 (m, 1H). |
| Example 94 | 5-(tert-butyl)-N-(2-methyl-4-(6-((tetrahydro-2H-pyran-4-yl)methyl)pyrrolo[2,1-f][1,2,4]triazin-4-yl)benzyl)-1,2,4-oxadiazole-3-carboxamide | SiO$_2$; 0-100% EtOAc/Hept 2.3 mg (28%) LCMS m/z = 489.3 [M + H]$^+$ $^1$H NMR (400 MHz, CDCl$_3$) δ: 8.50 (s, 1H), 7.88-8.04 (m, 2H), 7.78 (s, 1H), 7.53 (br d, 1H), 7.24 (br s, 1H), 6.90 (s, 1H), 4.78 (d, 2H), 3.98 (br dd, 2H), 3.28-3.48 (m, 2H), 2.63-2.79 (m, 2H), 2.52 (s, 3H), 1.82 (ddd, 1H), 1.49 (s, 9H), 1.32-1.65 (m, 4H). |

| Example Number | Name Structure | HPLC Method/Yield/Data |
|---|---|---|
| Example 95 | 5-(tert-butyl)-N-(2-methyl-4-(6-(tetrahydrofuran-3-yl)pyrrolo[2,1-f][1,2,4]triazin-4-yl)benzyl)-1,2,4-oxadiazole-3-carboxamide | SiO$_2$; 0-100% EtOAc/Hept<br>7.2 mg (75%)<br>LCMS m/z = 461.3 [M + H]$^+$<br>$^1$H NMR (400 MHz, CDCl$_3$) δ: 8.44-8.55 (m, 1H), 7.86-7.96 (m, 2H), 7.81 (d, 1H), 7.50 (d, 1H), 7.22 (br s, 1H), 6.91 (d, 1H), 4.77 (d, 2H), 4.14-4.21 (m, 1H), 4.02-4.10 (m, 1H), 3.91-3.99 (m, 1H), 3.75-3.81 (m, 1H), 3.55-3.63 (m, 1H), 2.49-2.53 (m, 3H), 2.38-2.48 (m, 1H), 1.98-2.11 (m, 1H), 1.47-1.49 (m, 9H). |
| Example 96 | 5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide | SiO$_2$; 0-30% DCM/MeOH<br>52.5 mg (15%)<br>LCMS m/z = 503.2 [M + H]$^+$<br>$^1$H NMR (400 MHz, MeOH-d$_4$) δ: 8.28-8.40 (m, 1H), 7.71-7.91 (m, 3H), 7.51 (d, 1H), 6.61 (d, 1H), 4.70 (s, 2H), 3.48-3.63 (m, 2H), 2.86-3.02 (m, 2H), 2.41-2.64 (m, 5H), 2.29-2.39 (m, 4H), 1.50 (s, 9H), 1.15-1.22 (m, 3H). |
| Example 97 | 3-(tert-butyl)-N-(4-(6-(4-methoxypiperidin-1-yl)pyrrolo[2,1-f][1,2,4]triazin-4-yl)-2-methylbenzyl)-1,2,4-oxadiazole-5-carboxamide | SiO$_2$; 0-100% EtOAc/Hept<br>9 mg (5%)<br>LCMS m/z = 504.3 [M + H]$^+$<br>$^1$H NMR (400 MHz, MeOH-d$_4$) δ: 8.33 (d, 1H), 7.77-7.89 (m, 3H), 7.53 (d, 1H), 6.55-6.63 (m, 1H), 4.64-4.74 (m, 2H), 3.48-3.57 (m, 2H), 3.43-3.47 (m, 1H), 3.38-3.42 (m, 3H), 2.95-3.07 (m, 2H), 2.44-2.55 (m, 3H), 1.98-2.11 (m, 2H), 1.62-1.76 (m, 2H), 1.38-1.47 (m, 9H). |

| Example Number | Name Structure | HPLC Method/Yield/Data |
|---|---|---|
| Example 98 | 2-(tert-butyl)-N-(4-(6-(3,4-dimethylpiperazin-1-yl)pyrrolo[2,1-f][1,2,4]triazin-4-yl)-2-methylbenzyl)-2H-tetrazole-5-carboxamide trifluoroacetate | Method B; 10-90% 7.5 mg (4%) LCMS m/z = 503.3 [M + H]+ ¹H NMR (400 MHz, MeOH-d₄) δ: 9.49 (s, 1H), 8.40-8.44 (m, 1H), 7.94-8.03 (m, 1H), 7.83-7.90 (m, 2H), 7.52-7.60 (m, 1H), 6.75-6.83 (m, 1H), 4.70-4.78 (m, 2H), 3.85-4.04 (m, 2H), 3.59-3.69 (m, 1H), 3.33-3.56 (m, 3H), 3.15 (br dd, 1H), 2.51-2.57 (m, 3H), 1.82 (s, 9H), 1.48 (d, 3H). |
| Example 99 | 3-(tert-butyl)-N-(4-(6-(3,4-dimethoxypyrrolidin-1-yl)pyrrolo[2,1-f][1,2,4]triazin-4-yl)-2-methylbenzyl)-1,2,4-oxadiazole-5-carboxamide trifluoroacetate | Method B; 10-90% 2 mg (2%) LCMS m/z = 520.3 [M + H]+ ¹H NMR (400 MHz, MeOH-d₄) δ: 8.50 (s, 2H), 7.76-7.89 (m, 2H), 7.58-7.69 (m, 1H), 6.68-6.75 (m, 1H), 4.65-4.76 (m, 2H), 4.09-4.25 (m, 2H), 3.59-3.67 (m, 2H), 3.47 (s, 8H), 2.54-2.59 (m, 3H), 1.42 (s, 9H). |
| Example 100 | 3-(tert-butyl)-N-(4-(6-(2-isopropylmorpholino)pyrrolo[2,1-f][1,2,4]triazin-4-yl)-2-methylbenzyl)-1,2,4-oxadiazole-5-carboxamide trifluoroacetate | Method B; 10-90% 8 mg (10%) LCMS m/z = 518.3 [M + H]+ ¹H NMR (400 MHz, MeOH-d₄) δ: 8.49 (s, 1H), 8.41-8.44 (m, 1H), 7.81-7.87 (m, 2H), 7.60-7.64 (m, 1H), 6.88-6.91 (m, 1H), 4.70-4.73 (m, 2H), 4.03 (s, 1H), 3.70-3.78 (m, 1H), 3.63-3.69 (m, 1H), 3.52-3.59 (m, 1H), 3.33-3.37 (m, 1H), 2.91-3.00 (m, 1H), 2.69-2.77 (m, 1H), 2.56 (s, 3H), 1.73-1.85 (m, 1H), 1.43 (s, 9H), 1.00-1.05 (m, 6H). |

| Example Number | Name Structure | HPLC Method/Yield/Data |
|---|---|---|
| Example 101 | 5-(tert-butyl)-N-(4-(6-(3,6-dihydro-2H-thiopyran-4-yl)pyrrolo[2,1-f][1,2,4]triazin-4-yl)-2-methylbenzyl)-1,2,4-oxadiazole-3-carboxamide | SiO$_2$; 0-100% EtOAc/Hept yellow solid: 12 mg, 69% LCMS m/z = 489.2 [M + H]$^+$ $^1$H NMR (500 MHz, DMSO-d$_6$) δ: 9.52 (t, 1H), 8.56 (s, 1H), 8.34 (d, 1H), 7.97-8.00 (m, 1H), 7.96 (s, 1H), 7.45 (d, 1H), 7.28 (d, 1H), 6.61-6.67 (m, 1H), 4.55 (d, 2H), 3.32-3.34 (m, 2H), 2.86 (t, 2H), 2.65-2.72 (m, 2H), 2.46 (s, 3H), 1.44 (s, 9H). |
| Example 102 | 5-(tert-butyl)-N-(4-(6-cyanopyrrolo[2,1-f][1,2,4]triazin-4-yl)-2-methylbenzyl)-1,2,4-oxadiazole-3-carboxamide | SiO$_2$; 0-100% EtOAc/Hept yellow solid: 43 mg, 58% LCMS m/z = 416.2 [M + H]$^+$ $^1$H NMR (500 MHz, DMSO-d$_6$) δ: 9.53 (t, 1H), 8.89 (s, 1H), 8.80 (s, 1H), 7.96-8.02 (m, 2H), 7.84 (s, 1H), 7.47 (d, 1H), 4.56(br d, 2H), 2.47 (s, 3H), 1.44 (s, 9H). |
| Example 103 | 3-(tert-butyl)-N-(4-(6-(3,6-dihydro-2H-pyran-4-yl)pyrrolo[2,1-f][1,2,4]triazin-4-yl)-2-methylbenzyl)-1,2,4-oxadiazole-5-carboxamide | SiO$_2$; 0-100% EtOAc/Hept yellow solid: 7 mg, 15% LCMS m/z = 473.2 [M + H]$^+$ $^1$H NMR (500 MHz, DMSO-d$_6$) δ: 9.90 (t, 1H), 8.53-8.60 (m, 1H), 8.35 (d, 1H), 7.98 (d, 1H), 7.96 (s, 1H), 7.49 (d, 1H), 7.28 (d, 1H), 6.48 (br s, 1H), 4.56 (d, 2H), 4.24 (br d, 2H), 3.83 (t, 2H), 2.47 (s, 3H), 1.37 (s, 9H). |
| Example 104 | 5-(tert-butyl)-N-(2-methyl-4-(6-(1-(oxetan-3-yl)-1H-pyrazol-4-yl)pyrrolo[2,1-f][1,2,4]triazin-4-yl)benzyl)-1,2,4-oxadiazole-3-carboxamide | SiO$_2$; 0-100% EtOAc/EtOH (3:1): Hept yellow solid: 24 mg, 30% LCMS m/z = 513.4 [M + H]$^+$ $^1$H NMR (500 MHz, DMSO-d$_6$) δ: 9.53 (br t, 1H), 8.57 (s, 1H), 8.45-8.51 (m, 1H), 8.11 (s, 1H), 7.96-8.03 (m, 2H), 7.42-7.49 (m, 2H), 5.58 (dt, 1H), 4.88-5.00 (m, 4H), 4.56 (br d, 2H), 2.48 (s, 3H), 1.44 (s, 9H). |

-continued

| Example Number | Name Structure | HPLC Method/Yield/Data |
|---|---|---|
| Example 105 | 3-(tert-butyl)-N-(2-methyl-4-(6-morpholinopyrrolo[2,1-f][1,2,4]triazin-4-yl)benzyl)-1,2,4-oxadiazole-5-carboxamide | SiO$_2$; 0-100% EtOAc/EtOH (3:1): Hept<br>yellow solid: 17 mg, 27%<br>LCMS m/z = 476.3 [M + H]$^+$<br>$^1$H NMR (500 MHz, DMSO-d$_6$) δ: 9.89 (t, 1H), 8.48 (s, 1H), 7.99 (d, 1H), 7.91-7.95 (m, 2H), 7.46 (d, 1H), 6.72 (d, 1H), 4.55 (d, 2H), 3.71-3.79 (m, 4H), 3.08-3.21 (m, 4H), 2.45 (s, 3H), 1.37 (s, 9H). |
| Example 106 | 5-(tert-butyl)-N-(2-methyl-4-(6-(1-methyl-1H-1,2,3-triazol-4-yl)pyrrolo[2,1-f][1,2,4]triazin-4-yl)benzyl)-1,2,4-oxadiazole-3-carboxamide trifluoroacetate | SiO$_2$; 0-100% EtOAc/Hept then Method B; 10-90%.<br>yellow solid: 20 mg, 20%<br>LCMS m/z = 472.2 [M + H]$^+$<br>$^1$H NMR (400 MHz, DMSO-d$_6$) δ: 9.54 (t, 1H), 8.71 (s, 1H), 8.70 (d, 1H), 8.16 (s, 1H), 8.04 (d, 1H), 8.01 (s, 1H), 7.59 (d, 1H), 7.48 (d, 1H), 4.57 (d, 2H), 4.24 (s, 3H), 2.48 (s, 3H), 1.44 (s, 9H). |
| Example 107 | 5-(tert-butyl)-N-(4-(6-(1-(difluoromethyl)-1H-pyrazol-4-yl)pyrrolo[2,1-f][1,2,4]triazin-4-yl)-2-methylbenzyl)-1,2,4-oxadiazole-3-carboxamide trifluoroacetate | SiO$_2$; 0-100% EtOAc/Hept then Method B; 10-90%<br>yellow solid: 35 mg, 33%<br>LCMS m/z = 507.2 [M + H]$^+$<br>$^1$H NMR (400 MHz, DMSO-d$_6$) δ: 9.54 (t, 1H), 8.80 (s, 1H), 8.56-8.63 (m, 2H), 8.36 (s, 1H), 7.96-8.05 (m, 2H), 7.69-7.90 (m, 1H), 7.58 (d, 1H), 7.47 (d, 1H), 4.57 (d, 2H), 2.49 (br s, 3H), 1.44 (s, 9H). |
| Example 108 | 5-(tert-butyl)-N-(4-(6-(1,3-dimethyl-1H-pyrazol-4-yl)pyrrolo[2,1-f][1,2,4]triazin-4-yl)-2-methylbenzyl)-1,2,4-oxadiazole-3-carboxamide | SiO$_2$; 0-100% EtOAc/Hept<br>yellow film: 45 mg, 65%<br>LCMS m/z = 485.2 [M + H]$^+$<br>$^1$H NMR (500 MHz, DMSO-d$_6$) δ: 9.52 (t, 1H), 8.58 (s, 1H), 8.32 (d, 1H), 8.11 (s, 1H), 7.94-8.02 (m, 2H), 7.46 (d, 1H), 7.26 (d, 1H), 4.56 (d, 2H), 3.79 (s, 3H), 2.47 (s, 3H), 2.37 (s, 3H), 1.44 (s, 9H). |

| Example Number | Name Structure | HPLC Method/Yield/Data |
|---|---|---|
| Example 109 | 5-(tert-butyl)-N-(4-(6-(1,5-dimethyl-1H-pyrazol-4-yl)pyrrolo[2,1-f][1,2,4]triazin-4-yl)-2-methylbenzyl)-1,2,4-oxadiazole-3-carboxamide | SiO$_2$; 0-100% EtOAc/Hept yellow solid: 70 mg, 77% LCMS m/z = 485.2 [M + H]$^+$ $^1$H NMR (500 MHz, DMSO-d$_6$) δ: 9.52 (t, 1H), 8.58 (s, 1H), 8.37 (d, 1H), 8.01 (dd, 1H), 7.98 (s, 1H), 7.81 (s, 1H), 7.47 (d, 1H), 7.28 (d, 1H), 4.56 (d, 2H), 3.79 (s, 3H), 2.47 (s, 3H), 2.46 (s, 3H), 1.44 (s, 9H). |
| Example 110 | 5-(tert-butyl)-N-(2-methyl-4-(6-(oxazol-5-yl)pyrrolo[2,1-f][1,2,4]triazin-4-yl)benzyl)-1,2,4-oxadiazole-3-carboxamide | SiO$_2$; 0-100% EtOAc/Hept yellow solid: 16 mg, 37% LCMS m/z = 458.2 [M + H]$^+$ $^1$H NMR (400 MHz, DMSO-d$_6$) δ: 9.54 (t, 1H), 8.67 (s, 1H), 8.59 (d, 1H), 8.47 (s, 1H), 7.95-8.05 (m, 2H), 7.70 (s, 1H), 7.52 (d, 1H), 7.48 (d, 1H), 4.57 (d, 2H), 2.48 (s, 3H), 1.44 (s, 9H). |
| Example 111 | 5-(tert-butyl)-N-(2-methyl-4-(6-(1-methyl-1H-imidazol-4-yl)pyrrolo[2,1-f][1,2,4]triazin-4-yl)benzyl)-1,2,4-oxadiazole-3-carboxamide trifluoroacetate | SiO$_2$; 0-100% EtOAc/Hept then Method A; 10-90% yellow solid: 6 mg, 36% LCMS m/z = 471.2 [M + H]$^+$ $^1$H NMR (500 MHz, DMSO-d$_6$) δ: 9.56 (t, 1H), 8.94 (br s, 1H), 8.69 (s, 1H), 8.59 (d, 1H), 8.08 (s, 1H), 7.94-8.02 (m, 2H), 7.61 (d, 1H), 7.49 (d, 1H), 4.57 (d, 2H), 3.88 (s, 3H), 1.44 (s, 9H). |
| Example 112 | 5-(tert-butyl)-N-(3-fluoro-2-methyl-4-(6-(1-methyl-1H-pyrazol-4-yl)pyrrolo[2,1-f][1,2,4]triazin-4-yl)benzyl)-1,2,4-oxadiazole-3-carboxamide | SiO$_2$; 0-100% EtOAc/Hept yellow solid: 6 mg, 36% LCMS m/z = 489.2 [M + H]$^+$ $^1$H NMR (500 MHz, DMSO-d$_6$) δ: 9.58 (t, 1H), 8.58 (s, 1H), 8.49 (d, 1H), 8.17 (s, 1H), 7.91 (s, 1H), 7.61 (t, 1H), 7.30 (d, 1H), 7.01 (dd, 1H), 4.58 (d, 2H), 3.85 (s, 3H), 2.36 (d, 3H), 1.44 (s, 9H). |

| Example Number | Name Structure | HPLC Method/Yield/Data |
|---|---|---|
| Example 113 | 2-(tert-butyl)-N-(2-methyl-4-(6-(1-methyl-1H-pyrazol-4-yl)pyrrolo[2,1-f][1,2,4]triazin-4-yl)benzyl)-2H-tetrazole-5-carboxamide trifluoroacetate | Method B; 10-90% yellow solid: 61 mg, 53% LCMS m/z = 471.2 [M + H]+ $^1$H NMR (500 MHz, DMSO-$d_6$) δ: 9.61 (t, 1H), 8.56 (s, 1H), 8.46 (d, 1H), 8.20 (s, 1H), 7.96-8.00 (m, 2H), 7.95 (s, 1H), 7.48 (d, 1H), 7.40 (d, 1H), 4.59 (d, 2H), 3.87 (s, 3H), 1.75 (s, 9H). |
| Example 114 | 2-(tert-butyl)-N-(2-methyl-4-(6-morpholinopyrrolo[2,1-f][1,2,4]triazin-4-yl)benzyl)-2H-tetrazole-5-carboxamide | SiO$_2$; 0-100% EtOAc/Hept yellow solid: 20 mg, 18% LCMS m/z = 476.3 [M + H]+ $^1$H NMR (500 MHz, DMSO-$d_6$) δ: 9.58 (t, 1H), 8.47 (s, 1H), 7.99 (d, 1H), 7.89-7.95 (m, 2H), 7.43 (d, 1H), 6.72 (d, 1H), 4.57 (d, 2H), 3.69-3.80 (m, 4H), 3.12-3.20 (m, 4H), 2.46 (s, 3H), 1.74 (s, 9H). |
| Example 115 | 3-(tert-butyl)-N-(4-(6-(3,4-dimethylpiperazin-1-yl)pyrrolo[2,1-f][1,2,4]triazin-4-yl)-3-fluoro-2-methylbenzyl)-1,2,4-oxadiazole-5-carboxamide | SiO$_2$; 0-30% MeOH/DCM solid: 130 mg, 70% LCMS m/z = 521.3 [M + H]+ |
| Example 116 | (S)-5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide | Chiral SFC (Chiralpak AD-H, 30 × 250 mm, 5 μm, 40% EtOH + 0.1% DEA in CO$_2$) 9 mg (18%) LCMS m/z = 503.3 [M + H]+; $^1$H NMR (400 MHz, MeOH-$d_4$) δ: 8.34 (s, 1H), 7.77-7.89 (m, 3H), 7.52 (d, 1H), 6.62 (d, 1H), 4.70 (s, 2H), 3.47-3.63 (m, 2H), 2.87-2.99 (m, 2H), 2.44-2.62 (m, 5H), 2.30-2.40 (m, 4H), 1.45-1.57 (m, 9H), 1.19 (d, 3H). |

(absolute stereochemistry arbitrarily assigned)

| Example Number | Name Structure | HPLC Method/Yield/Data |
|---|---|---|
| Example 117 | (R)-5-(tert-butyl)-N-(4-(6-(3,4-dimethylpiperazin-1-yl)pyrrolo[2,1-f][1,2,4]triazin-4-yl)-2-methylbenzyl)-1,2,4-oxadiazole-3-carboxamide<br><br>(absolute stereochemistry arbitrarily assigned) | Chiral SFC (Chiralpak AD-H, 30 × 250 mm, 5 μm, 40% EtOH + 0.1% DEA in $CO_2$) 16 mg (33%) LCMS m/z = 503.3 [M + H]$^+$; $^1$H NMR (400 MHz, MeOH-$d_4$) δ: 8.28-8.40 (m, 1H), 7.71-7.91 (m, 3H), 7.51 (d, 1H), 6.61 (d, 1H), 4.70 (s, 2H), 3.48-3.63 (m, 2H), 2.86-3.02 (m, 2H), 2.41-2.64 (m, 5H), 2.29-2.39 (m, 4H), 1.50 (s, 9H), 1.15-1.22 (m, 3H). |
| Example 118 | 3-(tert-butyl)-N-(3-fluoro-2-methyl-4-(2-morpholinopyrazolo[1,5-a]pyrimidin-7-yl)benzyl)-1,2,4-oxadiazole-5-carboxamide | Method C; 10-90% yellow solid: 23 mg, 32% LCMS m/z = 494.1 [M + H]$^+$, $^1$H NMR (500 MHz, MeOH-$d_4$) δ: 8.32 (br d, 1H), 7.63-7.56 (m, 1H), 7.33 (br d, 1H), 6.79 (br d, 1H), 6.10 (s, 1H), 4.69 (s, 2H), 4.59(s, 2H), 3.82-3.73 (m, 4H), 2.38(d, 3H), 1.42 (s, 9H). |
| Example 119 | (S)-5-(tert-butyl)-N-(4-(6-(7,7-difluorohexahydropyrrolo[1,2-a]pyrazin-2(1H)-yl)pyrrolo[2,1-f][1,2,4]triazin-4-yl)-2-methylbenzyl)-1,2,4-oxadiazole-3-carboxamide | Method C; 10-70% yellow solid: 5 mg, 74% LCMSm/z = 551.1 [M + H]$^+$ $^1$H NMR (500 MHz, DMSO-$d_6$) δ: 9.46-9.59 (m, 1H), 8.46 (s, 1H), 7.88-8.02 (m, 3H), 7.42 (d, 1H), 6.71 (d, 1H), 4.54 (d, 2H), 3.84 (br d, 2H), 3.69 (br d, 2H), 2.98-3.04 (m, 1H), 2.84 (td, 2H), 2.58-2.62 (m, 3H), 2.45 (s, 3H), 2.34-2.42 (m, 1H), 1.90-2.06 (m, 1H), 1.90-2.06 (m, 1H), 1.44 (s, 9H). |

| Example Number | Name Structure | HPLC Method/Yield/Data |
|---|---|---|
| Example 120 | 5-(tert-butyl)-N-(4-(6-(5,6-dihydroimidazo[1,2-a]pyrazin-7(8H)-yl)pyrrolo[2,1-f][1,2,4]triazin-4-yl)-2-methylbenzyl)-1,2,4-oxadiazole-3-carboxamide trifluoroacetate | Method B; 5-45% yellow solid: 26 mg, 46% LCMS m/z = 512.1 [M + H]+ $^1$H NMR (500 MHz, DMSO-d$_6$) δ: 9.51-9.59 (m, 1H), 8.54 (s, 1H), 8.18 (d, 1H), 7.89-8.00 (m, 2H), 7.67 (s, 2H), 7.44 (br d, 1H), 6.91 (d, 1H), 4.79 (s, 2H), 4.55 (br d, 2H), 4.32 (br d, 2H), 3.80-3.95 (m, 2H), 2.46 (s, 3H), 1.44 (s, 9H). |
| Example 121 | 3-(tert-butyl)-N-(4-(6-(5,6-dihydroimidazo[1,2-a]pyrazin-7(8H)-yl)pyrrolo[2,1-f][1,2,4]triazin-4-yl)-2-methylbenzyl)-1,2,4-oxadiazole-3-carboxamide trifluoroacetate | Method B; 5-45% orange solid: 22 mg, 39% LCMS m/z = 512.1 [M + H]+ $^1$H NMR (500 MHz, DMSO-d$_6$) δ: 9.88-10.00 (m, 1H), 8.54 (s, 1H), 8.19 (d, 1H), 7.90-8.01 (m, 2H), 7.67 (s, 2H), 7.48 (br d, 1H), 6.91 (d, 1H), 4.79 (s, 2H), 4.56 (br d, 2H), 4.28-4.38 (m, 2H), 3.82-3.94 (m, 2H), 2.47 (s, 3H), 1.38 (s, 9H). |
| Example 122 | 5-(tert-butyl)-N-(4-(6-((3R,4S)-3,4-difluoropyrrolidin-1-yl)pyrrolo[2,1-f][1,2,4]triazin-4-yl)-2-methylbenzyl)-1,2,4-oxadiazole-3-carboxamide | SiO$_2$; 0-100% EtOAc: Hept yellow solid: 59 mg, 50% LCMS m/z = 496.2 [M + H]+ $^1$H NMR (500 MHz, DMSO-d$_6$) δ: 9.51 (t, 1H), 8.46 (s, 1H), 7.90-7.98 (m, 2H), 7.84 (d, 1H), 7.42 (d, 1H), 6.52 (d, 1H), 5.33-5.55 (m, 2H), 4.54 (d, 2H), 3.62-3.76 (m, 2H), 3.46-3.59 (m, 2H), 2.45 (s, 3H), 1.44 (s, 9H). |

| Example Number | Name Structure | HPLC Method/Yield/Data |
|---|---|---|
| Example 123 | (S)-3-(tert-butyl)-N-(4-(6-(7,7-difluorohexahydropyrrolo[1,2-a]pyrazin-2(1H)-yl)pyrrolo[2,1-f][1,2,4]triazin-4-yl)-2-methylbenzyl)-1,2,4-oxadiazole-5-carboxamide | Method C; 10-70% yellow solid: 8 mg, 12% LCMS m/z = 551.1 [M + H]⁺ ¹H NMR (500 MHz, DMSO-d₆) δ: 9.85-9.97 (m, 1H), 8.47 (s, 1H), 7.87-8.03 (m, 3H), 7.46 (d, 1H), 6.71 (d, 1H), 4.55 (d, 2H), 3.85(br d, 1H), 3.66-3.74 (m, 1H), 2.97-3.08 (m, 1H), 2.85 (td, 1H), 2.54-2.62 (m, 5H), 2.46 (s, 3H), 2.34-2.43 (m, 1H), 1.91-2.06 (m, 1H), 1.34-1.42 (m, 9H). |
| Example 124 | 2-(tert-butyl)-N-(4-(6-(3,6-dihydro-2H-pyran-4-yl)pyrrolo[2,1-f][1,2,4]triazin-4-yl)-2-methylbenzyl)oxazole-4-carboxamide | Method C; 10-70% yellow solid: 4 mg, 9% LCMS m/z = 472.0 [M + H]⁺; ¹H NMR (500 MHz, DMSO-d₆) δ: 8.69-8.65 (m, 2H), 8.56 (d, 1H), 8.34 (d, 1H), 7.98 (dd, 1H), 7.95 (s, 1H), 7.42 (d, 1H), 7.29 (d, 1H), 6.48 (m, 1H), 4.51 (br d, 2H), 4.26-4.20 (m, 2H), 3.83 (br t, 2H), THP-CH2: under DMSO peak, 2.45 (s, 3H), 1.37 (s, 9H). |
| Example 125 | 2-(tert-butyl)-N-(4-(6-(3,6-dihydro-2H-pyran-4-yl)pyrrolo[2,1-f][1,2,4]triazin-4-yl)-2-methylbenzyl)oxazole-5-carboxamide | Method C; 5-65% yellow solid: 2 mg, 4% LCMS m/z = 472.0 [M + H]⁺; ¹H NMR (500 MHz, DMSO-d₆) δ: 9.05 (br t, 1H), 8.57 (s, 1H), 8.34 (br d, 1H), 8.00 (br dd, 1H), 7.96 (s, 1H), 7.70 (s, 1H), 7.44 (br d, 1H), 7.29 (b rd, 1H), 6.51-6.46 (m, 1H), 4.53 (br d, 2H),4.23 (br d, 2H), 3.83 (br t, 2H), THP-CH2: under DMSO peak 2.46 (s, 3H), 1.37 (s, 9H). |
| Example 126 | 1-(tert-butyl)-N-(4-(6-(3,6-dihydro-2H-pyran-4-yl)pyrrolo[2,1-f][1,2,4]triazin-4-yl)-2-methylbenzyl)-1H-pyrazole-4-carboxamide | Method C; 5-55% yellow solid: 1 mg, 1% LCMS m/z = 471.2 [M + H]⁺; ¹HNMR (500 MHz, DMSO-d₆) δ: 8.57-8.55 (m, 2H), 8.34 (br s, 1H), 8.05-7.94 (m, 3H), 7.45-7.44 (m, 2H), 7.28 (br d, 1H), 6.48 (s, 1H), 4.50 (br d, 2H),4.23 (br d, 2H), 3.87-3.78 (m, 2H), 2.63 (br d, 1H), 2.45 (s, 3H), THP-CH2 & CH3: under DMSO peak 1.53 (s, 9H). |

| Example Number | Name Structure | HPLC Method/Yield/Data |
|---|---|---|
| Example 127 | 1-(tert-butyl)-N-(4-(6-(3,6-dihydro-2H-pyran-4-yl)pyrrolo[2,1-f][1,2,4]triazin-4-yl)-2-methylbenzyl)-1H-pyrazole-3-carboxamide 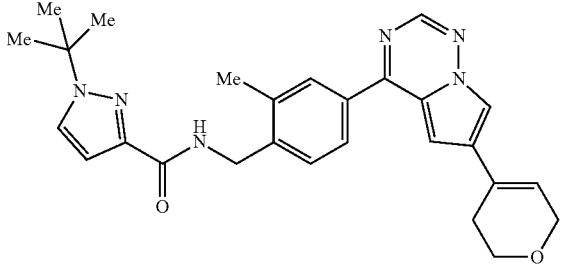 | Method C; 5-65% yellow solid: 5 mg, 11% LCMS m/z = 471.0 [M + H]⁺; ¹HNMR (500 MHz, DMSO-d₆) δ: 8.60-8.53 (m, 2H), 8.33 (d, 1H), 7.98 (br d, 1H), 7.95 (s, 1H), 7.93 (d, 1H), 7.44 (d, 1H), 7.29 (d, 1H), 6.67 (d, 1H), 6.48 (br s, 1H), 4.52 (br d, 2H), 4.23 (brd, 2H), 3.83 (br t, 2H), THP-CH2: under DMSO peak 2.46 (s, 3H), 1.57 (s, 9H). |
| Example 128 | 2-(tert-butyl)-N-(4-(6-(3,6-dihydro-2H-pyran-4-yl)pyrrolo[2,1-f][1,2,4]triazin-4-yl)-2-methylbenzyl)-2H-tetrazole-5-carboxamide 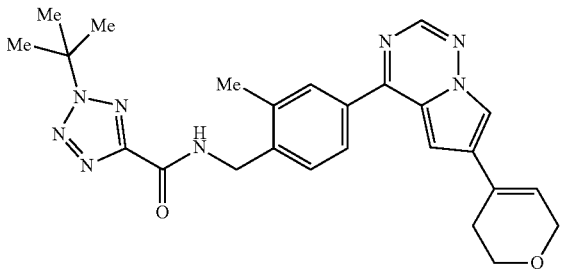 | Method C; 5-60% yellow oil: 57 mg, 100% LCMS m/z = 473.0 [M + H]⁺; ¹H NMR (500 MHz, DMSO-d₆) δ: 9.61-9.59 (m, 1H), 8.57 (s, 1H), 8.34 (br d, 1H), 7.99-7.95 (m, 2H), 7.46 (br d, 1H), 7.28 (d, 1H), 6.51-6.46 (m, 1H), 4.58 (brd, 2H), 4.23 (br d, 2H), 3.83 (br t, 2H), THP-CH2: under DMSO peak , 2.47 (s, 3H), 1.74 (s, 9H). |
| Example 129 | 2-(tert-butyl)-N-(4-(6-(1,5-dimethyl-1H-pyrazol-4-yl)pyrrolo[2,1-f][1,2,4]triazin-4-yl)-2-methylbenzyl)-2H-tetrazole-5-carboxamide 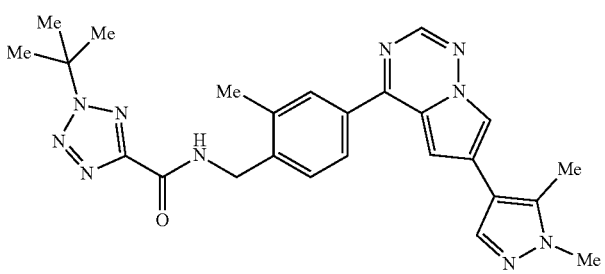 | Method B; 5-55% yellow solid: 6 mg, 15% LCMS m/z = 485.0 [M + H]⁺; ¹H NMR (500 MHz, DMSO-d₆) δ: 9.60 (s, 1H), 8.58 (s, 1H), 8.37 (d, 1H), 8.02-7.98 (m, 2H), 7.81 (s, 1H), 7.47 (d, 1H), 7.28 (d, 1H), 4.59 (d, 2H), 3.79 (s, 3H), 2.48 (s, 3H), 2.46 (s, 3H), 1.75 (s, 9H). |
| Example 130 | 2-(tert-butyl)-N-(4-(6-(1,5-dimethyl-1H-pyrazol-4-yl)pyrrolo[2,1-f][1,2,4]triazin-4-yl)-2-methylbenzyl)-oxazole-4-carboxamide 2-(tert-butyl)-N-(4-(6-(1,5-dimethyl-1H-pyrazol-4-yl)pyrrolo[2,1-f][1,2,4]triazin-4-yl)-2-methylbenzyl)-2H-tetrazole-5-carboxamide 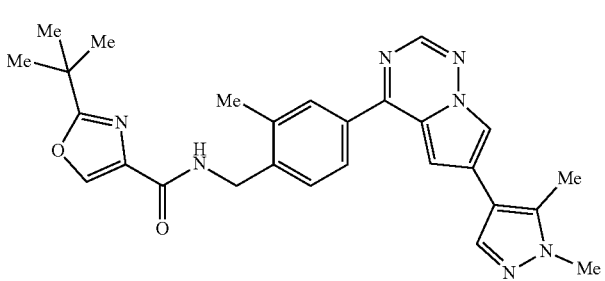 | Method B; 5-60% yellow solid: 3 mg, 6% LCMS m/z = 484.0 [M + H]⁺; ¹H NMR (500 MHz, DMSO-d₆) δ: 8.68 (br t, 1H), 8.58 (s, 1H), 8.56 (s, 1H), 8.37 (br d, 1H), 8.03-7.99 (m, 1H), 8.02-7.99 (m, 1H), 7.98-7.96 (br s, 1H), 7.81 (s, 1H), 7.44-7.43 (br d, 1H), 7.29 (br d, 1H), 4.52 (br d, 1H), 3.79 (s, 3H), 2.50 (s, 3H, CH3, under DMSO) 2.46 (s, 3H), 1.37 (s, 9H). |

| Example Number | Name Structure | HPLC Method/Yield/Data |
|---|---|---|
| Example 131 | 2-(tert-butyl)-N-(4-(6-(1,5-dimethyl-1H-pyrazol-4-yl)pyrrolo[2,1-f][1,2,4]triazin-4-yl)-2-methylbenzyl)-oxazole-5-carboxamide | Method B; 5-55% 1 mg (1%) LCMS m/z = 484.0 [M + H]+ |
| Example 132 | 5-(tert-butyl)-N-(2-chloro-5-fluoro-4-(pyrrolo[2,1-f][1,2,4]triazin-4-yl)benzyl)-1,2,4-oxadiazole-3-carboxamide | Method B; 10-70% yellow solid: 17 mg, 35% LCMS m/z = 529.0 [M + H]+; 1H NMR (500 MHz, DMSO-d6) δ: 9.91 (br t, 1H), 8.67 (s, 1H), 8.24 (dd, 1H), 7.91 (br d, 1H), 7.61 (br d, 1H), 7.12 (dd, 1H), 6.92-6.90 (m, 1H), 4.61 (d, 2H), 1.38 (s, 9H). |
| Example 133 | 3-(tert-butyl)-N-(2-chloro-5-fluoro-4-(pyrrolo[2,1-f][1,2,4]triazin-4-yl)benzyl)-1,2,4-oxadiazole-5-carboxamide | Method B; 5-70% yellow solid: 22 mg, 46% LCMS m/z = 428.9 [M + H]+; 1H NMR (500 MHz, DMSO-d6) δ: 9.59 (br t, 2H), 8.67 (s, 1H), 8.24 (dd, 1H), 7.91 (d, 1H), 7.45 (d, 1H), 7.12 (dd, 1H), 6.90 (m, 1H), 4.61 (d, 2H), 1.45 (s, 9H). |
| Example 134 | 2-(tert-butyl)-N-(2-chloro-5-fluoro-4-(pyrrolo[2,1-f][1,2,4]triazin-4-yl)benzyl)-oxazole-4-carboxamide | Method B; 10-70% yellow solid: 17 mg, 36% LCMS m/z = 427.9 [M + H]+; 1H NMR (500 MHz, DMSO-d6) δ: 8.83 (br t, 2H), 8.67 (s, 1H), 8.59 (s, 1H), 8.24 (dd, 1H), 7.90 (d, 1H), 7.32 (d, 1H), 7.12 (dd, 1H), 6.92-6.90 (m, 1H), 4.57 (d, 2H), 1.38 (s, 9H). |
| Example 135 | 5-(tert-butyl)-N-(2-chloro-5-fluoro-4-(pyrrolo[2,1-f][1,2,4]triazin-4-yl)benzyl)isoxazole-3-carboxamide | Method B; 20-75% yellow solid: 16 mg, 32% LCMS m/z = 428.0 [M + H]+; 1H NMR (500 MHz, DMSO-d6) δ: 9.41 (br t, 1H), 8.67 (s, 1H), 8.24 (dd, 1H), 7.91 (d, 1H), 7.40 (d, 1H), 7.12 (dd, 1H), 6.92-6.90 (m, 1H), 6.64 (s, 1H), 4.60 (d, 2H), 1.34 (s, 9H). |

-continued

| Example Number | Name Structure | HPLC Method/Yield/Data |
|---|---|---|
| Example 136 | 2-(tert-butyl)-N-(2-chloro-5-fluoro-4-(pyrrolo[2,1-f][1,2,4]triazin-4-yl)benzyl)-2H-tetrazole-5-carboxamide | Method B; 5-65% yellow solid: 14 mg, 28% LCMS m/z = 429.0 [M + H]+; 1HNMR (500 MHz, DMSO-$d_6$) δ: 9.68 (br t, 1H), 8.67 (s, 1H), 8.24 (dd, 1H), 7.91 (d, 1H), 7.45 (d, 1H), 7.12 (dd, 1H), 6.92-6.90 (m, 4.3 Hz, 1H),4.65 (d, 2H), 1.75 (s, 9H). |
| Example 137 | (R)-3-(tert-butyl)-N-(2-methyl-4-(6-(2-methylmorpholino)pyrrolo[2,1-f][1,2,4]triazin-4-yl)benzyl)-1,2,4-oxadiazole-5-carboxamide<br>(absolute stereochemistry arbitrarily assigned) | Chiral SFC (Chiralpak AD-H, 30 × 250 mm, 5 μm, 40% MeOH + 0.1% DEA in $CO_2$) 11 mg (19%) LCMS m/z = 490.2 [M + H]+; 1H NMR (500 MHz, DMSO-$d_6$) δ: 9.90 (s, 1H), 8.47 (s, 1H), 7.98 (d, 1H), 7.89-7.95 (m, 2H), 7.45 (d, 1H), 6.71 (d, 1H), 4.55 (d, 2H), 3.90 (br d, J = 10.4 Hz, 1H), 3.59-3.71 (m, 3H), 3.52 (br d, 1H), 2.67-2.75 (m, 1H), 2.45 (s, 3H), 2.38-2.43 (m, 1H), 1.37 (s, 9H), 1.15 (d, 3H). |
| Example 138 | (S)-3-(tert-butyl)-N-(2-methyl-4-(6-(2-methylmorpholino)pyrrolo[2,1-f][1,2,4]triazin-4-yl)benzyl)-1,2,4-oxadiazole-5-carboxamide<br>(absolute stereochemistry arbitrarily assigned) | Chiral SFC (Chiralpak AD-H, 30 × 250 mm, 5 μm, 40% MeOH + 0.1% DEA in $CO_2$) 11 mg (19%) LCMS m/z = 490.2 [M + H]+; 1HNMR (500 MHz, DMSO-$d_6$) δ: 9.90 (s, 1H), 8.47 (s, 1H), 7.98 (d, 1H), 7.89-7.96 (m, 2H), 7.46 (d, 1H), 6.71 (d, 1H), 4.55 (d, 2H), 3.90 (br d, 1H), 3.59-3.71 (m, 3H), 3.52 (br d, 1H), 2.67-2.75 (m, 1H), 2.45 (s, 3H),2.40 (d, 1H), 1.37 (s, 9H), 1.15 (d, 3H). |
| Example 139 | (R)-2-(tert-butyl)-N-(2-methyl-4-(6-(2-methylmorpholino)pyrrolo[2,1-f][1,2,4]triazin-4-yl)benzyl)-2H-tetrazole-5-carboxamide<br>(absolute stereochemistry arbitrarily assigned) | Chiral SFC (Chiralpak AD-H, 30 × 250 mm, 5 μm, 40% IPA + 0.1% DEA in $CO_2$) 13 mg (27%) LCMS m/z = 490.2 [M + H]+; 1H NMR (500 MHz, DMSO-$d_6$) δ: 9.02-9.10 (m, 1H), 8.72 (s, 1H), 8.46 (s, 1H), 7.97 (d, 1H), 7.89-7.93 (m, 2H), 7.41 (d, 1H), 6.71 (d, 1H), 4.53 (d, 2H), 3.89 (br d, 1H), 3.59-3.70 (m, 3H), 3.51 (br d, 1H), 2.67-2.73 (m, 1H), 2.45 (s, 3H), 2.39 (d, 1H), 1.64 (s, 9H), 1.15 (d, 3H) |

-continued

| Example Number | Name Structure | HPLC Method/Yield/Data |
|---|---|---|
| Example 140 | (S)-2-(tert-butyl)-N-(2-methyl-4-(6-(2-methylmorpholino)pyrrolo[2,1-f][1,2,4]triazin-4-yl)benzyl)-2H-tetrazole-5-carboxamide<br><br>(absolute stereochemistry arbitrarily assigned) | Chiral SFC (Chiralpak AD-H, 30 × 250 mm, 5 μm, 40% IPA + 0.1% DEA in $CO_2$)<br>6 mg (12%)<br>LCMS m/z = 490.2 [M + H]$^+$; $^1$H NMR (500 MHz, DMSO-d$_6$) δ: 9.07 (s, 1H), 8.72 (s, 1H), 8.46 (s, 1H), 7.97 (d, 1H), 7.88-7.94 (m, 2H), 7.41 (d, 1H), 6.71 (d, 1H), 4.53 (d, 2H), 3.88 (s, 1H), 3.59-3.70 (m, 3H), 3.51 (br d, 1H), 2.67-2.74 (m, 1H), 2.45 (s, 3H), 2.39 (d, 1H), 1.64 (s, 9H), 1.15 (d, 3H). |
| Example 141 | (S)-5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide<br><br>(absolute stereochemistry arbitrarily assigned) | Chiral SFC (Chiralpak AD-H, 30 × 250 mm, 5 μm, 40% MeOH:DCM (1:1) + 0.1% DEA in $CO_2$)<br>16 mg (17%)<br>LCMS m/z = 478.2 [M + H]$^+$; $^1$H NMR (500 MHz, DMSO-d$_6$) δ: 9.51 (t, 1H), 8.44 (s, 1H), 7.89-7.98 (m, 2H), 7.81 (d, 1H), 7.42 (d, 1H), 6.47 (d, 1H), 5.35-5.57 (m, 1H), 4.54 (d, 2H), 3.55 (s, 1H), 3.49 (d, 1H), 3.35-3.44 (m, 2H), 2.45 (s, 3H), 2.16-2.30 (m, 2H), 1.44 (s, 9H). |
| Example 142 | (R)-5-(tert-butyl)-N-(4-(6-(3-fluoropyrrolidin-1-yl)pyrrolo[2,1-f][1,2,4]triazin-4-yl)-2-methylbenzyl)-1,2,4-oxadiazole-3-carboxamide<br><br>(absolute stereochemistry arbitrarily assigned) | Chiral SFC (Chiralpak AD-H, 30 × 250 mm, 5 μm, 40% MeOH:DCM (1:1) + 0.1% DEA in $CO_2$)<br>12 mg (12%)<br>LCMS m/z = 478.2 [M + H]$^+$; $^1$H NMR (500 MHz, DMSO-d$_6$) δ: 9.55-9.44 (m, 1H), 8.44 (s, 1H), 7.89-7.96 (m, 2H), 7.81 (d, 1H), 7.42 (d, 1H), 6.47 (d, 1H), 5.31-5.59 (m, 1H), 4.54 (d, 2H), 3.55(s, 1H), 3.47-3.51 (m, 1H), 3.36-3.44 (m, 2H), 2.45 (s, 3H), 2.11-2.30 (m, 2H), 1.44 (s, 9H). |

| Example Number | Name Structure | HPLC Method/Yield/Data |
| --- | --- | --- |
| Example 143 | (R)-2-(tert-butyl)-N-(2-methyl-4-(6-(2-methylmorpholino)pyrrolo[2,1-f][1,2,4]triazin-4-yl)benzyl)oxazole-4-carboxamide<br>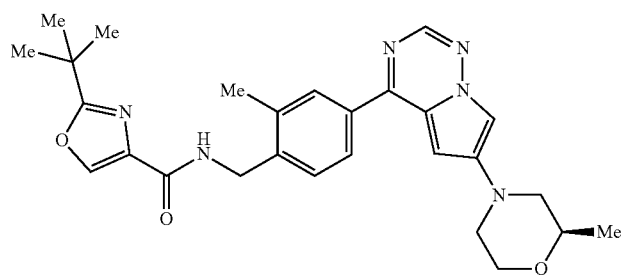<br>(absolute stereochemistry arbitrarily assigned) | Chiral SFC (Chiralpak AD-H, 30 × 250 mm, 5 μm, 40% EtOH + 0.1% DEA in $CO_2$) 13 mg (27%) LCMS m/z = 489.2 [M + H]$^+$; $^1$H NMR (500 MHz, DMSO-d$_6$) δ: 8.62-8.67 (m, 1H), 8.55 (s, 1H), 8.46 (s, 1H), 7.97 (br d, 1H), 7.88-7.95 (m, 1H), 7.39 (br d, 2H), 6.71 (br d, 1H), 4.50 (br d, 2H), 3.85-3.95 (m, 1H), 3.59-3.72 (m, 2H), 3.51 (brd, 1H), 2.66-2.75 (m, 2H), 2.44 (s, 3H), 2.33-2.42 (m, 1H), 1.37 (s, 9H), 1.15 (br d, 3H). |
| Example 144 | (S)-2-(tert-butyl)-N-(2-methyl-4-(6-(2-methylmorpholino)pyrrolo[2,1-f][1,2,4]triazin-4-yl)benzyl)oxazole-4-carboxamide<br>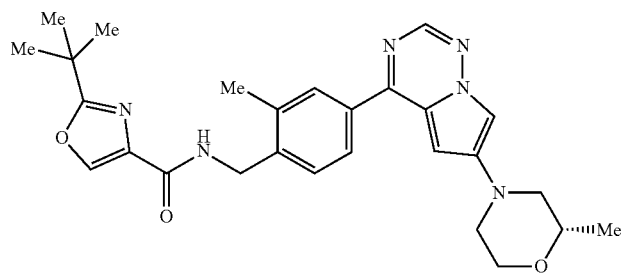<br>(absolute stereochemistry arbitrarily assigned) | Chiral SFC (Chiralpak AD-H, 30 × 250 mm, 5 μm, 40% EtOH + 0.1% DEA in $CO_2$) 16 mg (33%) LCMS m/z = 489.2 [M + H]$^+$; $^1$HNMR (500 MHz, DMSO-d$_6$) δ: 8.64 (br d, 1H), 8.55 (s, 1H), 8.46 (s, 1H), 7.97 (br d, 1H), 7.87-7.95 (m, 2H), 7.39 (br d, 1H), 6.71 (br d, 1H), 4.50 (br d, 2H), 3.89 (brd, 1H), 3.59-3.71 (m, 3H), 3.51 (brd, 1H), 2.70 (br dd, 2H), 2.44 (s, 3H), 2.34-2.37 (m, 1H), 1.37 (s, 9H), 1.15 (br d, 3H). |
| Example 145 | 1-(tert-butyl)-N-(4-(6-(1-(2,2-difluoroethyl)-1H-pyrazol-4-yl)pyrrolo[2,1-f][1,2,4]triazin-4-yl)-2-methylbenzyl)-1H-pyrazole-4-carboxamide<br>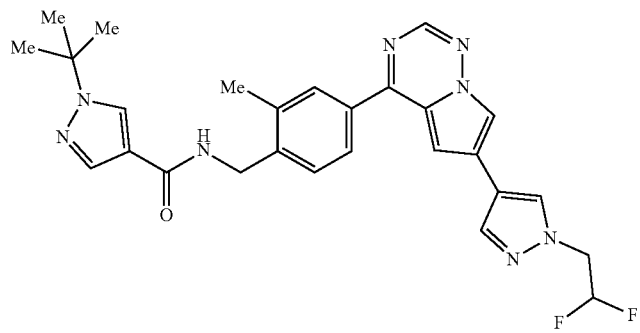 | Method B; 5-55% yellow solid: 2 mg, 3% LCMS m/z = 518.9 [M + H]$^+$; $^1$H NMR (500 MHz, DMSO-d$_6$) δ: 8.58-8.55 (m, 1H), 8.50 (br d, 1H), 8.35 (s, 1H), 8.30 (s, 1H), 8.08 (s, 1H), 8.01-7.99 (m, 1H), 7.98 (s, 1H), 7.94 (s, 1H), 7.47-7.43 (m, 2H), 6.39 (tt, 1H), 4.65 (td, 1H), 4.51 (br d, 1H), 3.34 (s, 2H), 2.46 (s, 3H), 1.54 (m, 9H) |

-continued

| Example Number | Name Structure | HPLC Method/Yield/Data |
|---|---|---|
| Example 146 | 2-(tert-butyl)-N-(4-(6-(1-(2,2-difluoroethyl)-1H-pyrazol-4-yl)pyrrolo[2,1-f][1,2,4]triazin-4-yl)-2-methylbenzyl)-2H-tetrazole-5-carboxamide 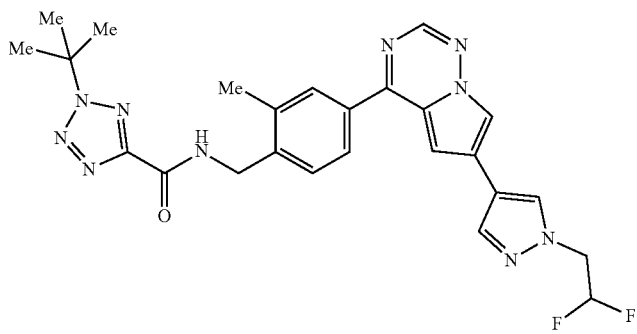 | Method B; 5-60% yellow solid: 15 mg, 23% LCMS m/z = 521.0 [M + H]+; 1H NMR (500 MHz, DMSO-d6) δ: 9.61 (br t, 1H), 8.57 (s, 1H), 8.51 (d, 1H), 8.30 (s, 1H), 8.07 (s, 1H), 8.01-7.97 (m, 2H), 7.48 (d, 1H), 7.44 (d, 1H), 6.39 (tt, 1H), 4.65 (td, 2H), 4.59 (d, 2H), 2.49 (s, 3H), 1.75 (s, 9H). |
| Example 147 | N-(4-(6-(1-(but-2-enoyl)-1H-pyrazol-4-yl)pyrrolo[2,1-f][1,2,4]triazin-4-yl)-2-methylbenzyl)-5-(tert-butyl)-1,2,4-oxadiazole-3-carboxamide 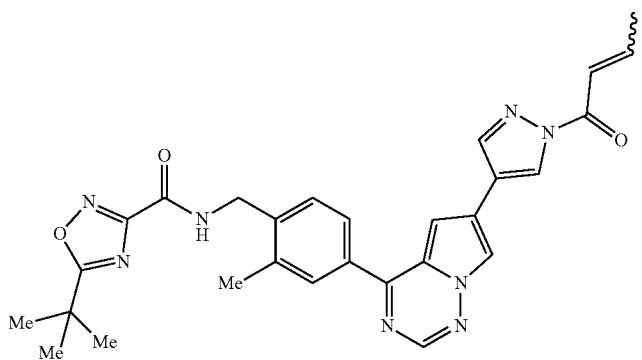 | SiO2; 0-100% EtOAc/Hept yellow solid: 18 mg, 49% LCMS m/z = 524.9 [M + H]+; 1H NMR (500 MHz, DMSO-d6) δ: 9.55 (t, 1H), 9.13-9.04 (m, 1H), 8.70 (d, 1H), 8.61 (s, 1H), 8.56-8.48 (m, 1H), 8.07-7.97 (m, 2H), 7.78-7.68 (m, 1H), 7.47 (d, 1H), 7.37-7.24 (m, 2H), 4.57 (d, 2H), 2.07-1.99 (m, 3H), 1.49-1.40 (m, 9H). |
| Example 148 | 5-(tert-butyl)-N-(2-methyl-4-(6-(6-methyl-3,6-diazabicyclo[3.1.1]heptan-3-yl)pyrrolo[2,1-f][1,2,4]triazin-4-yl)benzyl)-1,2,4-oxadiazole-3-carboxamide trifluoroacetate 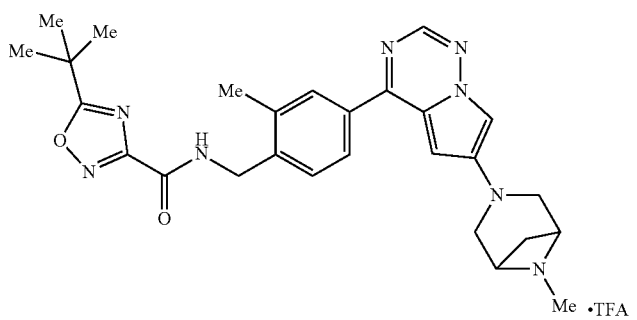 | Method B; 10-90% orange solid: 3 mg, 8% LCMS m/z = 501.3 [M + H]+; 1H NMR (400 MHz, MeOH-d4) δ: 10.34 (br s, 1H), 9.46-9.57 (m, 1H), 9.07 (br s, 1H), 8.51 (d, 1H), 7.91-8.06 (m, 2H), 7.44 (d, 1H), 6.63 (d, 1H), 4.55 (d, 2H), 4.49 (br s, 1H), 4.34 (br d, 1H), 3.67-3.91 (m, 4H), 3.31-3.42 (m, 1H), 3.05 (d, 2H), 2.80-2.92 (m, 1H), 2.46 (s, 3H), 1.98-2.07 (m, 1H), 1.44 (s, 9H). |

-continued

| Example Number | Name Structure | HPLC Method/Yield/Data |
|---|---|---|
| Example 149 | 5-(tert-butyl)-N-(2-methyl-4-(6-(1-methylpyrrolidin-3-yl)pyrrolo[2,1-f][1,2,4]triazin-4-yl)benzyl)-1,2,4-oxadiazole-3-carboxamide trifluoroacetate | Method B; 10-90% 29 mg (28%) LCMS m/z = 474.3 [M + H]+, 1H NMR (400 MHz, MeOH-d4) δ: 9.17-9.30 (m, 1H), 7.26-7.34 (m, 1H), 7.07-7.20 (m, 3H), 6.65-6.75 (m, 1H), 5.49-5.73 (m, 2H), 4.56-4.60 (m, 2H), 4.29-4.45 (m, 1H), 3.36-3.85 (m, 5H), 2.78-3.28 (m, 4H), 2.35-2.40 (m, 3H), 1.47-1.52 (m, 9H). |
| Example 150 | 5-(tert-butyl)-N-(4-(6-(1-cyclopropyl-1H-pyrazol-4-yl)pyrrolo[2,1-f][1,2,4]triazin-4-yl)-2-methylbenzyl)-1,2,4-oxadiazole-3-carboxamide hydrochloride | Method A; 35-55% yellow solid: 58 mg, 36% LCMS m/z = 497.2 [M + H]+ 1H NMR (400 MHz, DMSO-d6) δ: 9.56-9.53 (m, 1H), 8.55 (s, 1H), 8.46 (s, 1H), 8.31 (s, 1H), 7.99-7.94 (m, 3H), 7.47-7.41 (m, 2H), 4.56-4.55 (d, 2H), 3.76-3.70 (m, 1 H), 2.47 (s, 3H), 1.44 (s, 9H), 1.06-0.98 (m, 4H). |
| Example 151 | 5-(tert-butyl)-N-(2-methyl-4-(pyrrolo[2,1-f][1,2,4]triazin-4-yl)benzyl)-1,2,4-oxadiazole-3-carboxamide | Method B; 5-95% yellow solid: 22 mg, 17% LCMS m/z = 391.3 [M + H]+, 1H NMR (400 MHz, DMSO-d6) δ: 9.52 (br s, 1H), 8.61 (d, 1H), 8.18 (br d, 1H), 8.00-7.91 (m, 2H), 7.46 (br d, 1H), 7.23 (dd, 1H), 7.10 (br dd, 1H), 4.55 (br d, 2H), 2.46 (s, 3H), 1.45-1.40 (m, 9H). |
| Example 152 | 3-(tert-butyl)-N-(2-methyl-4-(pyrrolo[2,1-f][1,2,4]triazin-4-yl)benzyl)-1,2,4-oxadiazole-5-carboxamide trifluoroacetate | Method B; 5-95% yellow solid: 18 mg, 14% LCMS m/z = 391.3 [M + H]+ 1H NMR (400 MHz, DMSO-d6) δ: 9.90 (s, 1H), 8.61 (s, 1H), 8.18 (dd, 1H), 7.98-7.94 (m, 2H), 7.50 (d, 1H), 7.22 (dd, 1H), 7.10 (dd, 1H), 4.56 (d, 2H), 2.46 (s, 3H), 1.37 (s, 9H). |

-continued

| Example Number | Name Structure | HPLC Method/Yield/Data |
|---|---|---|
| Example 153 | 3-(tert-butyl)-N-(2-cyclopropyl-3-fluoro-4-(pyrrolo[2,1-f][1,2,4]triazin-4-yl)benzyl)-1,2,4-oxadiazole-5-carboxamide trifluoroacetate | Method B; 20-80% yellow solid: 20 mg, 16%<br>LCMS m/z = 435.6 [M + H]+<br>1H NMR (400 MHz, CDl3) δ: 8.65 (s, 1H), 8.10 (dd, 1H), 7.65-7.59 (m, 1H), 7.53 (br d, 1H), 7.35 (d, 1H), 7.17 (dd, 1H), 7.09-7.05 (m, 1H), 4.99 (d, 2H), 1.84-1.75 (m, 1H), 1.42 (s, 9H), 1.20-1.14 (m, 2H), 0.92-0.86 (m, 2H). |
| Example 154 | 5-(tert-butyl)-N-(2-chloro-3-fluoro-4-(6-morpholinopyrrolo[2,1-f][1,2,4]triazin-4-yl)benzyl)-1,2,4-oxadiazole-3-carboxamide trifluoroacetate | Method B; 10-95% yellow solid: 2 mg, 4%<br>LCMS m/z = 514.2 [M + H]+<br>1H NMR (400 MHz, CDCl3) δ: 8.58 (s, 1H), 7.82 (d,), 7.65 (dd, 1H), 7.56 (br t, 1H), 7.48 (d, 1H), 6.35-6.31 (m, 1H), 4.87 (d, 2H), 3.92-3.86 (m, 4H), 3.23 (dd, 4H), 1.49 (s, 9H). |
| Example 155 | 1-(tert-butyl)-N-(2-chloro-3-fluoro-4-(6-morpholinopyrrolo[2,1-f][1,2,4]triazin-4-yl)benzyl)-1,2,4-oxadiazole-3-carboxamide trifluoroacetate | Method B; 10-95% yellow solid: 3 mg, 4%<br>LCMS m/z = 512.3 [M + H]+<br>1H NMR (400 MHz, CDCl3) δ: 8.57 (s, 1H), 8.10 (s, 1H), 7.89 (s, 1H), 7.85 (d, 1H), 7.63 (dd, 1H), 7.45 (d, 1H), 6.53 (br t, 1H), 6.37-6.33 (m, 1H), 4.80 (d, 2H), 3.94-3.86 (m, 4H), 3.27-3.21 (m, 4H), 1.62 (s, 9H). |
| Example 156 | 5-(tert-butyl)-N-(2-chloro-3-fluoro-4-(6-morpholinopyrrolo[2,1-f][1,2,4]triazin-4-yl)benzyl)-1,3,4-oxadiazole-3-carboxamide trifluoroacetate | Method B; 10-95% red solid: 4 mg, 5%<br>LCMS m/z = 514.3 [M + H]+<br>1H NMR (400 MHz, CDCl3) δ: 8.52 (s, 1H), 7.69 (d, 1H), 7.68-7.66 (m, 1H), 7.53 (s, 1H), 7.45 (d, 1H), 6.27-6.24 (m, 1H), 4.85 (d, 2H), 3.92-3.87 (m, 4H), 3.21-3.17 (m, 4H), 1.49 (s, 9H). |

| Example Number | Name Structure | HPLC Method/Yield/Data |
| --- | --- | --- |
| Example 157 | 1-(tert-butyl)-N-(2-chloro-3-fluoro-4-(6-morpholinopyrrolo[2,1-f][1,2,4]triazin-4-yl)benzyl)-1H-1,2,3-trizole-carboxamide trifluoroacetate | Method B; 10-95% red solid: 9 mg, 8% LCMS m/z = 513.3 [M + H]+ $^1$H NMR (500 MHz, CDCl$_3$) δ: 8.56 (s, 1H), 8.23 (s, 1H), 7.80-7.76 (m, 1H), 7.75 (d, 1H), 7.65-7.62 (m, 1H), 7.45 (d, 1H), 6.32-6.27 (m, 1H), 4.86 (d, 2H), 3.92-3.86 (m, 4H), 3.23-3.18 (m, 4H), 1.75-1.70 (m, 9H). |
| Example 158 | 1-(tert-butyl)-N-(2-chloro-3-fluoro-4-(6-morpholinopyrrolo[2,1-f][1,2,4]triazin-4-yl)benzyl)-1H-pyrazole-3-carboxamide trifluoroacetate | Method B; 10-95% red solid: 11 mg, 10% LCMS m/z = 512.5 [M + H]+ $^1$H NMR (400 MHz, CDCl$_3$) δ: 8.63 (s, 1H), 8.00 (d, 1H), 7.75 (br t, 1H), 7.66-7.61 (m, 1H), 7.60-7.57 (m, 1H), 7.49 (d, 1H), 6.83 (d, 1H), 6.47 (t, 1H), 4.85 (d, 2H), 3.95-3.85 (m, 4H), 3.34-3.24 (m, 4H), 1.63 (s, 9H). |
| Example 159 | 3-(tert-butyl)-N-(2-chloro-4-(6-morpholinopyrrolo[2,1-f][1,2,4]triazin-4-yl)benzyl)-1,2,4-oxadiazole-5-carboxamide | Method B; 10-90% red solid: 8 mg, 7% LCMS m/z = 496.3 [M + H]+ $^1$H NMR (500 MHz, MeOH-d$_4$) δ: 8.45 (s, 1H), 8.15 (d, 1H), 8.08 (d, 1H), 7.98 (dd, 1H), 7.70-7.67 (m, 1H), 6.76 (d, 1H), 4.80-4.76 (m, 2H), 3.86-3.81 (m, 4H), 3.28-3.22 (m, 4H), 1.45-1.41 (m, 9H). |
| Example 160 | 1-(tert-butyl)-N-(2-chloro-4-(6-morpholinopyrrolo[2,1-f][1,2,4]triazin-4-yl)benzyl)-1H-pyrazole-4-carboxamide | Method B; 10-90% red solid: 7 mg, 6% LCMS m/z = 494.2 [M + H]+ $^1$H NMR (500 MHz, CDCl$_3$) δ: 8.56 (s, 1H), 8.10 (s, 1H), 8.00 (d, 1H), 7.88 (s, 1H), 7.85 (dd, 1H), 7.82 (d, 1H), 7.67 (d, 1H), 6.60-6.53 (m, 2H), 4.78 (d, 2H), 3.93-3.89 (m, 4H), 3.27-3.21 (m, 4H), 1.61 (s, 9H). |

| Example Number | Name Structure | HPLC Method/Yield/Data |
|---|---|---|
| Example 161 | 5-(tert-butyl)-N-(2-chloro-4-(6-morpholinopyrrolo[2,1-f][1,2,4]triazin-4-yl)benzyl)-1,3,4-oxadiazole-2-carboxamide | Method B; 10-90% red solid: 13 mg, 11% LCMS m/z = 496.2 [M + H]+ $^1$H NMR (500 MHz, CDCl$_3$) δ: 8.58 (s, 1H), 8.02 (d, 1H), 7.91-7.82 (m, 2H), 7.75 (brt, 1H), 7.69 (d, 1H), 6.55 (d, 1H), 4.84 (d, 2H), 3.94-3.88 (m, 4H), 3.28-3.21 (m, 4H), 1.51-1.45 (m, 9H). |
| Example 162 | 1-(tert-butyl)-N-(2-chloro-4-(6-morpholinopyrrolo[2,1-f][1,2,4]triazin-4-yl)benzyl)-1H-1,2,3-triazole-4-carboxamide | Method B; 10-90% orange solid: 9 mg, 9% LCMS m/z = 495.2 [M + H]+ $^1$H NMR (500 MHz, CDCl$_3$) δ: 8.47 (s, 1H), 8.23-8.18 (m, 1H), 8.10 (d, 1H), 7.94 (dd, 1H), 7.74 (br t, 1H), 7.64 (d, 1H), 7.61 (d, 1H), 6.48 (d, 1H), 4.85 (d, 2H), 3.95-3.88 (m, 4H), 3.22-3.15 (m, 4H), 1.76-1.71 (m, 9H). |
| Example 163 | 5-(tert-butyl)-N-(2-cyclopropyl-3-fluoro-4-(6-morpholinopyrrolo[2,1-f][1,2,4]triazin-4-yl)benzyl)-1,3,4-oxadiazole-2-carboxamide | SiO$_2$; 0-100% EtOAc/Hept followed by prep TLC, 3:1 EtOAc/Hept orange solid: 4 mg, 3% LCMS m/z = 520.3 [M + H]+ $^1$H NMR (500 MHz, CDCl$_3$) δ: 8.49 (s, 1H), 7.68-7.58 (m, 2H), 7.58-7.49 (m, 1H), 7.32-7.28 (m, 1H), 6.22 (br s, 1H), 4.95 (d, 2H), 3.91-3.86 (m, 4H), 3.21-3.13 (m, 4H), 1.85-1.76 (m, 1H), 1.52-1.46 (m, 9H), 1.17-1.11 (m, 2H), 0.90-0.83 (m, 2H). |
| Example 164 | 1-(tert-butyl)-N-(2-cyclopropyl-3-fluoro-4-(6-morpholinopyrrolo[2,1-f][1,2,4]triazin-4-yl)benzyl)-1H-1,2,3-triazole-4-carboxamide | Method B; 10-90% orange solid: 8 mg, 7% LCMS m/z = 519.3 [M + H]+ $^1$H NMR (500 MHz, CDCl$_3$) δ: 8.48 (s, 1H), 8.22-8.18 (m, 1H), 7.66-7.54 (m, 2H), 7.34-7.29 (m, 1H), 6.23 (br s, 1H), 4.95 (d, 2H), 3.91-3.85 (m, 4H), 3.20-3.13 (m, 4H), 1.87-1.79 (m, 1H), 1.72 (s, 9H), 1.17-1.11 (m, 2H), 0.91-0.84 (m, 2H). |

| Example Number | Name Structure | HPLC Method/Yield/Data |
|---|---|---|
| Example 165 | 5-(tert-butyl)-N-(2-methyl-4-(6-(1-methyl-1H-pyrazol-4-yl)pyrrolo[2,1-f][1,2,4]triazin-4-yl)benzyl)-1,3,4-oxadiazole-2-carboxamide | Method B; 10-90% yellow solid: 34 mg, 34% LCMS m/z = 471.3 [M + H]+ $^1$H NMR (400 MHz, CDCl$_3$) δ: 8.61 (s, 1H), 8.18 (s, 1H), 7.99-7.88 (m, 2H), 7.86 (s, 1H), 7.72 (s, 1H), 7.58 (d, 1H), 7.49 (br s, 1H), 4.77 (d, 2H), 4.02 (s, 3H), 2.54 (s, 3H), 1.52-1.47 (m, 9H). |
| Example 166 | 1-(tert-butyl)-N-(2-methyl-4-(6-(1-methyl-1H-pyrazol-4-yl)pyrrolo[2,1-f][1,2,4]triazin-4-yl)benzyl)-1H-1,2,3-triazole-4-carboxamide | Prep-TLC, 2:1 EtOAc/Hept yellow solid: 78 mg, 68% LCMS m/z = 470.2 [M + H]+ $^1$H NMR (400 MHz, CDCl$_3$) δ: 8.58 (s, 1H), 8.26 (s, 1H), 8.13 (d, 1H), 7.94-7.85 (m, 2H), 7.84 (s, 1H), 7.71 (s, 1H), 7.67 (br t, 1H), 7.56 (d, 1H), 7.33-7.31 (m, 1H), 7.22 (s, 1H), 4.77 (d, 2H), 4.06-3.98 (m, 3H), 2.52 (s, 3H), 1.74-1.69 (m, 9H), |
| Example 167 | 1-(tert-butyl)-N-(2-methyl-4-(6-(1-methyl-1H-pyrazol-4-yl)pyrrolo[2,1-f][1,2,4]triazin-4-yl)benzyl)-1H-pyrazole-4-carboxamide | Method B; 10-90% yellow solid: 23 mg, 34% LCMS m/z = 469.3 [M + H]+ $^1$H NMR (500 MHz, CDCl$_3$) δ: 8.55 (s, 1H), 8.12 (d, 2H), 7.92-7.84 (m, 3H), 7.81 (s, 1H), 7.70 (s, 1H), 7.51 (d, 1H), 7.23-7.18 (m, 1H), 6.38 (br s, 1H), 4.70 (d, 2H), 4.02-3.97 (m, 3H), 2.53-2.46 (m, 3H), 1.65-1.59 (m, 9H). |
| Example 168 | 1-(tert-butyl)-N-(2-methyl-4-(6-(1-methyl-1H-pyrazol-4-yl)pyrrolo[2,1-f][1,2,4]triazin-4-yl)benzyl)-1H-pyrazole-3-carboxamide | Method B; 10-90% + prep-TLC (2:1 EtOAc/Hept) yellow solid: 22 mg, 27% LCMS m/z = 469.3 [M + H]+ $^1$H NMR (500 MHz, CDCl$_3$) δ: 8.65-8.56 (m, 1H), 8.14 (s, 1H), 7.94-7.87 (m, 2H), 7.83 (s, 1H), 7.70 (s, 1H), 7.63-7.54 (m, 2H), 7.42-7.32 (m, 1H), 7.24 (s, 1H), 6.85 (d, 1H), 4.75 (d, 2H), 4.05-3.97 (m, 3H), 2.52 (s, 3H), 1.66-1.58 (m, 9H). |

-continued

| Example Number | Name Structure | HPLC Method/Yield/Data |
|---|---|---|
| Example 169 | 5-(tert-butyl)-N-(2-methyl-4-(6-(pyridin-3-yl)pyrrolo[2,1-f][1,2,4]triazin-4-yl)benzyl)-1,2,4-oxadiazole-3-carboxamide | Method B; 10-90% yellow solid: 25 mg, 60%<br>LCMS m/z = 468.2 [M + H]+<br>$^1$H NMR (500 MHz, MeOH-d$_4$) δ: 9.28 (d, 1H), 8.93-8.85 (m, 1H), 8.74-8.67 (m, 1H), 8.63 (d, 1H), 8.55-8.50 (m, 1H), 8.04-7.92 (m, 3H), 7.69 (d, 1H), 7.54 (d, 1H), 4.70 (s, 2H), 2.53 (s, 3H), 1.52-1.47 (m, 9H). |
| Example 170 | 5-(tert-butyl)-N-(2-methyl-4-(6-(6-methylpyridazin-4-yl)pyrrolo[2,1-f][1,2,4]triazin-4-yl)benzyl)-1,2,4-oxadiazole-3-carboxamide trifluoroacetate | Method B; 10-90% yellow solid: 31 mg, 53%<br>LCMS m/z = 483.5 [M + H]+<br>$^1$H NMR (500 MHz, CDCl$_3$) δ: 11.31 (br s, 1H), 9.47 (d, 1H), 8.67-8.57 (m, 1H), 8.41 (d, 1H), 7.99-7.88 (m, 3H), 7.55 (d, 1H), 7.48 (d, 1H), 7.35 (br t, 1H), 4.78 (d, 2H), 2.95-2.84 (m, 3H), 2.58-2.50 (m, 3H), 1.55-1.43 (m, 9H). |
| Example 171 | 3-(tert-butyl)-N-(2-methyl-4-(6-(6-methylpyridazin-4-yl)pyrrolo[2,1-f][1,2,4]triazin-4-yl)benzyl)-1,2,4-oxadiazole-3-carboxamide trifluoroacetate | Method B; 10-90% yellow solid: 9 mg, 15%<br>LCMS m/z = 483.5 [M + H]+<br>$^1$H NMR (500 MHz, CDCl$_3$) δ: 9.50 (s, 1H), 8.69-8.59 (m, 1H), 8.44 (s, 1H), 8.04-7.88 (m, 3H), 7.58 (br d, 1H), 7.54-7.46 (m, 1H), 7.42 (br t, 1H), 7.49-7.15 (br s, 1H), 4.79 (d, 2H), 2.94 (s, 3H), 2.55 (s, 3H), 1.44-1.36 (m, 9H). |
| Example 172 | 5-(tert-butyl)-N-(4-(6-(isothiazol-4-yl)pyrrolo[2,1-f][1,2,4]triazin-4-yl)-2-methylbenzyl)-1,2,4-oxadiazole-3-carboxamide trifluoroacetate | Method B; 10-90% yellow solid: 44 mg, 70%<br>LCMS m/z = 474.1 [M + H]+<br>$^1$H NMR (500 MHz, CDCl$_3$) δ: 11.36-10.60 (brs, 1H), 8.92-8.79 (m, 2H), 8.65 (s, 1H), 8.37-8.24 (m, 1H), 7.96-7.82 (m, 2H), 7.64-7.52 (m, 1H), 7.39 (br s, 2H), 4.80 (br d, 2H), 2.59-2.48 (m, 3H), 1.53-1.43 (m, 9H). |

| Example Number | Name Structure | HPLC Method/Yield/Data |
|---|---|---|
| Example 173 | 3-(tert-butyl)-N-(4-(6-(isothiazol-4-yl)pyrrolo[2,1-f][1,2,4]triazin-4-yl)-2-methylbenzyl)-1,2,4-oxadiazole-5-carboxamide trifluoroacetate 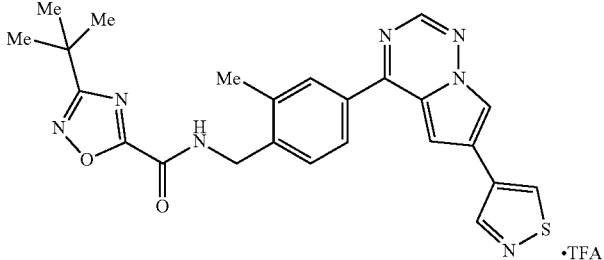 | Method B; 10-90% yellow solid: 10 mg, 13% LCMS m/z = 474.1 [M + H]+ $^1$H NMR (500 MHz, CDCl$_3$) δ: 1.41 (s, 9H), 2.54 (s, 3H), 4.79 (d, 2H), 6.04 (br s, 1H), 131-132 (m, 1H), 7.39 (br s, 1H), 7.59 (d, 1H), 7.93 (br s, 2H), 8.28 (d, 1H), 8.64 (s, 1H), 8.83 (d, 2H), |
| Example 174 | 5-(tert-butyl)-N-(4-(6-((2-methoxyethyl)(methyl)amino)pyrrolo[2,1-f][1,2,4]triazin-4-yl)-2-methylbenzyl-1,2,4-oxadiazole-3-carboxamide 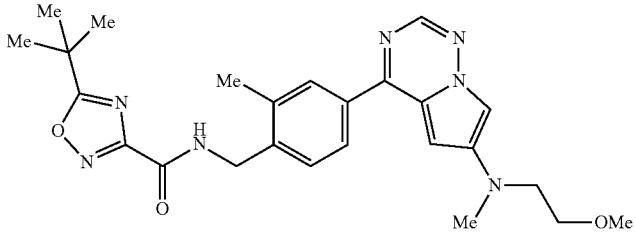 | SiO$_2$; Hept/EtOAc 0-100% yellow solid: 19 mg, 22% LCMS m/z = 478.2 [M + H]+ $^1$H NMR (500 MHz, CDCl$_3$) δ: 8.44-8.36 (m, 1H), 7.94-7.83 (m, 2H), 7.53-7.45 (m, 2H), 7.27-7.20 (m, 1H), 6.31 (d, 1H), 4.75 (d, 2H), 3.60 (t, 2H), 3.50-3.42 (m, 2H), 3.36 (s, 3H), 3.05-2.95 (m, 3H), 2.54-2.45 (m, 3H), 1.55-1.42 (m, 9H), |
| Example 175 | 1-(tert-butyl)-N-(2-methyl-4-(6-morpholinopyrrolo[2,1-f][1,2,4]triazin-4-yl)benzyl)-1H-pyrazole-3-carboxamide 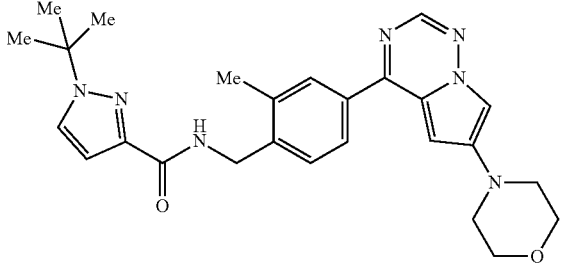 | Method B; 10-90% orange solid: 11 mg, 15% LCMS m/z = 474.3 [M + H]+ $^1$H NMR (500 MHz, CDCl$_3$) δ: 8.66-8.57 (m, 1H), 7.87-7.75 (m, 3H), 7.61-7.53 (m, 2H), 7.35 (br t, 1H), 6.83 (d, 1H), 6.63 (d, 1H), 4.73 (d, 2H), 3.96-3.83 (m, 4H), 3.27-3.19 (m, 4H), 2.50 (s, 3H), 1.64-1.58 (m, 9H). |
| Example 176 | 2-(tert-butyl)-N-(2-methyl-4-(6-morpholinopyrrolo[2,1-f][1,2,4]triazin-4-yl)benzyl)oxazole-4-carboxamide 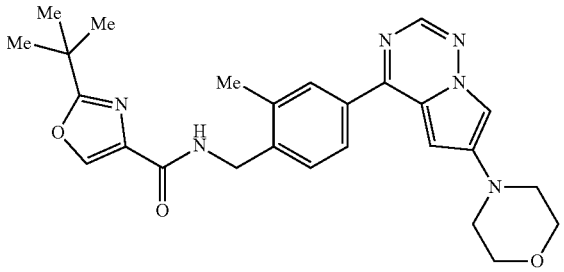 | Method B; 10-90% orange solid: 18 mg, 25% LCMS m/z = 475.2 [M + H]+ $^1$H NMR (500 MHz, CDCl$_3$) δ: 8.58 (s, 1H), 8.15 (s, 1H), 7.88-7.79 (m, 2H), 7.75 (d, 1H), 7.52 (d, 1H), 7.32 (br t, 1H), 6.58 (d, 1H), 4.70 (d, 2H), 3.95-3.85 (m, 4H), 3.26-3.14 (m, 4H), 2.49 (s, 3H), 1.43-1.35 (m, 9H). |

-continued

| Example Number | Name Structure | HPLC Method/Yield/Data |
|---|---|---|
| Example 177 | 5-(tert-butyl)-N-(2-methyl-4-(6-(4-methyl-3-oxopiperazin-1-yl)pyrrolo[2,1-f][1,2,4]triazin-4-yl)benzyl)-1,2,4-oxadiazole 3-carboxamide | SiO$_2$ (0-10% EtOAc/MeOH) orange solid: 76 mg, 52%<br>LCMS m/z = 503.2 [M + H]$^+$<br>$^1$H NMR (500 MHz, CDCl$_3$) δ: 8.54-8.47 (m, 1H), 7.98-7.86 (m, 2H), 7.67-7.58 (m, 1H), 7.52 (d, 1H), 7.25 (br s, 1H), 6.52 (s, 1H), 4.78 (d, 2H), 3.92-3.87 (m, 2H), 3.59-3.53 (m, 2H), 3.53-3.46 (m, 2H), 3.11-3.04 (m, 3H), 2.54-2.48 (m, 3H), 1.53-1.46 (m, 9H). |
| Example 178 | 5-(tert-butyl)-N-(2-chloro-4-(pyrrolo[2,1-f][1,2,4]triazin-4-yl)benzyl)-1,2,4-oxadiazole-3-carboxamide hydrochloride | Method A; 45-65% yellow solid: 34 mg, 16%<br>LCMS m/z = 411.0 [M+H]$^+$<br>$^1$H NMR (500 MHz, DMSO-d$_6$) δ: 9.64 (t, 1H), 8.65 (s, 1H), 8.24-8.22 (m, 1H), 8.15 (d, 1H), 8.14-8.11 (m, 1H), 7.58 (d, 1H), 7.25 (dd, 1H), 7.16-7.13 (m, 1H), 4.64 (d, 2H), 1.45 (s, 9H). |
| Example 179 | 5-(tert-butyl)-N-(4-(pyrrolo[2,1-f][1,2,4]triazin-4-yl)-2-(trifluoromethyl)benzyl)-1,2,4-oxadiazole-3-carboxamide hydrochloride | Method A; 34-54% yellow solid: 83 mg, 30%<br>LCMS m/z = 445.1 [M+H]$^+$<br>H NMR (400 MHz, MeOH-d$_4$) δ: 9.70 (s, 1H), 8.68 (s, 1H), 8.47-8.42 (t, 2H), 8.25 (d, 1H), 7.75 (d, 1H), 7.25 (d, 1H), 7.16-7.15 (m, 1H), 4.76 (d, 2H), 1.45 (s, 9H). |
| Example 180 | 5-(tert-butyl)-N-(3-fluoro-2-methoxy-4-(pyrrolo[2,1-f][1,2,4]triazin-4-yl)benzyl)-1,2,4-oxadiazole-3-carboxamide hydrochloride | Method A; 34-54% yellow solid: 40 mg, 25%<br>LCMS m/z = 425.1 [M + H]$^+$<br>$^1$H NMR (400 MHz, DMSO-d$_6$) δ: 9.55-9.52 (m, 1H), 8.66 (s, 1H), 8.23-8.22 (m, 1H), 7.53-7.49 (m, 1H), 7.28 (d, 1H), 7.12-7.10 (m, 1H), 6.91 (d, 1H), 4.60 (d, 2H), 3.99 (s, 3H), 1.44 (s, 9H). |

| Example Number | Name Structure | HPLC Method/Yield/Data |
|---|---|---|
| Example 181 | 5-(tert-butyl)-N-(2-(difluoromethyl)-4-(pyrrolo[2,1-f][1,2,4]triazin-4-yl)benzyl)-1,2,4-oxadiazole-3-carboxamide hydrochloride 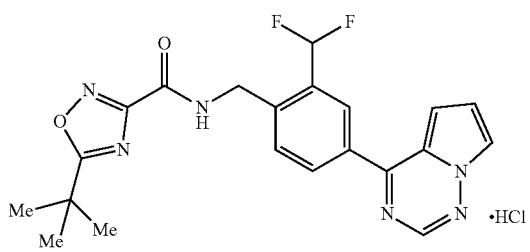 | Method A; 44-64% yellow solid: 116 mg, 42%<br>LCMS m/z = 427.1 [M + H]$^+$<br>$^1$H NMR (400 MHz, MeOH-d$_4$) δ: 8.63 (s, 1H), 8.42-8.39 (m, 1H), 8.29 (s, 1H), 8.24-8.20 (m, 1H), 7.82 (d, 1H), 7.54 (dd, 1H), 7.46-7.17 (m, 2H), 4.85 (s, 2H), 1.48 (s, 9H). |
| Example 182 | 1-(tert-butyl)-N-(2-methyl-4-(pyrrolo[2,1-f][1,2,4]triazin-4-yl)benzyl)-1H-pyrazole-3-carboxamide hydrochloride 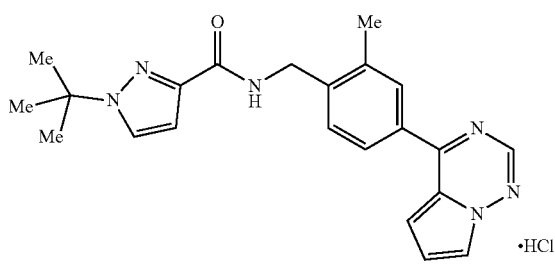 | Method A; 38-58% yellow solid: 69 mg, 41%<br>LCMS m/z = 389.1 [M + H]$^+$<br>$^1$H NMR (400 MHz, MeOH-d$_4$) δ: 8.71 (s, 1H), 8.64-8.62 (m, 1H), 7.93-7.89 (m, 2H), 7.85 (dd, 1H), 7.83 (d, 1H), 7.66 (d, 1H), 7.51 (dd, 2.0 Hz, 1H), 6.75 (d, 1H), 4.70 (s, 2H), 2.56 (s, 3H), 1.63 (s, 9H). |
| Example 183 | 1-(tert-butyl)-N-(2-methyl-4-(pyrrolo[2,1-f][1,2,4]triazin-4-yl)benzyl)-1H-pyrazole-4-carboxamide hydrochloride 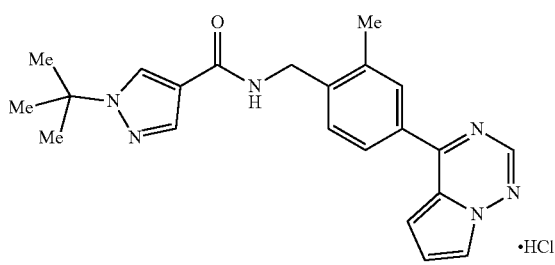 | Method A; 31-51% yellow solid: 68 mg, 49%<br>LCMS m/z = 389.1 [M + H]$^+$<br>$^1$H NMR (400 MHz, DMSO-d$_4$) δ: 8.65-8.60 (m, 2H), 8.36 (s, 1H), 8.23-8.20 (m, 1H), 7.95-7.90 (m, 3H), 7.44 (d, 1H), 7.26 (dd, 1H), 7.12 (dd, 1H), 4.47 (d, 2H), 2.42 (s, 3H), 1.50 (s, 9H). |
| Example 184 | 1-(tert-butyl)-N-(2-methyl-4-(pyrrolo[2,1-f][1,2,4]triazin-4-yl)benzyl)-1H-1,2,3-triazole-4-carboxamide hydrochloride 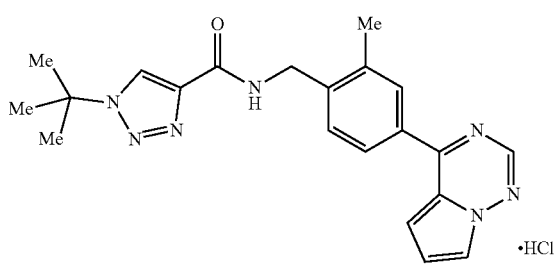 | Method A; 33-53% yellow solid: 67 mg, 49%<br>LCMS m/z = 390.1 [M + H]$^+$<br>$^1$H NMR (400 MHz, MeOH-d$_4$) δ: 9.10 (t, 1H), 8.72 (s, 1H), 8.61 (s, 1H), 8.24-8.21 (m, 1H), 7.93-7.89 (m, 2H), 7.45-7.41 (m, 1H), 7.29-7.25 (m, 1H), 7.12 (dd, 1H), 4.52 (d, 2H), 2.43 (s, 3H), 1.61 (s, 9H). |

| Example Number | Name Structure | HPLC Method/Yield/Data |
|---|---|---|
| Example 185 | 5-(tert-butyl)-N-(2-methyl-4-(pyrrolo[2,1-f][1,2,4]triazin-4-yl)benzyl)-1,3,4-oxadiazole-2-carboxamide hydrochloride 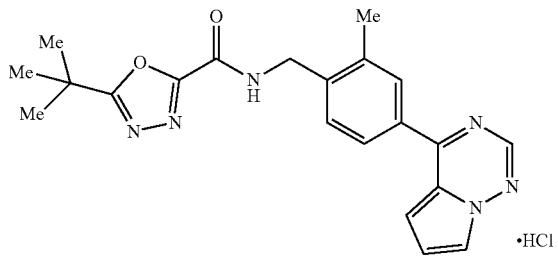 | Method A; 33-53% yellow solid: 73 mg, 24% LCMS m/z = 391.1 [M + H]$^+$ $^1$H NMR (400 MHz, DMSO-d$_6$) δ: 9.86-9.83 (m, 1H), 8.60 (s, 1H), 8.17 (d, 1H), 7.95 (d, 1H), 7.48 (d, 1H), 7.21 (d, 1H), 7.11-7.09 (m, 1H), 4.55 (d, 2H), 2.46 (s, 3H), 1.40 (s, 9H). |
| Example 186 | 3-(tert-butyl)-N-(4-(6-morpholinopyrrolo[2,1-f][1,2,4]triazin-4-yl)-2-(trifluoromethyl)benzyl)-1,2,4-oxadiazole-5-carboxamide hydrochloride 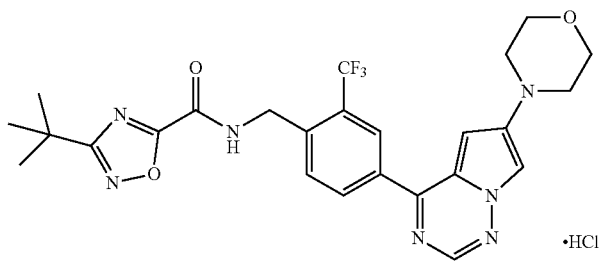 | Method A; 58-78% red solid: 45 mg, 50% LCMS m/z = 530.3 [M + H]$^+$ $^1$H NMR (500 MHz, DMSO-d$_6$) δ: 10.09 (t, 1H), 8.58 (s, 1H), 8.44-8.41 (m, 2H), 8.16 (s, 1H), 7.78 (d, 1H), 6.82 (d, 1H), 4.76 (d, 2H), 3.79-3.75 (m, 4H), 3.21-3.18 (m, 4H), 1.40 (m, 9H). |
| Example 187 | 1-(tert-butyl)-N-(4-(6-morpholinopyrrolo[2,1-f][1,2,4]triazin-4-yl)-2-(trifluoromethyl)benzyl)-1H-1,2,3-triazole-4-carboxamide hydrochloride 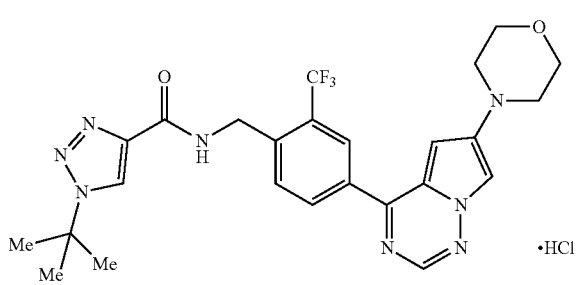 | Method A; 50-70% red solid: 56 mg, 63% LCMS m/z = 529.2 [M + H]$^+$ $^1$H NMR (500 MHz, DMSO-d$_6$) δ: 9.33 (t, 1H), 8.79 (s, 1H), 8.58 (s, 1H), 8.44-8.41 (m, 2H), 8.17 (d, 1H), 7.70 (d, 1H), 6.84 (d, 1H), 4.76 (d, 2H), 3.77-3.74 (m, 4H), 3.21-3.18 (m, 4H), 1.67 (m, 9H). |
| Example 188 | 1-(tert-butyl)-N-(2-methoxy-4-(6-(1-methyl-1H-pyrazol-4-yl)pyrrolo[2,1-f][1,2,4]triazin-4-yl)benzyl)-1H-1,2,3-triazole-4-carboxamide hydrochloride 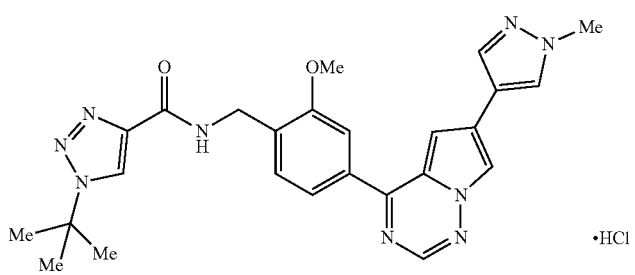 | Method A; yellow solid: 29 mg, 40% LCMS m/z = 527.2 [M + H]$^+$ $^1$H NMR (500 MHz, DMSO-d$_6$) δ: 9.01 (t, 1H), 8.73 (s, 1H), 8.58 (s, 1H), 8.49 (d, 1H), 8.20 (s, 1H), 7.95 (d, 1H), 7.75 (dd, 1H), 7.68 (d, 1H), 7.44 (d, 1H), 131 (d, 1H), 4.54 (d, 2H), 3.98 (s, 3H), 3.86 (s, 3H), 1.65 (s, 9H). |

| Example Number | Name Structure | HPLC Method/Yield/Data |
|---|---|---|
| Example 189 | 3-(tert-butyl)-N-(2-methoxy-4-(6-(1-methyl-1H-pyrazol-4-yl)pyrrolo[2,1-f][1,2,4]triazin-4-yl)benzyl)-1,2,4-oxadiazole-5-carboxamide hydrochloride | Method A; 49-69% orange solid: 21 mg, 40% LCMS m/z = 487.1 [M + H]$^+$ $^1$H NMR (400 MHz, DMSO-d$_6$) δ: 9.83 (s, 1H), 8.58 (s, 1H), 8.48 (s, 1H), 8.20 (s, 1H), 7.95 (s, 1H), 7.76 (s, 1H), 7.68 (s, 1H), 7.42 (s, 2H), 4.54 (s, 2H), 3.97 (s, 3H), 3.86 (s, 3H), 1.38 (s, 9H). |
| Example 190 | 3-(tert-butyl)-N-(2-(difluoromethyl)-4-(6-(1-methyl-1H-pyrazol-4-yl)pyrrolo[2,1-f][1,2,4]triazin-4-yl)benzyl)-1,2,4-oxadiazole-5-carboxamide | Method E; 55-80% yellow solid: 21 mg, 32% LCMS m/z = 507.2 [M + H]$^+$ $^1$H NMR (400 MHz, DMSO-d$_6$) δ: 10.04 (t, 1H), 8.62 (s, 1H), 8.52 (d, 1H), 8.40-8.35 (m, 2H), 8.20 (s, 1H), 7.95 (s, 1H), 7.73 (d, 1H), 7.48-7.34 (m, 2H), 4.77 (d, 2H), 3.88(s, 3H), 1.39 (s, 9H). |
| Example 191 | 5-(tert-butyl)-N-(2-(difluoromethyl)-4-(6-(1-methyl-1H-pyrazol-4-yl)pyrrolo[2,1-f][1,2,4]triazin-4-yl)benzyl)-1,3,4-oxadiazole-2-carboxamide | Method D; 38-68% yellow solid: 25 mg, 35% LCMS m/z = 507.2 [M + H]$^+$ $^1$H NMR (400 MHz, DMSO-d$_6$) δ: 9.99 (t, 1H), 8.62 (s, 1H), 8.53-8.52 (m, 1H), 8.36-8.35 (m, 2H), 8.21 (s, 1H), 7.96 (s, 1H), 7.73-7.70 (m, 1H), 7.49-7.35 (m, 2H), 4.76 (d, 2H), 3.88 (s, 3H), 1.42 (s, 9H). |
| Example 192 | 3-(tert-butyl)-N-(2-(difluoromethyl)-4-(6-morpholinopyrrolo[2,1-f][1,2,4]triazin-4-yl)benzyl)-1,2,4-oxadiazole-5-carboxamide | Method E; 60-90% yellow solid: 14 mg, 28% LCMS m/z = 511.9 [M + H]$^+$ $^1$H NMR (500 MHz, DMSO-d$_6$) δ: 10.02 (t, 1H), 8.54 (s, 1H), 8.34-8.30 (m, 2H), 8.07 (d, 1H), 7.68 (d, 1H), 7.57-7.34 (m, 1H), 6.77 (d, 1H), 4.76-4.74 (m, 2H), 3.78-3.75 (m, 4H), 3.20-3.17 (m, 4H), 1.39 (s, 9H). |

-continued

| Example Number | Name Structure | HPLC Method/Yield/Data |
|---|---|---|
| Example 193 | 5-(tert-butyl)-N-(2-(difluoromethyl)-4-(6-morpholinopyrrolo[2,1-f][1,2,4]triazin-4-yl)benzyl)-1,3,4-oxadiazole-2-carboxamide | Method D; 35-65% yellow solid: 13 mg, 22% LCMS m/z = 512.1 [M + H]$^+$ $^1$H NMR (500 MHz, DMSO-d$_6$) δ: 9.97 (t, 1H), 8.54 (s, 1H), 8.33-8.30 (m, 2H), 8.07 (d, 1H), 7.67 (d, 1H), 7.58-7.47 (m, 1H), 6.77 (d, 1H), 4.74 (d, 2H), 3.78-3.75 (m, 4H), 3.20-3.17 (m, 4H), 1.42 (s, 9H). |
| Example 194 | 3-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,2,4-oxadiazole-5-carboxamide | Method E; 45-75% yellow solid: 39 mg, 67% LCMS m/z = 525.1 [M + H]$^+$ $^1$H NMR (500 MHz, DMSO-d$_6$) δ: 10.05 (t, 1H), 8.63 (s, 1H), 8.55 (d, 1H), 8.19 (s, 1H), 8.00 (t, 1H), 7.93 (s, 1H), 7.65-7.44 (m, 2H), 7.06 (s, 1H), 4.82 (d, 2H), 3.86 (s, 3H), 1.39 (s, 9H). |
| Example 195 | 1-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1H-1,2,3-triazole-4-carboxamide | Method E; 58-78% yellow solid: 36 mg, 57% LCMS m/z = 524.1 [M + H]$^+$ $^1$H NMR (500 MHz, DMSO-d$_6$) δ: 9.32 (t, 1H), 8.76 (s, 1H), 8.62 (s, 1H), 8.55 (d, 1H), 8.19 (s, 1H), 7.98(t, 1H), 7.92 (s, 1H), 7.70-7.47 (m, 2H), 7.05 (s, 1H), 4.80 (d, 2H), 3.86 (s, 3H), 1.66 (s, 9H). |
| Example 196 | 5-(tert-butyl)-N-(2-(difluoromethyl)-3-fluoro-4-(6-(1-methyl-1H-pyrazol-4-yl)pyrrolo[2,1-f][1,2,4]triazin-4-yl)benzyl)-1,3,4-oxadiazole-2-carboxamide | Method D; 35-65% yellow solid: 24 mg, 41% LCMS m/z = 525.1 [M + H]$^+$ $^1$H NMR (500 MHz, DMSO-d$_6$) δ: 10.00 (t, 1H), 8.63 (s, 1H), 8.55 (d, 1H), 8.19(s, 1H), 8.00 (t, 1H), 7.93 (s, 1H), 7.66-7.44 (m, 2H), 7.06 (s, 1H), 4.81 (d, 2H), 3.86 (s, 3H), 1.42 (s, 9H). |

| Example Number | Name Structure | HPLC Method/Yield/Data |
|---|---|---|
| Example 197 | 5-(tert-butyl)-N-(2-methoxy-4-(6-(1-methyl-1H-pyrazol-4-yl)pyrrolo[2,1-f][1,2,4]triazin-4-yl)benzyl)-1,3,4-oxadiazole-2-carboxamide | Method D; 35-65% yellow solid: 38 mg, 44%<br>LCMS m/z = 487.1 [M + H]+<br>$^1$H NMR (500 MHz, CDCl$_3$) δ: 8.50 (s, 1H), 8.03 (s, 1H), 7.77 (s, 1H), 7.69 (m, 2H), 7.66 (m, 2H), 7.55 (d, 1H), 7.11 (s, 1H), 4.73 (d, 2H), 4.04 (s, 3H), 3.98 (s, 3H), 1.47 (s, 9H). |
| Example 198 | 2-(tert-butyl)-N-(2-(difluoromethyl)-4-(6-morpholinopyrrolo[2,1-f][1,2,4]triazin-4-yl)benzyl)oxazole-4-carboxamide hydrochloride | Method A; 46-76% red solid: 17 mg, 29%<br>LCMS m/z = 511.1 [M + H]$^+$<br>$^1$H NMR (500 MHz, DMSO-d$_6$) δ: 8.88-8.84 (m, 1H), 8.58 (s, 1H), 8.55 (s, 1H), 8.32-8.30 (m, 2H), 8.11 (d, 1H), 7.64-7.40 (m, 2H), 6.79 (d, 1H), 4.69 (d, 2H), 3.78-3.75 (m, 4H), 3.20-3.17 (m, 4H), 1.39 (s, 9H). |
| Example 199 | 5-(tert-butyl)-N-(2-(difluoromethyl)-3-fluoro-4-(6-morpholinopyrrolo[2,1-f][1,2,4]triazin-4-yl)benzyl)-1,3,4-oxadiazole-2-carboxamide | Method D; 40-70% yellow solid: 43 mg, 61%<br>LCMS m/z = 530.2 [M + H]+<br>$^1$H NMR (500 MHz, DMSO-d$_6$) δ: 9.92 (t, 1H), 8.49 (s, 1H), 8.05 (d, 1H), 7.89 (t, 1H), 7.61-7.34 (m, 2H), 6.33 (s, 1H), 4.75 (d, 2H), 3.71-3.68 (m, 4H), 3.11-3.08 (m, 4H), 1.38 (s, 9H). |
| Example 200 | 1-(tert-butyl)-N-(3-fluoro-2-methoxy-4-(6-(1-methyl-1H-pyrazol-4-yl)pyrrolo[2,1-f][1,2,4]triazin-4-yl)benzyl)-1H-1,2,3-triazole-4-carboxamide | Method E; 45-68% yellow solid: 37 mg, 57%<br>LCMS m/z = 504.1 [M + H]+<br>$^1$H NMR (500 MHz, DMSO-d$_6$) δ: 9.17-9.14 (m, 1H), 8.74 (s, 1H), 8.60 (s, 1H), 8.52 (s, 1H), 8.19 (s, 1H), 7.94 (s, 1H), 7.52-7.49 (m, 1H), 7.28 (d, 1H), 7.06 (s, 1H), 4.62 (d, 2H), 4.02 (s, 3H), 3.86 (s, 3H), 1.65 (s, 9H). |

| Example Number | Name Structure | HPLC Method/Yield/Data |
|---|---|---|
| Example 201 | 5-(tert-butyl)-N-(3-fluoro-2-methoxy-4-(6-(1-methyl-1H-pyrazol-4-yl)pyrrolo[2,1-f][1,2,4]triazin-4-yl)benzyl)-1,3,4-oxadiazole-2-carboxamide | Method D; 33-63% yellow solid: 22 mg, 35%<br>LCMS m/z = 505.1 [M + H]+<br>$^1$H NMR (500 MHz, DMSO-$d_6$) δ: 9.89 (t, 1H), 8.61 (s, 1H), 8.53 (d, 1H), 8.20 (s, 1H), 7.94-7.93 (m, 1H), 7.53-7.50 (m, 1H), 7.35-7.32 (m, 1H), 7.07-7.05 (m, 1H), 4.61 (d, 2H), 4.01 (d, 3H), 3.86 (s, 3H), 1.42 (s, 9H). |
| Example 202 | 1-(tert-butyl)-N-(3-fluoro-2-methoxy-4-(6-morpholinopyrrolo[2,1-f][1,2,4]triazin-4-yl)benzyl)-1H-pyrazole-3-carboxamide formate | Method E; 51-74% yellow solid: 22 mg, 35%<br>LCMS m/z = 508.2 [M + H]+<br>$^1$H NMR (400 MHz, DMSO-$d_6$) δ: 8.58 (t, 1H), 8.48 (s, 1H), 8.03 (d, 1H), 7.92 (d, 1H), 7.47-7.39 (m, 1H), 7.21 (d, 1H), 6.65 (d, 1H), 6.34 (s, 1H), 4.55 (d, 2H), 3.97 (s, 3H), 3.76-3.66 (m, 4H), 3.15-3.06 (m, 4H), 1.56 (s, 9H). |
| Example 203 | 3-(tert-butyl)-N-(3-fluoro-2-methoxy-4-(6-morpholinopyrrolo[2,1-f][1,2,4]triazin-4-yl)benzyl)-1,2,4-oxadiazole-5-carboxamide formate | Method E; 50-77% yellow solid: 20 mg, 30%<br>LCMS m/z = 510.2 [M + H]+<br>$^1$H NMR (400 MHz, DMSO-$d_6$) δ: 9.90 (t, 1H), 8.49 (s, 1H), 8.05 (d, 1H), 7.48-7.39 (m, 1H), 7.33-7.22 (m, 1H), 6.34 (s, 1H), 4.57 (d, 2H), 3.96 (s, 3H), 3.74-3.68 (m, 4H), 3.16-3.06 (m, 4H), 1.36 (s, 9H). |
| Example 204 | (R)-5-(tert-butyl)-N-(1-(2-chloro-4-(6-morpholinopyrrolo[2,1-f][1,2,4]triazin-4-yl)phenyl)ethyl)-1,3,4-oxadiazole-2-carboxamide | Method D; 0-100% yellow solid: 18 mg, 14%<br>LCMS m/z = 510.4 [M + H]+<br>$^1$H NMR (400 MHz, DMSO-$d_6$) δ: 10.05 (d, 1H), 8.50 (s, 1H), 8.13-8.08 (m, 2H), 8.05 (d, 1H), 7.75 (d, 1H), 6.77 (d, 1H), 5.49 (t, 1H), 3.77-3.73 (m, 4H), 3.19-3.16 (m, 4H), 1.54 (d, 3H), 1.39 (s, 9H). |

| Example Number | Name Structure | HPLC Method/Yield/Data |
|---|---|---|
| Example 205 | 1-(tert-butyl)-N-(2-cyclopropyl-4-(6-morpholinopyrrolo[2,1-f][1,2,4]triazin-4-yl)benzyl)-1H-1,2,3-triazole-4-carboxamide formate | Method E; 48-74%<br>red solid: 19 mg, 37%<br>LCMS m/z = 523.0<br>[M + H]$^+$<br>$^1$H NMR (400 MHz, DMSO-d$_6$) δ: 9.16-9.03 (m, 1H), 8.69 (s, 1H), 8.45 (s, 1H), 7.96 (d, 1H), 7.88 (d, 1H), 7.65 (s, 1H), 7.37 (d, 1H), 6.61 (s, 1H), 4.72 (d, 2H), 3.73-3.69 (m, 4H), 3.13-3.09 (m, 4H), 2.17-2.10 (m, 1H), 1.62 (s, 9H), 1.02-0.96 (m, 2H), 0.73-0.69 (m, 2H). |
| Example 206 | 3-(tert-butyl)-N-(2-cyclopropl-4-(6-morpholinopyrrolo[2,1-f][1,2,4]triazin-4-yl)benzyl)-1,2,4-oxadiazole-5-carboxamide hydrochloride | Method A; 43-63%<br>red solid: 17 mg, 27%<br>LCMS m/z = 524.1<br>[M + Na]$^+$<br>$^1$H NMR (400 MHz, DMSO-d$_6$) δ: 9.93 (t, 1H), 8.53 (s, 1H), 8.15 (s, 1H), 7.91 (d, 1H), 7.67 (s, 1H), 7.48 (d, 1H), 6.70 (s, 1H), 4.76 (d, 2H), 3.73 (s, 4H), 3.17 (t, 4H), 2.18-2.12 (m, 1H), 1.37 (s, 9H), 1.04-1.00 (m, 2H), 0.77-0.74 (m, 2H). |
| Example 207 | 3-(tert-butyl)-N-(2-(2,2-difluoroethyl)-4-(6-(1-methyl-1H-pyrazol-4-yl)pyrrolo[2,1-f][1,2,4]triazin-4-yl)benzyl)-1,2,4-oxadiazole-5-carboxamide hydrochloride | Method A; 45-65%<br>red solid: 53 mg, 53%<br>LCMS m/z = 521.2<br>[M + H]$^+$<br>$^1$H NMR (400 MHz, DMSO-d$_6$) δ: 9.98 (br t, 1H), 8.58 (s, 1H), 8.49 (d, 1H), 8.17 (s, 1H), 8.13-8.06 (m, 2H), 7.93 (s, 1H), 7.62 (d, 1H), 7.40 (d, 1H), 6.58 - 6.23 (m, 1H), 4.64 (d, 2H), 3.87 (s, 3H), 3.55 (m, 2H), 1.37 (s, 9H). |
| Example 208 | 1-(tert-butyl)-N-(2-(difluoromethyl)-4-(6-(3,6-dihydro-2H-pyran-4-yl)pyrrolo[2,1-f][1,2,4]triazin-4-yl)benzyl)-1H-pyrazole-4-carboxamide hydrochloride | Method A; 46-66%<br>red solid: 46 mg, 32%<br>LCMS m/z = 507.3<br>[M + H]$^+$<br>$^1$H NMR (400 MHz, DMSO-d$_6$) δ: 8.82 (t, 1H), 8.62 (s, 1H), 8.41 (d, 1H), 8.37-8.32 (m, 3H), 7.95 (s, 1H), 7.64 (d, 1H), 7.61-7.32 (m, 1H), 7.32 (d, 1H), 6.49 (s, 1H), 4.68 (d, 2H), 4.23 (d, 2H), 3.82 (t, 2H), 2.52 (s, 2H), 1.53 (s, 9H). |

| Example Number | Name Structure | HPLC Method/Yield/Data |
|---|---|---|
| Example 209 | 1-(tert-butyl)-N-(4-(6-(1-(2,2-difluoroethyl)-1H-pyrazol-4-yl)pyrrolo[2,1-f][1,2,4]triazin-4-yl)-2-(difluoromethyl)benzyl)-1H-pyrazole-4-carboxamide<br>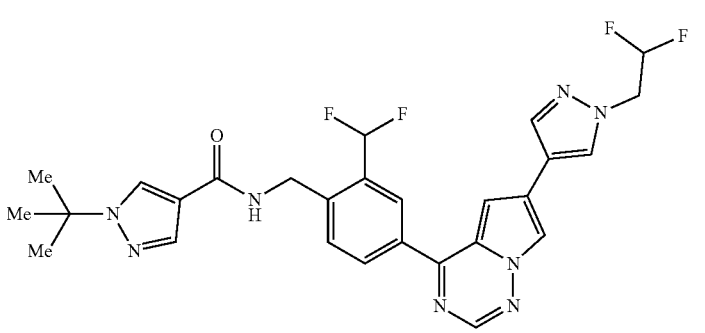 | Method D; 40-70%<br>red solid: 47 mg, 6%<br>LCMS m/z = 555.1 [M + H]$^+$<br>$^1$H NMR (400 MHz, DMSO-d$_6$) δ: 8.78-8.75 (m, 1H), 8.61 (s, 1H), 8.56 (s, 1H), 8.38-8.35 (m, 3H), 8.29 (s, 1H), 8.07 (s, 1H), 7.95 (s, 1H), 7.66-7.34 (m, 3H), 6.54-6.24 (m, 1H), 4.70-4.62 (m, 4H), 1.54 (s, 9H). |
| Example 210 | 2-(tert-butyl)-N-(4-(6-(1-(2,2-difluoroethyl)-1H-pyrazol-4-yl)pyrrolo[2,1-f][1,2,4]triazin-4-yl)-2-(difluoromethyl)benzyl)oxazole-4-carboxamide hydrochloride<br>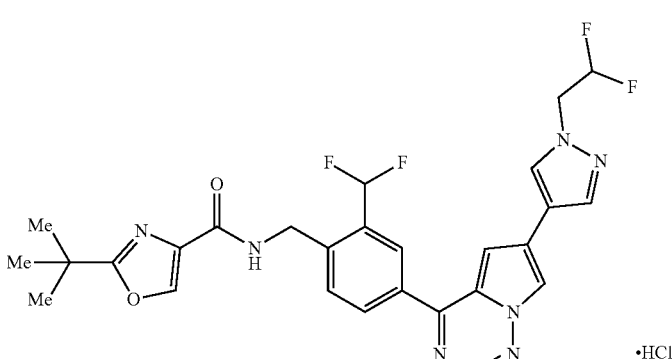 | Method A; 52-72%<br>red solid: 24 mg, 13%<br>LCMS m/z = 556.1 [M + H]$^+$<br>$^1$H NMR (400 MHz, DMSO-d$_6$) δ: 8.88-8.85 (m, 1H), 8.61 (s, 1H), 8.58-8.56 (m, 2H), 8.37-8.29 (m, 3H), 8.07 (s, 1H), 7.67-7.37 (m, 3H), 6.54-6.24 (m, 1H), 4.70-4.61 (m, 4H), 1.37 (s, 9H). |
| Example 211 | 2-(tert-butyl)-N-(2-(difluoromethyl)-4-(6-(1-methyl-1H-pyrazol-4-yl)pyrrolo[2,1-f][1,2,4]triazin-4-yl)benzyl)oxazole-4-carboxamide hydrochloride<br>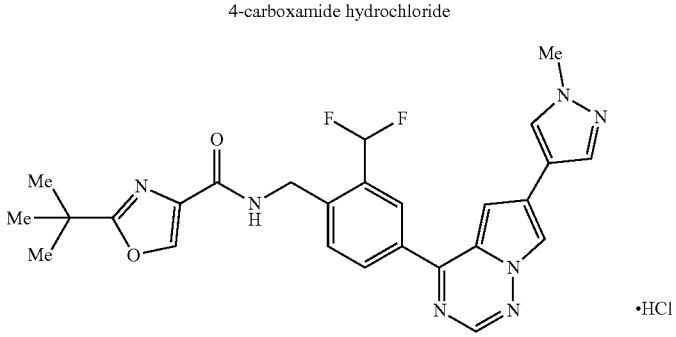 | Method A; 51-71%<br>yellow solid: 62 mg, 32%<br>LCMS m/z = 506.1 [M + H]$^+$<br>$^1$H NMR (400 MHz, DMSO-d$_6$) δ: 8.90-8.87 (m, 1H), 8.61-8.59 (d, 1H), 8.53-8.52 (d, 1H), 8.37 (s, 1H), 8.36-8.35 (m, 2H), 8.20 (s, 1H), 7.96 (s, 1H), 7.68-7.38 (m, 3 H), 4.71-4.69 (d, 2H), 3.87 (s, 3H), 1.38 (s, 9H). |

-continued

| Example Number | Name Structure | HPLC Method/Yield/Data |
|---|---|---|
| Example 212 | 1-(tert-butyl)-N-(2-(difluoromethyl)-4-(6-(1-methyl-1H-pyrazol-4-yl)pyrrolo[2,1-f][1,2,4]triazin-4-yl)benzyl)-1H-pyrazole-4-carboxamide hydrochloride 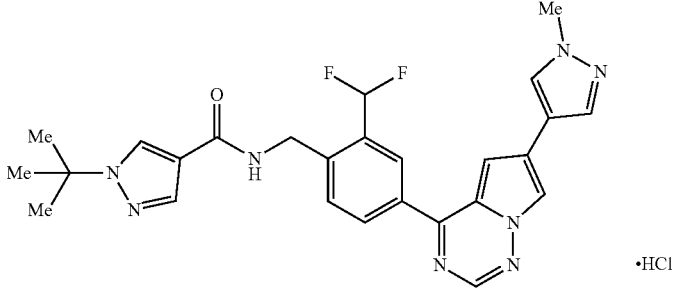 | Method A; 43-63% yellow solid: 63 mg, 34% LCMS m/z = 505.1 [M + H]$^+$ $^1$H NMR (400 MHz, DMSO-d$_6$) δ: 8.84-8.83 (m, 1H), 8.61 (s, 1H), 8.53 (s, 1H), 8.52-8.34 (m, 3H), 8.20 (s, 1H), 7.96-7.95 (d, 2H), 7.67-7.35 (m, 3 H), 4.69-4.68 (m, 2H), 3.86 (s, 3H), 1.54 (s, 9H). |
| Example 213 | 5-(tert-butyl)-N-(2-(difluoromethyl)-4-(6-(3,6-dihydro-2H-pyran-4-yl)pyrrolo[2,1-f][1,2,4]triazin-4-yl)benzyl)-1,3,4-oxadiazole-2-carboxamide 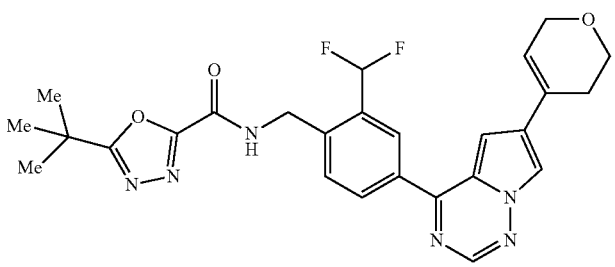 | Method D; 45-75% yellow solid: 37 mg, 17% LCMS m/z = 509.1 [M + H]$^+$ $^1$H NMR (400 MHz, DMSO-d$_6$) δ: 9.97-9.94 (m, 1H), 8.62-8.61 (d, 1H), 8.40-8.34 (m, 3H), 7.70-7.60 (m, 1H), 7.46 (s, 1H), 7.33-7.31 (m, 1H), 6.48 (s, 1 H), 4.74-4.73 (d, 2H), 4.24-4.23 (d, 2H), 3.84-3.82 (m, 2H), 2.50-2.40 (m, 2H), 1.40 (s, 9H). |
| Example 214 | 2-(tert-butyl)-N-(2-methyl-4-(pyrrolo[2,1-f][1,2,4]triazin-4-yl)benzyl)-2H-tetrazole-5-carboxamide 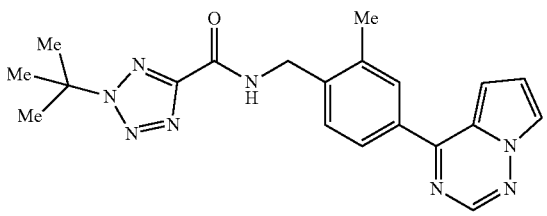 | 10.2 mg LCMS m/z = 391.2 [M + H]$^+$ |
| Example 215 | 5-(tert-butyl)-N-(2-methyl-4-(6-(morpholine-4-carbonyl)pyrrolo[2,1-f][1,2,4]triazin-4-yl)benzyl)-1,2,4-oxadiazole-3-carboxamide hydrochloride 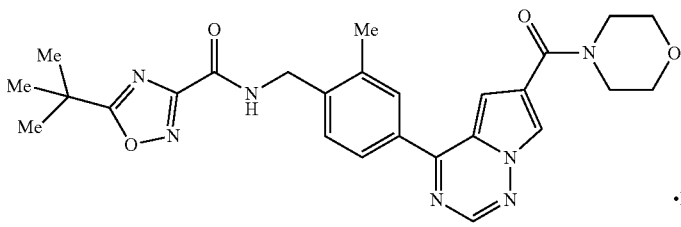 | Method A; 33-53% yellow solid: 38 mg, 55% LCMS m/z = 526.1 [M + Na]$^+$ $^1$H NMR (400 MHz, MeOH-d$_4$) δ: 9.57-9.54 (m, 1H), 8.70 (s, 1H), 8.41 (s, 1H), 7.80-7.97 (m, 2H), 7.47 (d, 1H), 7.34 (s, 1H), 4.56 (d, 2H), 3.64 (s, 8H), 2.47 (s, 3H), 1.44 (s, 9H). |

-continued

| Example Number | Name Structure | HPLC Method/Yield/Data |
|---|---|---|
| Example 216 | 5-(tert-butyl)-N-(2-methyl-4-(6-(4-methylpiperazine-1-carbonyl)pyrrolo[2,1-f][1,2,4]triazin-4-yl)benzyl)-1,2,4-oxadiazole-3-carboxamide hydrochloride 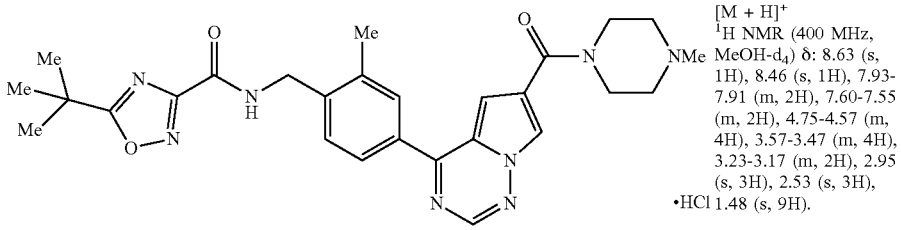 | Method A; 20-35% yellow solid: 35 mg, 53% LCMS m/z = 517.1 [M + H]+ $^1$H NMR (400 MHz, MeOH-$d_4$) δ: 8.63 (s, 1H), 8.46 (s, 1H), 7.93-7.91 (m, 2H), 7.60-7.55 (m, 2H), 4.75-4.57 (m, 4H), 3.57-3.47 (m, 4H), 3.23-3.17 (m, 2H), 2.95 (s, 3H), 2.53 (s, 3H), 1.48 (s, 9H). |
| Example 217 | 5-(tert-butyl)-N-(4-(6-(3-methoxyazetidine-1-carbonyl)pyrrolo[2,1-f][1,2,4]triazin-4-yl)-2-methylbenzyl)-1,2,4-oxadiazole-3-carboxamide 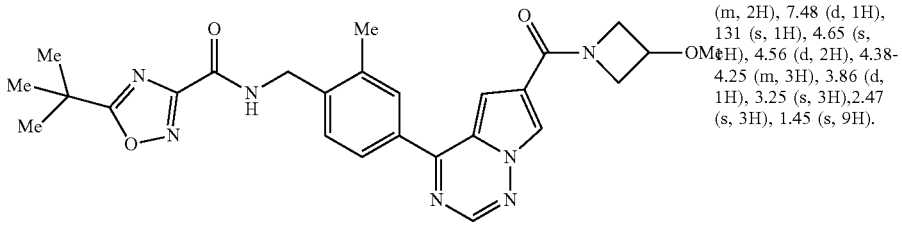 | Method D; 33-63% yellow solid: 19 mg, 30% LCMS m/z = 526.2 [M + Na]+ $^1$H NMR (500 MHz, MeOH-$d_4$) δ: 9.56-9.53 (m, 1H), 8.72 (s, 1H), 8.46 (s, 1H), 8.00-7.96 (m, 2H), 7.48 (d, 1H), 131 (s, 1H), 4.65 (s, 1H), 4.56 (d, 2H), 4.38-4.25 (m, 3H), 3.86 (d, 1H), 3.25 (s, 3H), 2.47 (s, 3H), 1.45 (s, 9H). |
| Example 218 | 5-(tert-butyl)-N-(3-fluoro-2-methyl-4-(pyrrolo[2,1-f][1,2,4]triazin-4-yl)benzyl)-1,2,4-oxadiazole-3-carboxamide hydrochloride 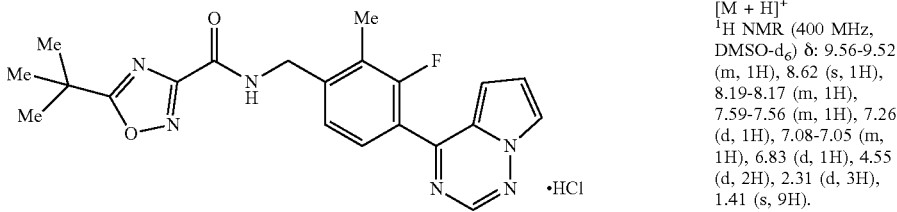 | Method A; 40-60% yellow solid: 55 mg, 39% LCMS m/z = 409.1 [M + H]+ $^1$H NMR (400 MHz, DMSO-$d_6$) δ: 9.56-9.52 (m, 1H), 8.62 (s, 1H), 8.19-8.17 (m, 1H), 7.59-7.56 (m, 1H), 7.26 (d, 1H), 7.08-7.05 (m, 1H), 6.83 (d, 1H), 4.55 (d, 2H), 2.31 (d, 3H), 1.41 (s, 9H). |
| Example 219 | 5-(tert-butyl)-N-(2-(2,2-difluoroethyl)-4-(6-(1-methyl-1H-pyrazol-4-yl)pyrrolo[2,1-f][1,2,4]triazin-4-yl)benzyl)-1,2,4-oxadiazole-3-carboxamide hydrochloride 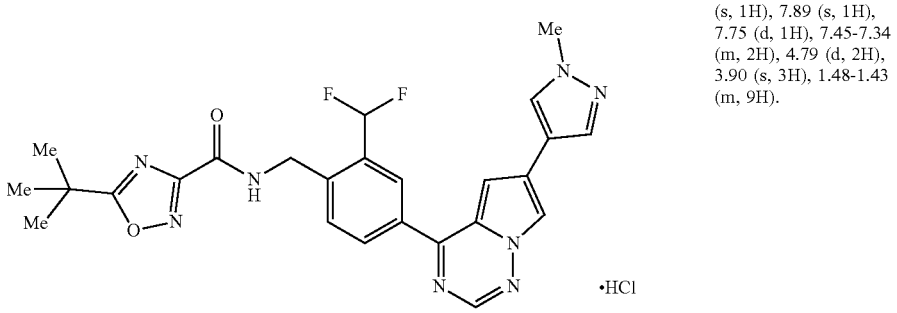 | Method A; 50-70% red solid: 21 mg, 32% LCMS m/z = 507.2 [M + H]+ $^1$H NMR (500 MHz, DMSO-$d_6$) δ: 9.28-9.26 (m, 1H), 8.58 (s, 1H), 8.41-8.35 (m, 3H), 8.12 (s, 1H), 7.89 (s, 1H), 7.75 (d, 1H), 7.45-7.34 (m, 2H), 4.79 (d, 2H), 3.90 (s, 3H), 1.48-1.43 (m, 9H). |

| Example Number | Name Structure | HPLC Method/Yield/Data |
|---|---|---|
| Example 220 | 5-(tert-butyl)-N-(2-(difluoromethyl)-4-(6-morpholinopyrrolo[2,1-f][1,2,4]triazin-4-yl)benzyl)-1,2,4-oxadiazole-3-carboxamide hydrochloride 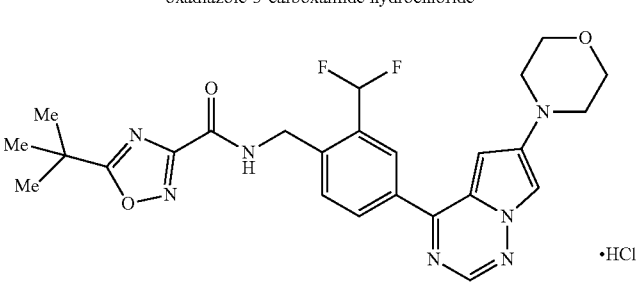 | Method A; 40-70% red solid: 20 mg, 26% LCMS m/z = 512.2 [M + H]$^+$ $^1$H NMR (400 MHz, DMSO-d$_6$) δ: 9.66 (t, 1H), 8.55 (s, 1H), 8.32-8.30 (m, 2H), 8.12 (s, 1H), 7.64 (d, 1H), 7.61-7.33 (m, 1H), 6.79 (s, 1H), 4.74 (d, 2H), 3.78-3.74 (m, 4H), 3.20-3.17 (m, 4H), 1.45 (s, 9H). |
| Example 221 | 5-(tert-butyl)-N-(2-(difluoromethyl)-3-fluoro-4-(6-morpholinopyrrolo[2,1-f][1,2,4]triazin-4-yl)benzyl)-1,2,4-oxadiazole-3-carboxamide 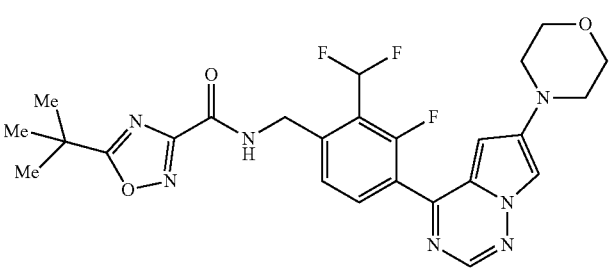 | Method E; 49-75% yellow solid: 25 mg, 50% LCMS m/z = 530.1 [M + H]$^+$ $^1$H NMR (400 MHz, DMSO-d$_6$) δ: 9.64-9.60 (m, 1H), 8.49 (s, 1H), 8.05 (s, 1H), 7.93-7.88 (m, 1H), 7.62-7.34 (m, 2H), 6.33 (s, 1H), 4.75 (d, 2H), 3.70 (t, 4H), 3.10 (t, 4H), 1.41 (s, 9H). |
| Example 222 | 4-(tert-butyl)-N-(2-(difluoromethyl)-4-(6-morpholinopyrrolo[2,1-f][1,2,4]triazin-4-yl)benzyl)oxazole-2-carboxamide hydrochloride 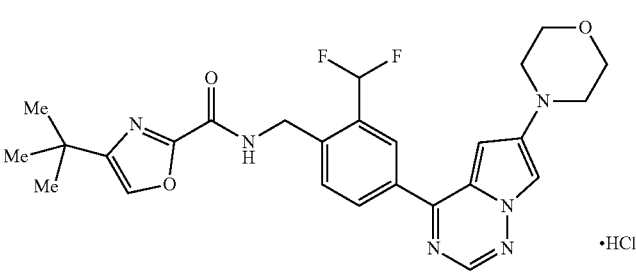 | Method A; 40-70% yellow solid: 14 mg, 22% LCMS m/z = 511.1 [M + H]$^+$ $^1$H NMR (400 MHz, DMSO-d$_6$) δ: 9.47 (t, 1H), 8.50 (s, 1H), 8.28-8.26 (m, 2H), 8.07-8.03 (m, 2H), 7.61-7.29 (m, 2H), 6.75 (d, 1H), 4.66 (d, 2H), 3.74-3.70 (m, 4H), 3.16-3.13 (m, 4H), 1.24 (s, 9H). |
| Example 223 | 5-(tert-butyl)-N-(3-fluoro-2-methoxy-4-(6-morpholinopyrrolo[2,1-f][1,2,4]triazin-4-yl)benzyl)-1,2,4-oxadiazole-3-carboxamide 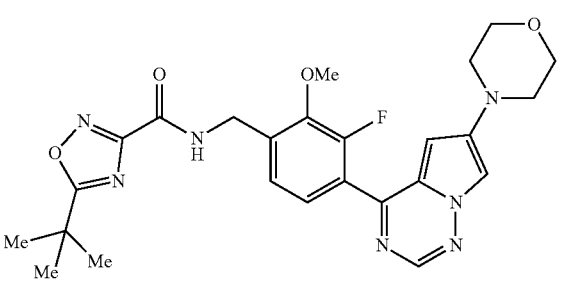 | Method E; 47-74% yellow solid: 21 mg, 30% LCMSm/z = 510.2 [M + H]$^+$ $^1$H NMR (500 MHz, DMSO-d$_6$) δ: 9.54 (t, 1H), 8.51 (s, 1H), 8.07 (d, 1H), 7.49-7.45 (m, 1H), 7.26 (d, 1H), 6.36 (s, 1H), 4.59 (d, 2H), 3.99 (s, 3H), 3.78-3.69 (m, 4H), 3.19-3.09 (m, 4H), 1.45 (s, 9H). |

-continued

| Example Number | Name Structure | HPLC Method/Yield/Data |
|---|---|---|
| Example 224 | 5-(tert-butyl)-N-(4-(6-(4-fluorophenyl)pyrrolo[2,1-f][1,2,4]triazin-4-yl)-2-methylbenzyl)-1,2,4-oxadiazole-3-carboxamide hydrochloride 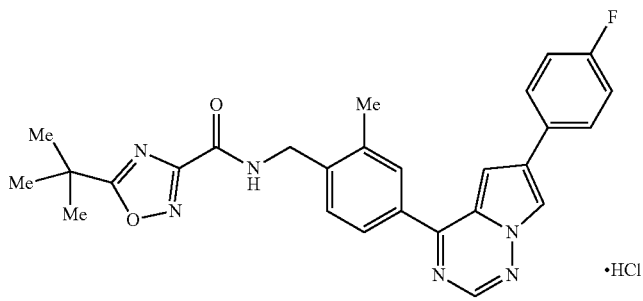 | Method A; 63-83% yellow solid: 27 mg, 34% LCMS m/z = 485.1 [M + H]+ $^1$H NMR (500 MHz, DMSO-$d_6$) δ: 9.57 (t, 1H), 8.74 (d, 1H), 8.63 (s, 1H), 8.08-8.05 (m, 1H), 8.03-8.00 (m, 3H), 7.65 (d, 1H), 7.48 (d, 1H), 7.31-7.27 (m, 2H), 4.58 (d, 2H), 2.50-2.49 (m, 3H), 1.45 (s, 9H). |
| Example 225 | 5-(tert-butyl)-N-(4-(6-(4-cyanophenyl)pyrrolo[2,1-f][1,2,4]triazin-4-yl)-2-methylbenzyl)-1,2,4-oxadiazole-3-carboxamide 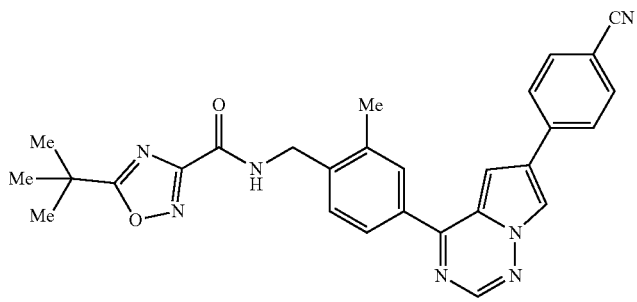 | Method D; 55-85% yellow solid: 30 mg, 25% LCMS m/z = 492.3 [M + H]+ $^1$H NMR (400 MHz, DMSO-$d_6$) δ: 9.67-9.53 (m, 1H), 8.89 (s, 1H), 8.65 (s, 1H), 8.18 (d, 2H), 8.10-8.01 (m, 2H), 7.91 (d, 2H), 7.80 (s, 1H), 7.47 (d, 1H), 4.57 (d, 2H), 2.48-2.47 (m, 3H), 1.44 (s, 9H). |
| Example 226 | 5-(tert-butyl)-N-(2-methyl-4-(6-(pyrimidin-5-yl)pyrrolo[2,1-f][1,2,4]triazin-4-yl)benzyl)-1,2,4-oxadiazole-3-carboxamide hydrochloride 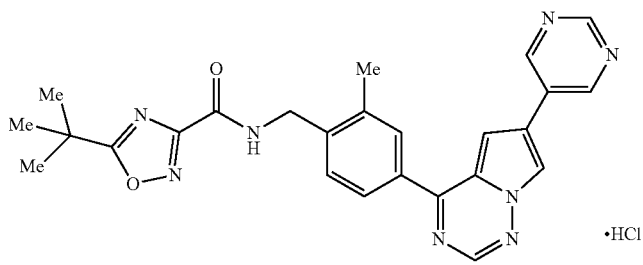 | Method A; 49-69% yellow solid: 18 mg, 12% LCMS m/z = 469.2 [M + H]+ $^1$H NMR (400 MHz, DMSO-$d_6$) δ: 9.56 (t, 1H), 9.44 (s, 2H), 9.13 (s, 1H), 8.92 (s, 1H), 8.67 (s, 1H), 8.10-8.01 (m, 2H), 7.89 (s, 1H), 7.48 (d, 1H), 4.57 (d, 2H), 2.52-2.51 (m, 3H), 1.44 (s, 9H). |
| Example 227 | 5-(tert-butyl)-N-(2-methyl-4-(6-(2-methylpyridin-4-yl)pyrrolo[2,1-f][1,2,4]triazin-4-yl)benzyl)-1,2,4-oxadiazole-3-carboxamide hydrochloride 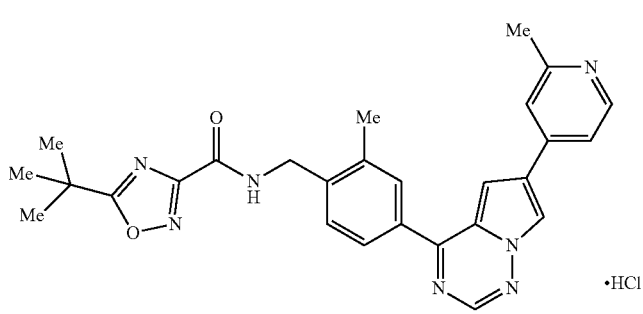 | Method A; 35-55% yellow solid: 10 mg, 14% LCMS m/z = 481.8 [M + H]+ $^1$H NMR (400 MHz, MeOH-$d_4$) δ: 8.97 (s, 1H), 8.64 (s, 2H), 8.44 (s, 1H), 8.34 (d, 1H), 8.02 (d, 3H), 7.61 (d, 1H), 4.72 (s, 2H), 2.82 (s, 3H), 2.56 (s, 3H), 1.50 (s, 9H). |

| Example Number | Name Structure | HPLC Method/Yield/Data |
|---|---|---|
| Example 228 | 5-(tert-butyl)-N-(4-(6-(2-methoxypyridin-4-yl)pyrrolo[2,1-f][1,2,4]triazin-4-yl)-2-methylbenzyl)-1,2,4-oxadiazole-3-carboxamide hydrochloride | Method A; 55-75% yellow solid: 20 mg, 24%<br>LCMS m/z = 498.1 [M + H]+<br>1H NMR (400 MHz, MeOH-d4) δ: 8.83 (s, 1H), 8.57 (s, 1H), 8.26 (d, 1H), 8.01 (d, 2H), 7.85 (s, 1H),7.81 (d, 1H), 7.77 (s, 1H), 7.58 (d, lH),4.71(s, 2H), 4.21 (s, 3H),2.55(s, 3H), 1.49 (s, 9H). |
| Example 229 | 5-(tert-butyl)-N-(2-methyl-4-(6-(3-methylmorpholino)pyrrolo[2,1-f][1,2,4]triazin-4-yl)benzyl)-1,2,4-oxadiazole-3-carboxamide hydrochloride | Method A; 35-55% yellow solid: 35 mg, 61%<br>LCMS m/z = 490.2 [M + H]+<br>1H NMR (400 MHz, DMSO-d6) δ: 9.53 (t, 1H), 8.59 (s, 1H), 8.41 (s, 1H), 7.87-7.83 (m, 2H), 7.44 (d, 1H), 6.84 (s, 1H), 4.52 (d, 2H), 3.68-3.66 (m, 4H), 3.58-3.53 (m, 1H), 3.38-3.34 (m, 1H), 3.14-3.08 (m, 1H), 2.43 (s, 3H), 1.40 (s, 9H), 1.09 (d, 3H). |
| Example 230 | 5-(tert-butyl)-N-(2-methyl-4-(6-(pyridin-2-yl)pyrrolo[2,1-f][1,2,4]triazin-4-yl)benzyl)-1,2,4-oxadiazole-3-carboxamide hydrochloride | Method A; 40-60% yellow solid: 25 mg, 25%<br>LCMS m/z = 468.2 [M + H]+<br>1H NMR (400 MHz, DMSO-d6) δ: 9.54 (t, 1H), 9.02 (s, 1H), 8.74-8.69 (m, 2H), 8.41 (d, 1H), 8.33-8.25 (m, 1H), 8.09 (s, 1H), 8.04-8.01 (m, 2H), 7.65 (t, 1H), 7.46 (d, 1H), 4.54 (d, 2H), 2.50 (s, 3H), 1.41 (s, 9H). |
| Example 231 | 3-(tert-butyl)-N-(2-(2,2-difluoroethyl)-4-(6-(1-methyl-1H-pyrazol-4-yl)pyrrolo[2,1-f][1,2,4]triazin-4-yl)benzyl)-1,2,4-oxadiazole-3-carboxamide hydrochloride | Method A yellow solid: 51 mg, 51%<br>LCMS m/z = 521.2 [M + H]+<br>1H NMR (400 MHz, DMSO-d6) δ: 9.62 (t, 1H), 8.59 (s, 1H), 8.49 (d, 1H), 8.18 (s, 1H), 8.11-8.07 (m, 2H), 7.94 (d, 1H), 7.59 (d, 1H), 7.41 (d, 1H), 6.57-6.26 (m, 1H), 4.63 (d, 2H), 3.87 (br s, 3H), 3.55 (dt, 2H), 1.43 (s, 9H). |

| Example Number | Name Structure | HPLC Method/Yield/Data |
|---|---|---|
| Example 232 | 5-(tert-butyl)-N-(2-(2,2-difluoroethyl)-4-(6-morpholinopyrrolo[2,1-f][1,2,4]triazin-4-yl)benzyl)-1,2,4-oxadiazole-3-carboxamide hydrochloride | Method A red solid: 33 mg, 29% LCMS m/z = 526.2 [M + H]$^+$ $^1$H NMR (400 MHz, DMSO-$d_6$) δ: 9.59 (brt, 1H), 8.53 (s, 1H), 8.13-7.97 (m, 3H), 7.56 (d, 1H), 6.77 (s, 1H), 6.58-6.18 (m, 1H), 4.61 (br d, 2H), 3.79-3.71 (m, 4H), 3.60-3.47 (m, 2H), 3.21-3.11 (m, 4H), 1.43 (s, 9H). |
| Example 233 | 5-(tert-butyl)-N-(2-(2,2-difluoroethyl)-3-fluoro-4-(6-(1-methyl-1H-pyrazol-4-yl)pyrrolo[2,1-f][1,2,4]triazin-4-yl)benzyl)-1,2,4-oxadiazole-3-carboxamide hydrochloride | Method A; 50-70% yellow solid: 44 mg, 49% LCMS m/z = 539.1 [M + H]$^+$ $^1$H NMR (400 MHz, DMSO-$d_6$) δ: 9.65 (t, 1H), 8.60 (s, 1H), 8.51 (s, 1H),8.15(s, 1H), 7.90 (s, 1H), 7.77 (t, 1H), 7.42 (d, 1H), 7.04 (s, 1H), 6.42 (t, 1H), 4.64 (d, 2H),3.85 (s, 3H), 3.56 (t, 2H), 1.43 (s, 9H). |
| Example 234 | 5-(tert-butyl)-N-(2-(2,2-difluoroethyl)-3-fluoro-4-(6-morpholinopyrrolo[2,1-f][1,2,4]triazin-4-yl)benzyl)-1,2,4-oxadiazole-3-carboxamide hydrochloride | Method A; 40-60% red solid: 25 mg, 18% LCMS m/z = 566.1 [M + Na]$^+$ $^1$H NMR (400 MHz, DMSO-$d_6$) δ: 9.62 (t, 1H), 8.51 (s, 1H), 8.08 (s, 1H), 7.71 (t, 1H), 7.39 (d, 1H), 6.40 (t, 1H), 6.35 (s, 1H),4.61 (d, 2H), 3.72 (t, 4H), 3.55 (d, 2H),3.12(t, 4H), 1.42 (s, 9H). |
| Example 235 | 5-(tert-butyl)-N-(3-fluoro-2-methoxy-4-(6-(1-methyl-1H-pyrazol-4-yl)pyrrolo[2,1-f][1,2,4]triazin-4-yl)benzyl)-1,2,4-oxadiazole-3-carboxamide hydrochloride | Method A; 38-53% yellow solid: 22 mg, 31% LCMS m/z = 505.1 [M + H]$^+$ $^1$H NMR (400 MHz, DMSO-$d_6$) δ: 9.55 (t, 1H), 8.59 (s, 1H), 8.51 (s, 1H), 8.18 (s, 1H), 7.92 (s, 1H),7.51 (t, 1H), 7.28 (d, 1H), 7.05 (s, 1H), 4.60 (d, 2H), 4.00(s, 3H), 3.85 (s, 3H), 1.44 (s, 9H). |

-continued

| Example Number | Name Structure | HPLC Method/Yield/Data |
|---|---|---|
| Example 236 | 5-(tert-butyl)-N-(4-(6-(1-ethyl-1H-pyrazol-4-yl)pyrrolo[2,1-f][1,2,4]triazin-4-yl)-2-methylbenzyl)-1,2,4-oxadiazole-3-carboxamide hydrochloride 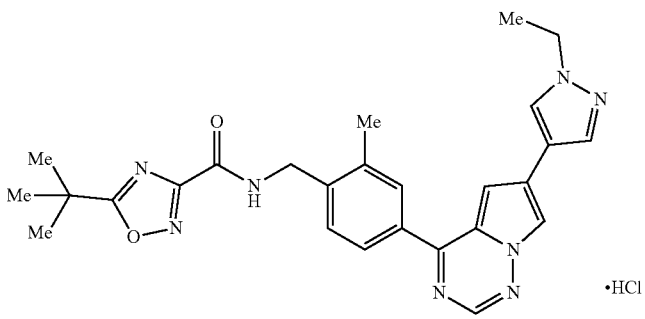 | Method A; 35-55% yellow solid: 25 mg, 11% LCMS m/z = 485.1 [M + H]+ $^1$H NMR (400 MHz, DMSO-$d_6$) δ: 9.54 (t, 1H), 8.55 (s, 1H), 8.45 (s, 1H), 8.25 (s, 1H), 7.99-7.95 (m, 3H), 7.45 (d, 1H), 7.39 (s, 1H), 4.55 (d, 2H), 4.17-4.11(m,2H), 2.47 (s, 3H), 1.43 (s, 9H), 1.40 (t, 3H). |
| Example 237 | 5-(tert-butyl)-N-(4-(6-(1-cyclopropyl-1H-pyrazol-4-yl)pyrrolo[2,1-f][1,2,4]triazin-4-yl)-2-methylbenzyl)-1,2,4-oxadiazole-3-carboxamide hydrochloride 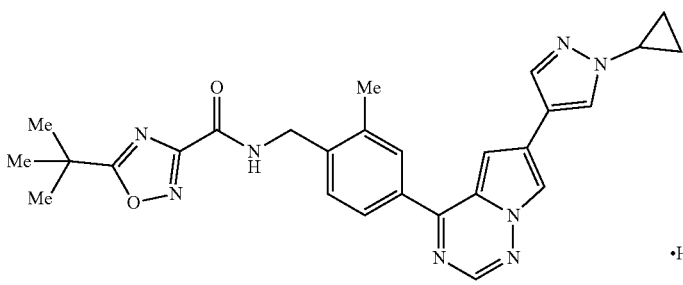 | Method A; 35-55% yellow solid: 58 mg, 36% LCMS m/z = 497.2 [M+H]+ $^1$H NMR (400 MHz, DMSO-$d_6$) δ: 9.56-9.53 (m, 1H), 8.55 (s, 1H), 8.46 (s, 1H), 8.31 (s, 1H), 7.99-7.94 (m, 3H), 7.47-7.41 (m, 2H), 4.56-4.55 (d, 2H), 3.76-3.70 (m, 1 H), 2.47 (s, 3H), 1.44 (s, 9H), 1.06-0.98 (m, 4H). |

In Vitro BTK Kinase Assay: Btk-PolyGAT-LS Assay

The purpose of the BTK in vitro assay is to determine compound potency against BTK through the measurement of $IC_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 pL aliquot of a ATP/peptide master mix (final concentration; ATP 10 μM, polyGAT 100 nM) in kinase buffer (10 mM Tris-HCl pH 7.5, 10 mM MgCl2, 200 μM $Na_3PO_4$, 5 mM DTT, 0.01% Triton X-100, and 0.2 mg/ml casein) is added to each well. Next, 1 pL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 pL of a 50 mM EDTA solution. Aliquots (5 uL) of the kinase reaction are transferred to a low volume white 384 well plate (Corning 3674), and 5 pL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. $IC_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-237 herein.

TABLE 1

| $IC_{50}$ (nM) | Example No. |
|---|---|
| † | 20, 46, 47, 53, 60, 71, 93, 94, 134, 135, 136, 172, 182, 184, 185, 215, 216 |
| †† | 17, 18, 19, 21, 22, 48, 49, 50, 51, 52, 54, 60, 62, 63, 70, 72, 75, 76, 77, 79, 81, 82, 84, 89, 92, 95, 99, 100, 102, 118, 131, 132, 133, 140, 148, 149, 151, 152, 153, 158, 161, 162, 163, 164, 175, 176, 178, 179, 180, 181, 183, 188, 193, 195, 197, 199, 200, 201, 202, 204, 205, 213, 214, 222, 229, 234 |
| ††† | 1, 2, 3, 4, 5, 6, 7, 8, 9, 10, 11, 12, 14, 15, 16, 23, 24, 25, 26, 27, 28, 29, 30, 31, 32, 33, 34, 35, 36, 37, 38, 39, 40, 41, 42, 43, 44, 45, 55, 56, 57, 58, 59, 61, 64, 65, 66, 67, 68, 69, 73, 74, 78, 80, 83, 85, 86, 87, 88, 96, 97, 98, 101, 103, 104, 105, 106, 107, 108, 109, 110, 111, 112, 113, 114, 116, 117, 120, 121, 122, 123, 124, 125, 127, 128, 129, 130, 137, 138, 139, 141, 142, 143, 144, 145, 146, 147, 150, 154, 155, 156, 157, 159, 160, 165, 166, 167, 168, 169, 170, 171, 173, 174, 177, 186, 187, 189, 190, 191, 192, 194, 196, 198, 203, 206, 207, 208, 209, 210, 211, 212, 217, 218, 219, 220, 221, 223, 224, 225, 226, 227, 228, 230, 231, 232, 233, 235, 236, 237 |

"†" represents an $IC_{50}$ of greater than 10 nM (10 nM < $IC_{50}$).
"††" represents an $IC_{50}$ of greater than 1 nM and equal to or less than 10 nM (1 nM < $IC_{50}$ ≤ 10 nM).
"†††" represents an $IC_{50}$ of equal to or less than 1 nM ($IC_{50}$ ≤ 1 nM)

In Vitro Whole Blood CD69 Assay

Human heparinized venous blood from health donors was aliquoted into 96-well plate and "spiked" with serial dilutions of formula I compounds in DMSO or with DMSO without drug. The final concentration of DMSO in all wells was 0.1%. The plate was incubated at 37° C. for 30 min. Drug-containing samples were stimulated with 0.1 µg/mL mouse anti-human IgD-dextran (1A62) or 20 µg/mL polyclonal rabbit F(ab')2 anti-human IgD. Phosphate-buffered saline (PBS) was added to the negative control unstimulated sample and the plates were incubated overnight (18 to 22 hours) at 37° C. Cells were stained with fluorochrome-conjugated anti-CD19 and anti-CD69 antibodies. Lyse/fix solution was used to remove red blood cells by hypotonic lysis and to fix the remaining cells, which were then analyzed by flow cytometry. CD19+ B cells were gated and analyzed for CD69 expression. The percentage of B cells expressing CD69 was plotted versus the log 10 of the concentration of the drug and the best-fit curves (variable Hill slope) were generated to obtain the $IC_{50}$ value.

Table 2 shows the activity of selected compounds of this invention in the Whole Blood CD69 inhibition assay, wherein each compound number corresponds to the compound numbering set forth in Examples 1-237 described herein.

TABLE 2

| $IC_{50}$ (nM) | Compound No. |
|---|---|
| * | 1, 37 |
| ** | 2, 5, 6, 8, 9, 10, 11, 12, 14, 15, 16, 24, 26, 28, 30, 31, 32, 33, 34, 35, 36, 38, 39, 40, 44, 45, 56, 57 |
| *** | 4, 6, 7, 58 |

"*" represents an $IC_{50}$ of greater than 1 µM (1 µM < $IC_{50}$).
"**" represents an $IC_{50}$ of greater than 0.1 µM and equal to or less than 1 µM (0.1 µM < $IC_{50}$ ≤ 1 µM).
"***" represents an $IC_{50}$ of equal to or less than 0.1 µM ($IC_{50}$ ≤ 0.1 µM).

What is claimed is:
1. A compound represented by Formula (I):

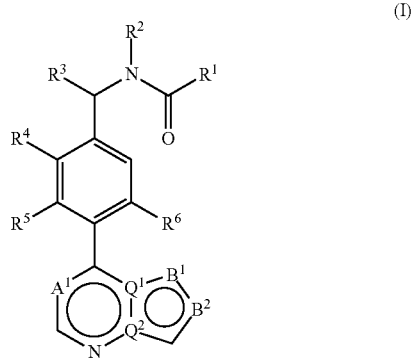

(I)

or a pharmaceutically acceptable salt thereof, wherein:
$A^1$ is selected from $CR^7$ and N;
$B^1$ and $B^2$ are each independently selected from $CR^8$, N, and $NR^8$;
one of $Q^1$ and $Q^2$ is N, and the other one is C;
$R^1$ is selected from $-N(R^{1a})_2$, 3- to 7-membered monocyclic carbocyclyl, 3- to 7-membered monocyclic heterocyclyl, 7- to 10-membered bicyclic carbocyclyl, and 7- to 10-membered bicyclic heterocyclyl; wherein the 3- to 7-membered monocyclic carbocyclyl, 3- to 7-membered monocyclic heterocyclyl, 7- to 10-membered bicyclic carbocyclyl, and 7- to 10-membered bicyclic heterocyclyl represented by $R^1$ are each optionally substituted with one or more $R^{10}$;

$R^{1a}$, for each occurrence, is independently selected from H, $C_{1-6}$ alkyl, $C_{2-6}$ alkenyl, $C_{2-6}$alkynyl, wherein the $C_{1-6}$ alkyl, $C_{2-6}$ alkenyl, and $C_{2-6}$ alkynyl represented by $R^{1a}$ are each optionally substituted with one or more $R^{10}$;

$R^{10}$, for each occurrence, is independently selected from halogen, $-OR^{10a}$, $-S(O)_2R^{10a}$, $-CN$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{10}$ are each optionally substituted with one or more $R^{15}$;

$R^{10a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{15}$, for each occurrence, is independently selected from $C_{1-6}$ alkyl, halogen, $-CN$, and $-OR^{15a}$, or two $R^{15}$, taken together with their intervening atom, form 3- to 7-membered monocyclic carbocyclyl or 4- to 6-membered monocyclic heterocyclyl;

$R^{15a}$ is H or $C_{1-6}$ alkyl;

$R^2$ is selected from H, $C_{1-6}$ alkyl, $C_{2-6}$ alkenyl, and $C_{2-6}$ alkynyl;

$R^3$ is selected from H, $C_{1-6}$ alkyl, $C_{2-6}$ alkenyl, $C_{2-6}$ alkynyl, $-C(O) N(R^{3a})_2$, $-C(O)OR^{3a}$, and $-C(O) R^{3a}$, wherein the $C_{1-6}$ alkyl, $C_{2-6}$ alkenyl, and $C_{2-6}$alkynyl represented by $R^3$ are each optionally substituted with one or more $R^{30}$;

$R^{3a}$, for each occurrence, is independently selected from H, $C_{1-6}$ alkyl, $C_{2-6}$ alkenyl, $C_{2-6}$ alkynyl, wherein the $C_{1-6}$ alkyl, $C_{2-6}$ alkenyl, and $C_{2-6}$ alkynyl represented by $R^{3a}$ are each optionally substituted with one or more $R^{30}$;

$R^{30}$, for each occurrence, is independently selected from halogen, $-OR^{30a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl;

$R^{30a}$ is selected from H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl;

or alternatively $R^2$ and $R^3$, taken together with their intervening atoms, form a Ring A that is selected from 3- to 7-membered monocyclic heterocyclyl and 7- to 10-membered bicyclic heterocyclyl; wherein Ring A is optionally substituted with one or more $R^{200}$;

$R^{200}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $-CN$, $-C(O)R^{200a}$, $-C(O)_2R^{200a}$, $-C(O)N(R^{200a})_2$, $-N(R^{200a})_2$, $-N(R^{200a})C(O)R^{200a}$, $-N(R^{200a})C(O)_2R^{200a}$, $-N(R^{200a})C(O)N(R^{200a})_2$, $-N(R^{200a})S(O)_2R^{200a}$, $-OR^{200a}$, $-OC(O) R^{200a}$, $-OC(O) N(R^{200a})_2$, $-SR^{200a}$, $-S(O) R^{200a}$, $-S(O)_2R^{200a}$, $-S(O) N(R^{200a})_2$, $-S(O)_2N(R^{200a})_2$; wherein the $C_{1-6}$alkyl, $C_{2-6}$alkenyl, $C_{2-6}$alkynyl, 3- to 7-membered monocyclic carbocyclyl, 4- to 6-membered monocyclic heterocyclyl represented by $R^{200}$ are each optionally substituted with one or more $R^{250}$; or two $R^{200}$ taken together with their intervening atom, form 4- to 6-membered monocyclic heterocyclyl or 3- to 7-membered monocyclic carbocyclyl, each of which is optionally substituted with one or more $R^{250}$;

$R^{200a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{200a}$ are each optionally substituted with one or more $R^{250}$;

$R^{250}$, for each occurrence, is independently selected from $C_{1-6}$ alkyl, halogen and $-OR^{250a}$;

$R^{250a}$ is H or $C_{1-6}$ alkyl;

$R^4$ is selected from H, $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $-NO_2$, $-CN$, $-OR^{4a}$, $-SR^{4a}$, $-N(R^{4a})_2$, $-C(O)R^{4a}$, $-C(O)OR^{4a}$, $-S(O)R^{4a}$, $-S(O)_2R^{4a}$, $-C(O)N(R^{4a})_2$, $-SO_2N(R^{4a})_2$, $-OC(O)R^{4a}$, $-N(R)C(O)R^{4a}$, $-N(R)C(O)OR^{4a}$, $-N(R)SO_2R^{4a}$, and $-OC(O)N(R^{4a})_2$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^4$ are each optionally substituted with one or more $R^{40}$;

$R^{4a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{4a}$ are each optionally substituted with one or more $R^{40}$;

$R^{40}$, for each occurrence, is independently selected from halogen, $-OR^{40a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{40}$ are each optionally substituted with one or more $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl are each optionally substituted with one or more $R^{45}$;

$R^{45}$, for each occurrence, is independently selected from $C_{1-6}$ alkyl, halogen and $-OR^{45a}$;

$R^{45a}$ is H or $C_{1-6}$ alkyl;

or alternatively $R^3$ and $R^4$, taken together with their intervening atoms form Ring B that is selected from 5- to 7-membered monocyclic carbocyclyl and 5- to 7-membered monocyclic heterocyclyl having 1-2 heteroatoms independently selected from O, N and S; wherein Ring B is optionally substituted with one or more $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, $-C(O)R^{300a}$, $-OR^{300a}$, and $-S(O)_2R^{300a}$, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more $R^{350}$;

$R^{350}$, for each occurrence, is independently selected from $C_{1-6}$ alkyl, halogen, $-CN$, $-C(O)R^{350a}$, $-C(O)N(R^{350a})_2$, $-C(R^{350a})_2N(R^{350a})_2$, and $-OR^{350a}$;

$R^{350a}$, for each occurrence, is independently H or $C_{1-6}$ alkyl optionally substituted with one to three halogen, or two $R^{350a}$ together with the N atom from which they are attached form 4- to 6-membered monocyclic heterocyclyl with 1-2 heteroatoms selected from N and O;

$R^5$ is selected from H, $C_{1-6}$ alkyl, $C_{2-6}$ alkenyl, $C_{2-6}$ alkynyl, halogen, and $-OR^{5a}$, wherein the $C_{1-6}$ alkyl, $C_{2-6}$ alkenyl, and $C_{2-6}$ alkynyl represented by $R^5$ are optionally substituted with one or more halogen;

$R^{5a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl represented by $R^{5a}$ are each optionally substituted with one or more halogen;

$R^6$ is selected from H, $C_{1-6}$ alkyl, $C_{2-6}$ alkenyl, $C_{2-6}$ alkynyl, halogen, $-OR^{6a}$, wherein the $C_{1-6}$ alkyl, $C_{2-6}$ alkenyl and $C_{2-6}$ alkynyl represented by $R^6$ are each optionally substituted with one or more halogen;

$R^{6a}$ is H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{6a}$ are each optionally substituted with one or more halogen;

$R^7$ is selected from H, $C_{1-6}$ alkyl, $C_{2-6}$ alkenyl, $C_{2-6}$ alkynyl, $-CN$, $-OR^{7a}$, $-C(O)N(R^{7a})_2$, $-C(O)OR^{7a}$, and $-C(O)R^{7a}$, wherein the $C_{1-6}$ alkyl, $C_{2-6}$ alkenyl, and $C_{2-6}$ alkynyl represented by $R^7$ are each optionally substituted one or more $R^{70}$;

$R^{7a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{7a}$ are each optionally substituted with one or more $R^{70}$;

$R^{70}$, for each occurrence, is independently selected from halogen, $-OR^{70a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{70}$ are optionally substituted with one or more $R^{75}$;

$R^{70a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{70a}$ are each optionally substituted one or more $R^{75}$;

$R^{75}$, for each occurrence, is independently selected from $C_{1-6}$ alkyl, halogen and —$OR^{75a}$, $R^{75a}$ is H or $C_{1-6}$ alkyl;

$R^8$, for each occurrence, is independently selected from H, halogen, $C_{1-6}$ alkyl, $C_{2-6}$ alkenyl, $C_{2-6}$ alkynyl, —CN, —$C(O)R^{8a}$, —$C(O)^2R^{8a}$, —$C(O)N(R^{8a})_2$, —$N(R^{8a})_2$, —$N(R^{8a})C(O)R^{8a}$, —$N(R^{8a})C(O)_2R^{8a}$, —$N(R^{8a})C(O)N(R^{8a})_2$, —$N(R^{8a})S(O)_2R^{8a}$, —$OR^{8a}$, —$OC(O)R^{8a}$, —$OC(O)N(R^{8a})_2$, —$SR^{8a}$, —$S(O)R^{8a}$, —$S(O)_2R^{8a}$, —$S(O)N(R^{8a})_2$, —$S(O)_2N(R^{8a})_2$, 3- to 7-membered monocyclic carbocyclyl, 4- to 6-membered monocyclic heterocyclyl, and 7- to 10-membered bicyclic heterocyclyl; wherein the $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl and 7- to 10-membered bicyclic heterocyclyl represented by $R^8$ are each optionally substituted with one or more $R^{80}$;

$R^{8a}$, for each occurrence, is independently selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{8a}$ are each optionally substituted with one or more $R^{80}$; or two $R^{8a}$, taken together with their intervening atom, form 4- to 6-membered monocyclic heterocyclyl optionally substituted with one or more $R^{80}$;

$R^{80}$, for each occurrence, is independently selected from halogen, $C_{1-6}$ alkyl, $C_{2-6}$ alkenyl, $C_{2-6}$ alkynyl, —CN, —$C(O)R^{80a}$, —$C(O)_2R^{80a}$, —$C(O)N(R^{80a})_2$, —$N(R^{80a})_2$, —$N(R^{80a})C(O)R^{80a}$, —$N(R^{80a})C(O)_2R^{80a}$, —$N(R^{80a})C(O)N(R^{80a})_2$, —$N(R^{80a})S(O)_2R^{80a}$, —$OR^{80a}$, —$OC(O)R^{80a}$, —$OC(O)N(R^{80a})_2$, —$SR^{80a}$, —$S(O)R^{80a}$, —$S(O)_2R^{80a}$, —$S(O)N(R^{80a})_2$, —$S(O)_2N(R^{80a})_2$, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{80}$ are each optionally substituted with one or more $R^{85}$; or two $R^{80}$ together the carbon atom from which they are attached form an oxo group (—C=O—);

$R^{80a}$, for each occurrence, is independently selected from H, $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 6-membered monocyclic carbocyclyl, and 4- to 6-membered monocyclic heterocyclyl represented by $R^{80a}$ are each optionally substituted with one or more $R^{85}$;

$R^{85}$, for each occurrence, is independently $C_{1-6}$ alkyl, halogen and —$OR^{85a}$, and $R^{85a}$ is H or $C_{1-6}$ alkyl.

2. The compound of claim 1, wherein the compound is represented by Formula (II) or Formula (III):

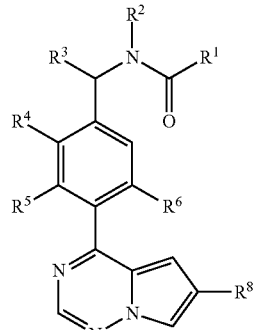

(II)

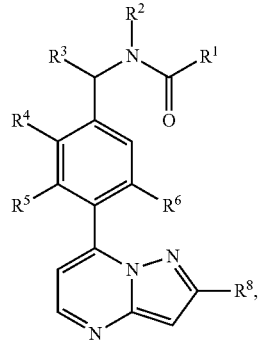

(III)

or a pharmaceutically acceptable salt thereof.

3. The compound of claim 2, or a pharmaceutically acceptable salt thereof, wherein:

$R^1$ is 5- to 6-membered monocyclic heteroaryl having 1-4 heteroatoms independently selected from O, N and S; wherein the 5- to 6-membered monocyclic heteroaryl represented by $R^1$ is optionally substituted with one or two $R^{10}$.

4. The compound of claim 3, wherein:

$R^1$ is a 5-membered heteroaryl selected from pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl, each of which is optionally substituted with one or two $R^{10}$.

5. The compound of claim 4, or a pharmaceutically acceptable salt thereof, or a pharmaceutically acceptable salt thereof, wherein $R^1$ is represented by the following formulas:

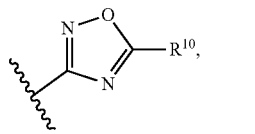 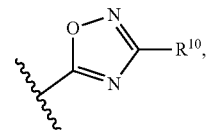

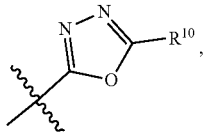 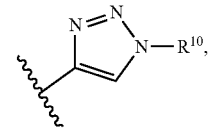

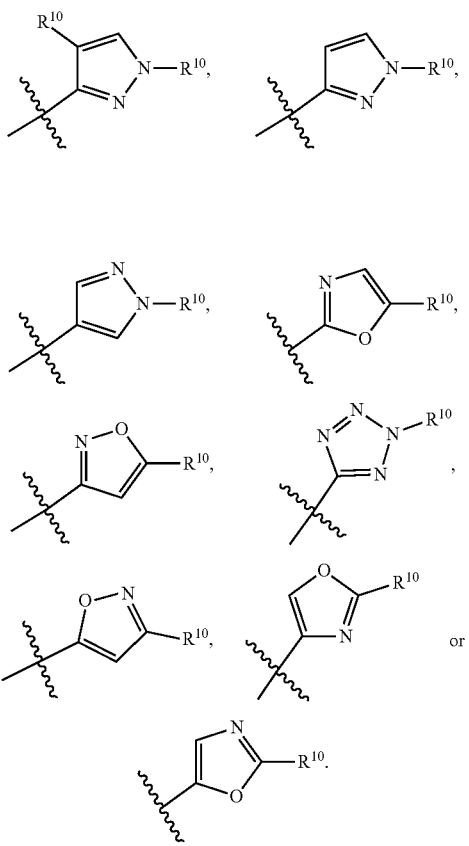

6. The compound of claim 1, or a pharmaceutically acceptable salt thereof, wherein:

$R^{10}$, for each occurrence, is independently selected from halogen, —$OR^{10a}$, —$S(O)_2R^{10a}$, —CN, $C_{1-6}$ alkyl, $C_{3-6}$ cycloalkyl, and phenyl; wherein the $C_{1-6}$ alkyl, $C_{3-6}$ cycloalkyl, and phenyl represented by $R^{10}$ are each optionally substituted with one to three $R^{15}$;

$R^{10a}$, for each occurrence, is independently selected from H and $C_{1-3}$ alkyl;

$R^{15}$, for each occurrence, is independently selected from $C_{1-6}$alkyl, halogen, —CN and —$OR^{15a}$, and $R^{15a}$ is H or $C_{1-3}$ alkyl.

7. The compound of claim 1, or a pharmaceutically acceptable salt thereof, wherein $R^2$ is H or methyl, and $R^3$ is H.

8. The compound of claim 1, or a pharmaceutically acceptable salt thereof, wherein:

$R^4$ is selected from halogen, —CN, —$OR^{4a}$, $C_{1-6}$ alkyl, and $C_{3-6}$ cycloalkyl, wherein the $C_{1-6}$ alkyl and $C_{3-6}$cycloalkyl represented by $R^4$ are each optionally substituted with one to three halogen; and $R^{4a}$ is $C_{1-4}$alkyl optionally substituted with one to three halogen.

9. The compound of claim 1, or a pharmaceutically acceptable salt thereof, wherein $R^3$ and $R^4$, taken together with their intervening atoms form Ring B that is a 7-membered monocyclic carbocyclyl or 7-membered monocyclic heterocyclyl having one heteroatom selected from O and N.

10. The compound of claim 9, wherein the compound is represented by one of the following formula:

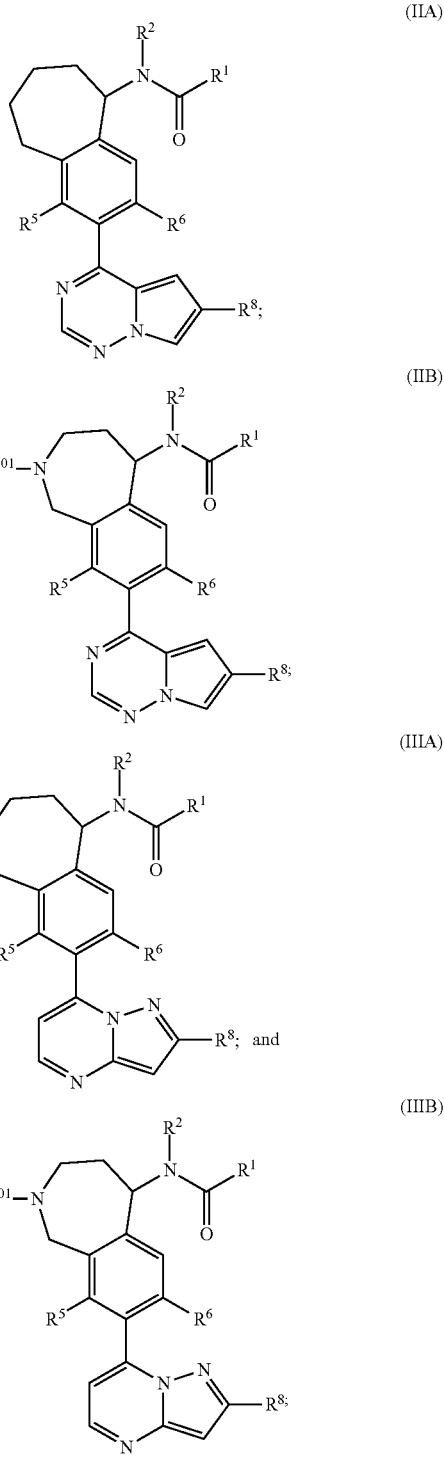

or a pharmaceutically acceptable salt thereof, wherein:

$R^{301}$ is H or $R^{300}$;

$R^{300}$ is selected from $C_{1-6}$ alkyl, $C_{2-6}$ alkenyl, $C_{2-6}$ alkynyl, 4- to 6-membered monocyclic heterocyclyl, —$C(O)R^{300a}$, —$OR^{300a}$, and —$S(O)_2R^{300a}$, wherein the $C_{1-6}$ alkyl, $C_{2-6}$ alkenyl, $C_{2-6}$ alkynyl and 4- to 6-membered monocyclic heterocyclyl represented by $R^{300}$ are each optionally substituted with one to three $R^{350}$;

$R^{300a}$ is selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl are each optionally substituted with one to three $R^{350}$;

$R^{350}$, for each occurrence, is independently selected from $C_{1-6}$ alkyl, halogen, —CN, —N($R^{350a}$)$_2$, —C(O)$R^{350a}$, —C(O)N($R^{350a}$)$_2$, —C($R^{350a}$)$_2$N($R^{350a}$)$_2$, and —O$R^{350a}$, wherein the $C_{1-6}$alkyl is optionally substituted with one to three halogen; and $R^{350a}$, for each occurrence, is independently H or $C_{1-6}$ alkyl optionally substituted with one to three halogen, or two $R^{350a}$ together with the N atom from which they are attached form 4- to 6-membered monocyclic heterocyclyl with 1-2 heteroatoms selected from N and O.

11. The compound of claim 10, or a pharmaceutically acceptable salt thereof, wherein $R^5$ is H or halogen, and $R^6$ is H or halogen.

12. The compound of claim 10, or a pharmaceutically acceptable salt thereof, wherein:

$R^8$, for each occurrence, is independently selected from H, halogen, $C_{2-6}$ alkynyl, —C(O)$R^{8a}$, —C(O)N($R^{8a}$)$_2$, —N($R^{8a}$)$_2$, —O$R^{8a}$, —CN, $C_{1-6}$ alkyl, $C_{2-6}$ alkenyl, phenyl, $C_{3-6}$ cycloalkyl, 4- to 6-membered monocyclic heterocyclyl having 1-2 heteroatoms independently selected from O, N and S, and 7- to 10-membered bicyclic heterocyclyl having 1-4 heteroatoms independently selected from O, N and S; wherein the $C_{1-6}$ alkyl, $C_{2-6}$ alkenyl, $C_{2-6}$ alkynyl, phenyl, $C_{3-6}$ cycloalkyl, 4- to 6-membered monocyclic heterocyclyl, and 7- to 10-membered bicyclic heterocyclyl represented by $R^8$ are each optionally substituted with one to three $R^{80}$;

$R^{8a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{8a}$ are each optionally substituted with one or three $R^{80}$; or two $R^{8a}$, taken together with their intervening atom, form 4- to 6-membered monocyclic heterocyclyl optionally substituted with one to three $R^{80}$, $R^{80}$, for each occurrence, is independently selected from halogen, —CN, —C(O)$R^{80a}$, —O$R^{80a}$, $C_{1-6}$ alkyl, $C_{2-6}$ alkenyl, $C_{2-6}$ alkynyl, $C_{3-6}$ cycloalkyl, and 4- to 6-membered monocyclic heterocyclyl, wherein the $C_{1-6}$ alkyl, $C_{2-6}$ alkenyl, $C_{2-6}$ alkynyl, $C_{3-6}$ cycloalkyl, and 4- to 6-membered monocyclic heterocyclyl represented by $R^{80}$ are each optionally substituted with one or three $R^{85}$, or two $R^{80}$ together the carbon atom from which they are attached form an oxo group (—C=O—); and $R^{80a}$, for each occurrence, is independently selected from H, $C_{1-6}$ alkyl, $C_{2-6}$ alkenyl, $C_{2-6}$ alkynyl, $C_{3-6}$ cycloalkyl, and 4- to 6-membered monocyclic heterocyclyl having 1-2 heteroatoms independently selected from O, N and S;

$R^{85}$, for each occurrence, is independently selected from halogen and —O$R^{85a}$;

$R^{85a}$ is H or $C_{1-6}$ alkyl.

13. The compound of claim 12, or a pharmaceutically acceptable salt thereof, wherein $R^8$ is selected from H, —CH$_3$, —CH$_2$OCH$_3$, F, Br, —CN, —OCH$_3$, —OC$_2$H$_5$OCH$_3$, —N(CH$_3$)(CH$_2$CH$_2$OCH$_3$), —C(O)N(CH$_3$)$_2$,

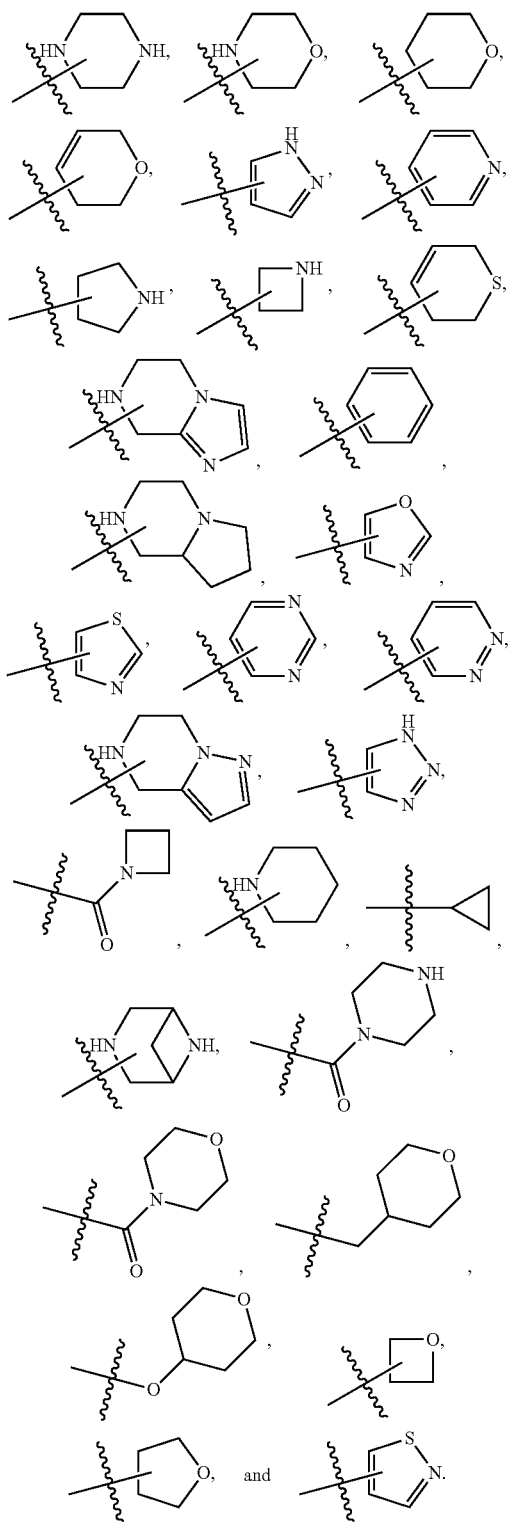

14. The compound of claim 12, or a pharmaceutically acceptable salt thereof, wherein:

$R^{80}$ is selected from halogen, —CN, —C(O)$R^{80a}$, —O$R^{80a}$, $C_{1-3}$ alkyl, $C_{3-6}$ cycloalkyl, and 4- to 6-membered monocyclic heterocyclyl having 1-2 heteroatoms selected from O and N; wherein the $C_{1-3}$ alkyl, $C_{3-6}$ cycloalkyl, and 4- to 6-membered monocyclic heterocyclyl represented by $R^{80}$ are each optionally substituted with one to three $R^{85}$; or two $R^{80}$ together with the carbon atom from which they are attached from an oxo (—C(=O)) group; and $R^{80a}$, for each occurrence, is independently selected from $C_{1-4}$ alkyl and $C_{2-4}$ alkenyl;

$R^{85}$, for each occurrence, is independently selected from F, —OH or $C_{1-3}$ alkoxy.

15. The compound of claim 1, wherein the compound is represented by the following formulas:

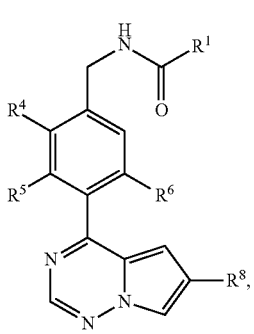

(IV)

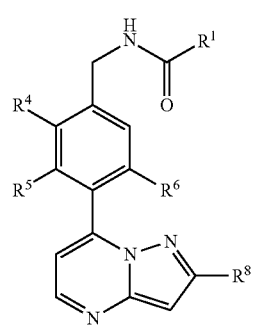

(V)

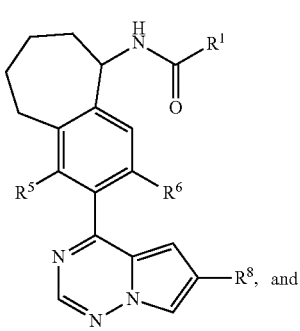

(VI)

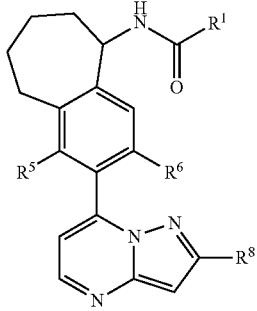

(VII)

or a pharmaceutically acceptable salt thereof, wherein:

$R^1$ is a 5-membered heteroaryl selected from 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl, each of which is optionally substituted with one or two $R^{10}$;

$R^{10}$, for each occurrence, is independently selected from halogen, —O$R^{10a}$, —S(O)$_2R^{10a}$, —CN, $C_{1-6}$ alkyl, $C_{3-6}$cycloalkyl, and phenyl; wherein the $C_{1-6}$ alkyl, $C_{3-6}$cycloalkyl, and phenyl represented by $R^{10}$ are each optionally substituted with one to three $R^{15}$;

$R^{10a}$, for each occurrence, is independently selected from H and $C_{1-3}$alkyl;

$R^{15}$, for each occurrence, is independently selected from $C_{1-6}$ alkyl, halogen, —CN and —O$R^{15a}$;

$R^{15a}$ is H or $C_{1-3}$ alkyl;

$R^4$ is selected from halogen, —CN, —O$R^{4a}$, $C_{1-6}$ alkyl, and $C_{3-6}$ cycloalkyl; wherein the $C_{1-6}$ alkyl and $C_{3-6}$ cycloalkyl represented by $R^4$ are each optionally substituted with 1-3 halogen; and $R^{4a}$ is $C_{1-4}$ alkyl optionally substituted with one to three halogen;

$R^5$ is H or halogen;

$R^6$ is H or halogen;

$R^8$ is H, —O$R^{8a}$ or 4- to 6-membered monocyclic heterocyclyl having 1-2 heteroatoms independently selected from O and N, wherein the 4- to 6-membered monocyclic heterocyclyl is optionally substituted with one or two $R^{80}$, $R^{8a}$ is $C_{1-6}$ alkyl optionally substituted with one to three $R^{80}$;

$R^{80}$, for each occurrence, is independently selected from halogen, —O$R^{80a}$, and $C_{1-3}$ alkyl optionally substituted with one to three $R^{85}$;

$R^{80a}$, for each occurrence, is independently selected from H, $C_{1-6}$ alkyl and $C_{2-6}$ alkenyl;

$R^{85}$, for each occurrence, is independently selected from halogen and —O$R^{85a}$, and $R^{85a}$ is H or $C_{1-3}$ alkyl.

16. The compound of claim 15, or a pharmaceutically acceptable salt thereof, wherein $R^1$ is

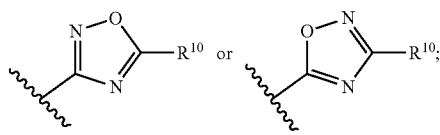

and $R^{10}$ is $C_{1-4}$alkyl or $C_{3-6}$cycloalkyl optionally substituted with halogen or $C_{1-3}$alkyl.

17. The compound of claim 15, or a pharmaceutically acceptable salt thereof, wherein $R^8$ is selected from H, $-OR^{8a}$,

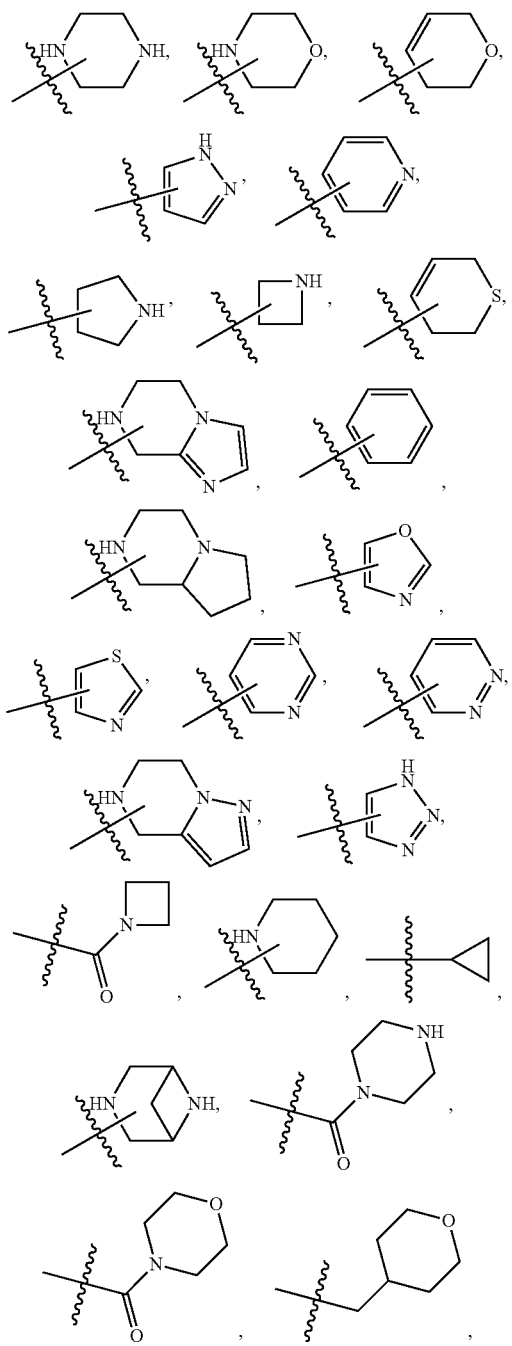

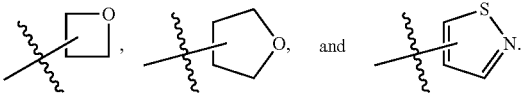

18. The compound of claim 17, or a pharmaceutically acceptable salt thereof, wherein $R^8$ is H

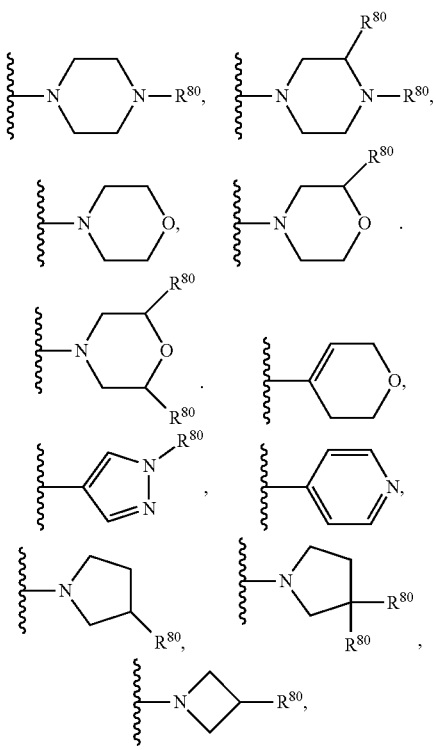

or $-OR^{8a}$, and $R^{80}$, for each occurrence, is independently selected from F, $-CH_3$,

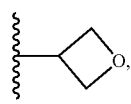

$CH_2CH_2OCH_3$, $-OCH_3$, and $-CH_2CHF_2$.

19. A pharmaceutical composition comprising a compound of claim 1 or a pharmaceutically acceptable salt thereof, and a pharmaceutically acceptable excipient.

20. A method of treating a disorder responsive to inhibition of Bruton's tyrosine kinase in a subject comprising administering to the subject an effective amount of the compound according to claim 1, or a pharmaceutically acceptable salt thereof, wherein the disorder is an autoimmune disorder, or multiple sclerosis.

* * * * *